(12) United States Patent
Nagase et al.

(10) Patent No.: US 6,177,438 B1
(45) Date of Patent: *Jan. 23, 2001

(54) MORPHINAN DERIVATIVES AND PHARMACEUTICAL USE THEREOF

(75) Inventors: Hiroshi Nagase, Kamakura; Jun Hayakawa, Yokohama; Kuniaki Kawamura; Koji Kawai, both of Kamakura; Takashi Endoh, Chigasaki, all of (JP)

(73) Assignee: Toray Industries, Inc., Tokyo (JP)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/754,750

(22) Filed: Nov. 21, 1996

Related U.S. Application Data

(63) Continuation of application No. 08/279,030, filed on Jul. 22, 1994, now abandoned.

(30) Foreign Application Priority Data

Jul. 23, 1993 (JP) .................................................. 5-202127

(51) Int. Cl.[7] ..................... C07D 491/08; A61K 31/4355

(52) U.S. Cl. ............................ 514/280; 546/44; 546/45; 546/46

(58) Field of Search .................................. 514/281, 282; 546/44, 45, 46

(56) References Cited

U.S. PATENT DOCUMENTS

| | | | |
|---|---|---|---|
| 3,819,635 | * 6/1974 | Pachter . | |
| 4,241,067 | * 12/1980 | Kobylecki et al. | 546/45 |
| 4,362,870 | * 12/1982 | Portoghese | 546/44 |
| 4,401,672 | * 8/1983 | Portoghese | 514/282 |
| 4,767,718 | * 8/1988 | Meyers | 546/45 |
| 4,806,556 | * 2/1989 | Portoghese | 546/44 |
| 4,816,586 | * 3/1989 | Portoghese | 545/31 |
| 4,925,848 | * 5/1990 | Lewis | 514/282 |
| 5,219,861 | * 6/1993 | Kanematsu | 514/282 |
| 5,972,953 | * 10/1999 | Nagase et al. | 514/282 |

FOREIGN PATENT DOCUMENTS

| | | |
|---|---|---|
| 74152 | 2/1982 | (AU) . |
| 37115 | 12/1984 | (AU) . |
| 57637 | 5/1986 | (AU) . |
| 23894 | 2/1993 | (AU) . |
| 622231 | 11/1935 | (DE) . |
| 374919 | 6/1990 | (EP) . |
| 577847 | 1/1994 | (EP) . |
| 657163 | 6/1995 | (EP) . |
| 864107 | 3/1961 | (GB) . |
| 919311 | 2/1963 | (GB) . |
| 2254298 | 5/1974 | (GB) . |
| 61-271275 | 12/1986 | (JP) . |
| 62-258380 | 11/1987 | (JP) . |
| 62-277324 | 12/1987 | (JP) . |
| 1-149788 | 6/1989 | (JP) . |
| 290054 | 6/1965 | (NL) . |
| 93 03051 | 2/1993 | (WO) . |
| 93-15081 | * 8/1993 | (WO) . |

OTHER PUBLICATIONS

Journal of Medicinal Chemistry, vol. 29, No. 8, 1986, Washington, US, pp. 1551–1553, M.S. Mohamed et al. "Activity of N–methyl–alpha– and –beta–funaltrexamine at opioid receptors.".

Chemical Abstracts, vol. 107, No. 21, Nov. 23, 1987, Columbus, Ohio, US; abstract No. 190810p. L.A. Dykstra et al., "Kappa opioids in rhesus monkeys. II. Analysis of the antagonistic actions of quadazocine and beta–funaltrexamine," p. 58.

Mucha et al. Pyschopharmocology, vol. 86 pp. 274–280, 1985.*

Leander, J. Pharm. Expt'l Therap. vol. 227, pp. 35–11, 1983.*

O'Neill, Japanese Names, Weatherhill, NY, NY pp. X,XI, 1984.*

Casy et al. Opioid Analgesics, Plenum Press, NY NY pp. 68–69, 76–77.*

PTCJ, vol. 58, No. 1433, pp. 318–320 Jul. 15, 1999 in Regan to Odetics v Horage Tech, 1999.*

Burger, Medicina Chemistry, 2d Ed Interscience, New York (1960) p. 43.*

Nagase et al. Chem. Abstr vol. 120 Entry 164625 (Abst. Wo–93 15081) 1993.*

* cited by examiner

Primary Examiner—John M. Ford
(74) Attorney, Agent, or Firm—Birch, Stewart, Kolasch & Birch, LLP

(57) ABSTRACT

A morphinan derivative or its pharmaceutically acceptable acid addition salt represented with, for example,

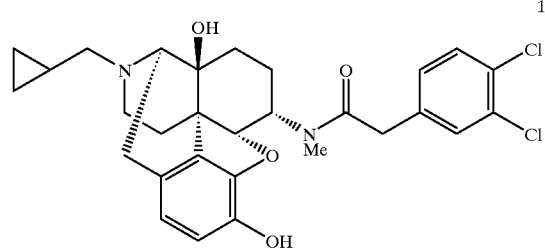

and an analgesic, diuretic, antitussive and brain cell protector having its derivative or its salt as the active ingredient are described.

The compound of the present invention possesses strong analgesic activity, diuretic action and antitussive action as a highly selective κ-opioid agonist, allowing it to be used as a useful analgesic, diuretic and antitussive. On the other hand, the compound of the present invention also possesses remarkable cerebro-neuroprotective activity, thus allowing it be used as a useful cerebro-neuroprotective agents.

6 Claims, No Drawings

MORPHINAN DERIVATIVES AND PHARMACEUTICAL USE THEREOF

This application is a continuation of application Ser. No. 08/279,030 filed on Jul. 22, 1994, now abandoned.

TECHNICAL FIELD

The present invention relates to an analgesic, diuretic, antitussive, or new preventive or therapeutic drug for ischemic brain disorders, cerebral nerve cell disorders and dementia having for its active ingredient a morphinan derivative or pharmacologically acceptable acid addition salt thereof.

Background Art

Morphine has long been known as a powerful analgesic having a morphinan skeleton, and is widely used even at present. However, this drug has serious side effects that present clinical problems, including drug dependence and respiratory suppression and inhibitory action of smooth muscle movement (constipation). Thus, its use is required to be carefully monitored. There is therefore a need for a powerful analgesic that acts on the central nervous system and that also can be used safely.

In addition, it has also been reported that drugs that act on opioid receptors effect urination (J. D. Leander, J. Pharmacol. Exp. Ther., 227, 35 (1983)), and thus the effective use of that action is also desired.

On the other hand, known examples of powerful antitussives that act on the central nervous system include codeine and dextromethorphan. Although these drugs are used not only for medical purposes, but are also widely used as one ingredient of comprehensive cold medications, they too essentially have serious side effects that present clinical problems, including drug dependency, respiratory suppression and inhibitory action of smooth muscle movement (constipation) and psychotomimetics. In particular, in view of the seriousness of the abuse of antitussives containing codeine and the psychotomimetics of dextromethorphan, a powerful yet safe antitussive is desired that acts on the central nervous system.

Aside from the above, there has been an increase in recent years in various types of ischemic diseases of the cerebroiuasciilar and cardiovascular system accompanying increasing of aged people. Cerebral infarction, cerebral hemorrhage, cerebral arteriosclerosis and cerebral phlebothrombosis, cerebrovascular disorders caused by intracerebral hemorrhage and intracerebral thrombus, and functional brain damage caused by head injury and so forth bring about a shortage of glucose and oxygen used as energy sources for nerve cell activity. Due to the resulting necrosis of nerve cells at the ischemic site, various symptoms are manifest as sequela of this necrosis, including cerebrovascular dementia and other disorders. In addition, accompanying the increasing proportion of elderly persons in society resulting from prolongation of the average life span, the problem of such diseases as Alzheimer's disease is becoming a serious problem both medically and socially. In the past, drugs that were developed against these ischemic cerebrovascular disorders and psychoneurotic symptoms accompanying senile dementia consisted primarily of those that mainly increased blood flow to the brain to promote the supply of glucose, oxygen and so forth to the ischemic site. Although these drugs are referred with obscure expressions such as cerebral circulatory improvers, cerebral metabolic activators and cerebral function improvers in terms of their action and mechanism, despite being considered to be effective in improving peripheral symptoms such as volitional disorders, emotional disorders and behavioral abnormalities, their effects are not clear with respect to improvement of the core symptoms of dementia such as memory disorders. Thus, at present, since there is no drug which is able to effectively treat these diseases, the development of a therapeutic drug is desired that demonstrates more reliable action and effects while also being safe and easy to use.

DISCLOSURE OF THE INVENTION

The existence of opioid receptors has been clearly established as receptors involved in analgesic action on the central nervous system. Moreover, these receptors are known to be able to be classified into the three types $\mu$, $\delta$ and $\kappa$. In addition, $\sigma$ receptors are also known to demonstrate psychotomimetics. Those agonists having affinity for $\kappa$-receptors or $\sigma$-receptors have been shown to have strong analgesic activity, while not demonstrating serious side effects that present clinical problems such as drug dependence, respiratory suppression and inhibitory action of smooth muscle movement, that are observed in the case of morphine and so forth, which are $\mu$-receptor agonists. In addition, the psychotomimetics observed in existing $\kappa$-receptor agonists is reported to be caused by affinity to $\sigma$ receptors. Moreover, $\kappa$-receptor agonists do not demonstrate cross tolerance with $\mu$-receptor agonists such as morphine. Analgesics free of such side effects have a high degree of usefulness since they can be applied in not only the control of pain in patients having post-operative pain and cancer patients, but can also be widely applied for general pain. In addition, the absence of cross tolerance indicates that these analgesics are effective even in patients that have developed tolerance to analgesics such as morphine. Namely, the object of the present invention is to provide a $\kappa$-receptor agonist or $\sigma$-receptor agonist that has powerful analgesic action while not having serious side effects like those of morphine, not having cross tolerance with morphine and so forth, and not demonstrating any affinity whatsoever for a receptors.

In addition, a second object of the present invention is to provide a useful diuretic that takes advantage of the effects of opioid action drugs on urination.

On the other hand, although antitussives such as morphine and codeine, which act on $\mu$ receptors, and dextromethorphan, which acts on $\sigma$ receptors, have been long known, it has not been possible to avoid serious side effects such as drug dependency, respiratory suppression, inhibitory action of smooth muscle movement (constipation) and psychotomimetics. However, those agonists that have affinity for $\kappa$ receptors have been shown not to demonstrate serious side effects that present clinical problems, such as drug dependency, respiratory suppression, inhibitory action of smooth muscle movement and so forth observed in morphine and so forth, which are $\mu$-receptor agonists. In addition, the psychotomimetics observed in existing $\kappa$-receptor agonists is reported to be caused by affinity to $\sigma$ receptors. Namely, a third object of the present invention is to provide a $\kappa$-receptor agonist having powerful antitussive activity that is free of the serious side effects observed in $\mu$-receptor agonists and $\sigma$-receptor agonists.

Moreover, aside from the above, a fourth object of the present invention is to provide a new preventive and therapeutic drug for ischemic brain disorders, cerebroneuronal disorders and dementia.

As a result of earnest studies to solve the abovementioned problems, the inventors of the present invention found that the morphinan derivative indicated with general formula (I) is a compound that demonstrates analgesic action, diuretic action, antitussive action and new preventive or therapeutic effects against ischemic brain disorders, cerebroneuronal disorders and dementia while also having the excellent characteristics described above, thus leading to completion of the present invention.

Namely, the present invention relates to a morphinan derivative represented with general formula (I) below or pharmacologically acceptable acid salt thereof, its production process, as well as its pharmaceutical applications:

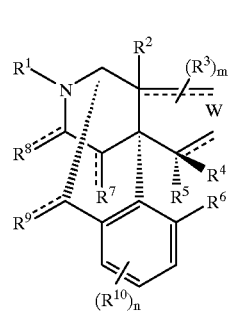

(I)

[wherein, ‒‒‒‒‒ represents a single or double bond;

$R^1$ represents an alkyl group having 1–5 carbon atoms, a cycloalkylalkyl group having 4–7 carbon atoms, a cycloalkenylalkyl group having 5–7 carbon atoms, an aryl group having 6–12 carbon atoms, an aralkyl group having 7–13 carbon atoms, an alkenyl group having 4–7 carbon atoms, an allyl group, a furan-2-ylalkyl group having 1–5 carbon atoms or a thiophen-2-ylalkyl group having 1–5 carbon atoms;

$R^2$ represents —A—B—$R^{11}$ (wherein, A is a valence bond, —C(=O)—, —XC(=Y)—, —XC(=Y)Z—, —X—, —XSO$_2$— or —OC(OR$^{12}$)R$^{12}$— (where, X, Y and Z each independently represent NR$^{12}$, S or O, R$^{12}$ represents a hydrogen atom, a straight chain or branched chain alkyl group having 1–5 carbon atoms or an aryl group having 6–12 carbon atoms, and wherein $R^{12}$ may be identical or different), B represents a valence bond, straight chain or branched chain alkylene group having 1–14 carbon atoms (which may be substituted with at least one type of substituent group selected from the group consisting of alkoxy group having 1–5 carbon atoms, an alkanoyloxy group having 1–5 carbon atoms, a hydroxy group, fluorine, chlorine, bromine, iodine, an amino group, a nitro group, a cyano group, a trifluoromethyl group and a phenoxy group, and wherein from 1 to 3 methylene groups may be replaced with carbonyl groups), a straight claim or branched claim a cyclic unsaturated hydrocarbon containing 1 to 3 double bonds and for triple bonds (which may be substituted with at least one type of substituent selected from the group consisting of alkoxy having 1 to 5 carbon atoms, alkonoyloxy having 1 to 5 carbon atoms, hydroxy, fluorine, chlorine, bromine, iodine, amino, nitro, cyano, trifluoromethyl or phenoxy, and wherein 1 to 3 methylene groups may be replaced with carbonyl) or a straight chain or branched chain saturated or unsaturated hydrocarbon group containing from 1 to 5 of at least one type of bond selected from the group consisting of a thioether bond, ether bond and amino bond, and having 1–14 carbon atoms (wherein hetero atoms are not bonded directly to A, and 1 to 3 methylene groups may be replaced with carbonyl groups); and, $R^{11}$ represents a hydrogen atom, a nitro group, fluorine, chlorine, bromine, iodine or an organic group having the basic skeleton group A shown below:

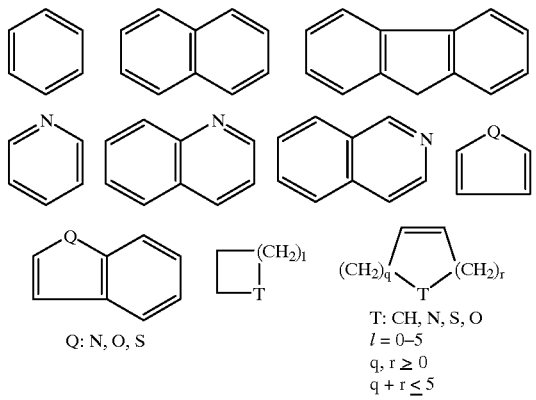

(which may be substituted with at least one type of substituent group selected from the group consisting of an alkyl group having 1–5 carbon atoms, an alkoxy group having 1–5 carbon atoms, an alkanoyloxy group having 1–5 carbon atoms, a hydroxy group, fluorine, chlorine, bromine, iodine, an amino group, a nitro group, a cyano group, an isothiocyanato group, a trifluoromethyl group, a trifluoromethoxy group and a methylenedioxy group);

$R^3$ represents —A—B—$R^{11}$ (wherein A, B and $R^{11}$ are the same as previously defined);

m is an integer from 1 to 10, which may be selected as desired within the range of the number of hydrogen atoms that can bond with carbon chain W, and $R^3$ may be identical or different in the case of m being equal to 2 or more;

$R^4$ represents —A—B—$R^{11}$ (wherein A, B and $R^{11}$ are the same as previously defined);

$R^5$ represents a hydrogen atom;

$R^6$ represents a hydrogen atom, a hydroxy group, fluorine, chlorine, bromine, iodine, —SO$_3$H, —OSO$_3$H, a nitro group, an amino group, an alkanoyloxy group having 1–5 carbon atoms, or an alkoxy group having 1–5 carbon atoms, or alternatively, $R^5$ and $R^6$ collectively represent —O—, —CH2— or —S—;

$R^7$ represents a hydrogen atom, a hydroxy group, fluorine, chlorine, bromine, iodine, an oxime group, an alkyl group having 1–5 carbon atoms (which may be substituted with a hydroxy group), an alkanoyl group having 1–5 carbon atoms, or a carbonyl group;

$R^8$ represents a hydrogen atom, an alkyl group having 1–5 carbon atoms, a cyano group, —COOH, an alkylamido group having 1–5 carbon atoms, or a carbonyl group;

$R^9$ represents a hydrogen atom, a hydroxy group, fluorine, chlorine, bromine, iodine, or a carbonyl group;

$R^{10}$ represents a hydrogen atom, a hydroxy group, fluorine, chlorine, bromine, iodine, —SO$_3$H, —OSO$_3$H, a nitro group, an amino group, an alkyl group having 1–5 carbon atoms, an alkanoyl group having 1–5 carbon atoms, an alkanoyloxy group having 1–5 carbon atoms, or an alkoxy group having 1–5 carbon atoms;

n represents an integer from 1 to 3;

W represents an alkylene group having 2–5 carbon atoms, or an unsaturated hydrocarbon group having 2–5 carbon atoms; and, the general formula (I) includes the (+) form, (−) form and (±) form].

Among the above-mentioned morphinan derivatives, the morphinan derivatives or their pharmacologically acceptable acid addition salts represented with general formula (I) (wherein $R^1$, $R^2$, $R^3$, $R^4$, $R^5$, $R^6$, $R^7$, $R^8$, $R^9$, $R^{10}$, m, n and W are the same as previously defined, but one of either $R^7$, $R^8$ or $R^9$ is a substituent group other than a hydrogen atom in the case of the compound represented with general formula (I-E):

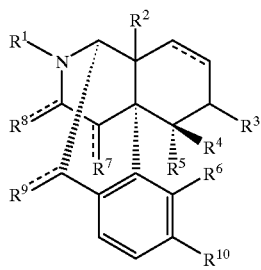

(I-E)

(wherein, ___ represents a double bond or single bond, $R^1$, $R^2$, $R^3$, $R^4$, $R^5$, $R^6$, $R^7$, $R^8$, $R^9$ and $R^{10}$ are the same as previously defined, and the general formula (I-E) includes the (+) form, (−) form and (±) form)) are preferable.

Among the above-mentioned preferable compounds, (1) morphinan derivatives or their pharmacologically acceptable acid addition salts represented with general formula (I-A):

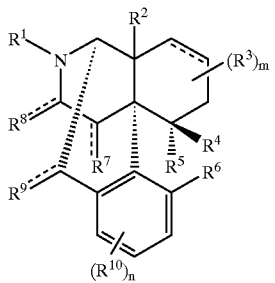

(I-A)

[wherein, ___ represents a double bond or single bond, $R^1$, $R^2$, $R^3$, $R^4$, $R^5$, $R^6$, $R^7$, $R^8$, $R^9$, $R^{10}$, m and n are the same as previously defined (provided that one of either $R^7$, $R^8$ or $R^9$ is a substituent group other than a hydrogen atom when both m and n are 1, $R^3$ is bonded to the carbon atom adjacent to the binding carbon atom of $R^4$, and $R^{10}$ is bonded to the carbon atom adjacent to the binding carbon atom of $R^6$), and the general formula (I-A) includes the (+) form, (−) form and (±) form]; (2) morphinan derivatives or their pharmacologically acceptable acid addition salts wherein W is an alkylene group having 2 or 4–5 carbon atoms or an unsaturated hydrocarbon group having 2 or 4–5 carbon atoms in the general formula (I); and, (3) morphinan derivatives or their pharmacologically acceptable acid addition salts represented with general formula (I-F):

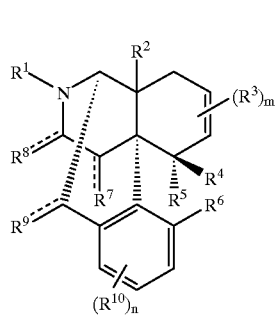

(I-F)

(wherein, $R^1$, $R^2$, $R^3$, $R^4$, $R^5$, $R^6$, $R^7$, $R^8$, $R^9$, $R^{10}$, m and n are the same as previously defined, and the general formula (I-F) includes the (+) form, (−) form and (±) form) are preferable.

Examples of the morphinan derivatives listed in (1) through (3) in the case of (1) include: a. morphinan derivatives wherein m is an integer from 2 to 6 in general formula (I-A); b. morphinan derivatives represented with general formula (I-G) or (I-H):

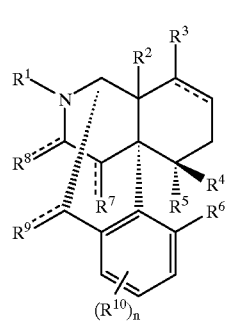

(I-G)

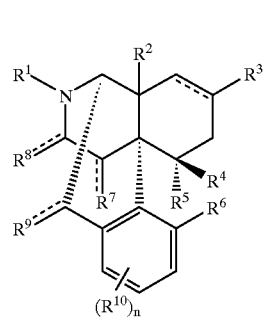

(I-H)

(wherein, . . . represents a double bond or single bond, $R^1$, $R^2$, $R^3$, $R^4$, $R^5$, $R^6$, $R^7$, $R^8$, $R^9$, $R^{10}$ and n are the same as previously defined, and the general formula (I-G) and (I-H) include the (+) form, (−) form and (±) form); and c. morphinan derivatives represented with general formula (I-J):

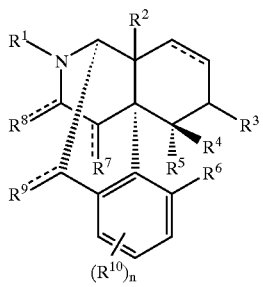

(I-J)

[wherein, ⋯ represents a double bond or single bond, $R^1$, $R^2$, $R^3$, $R^4$, $R^5$, $R^6$, $R^7$, $R^8$, $R^9$, $R^{10}$ and n are the same as previously defined (provided that one of either $R^7$, $R^8$ or $R^9$ is a substituent group other than a hydrogen atom when n is 1, and $R^{10}$ is bonded to the carbon atom adjacent to the binding carbon atom of $R^6$) and the general formula (I-J) includes the (+) form, (−) form and (±) form].

The present invention additionally provides a morphinan derivative or its pharmacologically acceptable acid addition salt as set forth in claim 1 represented with general formula (I-B):

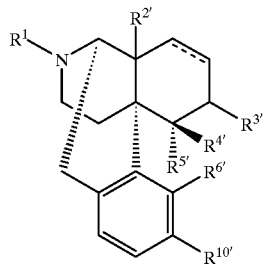

(I-B)

(wherein, ⋯ represents a double bond or single bond;

$R^{2'}$ represents a hydrogen atom, a hydroxy group, a nitro group, an alkanoyloxy group having 1–5 carbon atoms, an alkoxy group having 1–5 carbon atoms, a straight chain or branched chain alkyl group having 1–5 carbon atoms, or —$NR^{13}R^{14}$ (where, $R^{13}$ represents a hydrogen atom or a straight chain or branched chain alkyl group having 1–5 carbon atoms, and $R^{14}$ represents a hydrogen atom, an alkyl group having 1–5 carbon atoms or —C(=O)$R^{15}$ (where, $R^{15}$ represents a hydrogen atom, a phenyl group or an alkyl group having 1–5 carbon atoms));

$R^{3'}$ represents —A'—B—$R^{11'}$ (where, A' represents —XC(=Y)—, —XC(=Y)Z—, —X—, —$XSO_2$— or —OC(O$R^{12}$)$R^{12}$— (where, X, Y, Z and $R^{12}$ are the same as previously defined, and wherein $R^{12}$ may be identical or different), $R^{11'}$ is a hydrogen atom or the basic skeleton group A, and B is the same as previously defined);

$R^{4'}$ represents a hydrogen atom, a straight chain or branched chain alkyl group having 1–5 carbon atoms, or an alkanoyl group having 1–5 carbon atoms;

$R^{5'}$ represents a hydrogen atom; $R^{6'}$ represents a hydrogen atom, a hydroxy group, an alkanoyloxy group having 1–5 carbon atoms, or an alkoxy group having 1–5 carbon atoms, or alternatively, $R^{5'}$ and $R^{6'}$ collectively represent —O—, —$CH_2$— or —S—;

$R^{10'}$ represents a hydrogen atom, a hydroxy group, an alkanoyloxy group having 1–5 carbon atoms, or an alkoxy group having 1–5 carbon atoms; and the general formula (I-B) includes the (+) form, (−) form and (±) form).

Here, preferable examples of $R^1$ include an alkyl group having 1–5 carbon atoms, a cycloalkylmethyl group having 4–7 carbon atoms, a cycloalkenylmethyl group having 5–7 carbon atoms, a phenylalkyl group having 7–13 carbon atoms, an alkenyl group having 4–7 carbon atoms, an allyl group, a furan-2-yl-alkyl group having 1–5 carbon atoms, and a thiophen-2-yl-alkyl group having 1–5 carbon atoms, while particularly preferable examples include methyl, ethyl, cyclopropylmethyl, cyclobutylmethyl, cyclopentylmethyl, cyclopentenylmethyl, cyclohexenylmethyl, benzyl, phenetyl, trans-2-butenyl, 2-methyl-2-butenyl, allyl, furan-2-yl-methyl and thiophen-2-yl-methyl groups.

Among the —A—B—$R^{11}$ groups represented by $R^2$, $R^3$ and $R^4$, preferable examples of A include —$NR^{12}C(=O)$—, —$NR^{12}C(=S)$—, —$NR^{12}C(=O)O$—, —$NR^{12}C(=O)NR^{12}$—, —$NR^{12}C(=S)NR^{12}$—, —$NR^{12}C(=O)S$—, —OC(=O)—, —OC(=O)O—, —SC(=O)—, —$NR^{12}$—, —O—, —$NR^{12}SO_2$—, and —$OSO_2$—, while particularly preferable examples include —$NR^{12}C(=O)$—, —$NR^{12}C(=S)$—, —$NR^{12}C(=O)O$—, —$NR^{12}C(=O)NR^{12}$—, —$NR^{12}C(=S)NR^{12}$— and —$NR^{12}SO_2$—. Preferable examples of $R^{12}$ include a hydrogen atom, a straight chain or branched chain alkyl group having 1–5 carbon atoms and a phenyl group, while particularly preferable examples include straight chain or branched chain alkyl groups having 1–5 carbon atoms such as methyl, ethyl, propyl, isopropyl, butyl and isobutyl groups.

Among the —A—B—$R^{11}$ groups represented by $R^2$, $R^3$ and $R^4$, preferable examples of B include —($CH_2$)p- (p=0–6), —($CH_2$)p-C(=O)— (p=1–4), —CH=CH—($CH_2$)p- (p=0–4), —C≡C—($CH_2$)p- (p=0–4), —$CH_2$—O—, —$CH_2$—S—, —$CH_2$—O—($CH_2$)$_2$—O—($CH_2$)$_2$—, —$CH_2$—O—$CH_2$—NH—$CH_2$—O—$CH_2$—, and —$CH_2$—O—$CH_2$—S—$CH_2$—O—$CH_2$—, while particularly preferable examples include —($CH_2$)p- (p=0–6), —CH=CH—($CH_2$)p- (p=0–4), —C≡C—($CH_2$)p- (p=0–4), —$CH_2$—O— and —$CH_2$—S—.

Among the —A—B—$R^{11}$ groups represented by $R^2$, $R^3$ and $R^4$, preferable examples of $R^{11}$ include a hydrogen atom or organic groups having the basic skeletons shown below:

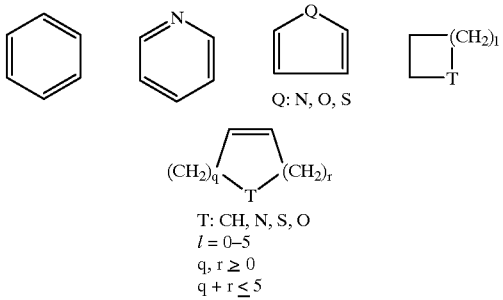

Q: N, O, S

T: CH, N, S, O
$l = 0–5$
$q, r \geq 0$
$q + r \leq 5$ (which may be substituted with at least one type of substituent group selected from the group consisting of an alkyl group having 1–5 carbon atoms, an alkoxy group having 1–5 carbon atoms, an alkanoyloxy group having 1–5 carbon atoms, a hydroxy group, fluorine, chlorine, bromine, an amino group, a nitro group, a cyano group, an isothiocyanato group, a trifluoromethyl group, and a trifluoromethoxy group), while particularly preferable examples include a hydrogen atom, phenyl, 3,4-dichlorophenyl, 4-chlorophenyl, 3-chlorophenyl, 2-chlorophenyl, 3,4-difluorophenyl, 4-fluorophenyl, 3-fluorophenyl, 2-fluorophenyl, 4-bromophenyl, 3-bromophenyl, 2-bromophenyl, 4-nitrophenyl, 3-nitrophenyl, 2-nitrophenyl 4-trifluoromethylphenyl, 3-trifluoromethylphenyl, 2-trifluoromethylphenyl, 4-methylphenyl, 3-methylphenyl, 2-methylphenyl, 4-methoxyphenyl, 3-methoxyphenyl, 2-methoxyphenyl, 3-furyl, 2-methyl-3-furyl, 4-methyl-3-furyl, 5-methyl-3-furyl, 2-bromo-3-furyl, 4-bromo-3-furyl, 5-bromo-3-furyl, 2-chloro-3-furyl, 4-chloro-3-furyl, 5-chloro-3-furyl, 2-furyl, 3-methyl-2-furyl, 4-methyl-2-furyl, 5-methyl-2-furyl, 3-bromo-2-furyl, 4-bromo-2-furyl, 5-bromo-2-furyl, 3-chloro-2-furyl, 4-chloro-2-furyl, 5-chloro-2-furyl, 3-thienyl, 2-methyl-3-thienyl, 4-methyl-3-thienyl, 5-methyl-3-thienyl, 2-bromo-3-thienyl, 4-bromo-3-thienyl, 5-bromo-3-thienyl, 2-chloro-3-thienyl, 4-chloro-3 -thienyl, 5-chloro-3-thienyl, 2-thienyl, 3-methyl-2-thienyl, 4-methyl-2-thienyl, 5-methyl-2-thienyl, 3-bromo-2-thienyl, 4-bromo-2-thienyl, 5-bromo-2-thienyl, 3-chloro-2-thienyl, 4-chloro-2-thienyl, 5-chloro-2-thienyl, cyclopentyl, cyclohexyl, 2-trifluoromethoxyphenyl, 3-trifluoromethoxyphenyl and 4-trifluoromethoxyphenyl groups.

In addition, preferable examples of $R^2$ include a hydrogen atom, hydroxy, nitro, acetoxy, methoxy, methyl, ethyl, propyl, amino, dimethylamino, acetylamino and benzoylamino groups, while particularly preferable examples include a hydrogen atom, hydroxy, acetoxy, methoxy, methyl and dimethylamino groups. In addition, preferable examples of $R^4$ include a hydrogen atom, methyl, ethyl, propyl, acetyl, propioyl and benzoyl groups, while particularly preferable examples include a hydrogen atom, methyl, acetyl and benzoyl groups. Moreover, m is preferably 1 or 2.

Preferable examples of $R^6$ include that which forms —O— collectively with $R^5$, a hydrogen atom, a hydroxy group, chlorine, bromine, a nitro group, an alkanoyloxy group having 1–5 carbon atoms and an alkoxy group having 1–5 carbon atoms, while particularly preferable examples include that which forms —O— collectively with $R^5$, acetoxy and methoxy groups.

Preferable examples of $R^7$ include a hydrogen atom, a hydroxy group, chlorine, bromine, an alkyl group having 1–5 carbon atoms, an alkanoyl group having 1–5 carbon atoms and a carbonyl group, while particularly preferable examples a hydrogen atom, hydroxy, acetyl and carbonyl groups.

Preferable examples of $R^8$ include a hydrogen atom, an alkyl group having 1–5 carbon atoms and a cyano group, while particularly preferable examples include a hydrogen atom and a cyano group, with a hydrogen atom being especially preferable.

Preferable examples of $R^9$ include a hydrogen atom, a hydroxy group, chlorine, bromine and a carbonyl group, while particularly preferable examples include a hydrogen atom and a carbonyl group, with a hydrogen atom being especially preferable.

Preferable examples of $R^{10}$ include a hydrogen atom, a hydroxy group, chlorine, bromine, a nitro group, an alkyl group having 1–5 carbon atoms, an alkanoyl group having 1–5 carbon atoms, an alkanoyloxy group having 1–5 carbon atoms, and an alkoxy group having 1–5 carbon atoms, while particularly preferable examples include a hydrogen atom, hydroxy, chlorine, bromine, nitro, methyl, ethyl, propyl, acetyl, propioyl, acetoxy and methoxy groups, with a hydrogen atom, hydroxy, acetoxy and methoxy groups being especially preferable. In addition, n is preferably 1 or 2.

Preferable examples of W include an alkylene group having 2–5 carbon atoms, and an unsaturated hydrocarbon group having 3–4 carbon atoms, while particularly preferable examples include $(CH_2)_2$, $(CH_2)_3$, $(CH_2)_4$, $CH=CH—CH_2$, $CH=CH—CH_2CH_2$ and $CH_2CH=CHCH_2$. However, preferable examples are not limited to these groups.

Examples of pharmacologically acceptable acid addition salts include inorganic acid salts such as hydrochloride, sulfate, nitrate, hydrobromide, hydroiodide and phosphate; organic carboxylates such as acetate, lactate, citrate, oxalate, glutarate malate, tartrate, fumarate, mandelate, maleate, benzoate and phthalate; and, organic sulfonates such as methanesulfonate, ethanesulfonate, benzenesulfonate, p-toluenesulfonate and camphasulfonate. Although hydrochloride, hydrobromide, phosphate, tartrate, and methanesulfonate and so forth are particularly preferable, pharmacologically acceptable acid salts are naturally not limited to these.

Compound 1 included in the compounds of general formula (I) of the present invention, wherein the line parallel to the solid line and broken line is a single bond, W is $(CH_2)_3$, $R^1$ is a cyclopropylmethyl group, $R^2$ and $R^{10}$ are hydroxy groups, $R^3$ is —A—B—$R^{11}$ wherein A is α-$NR^{12}C(=O)$—, $R^{12}$ is a methyl group, B is —$CH_2$— and $R^{11}$ is a 3,4-dichlorophenyl group, m and n are both 1, $R^4$ is a hydrogen atom, and $R^5$ and $R^6$ are collectively —O— (provided that binding position of $R^3$ and $R^{10}$ is as shown in the following structural formula),

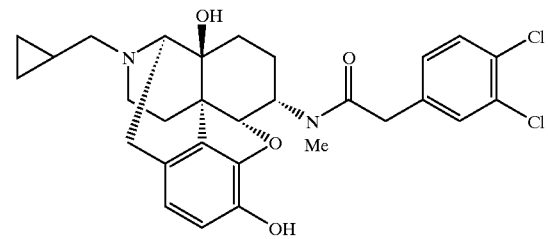

1 is named 17-cyclopropylmethyl-4,5α-epoxy-3,14β-dihydroxy-6α-(N-methyl-3,4-dichlorophenylacetamido) morphinan.

In accordance with the above nomenclature system, concrete examples of the compound of the present invention are as follows:

17-cyclopropylmethyl-4,5αepoxy-3,14β-dihydroxy-6α-(N-methylcinnamamido)morphinan,
17-cyclopropylmethyl-4,5α-epoxy-3,14β-dihydroxy-6α-(N-methylbenzyloxycarbamido)morphinan,
17-cyclopropylmethyl-4,5α-epoxy-3,14β-dihydroxy-6α-(N-methylphenylmethanesulfonamido)morphinan,
17-allyl-4,5α-epoxy-3,14β-dihydroxy-6α-(N-methyl-3,4-dichlorophenylacetamido)morphinan, 17-allyl-4,5α-epoxy-3,14β-dihydroxy-6α-(N-methylcinnamaido) morphinan, 17-allyl-4,5α-epoxy-3,14β-dihydroxy-6α-(N-methylbenzyloxycarbamido)morphinan,
17-allyl-4,5α-epoxy-3,14β-dihydroxy-6α-(N-methylphenylmethanesulfonamido)morphinan,
17-methyl-4,5α-epoxy-3,14β-dihydroxy-6α-(N-methyl-3,4-dichlorophenylacetamido)morphinan,
17-methyl-4,5α-epoxy-3,14β-dihydroxy-6α-(N-methylcinnamamido)morphinan, 17-methyl-4,5α-epoxy-3,14β-dihydroxy-6α-(N-methylbenzyloxycarbamido)morphinan, 17-methyl-4, 5α-epoxy-3,14β-dihydroxy-6α-(N-methylphenylmethanesulfonamido)morphinan, 17-phenethyl-4,5α-epoxy-3,14β-dihydroxy-6α-(N-methyl-3,4-dichlorophenylacetamido)morphinan, 17-phenethyl-4,5α-epoxy-3,14β-dihydroxy-6α-(N-methylcinnamamido)morphinan, 17-phenethyl-4,5α-epoxy-3,14β-dihydroxy-6α-(N-methylbenzyloxycarbamido)morphinan, 17-phenethyl-4,5α-epoxy-3,14β-dihydroxy-6α-(N-methylphenylmethanesulfonamido)morphinan, 17-cyclopropylmetyl-4,5α-epoxy-3-hydroxy-14β-acetoxy-6α-(N-methyl-3,4-dichlorophenylacetamido)morphinan, 17-cyclopropylmethyl-4,5α-epoxy-3-hydroxy-14β-acetoxy-6α-(N-methylcinnamamido)morphinan, 17-cyclopropylmethyl-4,5α-epoxy-3-hydroxy-14β-acetoxy-6α-(N-methylbenzyloxycarbamido)morphinan, 17-cyclopropylmethyl-4,5α-epoxy-3-hydroxy-14β-acetoxy-6α-(N-methylphenylmethanesulfonamido)morphinan, 17-allyl-4,5α-epoxy-3-hydroxy-14β-acetoxy-6α-(N-methyl-3,4-dichlorophenylacetamido)morphinan, 17-allyl-4.5α-epoxy-3-hydroxy-14β-acetoxy-6α-(N-methylcinnamamido)morphinan, 17-allyl-4,5α-epoxy-3-hydroxy-14β-acetoxy-6α-(N-methylbenzyloxycarbamido)morphinan, 17-allyl-4,5α-epoxy-3-hydroxy-14β-acetoxy-6α-(N-methylphenylmethanesulfonamido)morphinan, 17-methyl-4,5α-epoxy-3-hydroxy-14β-acetoxy-6α-(N-methyl-3,4-dichlorophenylacetamido)morphinan, 17-methyl-4,5α-epoxy-3-hydroxy-14β-acetoxy-6α-(N-methylcinnamamido)morphinan, 17-methyl-4,5α-epoxy-3-hydroxy-14β-acetoxy-6α-(N-methylbenzyloxycarbamido)morphinan, 17-methyl-4,5α-epoxy-3-hydroxy-14β-acetoxy-6α-(N-methylphenylmethanesulfonamido)morphinan, 17-phenethyl-4,5α-epoxy-3-hydroxy-14β-acetoxy-6α-(N-methyl-3,4-dichlorophenylacetamido)morphinan, 17-phenethyl-4,5α-epoxy-3-hydroxy-14β-acetoxy-6α-(N-methylcinnamamido)morphinan, 17-phenethyl-4,5α-epoxy-3-hydroxy-14β-acetoxy-6α-(N-methylbenzyloxycarbamido)morphinan, 17-phenethyl-4,5α-epoxy-3-hydroxy-14β-acetoxy-6α-(N-methylphenylmethanesulfonamido)morphinan, 17-cyclopropylmethyl-4,5α-epoxy-14β-hydroxy-6α-(N-methyl-3,4-dichlorophenylacetamido)morphinan, 17-cyclopropylmetyl-4,5α-epoxy-14β-hydroxy-6α-(N-methylcinnamamido)morphinan, 17-cyclopropylmethyl-4,5α-epoxy-14β-hydroxy-6α-(N-methylbenzyloxycarbamido)morphinan, 17-cyclopropylmethyl-4,5α-epoxy-14β-hydroxy-6α-(N-methylphenylmethanesulfonamido)morphinan, 17-allyl-4,5α-epoxy-14β-hydroxy-6α-(N-methyl-3,4-dichlorophenylacetamido)morphinan, 17-allyl-4,5α-epoxy-14β-hydroxy-6α-(N-methylcinnamamido)morphinan, 17-allyl-4,5α-epoxy-14β-hydroxy-6α-(N-methylbenzyloxycarbamido)morphinan, 17-allyl-4,5α-epoxy-14β-hydroxy-6α-(N-methylphenylmethanesulfonamido)morphinan, 17-methyl-4,5α-epoxy-14β-hydroxy-6α-(N-methyl-3,4-dichlorophenylacetoamido)morphinan, 17-methyl-4,5α-epoxy-14β-hydroxy-6α-(N-methylcinnamamido)morphinan, 17-methyl-4,5α-epoxy-14β-hydroxy-6α-(N-methylbenzyloxycarbamido)morphinan, 17-methyl-4,5α-epoxy-14β-hydroxy-6α-(N-methylphenylmethanesulfonamido)morphinan, 17-phenethyl-4,5α-epoxy-14β-hydroxy-6α-(N-methyl-3,4-dichlorophenylacetamido)morphinan, 17-phenethyl-4,5α-epoxy-14β-hydroxy-6α-(N-methylcinnamamido)morphinan, 17-phenethyl-4,5α-epoxy-14β-hydroxy-6α-(N-methylbenzyloxycarbamido)morphinan, 17-phenethyl-4,5α-epoxy-14β-hydroxy-6α-(N-methylphenylmethanesulfonamido)morphinan, 17-cyclopropylmethyl-4,5α-epoxy-14β-acetoxy-6α-(N-methyl-3,4-dichlorophenylacetamido)morphinan, 17-cyclopropylmethyl-4,5α-epoxy-14β-acetoxy-6α-(N-methylcinnamamido)morphinan, 17-cyclopropylmethyl-4,5α-epoxy-14β-acetoxy-6α-(N-methylbenzyloxycarbamido)morphinan, 17-cyclopropylmethyl-4,5α-epoxy-14β-acetoxy-6α-(N-methylphenylmethanesulfonamido)morphinan, 17-allyl-4,5α-epoxy-14β-acetoxy-6α-(N-methyl-3,4-dichlorophenylacetamido)morphinan, 17-allyl-4,5α-epoxy-14β-acetoxy-6α-(N-methylcinnamamido)morphinan, 17-allyl-4,5α-epoxy-14β-acetoxy-6α-(N-methylbenzyloxycarbamido)morphinan, 17-allyl-4,5α-epoxy-14β-acetoxy-6α-(N-methylphenylmethanesulfonamido)morphinan, 17-methyl-4,5α-epoxy-14β-acetoxy-6α-(N-methyl-3,4-dichlorophenylacetamido)morphinan, 17-methyl-4,5α-epoxy-14β-acetoxy-6α-(N-methylcinnamamido)morphinan, 17-methyl-4,5α-epoxy-14β-acetoxy-6α-(N-methylbenzyloxycarbamido)morphinan, 17-methyl-4,5α-epoxy-14β-acetoxy-6α-(N-methylphenylmethanesulfonamido)morphinan, 17-phenethyl-4,5α-epoxy-14β-acetoxy-6α-(N-methyl-3,4-dichlorophenylacetamido)morphinan, 17-phenethyl-4,5α-epoxy-14β-acetoxy-6α-(N-methylcinnamamido)morphinan, 17-phenethyl-4,5α-epoxy-14β-acetoxy-6α-(N-methylbenzyloxycarbamido)morphinan, 17-phenethyl-4,5α-epoxy-14β-acetoxy-6α-(N-methylphenylmethanesulfonamido)morphinan, 17-cyclopropylmethyl-4,5α-epoxy-3-methoxy-14β-hydroxy-6α-N-methyl-3,4-dichlorophenylacetamido)morphinan, 17-cyclopropylmethyl-4,5α-epoxy-3-methoxy-14β-hydroxy-6α-(N-methylcinnamamido)morphinan, 17-cyclopropylmethyl-4,5α-epoxy-3-methoxy-14β-hydroxy-6α-(N-methylbenzyloxycarbamido)morphinan, 17-cyclopropylmethyl-4,5α-epoxy-3-methoxy-14β-hydroxy-6α-(N-methylphenylmethanesulfonamido)morphinan, 17-allyl-4,5α-epoxy-3-methoxy-14β-hydroxy-6α-(N-methyl-3,4-dichlorophenylacetamido)morphinan, 17-allyl-4,5α-epoxy-3-methoxy-14β-hydroxy-6α-(N-methylcinamamido)morphinan, 17-allyl-4,5α-epoxy-3-methoxy-14β-hydroxy-6α-(N-methylbenzyloxycarbamido)morphinan, 17-allyl-4,5α-epoxy-3-methoxy-14β-hydroxy-6α-(N-methylphenylmethanesulfonamido)morphinan, 17-methyl-4,5α-epoxy-3-methoxy-14β-hydroxy-6α-(N-methyl-3,4-dichlorophenylacetamido)morphinan, 17-methyl-4,5α-epoxy-3-methoxy-14β-hydroxy-6α-(N-methylcinnamamido)morphinan, 17-methyl-4,5α-epoxy-3-methoxy-14β-hydroxy-6α-(N-methylbenzyloxycarbamido)morphinan, 17-methyl-4,5α-epoxy-3-methoxy-14β-hydroxy-6α-(N-methylphenylmethanesulfonamido)morphinan, 17-phenethyl-4,5α-epoxy-3-methoxy-14β-hydroxy-6α-(N-methyl-3,4 -dichlorophenylacetamido)morphinan, 17-phenethyl-4,5α-epoxy-3-methoxy-14β-hydroxy-6α-(N-methylcinnamamido)morphinan, 17-phenethyl-4,5α-epoxy-3-methoxy-14β-hydroxy-6α-(N-methylbenzyloxycarbamido)morphinan, 17-phenethyl-4,5α-epoxy-3-methoxy-14β-hydroxy-6α-(N-methylphenylmethanesulfonamido)morphinan, 17-cyclopropylmetyl-4,5α-epoxy-3-methoxy-14β-acetoxy-6α-(N-methyl-3,4-dichlorophenylacetamido)morphinan, 17-cyclopropylmethyl-4,5α-epoxy-3-methoxy-14β-acetoxy-6α-(N-methylcinnamamido)morphinan, 17-cyclopropylmethyl-4,5α-epoxy-3-methoxy-14β-acetoxy-6α-(N-methylbenzyloxycarbamido)morphinan, 17-cyclopropylmethyl-4,5α-epoxy-3-methoxy-14β-acetoxy-6α-(N-methylphenylmethanesulfonamido)morphinan, 17-allyl-4,5α-epoxy-3-methoxy-14β-acetoxy-6α-(N-methyl-3,4-dichlorophenylacetamido)morphinan, 17-allyl-4,5α-epoxy-3-methoxy-14β-acetoxy-6α-(N-methylcinnamamido)morphinan, 17-allyl-4,5α-epoxy-3-methoxy-14β-acetoxy-6α-(N-methylbenzyloxycarbamido)morphinan, 17-allyl-4,5α-epoxy-3-methoxy-14β-acetoxy-6β-(N-methylphenylmethanesulfonamido)morphinan, 17-methyl-4,5α-epoxy-3-methoxy-14β-acetoxy-6α-(N-methyl-3,4-dichlorophenylacetamido)morphinan, 17-methyl-4,5α-epoxy-3-methoxy-14β-acetoxy-6α-(N-methylcinnamamido)morphinan, 17-methyl-4,5α-epoxy-3-methoxy-14β-acetoxy-6α-(N-methylbenzyloxycarbamido)morphinan, 17-methyl-4,5α-epoxy-3-methoxy-14β-acetoxy-6α-(N-methylphenylmethanesulfonamido)morphinan, 17-phenethyl-4,5α-epoxy-3-methoxy-14β-acetoxy-6α-(N-methyl-3,4-dichlorophenylacetamido)morphinan, 17-phenethyl-4,5α-epoxy-3-methoxy-14β-acetoxy-6α-(N-methylcinnamamido)morphinan, 17-phenethyl-4,5α-epoxy-3-methoxy-14β-acetoxy-6α-(N-methylbenzyloxycarbamido)morphinan, 17-phenethyl-4,5α-epoxy-3-methoxy-14β-acetoxy-6α-(N-methylphenylmethanesulfonamido)morphinan, 17-cyclopropylmethyl-4,5α-epoxy-3-acetoxy-14β-hydroxy-6α-(N-methyl-3,4-dichlorophenylacetamido)morphinan, 17-cyclopropylmethyl-4,5α-epoxy-3-acetoxy-14β-hydroxy-6α-(N-methylcinnamamido)morphinan, 17-cyclopropylmethyl-4,5α-epoxy-3-acetoxy-14β-hydroxy-6α-(N-methylbenzyloxycarbamido)morphinan, 17-cyclopropylmethyl-4,5α-epoxy-3-acetoxy-14β-hydroxy-6α-(N-methylphenylmethanesulfonamido)morphinan, 17-allyl-4,5α-epoxy-3-acetoxy-14β-hydroxy-6α-(N-methyl-3,4-dichlorophenylacetamido)morphinan, 17-allyl-4,5α-epoxy-3-acetoxy-14β-hydroxy-6α-(N-methylcinnamamido)morphinan, 17-allyl-4,5α-epoxy-3-acetoxy-14β-hydroxy-6α-(N-methylbenzyloxycarbamido)morphinan, 17-allyl-4,5α-epoxy-3-acetoxy-14β-hydroxy-6α-(N-methylphenylmethanesulfonamido)morphinan, 17-methyl-4,5α-epoxy-3-acetoxy-14β-hydroxy-6α-(N-methyl-3,4-dichlorophenylacetamido)morphinan, 17-methyl-4,5α-epoxy-3-acetoxy-14β-hydroxy-6α-(N-methylcinnamamido)morphinan, 17-methyl-4,5α-epoxy-3-acetoxy-14β-hydroxy-6α-(N-methylbenzyloxycarbamido)morphinan, 17-methyl-4,5α-epoxy-3-acetoxy-14β-hydroxy-6α-(N-methylphenylmethanesulfonamido)morphinan, 17-phenethyl-4,5α-epoxy-3-acetoxy-14β-hydroxy-6α-(N-methyl-3,4-dichlorophenylacetamido)morphinan, 17-phenethyl-4,5α-epoxy-3-acetoxy-14β-hydroxy-6α-(N-methylcinnamamido)morphinan, 17-phenethyl-4,5α-epoxy-3-acetoxy-14β-hydroxy-6α-(N-methylbenzyloxycarbamido)morphinan, 17-phenethyl-4,5α-epoxy-3-acetoxy-14β-hydroxy-6α-(N-methylphenylmethanesulfonamido)morphinan, 17-cyclopropylmethyl-4,5α-epoxy-3,14β-diacetoxy-6α-(N-methyl-3,4-dichlorophenylacetamido)morphinan, 17-cyclopropylmethyl-4,5α-epoxy-3,14β-diacetoxy-6α-(N-methylcinnamamido)morphinan, 17-cyclopropylmethyl-4,5α-epoxy-3,14β-diacetoxy-6α-(N-methylbenzyloxycarbamido)morphinan, 17-cyclopropylmethyl-4,5α-epoxy-3,14β-diacetoxy-6α-(N-methylphenylmethanesulfonamido)morphinan, 17-allyl-4,5α-epoxy-3,14β-diacetoxy-6α-(N-methyl-3,4-dichlorophenylacetamido)morphinan, 17-allyl-4,5α-epoxy-3,14β-diacetoxy-6α-(N-methylcinnamamido)morphinan, 17-allyl-4,5α-epoxy-3,14β-diacetoxy-6α-(N-methylbenzyloxycarbamido)morphinan, 17-allyl-4,5α-epoxy-3,14β-diacetoxy-6α-(N-methylphenylmethanesulfonamido)morphinan, 17-methyl-4,5α-epoxy-3,14β-diacetoxy-6α-(N-methyl-3,4-dichlorophenylacetamido)morphinan, 17-methyl-4,5α-epoxy-3,14β-diacetoxy-6α-(N-methylcinnamamido)morphinan, 17-methyl-4,5α-epoxy-3,14β-diacetoxy-6α-(N-methylbenzyloxycarbamido)morphinan, 17-methyl-4,5α-epoxy-3,14β-diacetoxy-6α-(N-methylphenylmethanesulfonamido)morphinan, 17-phenethyl-4,5α-epoxy-3,14β-diacetoxy-6α-(N-methyl-3,4-dichlorophenylacetamido)morphinan, 17-phenethyl-4,5α-epoxy-3,14β-diacetoxy-6α-(N-methylcinnamamido)morphinan, 17-phenethyl-4,5α-epoxy-3,14β-diacetoxy-6α-(N-methylbenzyloxycarbamido)morphinan, 17-phenethyl-4,5α-epoxy-3,14β-diacetoxy-6α-(N-methylphenylmethanesulfonamido)morphinan, 17-cyclopropylmethyl-4,5α-epoxy-3,14β-dihydroxy-6α-(N-isobutyl-3,4-dichlorophenylacetamido)morphinan, 17-cyclopropylmetyl-4,5α-epoxy-3,14β-dihydroxy-6α-(N-isobutylcinnamamido)morphinan, 17-cyclopropylmethyl-4,5α-epoxy-3,14β-dihydroxy-6α-(N-isobutylbenzyloxycarbamido)morphinan, 17-cyclopropylmethyl-4,5α-epoxy-3,14β-dihydroxy-6α-(N-isobutylphenylmethanesulfonamamido)morphinan, 17-allyl-4,5α-epoxy-3,14β-dihydroxy-6α-(N-isobutyl-3,4-dichlorophenylacetamido)morphinan, 17-allyl-4,5α-epoxy-3,14β-dihydroxy-6α-(N-isobutylcinnamamido)morphinan, 17-allyl-4,5α-epoxy-3,14β-dihydroxy-6α-(N-isobutylbenzyloxycarbamido)morphinan, 17-allyl-4,5α-epoxy-3,14β-dihydroxy-6α-(N-isobutylphenylmethanesulfonamido)morphinan, 17-metyl-4,5α-epoxy-3,14β-dihydroxy-6α-(N-isobutyl-3,4-dichlorophenylacetamido)morphinan, 17-methyl-4,5α-epoxy-3,14β-dihydroxy-6α-(N-isobutylcinnamamido)morphinan, 17-metyl-4,5α-epoxy-3,14β-dihydroxy-6α-(N-isobutylbenzyloxycarbamido)morphinan, 17-metyl-4,5α-epoxy-3,14β-dihydroxy-6α-(N-isobutylphenylmethanesulfonamido)morphinan, 17-phenethyl-4,5α-epoxy-3,14β-dihydroxy-6α-(N-isobutyl-3,4-dichlorophenylacetamido)morphinan, 17-phenethyl-4,5α-epoxy-3,14β-dihydroxy-6α-(N-isobutylcinnamamido)morphinan, 17-phenethyl-4,5α-epoxy-3,14β-dihydroxy-6α-(N-isobutylbenzyloxycarbamido)morphinan, 17-phenethyl-4,5α-epoxy-3,14β-dihydroxy-6α-(N-isobutylphenylmethanesulfonamido)morphinan, 17-cyclopropylmethyl-4,5α-epoxy-3-hydroxy-14β-acetoxy-6α-(N-isobutyl-3,4-dichlorophenylacetamido)morphinan, 17-cyclopropylmetyl-4,5α-epoxy-3-hydroxy-14β-acetoxy-6α-(N-isobutylcinnamamido)morphinan, 17-cyclopropylmethyl-4,5α-epoxy-3-hydroxy-14β-acetoxy-6α-(N-isobutylbenzyloxycarbamido)morphinan, 17-cyclopropylmethyl-4,5α-epoxy-3-hydroxy-14β-acetoxy-6α-(N-isobutylphenylmethanesulfonamido)morphinan, 17-allyl-4,5α-epoxy-3-hydroxy-14β-acetoxy-6α-(N-isobutyl-3,4-dichlorophenylacetamido)morphinan, 17-allyl-4,5α-epoxy-3-hydroxy-14β-acetoxy-6α-(N-isobutylcinnamamido)morphinan, 17-allyl-4,5α-epoxy-3-hydroxy-14β-acetoxy-6α-(N-isobutylbenzyloxycarbamido)morphinan, 17-allyl-4,5α-epoxy-3-hydroxy-14β-acetoxy-6α-(N-isobutylphenylmethanesulfonamido)morphinan, 17-methyl-4,5α-epoxy-3-hydroxy-14β-acetoxy-6α-(N-isobutyl-3,4-dichlorophenylacetamido)morphinan, 17-methyl-4,5α-epoxy-3-hydroxy-14β-acetoxy-6α-(N-isobutylcinnamamido)morphinan, 17-methyl-4,5α-epoxy-3-hydroxy-14β-acetoxy-6α-(N-isobutylbenzyloxycarbamido)mophinan, 17-methyl-4,5α-epoxy-3-hydroxy-14β-acetoxy-6α-(N-isobutylphenylmethanesulfonamido)morphinan, 17-phenethyl-4,5α-epoxy-3-hydroxy-14β-acetoxy-6α-(N-isobutyl-3,4-dichlorophenylacetamido)morphinan, 17-phenethyl-4,5α-epoxy-3-hydroxy-14β-acetoxy-6α-(N-isobutylcinnamamido)morphinan, 17-phenethyl-4,5α-epoxy-3-hydroxy-14β-acetoxy-6α-(N-isobutylbenzyloxycarbamido)morphinan, 17-phenethyl-4,5α-epoxy-3-hydroxy-14β-acetoxy-6α-(N-isobutylphenylmethanesulfonamido)morphinan, 17-cyclopropylmethyl-4,5α-epoxy-14β-hydroxy-6α-(N-isobutyl-3,4-dichlorophenylacetamido)morphinan, 17-cyclopropylmethyl-4,5α-epoxy-14β-hydroxy-6α-(N-isobutylcinnamamido)morphinan, 17-cyclopropylmethyl-4,5α-epoxy-14β-hydroxy-6α-(N-isobutylbenzyloxycarbamido)morphinan, 17-cyclopropylmethyl-4,5α-epoxy-14β-hydroxy-6α-(N-isobutylphenylmethanesulfonamido)morphinan, 17-allyl-4,5α-epoxy-14β-hydroxy-6α-(N-isobutyl-3,4-dichlorophenylacetamido)morphinan, 17-allyl-4,5α-epoxy-14β-hydroxy-6α-(N-isobutylcinnamamido)morphinan, 17-allyl-4,5α-epoxy-14β-hydroxy-6α-(N-isobutylbenzyloxycarbamido)morphinan, 17-allyl-4,5α-epoxy-14β-hydroxy-6α-(N-isobutylphenylmethanesulfonamido)morphinan, 17-methyl-4,5α-epoxy-14β-hydroxy-6α-((N-isobutyl-3,4-dichlorophenylacetamido)morphinan, 17-methyl-4,5α-epoxy-14β-hydroxy-6α-(N-isobutylcinnamamido)morphinan, 17-methyl-4,5α-epoxy-14β-hydroxy-6α-(N-isobutylbenzyloxycarbamido)morphinan, 17-methyl-4,5α-epoxy-14β-hydroxy-6α-(N-isobutylphenylmethanesulfonamido)morphinan, 17-phenethyl-4,5α-epoxy-14β-hydroxy-6α-(N-isobutyl-3,4-dichlorophenylacetamido)morphinan, 17-phenethyl-4,5α-epoxy-14β-hydroxy-6α-(N-isobutylcinnamamido)morphinan, 17-phenethyl-4,5α-epoxy-14β-hydroxy-6α-(N-isobutylbenzyloxycarbamido)morphinan, 17-phenethyl-4,5α-epoxy-14β-hydroxy-6α-(N-isobutylphenylmethanesulfonamido)morphinan, 17-cyclopropylmethyl-4,5α-epoxy-14β-acetoxy-6α-(N-isobutyl-3,4-dichlorophenylacetamido)morphinan, 17-cyclopropylmethyl-4,5α-epoxy-14β-acetoxy-6α-(N-isobutylcinnamamido)morphinan, 17-cyclopropylmethyl-4,5α-epoxy-14β-acetoxy-6α-(N-isobutylbenzyloxycarbamido)morphinan, 17-cyclopropylmethyl-4,5α-epoxy-14β-acetoxy-6α-(N-isobutylphenylmethanesulfonamido)morphinan, 17-allyl-4,5α-epoxy-14β-acetoxy-6α-(N-isobutyl-3,4-dichlorophenylacetamido)morphinan, 17-allyl-4,5α-epoxy-14β-acetoxy-6α-(N-isobutylcinnamamido)morphinan, 17-allyl-4,5α-epoxy-14β-acetoxy-6α-(N-isobutylbenzyloxycarbamido)morphinan, 17-allyl-4,5α-epoxy-14β-acetoxy-6α-(N-isobutylphenylmethanesulfonamido)morphinan, 17-methyl-4,5α-epoxy-14β-acetoxy-6α-(N-isobutyl-3,4-dichlorophenylacetamido)morphinan, 17-methyl-4,5α-epoxy-14β-acetoxy-6α-(N-isobutylcinnamamido)morphinan, 17-methyl-4,5α-epoxy-14β-acetoxy-6α-(N-isobutylbenzyloxycarbamido)morphinan, 17-methyl-4,5α-epoxy-14β-acetoxy-6α-(N-isobutylphenylmethanesulfonamido)morphinan, 17-phenethyl-4,5α-epoxy-14β-acetoxy-6α-(N-isobutyl-3,4-dichlorophenylacetamido)morphinan, 17-phenethyl-4,5α-epoxy-14β-acetoxy-6α-(N-isobutylcinnamamido)morphinan, 17-phenethyl-4,5α-epoxy-14β-acetoxy-6α-(N-isobutylbenzyloxycarbamido)morphinan, 17-phenethyl-4,5α-epoxy-14β-acetoxy-6α-(N-isobutylphenylmethanesulfonamido)morphinan, 17-cyclopropylmethyl-4,5α-epoxy-3-methoxy-14β-hydroxy-6α-(N-isobutyl-3,4-dichlorophenylacetamido)morphinan, 17-cyclopropylmethyl-4,5α-epoxy-3-methoxy-14β-hydroxy-6α-(N-isobutylcinnamamido)morphinan, 17-cyclopropylmethyl-4,5α-epoxy-3-methoxy-14β-hydroxy-6α-(N-isobutylbenzyloxycarbamido)morphinan, 17-cyclopropylmethyl-4,5α-epoxy-3-methoxy-14β-hydroxy-6α-(N-isobutylphenylmethanesulfonamido)morphinan, 17-allyl-4,5α-epoxy-3-methoxy-14β-hydroxy-6α-(N-isobutyl-3,4-dichlorophenylacetamido)morphinan, 17-allyl-4,5α-epoxy-3-methoxy-14β-hydroxy-6α-(N-isobutylcinnamamido)morphinan, 17-allyl-4,5α-epoxy-3-methoxy-14β-hydroxy-6α-(N-isobutylbenzyloxycarbamido)morphinan, 17-allyl-4,5α-epoxy-3-methoxy-14β-hydroxy-6α-(N-isobutylphenylmethanesulfonamido)morphinan, 17-methyl-4,5α-epoxy-3-methoxy-14β-hydroxy-6α-(N-isobutyl-3,4-dichlorophenylacetamido)morphinan, 17-methyl-4,5α-epoxy-3-methoxy-14β-hydroxy-6α-(N-isobutylcinnamamido)morphinan, 17-methyl-4,5α-epoxy-3-methoxy-14β-hydroxy-6α-(N-isobutylbenzyloxycarbamido)morphinan, 17-methyl-4,5α-epoxy-3-methoxy-14β-hydroxy-6α-(N-isobutylphenylmethanesulfonamido)morphinan, 17-phenethyl-4,5α-epoxy-3-methoxy-14β-hydroxy-6α-(N-isobutyl-3,4-dichlorophenylacetamido)morphinan, 17-phenethyl-4,5α-epoxy-3-methoxy-14β-hydroxy-6α-(N-isobutylcinnamamido)morphinan, 17-phenethyl-4,5α-epoxy-3-methoxy-14β-hydroxy-6α-(N-isobutylbenzyloxycarbamido)morphinan, 17-phenethyl-4,5α-epoxy-3-methoxy-14β-hydroxy-6α-(N-isobutylphenylmethanesulfonamido)morphinan, 17-cyclopropylmethyl-4,5α-epoxy-3-methoxy-14β-acetoxy-6α-(N-isobutyl-3,4-dichlorophenylacetamido)morphinan, 17-cyclopropylmethyl-4,5α-epoxy-3-methoxy-14β-acetoxy-6α-(N-isobutylcinnamamido)

morphinan, 17-cyclopropylmethyl-4,5α-epoxy-3-methoxy-14β-acetoxy-6α-(N-isobutylbenzyloxycarbamido)morphinan, 17-cyclopropylmethyl-4,5α-epoxy-3-methoxy-14β-acetoxy-6α-(N-isobutylphenylmethanesulfonamido) morphinan, 17-allyl-4,5α-epoxy-3-methoxy-14β-acetoxy-6α-(N-isobutyl-3,4-dichlorophenylacetamido) morphinan, 17-allyl-4,5α-epoxy-3-methoxy-14β-acetoxy-6α-(N-isobutylcinnamamido)morphinan, 17-allyl-4,5α-epoxy-3-methoxy-14β-acetoxy-6α-(N-isobutylbenzyloxycarbamido)morphinan, 17-allyl-4,5α-epoxy-3-methoxy-14β-acetoxy-6α-(N-isobutylphenylmethanesulfonamido)morphinan, 17-methyl-4,5α-epoxy-3-methoxy-14β-acetoxy-6α-(N-isobutyl-3,4-dichlorophenylacetamido)morphinan, 17-methyl-4,5α-epoxy-3-methoxy-14β-acetoxy-6α-(N-isobutylcinnamamido)morphinan, 17-methyl-4,5α-epoxy-3-methoxy-14β-acetoxy-6α-(N-isobutylbenzyloxycarbamido)morphinan, 17-methyl-4,5α-epoxy-3-methoxy-14β-acetoxy-6α-(N-isobutylphenylmethanesulfonamido)morphinan, 17-phenethyl-4,5α-epoxy-3-methoxy-14β-acetoxy-6α-(N-isobutyl-3,4-dichlorophenylacetamido) morphinan, 17-phenethyl-4,5α-epoxy-3-methoxy-14β-acetoxy-6α-(N-isobutylcinnamamido)morphinan, 17-phenethyl-4,5α-epoxy-3-methoxy-14β-acetoxy-6α-(N-isobutylbenzyloxycarbamido)morphinan, 17-phenethyl-4,5α-epoxy-3-methoxy-14β-acetoxy-6α-(N-isobutylphenylmethanesulfonamido) morphinan,

17-cyclopropylmethyl-4,5α-epoxy-3-acetoxy-14β-hydroxy-6α-(N-isobutyl-3,4-dichlorophenylacetamido)morphinan, 17-cyclopropylmethyl-4,5α-epoxy-3-acetoxy-14β-hydroxy-6α-(N-isobutylcinnamamido)morphinan, 17-cyclopropylmethyl-4,5α-epoxy-3-acetoxy-14β-hydroxy-6α-(N-isobutylbenzyloxycarbamido) morphinan, 17-cyclopropylmethyl-4,5α-epoxy-3-acetoxy-14β-hydroxy-6α-(N-isobutylphenylmethanesulfonamido)morphinan, 17-allyl-4,5α-epoxy-3-acetoxy-14β-hydroxy-6α-(N-isobutyl-3,4-dichlorophenylacetamido)morphinan, 17-allyl-4,5α-epoxy-3-acetoxy-14β-hydroxy-6α-(N-isobutylcinnamamido)morphinan, 17-allyl-4,5α-epoxy-3-acetoxy-14β-hydroxy-6α-(N-isobutylbenzyloxycarbamido)morphinan, 17-allyl-4,5α-epoxy-3-acetoxy-14β-hydroxy-6α-(N-isobutylphenylmethanesulfonamido)morphinan, 17-methyl-4,5α-epoxy-3-acetoxy-14β-hydroxy-6α-(N-isobutyl-3,4-dichlorophenylacetamido)morphinan, 17-methyl-4,5α-epoxy-3-acetoxy-14β-hydroxy-6α-(N-isobutylcinnamamido)morphinan, 17-methyl-4,5α-epoxy-3-acetoxy-14β-hydroxy-6α-(N-isobutylbenzyloxycarbamido)morphinan, 17-methyl-4,5α-epoxy-3-acetoxy-14β-hydroxy-6α-(N-isobutylphenylmethanesulfonamido)morphinan, 17-phenethyl-4,5α-epoxy-3-acetoxy-14β-hydroxy-6α-(N-isobutyl-3,4-dichlorophenylacetamido)morphinan, 17-phenethyl-4,5α-epoxy-3-acetoxy-14β-hydroxy-6α-(N-isobutylcinnamamido)morphinan, 17-phenethyl-4,5α-epoxy-3-acetoxy-14β-hydroxy-6α-(N-isobutylbenzyloxycarbamido)morphinan, 17-phenethyl-4,5α-epoxy-3-acetoxy-14β-hydroxy-6α-(N-isobutylphenylmethanesulfonamido)morphinan, 17-cyclopropylmethyl-4,5α-epoxy-3,14β-diacetoxy-6α-(N-isobutyl-3,4-dichlorophenylacetamido)morphinan, 17-cyclopropylmethyl-4,5α-epoxy-3,14β-diacetoxy-6α-(N-isobutylcinnamamido)morphinan, 17-cyclopropylmethyl-4,5α-epoxy-3,14β-diacetoxy-6α-(N-isobutylbenzyloxycarbamido)morphinan, 17-cyclopropylmethyl-4,5α-epoxy-3,14β-diacetoxy-6α-(N-isobutylphenylmethanesulfonamido) morphinan, 17-allyl-4,5α-epoxy-3,14β-diacetoxy-6α-(N-isobutyl-3,4 -dichlorophenylacetamido)morphinan, 17-allyl-4,5α-epoxy-3,14β-diacetoxy-6α-(N-isobutylcinnamamido)morphinan, 17-allyl-4,5α-epoxy-3,14β-diacetoxy-6α-(N-isobutylbenzyloxycarbamido)morphinan, 17-allyl-4,5α-epoxy-3,14β-diacetoxy-6α-(N-isobutylphenylmethanesulfonamido)morphinan, 17-methyl-4,5α-epoxy-3,14β-diacetoxy-6α-(N-isobutyl-3,4-dichlorophenylacetamido)morphinan, 17-methyl-4,5α-epoxy-3,14β-diacetoxy-6α-(N-isobutylcinnamamido)morphinan, 17-methyl-4,5α-epoxy-3,14β-diacetoxy-6α-(N-isobutylbenzyloxycarbamido)morphinan, 17-methyl-4,5α-epoxy-3,14β-diacetoxy-6α-(N-isobutylphenylmethanesulfonamido)morphinan, 17-phenethyl-4,5α-epoxy-3,14β-diacetoxy-6α-(N-isobutyl-3,4-dichlorophenylacetamido)morphinan, 17-phenethyl-4,5α-epoxy-3,14β-diacetoxy-6α-(N-isobutylcinnamamido)morphinan, 17-phenethyl-4,5α-epoxy-3,14β-diacetoxy-6α-(N-isobutylbenzyloxycarbamido)morphinan, 17-phenethyl-4,5α-epoxy-3,14β-diacetoxy-6α-(N-isobutylphenylmethanesulfonamido)morphinan, 17-cyclopropylmethyl-4,5α-epoxy-3,14β-dihydroxy-6β-(N-methyl-3,4-dichlorophenylacetamido)morphinan, 17-cyclopropylmethyl-4,5α-epoxy-3,14β-dihydroxy-6β-(N-methylcinnamamido)morphinan, 17-cyclopropylmethyl-4,5α-epoxy-3,14β-dihydroxy-6β-(N-methylbenzyloxycarbamido)morphinan, 17-cyclopropylmethyl-4,5α-epoxy-3,14β-dihydroxy-6β-(N-metylphenylmethanesulfonamido)morphinan, 17-allyl-4,5α-epoxy-3,14β-dihydroxy-6β-(N-methyl-3,4-dichlorophenylacetamido)morphinan, 17-allyl-4,5α-epoxy-3,14β-dihydroxy-6β-(N-methylcinnamamido)morphinan, 17-allyl-4,5α-epoxy-3,14β-dihydroxy-6β-(N-methylbenzyloxycarbamido) morphinan, 17-allyl-4,5α-epoxy-3,14β-dihydroxy-6β-(N-methylphenylmethanesulfonamido)morphinan, 17-methyl-4,5α-epoxy-3,14β-dihydroxy-6β-(N-methyl-3,4-dichlorophenylacetamido)morphinan, 17-methyl-4,5α-epoxy-3,14β-dihydroxy-6β-(N-methylcinnamamido)morphinan, 17-methyl-4,5α-epoxy-3,14β-dihydroxy-6β-(N-methylbenzyloxycarbamido)morphinan, 17-methyl-4,5α-epoxy-3,14β-dihydroxy-6β-(N-methylphenylmethanesulfonamido)morphinan, 17-phenethyl-4,5α-epoxy-3,14β-dihydroxy-6β-(N-methyl-3,4-dichlorophenylacetamido)morphinan, 17-phenethyl-4,5α-epoxy-3,14β-dihydroxy-6β-(N-methylcinnamamido)morphinan, 17-phenethyl-4,5α-epoxy-3,14β-dihydroxy-6β-(N-methylbenzyloxycarbamido)morphinan, 17-phenethyl-4,5α-epoxy-3,14β-dihydroxy-6β-(N-methylphenylmethanesulfonamido)morphinan, 17-cyclopropylmethyl-4,5α-epoxy-3-hydroxy-14β-acetoxy-6β-(N-methyl-3,4-dichlorophenylacetamido) morphinan, 17-cyclopropylmethyl-4,5α-epoxy-3-hydroxy-14β-acetoxy-6β-(N-methylcinnamamido) morphinan, 17-cyclopropylmethyl-4,5α-epoxy-3-hydroxy-14β-acetoxy-6β-(N- methylbenzyloxycarbamido)morphinan, 17-cyclopropylmethyl-4,5α-epoxy-3-hydroxy-14β-acetoxy-6β-(N-methylphenylmethanesulfonamido)morphinan, 17-allyl-4,5α-epoxy-3-hydroxy-14β-acetoxy-6β-(N-methyl-3,4-dichlorophenylacetamido)morphinan, 17-allyl-4,5α-epoxy-3-hydroxy-14β-acetoxy-6β-(N-methylcinnamamido)morphinan, 17-allyl-4,5α-epoxy-3-hydroxy-14β-acetoxy-6β-(N-methylbenzyloxycarbamido)morphinan, 17-allyl-4,5α-epoxy-3-hydroxy-14β-acetoxy-6β-(N-methylphenylmethanesulfonamido)morphinan, 17-methyl-4,5α-epoxy-3-hydroxy-14β-acetoxy-6β-(N-methyl-3,4-dichlorophenylacetamido)morphinan, 17-methyl-4,5α-epoxy-3-hydroxy-14β-acetoxy-6β-(N-methylcinnamamido)morphinan, 17-methyl-4,5α-epoxy-3-hydroxy-14β-acetoxy-6β-(N-methylbenzyloxycarbamido)morphinan, 17-methyl-4,5α-epoxy-3-hydroxy-14β-acetoxy-6β-(N-methylphenylmethanesulfonamido)morphinan, 17-phenethyl-4,5α-epoxy-3-hydroxy-14β-acetoxy-6β-(N-methyl-3,4-dichlorophenylacetamido)morphinan, 17-phenethyl-4,5α-epoxy-3-hydroxy-14β-acetoxy-6β-(N-methylcinnamamido)morphinan, 17-phenethyl-4,5α-epoxy-3-hydroxy-14β-acetoxy-6β-(N-methylbenzyloxycarbamido)morphinan, 17-phenethyl-4,5α-epoxy-3-hydroxy-14β-acetoxy-6β-(N-methylphenylmethanesulfonamido)morphinan, 17-cyclopropylmethyl-4,5α-epoxy-14β-hydroxy-6β-(N-methyl-3,4-dichlorophenylacetamido)morphinan, 17-cyclopropylmethyl-4,5α-epoxy-14β-hydroxy-6β-(N-methylcinnamamido)morphinan, 17-cyclopropylmethyl-4,5α-epoxy-14β-hydroxy-6β-(N-methylbenzyloxycarbamido)morphinan, 17-cyclopropylmethyl-4,5α-epoxy-14β-hydroxy-6β-(N-methylphenylmethanesulfonamido)morphinan, 17-allyl-4,5α-epoxy-14β-hydroxy-6β-(N-methyl-3,4-dichlorophenylacetamido)morphinan, 17-allyl-4,5α-epoxy-14β-hydroxy-6β-(N-methylcinnamamido)morphinan, 17-allyl-4,5α-epoxy-14β-hydroxy-6β-(N-methylbenzyloxycarbamido)morphinan, 17-allyl-4,5α-epoxy-14β-hydroxy-6β-(N-methylphenylmethanesulfonamido)morphinan, 17-methyl-4,5α-epoxy-14β-hydroxy-6β-(N-methyl-3,4-dichlorophenylacetamido)morphinan, 17-methyl-4,5α-epoxy-14β-hydroxy-6β-(N-methylcinnamamido)morphinan, 17-methyl-4,5α-epoxy-14β-hydroxy-6β-(N-methylbenzyloxycarbamido)morphinan, 17-methyl-4,5α-epoxy-14β-hydroxy-6β-(N-methylphenylmethanesulfonamido)morphinan, 17-phenethyl-4,5α-epoxy-14β-hydroxy-6β-(N-methyl-3,4-dichlorophenylacetamido)morphinan, 17-phenethyl-4,5α-epoxy-14β-hydroxy-6β-(N-methylcinnamamido)morphinan, 17-phenethyl-4,5α-epoxy-14β-hydroxy-6β-(N-methylbenzyloxycarbamido)morphinan, 17-phenethyl-4,5α-epoxy-14β-hydroxy-6β-(N-methylphenylmethanesulfonamido)morphinan, 17-cyclopropylmethyl-4,5α-epoxy-14β-acetoxy-6β-(N-methyl-3,4-dichlorophenylacetamido)morphinan, 17-cyclopropylmethyl-4,5α-epoxy-14β-acetoxy-6β-(N-methylcinnamamido)morphinan, 17-cyclopropylmethyl-4,5α-epoxy-14β-acetoxy-6β-(N-methylbenzyloxycarbamido)morphinan, 17-cyclopropylmethyl-4,5α-epoxy-14β-acetoxy-6β-(N-methylphenylmethanesulfonamido)morphinan, 17-allyl-4,5α-epoxy-14β-acetoxy-6β-(N-methyl-3,4-dichlorophenylacetamido)morphinan, 17-allyl-4,5α-epoxy-14β-acetoxy-6β-(N-methylcinnamamido)morphinan, 17-allyl-4,5α-epoxy-14β-acetoxy-6β-(N-methylbenzyloxycarbamido)morphinan, 17-allyl-4,5α-epoxy-14β-acetoxy-6β-(N-methylphenylmethanesulfonamido)morphinan, 17-methyl-4,5α-epoxy-14β-acetoxy-6β-(N-methyl-3,4-dichlorophenylacetamido)morphinan, 17-methyl-4,5α-epoxy-14β-acetoxy-6β-(N-methylcinnamamido)morphinan, 17-methyl-4,5α-epoxy-14β-acetoxy-6β-(N-methylbenzyloxycarbamido)morphinan, 17-methyl-4,5α-epoxy-14β-acetoxy-6β-(N-methylphenylmethanesulfonamido)morphinan, 17-phenethyl-4,5α-epoxy-14β-acetoxy-6β-(N-methyl-3,4-dichlorophenylacetamido)morphinan, 17-phenethyl-4,5α-epoxy-14β-acetoxy-6β-(N-methylcinnamamido)morphinan, 17-phenethyl-4,5α-epoxy-14β-acetoxy-6β-(N-methylbenzyloxycarbamido)morphinan, 17-phenethyl-4,5α-epoxy-14β-acetoxy-6β-(N-methylphenylmethanesulfonamido)morphinan, 17-cyclopropylmethyl-4,5α-epoxy-3-methoxy-14β-hydroxy-6β-(N-methyl-3,4-dichlorophenylacetamido)morphinan, 17-cyclopropylmethyl-4,5α-epoxy-3-methoxy-14β-hydroxy-6β-(N-methylcinnamamido)morphinan, 17-cyclopropylmethyl-4,5α-epoxy-3-methoxy-14β-hydroxy-6β-(N-methylbenzyloxycarbamido)morphinan, 17-cyclopropylmethyl-4,5α-epoxy-3-methoxy-14β-hydroxy-6β-(N-methylphenylmethanesulfonamido)morphinan, 17-allyl-4,5α-epoxy-3-methoxy-14β-hydroxy-6β-(N-methyl-3,4-dichlorophenylacetamido)morphinan, 17-allyl-4,5α-epoxy-3-methoxy-14β-hydroxy-6β-(N-methylcinnamamido)morphinan, 17-allyl-4,5α-epoxy-3-methoxy-14β-hydroxy-6β-(N-methylbenzyloxycarbamido)morphinan, 17-allyl-4,5α-epoxy-3-methoxy-14β-hydroxy-6β-(N-methylphenylmethanesulfonamido)morphinan, 17-methyl-4,5α-epoxy-3-methoxy-14β-hydroxy-6β-(N-methyl-3,4-dichlorophenylacetamido)morphinan, 17-methyl-4,5α-epoxy-3-methoxy-14β-hydroxy-6β-(N-methylcinnamamido)morphinan, 17-methyl-4,5α-epoxy-3-methoxy-14β-hydroxy-6β-(N-methylbenzyloxycarbamido)morphinan, 17-methyl-4,5α-epoxy-3-methoxy-14β-hydroxy-6β-(N-methylphenylmethanesulfonamido)morphinan, 17-phenethyl- 4,5α-epoxy-3-methoxy-14β-hydroxy-6β-(N-methyl-3,4-dichlorophenylacetamido)morphinan, 17-phenethyl-4,5α-epoxy-3-methoxy-14β-hydroxy-6β-(N-methylcinnamamido)morphinan, 17-phenethyl-4,5α-epoxy-3-methoxy-14β-hydroxy-6β-(N-methylbenzyloxycarbamido)morphinan, 17-phenethyl-4,5α-epoxy-3-methoxy-14β-hydroxy-6β-(N-methylphenylmethanesulfonamido)morphinan, 17-cyclopropylmethyl-4,5α-epoxy-3-methoxy-14β-acetoxy-6β-(N-methyl-3,4-dichlorophenylacetamido)morphinan, 17-cyclopropylmethyl-4,5α-epoxy-3-methoxy-14β-acetoxy-6β-(N-methylcinnaimamido)morphinan, 17-cyclopropylmethyl-4,5α-epoxy-3-methoxy-14β-acetoxy-6β-(N-methylbenzyloxycarbamido)morphinan, 17-cyclopropylmethyl-4,5α-epoxy-3-methoxy-14β-acetoxy-6β-(N-methylphenylmethanesulfonamido)morphinan, 17-allyl-4,5α-epoxy-3-methoxy-14β-acetoxy-6β-(N-methyl-3,4-dichlorophenylacetamido)morphinan, 17-allyl-4,5α-epoxy-3-methoxy-14β-acetoxy-6β-(N-methylcinnamamido)morphinan, 17-allyl-4,5α-epoxy-3-methoxy-14β-acetoxy-6β-(N-methylbenzyloxycarbamido)morphinan,
17-allyl-4,5α-epoxy-3-methoxy-14β-acetoxy-6β-(N-methylphenylmethanesulfonamido)morphinan,
17-methyl-4,5α-epoxy-3-methoxy-14β-acetoxy-6β-(N-methyl-3,4-dichlorophenylacetamido)morphinan,
17-methyl-4,5α-epoxy-3-methoxy-14β-acetoxy-6β-(N-methylcinnamamido)morphinan,
17-methyl-4,5α-epoxy-3-methoxy-14β-acetoxy-6β-(N-methylbenzyloxycarbamido)morphinan,
17-methyl-4,5α-epoxy-3-methoxy-14β-acetoxy-6β-(N-methylphenylmethanesulfonamido)morphinan,
17-phenethyl-4,5α-epoxy-3-methoxy-14β-acetoxy-6β-(N-methyl-3,4-dichlorophenylacetamido)morphinan,
17-phenethyl-4,5α-epoxy-3-methoxy-14β-acetoxy-6β-(N-methylcinnamamido)morphinan,
17-phenethyl-4,5α-epoxy-3-methoxy-14β-acetoxy-6β-(N-methylbenzyloxycarbamido)morphinan,
17-phenethyl-4,5α-epoxy-3-methoxy-14β-acetoxy-6β-(N-methylphenylmethanesulfonamido)morphinan, 17-cyclopropylmethyl-4,5α-epoxy-3-acetoxy-14β-hydroxy-6β-(N-methyl-3,4-dichlorophenylacetamido)morphinan,
17-cyclopropylmethyl-4,5α-epoxy-3-acetoxy-14β-hydroxy-6β-(N-methylcinnamamido)morphinan,
17-cyclopropylmethyl-4,5α-epoxy-3-acetoxy-14β-hydroxy-6β-(N-methylbenzyloxycarbamido)morphinan,
17-cyclopropylmethyl-4,5α-epoxy-3-acetoxy-14β-hydroxy-6β-(N-methylphenylmethanesulfonamido)morphinan,
17-allyl-4,5α-epoxy-3-acetoxy-14β-hydroxy-6β-(N-methyl-3,4-dichlorophenylacetamido)morphinan,
17-allyl-4,5α-epoxy-3-acetoxy-14β-hydroxy-6β-(N-methylcinnamamido)morphinan,
17-allyl-4,5α-epoxy-3-acetoxy-14β-hydroxy-6β-(N-methylbenzyloxycarbamido)morphinan,
17-allyl-4,5α-epoxy-3-acetoxy-14β-hydroxy-6β-(N-methylphenylmethanesulfonamido)morphinan,
17-methyl-4,5α-epoxy-3-acetoxy-14β-hydroxy-6β-(N-methyl-3,4-dichlorophenylacetamido)morphinan,
17-methyl-4,5α-epoxy-3-acetoxy-14β-hydroxy-6β-(N-methylcinnamamido)morphinan,
17-methyl-4,5α-epoxy-3-acetoxy-14β-hydroxy-6β-(N-methylbenzyloxycarbamido)morphinan,
17-methyl-4,5α-epoxy-3-acetoxy-14β-hydroxy-6β-(N-methylphenylmethanesulfonamido)morphinan,
17-phenethyl-4,5α-epoxy-3-acetoxy-14β-hydroxy-6β-(N-methyl-3,4-dichlorophenylacetamido)morphinan,
17-phenethyl-4,5α-epoxy-3-acetoxy-14β-hydroxy-6β-(N-methylcinnamamido)morphinan,
17-phenethyl-4,5α-epoxy-3-acetoxy-14β-hydroxy-6β-(N-methylbenzyloxycarbamido)morphinan,
17-phenethyl-4,5α-epoxy-3-acetoxy-14β-hydroxy-6β-(N-methylphenylmethanesulfonamido)morphinan, 17-cyclopropylmethyl-4,5α-epoxy-3,14β-diacetoxy-6β-(N-methyl-3,4-dichlorophenylacetamido)morphinan,
17-cyclopropylmethyl-4,5α-epoxy-3,14β-diacetoxy-6β-(N-methylcinnamamido)morphinan,
17-cyclopropylmethyl-4,5α-epoxy-3,14β-diacetoxy-6β-(N-methylbenzyloxycarbamido)morphinan,
17-cyclopropylmethyl-4,5α-epoxy-3,14β-diacetoxy-6β-(N-methylphenylmethanesulfonamido)morphinan,
17-allyl-4,5α-epoxy-3,14β-diacetoxy-6β-(N-methyl-3,4-dichlorophenylacetamido)morphinan,
17-allyl-4,5α-epoxy-3,14β-diacetoxy-6β-(N-methylcinnamamido)morphinan,
17-allyl-4,5α-epoxy-3,14β-diacetoxy-6β-(N-methylbenzyloxycarbamido)morphinan,
17-allyl-4,5α-epoxy-3,14β-diacetoxy-6β-(N-methylphenylmethanesulfonamido)morphinan,
17-methyl-4,5α-epoxy-3,14β-diacetoxy-6β-(N-methyl-3,4-dichlorophenylacetamido)morphinan,
17-methyl-4,5α-epoxy-3,14β-diacetoxy-6β-(N-methylcinnamamido)morphinan, 17-methyl-4,5α-epoxy-3,14β-diacetoxy-6β-(N-methylbenzyloxycarbamido)morphinan, 17-methyl-4,5α-epoxy-3,14β-diacetoxy-6β-(N-methylphenylmethanesulfonamido)morphinan,
17-phenethyl-4,5α-epoxy-3,14β-diacetoxy-6β-(N-methyl-3,4-dichlorophenylacetamido)morphinan,
17-phenethyl-4,5α-epoxy-3,14β-diacetoxy-6β-(N-methylcinnamamido)morphinan, 17-phenethyl-4,5α-epoxy-3,14β-diacetoxy-6β-(N-methylbenzyloxycarbamido)morphinan, 17-phenethyl-4,5α-epoxy-3,14β-diacetoxy-6β-(N-methylphenylmethanesulfonamido)morphinan, 17-cyclopropylmethyl-4,5α-epoxy-3,14β-dihydroxy-6β-(N-isobutyl-3,4-dichlorophenylacetamido)morphinan,
17-cyclopropylmethyl-4,5α-epoxy-3,14β-dihydroxy-6β-(N-isobutylcinnamamido)morphinan,
17-cyclopropylmethyl-4,5α-epoxy-3,14β-dihydroxy-6β-(N-isobutylbenzyloxycarbamido)morphinan,
17-cyclopropylmethyl-4,5α-epoxy-3,14β-dihydroxy-6β-(N-isobutylphenylmethanesulfonamido)morphinan,
17-allyl-4,5α-epoxy-3,14β-dihydroxy-6β-(N-isobutyl-3,4-dichlorophenylacetamido)morphinan,
17-allyl4,5α-epoxy-3,14β-dihydroxy-6β-(N-isobutylcinnamamido)morphinan, 17-allyl-4,5α-epoxy-3,14β-dihydroxy-6β-(N-isobutylbenzyloxycarbamido)morphinan, 17-allyl4,5α-epoxy-3,14β-dihydroxy-6β-(N-isobutylphenylmethanesulfonamido)morphinan,
17-methyl-4,5α-epoxy-3,14β-dihydroxy-6β-(N-isobutyl-3,4-dichlorophenylacetamido)morphinan, 17-methyl-4,5α-epoxy-3,14β-dihydroxy-6β-(N-isobutylcinnamamido)morphinan, 17-methyl-4,5α-epoxy-3,14β-dihydroxy-6β-(N-isobutylbenzyloxycarbamido)morphinan, 17-methyl4,5α-epoxy-3,14β-dihydroxy-6β-(N-isobutylphenylmethanesulfonamido)morphinan,
17-phenethyl-4,5α-epoxy-3,14β-dihydroxy-6β-(N-isobutyl-3,4-dichlorophenylacetamido)morphinan, 17-phenethyl-4,5α-epoxy-3,14β-dihydroxy-6β-(N-isobutylcinnamamido)morphinan, 17-phenethyl-4,5α-epoxy-3,14β-dihydroxy-6β-(N-isobutylbenzyloxycarbamido)morphinan, 17-phenethyl-4,5α-epoxy-3,14β-dihydroxy-6β-(N-isobutylphenylmethanesulfonamido)morphinan, 17-cyclopropylmethyl-4,5α-epoxy-3-hydroxy-14β-acetoxy-6β-(N-isobutyl-3,4-dichlorophenylacetamido)morphinan, 17-cyclopropylmethyl-4,5αepoxy-3-hydroxy-14β-acetoxy-6β-(N-isobutylcinnamamido)morphinan, 17-cyclopropylmethyl-4,5α-epoxy-3-hydroxy-14β-acetoxy-6β-(N-isobutylbenzyloxycarbamido)morphinan, 17-cyclopropylmethyl-4,5α-(epoxy-3-hydroxy-14β-acetoxy-6β-(N-isobutylphenylmethanesulfonamido)morphinan, 17-allyl-4,5α-epoxy-3-hydroxy-14β-acetoxy-6β-(N-isobutyl-3,4-dichlorophenylacetamido)morphinan, 17-allyl-4,5α-epoxy-3-hydroxy-14β-acetoxy-6β-(N-isobutylcinnamamido)morphinan, 17-allyl-4,5α-epoxy-3-hydroxy-14β-acetoxy-6β-(N-isobutylbenzyloxycarbamido)morphinan, 17-allyl-4,5α-epoxy-3-hydroxy-14β-acetoxy-6β-(N-isobutylphenylmethanesulfonamido)morphinan,
17-methyl-4,5α-epoxy-3-hydroxy-14β-acetoxy-6β-(N-isobutyl-3,4-dichlorophenylacetamido)morphinan, 17-methyl-4,5α-epoxy-3-hydroxy-14β-acetoxy-6β-(N-isobutylcinnamamido)morphinan, 17-methyl-4,5α-epoxy-3-hydroxy-14β-acetoxy-6β-(N-isobutylbenzyloxycarbamido)morphinan, 17-methyl-4,5α-epoxy-3-hydroxy-14β-acetoxy-6β-(N-isobutylphenylmethanesulfonamido)morphinan, 17-phenethyl-4,5α-epoxy-3-hydroxy-14β-acetoxy-6β-(N-isobutyl-3,4-dichlorophenylacetamido)morphinan, 17-phenethyl-4,5α-epoxy-3-hydroxy-14β-acetoxy-6β-(N-isobutylcinnamamido)morphinan, 17-phenethyl-4,5α-epoxy-3-hydroxy-14β-acetoxy-6β-(N-isobutylbenzyloxycarbamido)morphinan, 17-phenethyl-4,5α-epoxy-3-hydroxy-14β-acetoxy-6β-(N-isobutylphenylmethanesulfonamido)morphinan, 17-cyclopropylmethyl-4,5α-epoxy-14β-hydroxy-6β-(N-isobutyl-3,4-dichlorophenylacetamido)morphinan, 17-cyclopropylmethyl-4,5α-epoxy-14β-hydroxy-6β-(N-isobutylcinnamamido)morphinan, 17-cyclopropylmethyl-4,5α-epoxy-14β-hydroxy-6β-(N-isobutylbenzyloxycarbamido)morphinan, 17-cyclopropylmethyl-4,5α-epoxy-14β-hydroxy-6β-(N-isobutylphenylmethanesulfonamido)morphinan, 17-allyl-4,5α-epoxy-14β-hydroxy-6β-(N-isobutyl-3,4-dichlorophenylacetamido)morphinan, 17-allyl-4,5α-epoxy-14β-hydroxy-6β-(N-isobutylcinnamamido)morphinan, 17-allyl-4,5α-epoxy-14β-hydroxy-6β-(N-isobutylbenzyloxycarbamido)morphinan, 17-allyl-4,5α-epoxy-14β-hydroxy-6β-(N-isobutylphenylmethanesulfonamido)morphinan, 17-methyl-4,5α-epoxy-14β-hydroxy-6β-(N-isobutyl-3,4-dichlorophenylacetamido)morphinan, 17-methyl-4,5α-epoxy-14β-hydroxy-6β-(N-isobutylcinnamamido)morphinan, 17-methyl-4,5α-epoxy-14β-hydroxy-6β-(N-isobutylbenzyloxycarbamido)morphinan, 17-methyl-4,5α-epoxy-14β-hydroxy-6β-(N-isobutylphenylmethanesulfonamido)morphinan, 17-phenethyl-4,5α-epoxy-14β-hydroxy-6β-(N-isobutyl-3,4-dichlorophenylacetamido)morphinan, 17-phenethyl-4,5α-epoxy-14β-hydroxy-6β-(N-isobutylcinnamamido)morphinan, 17-phenethyl-4,5α-epoxy-14β-hydroxy-6β-(N-isobutylbenzyloxycarbamido)morphinan, 17-phenethyl-4,5α-epoxy-14β-hydroxy-6β-(N-isobutylphenylmethanesulfonamido)morphinan, 17-cyclopropylmethyl-4,5α-epoxy-14β-acetoxy-6β-(N-isobutyl-3,4-dichlorophenylacetamido)morphinan, 17-cyclopropylmethyl-4,5α-epoxy-14β-acetoxy-6β-(N-isobutylcinnamamido)morphinan, 17-cyclopropylmethyl-4,5α-epoxy-14β-acetoxy-6β-(N-isobutylbenzyloxycarbamido)morphinan, 17-cyclopropylmethyl-4,5α-epoxy-14β-acetoxy-6β-(N-isobutylphenylmethanesulfonamido)morphinan, 17-allyl-4,5α-epoxy-14β-acetoxy-6β-(N-isobutyl-3,4-dichlorophenylacetamido)morphinan, 17-allyl-4,5α-epoxy-14β-acetoxy-6β-(N-isobutylcinnamamido)morphinan, 17-allyl-4,5α-epoxy-14β-acetoxy-6β-(N-isobutylbenzyloxycarbamido)morphinan, 17-allyl-4,5α-epoxy-14β-acetoxy-6β-(N-isobutylphenylmethanesulfonamido)morphinan, 17-methyl-4,5α-epoxy-14β-acetoxy-6β-(N-isobutyl-3,4-dichlorophenylacetamido)morphinan, 17-methyl-4,5α-epoxy-14β-acetoxy-6β-(N-isobutylcinnamamido)morphinan, 17-methyl-4,5α-epoxy-14β-acetoxy-6β-(N-isobutylbenzyloxycarbamido)morphinan, 17-methyl-4,5α-epoxy-14β-acetoxy-6β-(N-isobutylphenylmethanesulfonamido)morphinan, 17-phenethyl-4,5α-epoxy-14β-acetoxy-6β-(N-isobutyl-3,4-dichlorophenylacetamido)morphinan, 17-phenethyl-4,5α-epoxy-14β-acetoxy-6β-(N-isobutylcinnamamido)morphinan, 17-phenethyl-4,5α-epoxy-14β-acetoxy-6β-(N-isobutylbenzyloxycarbamido)morphinan, 17-phenethyl-4,5α-epoxy-14β-acetoxy-6β-(N-isobutylphenylmethanesulfonamido)morphinan, 17-cyclopropylmethyl-4,5α-epoxy-3-methoxy-14β-hydroxy-6β-(N-isobutyl-3,4-dichlorophenylacetamido)morphinan, 17-cyclopropylmethyl-4,5α-epoxy-3-methoxy-14β-hydroxy-6β-(N-isobutylcinnamamido)morphinan, 17-cyclopropylmethyl-4,5α-epoxy-3-methoxy-14β-hydroxy-6β-(N-isobutylbenzyloxycarbamido)morphinan, 17-cyclopropylmethyl-4,5α-epoxy-3-methoxy-14β-hydroxy-6β-(N-isobutylphenylmethanesulfonamido)morphinan, 17-allyl-4,5α-epoxy-3-methoxy-14β-hydroxy-6β-(N-isobutyl-3,4-dichlorophenylacetamido)morphinan, 17-allyl-4,5α-epoxy-3-methoxy-14β-hydroxy-6β-(N-isobutylcinnamamido)morphinan, 17-allyl-4,5α-epoxy-3-methoxy-14β-hydroxy-6β-(N-isobutylbenzyloxycarbamido)morphinan, 17-allyl-4,5α-epoxy-3-methoxy-14β-hydroxy-6β-(N-isobutylphenylmethanesulfonamido)morphinan, 17-methyl-4,5α-epoxy-3-methoxy-14β-hydroxy-6β-(N-isobutyl-3,4-dichlorophenylacetamido)morphinan, 17-methyl-4,5α-epoxy-3-methoxy-14β-hydroxy-6β-(N-isobutylcinnamamido)morphinan, 17-methyl-4,5α-epoxy-3-methoxy-14β-hydroxy-6β-(N-isobutylbenzyloxycarbamido)morphinan, 17-methyl-4,5α-epoxy-3-methoxy-14β-hydroxy-6β-(N-isobutylphenylmethanesulfonaimido)morphinan, 17-phenethyl-4,5α-epoxy-3-methoxy-14β-hydroxy-6β-(N-isobutyl-3,4-dichlorophenylacetamido)morphinan, 17-phenethyl-4,5α-epoxy-3-methoxy-14β-hydroxy-6β-(N-isobutylcinnamamido)morphinan, 17-phenethyl-4,5α-epoxy-3-methoxy-14β-hydroxy-6β-(N-isobutylbenzyloxycarbamido)morphinan, 17-phenethyl-4,5α-epoxy-3-methoxy-14β-hydroxy-6β-(N-isobutylphenylmethanesulfonamido)morphinan, 17-cyclopropylmethyl-4,5α-epoxy-3-methoxy-14β-acetoxy-6β-(N-isobutyl-3,4-dichlorophenylacetamido)morphinan, 17-cyclopropylmethyl-4,5α-epoxy-3-methoxy-14β-acetoxy-6β-(N-isobutylcinnamamido)morphinan, 17-cyclopropylmethyl-4,5α-epoxy-3-methoxy-14β-acetoxy-6β-(N-isobutylbenzyloxycarbamido)morphinan, 17-cyclopropylmethyl-4,5α-epoxy-3-methoxy-14β-acetoxy-6β-(N-isobutylphenylmethanesulfonamido)morphinan, 17-allyl-4,5α-epoxy-3-methoxy-14β-acetoxy-6β-(N-isobutyl-3,4-dichlorophenylacetamido)morphinan, 17-allyl-4,5α-epoxy-3-methoxy-14β-acetoxy-6β-(N-isobutylcinnamamido)morphinan, 17-allyl-4,5α-epoxy-3-methoxy-14β-acetoxy-6β-(N-isobutylbenzyloxycarbamido)morphinan, 17-allyl-4,5α-epoxy-3-methoxy-14β-acetoxy-6β-(N-isobutylphenylmethanesulfonamido)morphinan, 17-methyl-4,5α-epoxy-3-methoxy-14β-acetoxy-6β-(N-isobutyl-3,4-dichlorophenylacetamido)morphinan, 17-methyl-4,5α-epoxy-3-methoxy-14β-acetoxy-6β-(N-isobutylcinnamamido)morphinan, 17-methyl-4,5α-epoxy-3-methoxy-14β-acetoxy-6β-(N-isobutylbenzyloxycarbamido)morphinan, 17-methyl-4,5α-epoxy-3-methoxy-14β-acetoxy-6β-(N- isobutylphenylmethanesulfonamido)morphinan, 17-phenethyl-4,5α-epoxy-3-methoxy-14β-acetoxy-6β-(N-isobutyl-3,4-dichlorophenylacetamido)morphinan, 17-phenethyl-4,5α-epoxy-3-methoxy-14β-acetoxy-6β-(N-isobutylcinnamamido)morphinan, 17-phenethyl-4,5α-epoxy-3-methoxy-14β-acetoxy-6β-(N-isobutylbenzyloxycarbamido)morphinan, 17-phenethyl-4,5α-epoxy-3-methoxy-14β-acetoxy-6β-(N-isobutylphenylmethanesulfonamido)morphinan, 17-cyclopropylmethyl-4,5α-epoxy-3-acetoxy-14β-hydroxy-6β-(N-isobutyl-3,4-dichlorophenylacetamido)morphinan, 17-cyclopropylmethyl-4,5α-epoxy-3-acetoxy-14β-hydroxy-6β-(N-isobutylcinnamamido)morphinan, 17-cyclopropylmethyl-4,5α-epoxy-3-acetoxy-14β-hydroxy-6β-(N-isobutylbenzyloxycarbamido)morphinan, 17-cyclopropylmethyl-4,5α-epoxy-3-acetoxy-14β-hydroxy-6β-(N-isobutylphenylmethanesulfonamido)morphinan, 17-allyl-4,5α-epoxy-3-acetoxy-14β-hydroxy-6β-(N-isobutyl-3,4-dichlorophenylacetamido)morphinan, 17-allyl-4,5α-epoxy-3-acetoxy-14β-hydroxy-6β-(N-isobutylcinnamamido)morphinan, 17-allyl-4,5α-epoxy-3-acetoxy-14β-hydroxy-6β-(N-isobutylbenzyloxycarbamido)morphinan, 17-allyl-4,5α-epoxy-3-acetoxy-14β-hydroxy-6β-(N-isobutylphenylmethanesulfonamido)morphinan, 17-methyl-4,5α-epoxy-3-acetoxy-14β-hydroxy-6β-(N-isobutyl-3,4-dichlorophenylacetamido)morphinan, 17-methyl-4,5α-epoxy-3-acetoxy-14β-hydroxy-6β-(N-isobutylcinnamamido)morphinan, 17-methyl-4,5α-epoxy-3-acetoxy-14β-hydroxy-6β-(N-isobutylbenzyloxycarbamido)morphinan, 17-methyl-4,5α-epoxy-3-acetoxy-14β-hydroxy-6β-(N-isobutylphenylmethanesulfonamido)morphinan, 17-phenethyl-4,5α-epoxy-3-acetoxy-14β-hydroxy-6β-(N-isobutyl-3,4-dichlorophenylacetamido)morphinan, 17-phenethyl-4,5α-epoxy-3-acetoxy-14β-hydroxy-6β-(N-isobutylcinnamamido)morphinan, 17-phenethyl-4,5α-epoxy-3-acetoxy-14β-hydroxy-6β-(N-isobutylbenzyloxycarbamido)morphinan, 17-phenethyl-4,5α-epoxy-3-acetoxy-14β-hydroxy-6β-(N-isobutylphenylmethanesulfonamido)morphinan, 17-cyclopropylmethyl-4,5α-epoxy-3,14β-diacetoxy-6β-(N-isobutyl-3,4-dichlorophenylacetamido)morphinan, 17-cyclopropylmethyl-4,5α-epoxy-3,14β-diacetoxy-6β-(N-isobutylcinnamamido)morphinan, 17-cyclopropylmethyl-4,5α-epoxy-3,14β-diacetoxy-6β-(N-isobutylbenzyloxycarbamido)morphinan, 17-cyclopropylmethyl-4,5α-epoxy-3,14β-diacetoxy-6β-(N-isobutylphenylmethanesulfonamido)morphinan, 17-allyl-4,5α-epoxy-3,14β-diacetoxy-6β-(N-isobutyl-3,4-dichlorophenylacetamido)morphinan, 17-allyl-4,5α-epoxy-3,14β-diacetoxy-6β-(N-isobutylcinnamamido)morphinan, 17-allyl-4,5α-epoxy-3,14β-diacetoxy-6β-(N-isobutylbenzyloxycarbamido)morphinan, 17-allyl-4,5α-epoxy-3,14β-diacetoxy-6β-(N-isobutylphenylmethanesulfonamido)morphinan, 17-methyl-4,5α-epoxy-3,14β-diacetoxy-6β-(N-isobutyl-3,4-dichlorophenylacetamido)morphinan, 17-methyl-4,5α-epoxy-3,14β-diacetoxy-6β-(N-isobutylcinnamamido)morphinan, 17-methyl-4,5α-epoxy-3,14β-diacetoxy-6β-(N-isobutylbenzyloxycarbamido)morphinan, 17-methyl-4,5α-epoxy-3,14β-diacetoxy-6β-(N-isobutylphenylmethanesulfonamido)morphinan, 17-phenethyl-4,5α-epoxy-3,14β-diacetoxy-6β-(N-isobutyl-3,4-dichlorophenylacetamido)morphinan, 17-phenethyl-4,5α-epoxy-3,14β-diacetoxy-6β-(N-isobutylcinnamamido)morphinan, 17-phenethyl-4,5α-epoxy-3,14β-diacetoxy-6β-(N-isobutylbenzyloxycarbamido)morphinan, 17-phenethyl-4,5α-epoxy-3,14β-diacetoxy-6β-(N-isobutylphenylmethanesulfonamido)morphinan, 17-cyclopropylmethyl-4,5α-epoxy-3,14β-dihydroxy-6α-(N-methyl-3,4-dichlorobenzamido)morphinan, 17-allyl-4,5α-epoxy-3,14β-dihydroxy-6α-(N-methyl-3,4-dichlorobenzamido)morphinan, 17-cyclopropylmethyl-4,5α-epoxy-3,14β-dihydroxy-6β-(N-methyl-3,4-dichlorobenzamido)morphinan, 17-allyl-4,5α-epoxy-3,14β-dihydroxy-6β-(N-methyl-3,4-dichlorobenzamido)morphinan, 17-cyclopropylmethyl-4,5α-epoxy-3,14β-dihydroxy-6α-(N-ethyl-3,4-dichlorophenylacetamido)morphinan, 17-allyl-4,5α-epoxy-3,14β-dihydroxy-6α-(N-ethyl-3,4-dichlorophenylacetamido)morphinan, 17-cyclopropylmethyl-4,5α-epoxy-3,14β-dihydroxy-6β-(N-ethyl-3,4-dichlorophenylacetamido)morphinan, 17-allyl-4,5α-epoxy-3,14β-dihydroxy-6β-(N-ethyl-3,4-dichlorophenylacetamido)morphinan, 17-cyclopropylmethyl-4,5α-epoxy-3,14β-dihydroxy-6α-(N-methyl-3-phenylpropionamido)morphinan, 17-allyl-4,5α-epoxy-3,14β-dihydroxy-6α-(N-methyl-3-phenylpropionamido)morphinan, 17-cyclopropylmethyl-4,5α-epoxy-3,14β-dihydroxy-6β-(N-methyl-3-phenylpropionamido)morphinan, 17-allyl-4,5α-epoxy-3,14β-dihydroxy-6β-(N-methyl-3-phenylpropionamido)morphinan, 17-cyclopropylmethyl-4,5α-epoxy-3,14β-dihydroxy-6α-[N-methyl-3-(5-chlorobenzo[b]thienyl)acetamido]morphinan, 17-allyl-4,5α-epoxy-3,14β-dihydroxy-6α-[N-methyl-3-(5-chlorobenzo[b]thienyl)acetamido]morphinan, 17-cyclopropylmethyl-4,5α-epoxy-3,14β-dihydroxy-6β-[N-methyl-3-(5-chlorobenzo[b]thienyl)acetamido]morphinan, 17-allyl-4,5α-epoxy-3,14β-dihydroxy-6β-[N-methyl-3-(5-chlorobenzo[b]thienyl)acetamido]morphinan, 17-cyclopropylmethyl-4,5α-epoxy-3,14β-dihydroxy-6α-(N-methylphenylacetamido)morphinan, 17-allyl-4,5α-epoxy-3,14β-dihydroxy-6α-(N-methylphenylacetamido)morphinan, 17-cyclopropylmethyl-4,5α-epoxy-3,14β-dihydroxy-6β-(N-methylphenylacetamido)morphinan, 17-allyl-4,5α-epoxy-3,14β-dihydroxy-6β-(N-methylphenylacetamido)morphinan, 17-cyclopropylmethyl-4,5α-epoxy-3,14β-dihydroxy-6α-(N-methylcyclohexylacetamido)morphinan, 17-allyl-4,5α-epoxy-3,14β-dihydroxy-6α-(N-methylcyclohexylacetamido)morphinan, 17-cyclopropylmethyl-4,5α-epoxy-3,14β-dihydroxy-6β-(N-methylcyclohexylacetamido)morphinan, 17-allyl-4,5α-epoxy-3,14β-dihydroxy-6β-(N-methylcyclohexylacetamido)morphinan, 17-cyclopropylmethyl-4,5α-epoxy-3,14β-dihydroxy-6α-(N-methyl-3-bromophenylacetamido)morphinan, 17-allyl-4,5α-epoxy-3,14β-dihydroxy-6α-(N-methyl-3-bromophenylacetamido)morphinan, 17-cyclopropylmethyl-4,5α-epoxy-3,14β-dihydroxy-6β-(N-methyl-3-bromophenylacetamido)morphinan, 17-allyl-4,5α-epoxy-3,14β-dihydroxy-6β-(N-methyl-3-bromophenylacetamido)morphinan, 17-cyclopropylmethyl-4,5α-epoxy-3,14β-dihydroxy- 6α-(N-methyl-4-benzo[b]thienylacetamido) morphinan, 17-allyl4,5α-epoxy-3,14β-dihydroxy-6α-(N-methyl-4-benzo[b]thienylacetamido)morphinan, 17-cyclopropylmethyl-4,5α-epoxy-3,14β-dihydroxy-6β-(N-methyl-4-benzo[b]thienylacetamido) morphinan, 17-allyl-4,5α-epoxy-3,14β-dihydroxy-6β-(N-methyl-4-benzo[b]thienylacetamido)morphinan, 17-cyclopropylmethyl-4,5α-epoxy-3,14β-dihydroxy-6α-(N-methyl-3,4-dichlorocinnamamido)morphinan, 17-allyl-4,5α-epoxy-3,14β-dihydroxy-6α-(N-methyl-3,4-dichlorocinnamamido)morphinan, 17-cyclopropylmethyl-4,5α-epoxy-3,14β-dihydroxy-6β-(N-methyl-3,4-dichlorocinnamamido)morphinan, 17-allyl-4,5α-epoxy-3,14β-dihydroxy-6β-(N-methyl-3,4-dichlorocinnamamido)morphinan, 17-cyclopropylmethyl-4,5α-epoxy-3,14β-dihydroxy-6α-(N-methyl-4-bromophenylacetamido)morphinan, 17-allyl-4,5α-epoxy-3,14β-dihydroxy-6α-(N-methyl-4-bromophenylacetamido)morphinan, 17-cyclopropylmethyl-4,5α-epoxy-3,14β-dihydroxy-6β-(N-methyl-4-bromophenylacetamido)morphinan, 17-allyl-4,5α-epoxy-3,14β-dihydroxy-6β-(N-methyl-4-bromophenylacetamido)morphinan, 17-cyclopropylmethyl-4,5α-epoxy-3,14β-dihydroxy-6α-[(R)-N-methyl-2-phenylpropionamido]morphinan, 17-allyl-4,5α-epoxy-3,14β-dihydroxy-6α-[(R)-N-methyl-2-phenylpropionamido]morphinan, 17-cyclopropylmethyl-4,5α-epoxy-3,14β-dihydroxy-6β-[(R)-N-methyl-2-phenylpropionamido]morphinan, 17-allyl-4,5α-epoxy-3,14β-dihydroxy-6β-[(R)-N-methyl-2-phenylpropionamido]morphinan, 17-cyclopropylmethyl-4,5α-epoxy-3,14β-dihydroxy-6α-[(R)-N-methylmethoxyphenylacetamido]morphinan, 17-allyl-4,5α-epoxy-3,14β-dihydroxy-6α-[(R)-N-methylmethoxyphenylacetamido]morphinan, 17-cyclopropylmethyl-4,5α-epoxy-3,14β-dihydroxy-6β-[(R)-N-methylmethoxyphenylacetaimido]morphinan, 17-allyl-4,5α-epoxy-3,14β-dihydroxy-6β-[(R)-N-methylmethoxyphenylacetamido]morphinan, 17-cyclopropylmethyl-4,5α-epoxy-3,14β-dihydroxy-6α-[(S)-N-methylmethoxyphenylacetamido]morphinan, 17-allyl-4,5α-epoxy-3,14β-dihydroxy-6α-[(S)-N-methylmethoxyphenylacetamido]morphinan, 17-cyclopropylmethyl-4,5α-epoxy-3,14β-dihydroxy-6β-[(S)-N-methylmethoxyphenylacetamido]morphinan, 17-allyl-4,5α-epoxy-3,14β-dihydroxy-6β-[(S)-N-methylmethoxyphenylacetamido]morphinan, 17-cyclopropylmethyl-4,5α-epoxy-3,14β-dihydroxy-6α-(3,4-dichlorophenylacetamido)morphinan, 17-allyl-4,5α-epoxy-3,14β-dihydroxy-6α-(3,4-dichlorophenylacetamido)morphinan, 17-cyclopropylmethyl-4,5α-epoxy-3,14β-dihydroxy-6β-(3,4-dichlorophenylacetamido)morphinan, 17-allyl-4,5α-epoxy-3,14β-dihydroxy-6β-(3,4-dichlorophenylacetamido)morphinan, 17-cyclopropylmethyl-4,5α-epoxy-3,14β-dihydroxy-6α-(N-methyl-3,4-difluorophenylacetamido)morphinan, 17-allyl-4,5α-epoxy-3,14β-dihydroxy-6α-(N-methyl-3,4-difluorophenylacetamido)morphinan, 17-cyclopropylmethyl-4,5α-epoxy-3,14β-dihydroxy-6β-(N-methyl-3,4-difluorophenylacetamido)morphinan, 17-allyl-4,5α-epoxy-3,14β-dihydroxy-6β-(N-methyl-3,4-difluorophenylacetamido)morphinan, 17-cyclopropylmethyl-4,5α-epoxy-3,14β-dihydroxy-6α-(N-methyl-3-trifluoromethylphenylacetamido)morphinan, 17-allyl-4,5α-epoxy-3,14β-dihydroxy-6α-(N-methyl-3-trifluoromethylphenylacetamido) morphinan, 17-cyclopropylmethyl-4,5α-epoxy-3,14β-dihydroxy-6β-(N-methyl-3-trifluoromethylphenylacetamido)morphinan, 17-allyl-4,5α-epoxy-3,14β-dihydroxy-6β-(N-methyl-3-trifluoromethylphenylacetamido)morphinan, 17-cyclopropylmethyl-4,5α-epoxy-3,14β-dihydroxy-6α-[(S)-N-methyl-2-phenylpropionamido]morphinan, 17-allyl-4,5α-epoxy-3,14β-dihydroxy-6α-[(S)-N-methyl-2-phenylpropionamido]morphinan, 17-cyclopropylmethyl-4,5α-epoxy-3,14β-dihydroxy-6β-[(S)-N-methyl-2-phenylpropionamido]morphinan, 17-allyl-4,5α-epoxy-3,14β-dihydroxy-6β-[(S)-N-methyl-2-phenylpropionamido]morphinan, 17-cyclopropylmethyl-4,5α-epoxy-3,14β-dihydroxy-6α-[N-methyl-N-2-(3,4-dichlorophenyl)ethylamino]morphinan, 17-allyl-4,5α-epoxy-3,14β-dihydroxy-6α-[N-methyl-N-2-(3,4-dichlorophenyl)ethylamino]morphinan, 17-cyclopropylmethyl-4,5α-epoxy-3,14β-dihydroxy-6β-[N-methyl-N-2-(3,4-dichlorophenyl)ethylamino]morphinan, 17-allyl-4,5α-epoxy-3,14β-dihydroxy-6β-[N-methyl-N-2-(3,4-dichlorophenyl)ethylamino]morphinan, 17-cyclopropylmethyl-4,5α-epoxy-3,14β-dihydroxy-6α-(N-methyl-4-nitrophenylacetamido)morphinan, 17-allyl-4,5α-epoxy-3,14β-dihydroxy-6α-(N-methyl-4-nitrophenylacetamido)morphinan, 17-cyclopropylmethyl-4,5α-epoxy-3,14β-dihydroxy-6β-(N-methyl-4-nitrophenylacetamido)morphinan, 17-allyl-4,5α-epoxy-3,14β-dihydroxy-6β-(N-methyl-4-nitrophenylacetamido)morphinan, 17-cyclopropylmethyl-4,5α-epoxy-3,14β-dihydroxy-6α-(N-methyl-4-aminophenylacetamido)morphinan, 17-allyl-4,5α-epoxy-3,14β-dihydroxy-6α-(N-methyl-4-aminophenylacetamido)morphinan, 17-cyclopropylmethyl-4,5α-epoxy-3,14β-dihydroxy-6β-(N-methyl-4-aminophenylacetamido)morphinan, 17-allyl-4,5α-epoxy-3,14β-dihydroxy-6β-(N-methyl-4-aminophenylacetamido)morphinan, 17-cyclopropylmethyl-4,5αepoxy-3,14β-dihydroxy-6α-(N-methylcyclohexylcarboxyamido)morphinan, 17-allyl-4,5α-epoxy-3,14β-dihydroxy-6α-(N-methylcyclohexylcarboxyamido)morphinan, 17-cyclopropylmethyl-4,5α-epoxy-3,14(3-dihydroxy-6β-(N-methylcyclohexylcarboxyamido)morphinan, 17-allyl-4,5α-epoxy-3,14β-dihydroxy-6β-(N-methylcyclohexylcarboxyamido)morphinan, 17-cyclopropylmethyl-4,5α-epoxy-3,14β-dihydroxy-6α-(N-methylbenzamido)morphinan, 17-allyl-4,5α-epoxy-3,14β-dihydroxy-6α-(N-methylbenzamido)morphinan, 17-cyclopropylmethyl-4,5α-epoxy-3,14β-dihydroxy-6β-(N-methylbenzamido)morphinan, 17-allyl-4,5α-epoxy-3,14β-dihydroxy-6β-(N-methylbenzamido)morphinan, 17-cyclopropylmethyl-4,5α-epoxy-3,14β-dihydroxy-6α-(N-methyl-4-phenylbutyroamido)morphinan, 17-allyl-4,5α-epoxy-3,14β-dihydroxy-6α-(N-methyl-4-phenylbutyroamido)morphinan, 17-cyclopropylmethyl-4,5α-epoxy-3,14β-dihydroxy-6β-(N-methyl-4-phenylbutyroamido)morphinan, 17-allyl-4,5α-epoxy-3,14β-dihydroxy-6β-(N-methyl-4-phenylbutyroamido)morphinan, 17-cyclopropylmethyl-4,5α-epoxy-3,14β-dihydroxy-6α-(N-methyl-2-bromophenylacetamido)morphinan, 17-allyl-4,5α-epoxy-3,14β-dihydroxy-6α-(N-methyl-2-bromophenylacetamido)morphinan, 17-cyclopropylmethyl-4,5α-epoxy-3,14β-dihydroxy-6β-(N-methyl-2-bromophenylacetamido)morphinan, 17-allyl-4,5α-epoxy-3,14β-dihydroxy-6β-(N-methyl-2-bromophenylacetamido)morphinan, 17-cyclopropylmethyl-4,5α-epoxy-3,14β-dihydroxy-6α-(N-methyl-6-phenylhexanamido)morphinan, 17-allyl-4,5α-epoxy-3,14β-dihydroxy-6α-(N-methyl-6-phenylhexanamido)morphinan, 17-cyclopropylmethyl-4,5α-epoxy-3,14β-dihydroxy-6β-(N-methyl-6-phenylhexanamido)morphinan, 17-allyl-4,5α-epoxy-3,14β-dihydroxy-6β-(N-methyl-6-phenylhexanamido)morphinan, 17-cyclopropylmethyl-4,5α-epoxy-3,14β-dihydroxy-6α-(N-methyl-3-fluorophenylacetamido)morphinan, 17-allyl-4,5α-epoxy-3,14β-dihydroxy-6α-(N-methyl-3-fluorophenylacetamido)morphinan, 17-cyclopropylmethyl-4,5α-epoxy-3,14β-dihydroxy-6β-(N-methyl-3-fluorophenylacetamido)morphinan, 17-allyl-4,5α-epoxy-3,14β-dihydroxy-6β-(N-methyl-3-fluorophenylacetamido)morphinan, 17-cyclopropylmethyl-4,5α-epoxy-3,14β-dihydroxy-6α-[N-methyl-N'-(3,4-dichlorophenyl)ureido]morphinan, 17-allyl-4,5α-epoxy-3,14β-dihydroxy-6α-[N-methyl-N'-(3,4-dichlorophenyl)ureido]morphinan, 17-cyclopropylmethyl-4,5α-epoxy-3,14β-dihydroxy-6β-[N-methyl-N'-(3,4-dichlorophenyl)ureido]morphinan, 17-allyl-4,5α-epoxy-3,14β-dihydroxy-6β-[N-methyl-N'-(3,4-dichlorophenyl)ureido]morphinan, 17-cyclopropylmethyl-4,5α-epoxy-3,14β-dihydroxy-6α-(N-methyl-N'-benzylureido)morphinan, 17-allyl-4,5α-epoxy-3,14β-dihydroxy-6α-(N-methyl-N'-benzylureido)morphinan, 17-cyclopropylmethyl-4,5α-epoxy-3,14β-dihydroxy-6β-(N-methyl-N'-benzylureido)morphinan, 17-allyl-4,5α-epoxy-3,14β-dihydroxy-6β-(N-methyl-N'-benzylureido)morphinan, 17-cyclopropylmethyl-4,5α-epoxy-3,14β-dihydroxy-6α-(N-methyl-3-nitrophenylacetamido)morphinan, 17-allyl-4,5α-epoxy-3,14β-dihydroxy-6α-(N-methyl-3-nitrophenylacetamido)morphinan, 17-cyclopropylmethyl-4,5α-epoxy-3,14β-dihydroxy-6β-(N-methyl-3-nitrophenylacetamido)morphinan, 17-allyl-4,5α-epoxy-3,14β-dihydroxy-6β-(N-methyl-3-nitrophenylacetamido)morphinan, 17-cyclopropylmethyl-4,5α-epoxy-3,14β-dihydroxy-6α-(N-methyl-4-pyridylacetamido)morphinan, 17-allyl-4,5α-epoxy-3,14β-dihydroxy-6α-(N-methyl-4-pyridylacetamido)morphinan, 17-cyclopropylmethyl-4,5α-epoxy-3,14β-dihydroxy-6β-(N-methyl-4-pyridylacetamido)morphinan, 17-allyl-4,5α-epoxy-3,14β-dihydroxy-6β-(N-methyl-4-pyridylacetamido)morphinan, 17-cyclopropylmethyl-4,5α-epoxy-3,14β-dihydroxy-6α-[N-methyl-trans-3-(3-thienyl)acrylamido]morphinan, 17-allyl-4,5α-epoxy-3,14β-dihydroxy-6α-[N-methyl-trans-3-(3-thienyl)acrylamido]morphinan, 17-cyclopropylmethyl-4,5α-epoxy-3,14β-dihydroxy-6β-[N-methyl-trans-3-(3-thienyl)acrylamido]morphinan, 17-allyl-4,5α-epoxy-3,14β-dihydroxy-6β-[N-methyl-trans-3-(3-thienyl)acrylamido]morphinan, 17-cyclopropylmethyl-4,5α-epoxy-3,14β-dihydroxy-6α-(N-methylthiophenoxyacetamido)morphinan, 17-allyl-4,5α-epoxy-3,14β-dihydroxy-6α-(N-methylthiophenoxyacetamido)morphinan, 17-cyclopropylmethyl-4,5α-epoxy-3,14β-dihydroxy-6β-(N-methylthiophenoxyacetamido)morphinan, 17-allyl-4,5α-epoxy-3,14β-dihydroxy-6β-(N-methylthiophenoxyacetamido)morphinan, 17-cyclopropylmethyl-4,5α-epoxy-3,14β-dihydroxy-6α-(N-methylphenoxyacetamido)morphinan, 17-allyl-4,5α-epoxy-3,14β-dihydroxy-6α-(N-methylphenoxyacetamido)morphinan, 17-cyclopropylmethyl-4,5α-epoxy-3,14β-dihydroxy-6β-(N-methylphenoxyacetamido)morphinan, 17-allyl-4,5α-epoxy-3,14β-dihydroxy-6β(N-methylphenoxyacetamido)morphinan, 17-cyclopropylmethyl-4,5α-epoxy-3,14β-dihydroxy-6α-(N-methyl-4-nitrobenzyloxycarbamido)morphinan, 17-allyl-4,5α-epoxy-3,14β-dihydroxy-6α-(N-methyl-4-nitrobenzyloxycarbamido)morphinan, 17-cyclopropylmethyl-4,5α-epoxy-3,14β-dihydroxy-6β-(N-methyl-4-nitrobenzyloxycarbamido)morphinan, 17-allyl-4,5α-epoxy-3,14β-dihydroxy-6β-(N-methyl-4-nitrobenzyloxycarbamido)morphinan, 17-cyclopropylmethyl-4,5α-epoxy-3,14β-dihydroxy-6α-(N-methyl-3-pyridylmethoxycarbamido)morphinan, 17-allyl-4,5α-epoxy-3,14β-dihydroxy-6α-(N-methyl-3-pyridylmethoxycarbamido)morphinan, 17-cyclopropylmethyl-4,5α-epoxy-3,14β-dihydroxy-6β-(N-methyl-3-pyridylmethoxycarbamido)morphinan, 17-allyl-4,5α-epoxy-3,14β-dihydroxy-6β-(N-methyl-3-pyridylmethoxycarbamido)morphinan, 17-cyclopropylmethyl-4,5α-epoxy-3,14β-dihydroxy-6α-(N-methyl-3,4-dichlorophenylmethanesulfonamido)morphinan, 17-allyl-4,5α-epoxy-3,14β-dihydroxy-6α-(N-methyl-3,4-dichlorophenylmethanesulfonamido)morphinan, 17-cyclopropylmethyl-4,5α-epoxy-3,14β-dihydroxy-6β-(N-methyl-3,4-dichlorophenylmethanesulfonamido)morphinan, 17-allyl-4,5α-epoxy-3,14β-dihydroxy-6β-(N-methyl-3,4-dichlorophenylmethanesulfonamido)morphinan, 17-cyclopropylmethyl-4,5α-epoxy-3,14β-dihydroxy-6α-(N-methyl-N'-benzylthioureido)morphinan, 17-ally-4,5α-epoxy-3,14β-dihydroxy-6α-(N-methyl-N'-benzylthioureido)morphinan, 17-cyclopropylmethyl-4,5α-epoxy-3,14β-dihydroxy-6β-(N-methyl-N'-benzylthioureido)morphinan, 17-allyl-4,5α-epoxy-3,14β-dihydroxy-6β-N-methyl-N'-benzylthioureido)morphinan, 17-cyclopropylmethyl-4,5α-epoxy-3,14β-dihydroxy-6α-(N-methylhexanamido)morphinan, 17-allyl-4,5α-epoxy-3,14β-dihydroxy-6α-(N-methylhexanamido)morphinan, 17-cyclopropylmethyl-4,5α-epoxy-3,14βdihydroxy-6β-(N-methylhexanamido)morphinan, 17-allyl-4,5α-epoxy-3,14β-dihydroxy-6β-(N-methylhexanamido)morphinan, 17-cyclopropylmethyl-4,5α-epoxy-3,14β-dihydroxy-6α-(N-methylheptanamido)morphinan, 17-allyl-4,5α-epoxy-3,14β-dihydroxy-6α-(N-methylheptanamido)morphinan, 17-cyclopropylmethyl-4,5α-epoxy-3,14β-dihydroxy-6β-(N-methylheptanamido)morphinan, 17-allyl-4,5α-epoxy-3,14β-dihydroxy-6β-(N-ethylheptanamido)morphinan, 17-cyclopropylmethyl-4,5α-epoxy-3,14β-dihydroxy-6α-(N-methyl-3-aminophenylacetamido)morphinan, 17-allyl-4,5α-epoxy-3,14β-dihydroxy-6α-(N-methyl-3-aminophenylacetamido)morphinan, 17-cyclopropylmethyl-4,5α-epoxy-3,14β-dihydroxy-6β-(N-methyl-3-aminophenylacetamido)morphinan, 17-allyl-4,5α-epoxy-3,14β-dihydroxy-6β-(N-methyl-3-aminophenylacetamido)morphinan, 17-cyclopropylmethyl-4,5α-epoxy-3,14β-dihydroxy-6α-(N-methyl-2-pyridylacetamido)morphinan, 17-allyl-4,5α-epoxy-3,14β-dihydroxy-6β-(N-methyl- 2-pyridylacetamido)morphinan,
17-cyclopropylmethyl-4,5α-epoxy-3,14β-dihydroxy-6β-(N-methyl-2-pyridylacetamido)morphinan,
17-allyl-4,5α-epoxy-3,14β-dihydroxy-6β-(N-methyl-2-pyridylacetamido)morphinan, 17-cyclopropylmethyl-4,5α-epoxy-3,14β-dihydroxy-6α-[N-methyl-3-(3-pyridyl)propionamido]morphinan,
17-allyl-4,5α-epoxy-3,14β-dihydroxy-6α-[N-methyl-3-(3-pyridyl)propionamido]morphinan,
17-cyclopropylmethyl-4,5α-epoxy-3,14β-dihydroxy-6β-[N-methyl-3-(3-pyridyl)propionamido]morphinan,
17-allyl-4,5α-epoxy-3,14β-dihydroxy-6β-[N-methyl-3-(3-pyridyl)propionamido]morphinan, 17-cyclopropylmethyl-4,5α-epoxy-3,14β-dihydroxy-6α-(3-phenylpropioyloxy)morphinan, 17-allyl-4,5α-epoxy-3,14β-dihydroxy-6α-(3-phenylpropioyloxy)morphinan, 17-cyclopropylmethyl-4,5α-epoxy-3,14β-dihydroxy-6β-(3-phenylpropioyloxy)morphinan, 17-allyl-4,5α-epoxy-3,14β-dihydroxy-6β-(3-phenylpropioyloxy)morphinan, 17-cyclopropylmethyl-4,5α-epoxy-3,14β-dihydroxy-6α-[2-(3-furyl)ethenylsulfonyloxy]morphinan, 17-allyl-4,5α-epoxy-3,14β-dihydroxy-6α-[2-(3-furyl)ethenylsulfonyloxy]morphinan, 17-cyclopropylmethyl-4,5α-epoxy-3,14β-dihydroxy-6β-[2-(3-furyl)ethenylsulfonyloxy]morphinan, 17-allyl-4,5α-epoxy-3,14β-dihydroxy-6β-[2-(3-furyl)ethenylsulfonyloxy]morphinan, 17-cyclopropylmethyl-4,5α-epoxy-3,14β-dihydroxy-6α-(N-methyl-3-trifluoromethylcinnamamido)morphinan, 17-cyclopropylmethyl-4,5α-epoxy-3,14β-dihydroxy-6α-[N-methyl-trans-3-(3-furyl)acrylamido]morphinan, 17-cyclopropylmethyl-4,5α-epoxy-3,14β-dihydroxy-6α-(N-methyl-4-trifluoromethylcinnamamido)morphinan, 17-cyclopropylmethyl-4,5α-epoxy-3,14β-dihydroxy-6α-(N-methyl-3-phenylpropiolamido)morphinan, 17-allyl-4,5α-epoxy-3,14β-dihydroxy-6α-(N-methyl-3-trifluoromethylcinnamamido)morphinan, 17-allyl-4,5α-epoxy-3,14β-dihydroxy-6α-[N-methyl-trans-3-(3-furyl)acrylamido]morphinan, 17-allyl-4,5α-epoxy-3,14β-dihydroxy-6α-(N-methyl-4-trifluoromethylcinnamamido)morphinan, 17-allyl-4,5α-epoxy-3,14β-dihydroxy-6α-(N-methyl-3-phenylpropiolamido)morphinan, 17-methyl-4,5α-epoxy-3,14β-dihydroxy-6α-(N-methyl-3-trifluoromethylcinnamamido)morphinan, 17-methyl-4,5α-epoxy-3,14β-dihydroxy-6α-[N-methyl-trans-3-(3-furyl)acrylamido]morphinan, 17-methyl-4,5α-epoxy-3,14β-dihydroxy-6α-(N-methyl-4-trifluoromethylcinnamamido)morphinan, 17-methyl-4,5α-epoxy-3,14β-dihydroxy-6α-(N-methyl-3-phenylpropiolamido)morphinan, 17-phenethyl-4,5α-epoxy-3,14β-dihydroxy-6α-(N-methyl-3-trifluoromethylcinnamamido)morphinan, 17-phenethyl-4,5α-epoxy-3,14β-dihydroxy-6α-[N-methyl-trans-3-(3-furyl)acrylamido]morphinan, 17-phenethyl-4,5α-epoxy-3,14β-dihydroxy-6α-(N-methyl-4-trifluoromethylcinnamamido)morphinan, 17-phenethyl-4,5α-epoxy-3,14β-dihydroxy-6α-(N-methyl-3-phenylpropiolamido)morphinan, 17-cyclopropylmethyl-4,5α-epoxy-3-hydroxy-14β-acetoxy-6α-(N-methyl-3-trifluoromethylcinnamamido)morphinan, 17-cyclopropylmethyl-4,5α-epoxy-3-hydroxy-14β-acetoxy-6α-[N-methyl-trans-3-(3-furyl)acrylamido]morphinan, 17-cyclopropylmethyl-4,5α-epoxy-3-hydroxy-14β-acetoxy-6α-(N-methyl-4-trifluoromethylcinnamamido)morphinan, 17-cyclopropylmethyl-4,5α-epoxy-3-hydroxy-14β-acetoxy-6α-(N-methyl-3-phenylpropiolamido)morphinan, 17-allyl-4,5α-epoxy-3-hydroxy-14β-acetoxy-6α-(N-methyl-3-trifluoromethylcinnamamido)morphinan, 17-allyl-4,5α-epoxy-3-hydroxy-14β-acetoxy-6α-[N-methyl-trans-3-(3-furyl)acrylamido]morphinan, 17-allyl-4,5α-epoxy-3-hydroxy-14β-acetoxy-6α-(N-methyl-4-trifluoromethylcinnamamido)morphinan, 17-allyl-4,5α-epoxy-3-hydroxy-14β-acetoxy-6α-(N-methyl-3-phenylpropiolamido)morphinan, 17-methyl-4,5α-epoxy-3-hydroxy-14β-acetoxy-6α-(N-methyl-3-trifluoromethylcinnamamido)morphinan, 17-methyl-4,5α-epoxy-3-hydroxy-14β-acetoxy-6α-[N-methyl-trans-3-(3-furyl)acrylamido]morphinan, 17-methyl-4,5α-epoxy-3-hydroxy-14β-acetoxy-6α-(N-methyl-4-trifluoromethylcinnamamido)morphinan, 17-methyl-4,5α-epoxy-3-hydroxy-14β-acetoxy-6α-(N-methyl-3-phenylpropiolamido)morphinan, 17-phenethyl-4,5α-epoxy-3-hydroxy-14β-acetoxy-6α-(N-methyl-3-trifluoromethylcinnamamido)morphinan, 17-phenethyl-4,5α-epoxy-3-hydroxy-14β-acetoxy-6α-[N-methyl-trans-3-(3-furyl)acrylamido]morphinan, 17-phenethyl-4,5α-epoxy-3-hydroxy-14β-acetoxy-6α-(N-methyl-4-trifluoromethylcinnamamido)morphinan, 17-phenethyl-4,5α-epoxy-3-hydroxy-14β-acetoxy-6α-(N-methyl-3-phenylpropiolamido)morphinan, 17-cyclopropylmethyl-4,5α-epoxy-14β-hydroxy-6α-(N-methyl-3-trifluoromethylcinnamamido)morphinan, 17-cyclopropylmethyl-4,5α-epoxy-14β-hydroxy-6α-[N-methyl-trans-3-(3-furyl)acrylamido]morphinan, 17-cyclopropylmethyl-4,5α-epoxy-14β-hydroxy-6α-(N-methyl-4-trifluoromethylcinnamamido)morphinan, 17-cyclopropylmethyl-4,5α-epoxy-14β-hydroxy-6α-(N-methyl-3-phenylpropiolamido)morphinan, 17-allyl-4,5α-epoxy-14β-hydroxy-6α-(N-methyl-3-trifluoromethylcinnamamido)morphinan, 17-allyl-4,5α-epoxy-14β-hydroxy-6α-[N-methyl-trans-3-(3-furyl)acrylamido]morphinan, 17-allyl-4,5α-epoxy-14β-hydroxy-6α-(N-methyl-4-trifluoromethylcinnamamido)morphinan, 17-allyl-4,5α-epoxy-14β-hydroxy-6α-(N-methyl-3-phenylpropiolamido)morphinan, 17-methyl-4,5α-epoxy-14β-hydroxy-6β-(N-methyl-3-trifluoromethylcinnamamido)morphinan, 17-methyl-4,5α-epoxy-14β-hydroxy-6α-[N-methyl-trans-3-(3-furyl)acrylamido]morphinan, 17-methyl-4,5α-epoxy-14β-hydroxy-6α-(N-methyl-4-trifluoromethylcinnamamido)morphinan, 17-methyl-4,5α-epoxy-14β-hydroxy-6α-(N-methyl-3-phenylpropiolamido)morphinan, 17-phenethyl-4,5α-epoxy-14β-hydroxy-6α-(N-methyl-3-trifluoromethylcinnamamido)morphinan, 17-phenethyl-4,5α-epoxy-14β-hydroxy-6α-[N-methyl-trans-3-(3-furyl)acrylamido]-morphinan, 17-phenethyl-4,5α-epoxy-14β-hydroxy-6α-(N-methyl-4-trifluoromethylcinnamamido)morphinan, 17-phenethyl-4,5α-epoxy-14β-hydroxy-6α-(N-methyl-3-phenylpropiolamido)morphinan, 17-cyclopropylmethyl-4,5α-epoxy-14β-acetoxy-6α-(N-methyl-3-trifluoromethylcinnamamido)morphinan, 17-cyclopropylmethyl-4,5α-epoxy-14β-acetoxy-6α-[N-methyl-trans-3-(3-furyl)acrylamido]morphinan, 17-cyclopropylmethyl-4,5α-epoxy-14β-acetoxy-6α-(N-methyl-4-trifluoromethylcinnamamido)morphinan, 17-cyclopropylmethyl-4,5α-epoxy-14β-acetoxy-6α-(N-methyl-3-phenylpropiolamido)morphinan, 17-allyl-4,5α-epoxy-14β-acetoxy-6α-(N-methyl-3-trifluoromethylcinnamamido)morphinan, 17-allyl-4,5α-epoxy-14β-acetoxy-6α-[N-methyl-trans-3-(3-furyl)acrylamido]morphinan, 17-allyl-4,5α-epoxy-14β-acetoxy-6α-(N-methyl-4-trifluoromethylcinnamamido)morphinan, 17-allyl-4,5α-epoxy-14β-acetoxy-6α-(N-methyl-3-phenylpropiolamido)morphinan, 17-methyl-4,5α-epoxy-14β-acetoxy-6α-(N-methyl-3-trifluoromethylcinnamamido)morphinan, 17-methyl-4,5α-epoxy-14β-acetoxy-6α-[N-methyl-trans-3-(3-furyl)acrylamido]morphinan, 17-methyl-4,5α-epoxy-14β-acetoxy-6α-(N-methyl-4-trifluoromethylcinnamamido)morphinan, 17-methyl-4,5α-epoxy-14β-acetoxy-6β-(N-methyl-3-phenylpropiolamido)morphinan, 17-phenethyl-4,5α-epoxy-14β-acetoxy-6α-(N-methyl-3-trifluoromethylcinnamamido)morphinan, 17-phenethyl-4,5α-epoxy-14β-acetoxy-6α-[N-methyl-trans-3-(3-furyl)acrylamido]morphinan, 17-phenethyl-4,5α-epoxy-14β-acetoxy-6α-(N-methyl-4-trifluoromethylcinnamamido)morphinan, 17-phenethyl-4,5α-epoxy-14β-acetoxy-6α-(N-methyl-3-phenylpropiolamido)morphinan, 17-cyclopropylmethyl-4,5α-epoxy-3-methoxy-14β-hydroxy-6α-(N-methyl-3-trifluoromethylcinnamamido)morphinan, 17-cyclopropylmethyl-4,5α-epoxy-3-methoxy-14β-hydroxy-6α-[N-methyl-trans-3-(3-furyl)acrylamido]morphinan, 17-cyclopropylmethyl-4,5α-epoxy-3-methoxy-14β-hydroxy-6α-(N-methyl-4-trifluoromethylcinnamamido)morphinan, 17-cyclopropylmethyl-4,5α-epoxy-3-methoxy-14β-hydroxy-6α-(N-methyl-3-phenylpropiolamido)morphinan, 17-allyl-4,5α-epoxy-3-methoxy-14β-hydroxy-6α-(N-methyl-3-trifluoromethylcinnamamido)morphinan, 17-allyl-4,5α-epoxy-3-methoxy-14β-hydroxy-6α-[N-methyl-trans-3-(3-furyl)acrylamido]morphinan, 17-allyl-4,5α-epoxy-3-methoxy-14β-hydroxy-6α-(N-methyl-4-trifluoromethylcinnamamido)morphinan, 17-allyl-4,5α-epoxy-3-methoxy-14β-hydroxy-6α-(N-methyl-3-phenylpropiolamido)morphinan, 17-methyl-4,5α-epoxy-3-methoxy-14β-hydroxy-6α-(N-methyl-3-trifluoromethylcinnamamido)morphinan, 17-methyl-4,5α-epoxy-3-methoxy-14β-hydroxy-6α-[N-methyl-trans-3-(3 -furyl)acrylamido]morphinan, 17-methyl-4,5α-epoxy-3-methoxy-14β-hydroxy-6α-(N-methyl-4-trifluoromethylcinnamamido)morphinan, 17-methyl-4,5α-epoxy-3-methoxy-14β-hydroxy-6α-(N-methyl-3-phenylpropiolamido)morphinan, 17-phenethyl-4,5α-epoxy-3-methoxy-14β-hydroxy-6α-(N-methyl-3-trifluoromethylcinnamamido)morphinan, 17-phenethyl-4,5α-epoxy-3-methoxy-14β-hydroxy-6α-[N-methyl-trans-3-(3-furyl)acrylamido]morphinan, 17-phenethyl-4,5α-epoxy-3-methoxy-14β-hydroxy-6α-(N-methyl-4-trifluoromethylcinnamamidomorphinan, 17-phenethyl-4,5α-epoxy-3-methoxy-14β-hydroxy-6α-(N-methyl-3-phenylpropiolamido)morphinan, 17-cyclopropylmethyl-4,5α-epoxy-3-methoxy-14β-acetoxy-6α-(N-methyl-3-trifluoromethylcinnamamido)morphinan, 17-cyclopropylmethyl-4,5α-epoxy-3-methoxy-14β-acetoxy-6α-[N-methyl-trans-3-(3-furyl)acrylamido] morphinan, 17-cyclopropylmethyl-4,5α-epoxy-3-methoxy-14β-acetoxy-6α-(N-methyl-4-trifluoromethylcinnamamido)morphinan, 17-cyclopropylmethyl-4,5α-epoxy-3-methoxy-14β-acetoxy-6α-(N-methyl-3-phenylpropionamido)morphinan, 17-allyl-4,5α-epoxy-3-methoxy-14β-acetoxy-6α-(N-methyl-3-trifluoromethylcinnamamido)morphinan, 17-allyl-4,5α-epoxy-3-methoxy-14β-acetoxy-6α-[N-methyl-trans-3-(3-furyl)acrylamido]morphinan, 17-allyl-4,5α-epoxy-3-methoxy-14β-acetoxy-6α-(N-methyl-4-trifluoromethylcinnamamido)morphinan, 17-allyl-4,5α-epoxy-3-methoxy-14β-acetoxy-6α-(N-methyl-3-phenylpropiolamido)morphinan, 17-methyl-4,5α-epoxy-3-methoxy-14β-acetoxy-6α-(N-methyl-3-trifluoromethylcinnamamido)morphinan, 17-methyl-4,5α-epoxy-3-methoxy-14β-acetoxy-6α-[N-methyl-trans-3-(3-furyl)acrylamido]morphinan, 17-methyl-4,5α-epoxy-3-methoxy-14β-acetoxy-6β-(N-methyl-4-trifluoromethylcinnamamido)morphinan, 17-methyl-4,5α-epoxy-3-methoxy-14β-acetoxy-6α-(N-methyl-3-phenylpropiolamido)morphinan, 17-phenethyl-4,5α-epoxy-3-methoxy-14β-acetoxy-6α-(N-methyl-3-trifluoromethylcinnamamido)morphinan, 17-phenethyl-4,5α-epoxy-3-methoxy-14β-acetoxy-6α-[N-methyl-trans-3-(3-furyl)acrylamido]morphinan, 17-phenethyl-4,5α-epoxy-3-methoxy-14β-acetoxy-6α-(N-methyl-4-trifluoromethylcinnamamido)morphinan, 17-phenethyl-4,5α-epoxy-3-methoxy-14β-acetoxy-6α-(N-methyl-3-phenylpropiolamido)morphinan, 17-cyclopropylmethyl-4,5α-epoxy-3-acetoxy-14β-hydroxy-6α-(N-methyl-3-trifluoromethylcinnamamido)morphinan, 17-cyclopropylmethyl-4,5α-epoxy-3-acetoxy-14β-hydroxy-6α-[N-methyl-trans-3-(3-furyl)acrylamido]morphinan, 17-cyclopropylmethyl-4,5α-epoxy-3-acetoxy-14β-hydroxy-6α-(N-methyl-4-trifluoromethylcinnamamido)morphinan, 17-cyclopropylmethyl-4,5α-epoxy-3-acetoxy-14β-hydroxy-6α-(N-methyl-3-phenylpropiolamido)morphinan, 17-allyl-4,5α-epoxy-3-acetoxy-14β-hydroxy-6α-(N-methyl-3-trifluoromethylcinnamamido)morphinan, 17-allyl-4,5α-epoxy-3-acetoxy-14β-hydroxy-6α-[N-methyl-trans-3-(3-furyl)acrylamido]morphinan, 17-allyl-4,5α-epoxy-3-acetoxy-14β-hydroxy-6α-(N-methyl-4-trifluoromethylcinnamamido)morphinan, 17-allyl-4,5α-epoxy-3-acetoxy-14β-hydroxy-6α-(N-methyl-3-phenylpropiolamido)morphinan, 17-methyl-4,5α-epoxy-3-acetoxy-14β-hydroxy-6α-(N-methyl-3-trifluoromethylcinnamamido)morphinan, 17-methyl-4,5α-epoxy-3-acetoxy-14β-hydroxy-6α-[N-methyl-trans-3-(3-furyl)acrylamido]morphinan, 17-methyl-4,5α-epoxy-3-acetoxy-14β-hydroxy-6α-(N-methyl-4-trifluoromethylcinnamamido)morphinan, 17-methyl-4,5α-epoxy-3-acetoxy-14β-hydroxy-6α-(N-methyl-3-phenylpropiolamido)morphinan, 17-phenethyl-4,5α-epoxy-3-acetoxy-14β-hydroxy-6α-(N-methyl-3-trifluoromethylcinnamamido)morphinan, 17-phenethyl-4,5α-epoxy-3-acetoxy-14β-hydroxy-6α-[N-methyl-trans-3-(3-furyl)acrylamido]morphinan, 17-phenethyl-4,5α-epoxy-3-acetoxy-14β-hydroxy-6α-(N-methyl-4 -trifluoromethylcinnamamido)morphinan, 17-phenethyl-4,5α-epoxy-3-acetoxy-14β-hydroxy-6α-(N-methyl-3-phenylpropiolamido)morphinan, 17-cyclopropylmethyl-4,5α-epoxy-3,14β-diacetoxy-6α-(N-methyl-3-trifluoromethylcinnamamido)morphinan, 17-cyclopropylmethyl-4,5α-epoxy-3,14β-diacetoxy-6α-[N-methyl-trans-3-(3-furyl)acrylamido]morphinan, 17-cyclopropylmethyl-4,5α-epoxy-3,14β-diacetoxy-6α-(N-methyl-4-trifluoromethylcinnamamido)morphinan, 17-cyclopropylmethyl-4,5α-epoxy-3,14β-diacetoxy-6α-(N-methyl-3-phenylpropiolamido)morphinan, 17-allyl-4,5α-epoxy-3,14β-diacetoxy-6α-(N-methyl-3-trifluoromethylcinnamamido)morphinan, 17-allyl-4,5α-epoxy-3,14β-diacetoxy-6α-[N-methyl-trans-3-(3-furyl)acrylamido]-morphinan, 17-allyl-4,5α-epoxy-3,14β-diacetoxy-6α-(N-methyl-4-trifluoromethylcinnamamido)morphinan, 17-allyl-4,5α-epoxy-3,14β-diacetoxy-6α-(N-methyl-3-phenylpropiolamido)morphinan, 17-methyl-4,5α-epoxy-3,14β-diacetoxy-6α-(N-methyl-3-trifluoromethylcinnamamido)morphinan, 17-methyl-4,5α-epoxy-3,14β-diacetoxy-6α-[N-methyl-trans-3-(3-furyl)acrylamido]morphinan, 17-methyl-4,5α-epoxy-3,14β-diacetoxy-6α-(N-methyl-4-trifluoromethylcinnamamido)morphinan, 17-methyl-4,5α-epoxy-3,14β-diacetoxy-6α-(N-methyl-3-phenylpropiolamido)morphinan, 17-phenethyl-4,5α-epoxy-3,14β-diacetoxy-6α-(N-methyl-3-trifluoromethylcinnamamido)morphinan, 17-phenethyl-4,5α-epoxy-3,14β-diacetoxy-6α-[N-methyl-trans-3-(3-furyl)acrylamido]morphinan, 17-phenethyl-4,5α-epoxy-3,14β-diacetoxy-6α-(N-methyl-4-trifluoromethylcinnamamido)morphinan, 17-phenethyl-4,5α-epoxy-3,14β-diacetoxy-6α-(N-methyl-3-phenylpropiolamido)morphinan, 17-cyclopropylmethyl-4,5α-epoxy-3,14β-dihydroxy-6α-(N-isobutyl-3-trifluoromethylcinnamamido)morphinan, 17-cyclopropylmethyl-4,5α-epoxy-3,14β-dihydroxy-6α-[N-isobutyl-trans-3-(3-furyl)acrylamido]morphinan, 17-cyclopropylmethyl-4,5α-epoxy-3,14β-dihydroxy-6α-(N-isobutyl-4-trifluoromethylcinnamamido)morphinan, 17-cyclopropylmethyl-4,5α-epoxy-3,14β-dihydroxy-6α-(N-isobutyl-3-phenylpropiolamido)morphinan, 17-allyl-4,5α-epoxy-3,14β-dihydroxy-6β-(N-isobutyl-3-trifluoromethylcinnamamido)morphinan, 17-allyl-4,5α-epoxy-3,14β-dihydroxy-6α-[N-isobutyl-trans-3-(3-furyl)acrylamido]morphinan, 17-allyl-4,5α-epoxy-3,14β-dihydroxy-6α-(N-isobutyl-4-trifluoromethylcinnamamido)morphinan, 17-allyl-4,5α-epoxy-3,14β-dihydroxy-6α-(N-isobutyl-3-phenylpropiolamido)morphinan, 17-methyl-4,5α-epoxy-3,14β-dihydroxy-6α-(N-isobutyl-3-trifluoromethylcinnamamido)morphinan, 17-methyl-4,5α-epoxy-3,14β-dihydroxy-6α-[N-isobutyl-trans-3-(3-furyl)acrylamido]morphinan, 17-methyl-4,5α-epoxy-3,14β-dihydroxy-6α-(N-isobutyl-4-trifluoromethylcinnamamido)morphinan, 17-methyl-4,5α-epoxy-3,14β-dihydroxy-6α-(N-isobutyl-3-phenylpropiolamido)morphinan, 17-phenethyl-4,5α-epoxy-3,14β-dihydroxy-6α-(N-isobutyl-3-trifluoromethylcinnamamido)morphinan, 17-phenethyl-4,5α-epoxy-3,14β-dihydroxy-6α-[N-isobutyl-trans-3-(3-furyl)acrylamido]morphinan, 17-phenethyl-4,5α-epoxy-3,14β-dihydroxy-6α-(N-isobutyl-4-trifluoromethylcinnamamido)morphinan, 17-phenethyl-4,5α-epoxy-3,14β-dihydroxy-6α-(N-isobutyl-3-phenylpropiolamido)morphinan, 17-cyclopropylmethyl-4,5α-epoxy-3-hydroxy-14β-acetoxy-6α-(N-isobutyl-3-trifluoromethylcinnamamido)morphinan, 17-cyclopropylmethyl-4,5α-epoxy-3-hydroxy-14β-acetoxy-6α-[N-isobutyl-trans-3-(3-furyl)acrylamido]morphinan, 17-cyclopropylmethyl-4,5α-epoxy-3-hydroxy-14β-acetoxy-6α-(N-isobutyl-4-trifluoromethylcinnamamido)morphinan, 17-cyclopropylmethyl-4,5α-epoxy-3-hydroxy-14β-acetoxy-6α-(N-isobutyl-3-phenylpropiolamido)morphinan, 17-allyl-4,5α-epoxy-3-hydroxy-14β-acetoxy-6α-(N-isobutyl-3-trifluoromethylcinnamamido)morphinan, 17-allyl-4,5α-epoxy-3-hydroxy-14β-acetoxy-6α-[N-isobutyl-trans-3-(3-furyl)acrylamido]morphinan, 17-allyl-4,5α-epoxy-3-hydroxy-14β-acetoxy-6α-(N-isobutyl-4-trifluoromethylcinnamamido)morphinan, 17-allyl-4,5α-epoxy-3-hydroxy-14β-acetoxy-6α-(N-isobutyl-3-phenylpropiolamido)morphinan, 17-methyl-4,5α-epoxy-3-hydroxy-14β-acetoxy-6α-(N-isobutyl-3-trifluoromethylcinnamamido)morphinan, 17-methyl-4,5α-epoxy-3-hydroxy-14β-acetoxy-6α-[N-isobutyl-trans-3-(3-furyl)acrylamido]morphinan, 17-methyl-4,5α-epoxy-3-hydroxy-14β-acetoxy-6α-(N-isobutyl-4-trifluoromethylcinnamamido)morphinan, 17-methyl-4,5α-epoxy-3-hydroxy-14β-acetoxy-6α-(N-isobutyl-3-phenylpropiolamido)morphinan, 17-phenethyl-4,5α-epoxy-3-hydroxy-14β-acetoxy-6α-(N-isobutyl-3-trifluoromethylcinnamamido)morphinan, 17-phenethyl-4,5α-epoxy-3-hydroxy-14β-acetoxy-6α-[N-isobutyl-trans-3-(3-furyl)acrylamido]morphinan, 17-phenethyl-4,5α-epoxy-3-hydroxy-14β-acetoxy-6α-(N-isobutyl-4-trifluoromethylcinnamamido)morphinan, 17-phenethyl-4,5α-epoxy-3-hydroxy-14β-acetoxy-6α-(N-isobutyl-3-phenylpropiolamido)morphinan, 17-cyclopropylmethyl-4,5α-epoxy-14β-hydroxy-6α-(N-isobutyl-3-trifluoromethylcinnamamido)morphinan, 17-cyclopropylmethyl-4,5α-epoxy-14β-hydroxy-6α-[N-isobutyl-trans-3-(3-furyl)acrylamido]morphinan, 17-cyclopropylmethyl-4,5α-epoxy-14-hydroxy-6α-(N-isobutyl-4-trifluoromethylcinnamamido)morphinan, 17-cyclopropylmethyl-4,5α-epoxy-14β-hydroxy-6α-(N-isobutyl-3-phenylpropiolamido)morphinan, 17-allyl-4,5α-epoxy-14β-hydroxy-6α-(N-isobutyl-3-trifluoromethylcinnamamido)morphinan, 17-allyl-4,5α-epoxy-14β-hydroxy-6α-[N-isobutyl-trans-3-(3-furyl)acrylamido]morphinan, 17-allyl-4,5α-epoxy-14β-hydroxy-6α-(N-isobutyl-4-trifluoromethylcinnamamido)morphinan, 17-allyl-4,5α-epoxy-14β-hydroxy-6α-(N-isobutyl-3-phenylpropiolamido)morphinan, 17-methyl-4,5α-epoxy-14β-hydroxy-6α-(N-isobutyl-3-trifluoromethylcinnamamido)morphinan, 17-methyl-4,5α-epoxy-14β-hydroxy-6α-[N-isobutyl-trans-3-(3-furyl)acrylamido]morphinan, 17-methyl-4,5α-epoxy-14β-hydroxy-6α-(N-isobutyl-4-trifluoromethylcinnamamido)morphinan, 17-methyl-4,5α-epoxy-14β-hydroxy-6β-(N-isobutyl-3-phenylpropiolamido)morphinan, 17-phenethyl-4,5α-epoxy-14β-hydroxy-6α-(N-isobutyl-3-trifluoromethylcinnamamido)morphinan, 17-phenethyl-4,5α-epoxy-14β-hydroxy-6α-[N-isobutyl-trans-3-(3-furyl)acrylamido]morphinan, 17-phenethyl-4,5α-epoxy-14β-hydroxy-6α-(N-isobutyl-4-trifluoromethylcinnamamido)morphinan, 17-phenethyl-4,5α-epoxy-14β-hydroxy-6α-(N-isobutyl-3-phenylpropiolamido)morphinan, 17-cyclopropylmethyl-4,5α-epoxy-14β-acetoxy-6α-(N-isobutyl-3-trifluoromethylcinnamamido)

morphinan, 17-cyclopropylmethyl-4,5α-epoxy-14β-acetoxy-6α-[N-isobutyl-trans-3-(3-furyl)acrylamido]morphinan, 17-cyclopropylmethyl-4,5α-epoxy-14β-acetoxy-6α-(N-isobutyl-4-trifluoromethylcinnamamido)morphinan, 17-cyclopropylmethyl-4,5α-epoxy-14β-acetoxy-6α-(N-isobutyl-3-phenylpropiolamido)morphinan, 17-allyl-4,5α-epoxy-14β-acetoxy-6α-(N-isobutyl-3-trifluoromethylcinnamamido)morphinan, 17-allyl-4,5α-epoxy-14β-acetoxy-6α-[N-isobutyl-trans-3-(3-furyl)acrylamido]morphinan, 17-allyl-4,5α-epoxy-14β-acetoxy-6α-(N-isobutyl-4-trifluoromethylcinnamamido)morphinan, 17-allyl-4,5α-epoxy-14β-acetoxy-6α-(N-isobutyl-3-phenylpropiolamido)morphinan, 17-methyl-4,5α-epoxy-14β-acetoxy-6α-(N-isobutyl-3-trifluoromethylcinnamamido)morphinan, 17-methyl-4,5α-epoxy-14β-acetoxy-6α-(N-isobutyl-trans-3-(3-furyl)acrylamido]morphinan, 17-methyl-4,5α-epoxy-14β-acetoxy-6α-(N-isobutyl-4-trifluoromethylcinnamamido)morphinan, 17-methyl-4,5α-epoxy-14β-acetoxy-6α-(N-isobutyl-3-phenylpropiolamido)morphinan, 17-phenethyl-4,5α-epoxy-14β-acetoxy-6α-(N-isobutyl-3-trifluoromethylcinnamamido)morphinan, 17-phenethyl-4,5α-epoxy-14β-acetoxy-6α-[N-isobutyl-trans-3-(3-furyl)acrylamido]morphinan, 17-phenethyl-4,5α-epoxy-14β-acetoxy-6α-(N-isobutyl-4-trifluoromethylcinnamamido)morphinan, 17-phenethyl-4,5α-epoxy-14β-acetoxy-6α-(N-isobutyl-3-phenylpropiolamido)morphinan, 17-cyclopropylmethyl-4,5α-epoxy-3-methoxy-14β-hydroxy-6α-(N-isobutyl-3-trifluoromethylcinnamamido)morphinan, 17-cyclopropylmethyl-4,5α-epoxy-3-methoxy-14β-hydroxy-6α-[N-isobutyl-trans-3-(3-furyl)acrylamido]morphin, 17-cyclopropylmethyl-4,5α-epoxy-3-methoxy-14β-hydroxy-6α-(N-isobutyl-4-trifluoromethylcinnamamido)morphinan, 17-cyclopropylmethyl-4,5α-epoxy-3-methoxy-14β-hydroxy-6α-(N-isobutyl-3-phenylpropiolamido)morphinan, 17-allyl-4,5α-epoxy-3-methoxy-14β-hydroxy-6α-(N-isobutyl-3-trifluoromethylcinnamamido)morphinan, 17-allyl-4,5α-epoxy-3-methoxy-14β-hydroxy-6α-[N-isobutyl-trans-3-(3-furyl)acrylamido]morphinan, 17-allyl-4,5α-epoxy-3-methoxy-14β-hydroxy-6α-(N-isobutyl-4-trifluoromethylcinnamamido)morphinan, 17-allyl-4,5α-epoxy-3-methoxy-14β-hydroxy-6α-(N-isobutyl-3-phenylpropiolamido)morphinan, 17-methyl-4,5α-epoxy-3-methoxy-14β-hydroxy-6α-(N-isobutyl-3-trifluoromethylcinnamamido)morphinan, 17-methyl-4,5α-epoxy-3-methoxy-14β-hydroxy-6α-[N-isobutyl-trans-3-(3-furyl)acrylamido]morphinan, 17-methyl-4,5α-epoxy-3-methoxy-14β-hydroxy-6α-(N-isobutyl-4-trifluoromethylcinnamamido)morphinan, 17-methyl-4,5α-epoxy-3-methoxy-14β-hydroxy-6α-(N-isobutyl-3-phenylpropiolaimido)morphinan, 17-phenethyl- 4,5α-epoxy-3-methoxy-14β-hydroxy-6α-(N-isobutyl-3-trifluoromethylcinnamamido) morphinan, 17-phenethyl-4,5α-epoxy-3-methoxy-14β-hydroxy-6α-[N-isobutyl-trans-3-(3-furyl)acrylamido]morphinan, 17-phenethyl-4,5α-epoxy-3-methoxy-14β-hydroxy-6α-(N-isobutyl-4-trifluoromethylcinnamamido)morphinan, 17-phenethyl-4,5α-epoxy-3-methoxy-14β-hydroxy-6α-(N-isobutyl-3-phenylpropiolamido)morphinan, 17-cyclopropylmethyl-4,5α-epoxy-3-methoxy-14β-acetoxy-6α-(N-isobutyl-3-trifluoromethylcinnamamido)morphinan, 17-cyclopropylmethyl-4,5α-epoxy-3-methoxy-14β-acetoxy-6α-[N-isobutyl-trans-3-(3-furyl)acrylamido]morphinan, 17-cyclopropylmethyl-4,5α-epoxy-3-methoxy-14β-acetoxy-6α-(N-isobutyl-4-trifluoromethylcinnamamido)morphinan, 17-cyclopropylmethyl-4,5α-epoxy-3-methoxy-14β-acetoxy-6α-(N-isobutyl-3-phenylpropiolamido)morphinan, 17-allyl-4,5α-epoxy-3-methoxy-14β-acetoxy-6α-(N-isobutyl-3-trifluoromethylcinnamamido)morphinan, 17-allyl-4,5α-epoxy-3-methoxy-14β-acetoxy-6α-[N-isobutyl-trans-3-(3-furyl)acrylamido]morphinan, 17-allyl4,5α-epoxy-3-methoxy-14β-acetoxy-6α-(N-isobutyl-4-trifluoromethylcinnaimamido)morphinan, 17-allyl-4,5α-epoxy-3-methoxy-14β-acetoxy-6α-(N-isobutyl-3-phenylpropiolamido)morphinan, 17-methyl-4,5α-epoxy-3-methoxy-14β-acetoxy-6α-(N-isobutyl-3-trifluoromethylcinnamamido)morphinan, 17-methyl-4,5α-epoxy-3-methoxy-14β-acetoxy-6α-[N-isobutyl-trans-3-(3-furyl)acrylamido]morphinan, 17-methyl-4,5α-epoxy-3-methoxy-14β-acetoxy-6α-(N-isobutyl-4-trifluoromethylcinnamamido)morphinan, 17-methyl-4,5α-epoxy-3-methoxy-14β-acetoxy-6α-(N-isobutyl-3-phenylpropiolamido)morphinan, 17-phenethyl-4,5α-epoxy-3-methoxy-14β-acetoxy-6α-(N-isobutyl-3-trifluoromethylcinnamamido)morphinan, 17-phenethyl-4,5α-epoxy-3-methoxy-14β-acetoxy-6α-[N-isobutyl-trans-3-(3-furyl)acrylamido]morphinan, 17-phenethyl-4,5α-epoxy-3-methoxy-14β-acetoxy-6α-(N-isobutyl-4-trifluoromethylcinnamamido)morphinan, 17-phenethyl-4,5α-epoxy-3-methoxy-14-acetoxy-6α-(N-isobutyl-3-phenylpropiolamido)morphinan, 17-cyclopropylmethyl-4,5α-epoxy-3-acetoxy-14β-hydroxy-6α-(N-isobutyl-3-trifluoromethylcinnamamido)morphinan, 17-cyclopropylmethyl-4,5α-epoxy-3-acetoxy-14β-hydroxy-6α-[N-isobutyl-trans-3-(3-furyl)acrylamido]morphinan, 17-cyclopropylmethyl-4,5α-epoxy-3-acetoxy-14β-hydroxy-6α-(N-isobutyl-4-trifluoromethylcinnamamido)morphinan, 17-cyclopropylmethyl-4,5α-epoxy-3-acetoxy-14β-hydroxy-6α-(N-isobutyl-3-phenylpropiolamido)morphinan, 17-allyl-4,5α-epoxy-3-acetoxy-14β-hydroxy-6α-(N-isobutyl-3-trifluoromethylcinnamamido)morphinan, 17-allyl-4,5α-epoxy-3-acetoxy-14β-hydroxy-6α-[N-isobutyl-trans-3-(3-furyl)acrylamido]morphinan, 17-allyl-4,5α-epoxy-3-acetoxy-14β-hydroxy-6α-(N-isobutyl-4-trifluoromethylcinnamamido)morphinan, 17-allyl-4,5α-epoxy-3-acetoxy-14β-hydroxy-6α-(N-isobutyl-3-phenylpropiolamido)morphinan, 17-methyl-4,5α-epoxy-3-acetoxy-14β-hydroxy-6α-(N-isobutyl-3-trifluoromethylcinnamamido)morphinan, 17-methyl-4,5α-epoxy-3-acetoxy-14β-hydroxy-6α-[N-isobutyl-trans-3-(3-furyl)acrylamido]morphinan, 17-methyl-4,5α-epoxy-3-acetoxy-14β-hydroxy-6α-(N-isobutyl-4-trifluoromethylcinnamamido)morphinan, 17-methyl-4,5α-epoxy-3-acetoxy-14β-hydroxy-6α-(N-isobutyl-3-phenylpropiolamido)morphinan, 17-phenethyl-4,5α-epoxy-3-acetoxy-14β-hydroxy-6α-(N-isobutyl-3-trifluoromethylcinnamamido)morphinan, 17-phenethyl-4,5α-epoxy-3-acetoxy-14β-hydroxy-6α-[N-isobutyl-trans-3-(3-furyl)acrylamido]morphinan,
17-phenethyl-4,5α-epoxy-3-acetoxy-14β-hydroxy-6α-(N-isobutyl-4-trifluoromethylcinnamamido)morphinan, 17-phenethyl-4,5α-epoxy-3-acetoxy-14β-hydroxy-6α-(N-isobutyl-3-phenylpropiolamido)morphinan, 17-cyclopropylmethyl-4,5α-epoxy-3,14β-diacetoxy-6α-(N-isobutyl-3-trifluoromethylcinnamamido)morphinan, 17-cyclopropylmethyl-4,5α-epoxy-3,14β-diacetoxy-6α-[N-isobutyl-trans-3-(3-furyl)acrylamido]morphinan, 17-cyclopropylmethyl-4,5α-epoxy-3,14β-diacetoxy-6α-(N-isobutyl-4-trifluoromethylcinnamamido)morphinan, 17-cyclopropylmethyl-4,5α-epoxy-3,14β-diacetoxy-6α-(N-isobutyl-3-phenylpropiolamido)morphinan, 17-allyl-4,5α-epoxy-3,14β-diacetoxy-6α-(N-isobutyl-3-trifluoromethylcinnamamido)morphinan, 17-allyl-4,5α-epoxy-3,14β-diacetoxy-6α-[N-isobutyl-trans-3-(3-furyl)acrylamido]morphinan, 17-allyl-4,5α-epoxy-3,14β-diacetoxy-6α-(N-isobutyl-4-trifluoromethylcinnamamido)morphinan, 17-allyl-4,5α-epoxy-3,14β-diacetoxy-6α-(N-isobutyl-3-phenylpropiolamido)morphinan, 17-methyl-4,5α-epoxy-3,14β-diacetoxy-6α-(N-isobutyl-3-trifluoromethylcinnamamido)morphinan, 17-methyl-4,5α-epoxy-3,14β-diacetoxy-6α-[N-isobutyl-trans-3-(3-furyl)acrylamido]morphinan, 17-methyl-4,5α-epoxy-3,14β-diacetoxy-6α-(N-isobutyl-4-trifluoromethylcinnamamido)morphinan, 17-methyl-4,5α-epoxy-3,14β-diacetoxy-6α-(N-isobutyl-3-phenylpropiolamido)morphinan, 17-phenethyl-4,5α-epoxy-3,14-diacetoxy-6α-(N-isobutyl-3-trifluoromethylcinnamamido)morphinan, 17-phenethyl-4,5α-epoxy-3,14β-diacetoxy-6α-[N-isobutyl-trans-3-(3-furyl)acrylamido]morphinan, 17-phenethyl-4,5α-epoxy-3,14β-diacetoxy-6α-(N-isobutyl-4-trifluoromethylcinnamamido)morphinan, 17-phenethyl-4,5α-epoxy-3,14β-diacetoxy-6α-(N-isobutyl-3-phenylpropiolamido)morphinan, 17-cyclopropylmethyl-4,5α-epoxy-3,14β-dihydroxy-6β-(N-methyl-3-trifluoromethylcinnamamido)morphinan, 17-cyclopropylmethyl-4,5α-epoxy-3,14β-dihydroxy-6β-[N-methyl-trans-3-(3-furyl)acrylamido]morphinan, 17-cyclopropylmethyl-4,5α-epoxy-3,14β-dihydroxy-6β-(N-methyl-4-trifluoromethylcinnamamido)morphinan, 17-cyclopropylmethyl-4,5α-epoxy-3,14β-dihydroxy-6β-(N-methyl-3-phenylpropiolamido)morphinan, 17-allyl-4,5α-epoxy-3,14β-dihydroxy-6β-(N-methyl-3-trifluoromethylcinnamamido)morphinan, 17-allyl-4,5α-epoxy-3,14β-dihydroxy-6β-[N-methyl-trans-3-(3-furyl)acrylamido]morphinan, 17-allyl-4,5α-epoxy-3,14β-dihydroxy-6β-(N-methyl-4-trifluoromethylcinnamamido)morphinan, 17-allyl-4,5α-epoxy-3,14β-dihydroxy-6β-(N-methyl-3-phenylpropiolamido)morphinan, 17-methyl-4,5α-epoxy-3,14β-dihydroxy-6β-(N-methyl-3-trifluoromethylcinnamamido)morphinan, 17-methyl-4,5α-epoxy-3,14β-dihydroxy-6β-[N-methyl-trans-3-(3-furyl)acrylamido]morphinan, 17-methyl-4,5α-epoxy-3,14β-dihydroxy-6β-(N-methyl-4-trifluoromethylcinnamamido)morphinan, 17-methyl-4,5α-epoxy-3,14β-dihydroxy-6β-(N-methyl-3-phenylpropiolamido)morphinan, 17-phenethyl-4,5α-epoxy-3,14β-dihydroxy-6β-(N-methyl-3-trifluoromethylcinnamamido)morphinan, 17-phenethyl-4,5α-epoxy-3,14β-dihydroxy-6β-[N-methyl-trans-3-(3-furyl)acrylamido]morphinan, 17-phenethyl-4,5α-epoxy-3,14β-dihydroxy-6β-(N-methyl-4-trifluoromethylcinnamamido)morphinan, 17-phenethyl-4,5α-epoxy-3,14β-dihydroxy-6β-(N-methyl-3-phenylpropiolamido)morphinan, 17-cyclopropylmethyl-4,5α-epoxy-3-hydroxy-14β-acetoxy-6β-(N-methyl-3-trifluoromethylcinnamamido)morphinan, 17-cyclopropylmethyl-4,5α-epoxy-3-hydroxy-14β-acetoxy-6β-[N-methyl-trans-3-(3-furyl)acrylamido]morphinan, 17-cyclopropylmethyl-4,5α-epoxy-3-hydroxy-14β-acetoxy-6β-(N-methyl-4-trifluoromethylcinnamamido)morphinan, 17-cyclopropylmethyl-4,5α-epoxy-3-hydroxy-14β-acetoxy-6β-(N-methyl-3-phenylpropiolamido)morphinan, 17-allyl-4,5α-epoxy-3-hydroxy-14β-acetoxy-6β-(N-methyl-3-trifluoromethylcinnamamido)morphinan, 17-allyl-4,5α-epoxy-3-hydroxy-14β-acetoxy-6β-[N-methyl-trans-3-(3-furyl)acrylamido]morphinan, 17-allyl-4,5α-epoxy-3-hydroxy-14β-acetoxy-6β-(N-methyl-4-trifluoromethylcinnamamido)morphinan, 17-allyl-4,5α-epoxy-3-hydroxy-14β-acetoxy-6β-(N-methyl-3-phenylpropiolamido)morphinan, 17-methyl-4,5α-epoxy-3-hydroxy-14β-acetoxy-6β-(N-methyl-3-trifluoromethylcinnamamido)morphinan, 17-methyl-4,5α-epoxy-3-hydroxy-14β-acetoxy-6β-[N-methyl-trans-3-(3-furyl)acrylamido]morphinan, 17-methyl-4,5α-epoxy-3-hydroxy-14β-acetoxy-6β-(N-methyl-4-trifluoromethylcinnamamido)morphinan, 17-methyl-4,5α-epoxy-3-hydroxy-14β-acetoxy-6β-(N-methyl-3-phenylpropiolamido)morphinan, 17-phenethyl-4,5α-epoxy-3-hydroxy-14β-acetoxy-6β-(N-methyl-3-trifluoromethylcinnamamido)morphinan, 17-phenethyl-4,5α-epoxy-3-hydroxy-14β-acetoxy-6β-[N-methyl-trans-3-(3-furyl)acrylamido]morphinan, 17-phenethyl-4,5α-epoxy-3-hydroxy-14β-acetoxy-6β-(N-methyl-4-trifluoromethylcinnamamido)morphinan, 17-phenethyl-4,5α-epoxy-3-hydroxy-14β-acetoxy-6β-(N-methyl-3-phenylpropiolamido)morphinan, 17-cyclopropylmethyl-4,5α-epoxy-14β-hydroxy-6β-(N-methyl-3-trifluoromethylcinnamamido)morphinan, 17-cyclopropylmethyl-4,5α-epoxy-14β-hydroxy-6β-[N-methyl-trans-3-(3-furyl)acrylamido]morphinan, 17-cyclopropylmethyl-4,5α-epoxy-14β-hydroxy-6β-(N-methyl-4-trifluoromethylcinnamamido)morphinan, 17-cyclopropylmethyl-4,5α-epoxy-14β-hydroxy-6β-(N-methyl-3-phenylpropiolamido)morphinan, 17-allyl-4,5α-epoxy-14β-hydroxy-6β-(N-methyl-3-trifluoromethylcinnamamido)morphinan, 17-allyl-4,5α-epoxy-14β-hydroxy-6β-[N-methyl-trans-3-(3-furyl)acrylamido]morphinan, 17-allyl-4,5α-epoxy-14β-hydroxy-6β-(N-methyl-4-trifluoromethylcinnamamido)morphinan, 17-allyl-4,5α-epoxy-14β-hydroxy-6β-(N-methyl-3-phenylpropiolamido)morphinan, 17-methyl-4,5α-epoxy-14β-hydroxy-6β-(N-methyl-3-trifluoromethylcinnamamido)morphinan, 17-methyl-4,5α-epoxy-14β-hydroxy-6β-[N-methyl-trans-3-(3-furyl)acrylamido]morphinan, 17-methyl-4,5α-epoxy-14β-hydroxy-6β-(N-methyl-4-trifluoromethylcinnamamido)morphinan, 17-methyl-4,5α-epoxy-14β-hydroxy-6β-(N-methyl-3-phenylpropiolamido)morphinan, 17-phenethyl-4,5α-epoxy-14β-hydroxy-6β-(N-methyl-3-trifluoromethylcinnamamido)morphinan, 17-phenethyl-4,5α-epoxy-14β-hydroxy-6β-[N- methyl-trans-3-(3-furyl)acrylamido]morphinan, 17-phenethyl-4,5α-epoxy-14β-hydroxy-6β-(N-methyl-4-trifluoromethylcinnamamido)morphinan, 17-phenethyl-4,5-epoxy-14β-hydroxy-6β-(N-methyl-3-phenylpropiolamido)morphinan, 17-cyclopropylmethyl-4,5α-epoxy-14β-acetoxy-6β-(N-methyl-3-trifluoromethylcinnamamido)morphinan, 17-cyclopropylmethyl-4,5α-epoxy-14β-acetoxy-6β-[N-methyl-trans-3-(3-furyl)acrylamido]morphinan, 17-cyclopropylmethyl-4,5α-epoxy-14β-acetoxy-6β-(N-methyl-4-trifluoromethylcinnamamido)morphinan, 17-cyclopropylmethyl-4,5α-epoxy-14β-acetoxy-6β-(N-methyl-3-phenylpropiolamido)morphinan, 17-allyl-4,5α-epoxy-14β-acetoxy-6β-(N-methyl-3-trifluoromethylcinnamamido)morphinan, 17-allyl-4,5α-epoxy-14β-acetoxy-6β-[N-methyl-trans-3-(3-furyl)acrylamido]morphinan, 17-allyl-4,5α-epoxy-14β-acetoxy-6β-(N-methyl-4-trifluoromethylcinnamamido)morphinan, 17-allyl-4,5α-epoxy-14β-acetoxy-6β-(N-methyl-3-phenylpropiolamido)morphinan, 17-methyl-4,5α-epoxy-14β-acetoxy-6β-(N-methyl-3-trifluoromethylcinnamamido)morphinan, 17-methyl-4,5α-epoxy-14β-acetoxy-6β-[N-methyl-trans-3-(3-furyl)acrylamido]morphinan, 17-methyl-4,5α-epoxy-14β-acetoxy-6β-(N-methyl-4-trifluoromethylcinnamamido)morphinan, 17-methyl-4,5α-epoxy-14β-acetoxy-6β-(N-methyl-3-phenylpropiolamido)morphinan, 17-phenethyl-4,5α-epoxy-14β-acetoxy-6β-(N-methyl-3-trifluoromethylcinnamamido)morphinan, 17-phenethyl-4,5α-epoxy-14β-acetoxy-6β-[N-methyl-trans-3-(3-furyl)acrylamido]morphinan, 17-phenethyl-4,5α-epoxy-14β-acetoxy-6β-(N-methyl-4-trifluoromethylcinnamamido)morphinan, 17-phenethyl-4,5α-epoxy-14β-acetoxy-6β-(N-methyl-3-phenylpropiolamido)morphinan, 17-cyclopropylmethyl-4,5α-epoxy-3-methoxy-14β-hydroxy-6β-(N-methyl-3-trifluoromethylcinnamamido)morphinan, 17-cyclopropylmethyl-4,5α-epoxy-3-methoxy-14β-hydroxy-6β-[N-methyl-trans-3-(3-furyl)acrylamido]morphinan, 17-cyclopropylmethyl-4,5α-epoxy-3-methoxy-14β-hydroxy-6β-(N-methyl-4-trifluoromethylcinnamamido)morphinan, 17-cyclopropylmethyl-4,5α-epoxy-3-methoxy-14β-hydroxy-6β-(N-methyl-3-phenylpropiolamido)morphinan, 17-allyl-4,5α-epoxy-3-methoxy-14β-hydroxy-6β-(N-methyl-3-trifluoromethylcinnamamido)morphinan, 17-allyl-4,5α-epoxy-3-methoxy-14β-hydroxy-6β-[N-methyl-trans-3-(3-furyl)acrylamido]morphinan, 17-allyl-4,5α-epoxy-3-methoxy-14β-hydroxy-6β-(N-methyl-4-trifluoromethylcinnamamido)morphinan, 17-allyl-4,5α-epoxy-3-methoxy-14β-hydroxy-6β-(N-methyl-3-phenylpropiolamido)morphinan, 17-methyl-4,5α-epoxy-3-methoxy-14β-hydroxy-6β-(N-methyl-3-trifluoromethylcinnamamido)morphinan, 17-methyl-4,5α-epoxy-3-methoxy-14β-hydroxy-6β-[-methyl-trans-3-(3-furyl)acrylamido]morphinan, 17-methyl-4,5α-epoxy-3-methoxy-14β-hydroxy-6β-(N-methyl-4-trifluoromethylcinnamamido)morphinan, 17-methyl-4,5α-epoxy-3-methoxy-14β-hydroxy-6β-(N-methyl-3-phenylpropiolamido)morphinan, 17-phenethyl-4,5α-epoxy-3-methoxy-14β-hydroxy-6β-(N-methyl-3-trifluoromethylcinnamamido)morphinan, 17-phenethyl-4,5α-epoxy-3-methoxy-14β-hydroxy-6β-[N-methyl-trans-3-(3-furyl)acrylamido]morphinan, 17-phenethyl-4,5α-epoxy-3-methoxy-14β-hydroxy-6β-(N-methyl-4-trifluoromethylcinnamamido)morphinan, 17 -phenethyl-4,5α-epoxy-3-methoxy-14β-hydroxy-6β-(N-methyl-3-phenylpropiolamido)morphinan, 17-cyclopropylmethyl-4,5α-epoxy-3-methoxy-14β-acetoxy-6β-(N-methyl-3-trifluoromethylcinnamamido)morphinan, 17-cyclopropylmethyl-4,5α-epoxy-3-methoxy-14β-acetoxy-6β-[N-methyl-trans-3-(3-furyl)acrylamido]morphinan, 17-cyclopropylmethyl-4,5α-epoxy-3-methoxy-14β-acetoxy-6β-(N-methyl-4-trifluoromethylcinnamamido)morphinan, 17-cyclopropylmethyl-4,5α-epoxy-3-methoxy-14β-acetoxy-6β-(N-methyl-3-phenylpropiolamido)morphinan, 17-allyl-4,5α-epoxy-3-methoxy-14β-acetoxy-6β-(N-methyl-3-trifluoromethylcinnamamido)morphinan, 17-allyl-4,5α-epoxy-3-methoxy-14β-acetoxy-6β-[N-methyl-trans-3-(3-furyl)acrylamido]morphinan, 17-allyl-4,5α-epoxy-3-methoxy-14β-acetoxy-6β-(N-methyl-4-trifluoromethylcinnamamido)morphinan, 17-allyl-4,5α-epoxy-3-methoxy-14β-acetoxy-6β-(N-methyl-3-phenylpropiolamido)morphinan, 17-methyl-4,5α-epoxy-3-methoxy-14β-acetoxy-6β-(N-methyl-3-trifluoromethylcinnamamido)morphinan, 17-methyl-4,5α-epoxy-3-methoxy-14β-acetoxy-6β-[N-methyl-trans-3-(3-furyl)acrylamido]morphinan, 17-methyl-4,5α-epoxy-3-methoxy-14β-acetoxy-6β-(N-methyl-4-trifluoromethylcinnamamido)morphinan, 17-methyl-4,5α-epoxy-3-methoxy-14β-acetoxy-6β-(N-methyl-3-phenylpropiolamido)morphinan, 17-phenethyl-4,5α-epoxy-3-methoxy-14β-acetoxy-6β-(N-methyl-3-trifluoromethylcinnamamido)morphinan, 17-phenethyl-4,5α-epoxy-3-methoxy-14β-acetoxy-6β-[N-methyl-trans-3-(3-furyl)acrylamido]morphinan, 17-phenethyl-4,5α-epoxy-3-methoxy-14β-acetoxy-6β-(N-methyl-4-trifluoromethylcinnamamido)morphinan, 17-phenethyl-4,5α-epoxy-3-methoxy-14β-acetoxy-6β-(N-methyl-3-phenylpropiolamido)morphinan, 17-cyclopropylmethyl-4,5α-epoxy-3-acetoxy-14β-hydroxy-6β-(N-methyl-3-trifluoromethylcinnamamido)morphinan, 17-cyclopropylmethyl-4,5α-epoxy-3-acetoxy-14β-hydroxy-6β-[N-methyl-trans-3-(3-furyl)acrylamido]morphinan, 17 -cyclopropylmethyl-4,5α-epoxy-3-acetoxy-14β-hydroxy-6β-(N-methyl-4-trifluoromethylcinnamamido)morphinan, 17-cyclopropylmethyl-4,5α-epoxy-3-acetoxy-14β-hydroxy-6β-(N-methyl-3-phenylpropiolamido)morphinan, 17-allyl-4,5α-epoxy-3-acetoxy-14β-hydroxy-6β-(N-methyl-3-trifluoromethylcinnamamido)morphinan, 17-allyl-4,5α-epoxy-3-acetoxy-14β-hydroxy-6β-[N-methyl-trans-3-(3-furyl)acrylamido]morphinan, 17-allyl-4,5α-epoxy-3-acetoxy-14β-hydroxy-6β-(N-methyl-4-trifluoromethylcinnamamido)morphinan, 17-allyl-4,5α-epoxy-3-acetoxy-14β-hydroxy-6β-(N-methyl-3-phenylpropiolamido)morphinan, 17-methyl-4,5α-epoxy-3-acetoxy-14β-hydroxy-6β-(N-methyl-3-trifluoromethylcinnamamido)morphinan, 17-methyl-4,5α-epoxy-3-acetoxy-14β-hydroxy-6β[N-methyl-trans-3-(3-furyl)acrylamido]morphinan, 17-methyl-4,5α-epoxy-3-acetoxy-14β-hydroxy-6β-(N-methyl-4-trifluoromethylcinnamamido)morphinan, 17-methyl-4,5α-epoxy-3-acetoxy-14β-hydroxy-6β-(N-methyl-3-phenylpropiolamido)morphinan, 17-phenethyl-4,5α-epoxy-3-acetoxy-14β-hydroxy-6β-

(N-methyl-3-trifluoromethylcinnamamido)morphinan, 17-phenethyl-4,5α-epoxy-3-acetoxy-14β-hydroxy-6β-[N-methyl-trans-3-(3-furyl)acrylamido]morphinan, 17-phenethyl-4,5α-epoxy-3-acetoxy-14β-hydroxy-6β-(N-methyl-4-trifluoromethylcinnamamido)morphinan, 17-phenethyl-4,5α-epoxy-3-acetoxy-14β-hydroxy-6β-(N-methyl-3-phenylpropiolamido)morphinan, 17-cyclopropylmethyl-4,5α-epoxy-3,14β-diacetoxy-6β-(N-methyl-3-trifluoromethylcinnamamido)morphinan, 17-cyclopropylmethyl-4,5α-epoxy-3,14β-diacetoxy-6β-[N-methyl-trans-3-(3-furyl)acrylamido]morphinan, 17-cyclopropylmethyl-4,5α-epoxy-3,14β-diacetoxy-6β-(N-methyl-4-trifluoromethylcinnamamido)morphinan, 17-cyclopropylmethyl-4,5α-epoxy-3,14β-diacetoxy-6β-(N-methyl-3-phenylpropiolamido)morphinan, 17-allyl-4,5α-epoxy-3,14β-diacetoxy-6β-(N-methyl-3-trifluoromethylcinnamamido)morphinan, 17-allyl-4,5α-epoxy-3,14β-diacetoxy-6β-[N-methyl-trans-3-(3-furyl)acrylamido]morphinan, 17-allyl-4,5α-epoxy-3,14β-diacetoxy-6β-(N-methyl-4-trifluoromethylcinnamamido)morphinan, 17-allyl-4,5α-epoxy-3,14β-diacetoxy-6β-(N-methyl-3-phenylpropiolamido)morphinan, 17-methyl-4,5α-epoxy-3,14β-diacetoxy-6β-(N-methyl-3-trifluoromethylcinnamamido)morphinan, 17-methyl-4,5α-epoxy-3,14β-diacetoxy-6β-[N-methyl-trans-3-(3-furyl)acrylamido]morphinan, 17-methyl-4,5α-epoxy-3,14β-diacetoxy-6β-(N-methyl-4-trifluoromethylcinnamamido)morphinan, 17-methyl-4,5α-epoxy-3,14β-diacetoxy-6β-(N-methyl-3-phenylpropiolamido)morphinan, 17-phenethyl-4,5α-epoxy-3,14β-diacetoxy-6β-(N-methyl-3-trifluoromethylcinnamamido)morphinan, 17-phenethyl-4,5α-epoxy-3,14β-diacetoxy-6β-[N-methyl-trans-3-(3-furyl)acrylamido]morphinan, 17-phenethyl-4,5α-epoxy-3,14β-diacetoxy-6β-(N-methyl-4-trifluoromethylcinnamamido)morphinan, 17-phenethyl-4,5α-epoxy-3,14β-diacetoxy-6β-(N-methyl-3-phenylpropiolamido)morphinan, 17-cyclopropylmethyl-4,5α-epoxy-3,14β-dihydroxy-6β-(N-isobutyl-3-trifluoromethylcinnamamido)morphinan, 17-cyclopropylmethyl-4,5α-epoxy-3,14β-dihydroxy-6β-[N-isobutyl-trans-3-(3-furyl)acrylamido]morphinan, 17-cyclopropylmethyl-4,5α-epoxy-3,14β-dihydroxy-6β-(N-isobutyl-4-trifluoromethylcinnamamido)morphinan, 17-cyclopropylmethyl-4,5α-epoxy-3,14β-dihydroxy-6β-(N-isobutyl-3-phenylpropiolamido)morphinan, 17-allyl-4,5α-epoxy-3,14β-dihydroxy-6β-(N-isobutyl-3-trifluoromethylcinnamamido)morphinan, 17-allyl-4,5α-epoxy-3,14β-dihydroxy-6β-[N-isobutyl-trans-3-(3-furyl)acrylamido]morphinan, 17-allyl-4,5α-epoxy-3,14β-dihydroxy-6β-(N-isobutyl-4-trifluoromethylcinnamamido)morphinan, 17-allyl-4,5α-epoxy-3,14β-dihydroxy-6β-(N-isobutyl-3-phenylpropiolamido)morphinan, 17-methyl-4,5α-epoxy-3,14β-dihydroxy-6β-(N-isobutyl-3-trifluoromethylcinnamamido)morphinan, 17-methyl-4,5α-epoxy-3,14β-dihydroxy-6β-[N-isobutyl-trans-3-(3-furyl)acrylamido]morphinan, 17-methyl-4,5α-epoxy-3,14β-dihydroxy-6β-(N-isobutyl-4-trifluoromethylcinnamamido)morphinan, 17-methyl-4,5α-epoxy-3,14β-dihydroxy-6β-(N-isobutyl-3-phenylpropiolamido)morphinan, 17-phenethyl-4,5α-epoxy-3,14β-dihydroxy-6β-(N-isobutyl-3-trifluoromethylcinnamamido)morphinan, 17-phenethyl-4,5α-epoxy-3,14β-dihydroxy-6β-[N-isobutyl-trans-3-(3-furyl)acrylamido]morphinan, 17-phenethyl-4,5α-epoxy-3,14β-dihydroxy-6β-(N-isobutyl-4-trifluoromethylcinnamamido)morphinan, 17-phenethyl-4,5α-epoxy-3,14β-dihydroxy-6β-(N-isobutyl-3-phenylpropiolamido)morphinan, 17-cyclopropylmethyl-4,5α-epoxy-3-hydroxy-14β-acetoxy-6β-(N-isobutyl-3-trifluoromethylcinnamamido)morphinan, 17-cyclopropylmethyl-4,5α-epoxy-3-hydroxy-14β-acetoxy-6β-[N-isobutyl-trans-3-(3-furyl)acrylamido]morphinan, 17-cyclopropylmethyl-4,5-epoxy-3-hydroxy-14β-acetoxy-6β-(N-isobutyl-4-trifluoromethylcinnamamido)morphinan, 17-cyclopropylmethyl-4,5α-epoxy-3-hydroxy-14β-acetoxy-6β-(N-isobutyl-3-phenylpropiolamido)morphinan, 17-allyl-4,5α-epoxy-3-hydroxy-14β-acetoxy-6β-(N-isobutyl-3-trifluoromethylcinnamamido)morphinan, 17-allyl-4,5α-epoxy-3-hydroxy-14β-acetoxy-6β-[N-isobutyl-trans-3-(3-furyl)acrylamido]morphinan, 17-allyl-4,5α-epoxy-3-hydroxy-14β-acetoxy-6β-(N-isobutyl-4-trifluoromethylcinnamamido)morphinan, 17-allyl-4,5α-epoxy-3-hydroxy-14β-acetoxy-6β-(N-isobutyl-3-phenylpropiolamido)morphinan, 17-methyl-4,5α-epoxy-3-hydroxy-14β-acetoxy-6β-(N-isobutyl-3-trifluoromethylcinnamamido)morphinan, 17-methyl-4,5α-epoxy-3-hydroxy-14β-acetoxy-6β-[N-isobutyl-trans-3-(3-furyl)acrylamido]morphinan, 17-methyl-4,5α-epoxy-3-hydroxy-14β-acetoxy-6β-(N-isobutyl-4-trifluoromethylcinnamamido)morphinan, 17-methyl-4,5α-epoxy-3-hydroxy-14β-acetoxy-6β-(N-isobutyl-3-phenylpropiolamido)morphinan, 17-phenethyl-4,5α-epoxy-3-hydroxy-14β-acetoxy-6β-(N-isobutyl-3-trifluoromethylcinnamamido)morphinan, 17-phenethyl-4,5α-epoxy-3-hydroxy-14β-acetoxy-6β-[N-isobutyl-trans-3-(3-furyl)acrylamido]morphinan, 17-phenethyl-4,5α-epoxy-3-hydroxy-14β-acetoxy-6β-(N-isobutyl-4-trifluoromethylcinnamamido)morphinan, 17-phenethyl-4,5α-epoxy-3-hydroxy-14β-acetoxy-6β-(N-isobutyl-3-phenylpropiolamido)morphinan, 17-cyclopropylmethyl-4,5α-epoxy-14β-hydroxy-6β-(N-isobutyl-3-trifluoromethylcinnamamido)morphinan, 17-cyclopropylmethyl-4,5α-epoxy-14β-hydroxy-6β-[N-isobutyl-trans-3-(3-furyl)acrylamido]morphinan, 17-cyclopropylmethyl-4,5α-epoxy-14β-hydroxy-6β-(N-isobutyl-4-trifluoromethylcinnamamido)morphinan, 17-cyclopropylmethyl-4,5α-epoxy-14β-hydroxy-6β-(N-isobutyl-3-phenylpropiolamido)morphinan, 17-allyl-4,5α-epoxy-14β-hydroxy-6β-(N-isobutyl-3-trifluoromethylcinnamamido)morphinan, 17-allyl-4,5α-epoxy-14β-hydroxy-6β-[N-isobutyl-trans-3-(3-furyl)acrylamido]morphinan, 17-allyl-4,5α-epoxy-14β-hydroxy-6β-(N-isobutyl-4-trifluoromethylcinnamamido)morphinan, 17-allyl-4,5α-epoxy-14β-hydroxy-6β-(N-isobutyl-3-phenylpropiolamido)morphinan, 17-methyl-4,5α-epoxy-14β-hydroxy-6β-(N-isobutyl-3-trifluoromethylcinnamamido)morphinan, 17-methyl-4,5α-epoxy-14β-hydroxy-6β-[N-isobutyl-trans-3-(3-furyl)acrylamido]morphinan, 17-methyl-4,5α-epoxy-14β-hydroxy-6β-(N-isobutyl-4-trifluoromethylcinnamamido)morphinan, 17-methyl-4,5α-epoxy-14β-hydroxy-6β-(N-isobutyl-3-phenylpropiolamido)morphinan, 17-phenethyl-4,5α-epoxy-14β-hydroxy-6β-(N-isobutyl-3- trifluoromethylcinnamido)morphinan, 17-phenethyl-4,5α-epoxy-14β-hydroxy-6β-[N-isobutyl-trans-3-(3-furyl)acrylamido]morphinan, 17-phenethyl-4,5 α-epoxy-14β-hydroxy-6β-(N-isobutyl-4-trifluoromethylcinnamamido)morphinan, 17-phenethyl-4,5α-epoxy-14β-hydroxy-6β-(N-isobutyl-3-phenylpropiolamido)morphinan, 17-cyclopropylmethyl-4,5α-epoxy-14β-acetoxy-6β-(N-isobutyl-3-trifluoromethylcinnamamido)morphinan, 17-cyclopropylmethyl-4,5α-epoxy-14β-acetoxy-6β-[N-isobutyl-trans-3-(3-furyl)acrylamido]morphinan, 17-cyclopropylmethyl-4,5-epoxy-14β-acetoxy-6β-(N-isobutyl-4-trifluoromethylcinnamamido)morphinan, 17-cyclopropylmethyl-4,5α-epoxy-14β-acetoxy-6β-(N-isobutyl-3-phenylpropiolamido)morphinan, 17-allyl-4,5α-epoxy-14β-acetoxy-6β-(N-isobutyl-3-trifluoromethylcinnamamido)morphinan, 17-allyl-4,5α-epoxy-14β-acetoxy-6β-[N-isobutyl-3-(3-furyl)acrylamido]morphinan, 17-allyl-4,5α-epoxy-14β-acetoxy-6β-(N-isobutyl-4-trifluoromethylcinnamamido)morphinan, 17-allyl-4,5α-epoxy-14β-acetoxy-6β-(N-isobutyl-3-phenylpropiolamido)morphinan, 17-methyl-4,5α-epoxy-14β-acetoxy-6β-(N-isobutyl-3-trifluoromethylcinnamamido)morphinan, 17-methyl-4,5α-epoxy-14β-acetoxy-6β-[N-isobutyl-trans-3-(3-furyl)acrylamido]morphinan, 17-methyl-4,5α-epoxy-14β-acetoxy-6β-(N-isobutyl-4-trifluoromethylcinnamamido)morphinan, 17-methyl-4,5α-epoxy-14β-acetoxy-6β-(N-isobutyl-3-phenylpropiolamido)morphinan, 17-phenethyl-4,5α-[-epoxy-14β-acetoxy-6β-(N-isobutyl-3-trifluoromethylcinnamamido]morphinan, 17-phenethyl-4,5α-epoxy-14β-acetoxy-6β-[N-isobutyl-trans-3-(3-furyl)acrylamido]morphinan, 17-phenethyl-4,5α-epoxy-14β-acetoxy-6β-(N-isobutyl-4-trifluoromethylcinnamamido)morphinan, 17-phenethyl-4,5α-epoxy-14β-acetoxy-6β-(N-isobutyl-3 -phenylpropiolamido)morphinan, 17-cyclopropylmethyl-4,5α-epoxy-3-methoxy-14β-hydroxy-6β-(N-isobutyl-3-trifluoromethylcinnamamido)morphinan, 17-cyclopropylmethyl-4,5α-epoxy-3-methoxy-14β-hydroxy-6β-[N-isobutyl-trans-3-(3-furyl)acrylamido]morphinan, 17-cyclopropylmethyl-4,5α-epoxy-3-methoxy-14β-hydroxy-6β-(N-isobutyl-4-trifluoromethylcinnamamido)morphinan, 17-cyclopropylmethyl-4,5α-epoxy-3-methoxy-14β-hydroxy-6β-(N-isobutyl-3-phenylpropiolamido)morphinan, 17-allyl-4,5α-epoxy-3-methoxy-14β-hydroxy-6β-(N-isobutyl-3-trifluoromethylcinnamamido)morphinan, 17-allyl-4,5α-epoxy-3-methoxy-14β-hydroxy-6β-[N-isobutyl-trans-3-(3-furyl)acrylamido]morphinan, 17-allyl-4,5α-epoxy-3-methoxy-14β-hydroxy-6β-(N-isobutyl-4-trifluoromethylcinnamamido)morphinan, 17-allyl-4,5α-epoxy-3-methoxy-14β-hydroxy-6β-(N-isobutyl-3-phenylpropiolamido)morphinan, 17-methyl-4,5α-epoxy-3-methoxy-14β-hydroxy-6β-(N-isobutyl-3-trifluoromethylcinnamamido)morphinan, 17-methyl-4,5α-epoxy-3-methoxy-14β-hydroxy-6β-[N-isobutyl-trans-3-(3-furyl)acrylamido]morphinan, 17-methyl-4,5α-epoxy-3-methoxy-14β-hydroxy-6β-(N-isobutyl-4-trifluoromethylcinnamamido)morphinan, 17-methyl-4,5α-epoxy-3-methoxy-14β-hydroxy-6β-(N-isobutyl-3-phenylpropiolamido)morphinan, 17-phenethyl-4,5α-epoxy-3-methoxy-14β-hydroxy-6β-(N-isobutyl-3-trifluoromethylcinnamamido)morphinan, 17-phenethyl-4,5α-epoxy-3-methoxy-14β-hydroxy-6β-[N-isobutyl-trans-3-(3-furyl)acrylamido]morphinan, 17-phenethyl-4,5α-epoxy-3-methoxy-14β-hydroxy-6β-(N-isobutyl-4-trifluoromethylcinnamamido)morphinan, 17-phenethyl-4,5α-epoxy-3-methoxy-14β-hydroxy-6β-(N-isobutyl-3-phenylpropiolamido)morphinan, 17-cyclopropylmethyl-4,5α-epoxy-3-methoxy-14β-acetoxy-6β-(N-isobutyl-3-trifluoromethylcinnamamido)morphinan, 17-cyclopropylmethyl-4,5α-epoxy-3-methoxy-14β-acetoxy-6β-[N-isobutyl-trans-3-(3 -furyl)acrylamido]morphinan, 17-cyclopropylmethyl-4,5α-epoxy-3-methoxy-14β-acetoxy-6β-(N-isobutyl-4-trifluoromethylcinnamamido)morphinan, 17-cyclopropylmethyl-4,5α-epoxy-3-methoxy-14β-acetoxy-6β-(N-isobutyl-3-phenylpropiolamido)morphinan, 17-allyl-4,5α-epoxy-3-methoxy-14β-acetoxy-6β-(N-isobutyl-3-trifluoromethylcinnamamido)morphinan, 17-allyl-4,5α-epoxy-3-methoxy-14β-acetoxy-6β-[N-isobutyl-trans-3-(3-furyl)acrylamido]morphinan, 17-allyl-4,5α-epoxy-3-methoxy-14β-acetoxy-6β-(N-isobutyl-4-trifluoromethylcinnamamido)morphinan, 17-allyl-4,5α-epoxy-3-methoxy-14β-acetoxy-6β-(N-isobutyl-3-phenylpropiolamido)morphinan, 17-methyl-4,5α-epoxy-3-methoxy-14β-acetoxy-6β-(N-isobutyl-3-trifluoromethylcinnamamido)morphinan, 17-methyl-4,5α-epoxy-3-methoxy-14β-acetoxy-6β-[N-isobutyl-trans-3-(3-furyl)acrylamido]morphinan, 17-methyl-4,5α-epoxy-3-methoxy-14β-acetoxy-6β-(N-isobutyl-4-trifluoromethylcinnamamido)morphinan, 17-methyl-4,5α-epoxy-3-methoxy-14β-acetoxy-6β-(N-isobutyl-3-phenylpropiolamido)morphinan, 17-phenethyl-4,5α-epoxy-3-methoxy-14β-acetoxy-6β-(N-isobutyl-3-trifluoromethylcinnamamido)morphinan, 17-phenethyl-4,5α-epoxy-3-methoxy-14β-acetoxy-6β-[N-isobutyl-trans-3-(3-furyl)acrylamido]morphinan, 17-phenethyl-4,5α-epoxy-3-methoxy-14β-acetoxy-6β-(N-isobutyl-4-trifluoromethylcinnamamido)morphinan, 17-phenethyl-4,5α-epoxy-3-methoxy-14β-acetoxy-6β-(N-isobutyl-3-phenylpropiolamido)morphinan, 17-cyclopropylmethyl-4,5α-epoxy-3-acetoxy-14β-hydroxy-6β-(N-isobutyl-3-trifluoromethylcinnamamido)morphinan, 17-cyclopropylmethyl-4,5α-epoxy-3-acetoxy-14β-hydroxy-6β-[N-isobutyl-trans-3-(3-furyl)acrylamido]morphinan, 17-cyclopropylmethyl-4,5α-epoxy-3-acetoxy-14β-hydroxy-6β-(N-isobutyl-4-trifluoromethylcinnamamido)morphinan, 17-cyclopropylmethyl-4,5α-epoxy-3-acetoxy-14β-hydroxy-6β-(N-isobutyl-3-phenylpropiolamido)morphinan, 17-allyl-4,5α-epoxy-3-acetoxy-14β-hydroxy-6β-(N-isobutyl-3-trifluoromethylcinnamnamido)morphinan, 17-allyl-4,5α-epoxy-3-acetoxy-14β-hydroxy-6β-[N-isobutyl-trans-3-(3-furyl)acrylamido]morphinan, 17-allyl-4,5α-epoxy-3-acetoxy-14β-hydroxy-6β-(N-isobutyl-4-trifluoromethylcinnamamido)morphinan, 17-allyl-4,5α-epoxy-3-acetoxy-14β-hydroxy-6β-(N-isobutyl-3-phenylpropiolamido)morphinan, 17-methyl-4,5α-epoxy-3-acetoxy-14β-hydroxy-6β-(N-isobutyl-3-trifluoromethylcinnamamido)morphinan, 17-methyl-4,5α-epoxy-3-acetoxy-14β-hydroxy-6β-[N-isobutyl-trans-3-(3-furyl)acrylamido]morphinan, 17-methyl-4,5α-epoxy-3-acetoxy-14β-hydroxy-6β-(N-isobutyl-4-trifluoromethylcinnamamido)morphinan, 17-methyl-4,5α-epoxy-3-acetoxy-14β-hydroxy-6β-(N-isobutyl-3-phenylpropiolamido)morphinan, 17-phenethyl-4,5α-epoxy-3-acetoxy-14β-hydroxy-6β-(N-isobutyl-3-trifluoromethylcinnamamido)morphinan, 17-phenethyl-4,5α-epoxy-3-acetoxy-14β-hydroxy-6β-[N-isobutyl-trans-3-(3-furyl)acrylamido]morphinan, 17-phenethyl-4,5α-epoxy-3-acetoxy-14β-hydroxy-6β-(N-isobutyl-4-trifluoromethylcinnamamido)morphinan, 17-phenethyl-4,5α-epoxy-3-acetoxy-14β-hydroxy-6β-(N-isobutyl-3-phenylpropiolamido)morphinan, 17-cyclopropylmethyl-4,5α-epoxy-3,14β-diacetoxy-6β-(N-isobutyl-3-trifluoromethylcinnamamido)morphinan, 17-cyclopropylmethyl-4,5α-epoxy-3,14β-diacetoxy-6β-[N-isobutyl-trans-3-(3-furyl)acrylamido]morphinan, 17-cyclopropylmethyl-4,5α-epoxy-3,14β-diacetoxy-6β-(N-isobutyl-4-trifluoromethylcinnamamido)morphinan, 17-cyclopropylmethyl-4,5α-epoxy-3,14β-diacetoxy-6β-(N-isobutyl-3-phenylpropiolamido)morphinan, 17-allyl-4,5α-epoxy-3,14β-diacetoxy-6β-(N-isobutyl-3-trifluoromethylcinnamamido)morphinan, 17-allyl-4,5α-epoxy-3,14β-diacetoxy-6β-[N-isobutyl-trans-3-(3-furyl)acrylamido]morphinan, 17-allyl-4,5α-epoxy-3,14β-diacetoxy-6β-(N-isobutyl-4-trifluoromethylcinnamamido)morphinan, 17-allyl-4,5α-epoxy-3,14β-diacetoxy-6β-(N-isobutyl-3-phenylpropiolamido)morphinan, 17-methyl-4,5α-epoxy-3,14β-diacetoxy-6β-(N-isobutyl-3-trifluoromethylcinnamamido)morphinan, 17-methyl-4,5α-epoxy-3,14β-diacetoxy-6β-[N-isobutyl-trans-3-(3-furyl)acrylamido]morphinan, 17-methyl-4,5α-epoxy-3,14β-diacetoxy-6β-(N-isobutyl-4-trifluoromethylcinnamamido)morphinan, 17-methyl-4,5α-epoxy-3,14β-diacetoxy-6β-(N-isobutyl-3-phenylpropiolamido)morphinan, 17-phenethyl-4,5α-epoxy-3,14β-diacetoxy-6β-(N-isobutyl-3-trifluoromethylcinnamamido)morphinan, 17-phenethyl-4,5α-epoxy-3,14β-diacetoxy-6β-[N-isobutyl-trans-3-(3-furyl)acrylamido]morphinan, 17-phenethyl-4,5α-epoxy-3,14β-diacetoxy-6β-(N-isobutyl-4-trifluoromethylcinnamamido)morphinan, 17-phenethyl-4,5α-epoxy-3,14β-diacetoxy-6β-(N-isobutyl-3-phenylpropiolamido)morphinan, 17-cyclopropylmethyl-4,5α-epoxy-3,14β-dihydroxy-6α-(N-methyl-3-cyclohexylpropionamido)morphinan, 17-allyl-4,5α-epoxy-3,14β-dihydroxy-6α-(N-methyl-3-cyclohexylpropionamido)morphinan, 17-cyclopropylmethyl-4,5α-epoxy-3,14β-dihydroxy-6β-(N-methyl-3-cyclohexylpropionamido)morphinan, 17-allyl-4,5α-epoxy-3,14β-dihydroxy-6β-(N-methyl-3-cyclohexylpropionamido)morphinan, 17-cyclopropylmethyl-4,5α-epoxy-3,14β-dihydroxy-6α-(N-methylbutyloxycarbamido)morphinan, 17-allyl-4,5α-epoxy-3,14β-dihydroxy-6α-(N-methylbutyloxycarbamido)morphinan, 17-cyclopropylmethyl-4,5α-epoxy-3,14β-dihydroxy-6β-(N-methylbutyloxycarbamido)morphinan, 17-allyl-4,5α-epoxy-3,14β-dihydroxy-6β-(N-methylbutyloxycarbamido)morphinan, 17-cyclopropylmethyl-4,5α-epoxy-3,14β-dihydroxy-6α-(N-methyl-3-isothiocyanatophenylacetamido)morphinan, 17-allyl-4,5α-epoxy-3,14β-dihydroxy-6α-(N-methyl-3-isothiocyanatophenylacetamido)morphinan, 17-cyclopropylmethyl-4,5α-epoxy-3,14β-dihydroxy-6β-(N-methyl-3-isothiocyanatophenylacetamido)morphinan, 17-allyl-4,5α-epoxy-3,14β-dihydroxy-6β-(N-methyl-3-isothiocyanatophenylacetamido)morphinan, 17-cyclopropylmethyl-4,5α-epoxy-3,14β-dihydroxy-6α-(N-methyl-2-hexenamido)morphinan, 17-allyl-4,5α-epoxy-3,14β-dihydroxy-6α-(N-methyl-2-hexenamido)morphinan, 17-cyclopropylmethyl-4,5α-epoxy-3,14β-dihydroxy-6β-(N-methyl-2-hexenamido)morphinan, 17-allyl-4,5α-epoxy-3,14β-dihydroxy-6β-(N-methyl-2-hexenamido)morphinan, 17-cyclopropylmethyl-4,5α-epoxy-3,14β-dihydroxy-6α-(N-methyl-3-fluorocinnamamido)morphinan, 17-allyl-4,5α-epoxy-3,14β-dihydroxy-6α-(N-methyl-3-fluorocinnamamido)morphinan, 17-cyclopropylmethyl-4,5α-epoxy-3,14β-dihydroxy-6β-(N-methyl-3-fluorocinnamamido)morphinan, 17-allyl-4,5α-epoxy-3,14β-dihydroxy-6β-(N-methyl-3-fluorocinnamamido)morphinan, 17-cyclopropylmethyl-4,5α-epoxy-3,14β-dihydroxy-6α-(N-methyl-3-methoxycinnamamido)morphinan, 17-allyl-4,5α-epoxy-3,14β-dihydroxy-6α-(N-methyl-3-methoxycinnamamido)morphinan, 17-cyclopropylmethyl-4,5α-epoxy-3,14β-dihydroxy-6β-(N-methyl-3-methoxycinnamaimido)morphinan, 17-allyl-4,5α-epoxy-3,14β-dihydroxy-6β-(N-methyl-3-methoxycinnamamido)morphinan, 17-cyclopropylmethyl-4,5α-epoxy-3,14β-dihydroxy-6α-(N-methyl-2-cyclopentylpropionamido)morphinan, 17-allyl-4,5α-epoxy-3,14β-dihydroxy-6α-(N-methyl-2-cyclopentylpropionamido)morphinan, 17-cyclopropylmethyl-4,5α-epoxy-3,14β-dihydroxy-6β-(N-methyl-2-cyclopentylpropionamido)morphinan, 17-allyl- 4,5α-epoxy-3,14β-dihydroxy-6β-(N-methyl-2-cyclopentylpropionamido)morphinan, 17-cyclopropylmethyl-4,5α-epoxy-3,14β-dihydroxy-6α-(N-methyl-2-naphthamido)morphinan, 17-allyl-4,5α-epoxy-3,14β-dihydroxy-6α-(N-methyl-2-naphthamido)morphinan, 17-cyclopropylmethyl-4,5α-epoxy-3,14β-dihydroxy-6β-(N-methyl-2-naphthamido)morphinan, 17-allyl-4,5α-epoxy-3,14β-dihydroxy-6β-(N-methyl-2-naphthamido)morphinan, 17-cyclopropylmethyl-4,5α-epoxy-3,14β-dihydroxy-6α-(N-methyl-3-nitrocinnamamido)morphinan, 17-allyl-4,5α-epoxy-3,14β-dihydroxy-6α-(N-methyl-3-nitrocinnamamido)morphinan, 17-cyclopropylmethyl-4,5α-epoxy-3,14β-dihydroxy-6β-(N-methyl-3-nitrocinnamamido)morphinan, 17-allyl-4,5α-epoxy-3,14β-dihydroxy-6β-(N-methyl-3-nitrocinnamamido)morphinan, 17-cyclopropylmethyl-4,5α-epoxy-3,14β-dihydroxy-6α-(N-methyl-2-methoxyethoxycarbamido)morphinan, 17-allyl-4,5α-epoxy-3,14β-dihydroxy-6α-(N-methyl-2-methoxyethoxycarbamido)morphinan, 17-cyclopropylmethyl-4,5α-epoxy-3,14β-dihydroxy-6β-(N-methyl-2-methoxyethoxycarbamido)morphinan, 17-allyl-4,5α-epoxy-3,14β-dihydroxy-6β-(N-methyl-2-methoxyethoxycarbamido)morphinan, 17-cyclopropylmethyl-4,5α-epoxy-3,14β-dihydroxy-6α-(N-methyl-trans-3-cyclohexylacrylamido)morphinan, 17-allyl-4,5α-epoxy-3,14β-dihydroxy-6α-(N-methyl-trans-3-cyclohexylacrylamido)morphinan, 17-cyclopropylmethyl-4,5α-epoxy-3,14β-dihydroxy- 6β-(N-methyl-trans-3-cyclohexylacrylamido) morphinan, 17-allyl-4,5α-epoxy-3,14β-dihydroxy-6β-(N-methyl-trans-3-cyclohexylacrylamido)morphinan, 17-cyclopropylmethyl-4,5α-epoxy-3,14β-dihydroxy-6α-(N-methylbenzoylacetamido)morphinan, 17-allyl-4,5α-epoxy-3,14β-dihydroxy-6α-(N-methylbenzoylacetamido)morphinan, 17-cyclopropylmethyl-4,5α-epoxy-3,14β-dihydroxy-6β-(N-methylbenzoylacetamido)morphinan, 17-allyl-4,5α-epoxy-3,14β-dihydroxy-6β-(N-methylbenzoylacetamido)morphinan, 17-cyclopropylmethyl-4,5α-epoxy-3,14β-dihydroxy-6α-[N-methyl-trans-3-(2-furyl)acrylamido]morphinan, 17-allyl-4,5α-epoxy-3,14β-dihydroxy-6α-[N-methyl-trans-3-(2-furyl)acrylamido]morphinan, 17-cyclopropylmethyl-4,5α-epoxy-3,14β-dihydroxy-6β-[N-methyl-trans-3-(2-furyl)acrylamido]morphinan, 17-allyl-4,5α-epoxy-3,14β-dihydroxy-6β-[N-methyl-trans-3-(2-furyl)acrylamido]morphinan, 17-cyclopropylmethyl-4,5α-epoxy-3,14β-dihydroxy-6α-(N-methyl-2-trifluoromethylcinnamamido)morphinan, 17-allyl-4,5α-epoxy-3,14β-dihydroxy-6α-(N-methyl-2-trifluoromethylcinnamamido)morphinan, 17-cyclopropylmethyl-4,5α-epoxy-3,14β-dihydroxy-6β-(N-methyl-2-trifluoromethylcinnamamido) morphinan, 17-allyl-4,5α-epoxy-3,14β-dihydroxy-6β-(N-methyl-2-trifluoromethylcinnamamido)morphinan, 17-cyclopropylmethyl-4,5α-epoxy-3,14β-dihydroxy-6α-(N-methyl-3-isothiocyanatocinnamamido)morphinan, 17-allyl-4,5α-epoxy-3,14β-dihydroxy-6α-(N-methyl-3-isothiocyanatocinnamamido)morphinan, 17-cyclopropylmethyl-4,5α-epoxy-3,14β-dihydroxy-6β-(N-methyl-3-isothiocyanatocinnamamido) morphinan, 17-allyl-4,5α-epoxy-3,14β-dihydroxy-6β-(N-methyl-3-isothiocyanatocinnamamido)morphinan, 17-cyclopropylmethyl-4,5α-epoxy-3,14β-dihydroxy-6α-(N-methyl-3-methylcinnamamido)morphinan, 17-cyclopropylmethyl-4,5α-epoxy-3,14β-dihydroxy-6α-[N-methyl-3-(4-trifluoromethylphenyl)propiolamido]morphinan, 17-allyl-4,5α-epoxy-3,14β-dihydroxy-6α-(N-methyl-3-methylcinnamamido)morphinan, 17-allyl-4,5α-epoxy-3,14β-dihydroxy-6α-[N-methyl-3-(4-trifluoromethylphenyl)propiolamido]morphinan, 17-methyl-4,5α-epoxy-3,14β-dihydroxy-6α-(N-methyl-3-methylcinnamamido)morphinan, 17-methyl-4,5α-epoxy-3,14β-dihydroxy-6α-[N-methyl-3-(4-trifluoromethylphenyl)propiolamido]morphinan, 17-phenethyl-4,5α-epoxy-3,14β-dihydroxy-6α-(N-methyl-3-methylcinnamamido)morphinan, 17-phenethyl-4,5α-epoxy-3,14β-dihydroxy-6α-[N-methyl-3-(4-trifluoromethylphenyl)propiolamido]morphinan, 17-cyclopropylmethyl-4,5α-epoxy-14β-acetoxy-3-hydroxy-6α-(N-methyl-3-methylcinnamamido) morphinan, 17-cyclopropylmethyl-4,5α-epoxy-14β-acetoxy-3-hydroxy-6α-[N-methyl-3-(4-trifluoromethylphenyl)propiolamido]morphinan, 17-allyl-4,5α-epoxy-14β-acetoxy-3-hydroxy-6α-(N-methyl-3-methylcinnamamido)morphinan, 17-allyl-4,5α-epoxy-14β-acetoxy-3-hydroxy-6α-[N-methyl-3-(4-trifluoromethylphenyl)propiolamido]morphinan, 17-methyl-4,5α-epoxy-14β-acetoxy-3-hydroxy-6α-(N-methyl-3-methylcinnamamido)morphinan, 17-methyl-4,5α-epoxy-14β-acetoxy-3-hydroxy-6α-[N-methyl-3-(4-trifluoromethylphenyl)propiolamido]morphinan, 17-phenethyl-4,5α-epoxy-14β-acetoxy-3-hydroxy-6α-(N-methyl-3-methylcinnamamido) morphinan, 17-phenethyl-4,5α-epoxy-14β-acetoxy-3-hydroxy-6α-[N-methyl-3-(4-trifluoromethylphenyl)propiolamido]morphinan, 17-cyclopropylmethyl-4,5α-epoxy-14β-hydroxy-6α-(N-methyl-3-methylcinnamamido)morphinan, 17-cyclopropylmethyl-4,5α-epoxy-14β-hydroxy-6α-[N-methyl-3-(4-trifluoromethylphenyl)propiolamido] morphinan, 17-allyl-4,5α-epoxy-14β-hydroxy-6α-(N-methyl-3-methylcinnamamido)morphinan, 17-allyl-4,5α-epoxy-14β-hydroxy-6α-[N-methyl-3-(4-trifluoromethylphenyl)propiolamido]morphinan, 17-methyl-4,5α-epoxy-14β-hydroxy-6α-(N-methyl-3-methylcinnamamido)morphinan, 17-methyl-4,5α-epoxy-14β-hydroxy-6α-[N-methyl-3-(4-trifluoromethylphenyl)propiolamido]morphinan, 17-phenethyl-4,5α-epoxy-14β-hydroxy-6α-(N-methyl-3-methylcinnamamido)morphinan, 17-phenethyl-4,5α-epoxy-14β-hydroxy-6α-[N-methyl-3-(4-trifluoromethylphenyl)propiolamido] morphinan, 17-cyclopropylmethyl-4,5α-epoxy-14β-acetoxy-6α-(N-methyl-3-methylcinnamamido) morphinan, 17-cyclopropylmethyl-4,5α-epoxy-14β-acetoxy-6α-[N-methyl-3-(4-trifluoromethylphenyl)propiolamido] morphinan, 17-allyl-4,5α-epoxy-14β-acetoxy-6α-(N-methyl-3-methylcinnamamido)morphinan, 17-allyl-4,5α-epoxy-14β-acetoxy-6α-[N-methyl-3-(4-trifluoromethylphenyl)propiolamido]morphinan, 17-methyl-4,5α-epoxy-14β-acetoxy-6α-(N-methyl-3-methylcinnamamido)morphinan, 17-methyl-4,5α-epoxy-14β-acetoxy-6α-[N-methyl-3-(4-trifluoromethylphenyl)propiolamido]morphinan, 17-phenethyl-4,5α-epoxy-14β-acetoxy-6α-(N-methyl-3-methylcinnamamido)morphinan, 17-phenethyl-4,5α-epoxy-14β-acetoxy-6α-[N-methyl-3-(4-trifluoromethylphenyl)propiolamido]morphinan, 17-cyclopropylmethyl-4,5α-epoxy-14β-hydroxy-3-methoxy-6α-(N-methyl-3-methylcinnamamido) morphinan, 17-cyclopropylmethyl-4,5α-epoxy-14β-hydroxy-3-methoxy-6α-[N-methyl-3-(4-trifluoromethylphenyl)propiolamido]morphinan, 17-allyl-4,5α-epoxy-14β-hydroxy-3-methoxy-6α-(N-methyl-3-methylcinnamamido)morphinan, 17-allyl-4,5α-epoxy-14β-hydroxy-3-methoxy-6α-[N-methyl-3-(4-trifluoromethylphenyl)propiolamido]morphinan, 17-methyl-4,5α-epoxy-14β-hydroxy-3-methoxy-6α-(N-methyl-3-methylcinnamamido)morphinan, 17-methyl-4,5α-epoxy-14β-hydroxy-3-methoxy-6α-[N-methyl-3-(4-trifluoromethylphenyl)propiolamido]morphinan, 17-phenethyl-4,5α-epoxy-14β-hydroxy-3-methoxy-6α-(N-methyl-3-methylcinnamamido) morphinan, 17-phenethyl-4,5α-epoxy-14β-hydroxy-3-methoxy-6α-[N-methyl-3-(4-trifluoromethylphenyl)propiolamido]morphinan, 17-cyclopropylmethyl-4,5α-epoxy-14β-acetoxy-3-methoxy-6α-(N-methyl-3-methylcinnamamido) morphinan, 17-cyclopropylmethyl-4,5α-epoxy-14β-acetoxy-3-methoxy-6α-[N-methyl-3-(4-trifluoromethylphenyl)propiolamido]morphinan, 17-allyl-4,5α-epoxy-14β-acetoxy-3-methoxy- 6α-(N-methyl-3-methylcinnamamido)morphinan, 17-allyl-4,5α-epoxy-14β-acetoxy-3-methoxy-6α-[N-methyl-3-(4-trifluoromethylphenyl)propiolamido]morphinan, 17-methyl-4,5α-epoxy-14β-acetoxy-3-methoxy-6α-(N-methyl-3-methylcinnamamido)morphinan, 17-methyl-4,5α-epoxy-14β-acetoxy-3-methoxy-6α-

[N-methyl-3-(4-trifluoromethylphenyl)propiolamido]morphinan, 17-phenethyl-4,5α-epoxy-14β-acetoxy-3-methoxy-6α-(N-methyl-3-methylcinnamamido)morphinan, 17-phenethyl-4,5α-epoxy-14β-acetoxy-3-methoxy-6α-[N-methyl-3-(4-trifluoromethylphenyl)propiolamido]morphinan, 17-cyclopropylmethyl-4,5α-epoxy-14β-hydroxy-3-acetoxy-6α-(N-methyl-3-methylcinnamamido)morphinan, 17-cyclopropylmethyl-4,5α-epoxy-14β-hydroxy-3-acetoxy-6α-[N-methyl-3-(4-trifluoromethylphenyl)propiolamido]morphinan, 17-allyl-4,5α-epoxy-14β-hydroxy-3-acetoxy-6α-(N-methyl-3-methylcinnamamido)morphinan, 17-allyl-4,5α-epoxy-14β-hydroxy-3-acetoxy-6α-[N-methyl-3-(4-trifluoromethylphenyl)propiolamido]morphinan, 17-methyl-4,5α-epoxy-14β-hydroxy-3-acetoxy-6α-(N-methyl-3-methylcinnamamido)morphinan, 17-methyl-4,5α-epoxy-14β-hydroxy-3-acetoxy-6α-[N-methyl-3-(4-trifluoromethyl-phenyl)propiolamido]morphinan, 17-phenethyl-4,5α-epoxy-14β-hydroxy-3-acetoxy-6α-(N-methyl-3-methylcinnamamido)morphinan, 17-phenethyl-4,5α-epoxy-14β-hydroxy-3-acetoxy-6α-[N-methyl-3-(4-trifluoromethylphenyl)propiolamido]morphinan, 17-cyclopropylmethyl-4,5α-epoxy-3,14β-diacetoxy-6α-(N-methyl-3-methylcinnamamido)morphinan, 17-cyclopropylmethyl-4,5α-epoxy-3,14β-diacetoxy-6α-[N-methyl-3-(4-trifluoromethylphenyl)propiolamido]morphinan, 17-allyl-4,5α-epoxy-3,14β-diacetoxy-6α-(N-methyl-3-methylcinnamamido)morphinan, 17-allyl-4,5α-epoxy-3,14β-diacetoxy-6α-[N-methyl-3-(4-trifluoromethylphenyl)propiolamido]morphinan, 17-methyl-4,5α-epoxy-3,14β-diacetoxy-6α-(N-methyl-3-methylcinnamamido)morphinan, 17-methyl-4,5α-epoxy-3,14β-diacetoxy-6α-[N-methyl-3-(4-trifluoromethylphenyl)propiolamido]morphinan, 17-phenethyl-4,5α-epoxy-3,14β-diacetoxy-6α-(N-methyl-3-methylcinnamamido)morphinan, 17-phenethyl-4,5α-epoxy-3,14β-diacetoxy-6α-[N-methyl-3-(4-trifluoromethylphenyl)propiolamido]morphinan, 17-cyclopropylmethyl-4,5α-epoxy-3,14β-dihydroxy-6α-(N-isobutyl-3-methylcinnamamido)morphinan, 17-cyclopropylmethyl-4,5α-epoxy-3,14α-dihydroxy-6α-[N-isobutyl-3-(4-trifluoromethylphenyl)propiolamido]morphinan, 17-allyl-4,5α-epoxy-3,14β-dihydroxy-6α-(N-isobutyl-3-methylcinnamamido)morphinan, 17-allyl-4,5α-epoxy-3,14β-dihydroxy-6α-[N-isobutyl-3-(4-trifluoromethylphenyl)propiolamido]morphinan, 17-methyl-4,5α-epoxy-3,14β-dihydroxy-6α-(N-isobutyl-3-methylcinnamamido)morphinan, 17-methyl-4,5α-epoxy-3,14β-dihydroxy-6α-[N-isobutyl-3-(4-trifluoromethylphenyl)propiolamido]morphinan, 17-phenethyl-4,5α-epoxy-3,14β-dihydroxy-6α-(N-isobutyl-3-methylcinnamamido)morphinan, 17-phenethyl-4,5α-epoxy-3,14β-dihydroxy-6α-[N-isobutyl-3-(4-trifluoromethylphenyl)propiolamido]morphinan, 17-cyclopropylmethyl-4,5α-epoxy-14β-acetoxy-3-hydroxy-6α-(N-isobutyl-3-methylcinnamamido)morphinan, 17-cyclopropylmethyl-4,5α-epoxy-14β-acetoxy-3-hydroxy-6α-[N-isobutyl-3-(4-trifluoromethylphenyl)propiolamido]morphinan, 17-allyl-4,5α-epoxy-14β-acetoxy-3-hydroxy-6α-(N-isobutyl-3-methylcinnamamido)morphinan, 17-allyl-4,5α-epoxy-14β-acetoxy-3-hydroxy-6α-[N-isobutyl-3-(4-trifluoromethylphenyl)propiolamido]morphinan, 17-methyl-4,5α-epoxy-14β-acetoxy-3-hydroxy-6α-(N-isobutyl-3-methylcinnamamido)morphinan, 17-methyl-4,5α-epoxy-14β-acetoxy-3-hydroxy-6α-[N-isobutyl-3-(4-trifluoromethylphenyl)propiolamido]morphinan, 17-phenethyl-4,5α-epoxy-14β-acetoxy-3-hydroxy-6α-(N-isobutyl-3-methylcinnamamido)morphinan, 17-phenethyl-4,5α-epoxy-14β-acetoxy-3-hydroxy-6α-[N-isobutyl-3-(4-trifluoromethylphenyl)propiolamido]morphinan, 17-cyclopropylmethyl-4,5α-epoxy-14β-hydroxy-6α-(N-isobutyl-3-methylcinnamamido)morphinan, 17-cyclopropylmethyl-4,5α-epoxy-14β-hydroxy-6α-[N-isobutyl-3-(4-trifluoromethylphenyl)propiolamido]morphinan, 17-allyl-4,5α-epoxy-14β-hydroxy-6α-(N-isobutyl-3-methylcinnamamido)morphinan, 17-allyl-4,5α-epoxy-14β-hydroxy-6α-[N-isobutyl-3-(4-trifluoromethylphenyl)propiolamido]morphinan, 17-methyl-4,5α-epoxy-14β-hydroxy-6α-(N-isobutyl-3-methylcinnamamido)morphinan, 17-methyl-4,5α-epoxy-14β-hydroxy-6α-[N-isobutyl-3-(4-trifluoromethylphenyl)propiolamido]morphinan, 17-phenethyl-4,5α-epoxy-14β-hydroxy-6α-(N-isobutyl-3-methylcinnamamido)morphinan, 17-phenethyl-4,5α-epoxy-14β-hydroxy-6α-[N-isobutyl-3-(4-trifluoromethylphenyl)propiolamido]morphinan, 17-cyclopropylmethyl-4,5α-epoxy-14β-acetoxy-6α-(N-isobutyl-3-methylcinnamamido)morphinan, 17-cyclopropylmethyl-4,5α-epoxy-14β-acetoxy-6α-[N-isobutyl-3-(4-trifluoromethylphenyl)propiolamido]morphinan, 17-allyl-4,5α-epoxy-14β-acetoxy-6α-(N-isobutyl-3-methylcinnamamido)morphinan, 17-allyl-4,5α-epoxy-14β-acetoxy-6α-[N-isobutyl-3-(4-trifluoromethylphenyl)propiolamido]morphinan, 17-methyl-4,5α-epoxy-14β-acetoxy-6α-(N-isobutyl-3-methylcinnamamido)morphinan, 17-methyl-4,5α-epoxy-14β-acetoxy-6α-[N-isobutyl-3-(4-trifluoromethylphenyl)propiolamido]morphinan, 17-phenethyl-4,5α-epoxy-14β-acetoxy-6α-(N-isobutyl-3-methylcinnamamido)morphinan, 17-phenethyl-4,5α-epoxy-14β-acetoxy-6α-[N-isobutyl-3-(4-trifluoromethylphenyl)propiolamido]morphinan, 17-cyclopropylmethyl-4,5α-epoxy-14β-hydroxy-3-methoxy-6α-(N-isobutyl-3-methylcinnamamido)morphinan, 17-cyclopropylmethyl-4,5α-epoxy-14β-hydroxy-3-methoxy-6α-[N-isobutyl-3-(4-trifluoromethylphenyl)propiolamido]morphinan, 17-allyl-4,5α-epoxy-14β-hydroxy-3-methoxy-6α-(N-isobutyl-3-methylcinnamamido)morphinan, 17-allyl-4,5α-epoxy-14β-hydroxy-3-methoxy-6α-[N-isobutyl-3-(4-trifluoromethylphenyl)propiolamido]morphinan, 17-methyl-4,5α-epoxy-14β-hydroxy-3-methoxy-6α-(N-isobutyl-3-methylcinnamamido)morphinan, 17-methyl-4,5α-epoxy-14β-hydroxy-3-methoxy-6α-[N-isobutyl-3-(4-trifluoromethylphenyl)propiolamido]morphinan, 17-phenethyl-4,5α-epoxy-14β-hydroxy-3-methoxy-6α-(N-isobutyl-3-methylcinnamamido)morphinan, 17-phenethyl-4,5α-epoxy-14β-hydroxy-3-methoxy-6α-[N-isobutyl-3-(4-trifluoromethylphenyl)propiolamido]morphinan, 17-cyclopropylmethyl-4,5α-epoxy-14β-acetoxy-3-methoxy-6α-(N-isobutyl-3-methylcinnamamido)morphinan, 17-cyclopropylmethyl-4,5α-epoxy-14β-acetoxy-3-methoxy-6α-[N-isobutyl-3-(4-trifluoromethylphenyl)propiolamido]morphinan, 17-allyl-4,5α-epoxy-14β-acetoxy-3-methoxy-6α-(N-isobutyl-3-methylcinnamamido)morphinan, 17-allyl-4,5α-epoxy-14β-acetoxy-3-methoxy-6α-[N-isobutyl-3-(4-trifluoromethylphenyl)propiolamido]morphinan, 17-methyl-4,5α-epoxy-14β-acetoxy-3-methoxy-6α-(N-isobutyl-3-methylcinnamamido)morphinan, 17-methyl-4,5α-epoxy-14β-acetoxy-3-methoxy-6α-[N-isobutyl-3-(4-trifluoromethylphenyl)propiolamido]morphinan, 17-phenethyl-4,5α-epoxy-14β-acetoxy-3-methoxy-6α-(N-isobutyl-3-methylcinnamamido)morphinan, 17-phenethyl-4,5α-epoxy-14β-acetoxy-3-methoxy-6α-[N-isobutyl-3-(4-trifluoromethylphenyl)propiolamido]morphinan, 17-cyclopropylmethyl-4,5α-epoxy-14β-hydroxy-3-acetoxy-6α-(N-isobutyl-3-methylcinnamamido)morphinan, 17-cyclopropylmethyl-4,5α-epoxy-14β-hydroxy-3-acetoxy-6α-[N-isobutyl-3-(4-trifluoromethylphenyl)propiolamido]morphinan, 17-allyl-4,5α-epoxy-14β-hydroxy-3-acetoxy-6α-(N-isobutyl-3-methylcinnamamido)morphinan, 17-allyl-4,5α-epoxy-14β-hydroxy-3-acetoxy-6α-[N-isobutyl-3-(4-trifluoromethylphenyl)propiolamido]morphinan, 17-methyl-4,5α-epoxy-14β-hydroxy-3-acetoxy-6α-(N-isobutyl-3-methylcinnamamido)morphinan, 17-methyl-4,5α-epoxy-14β-hydroxy-3-acetoxy-6α-[N-isobutyl-3-(4-trifluoromethylphenyl)propiolamido]morphinan, 17-phenethyl-4,5α-epoxy-14β-hydroxy-3-acetoxy-6α-(N-isobutyl-3-methylcinnamamido)morphinan, 17-phenethyl-4,5α-epoxy-14β-hydroxy-3-acetoxy-6α-[N-isobutyl-3-(4-trifluoromethylphenyl)propiolamido]morphinan, 17-cyclopropylmethyl-4,5α-epoxy-3,14β-diacetoxy-6α-(N-isobutyl-3-methylcinnamamido)morphinan, 17-cyclopropylmethyl-4,5α-epoxy-3,14β-diacetoxy-6α-[N-isobutyl-3-(4-trifluoromethylphenyl)propiolamido]morphinan, 17-allyl-4,5α-epoxy-3,14β-diacetoxy-6α-(N-isobutyl-3-methylcinnamamido)morphinan, 17-allyl-4,5α-epoxy-3,14β-diacetoxy-6α-[N-isobutyl-3-(4-trifluoromethylphenyl)propiolamido]morphinan, 17-methyl-4,5α-epoxy-3,14β-diacetoxy-6α-(N-isobutyl-3-methylcinnamamido)morphinan, 17-methyl-4,5α-epoxy-3,14β-diacetoxy-6α-[N-isobutyl-3-(4-trifluoromethylphenyl)propiolamido]morphinan, 17-phenethyl-4,5α-epoxy-3,14β-diacetoxy-6α-(N-isobutyl-3-methylcinnamamido)morphinan, 17-phenethyl-4,5α-epoxy-3,14β-diacetoxy-6α-[N-isobutyl-3-(4-trifluoromethylphenyl)propiolamido]morphinan, 17-cyclopropylmethyl-4,5α-epoxy-3,14β-dihydroxy-6β-(N-methyl-3-methylcinnamamido)morphinan, 17-cyclopropylmethyl-4,5α-epoxy-3,14β-dihydroxy-6β-[N-methyl-3-(4-trifluoromethylphenyl)propiolamido]morphinan, 17-allyl-4,5α-epoxy-3,14β-dihydroxy-6β-(N-methyl-3-methylcinnamamido)morphinan, 17-allyl-4,5α-epoxy-3,14β-dihydroxy-6β-[N-methyl-3-(4-trifluoromethylphenyl)propiolamido]morphinan, 17-methyl-4,5α-epoxy-3,14β-dihydroxy-6β-(N-methyl-3-methylcinnamamido)morphinan, 17-methyl-4,5α-epoxy- 3,14β-dihydroxy-6β-[N-methyl-3-(4-trifluoromethylphenyl)propiolamido]morphinan, 17-phenethyl-4,5α-epoxy-3,14β-dihydroxy-6β-(N-methyl-3-methylcinnamamido)morphinan, 17-phenethyl-4,5α-epoxy-3,14β-dihydroxy-6β-[N-methyl-3-(4-trifluoromethylphenyl)propiolamido]morphinan, 17-cyclopropylmethyl-4,5α-epoxy-14β-acetoxy-3-hydroxy-6β-(N-methyl-3-methylcinnamamido)morphinan, 17-cyclopropylmethyl-4,5α-epoxy-14β-acetoxy-3-hydroxy-6β-[N-methyl-3-(4-trifluoromethylphenyl)propiolamido]morphinan, 17-allyl-4,5α-epoxy-14β-acetoxy-3-hydroxy-6β-(N-methyl-3-methylcinnamamido)morphinan, 17-allyl-4,5α-epoxy-14β-acetoxy-3-hydroxy-6β-[N-methyl-3-(4-trifluoromethylphenyl)propiolamido]morphinan, 17-methyl-4,5α-epoxy-14β-acetoxy-3-hydroxy-6β-(N-methyl-3-methylcinnamamido)morphinan, 17-methyl-4,5α-epoxy-14β-acetoxy-3-hydroxy-6β-[N-methyl-3-(4-trifluoromethylphenyl)propiolamido]morphinan, 17-phenethyl-4,5α-epoxy-14β-acetoxy-3-hydroxy-6β-(N-methyl-3-methylcinnamamido)morphinan, 17-phenethyl-4,5α-epoxy-14β-acetoxy-3-hydroxy-6β-[N-methyl-3-(4-trifluoromethylphenyl)propiolamido]morphinan, 17-cyclopropylmethyl-4,5α-epoxy-14β-hydroxy-6β-(N-methyl-3-methylcinnamamido)morphinan, 17-cyclopropylmethyl-4,5α-epoxy-14β-hydroxy-6β-[N-methyl-3-(4-trifluoromethylphenyl)propiolamido]morphinan, 17-allyl-4,5α-epoxy-14β-hydroxy-6β-(N-methyl-3-methylcinnamamido)morphinan, 17-allyl-4,5α-epoxy-14β-hydroxy-6β-[N-methyl-3-(4-trifluoromethylphenyl)propiolamido]morphinan, 17-methyl-4,5α-epoxy-14β-hydroxy-6β-(N-methyl-3-methylcinnamamido)morphinan, 17-methyl-4,5α-epoxy-14β-hydroxy-6-[N-methyl-3-(4-trifluoromethylphenyl)propiolamido]morphinan, 17-phenethyl-4,5α-epoxy-14β-hydroxy-6β-(N-methyl-3-methylcinnamamido)morphinan, 17-phenethyl-4,5α-epoxy-14β-hydroxy-6β-[N-methyl-3-(4-trifluoromethylphenyl)propiolamido]morphinan, 17-cyclopropylmethyl-4,5α-epoxy-14β-acetoxy-6β-(N-methyl-3-methylcinnamamido)morphinan, 17-cyclopropylmethyl-4,5α-epoxy-14β-acetoxy-6β-[N-methyl-3-(4-trifluoromethylphenyl)propiolamido]morphinan, 17-allyl-4,5α-epoxy-14β-acetoxy-6β-(N-methyl-3-methylcinnamamido)morphinan, 17-allyl-4,5α-epoxy-14β-acetoxy-6β-[N-methyl-3-(4-trifluoromethylphenyl)propiolamido]morphinan, 17-methyl-4,5α-epoxy-14β-acetoxy-6β-(N-methyl-3-methylcinnamamido)morphinan, 17-methyl-4,5α-epoxy-14β-acetoxy-6β-[N-methyl-3-(4-trifluoromethylphenyl)propiolamido]morphinan, 17-phenethyl-4,5α-epoxy-14β-acetoxy-6β-(N-methyl-3-methylcinnamasnido)morphinan, 17-phenethyl-4,5α-epoxy-14β-acetoxy-6β-[N-methyl-3-(4-trifluoromethylphenyl)propiolamido]morphinan, 17-cyclopropylmethyl-4,5α-epoxy-14β-hydroxy-3-methoxy-6β-(N-methyl-3-methylcinnamamido)morphinan, 17-cyclopropylmethyl-4,5α-epoxy-14β-hydroxy-3-methoxy-6β-[N-methyl-3-(4-trifluoromethylphenyl)propiolamido]morphinan, 17-allyl-4,5α-epoxy-14β-hydroxy-3-methoxy-6β-(N-methyl-3-methylcinnamamido)morphinan, 17-allyl-4,5α-epoxy-14β-hydroxy-3-methoxy-6β-[N-methyl-3-(4-trifluoromethylphenyl)propiolamido]morphinan, 17-methyl-4,5α-epoxy-14β-hydroxy-3-methoxy-6β-(N-methyl-3-methylcinnamamido)morphinan, 17-methyl-4,5α-epoxy-14β-hydroxy-3-methoxy-6β-[N-methyl-3-(4-trifluoromethylphenyl)propiolamido]morphinan, 17-phenethyl-4,5α-epoxy-14β-hydroxy-3-methoxy-6β-(N-methyl-3-methylcinnamamido)morphinan, 17-phenethyl-4,5α-epoxy-14β-hydroxy-3-methoxy-6β-[N-methyl-3-(4-trifluoromethylphenyl)propiolamido]morphinan, 17-cyclopropylmethyl-4,5α-epoxy-14β-acetoxy-3-methoxy-6β-(N-methyl-3-methylcinnamamido)morphinan, 17-cyclopropylmethyl-4,5α-epoxy-14β-acetoxy-3-methoxy-6β-[N-methyl-3-(4-trifluoromethylphenyl)propiolamido]morphinan, 17-allyl-4,5α-epoxy-14β-acetoxy-3-methoxy-6β-(N-methyl-3-methylcinnamamido)morphinan, 17-allyl-4,5α-epoxy-14β-acetoxy-3-methoxy-6β-[N-methyl-3-(4-trifluoromethylphenyl)propiolamido]morphinan, 17-methyl-4,5α-epoxy-14β-acetoxy-3-methoxy-6β-(N-methyl-3-methylcinnamamido)morphinan, 17-methyl-4,5α-epoxy-14β-acetoxy-3-methoxy-6β-[N-methyl-3-(4-trifluoromethylphenyl)propiolamido]morphinan, 17-phenethyl-4,5α-epoxy-14β-acetoxy-3-methoxy-6β-(N-methyl-3-methylcinnamamido)morphinan, 17-phenethyl-4,5α-epoxy-14β-acetoxy-3-methoxy-6β-[N-methyl-3-(4-trifluoromethylphenyl)propiolamido]morphinan, 17-cyclopropylmethyl-4,5α-epoxy-14β-hydroxy-3-acetoxy-6β-(N-methyl-3-methylcinnamamido)morphinan, 17-cyclopropylmethyl-4,5α-epoxy-14β-hydroxy-3-acetoxy-6β-[N-methyl-3-(4-trifluoromethylphenyl)propiolamido]morphinan, 17-allyl-4,5α-epoxy-14β-hydroxy-3-acetoxy-6β-(N-methyl-3-methylcinnamamido)morphinan, 17-allyl-4,5α-epoxy-14β-hydroxy-3-acetoxy-6β-[N-methyl-3-(4-trifluoromethylphenyl)propiolamido]morphinan, 17-methyl-4,5α-epoxy-14β-hydroxy-3-acetoxy-6β-(N-methyl-3-methylcinnamamido)morphinan, 17-methyl-4,5α-epoxy-14β-hydroxy-3-acetoxy-6β-[N-methyl-3-(4-trifluoromethylphenyl)propiolamido]morphinan, 17-phenethyl-4,5α-epoxy-14β-hydroxy-3-acetoxy-6β-(N-methyl-3-methylcinnamamido)morphinan, 17-phenethyl-4,5α-epoxy-14β-hydroxy-3-acetoxy-6β-[N-methyl-3-(4-trifluoromethylphenyl)propiolamido]morphinan, 17-cyclopropylmethyl-4,5α-epoxy-3,14β-diacetoxy-6β-(N-methyl-3-methylcinnamamido)morphinan, 17-cyclopropylmethyl-4,5α-epoxy-3,14β-diacetoxy-6β-[N-methyl-3-(4-trifluoromethylphenyl)propiolamido]morphinan, 17-allyl-4,5α-epoxy-3,14β-diacetoxy-6β-(N-methyl-3-methylcinnamamido)morphinan, 17-allyl-4,5α-epoxy-3,14β-diacetoxy-6β-[N-methyl-3-(4-trifluoromethylphenyl)propiolamido]morphinan, 17-methyl-4,5α-epoxy-3,14β-diacetoxy-6β-(N-methyl-3-methylcinnamamido)morphinan, 17-methyl-4,5α-epoxy-3,14β-diacetoxy-6β-[N-methyl-3-(4-trifluoromethylphenyl)propiolamido]morphinan, 17-phenethyl-4,5α-epoxy-3,14β-diacetoxy-6β-(N-methyl-3-methylcinnamamido)morphinan, 17-phenethyl-4,5α-epoxy-3,14β-diacetoxy-6β-[N-methyl-3-(4-trifluoromethylphenyl)propiolamido]morphinan, 17-cyclopropylmethyl-4,5α-epoxy-3,14β-dihydroxy-6β-(N-isobutyl-3-methylcinnamamido)morphinan, 17-cyclopropylmethyl-4,5α-epoxy-3,14β-dihydroxy-6β-[N-isobutyl-3-(4-trifluoromethylphenyl)propiolamido]morphinan, 17-allyl-4,5α-epoxy-3,14β-dihydroxy-6β-(N-isobutyl-3-methylcinnamamido)morphinan, 17-allyl-4,5α-epoxy-3,14β-dihydroxy-6β-[N-isobutyl-3-(4-trifluoromethylphenyl)propiolamido]morphinan, 17-methyl-4,5α-epoxy-3,14β-dihydroxy-6β-(N-isobutyl-3-methylcinnamamido)morphinan, 17-methyl-4,5α-epoxy-3,14β-dihydroxy-6β-[N-isobutyl-3-(4-trifluoromethylphenyl)propiolamido]morphinan, 17-phenethyl-4,5α-epoxy-3,14β-dihydroxy-6β-(N-isobutyl-3-methylcinnamamido)morphinan, 17-phenethyl-4,5α-epoxy-3,14β-dihydroxy-6β-[N-isobutyl-3-(4-trifluoromethylphenyl)propiolamido]morphinan, 17-cyclopropylmethyl-4,5α-epoxy-14β-acetoxy-3-hydroxy-6β-(N-isobutyl-3-methylcinnamamido)morphinan, 17-cyclopropylmethyl-4,5α-epoxy-14β-acetoxy-3-hydroxy-6β-[N-isobutyl-3-(4-trifluoromethylphenyl)propiolamido]morphinan, 17-allyl-4,5α-epoxy-14β-acetoxy-3-hydroxy-6β-(N-isobutyl-3-methylcinnamamido)morphinan, 17-allyl-4,5α-epoxy-14β-acetoxy-3-hydroxy-6β-[N-isobutyl-3-(4-trifluoromethylphenyl)propiolamido]morphinan, 17-methyl-4,5α-epoxy-14β-acetoxy-3-hydroxy-6β-(N-isobutyl-3-methylcinnamamido)morphinan, 17-methyl-4,5α-epoxy-14β-acetoxy-3-hydroxy-6β-[N-isobutyl-3-(4-trifluoromethylphenyl)propiolamido]morphinan, 17-phenethyl-4,5α-epoxy-14β-acetoxy-3-hydroxy-6β-(N-isobutyl-3-methylcinnamamido)morphinan, 17-phenethyl-4,5α-epoxy-14β-acetoxy-3-hydroxy-6β-[N-isobutyl-3-(4 -trifluoromethylphenyl)propiolamido]morphinan, 17-cyclopropylmethyl-4,5α-epoxy-14β-hydroxy-6β-(N-isobutyl-3-methylcinnamamido)morphinan, 17-cyclopropylmethyl-4,5α-epoxy-14β-hydroxy-6β-[N-isobutyl-3-(4-trifluoromethylphenyl)propiolamido]morphinan, 17-allyl-4,5α-epoxy-14β-hydroxy-6β-(N-isobutyl-3-methylcinnamamido)morphinan, 17-allyl-4,5α-epoxy-14β-hydroxy-6β-[N-isobutyl-3-(4-trifluoromethylphenyl)propiolamido]morphinan, 17-methyl-4,5α-epoxy-14β-hydroxy-6β-(N-isobutyl-3-methylcinnamamido)morphinan, 17-methyl-4,5α-epoxy-14β-hydroxy-6β-[N-isobutyl-3-(4-trifluoromethylphenyl)propiolamido]morphinan, 17-phenethyl-4,5α-epoxy-14β-hydroxy-6β-(N-isobutyl-3-methylcinnamamido)morphinan, 17-phenethyl-4,5α-epoxy-14β-hydroxy-6β-[N-isobutyl-3-(4-trifluoromethylphenyl)propiolamido]morphinan, 17-cyclopropylmethyl-4,5α-epoxy-14β-acetoxy-6β-(N-isobutyl-3-methylcinnamamido)morphinan, 17-cyclopropylmethyl-4,5α-epoxy-14β-acetoxy-6β-[N-isobutyl-3-(4-trifluoromethylphenyl)propiolamido]morphinan, 17-allyl-4,5α-epoxy-14β-acetoxy-6β-(N-isobutyl-3-methylcinnamamido)morphinan, 17-allyl-4,5α-epoxy-14β-acetoxy-6β-[N-isobutyl-3-(4-trifluoromethylphenyl)propiolamido]morphinan, 17-methyl-4,5α-epoxy-14β-acetoxy-6β-(N-isobutyl-3-methylcinnamamido)morphinan, 17-methyl-4,5α-epoxy-14β-acetoxy-6β-[N-isobutyl-3-(4-trifluoromethylphenyl)propiolamido]morphinan, 17-phenethyl-4,5α-epoxy-14β-acetoxy-6β-(N-isobutyl-3-methylcinnamamido)morphinan, 17-phenethyl-4,5α-epoxy-14β-acetoxy-6β-[N-isobutyl-3-(4-trifluoromethylphenyl)propiolamido]morphinan, 17-cyclopropylmethyl-4,5α-epoxy-14β-hydroxy-3-methoxy-6β-(N-isobutyl-3-methylcinnamamido)morphinan, 17-cyclopropylmethyl-4,5α-epoxy-14β-hydroxy-3-methoxy-6β-[N-isobutyl-3-(4-trifluoromethylphenyl)propiolamido]morphinan, 17-allyl-4,5α-epoxy-14β-hydroxy-3-methoxy-6β-(N-isobutyl-3-methylcinnamamido)morphinan, 17-allyl-4,5α-epoxy-14β-hydroxy-3-methoxy-6β-[N-isobutyl-3-(4-trifluoromethylphenyl)propiolamido]morphinan, 17-methyl-4,5α-epoxy-14β-hydroxy-3-methoxy-6β-(N-isobutyl-3-methylcinnamamido)morphinan, 17-methyl-4,5α-epoxy-14β-hydroxy-3-methoxy-6β-

[N-isobutyl-3-(4-trifluoromethylphenyl)propiolamido]morphinan, 17-phenethyl-4,5α-epoxy-14β-hydroxy-3-methoxy-6β-(N-isobutyl-3-methylcinnamamido)morphinan, 17-phenethyl-4,5α-epoxy-14β-hydroxy-3-methoxy-6β-[N-isobutyl-3-(4-trifluoromethylphenyl)propiolamido]morphinan, 17-cyclopropylmethyl-4,5α-epoxy-14β-acetoxy-3-methoxy-6β-(N-isobutyl-3-methylcinnamamido)morphinan, 17-cyclopropylmethyl-4,5α-epoxy-14β-acetoxy-3-methoxy-6β-[N-isobutyl-3-(4-trifluoromethylphenyl)propiolamido]morphinan, 17-allyl-4,5α-epoxy-14β-acetoxy-3-methoxy-6β-(N-isobutyl-3-methylcinnamamido)morphinan, 17-allyl-4,5α-epoxy-14β-acetoxy-3-methoxy-6β-[N-isobutyl-3-(4-trifluoromethylphenyl)propiolamido]morphinan, 17-methyl-4,5α-epoxy-14β-acetoxy-3-methoxy-6β-(N-isobutyl-3-methylcinnamamido)morphinan, 17-methyl-4,5α-epoxy-14β-acetoxy-3-methoxy-6β-[N-isobutyl-3-(4-trifluoromethylphenyl)propiolamido]morphinan, 17-phenethyl-4,5α-epoxy-14β-acetoxy-3-methoxy-6β-(N-isobutyl-3-methylcinnamamido)morphinan, 17-phenethyl-4,5α-epoxy-14β-acetoxy-3-methoxy-6β-[N-isobutyl-3-(4-trifluoromethylphenyl)propiolamido]morphinan, 17-cyclopropylmethyl-4,5α-epoxy-14β-hydroxy-3-acetoxy-6β-(N-isobutyl-3-methylcinnamamido)morphinan, 17-cyclopropylmethyl-4,5α-epoxy-14β-hydroxy-3-acetoxy-6β-[N-isobutyl-3-(4-trifluoromethylphenyl)propiolamido]morphinan, 17-allyl-4,5α-epoxy-14β-hydroxy-3-acetoxy-6β-(N-isobutyl-3-methylcinnamamido)morphinan, 17-allyl-4,5α-epoxy-14β-hydroxy-3-acetoxy-6β-[N-isobutyl-3-(4-trifluoromethylphenyl)propiolamido]morphinan, 17-methyl-4,5α-epoxy-14β-hydroxy-3-acetoxy-6β-(N-isobutyl-3-methylcinnamamido)morphinan, 17-methyl-4,5α-epoxy-14β-hydroxy-3-acetoxy-6β-[N-isobutyl-3-(4-trifluoromethylphenyl)propiolamido]morphinan, 17-phenethyl-4,5α-epoxy-14β-hydroxy-3-acetoxy-6β-(N-isobutyl-3-methylcinnamamido)morphinan, 17-phenethyl-4,5α-epoxy-14β-hydroxy-3-acetoxy-6β-[N-isobutyl-3-(4-trifluoromethylphenyl)propiolamido]morphinan, 17-cyclopropylmethyl-4,5α-epoxy-3,14β-diacetoxy-6β-(N-isobutyl-3-methylcinnamamido)morphinan, 17-cyclopropylmethyl-4,5α-epoxy-3,14β-diacetoxy-6β-[N-isobutyl-3-(4-trifluoromethylphenyl)propiolamido]morphinan, 17-allyl-4,5α-epoxy-3,14β-diacetoxy-6β-(N-isobutyl-3-methylcinnamamido)morphinan, 17-allyl-4,5α-epoxy-3,14β-diacetoxy-6β-[N-isobutyl-3-(4-trifluoromethylphenyl)propiolamido]morphinan, 17-methyl-4,5α-epoxy-3,14β-diacetoxy-6β-(N-isobutyl-3-methylcinnamamido)morphinan, 17-methyl-4,5α-epoxy-3,14β-diacetoxy-6β-[N-isobutyl-3-(4-trifluoromethylphenyl)propiolamido]morphinan, 17-phenethyl-4,5α-epoxy-3,14β-diacetoxy-6β-(N-isobutyl-3-methylcinnamamido)morphinan, 17-phenethyl-4,5α-epoxy-3,14β-diacetoxy-6β-[N-isobutyl-3-(4-trifluoromethylphenyl)propiolamido]morphinan, 17-cyclopropylmethyl-4,5α-epoxy-3,14β-dihydroxy-6α-[N-methyl-3-(3-trifluoromethylphenyl)propiolamido]morphinan, 17-allyl-4,5α-epoxy-3,14β-dihydroxy-6α-[N-methyl-3-(3-trifluoromethylphenyl)propiolamido]morphinan, 17-cyclopropylmethyl-4,5α-epoxy-3,14β-dihydroxy-6β-[N-methyl-3-(3-trifluoromethylphenyl)propiolamido]morphinan, 17-allyl-4,5α-epoxy-3,14β-dihydroxy-6β-[N-methyl-3-(3-trifluoromethylphenyl)propiolamido]morphinan, 17-cyclopropylmethyl-4,5α-epoxy-3,14β-dihydroxy-6α-[N-methyl-trans-3-(2-thienyl)acrylamido]morphinan, 17-allyl-4,5α-epoxy-3,14β-dihydroxy-6α-[N-methyl-trans-3-(2-thienyl)acrylamido]morphinan, 17-cyclopropylmethyl-4,5α-epoxy-3,14β-dihydroxy-6β-[N-methyl-trans-3-(2-thienyl)acrylamido]morphinan, 17-allyl-4,5α-epoxy-3,14β-dihydroxy-6β-[N-methyl-trans-3-(2-thienyl)acrylamido]morphinan, 17-cyclopropylmethyl-4,5α-epoxy-3-hydroxy-6α-(N-methyl-3-trifluoromethylcinnamamido)morphinan, 17-cyclopropylmethyl-4,5α-epoxy-3-hydroxy-6α-[N-methyl-trans-3-(3-furyl)acrylamido]morphinan, 17-cyclopropylmethyl-4,5α-epoxy-3-hydroxy-6α-(N-methyl-3-methylcinnamamido)morphinan, 17-cyclopropylmethyl-4,5α-epoxy-3-hydroxy-6α-[N-methyl-3-(4-trifluoromethylphenyl)propiolamido]morphinan, 17-allyl-4,5α-epoxy-3-hydroxy-6α-(N-methyl-3-trifluoromethylcinnamamido)morphinan, 17-allyl-4,5α-epoxy-3-hydroxy-6α-[N-methyl-trans-3-(3-furyl)acrylamido]morphinan, 17-allyl-4,5α-epoxy-3-hydroxy-6α-(N-methyl-3-methylcinnamamido)morphinan, 17-allyl-4,5α-epoxy-3-hydroxy-6α-[N-methyl-3-(4-trifluoromethylphenyl)propiolamido]morphinan, 17-methyl-4,5α-epoxy-3-hydroxy-6α-(N-methyl-3-trifluoromethylcinnamamido)morphinan, 17-methyl-4,5α-epoxy-3-hydroxy-6α-[N-methyl-trans-3-(3-furyl)acrylamido]morphinan, 17-methyl-4,5α-epoxy-3-hydroxy-6α-(N-methyl-3-methylcinnamamido)morphinan, 17-methyl-4,5α-epoxy-3-hydroxy-6α-[N-methyl-3-(4-trifluoromethylphenyl)propiolamido]morphinan, 17-phenethyl-4,5α-epoxy-3-hydroxy-6α-(N-methyl-3-trifluoromethylcinnamamido)morphinan, 17-phenethyl-4,5α-epoxy-3-hydroxy-6α-[N-methyl-trans-3-(3-furyl)acrylamido]morphinan, 17-phenethyl-4,5α-epoxy-3-hydroxy-6α-(N-methyl-3-methylcinnamamido)morphinan, 17-phenethyl-4,5α-epoxy-3-hydroxy-6α-[N-methyl-3-(4-trifluoromethylphenyl)propiolamido]morphinan, 17-cyclopropylmethyl-4,5α-epoxy-3-hydroxy-14β-nitro-6α-(N-methyl-3-trifluoromethylcinnamamido)morphinan, 17-cyclopropylmethyl-4,5α-epoxy-3-hydroxy-14β-nitro-6α-[N-methyl-trans-3-(3-furyl)acrylamido]morphinan, 17-cyclopropylmethyl-4,5α-epoxy-3-hydroxy-14β-nitro-6α-(N-methyl-3-methylcinnamamido)morphinan, 17-cyclopropylmethyl-4,5α-epoxy-3-hydroxy-14β-nitro-6α-[N-methyl-3-(4-trifluoromethylphenyl)propiolamido]morphinan, 17-allyl-4,5α-epoxy-3-hydroxy-14β-nitro-6α-(N-methyl-3-trifluoromethylcinnamamido)morphinan, 17-allyl-4,5α-epoxy-3-hydroxy-14β-nitro-6α-[N-methyl-trans-3-(3-furyl)acrylamido]morphinan, 17-allyl-4,5α-epoxy-3-hydroxy-14β-nitro-6α-(N-methyl-3-methylcinnamamido)morphinan, 17-allyl-4,5α-epoxy-3-hydroxy-14β-nitro-6α-[N-methyl-3-(4-trifluoromethylphenyl)propiolamido]morphinan, 17-methyl-4,5α-epoxy-3-hydroxy-14β-nitro-6α-(N-methyl-3-trifluoromethylcinnamamido)morphinan, 17-methyl-4,5α-epoxy-3-hydroxy-14β-nitro-6α-[N-methyl-trans-3-(3-furyl)acrylamido]morphinan, 17-methyl-4,5α-epoxy-3-hydroxy-14β-nitro-6α-(N-methyl-3-methylcinnamamido)morphinan, 17-methyl-4,5α-epoxy-3-hydroxy-14β-nitro-6α-[N-methyl-3-(4-trifluoromethylphenyl)propiolamido]morphinan, 17-phenethyl-4,5α-epoxy-3-hydroxy-14β-nitro-6α-(N-methyl-3-trifluoromethylcinnamamido)morphinan, 17-phenethyl-4,5α-epoxy-3-hydroxy-14β-nitro-6α-[N-methyl-trans-3-(3-furyl)acrylamido]morphinan, 17-phenethyl-4,5α-epoxy-3-hydroxy-14β-nitro-6α-(N-methyl-3-methylcinnamamido)morphinan, 17-phenethyl-4,5α-epoxy-3-hydroxy-14β-nitro-6α-[N-methyl-3-(4-trifluoromethylphenyl)propiolamido]morphinan, 17-cyclopropylmethyl-4,5α-epoxy-3-hydroxy-14β-dimethylamino-6α-(N-methyl-3-trifluoromethylcinnamamido)morphinan, 17-cyclopropylmethyl-4,5α-epoxy-3-hydroxy-14β-dimethylamino-6α-[N-methyl-trans-3-(3-furyl)acrylamido]morphinan, 17-cyclopropylmethyl-4,5α-epoxy-3-hydroxy-14β-dimethylamino-6α-(N-methyl-3-methylcinnamamido)morphinan, 17-cyclopropylmethyl- 4,5α-epoxy-3-hydroxy-14β-dimethylamino-6α-[N-methyl-3-(4-trifluoromethylphenyl)propiolamido]morphinan, 17-allyl-4,5α-epoxy-3-hydroxy-14β-dimethylamino-6α-(N-methyl-3-trifluoromethylcinnamamido)morphinan, 17-allyl-4,5α-epoxy-3-hydroxy-14β-dimethylamino-6α-[N-methyl-trans-3-(3-furyl)acrylamido]morphinan, 17-allyl-4,5α-epoxy-3-hydroxy-14β-dimethylamino-6α-(N-methyl-3-methylcinnamamido)morphinan, 17-allyl-4,5α-epoxy-3-hydroxy-14β-dimethylamino-6α-[N-methyl-3-(4-trifluoromethylphenyl)propiolamido]morphinan, 17-methyl-4,5α-epoxy-3-hydroxy-14β-dimethylamino-6α-(N-methyl-3-trifluoromethylcinnamamido)morphinan, 17-methyl-4,5α-epoxy-3-hydroxy-14β-dimethylamino-6α-[N-methyl-trans-3-(3-furyl)acrylamido]morphinan, 17-methyl-4,5α-epoxy-3-hydroxy-14β-dimethylamino-6α-(N-methyl-3-methylcinnamamido)morphinan, 17-methyl-4,5α-epoxy-3-hydroxy-14β-dimethylamino-6α-[N-methyl-3-(4-trifluoromethylphenyl)propiolamido]morphinan, 17-phenethyl-4,5α-epoxy-3-hydroxy-14β-dimethylamino-6α-(N-methyl-3-trifluoromethylcinnamamido)morphinan, 17-phenethyl-4,5α-epoxy-3-hydroxy-14β-dimethylamino-6α-[N-methyl-trans-3-(3-furyl)acrylamido]morphinan, 17-phenethyl-4,5α-epoxy-3-hydroxy-14β-dimethylamino-6α-(N-methyl-3-methylcinnamamido)morphinan, 17-phenethyl-4,5α-epoxy-3-hydroxy-14β-dimethylamino-6α-[N-methyl-3-(4-trifluoromethylphenyl)propiolamido]morphinan, 17-cyclopropylmethyl-4,5α-epoxy-3-hydroxy-14β-methyl-6α-(N-methyl-3-trifluoromethylcinnamamido)morphinan, 17-cyclopropylmethyl-4,5α-epoxy-3-hydroxy-14β-methyl-6α-[N-methyl-trans-3-(3-furyl)acrylamido]morphinan, 17-cyclopropylmethyl-4,5α-epoxy-3-hydroxy-14β-methyl-6α-(N-methyl-3-methylcinnamamido)morphinan, 17-cyclopropylmethyl-4,5α-epoxy-3-hydroxy-14β-methyl-6α-[N-methyl-3-(4-trifluoromethylphenyl)propiolamido]morphinan, 17-allyl-4,5α-epoxy-3-hydroxy-14β-methyl-6α-(N-methyl-3-trifluoromethylcinnamamido)morphinan, 17-allyl-4,5α-epoxy-3-hydroxy-14β-methyl-6α-[N-methyl-trans-3-(3-furyl)acrylamido]morphinan, 17-allyl-4,5α-epoxy-3-hydroxy-14β-methyl-6α-(N-methyl-3-methylcinnamamido)morphinan, 17-allyl-4,5α-epoxy-3-hydroxy-14β-methyl-6α-[N-methyl-3-(4-trifluoromethylphenyl)propiolamido]morphinan, 14β,17-dimethyl-4,5α-epoxy-3-hydroxy-6α-(N-methyl-3-trifluoromethylcinnamamido)morphinan, 14β,17-dimethyl-4,5α-epoxy-3-hydroxy-6α-[N-methyl-trans-3-(3-furyl)acrylamido]morphinan, 14β,17-dimethyl-4,5α-epoxy-3-hydroxy-6α-(N-methyl-3-methylcinnamamido)morphinan, 14β,17-dimethyl-4,5α-epoxy-3-hydroxy-6α-[N-methyl-3-(4-trifluoromethylphenyl)propiolamido]morphinan, 17-phenethyl-4,5α-epoxy-3-hydroxy-14β-methyl-6α-(N-methyl-3-trifluoromethylcinnamamido)morphinan, 17-phenethyl-4,5α-epoxy-3-hydroxy-14β-methyl-6α-[N-methyl-trans-3-(3-furyl)acrylamido]morphinan, 17-phenethyl-4,5α-epoxy-3-hydroxy-14β-methyl-6α-(N-methyl-3-methylcinnamamido)morphinan, 17-phenethyl-4,5α-epoxy-3-hydroxy-14β-methyl-6α-[N-methyl-3-(4-trifluoromethylphenyl)propiolamido]morphinan, 17-cyclopropylmethyl-3,14β-dihydroxy-6α-(N-methyl-3-trifluoromethylcinnamamido)morphinan, 17-cyclopropylmethyl-3,14β-dihydroxy-6α-[N-methyl-trans-3-(3-furyl)acrylamido]morphinan, 17-cyclopropylmethyl-3,14β-dihydroxy-6α-(N-methyl-3-methylcinnamamido)morphinan, 17-cyclopropylmethyl-3,14β-dihydroxy-6α-[N-methyl-3-(4-trifluoromethylphenyl)propiolamido]morphinan, 17-allyl-3,14β-dihydroxy-6α-(N-methyl-3-trifluoromethylcinnamamido)morphinan, 17-allyl-3,14β-dihydroxy-6α-[N-methyl-trans-3-(3-furyl)acrylamido]morphinan, 17-allyl-3,14β-dihydroxy-6α-(N-methyl-3-methylcinnamamido)morphinan, 17-allyl-3,14β-dihydroxy-6α-[N-methyl-3-(4-trifluoromethylphenyl)propiolamido]morphinan, 17-methyl-3,14β-dihydroxy-6α-(N-methyl-3-trifluoromethylcinnamamido)morphinan, 17-methyl-3,14β-dihydroxy-6α-[N-methyl-trans-3-(3-furyl)acrylamido]morphinan, 17-methyl-3,14β-dihydroxy-6α-(N-methyl-3-methylcinnamamido)morphinan, 17-methyl-3,14β-dihydroxy-6α-[N-methyl-3-(4-trifluoromethylphenyl)propiolamido]morphinan, 17-phenethyl-3,14β-dihydroxy-6α-(N-methyl-3-trifluoromethylcinnamamido)morphinan, 17-phenethyl-3,14β-dihydroxy-6α-[N-methyl-trans-3-(3-furyl)acrylamido]morphinan, 17-phenethyl-3,14β-dihydroxy-6α-(N-methyl-3-methylcinnamamido)morphinan, 17-phenethyl-3,14β-dihydroxy-6α-[N-methyl-3-(4-trifluoromethylphenyl)propiolamido]morphinan, 17-cyclopropylmethyl-3,14β-dihydroxy-4-methoxy-6α-(N-methyl-3-trifluoromethylcinnamamido)morphinan, 17-cyclopropylmethyl-3,14β-dihydroxy-4-methoxy-6α-[N-methyl-trans-3-(3-furyl)acrylamido]morphinan, 17-cyclopropylmethyl-3,14β-dihydroxy-4-methoxy-6α-(N-methyl-3-methylcinnamamido)morphinan, 17-cyclopropylmethyl-3,14β-dihydroxy-4-methoxy-6α-[N-methyl-3-(4-trifluoromethylphenyl)propiolamido]morphinan, 17-allyl-3,14β-dihydroxy-4-methoxy-6α-(N-methyl-3-trifluoromethylcinnamamido)morphinan, 17-allyl-3,14β-dihydroxy-4-methoxy-6α-[N-methyl-trans-3-(3-furyl)acrylamido]morphinan, 17-allyl-3,14β-dihydroxy-4-methoxy-6α-(N-methyl-3-methylcinnamamido)morphinan, 17-allyl-3,14β-dihydroxy-4-methoxy-6α-[N-methyl-3-(4-trifluoromethylphenyl)propiolamido]morphinan, 17-methyl-3,14β-dihydroxy-4-methoxy-6α-(N-methyl-3-trifluoromethylcinnamamido)morphinan, 17-methyl-3,14β-dihydroxy-4-methoxy-6α-[N-methyl-trans-3-(3-furyl)acrylamido]morphinan, 17-methyl-3,14β-dihydroxy-4-methoxy-6α-(N-methyl-3-methylcinnamamido)morphinan, 17-methyl-3,14β-dihydroxy-4-methoxy-6α-[N-methyl-3-(4-trifluoromethylphenyl)propiolamido]morphinan, 17-phenethyl-3,14β-dihydroxy-4-methoxy-6α-(N-methyl-3-trifluoromethylcinnamamido)morphinan, 17-phenethyl-3,14β-dihydroxy-4-methoxy-6α-[N-methyl-trans-3-(3-furyl)acrylamido]morphinan, 17-phenethyl-3,14β-dihydroxy-4-methoxy-6α-(N-methyl-3-methylcinnamamido)morphinan, 17-phenethyl-3,14β-dihydroxy-4-methoxy-6α-[N-methyl-3-(4-trifluoromethylphenyl)propiolamido]morphinan, 17-cyclopropylmethyl-4,5α-epoxy-3,14β-dihydroxy-5β-methyl-6α-(N-methyl-3-trifluoromethylcinnamamido)morphinan, 17-cyclopropylmethyl-4,5α-epoxy-3,14β-dihydroxy-5β-methyl-6α-[N-methyl-trans-3-(3-furyl)acrylamido]morphinan, 17-cyclopropylmethyl-4,5α-epoxy-3,14β-dihydroxy-5β-methyl-6α-(N-methyl-3-methylcinnamamido)morphinan, 17-cyclopropylmethyl-4,5α-epoxy-3,14β-dihydroxy-5β-methyl-6α-[N-methyl-3-(4-trifluoromethylphenyl)propiolamido]morphinan, 17-allyl-4,5α-epoxy-3,14β-dihydroxy-5β-methyl-6α-(N-methyl-3-trifluoromethylcinnamamido)morphinan, 17-allyl-4,5α-epoxy-3,14β-dihydroxy-5β-methyl-6α-[N-methyl-trans-3-(3-furyl)acrylamido]morphinan, 17-allyl-4,5α-epoxy-3,14β-dihydroxy-5β-methyl-6α-(N-methyl-3-methylcinnamamido)morphinan, 17-allyl-4,5α-epoxy-3,14β-dihydroxy-5β-methyl-6α-[N-methyl-3-(4-trifluoromethylphenyl)propiolamido]morphinan, 5β,17-dimethyl-4,5α-epoxy-3,14β-dihydroxy-6α-(N-methyl-3-trifluoromethylcinnamamido)morphinan, 5β,17-dimethyl-4,5α-epoxy-3,14β-dihydroxy-6α-[N-methyl-trans-3-(3-furyl)acrylamido]morphinan, 5β,17-dimethyl-4,5α-epoxy-3,14β-dihydroxy-6α-(N-methyl-3-methylcinnamamido)morphinan, 5β,17-dimethyl-4,5α-epoxy-3,14β-dihydroxy-6α-[N-methyl-3-(4-trifluoromethylphenyl)propiolamido]morphinan, 17-phenethyl-4,5α-epoxy-3,14β-dihydroxy-5β-methyl-6α-(N-methyl-3-trifluoromethylcinnamamido)morphinan, 17-phenethyl-4,5α-epoxy-3,14β-dihydroxy-5β-methyl-6α-[N-methyl-trans-3-(3-furyl)acrylamido]morphinan, 17-phenethyl-4,5α-epoxy-3,14β-dihydroxy-5β-methyl-6α-(N-methyl-3-methylcinnamamido)morphinan, 17-phenethyl-4,5α-epoxy-3,14β-dihydroxy-5β-methyl-6α-[N-methyl-3-(4-trifluoromethylphenyl)propiolamido]morphinan, 17-cyclopropylmethyl-7,8-didehydro-4,5α-epoxy-3,14β-dihydroxy-6α-(N-methyl-3-trifluoromethylcinnamamido)morphinan, 17-cyclopropylmethyl-7,8-didehydro-4,5α-epoxy-3,14β-dihydroxy-6α-[N-methyl-trans-3-(3-furyl)acrylamido]morphinan, 17-cyclopropylmethyl-7,8-didehydro-4,5α-epoxy-3,14β-dihydroxy-6α-(N-methyl-3-methylcinnamamido)morphinan, 17-cyclopropylmethyl-7,8-didehydro-4,5α-epoxy-3,14β-dihydroxy-6α-[N-methyl-3-(4-trifluoromethylphenyl)propiolamido]morphinan, 17-allyl-7,8-didehydro-4,5α-epoxy-3,14β-dihydroxy-6α-(N-methyl-3-trifluoromethylcinnamamido)morphinan, 17-allyl-7,8-didehydro-4,5α-epoxy-3,14β-dihydroxy-6α-[N-methyl-trans-3-(3-furyl)acrylamido]morphinan, 17-allyl-7,8-didehydro-4,5α-epoxy-3,14β-dihydroxy-6α-(N-methyl-3-methylcinnamamido)morphinan, 17-allyl-7,8-didehydro-4,5α-epoxy-3,14β-dihydroxy-6α-[N-methyl-3-(4-trifluoromethylphenyl)propiolamido]morphinan, 17-methyl-7,8-didehydro-4,5α-epoxy-3,14β-dihydroxy-6α-(N-methyl-3-trifluoromethylcinnamamido)morphinan, 17-methyl-7,8-didehydro-4,5α-epoxy-3,14β-dihydroxy-6α-[N-methyl-trans-3-(3-furyl)acrylamido]morphinan, 17-methyl-7,8-didehydro-4,5α-epoxy-3,14β-dihydroxy-6α-(N-methyl-3-methylcinnamamido)morphinan, 17-methyl-7,8-didehydro-4,5α-epoxy-3,14β-dihydroxy-6α-[N-methyl-3-(4-trifluoromethylphenyl)propiolamido]morphinan, 17-phenethyl-7,8-didehydro-4,5α-epoxy-3,14β-dihydroxy-6α-(N-methyl-3-trifluoromethylcinnamamido)morphinan, 17-phenethyl-7,8-didehydro-4,5α-epoxy-3,14β-dihydroxy-6α-[N-methyl-trans-3-(3-furyl)acrylamido]morphinan, 17-phenethyl-7,8-didehydro-4,5α-epoxy-3,14β-dihydroxy-6α-(N-methyl-3-methylcinnamamido)morphinan, 17-phenethyl-7,8-didehydro-4,5α-epoxy-3,14β-dihydroxy-6α-[N-methyl-3-(4-trifluoromethylphenyl)propiolamido]morphinan, 17-cyclopropylmethyl-4,5α-epoxy-3-hydroxy-6β-(N-methyl-3-trifluoromethylcinnamamido)morphinan, 17-cyclopropylmethyl-4,5α-epoxy-3-hydroxy-6β-[N-methyl-trans-3-(3-furyl)acrylamido]morphinan, 17-cyclopropylmethyl-4,5α-epoxy-3-hydroxy-6β-(N-methyl-3-methylcinnamamido)morphinan, 17-cyclopropylmethyl-4,5α-epoxy-3-hydroxy-6β-[N-methyl-3-(4-trifluoromethylphenyl)propiolamido]morphinan, 17-allyl-4,5α-epoxy-3-hydroxy-6β-(N-methyl-3-trifluoromethylcinnainamido)morphinan, 17-allyl-4,5α-epoxy-3-hydroxy-6β-[N-methyl-trans-3-(3-furyl)acrylamido]morphinan, 17-allyl-4,5α-epoxy-3-hydroxy-6β-(N-methyl-3-methylcinnamamido)morphinan, 17-allyl-4,5α-epoxy-3-hydroxy-6β-[N-methyl-3-(4-trifluoromethylphenyl)propiolamido]morphinan, 17-methyl-4,5α-epoxy-3-hydroxy-6β-(N-methyl-3-trifluoromethylcinnamamido)morphinan, 17-methyl-4,5α-epoxy-3-hydroxy-6β-[N-methyl-trans-3-(3-furyl)acrylamido]morphinan, 17-methyl-4,5α-epoxy-3-hydroxy-6β-(N-methyl-3-methylcinnamamido)morphinan, 17-methyl-4,5α-epoxy-3-hydroxy-6β-[N-methyl-3-(4-trifluoromethylphenyl)propiolamido]morphinan, 17-phenethyl-4,5α-epoxy-3-hydroxy-6β-(N-methyl-3-trifluoromethylcinnamamido)morphinan, 17-phenethyl-4,5α-epoxy-3-hydroxy-6β-[N-methyl-trans-3-(3-furyl)acrylamido]morphinan, 17-phenethyl-4,5α-epoxy-3-hydroxy-6β-(N-methyl-3-methylcinnamamido)morphinan, 17-phenethyl-4,5α-epoxy-3-hydroxy-6β-[N-methyl-3-(4-trifluoromethylphenyl)propiolamido]morphinan, 17-cyclopropylmethyl-4,5α-epoxy-3-hydroxy-14β-nitro-6β-(N-methyl-3-trifluoromethylcinnamamido)morphinan, 17-cyclopropylmethyl-4,5α-epoxy-3-hydroxy-14β-nitro-6β-[N-methyl-trans-3-(3-furyl)acrylamido]morphinan, 17-cyclopropylmethyl-4,5α-epoxy-3-hydroxy-14β-nitro-6β-(N-methyl-3-methylcinnamamido)morphinan, 17-cyclopropylmethyl-4,5α-epoxy-3-hydroxy-14β-nitro-6β-[N-methyl-3-(4-trifluoromethylphenyl)propiolamido]morphinan, 17-allyl-4,5α-epoxy-3-hydroxy-14β-nitro-6β-(N-methyl-3-trifluoromethylcinnamamido)morphinan, 17-allyl-4,5α-epoxy-3-hydroxy-14β-nitro-6β-[N-methyl-trans-3-(3-furyl)acrylamido]morphinan, 17-allyl-4,5α-epoxy-3-hydroxy-14β-nitro-6β-(N-methyl-3-methylcinnamamido)morphinan, 17-allyl-4,5α-epoxy-3-hydroxy-14β-nitro-6β-[N-methyl-3-(4-trifluoromethylphenyl)propiolamido]morphinan, 17-methyl-4,5α-epoxy-3-hydroxy-14β-nitro-6β-(N-methyl-3-trifluoromethylcinnamamido)morphinan, 17-methyl-4,5α-epoxy-3-hydroxy-14β-nitro-6β-[N-methyl-trans-3-(3-furyl)acrylamido]morphinan, 17-methyl-4,5α-epoxy-3-hydroxy-14β-nitro-6β-(N-methyl-3-methylcinnamamido)morphinan, 17-methyl-4,5α-epoxy-3-hydroxy-14β-nitro-6β-[N-methyl-3-(4-trifluoromethylphenyl)propiolamido]morphinan, 17-phenethyl-4,5α-epoxy-3-hydroxy-14β-nitro-6β-(N-methyl-3-trifluoromethylcinnamamido)morphinan, 17-phenethyl-4,5α-epoxy-3-hydroxy-14β-nitro-6β-[N-methyl-trans-3-(3-furyl)acrylamido]morphinan, 17-phenethyl-4,5α-epoxy-3-hydroxy-14β-nitro-6β-(N-methyl-3-methylcinnamamido)morphinan, 17-phenethyl-4,5α-epoxy-3-hydroxy-14β-nitro-6β-[N-methyl-3-(4-trifluoromethylphenyl)propiolamido]morphinan, 17-cyclopropylmethyl-4,5α-epoxy-3-hydroxy-14β-dimethylamino-6β-(N-methyl-3-trifluoromethylcinnamamido)morphinan, 17-cyclopropylmethyl-4,5α-epoxy-3-hydroxy-14β-dimethylamino-6β-[N-methyl-trans-3-(3-furyl)acrylamido]morphinan, 17-cyclopropylmethyl-4,5α-epoxy-3-hydroxy-14β-dimethylamino-6β-(N-methyl-3-methylcinnamamido)morphinan, 17-cyclopropylmethyl-4,5α-epoxy-3-hydroxy-14β-dimethylamino-6β-[N-methyl-3-(4-trifluoromethylphenyl)propiolamido]morphinan, 17-allyl-4,5α-epoxy-3-hydroxy-14β-dimethylamino-6β-(N-methyl-3-trifluoromethylcinnamamido)morphinan, 17-allyl-4,5α-epoxy-3-hydroxy-14β-dimethylamino-6β-[N-methyl-trans-3-(3-furyl)acrylamido]morphinan, 17-allyl-4,5α-epoxy-3-hydroxy-14β-dimethylamino-6β-(N-methyl-3-methylcinnamamido)morphinan, 17-allyl-4,5α-epoxy-3-hydroxy-14β-dimethylamino-6β-[N-methyl-3-(4-trifluoromethylphenyl)propiolamido]morphinan, 17-methyl-4,5α-epoxy-3-hydroxy-14β-dimethylamino-6β-(N-methyl-3-trifluoromethylcinnamamido)morphinan, 17-methyl-4,5α-epoxy-3-hydroxy-14β-dimethylamino-6β-[N-methyl-trans-3-(3-furyl)acrylamido]morphinan, 17-methyl-4,5α-epoxy-3-hydroxy-14β-dimethylamino-6β-(N-methyl-3-methylcinnamamido)morphinan, 17-methyl-4,5α-epoxy-3-hydroxy-14β-dimethylamino-6β-[N-methyl-3-(4-trifluoromethylphenyl)propiolamido]morphinan, 17-phenethyl-4,5α-epoxy-3-hydroxy-14β-dimethylamino-6β-(N-methyl-3-trifluoromethylcinnamamido)morphinan, 17-phenethyl-4,5α-epoxy-3-hydroxy-14β-dimethylamino-6β-[N-methyl-trans-3-(3-furyl)acrylamido]morphinan, 17-phenethyl-4,5α-epoxy-3-hydroxy-14β-dimethylamino-6β-(N-methyl-3-methylcinnamamido)morphinan, 17-phenethyl-4,5α-epoxy-3-hydroxy-14β-dimethylamino-6β-[N-methyl-3-(4-trifluoromethylphenyl)propiolamido]morphinan, 17-cyclopropylmethyl-4,5α-epoxy-3-hydroxy-14β-methyl-6β-(N-methyl-3-trifluoromethylcinnamamido)morphinan, 17-cyclopropylmethyl-4,5α-epoxy-3-hydroxy-14β-methyl-6β-[N-methyl-trans-3-(3-furyl)acrylamido]morphinan, 17-cyclopropylmethyl-4,5α-epoxy-3-hydroxy-14β-methyl-6β-(N-methyl-3-methylcinnamamido)morphinan, 17-cyclopropylmethyl-4,5α-epoxy-3-hydroxy-14β-methyl-6β-[N-methyl-3-(4-trifluoromethylphenyl)propiolamido]morphinan, 17-allyl-4,5α-epoxy-3-hydroxy-14β-methyl-6β-(N-methyl-3-trifluoromethylcinnamamido)morphinan, 17-allyl-4,5α-epoxy-3-hydroxy-14β-methyl-6β-[N-methyl-trans-3-(3-furyl)acrylamido]morphinan, 17-allyl-4,5α-epoxy-3-hydroxy-14β-methyl-6β-(N-methyl-3-methylcinnamamido)morphinan, 17-allyl-4,5α-epoxy-3-hydroxy-14β-methyl-6β-[N-methyl-3-(4-trifluoromethylphenyl)propiolamido]morphinan, 14β,17-dimethyl-4,5α-epoxy-3-hydroxy-6β-(N-methyl-3-trifluoromethylcinnamamido)morphinan, 14β,17-dimethyl-4,5α-epoxy-3-hydroxy-6β-[N-methyl-trans-3-(3-furyl)acrylamido]morphinan, 14β,17-dimethyl-4,5α-epoxy-3-hydroxy-6β-(N-methyl-3-methylcinnamamido)morphinan, 14β,17-dimethyl-4,5α-epoxy-3-hydroxy-6β-[N-methyl-3-(4-trifluoromethylphenyl)propiolamido]morphinan, 17-phenethyl-4,5α-epoxy-3-hydroxy-14β-methyl-6β-(N-methyl-3-trifluoromethylcinnamamido)morphinan, 17-phenethyl-4,5α-epoxy-3-hydroxy-14β-methyl-6β-[N-methyl-trans-3-(3-furyl)acrylamido]morphinan, 17-phenethyl-4,5α-epoxy-3-hydroxy-14β-methyl-6β-(N-methyl-3-methylcinnamamido)morphinan, 17-phenethyl-4,5α-epoxy-3-hydroxy-14β-methyl-6β-[N-methyl-3-(4-trifluoromethylphenyl)propiolamido]morphinan, 17-cyclopropylmethyl-3,14β-dihydroxy-6β-(N-methyl-3-trifluoromethylcinnamamido)morphinan, 17-cyclopropylmethyl-3,14β-dihydroxy-6β-[N-methyl-trans-3-(3-furyl)acrylamido]morphinan, 17-cyclopropylmethyl-3,14β-dihydroxy-6β-(N-methyl-3-methylcinnamamido)morphinan, 17-cyclopropylmethyl-3,14β-dihydroxy-6β-[N-methyl-3-(4-trifluoromethylphenyl)propiolamido]morphinan, 17-allyl-3,14β-dihydroxy-6β-(N-methyl-3-trifluoromethylcinnamamido)morphinan, 17-allyl-3,14β-dihydroxy-6β-[N-methyl-trans-3-(3-furyl)acrylamido]morphinan, 17-allyl-3,14β-dihydroxy-6β-(N-methyl-3-methylcinnamamido)morphinan, 17-allyl-3,14β-dihydroxy-6β-[N-methyl-3-(4-trifluoromethylphenyl)propiolamido]morphinan, 17-methyl-3,14β-dihydroxy-6β-(N-methyl-3-trifluoromethylcinnamamido)morphinan, 17-methyl-3,14β-dihydroxy-6β-[N-methyl-trans-3-(3-furyl)acrylamido]morphinan, 17-methyl-3,14β-dihydroxy-6β-(N-methyl-3-methylcinnamamido)morphinan, 17-methyl-3,14β-dihydroxy-6β-[N-methyl-3-(4-trifluoromethylphenyl)propiolamido]morphinan, 17-phenethyl-3,14β-dihydroxy-6β-(N-methyl-3-trifluoromethylcinnamamido)morphinan, 17-phenethyl-3,14β-dihydroxy-6β-[N-methyl-trans-3-(3-furyl)acrylamido]morphinan, 17-phenethyl-3,14β-dihydroxy-6β-(N-methyl-3-methylcinnamamido)morphinan, 17-phenethyl-3,14β-dihydroxy-6β-[N-methyl-3-(4-trifluoromethylphenyl)propiolamido]morphinan, 17-cyclopropylmethyl-3,14β-dihydroxy-4-methoxy-6β-(N-methyl-3-trifluoromethylcinnamamido)morphinan, 17-cyclopropylmethyl-3,14β-dihydroxy-4-methoxy-6β-[N-methyl-trans-3-(3-furyl)acrylamido]morphinan, 17-cyclopropylmethyl-3,14β-dihydroxy-4-methoxy-6β-(N-methyl-3-methylcinnamamido)morphinan, 17-cyclopropylmethyl-3,14β-dihydroxy-4-methoxy-6β-[N-methyl-3-(4-trifluoromethylphenyl)propiolamido]morphinan, 17-allyl-3,14β-dihydroxy-4- methoxy-6β-(N-methyl-3-trifluoromethylcinnamamido)morphinan, 17-allyl-3,14β-dihydroxy-4-methoxy-6β-[N-methyl-trans-3-(3-furyl)acrylamido]morphinan, 17-allyl-3,14β-dihydroxy-4-methoxy-6β-(N-methyl-3-methylcinnamamido)morphinan, 17-allyl-3,14β-dihydroxy-4-methoxy-6β-[N-methyl-3-(4-trifluoromethylphenyl)propiolamido]morphinan, 17-methyl-3,14β-dihydroxy-4-methoxy-6β-(N-methyl-3-trifluoromethylcinnamamido)morphinan, 17-methyl-3,14β-dihydroxy-4-methoxy-6β-[N-methyl-trans-3-(3-furyl)acrylamido]morphinan, 17-methyl-3,14β-dihydroxy-4-methoxy-6β-(N-methyl-3-methylcinnamamido)morphinan, 17-methyl-3,14β-dihydroxy-4-methoxy-6β-[N-methyl-3-(4-trifluoromethylphenyl)propiolamido]morphinan, 17-phenethyl-3,14β-dihydroxy-4-methoxy-6β-(N-methyl-3-trifluoromethylcinnamamido)morphinan, 17-phenethyl-3,14β-dihydroxy-4-methoxy-6β-[N-methyl-trans-3-(3-furyl)acrylamido]morphinan, 17-phenethyl-3,14β-dihydroxy-4-methoxy-6β-(N-ethyl-3-methylcinnamamido)morphinan, 17-phenethyl-3,14β-dihydroxy-4-methoxy-6β-[N-methyl-3-(4-trifluoromethylphenyl)propiolamido]morphinan, 17-cyclopropylmethyl-4,5α-epoxy-3,14β-dihydroxy-5β-methyl-6β-(N-methyl-3-trifluoromethylcinnamamido)morphinan, 17-cyclopropylmethyl-4,5α-epoxy-3,14β-dihydroxy-5β-methyl-6β-[N-methyl-trans-3-(3-furyl)acrylamido]morphinan, 17-cyclopropylmethyl-4,5α-epoxy-3,14β-dihydroxy-5β-methyl-6β-(N-methyl-3-methylcinnamamido)morphinan, 17-cyclopropylmethyl-4,5α-epoxy-3,14β-dihydroxy-5β-methyl-6β-[N-methyl-3-(4-trifluoromethylphenyl)propiolamido]morphinan, 17-allyl-4,5α-epoxy-3,14β-dihydroxy-5β-methyl-6β-(N-methyl-3-trifluoromethylcinnamamido)morphinan, 17-allyl-4,5α-epoxy-3,14β-dihydroxy-5β-methyl-6β-[N-methyl-trans-3-(3-furyl)acrylamido]morphinan, 17-allyl-4,5α-epoxy-3,14β-dihydroxy-5β-methyl-6β-(N-methyl-3-methylcinnamamido)morphinan, 17-allyl-4,5α-epoxy-3,14β-dihydroxy-5β-methyl-6β-[N-methyl-3-(4-trifluoromethylphenyl)propiolamido]morphinan, 5β,17-dimethyl-4,5α-epoxy-3,14β-dihydroxy-6β-(N-methyl-3-trifluoromethylcinnamamido)morphinan, 5β,17-dimethyl-4,5α-epoxy-3,14β-dihydroxy-6β-[N-methyl-trans-3-(3-furyl)acrylamido]morphinan, 5β,17-dimethyl-4,5α-epoxy-3,14β-dihydroxy-6β-(N-methyl-3-methylcinnamamido)morphinan, 5β,17-dimethyl-4,5α-epoxy-3,14β-dihydroxy-6β-[N-methyl-3-(4-trifluoromethylphenyl)propiolamido]morphinan, 17-phenethyl-4,5α-epoxy-3,14β-dihydroxy-5β-methyl-6β-(N-methyl-3-trifluoromethylcinnamamido)morphinan, 17-phenethyl-4,5α-epoxy-3,14β-dihydroxy-5β-methyl-6β-[N-methyl-trans-3-(3-furyl)acrylamido]morphinan, 17-phenethyl-4,5α-epoxy-3,14β-dihydroxy-5β-methyl-6β-(N-methyl-3-methylcinnamamido)morphinan, 17-phenethyl-4,5α-epoxy-3,14β-dihydroxy-5β-methyl-6β-[N-methyl-3-(4-trifluoromethylphenyl)propiolamido]morphinan, 17-cyclopropylmethyl-7,8-didehydro-4,5α-epoxy-3,14β-dihydroxy-6β-(N-methyl-3-trifluoromethylcinnamamido)morphinan, 17-cyclopropylmethyl-7,8-didehydro-4,5α-epoxy-3,14β-dihydroxy-6β-[N-methyl-trans-3-(3-furyl)acrylamido]morphinan, 17-cyclopropylmethyl-7,8-didehydro-4,5α-epoxy-3,14β-dihydroxy-6β-(N-methyl-3-methylcinnamamido)morphinan, 17-cyclopropylmethyl-7,8-didehydro-4,5α-epoxy-3,14β-dihydroxy-6β-[N-methyl-3-(4-trifluoromethylphenyl)propiolamido]morphinan, 17-allyl-7,8-didehydro-4,5α-epoxy-3,14β-dihydroxy-6β-(N-methyl-3-trifluoromethylcinnamamido)morphinan, 17-allyl-7,8-didehydro-4,5α-epoxy-3,14β-dihydroxy-6β-[N-methyl-trans-3-(3-furyl)acrylamido]morphinan, 17-allyl-7,8-didehydro-4,5α-epoxy-3,14β-dihydroxy-6β-(N-methyl-3-methylcinnamamido)morphinan, 17-allyl-7,8-didehydro-4,5α-epoxy-3,14β-dihydroxy-6β-[N-methyl-3-(4-trifluoromethylphenyl)propiolamido]morphinan, 17-methyl-7,8-didehydro-4,5α-epoxy-3,14β-dihydroxy-6β-(N-methyl-3-trifluoromethylcinnamamido)-morphinan, 17-methyl-7,8-didehydro-4,5α-epoxy-3,14β-dihydroxy-6β-[N-methyl-trans-3-(3-furyl)acrylamido]morphinan, 17-methyl-7,8-didehydro-4,5α-epoxy-3,14β-dihydroxy-6β-(N-methyl-3-methylcinnamamido)morphinan, 17-methyl-7,8-didehydro-4,5α-epoxy-3,14β-dihydroxy-6β-[N-methyl-3-(4-trifluoromethylphenyl)propiolamido]-morphinan, 17-phenethyl-7,8-didehydro-4,5α-epoxy-3,14β-dihydroxy-6β-(N-methyl-3-trifluoromethylcinnamamido)morphinan, 17-phenethyl-7,8-didehydro-4,5α-epoxy-3,14β-dihydroxy-6β-[N-methyl-trans-3-(3-furyl)acrylamido]morphinan, 17-phenethyl-7,8-didehydro-4,5α-epoxy-3,14β-dihydroxy-6β-(N-methyl-3-methylcinnamamido)morphinan, 17-phenethyl-7,8-didehydro-4,5α-epoxy-3,14β-dihydroxy-6β-[N-methyl-3-(4-trifluoromethylphenyl)propiolamido]morphinan, 17-cyclopropylmethyl-4,5α-epoxy-3,14β-dihydroxy-6α-[N-methyl-3-(3-methylphenyl)propiolamido]morphinan, 17-allyl-4,5α-epoxy-3,14β-dihydroxy-6α-[N-methyl-3-(3-methylphenyl)propiolamido]morphinan, 17-methyl-4,5α-epoxy-3,14β-dihydroxy-6α-[N-methyl-3-(3-methylphenyl)propiolamido]morphinan, 17-phenethyl-4,5α-epoxy-3,14β-dihydroxy-6α-[N-methyl-3-(3-methylphenyl)propiolamido]morphinan, 17-cyclopropylmethyl-4,5α-epoxy-14β-acetoxy-3-hydroxy-6α-[N-methyl-3-(3-methylphenyl)propiolamido]morphinan, 17-allyl-4,5α-epoxy-14β-acetoxy-3-hydroxy-6α-[N-methyl-3-(3-methylphenyl)propiolamido]morphinan, 17-methyl-4,5α-epoxy-14β-acetoxy-3-hydroxy-6α-[N-methyl-3-(3-methylphenyl)propiolamido]morphinan, 17-phenethyl-4,5α-epoxy-14β-acetoxy-3-hydroxy-6α-[N-methyl-3-(3-methylphenyl)propiolamido]morphinan, 17-cyclopropylmethyl-4,5α-epoxy-14β-hydroxy-6α-[N-methyl-3-(3-methylphenyl)propiolamido]morphinan, 17-allyl-4,5α-epoxy-14β-hydroxy-6α-[N-methyl-3-(3-methylphenyl)propiolamido]morphinan, 17-methyl-4,5α-epoxy-14β-hydroxy-6α-[N-methyl-3-(3-methylphenyl)propiolamido]morphinan, 17-phenethyl-4,5α-epoxy-14β-hydroxy-6α-[N-methyl-3-(3-methylphenyl)propiolamido]morphinan, 17-cyclopropylmethyl-4,5α-epoxy-14β-acetoxy-6α-[N-methyl-3-(3-methylphenyl)propiolamido]morphinan, 17-allyl-4,5α-epoxy-14β-acetoxy-6α-[N-methyl-3-(3-methylphenyl)propiolamido]morphinan, 17-methyl-4,5α-epoxy-14β-acetoxy-6α-[N-methyl-3-(3-methylphenyl)propiolamido]morphinan, 17-phenethyl-4,5α-epoxy- 14β-acetoxy-6α-[N-methyl-3-(3-methylphenyl) propiolamido]morphinan, 17-cyclopropylmethyl-4,5α-epoxy-14β-hydroxy-3-methoxy-6α-[N-methyl-3-(3-methylphenyl)propiolamido]morphinan, 17-allyl-4,5α-epoxy-14β-hydroxy-3-methoxy-6α-[N-methyl-3-(3-methylphenyl)propiolamido]morphinan, 17-methyl-4,5α-epoxy-14β-hydroxy-3-methoxy-6α-[N-methyl-3-(3-methylphenyl)propiolamido]morphinan, 17-phenethyl-4,5α-epoxy-14β-hydroxy-3-methoxy-6α-[N-methyl-3-(3-methylphenyl)propiolamido] morphinan, 17-cyclopropylmethyl-4,5α-epoxy-14β-acetoxy-3-methoxy-6α-[N-methyl-3-(3-methylphenyl) propiolamido]morphinan, 17-allyl-4,5α-epoxy- 14β-acetoxy-3-methoxy-6α-[N-methyl-3-(3-methylphenyl) propiolamido]morphinan, 17-methyl-4,5α-epoxy-14β-acetoxy-3-methoxy-6α-[N-methyl-3-(3-methylphenyl) propiolamido]morphinan, 17-phenethyl-4,5α-epoxy-14β-acetoxy-3-methoxy-6α-[N-methyl-3-(3-methylphenyl)propiolamido]morphinan, 17-cyclopropylmethyl-4,5α-epoxy-14β-hydroxy-3-acetoxy-6α-[N-methyl-3-(3-methylphenyl) propiolamido]morphinan, 17-allyl-4,5α-epoxy-14β-hydroxy-3-acetoxy-6α-[N-methyl-3-(3-methylphenyl) propiolamido]morphinan, 17-methyl-4,5α-epoxy-14β-hydroxy-3-acetoxy-6α-[N-methyl-3-(3-methylphenyl) propiolamido]morphinan, 17-phenethyl-4,5α-epoxy-14β-hydroxy-3-acetoxy-6α-[N-methyl-3-(3-methylphenyl)propiolamido]morphinan, 17-cyclopropylmethyl-4,5α-epoxy-3,14β-diacetoxy-6α-[N-methyl-3-(3-methylphenyl)propiolamido] morphinan, 17-allyl-4,5α-epoxy-3,14β-diacetoxy-6α-[N-methyl-3-(3-methylphenyl)propiolamido] morphinan, 17-methyl-4,5α-epoxy-3,14β-diacetoxy-6α-[N-methyl-3-(3-methylphenyl)propiolamido] morphinan, 17-phenethyl-4,5α-epoxy-3,14β-diacetoxy-6α-[N-methyl-3-(3-methylphenyl) propiolamido]morphinan, 17-cyclopropylmethyl-4,5α-epoxy-3,14β-dihydroxy-6α-[N-isobutyl-3-(3-methylphenyl)propiolamido]morphinan, 17-allyl-4,5α-epoxy-3,14β-dihydroxy-6α-[N-isobutyl-3-(3-methylphenyl)propiolamido]morphinan, 17-methyl-4,5α-epoxy-3,14β-dihydroxy-6α-[N-isobutyl-3-(3-methylphenyl)propiolamido]morphinan, 17-phenethyl-4,5α-epoxy-3,14β-dihydroxy-6α-[N-isobutyl-3-(3-methylphenyl)propiolamido]morphinan, 17-cyclopropylmethyl-4,5α-epoxy-14β-acetoxy-3-hydroxy-6α-[N-isobutyl-3-(3-methylphenyl) propiolamido]morphinan, 17-allyl-4,5α-epoxy-14β-acetoxy-3-hydroxy-6α-[N-isobutyl-3-(3-methylphenyl)propiolamido]morphinan, 17-methyl-4,5α-epoxy-14β-acetoxy-3-hydroxy-6α-[N-isobutyl-3-(3-methylphenyl)propiolamido]morphinan, 17-phenethyl-4,5α-epoxy-14β-acetoxy-3-hydroxy-6α-[N-isobutyl-3-(3-methylphenyl)propiolamido] morphinan, 17-cyclopropylmethyl-4,5α-epoxy-14β-hydroxy-6α-[N-isobutyl-3-(3-methylphenyl) propiolamido]morphinan, 17-allyl-4,5α-epoxy-14β-hydroxy-6α-[N-isobutyl-3-(3-methylphenyl) propiolamido]morphinan, 17-methyl-4,5α-epoxy-14β-hydroxy-6α-[N-isobutyl-3-(3-methylphenyl) propiolamido]morphinan, 17-phenethyl-4,5α-epoxy-14β-hydroxy-6α-[N-isobutyl-3-(3-methylphenyl) propiolamido]morphinan, 17-cyclopropylmethyl-4,5α-epoxy-14β-acetoxy-6α-[N-isobutyl-3-(3-methylphenyl)propiolamido]morphinan, 17-allyl-4,5α-epoxy-14β-acetoxy-6α-[N-isobutyl-3-(3-methylphenyl)propiolamido]morphinan, 17-methyl-4,5α-epoxy-14β-acetoxy-6α-[N-isobutyl-3-(3-methylphenyl)propiolamido]morphinan, 17-phenethyl-4,5α-epoxy-14β-acetoxy-6α-[N-isobutyl-3-(3-methylphenyl)propiolamido]morphinan, 17-cyclopropylmethyl-4,5α-epoxy-14β-hydroxy-3-methoxy-6α-[N-isobutyl-3-(3-methylphenyl) propiolamido]morphinan, 17-allyl-4,5α-epoxy-14β-hydroxy-3-methoxy-6α-[N-isobutyl-3-(3-methylphenyl)propiolamido]morphinan, 17-methyl-4,5α-epoxy-14β-hydroxy-3-methoxy-6α-[N-isobutyl-3-(3-methylphenyl)propiolamido]morphinan, 17-phenethyl-4,5α-epoxy-14β-hydroxy-3-methoxy-6α-[N-isobutyl-3-(3-methylphenyl)propiolamido] morphinan, 17-cyclopropylmethyl-4,5α-epoxy-14β-acetoxy-3-methoxy-6α-[N-isobutyl-3-(3-methylphenyl)propiolamido]morphinan, 17-allyl-4,5α-epoxy-14β-acetoxy-3-methoxy-6α-[N-isobutyl-3-(3-methylphenyl)propiolamido]morphinan, 17-methyl-4,5α-epoxy-14β-acetoxy-3-methoxy-6α-[N-isobutyl-3-(3-methylphenyl)propiolamido]morphinan, 17-phenethyl-4,5α-epoxy-14β-acetoxy-3-methoxy-6α-[N-isobutyl-3-(3-methylphenyl)propiolamido] morphinan, 17-cyclopropylmethyl-4,5α-epoxy-14β-hydroxy-3-acetoxy-6α-[N-isobutyl-3-(3-methylphenyl)propiolamido]morphinan, 17-allyl-4,5α-epoxy-14β-hydroxy-3-acetoxy-6α-[N-isobutyl-3-(3-methylphenyl)propiolamido]morphinan, 17-methyl-4,5α-epoxy-14β-hydroxy-3-acetoxy-6α-[N-isobutyl-3-(3-methylphenyl)propiolamido]morphinan, 17-phenethyl-4,5α-epoxy-14β-hydroxy-3-acetoxy-6α-[N-isobutyl-3-(3-methylphenyl)propiolamido] morphinan, 17-cyclopropylmethyl-4,5α-epoxy-3,14β-diacetoxy-6α-[N-isobutyl-3-(3-methylphenyl) propiolamido]morphinan, 17-allyl-4,5α-epoxy-3,14β-diacetoxy-6α-[N-isobutyl-3-(3-methylphenyl) propiolamido]morphinan, 17-methyl-4,5α-epoxy-3,14β-diacetoxy-6α-[N-isobutyl-3-(3 -methylphenyl) propiolamido]morphinan, 17-phenethyl-4,5α-epoxy-3,14β-diacetoxy-6α-[N-isobutyl-3-(3-methylphenyl) propiolamido]morphinan, 17-cyclopropylmethyl-4,5α-epoxy-3,14β-dihydroxy-6β-[N-methyl-3-(3-methylphenyl)propiolamido]morphinan, 17-allyl-4,5α-epoxy-3,14β-dihydroxy-6β-[N-methyl-3-(3-methylphenyl)propiolamido]morphinan, 17-methyl-4,5α-epoxy-3,14β-dihydroxy-6β-[N-methyl-3-(3-methylphenyl)propiolamido]morphinan, 17-phenethyl-4,5α-epoxy-3,14β-dihydroxy-6β-[N-methyl-3-(3-methylphenyl)propiolamido]morphinan, 17-cyclopropylmethyl-4,5α-epoxy-14β-acetoxy-3-hydroxy-6β-[N-methyl-3-(3-methylphenyl) propiolamido]morphinan, 17-allyl-4,5α-epoxy-14β-acetoxy-3-hydroxy-6β-[N-methyl-3-(3-methylphenyl) propiolamido]morphinan, 17-methyl-4,5α-epoxy-14β-acetoxy-3-hydroxy-6β-[N-methyl-3-(3-methylphenyl) propiolamido]morphinan, 17-phenethyl-4,5α-epoxy-14β-acetoxy-3-hydroxy-6β-[N-methyl-3-(3-methylphenyl)propiolamido]morphinan, 17-cyclopropylmethyl-4,5α-epoxy-14β-hydroxy-6β-[N-methyl-3-(3-methylphenyl)propiolamido] morphinan, 17-allyl-4,5α-epoxy-14β-hydroxy-6β-[N-methyl-3-(3-methylphenyl)propiolamido]morphinan, 17-methyl-4,5α-epoxy-14β-hydroxy-6β-[N-methyl-3-(3-methylphenyl)propiolamido]morphinan, 17-phenethyl-4,5α-epoxy-14β-hydroxy-6β-[N-methyl-3-(3-methylphenyl)propiolamido]morphinan, 17-cyclopropylmethyl-4,5α-epoxy-14β-acetoxy-6β-[N-methyl-3-(3-methylphenyl)propiolamido]

morphinan, 17-allyl-4,5α-epoxy-14β-acetoxy-6β-[N-methyl-3-(3-methylphenyl)propiolamido]morphinan, 17-methyl-4,5α-epoxy-14β-acetoxy-6β-[N-methyl-3-(3-methylphenyl)propiolamido]morphinan, 17-phenethyl-4,5α-epoxy-14β-acetoxy-6β-[N-methyl-3-(3-methylphenyl)propiolamido]morphinan, 17-cyclopropylmethyl-4,5α-epoxy-14β-hydroxy-3-methoxy-6β-[N-methyl-3-(3-methylphenyl)propiolamido]morphinan, 17-allyl-4,5α-epoxy-14β-hydroxy-3-methoxy-6β-[N-methyl-3-(3-methylphenyl)propiolamido]morphinan, 17-methyl-4,5α-epoxy-14β-hydroxy-3-methoxy-6β-[N-methyl-3-(3-methylphenyl)propiolamido]morphinan, 17-phenethyl-4,5α-epoxy-14β-hydroxy-3-methoxy-6β-[N-methyl-3-(3-methylphenyl)propiolamido]morphinan, 17-cyclopropylmethyl-4,5α-epoxy-14β-acetoxy-3-methoxy-6β-[N-methyl-3-(3-methylphenyl)propiolamido]morphinan, 17-allyl-4,5α-epoxy-14β-acetoxy-3-methoxy-6β-[N-methyl-3-(3-methylphenyl)propiolamido]morphinan, 17-methyl-4,5α-epoxy-14β-acetoxy-3-methoxy-6β-[N-methyl-3-(3-methylphenyl)propiolamido]morphinan, 17-phenethyl-4,5α-epoxy-14β-acetoxy-3-methoxy-6β-[N-methyl-3-(3-methylphenyl)propiolamido]morphinan, 17-cyclopropylmethyl-4,5α-epoxy-14β-hydroxy-3-acetoxy-6β-[N-methyl-3-(3-methylphenyl)propiolamido]morphinan, 17-allyl-4,5α-epoxy-14β-hydroxy-3-acetoxy-6β-[N-methyl-3-(3-methylphenyl)propiolamido]morphinan, 17-methyl-4,5α-epoxy-14β-hydroxy-3-acetoxy-6β-[N-methyl-3-(3-methylphenyl)propiolamido]morphinan, 17-phenethyl-4,5α-epoxy-14β-hydroxy-3-acetoxy-6β-[N-methyl-3-(3-methylphenyl)propiolamido]morphinan, 17-cyclopropylmethyl-4,5α-epoxy-3,14β-diacetoxy-6β-[N-methyl-3-(3-methylphenyl)propiolamido]morphinan, 17-allyl-4,5α-epoxy-3,14β-diacetoxy-6β-[N-methyl-3-(3-methylphenyl)propiolamido]morphinan, 17-methyl-4,5α-epoxy-3,14β-diacetoxy-6β-[N-methyl-3-(3-methylphenyl)propiolamido]morphinan, 17-phenethyl-4,5α-epoxy-3,14β-diacetoxy-6β-[N-methyl-3-(3-methylphenyl)propiolamido]morphinan, 17-cyclopropylmethyl-4,5α-epoxy-3,14β-dihydroxy-6β-[N-isobutyl-3-(3-methylphenyl)propiolamido]morphinan, 17-allyl-4,5α-epoxy-3,14β-dihydroxy-6β-[N-isobutyl-3-(3-methylphenyl)propiolamido]morphinan, 17-methyl-4,5α-epoxy-3,14β-dihydroxy-6β-[N-isobutyl-3-(3-methylphenyl)propiolamido]morphinan, 17-phenethyl-4,5α-epoxy-3,14β-dihydroxy-6β-[N-isobutyl-3-(3-methylphenyl)propiolamido]morphinan, 17-cyclopropylmethyl-4,5α-epoxy-14β-acetoxy-3-hydroxy-6β-[N-isobutyl-3-(3-methylphenyl)propiolamido]morphinan, 17-allyl-4,5α-epoxy-14β-acetoxy-3-hydroxy-6β-[N-isobutyl-3-(3-methylphenyl)propiolamido]morphinan, 17-methyl-4,5α-epoxy-14β-acetoxy-3-hydroxy-6β-[N-isobutyl-3-(3-methylphenyl)propiolamido]morphinan, 17-phenethyl-4,5α-epoxy-14β-acetoxy-3-hydroxy-6β-[N-isobutyl-3-(3-methylphenyl)propiolamido]morphinan, 17-cyclopropylmethyl-4,5α-epoxy-14β-hydroxy-6β-[N-isobutyl-3-(3-methylphenyl)propiolamido]morphinan, 17-allyl-4,5α-epoxy-14β-hydroxy-6β-[N-isobutyl-3-(3-methylphenyl)propiolamido]morphinan, 17-methyl-4,5α-epoxy-14β-hydroxy-6β-[N-isobutyl-3-(3-methylphenyl)propiolamido]morphinan, 17-phenethyl-4,5α-epoxy-14β-hydroxy-6β-[N-isobutyl-3-(3-methylphenyl)propiolamido]morphinan, 17-cyclopropylmethyl-4,5α-epoxy-14β-acetoxy-6β-[N-isobutyl-3-(3-methylphenyl)propiolamido]morphinan, 17-allyl-4,5α-epoxy-14β-acetoxy-6β-[N-isobutyl-3-(3-methylphenyl)propiolamido]morphinan, 17-methyl-4,5α-epoxy-14β-acetoxy-6β-[N-isobutyl-3-(3-methylphenyl)propiolamido]morphinan, 17-phenethyl-4,5α-epoxy-14β-acetoxy-6β-[N-isobutyl-3-(3-methylphenyl)propiolamido]morphinan, 17-cyclopropylmethyl-4,5α-epoxy-14β-hydroxy-3-methoxy-6β-[N-isobutyl-3-(3-methylphenyl)propiolamido]morphinan, 17-allyl-4,5α-epoxy-14β-hydroxy-3-methoxy-6β-[N-isobutyl-3-(3-methylphenyl)propiolamido)morphinan, 17-methyl-4,5α-epoxy-14β-hydroxy-3-methoxy-6β-[N-isobutyl-3-(3-methylphenyl)propiolamido]morphinan, 17-phenethyl-4,5α-epoxy-14β-hydroxy-3-methoxy-6β-[N-isobutyl-3-(3-methylphenyl)propiolamido]morphinan, 17-cyclopropylmethyl-4,5α-epoxy-14β-acetoxy-3-methoxy-6β-[N-isobutyl-3-(3-methylphenyl)propiolamido]morphinan, 17-allyl-4,5α-epoxy-14β-acetoxy-3-methoxy-6β-[N-isobutyl-3-(3-methylphenyl)propiolamido]morphinan, 17-methyl-4,5α-epoxy-14β-acetoxy-3-methoxy-6β-[N-isobutyl-3-(3-methylphenyl)propiolamido]morphinan, 17-phenethyl-4,5α-epoxy-14β-acetoxy-3-methoxy-6β-[N-isobutyl-3-(3-methylphenyl)propiolamido]morphinan, 17-cyclopropylmethyl-4,5α-epoxy-14β-hydroxy-3-acetoxy-6β-[N-isobutyl-3-(3-methylphenyl)propiolamido]morphinan, 17-allyl-4,5α-epoxy-14β-hydroxy-3-acetoxy-6β-[N-isobutyl-3-(3-methylphenyl)propiolamido]morphinan, 17-methyl-4,5α-epoxy-14β-hydroxy-3-acetoxy-6β-[N-isobutyl-3-(3-methylphenyl)propiolamido]morphinan, 17-phenethyl-4,5α-epoxy-14β-hydroxy-3-acetoxy-6β-[N-isobutyl-3-(3-methylphenyl)propiolamido]morphinan, 17-cyclopropylmethyl-4,5α-epoxy-3,14β-diacetoxy-6β-[N-isobutyl-3-(3-methylphenyl)propiolamido]morphinan, 17-allyl-4,5α-epoxy-3,14β-diacetoxy-6β-[N-isobutyl-3-(3-methylphenyl)propiolamido]morphinan, 17-methyl-4,5α-epoxy-3,14β-diacetoxy-6β-[N-isobutyl-3-(3-methylphenyl)propiolamido]morphinan, 17-phenethyl-4,5α-epoxy-3,14β-diacetoxy-6β-[N-isobutyl-3-(3-methylphenyl)propiolamido]morphinan, 17-cyclopropylmethyl-4,5α-epoxy-3-hydroxy-6α-[N-methyl-3-(3-methylphenyl)propiolamido]morphinan, 17-allyl-4,5α-epoxy-3-hydroxy-6α-[N-methyl-3-(3-methylphenyl)propiolamido]morphinan, 17-methyl-4,5α-epoxy-3-hydroxy-6α-[N-methyl-3-(3-methylphenyl)propiolamido]morphinan, 17-phenethyl-4,5α-epoxy-3-hydroxy-6α-[N-methyl-3-(3-methylphenyl)propiolamido]morphinan, 17-cyclopropylmethyl-4,5α-epoxy-3-hydroxy-14β-nitro-6α-[N-methyl-3-(3-methylphenyl)propiolamido]morphinan, 17-allyl-4,5α-epoxy-3-hydroxy-14β-nitro-6α-[N-methyl-3-(3-methylphenyl)propiolamido]morphinan, 17-methyl-4,5α-epoxy-3-hydroxy-14β-nitro-6α-[N-methyl-3-(3-methylphenyl)propiolamido]morphinan, 17-phenethyl-4,5α-epoxy-3-hydroxy-14β-nitro-6α-[N-methyl-3-(3-methylphenyl)propiolamido]morphinan, 17-cyclopropylmethyl-4,5α-epoxy-3-hydroxy-14β-dimethylamino-6α-[N-methyl-3-(3-methylphenyl)propiolamido]morphinan, 17-allyl-4,5α-epoxy-3-hydroxy-14β-dimethylamino-6α-[N-methyl-3-(3-methylphenyl)propiolamido]morphinan, 17-methyl-4,5α-epoxy-3-hydroxy-14β-dimethylamino-6α-[N- methyl-3-(3-methylphenyl)propiolamido]morphinan, 17-phenethyl-4,5α-epoxy-3-hydroxy-14β-dimethylamino-6α-[N-methyl-3-(3-methylphenyl)propiolamido]morphinan, 17-cyclopropylmethyl-4,5α-epoxy-3-hydroxy-14β-methyl-6α-[N-methyl-3-(3-methylphenyl)propiolamido]morphinan, 17-allyl-4,5α-epoxy-3-hydroxy-14β-methyl-6α-[N-methyl-3-(3-methylphenyl)propiolamido]morphinan, 14β,17-dimethyl-4,5α-epoxy-3-hydroxy-6α-[N-methyl-3-(3-methylphenyl)propiolamido]morphinan, 17-phenethyl-4,5α-epoxy-3-hydroxy-14β-methyl-6α-[N-methyl-3-(3-methylphenyl)propiolamido]morphinan, 17-cyclopropylmethyl-3,14β-dihydroxy-6α-[N-methyl-3-(3-methylphenyl)propiolamido]morphinan, 17-allyl-3,14β-dihydroxy-6α-[N-methyl-3-(3-methylphenyl)propiolamido]morphinan, 17-methyl-3,14β-dihydroxy-6α-[N-methyl-3-(3-methylphenyl)propiolamido]morphinan, 17-phenethyl-3,14β-dihydroxy-6α-[N-methyl-3-(3-methylphenyl)propiolamido]morphinan, 17-cyclopropylmethyl-3,14β-dihydroxy-4-methoxy-6α-[N-methyl-3-(3-methylphenyl)propiolamido]morphinan, 17-allyl-3,14β-dihydroxy-4-methoxy-6α-[N-methyl-3-(3-methylphenyl)propiolamido]morphinan, 17-methyl-3,14β-dihydroxy-4-methoxy-6α-[N-methyl-3-(3-methylphenyl)propiolamido]morphinan, 17-phenethyl-3,14β-dihydroxy-4-methoxy-6α-[N-methyl-3-(3-methylphenyl)propiolamido]morphinan, 17-cyclopropylmethyl-4,5α-epoxy-3,14β-dihydroxy-5β-methyl-6α-[N-methyl-3-(3-methylphenyl)propiolamido]morphinan, 17-allyl-4,5α-epoxy-3,14β-dihydroxy-5β-methyl-6α-[N-methyl-3-(3-methylphenyl)propiolamido]morphinan, 5β,17-dimethyl-4,5α-epoxy-3,14β-dihydroxy-6α-[N-methyl-3-(3-methylphenyl)propiolamido]morphinan, 17-phenethyl-4,5α-epoxy-3,14β-dihydroxy-5β-methyl-6α-[N-methyl-3-(3-methylphenyl)propiolamido]morphinan, 17-cyclopropylmethyl-7,8-didehydro-4,5α-epoxy-3,14β-dihydroxy-6α-[N-methyl-3-(3-methylphenyl)propiolamido]morphinan, 17-allyl-7,8-didehydro-4,5α-epoxy-3,14β-dihydroxy-6α-[N-methyl-3-(3-methylphenyl)propiolamido]morphinan, 17-methyl-7,8-didehydro-4,5α-epoxy-3,14β-dihydroxy-6α-[N-methyl-3-(3-methylphenyl)propiolamido]morphinan, 17-phenethyl-7,8-didehydro-4,5α-epoxy-3,14β-dihydroxy-6α-[N-methyl-3-(3-methylphenyl)propiolamido]morphinan, 17-cyclopropylmethyl-4,5α-epoxy-3-hydroxy-6β-[N-methyl-3-(3-methylphenyl)propiolamido]morphinan, 17-allyl-4,5α-epoxy-3-hydroxy-6β-[N-methyl-3-(3-methylphenyl)propiolamido]morphinan, 17-methyl-4,5α-epoxy-3-hydroxy-6β-[N-methyl-3-(3-methylphenyl)propiolamido]morphinan, 17-phenethyl-4,5α-epoxy-3-hydroxy-6β-[N-methyl-3-(3-methylphenyl)propiolamido]morphinan, 17-cyclopropylmethyl-4,5α-epoxy-3-hydroxy-14β-nitro-6β-[N-methyl-3-(3-methylphenyl)propiolamido]morphinan, 17-allyl-4,5α-epoxy-3-hydroxy-14β-nitro-6β-[N-methyl-3-(3-methylphenyl)propiolamido]morphinan, 17-methyl-4,5α-epoxy-3-hydroxy-14β-nitro-6β-[N-methyl-3-(3-methylphenyl)propiolamido]morphinan, 17-phenethyl-4,5α-epoxy-3-hydroxy-14β-nitro-6β-[N-methyl-3-(3-methylphenyl)propiolamido]morphinan, 17-cyclopropylmethyl-4,5α-epoxy-3-hydroxy-14β-dimethylamino-6β-[N-methyl-3-(3-methylphenyl)propiolamido]morphinan, 17-allyl-4,5α-epoxy-3-hydroxy-14β-dimethylamino-6β-[N-methyl-3-(3-methylphenyl)propiolamido]morphinan, 17-methyl-4,5α-epoxy-3-hydroxy-14β-dimethylamino-6β-[N-methyl-3-(3-methylphenyl)propiolamido]morphinan, 17-phenethyl-4,5α-epoxy-3-hydroxy-14β-dimethylamino-6β-[N-methyl-3-(3-methylphenyl)propiolamido]morphinan, 17-cyclopropylmethyl-4,5α-epoxy-3-hydroxy-14β-methyl-6β-[N-methyl-3-(3-methylphenyl)propiolamido]morphinan, 17-allyl-4,5α-epoxy-3-hydroxy-14β-methyl-6β-[N-methyl-3-(3-methylphenyl)propiolamido]morphinan, 14β,17-dimethyl-4,5α-epoxy-3-hydroxy-6β-[N-methyl-3-(3-methylphenyl)propiolamido]morphinan, 17-phenethyl-4,5α-epoxy-3-hydroxy-14β-methyl-6β-[N-methyl-3-(3-methylphenyl)propiolamido]morphinan, 17-cyclopropylmethyl-3,14β-dihydroxy-6β-[N-methyl-3-(3-methylphenyl)propiolamido]morphinan, 17-allyl-3,14β-dihydroxy-6β-[N-methyl-3-(3-methylphenyl)propiolamido]morphinan, 17-methyl-3,14β-dihydroxy-6β-[N-methyl-3-(3-methylphenyl)propiolamido]morphinan, 17-phenethyl-3,14β-dihydroxy-6β-[N-methyl-3-(3-methylphenyl)propiolamido]morphinan, 17-cyclopropylmethyl-3,14β-dihydroxy-4-methoxy-6β-[N-methyl-3-(3-methylphenyl)propiolamido]morphinan, 17-allyl-3,14β-dihydroxy-4-methoxy-6β-[N-methyl-3-(3-methylphenyl)propiolamido]morphinan, 17-methyl-3,14β-dihydroxy-4-methoxy-6β-[N-methyl-3-(3-methylphenyl)propiolamido]morphinan, 17-phenethyl-3,14β-dihydroxy-4-methoxy-6β-[N-methyl-3-(3-methylphenyl)propiolamido]morphinan, 17-cyclopropylmethyl-4,5α-epoxy-3,14β-dihydroxy-5β-methyl-6β-[N-methyl-3-(3-methylphenyl)propiolamido]morphinan, 17-allyl-4,5α-epoxy-3,14β-dihydroxy-5β-methyl-6β-[N-methyl-3-(3-methylphenyl)propiolamido]morphinan, 5β,17-dimethyl-4,5α-epoxy-3,14β-dihydroxy-6β-[N-methyl-3-(3-methylphenyl)propiolamido]morphinan, 17-phenethyl-4,5α-epoxy-3,14β-dihydroxy-5β-methyl-6β-[N-methyl-3-(3-methylphenyl)propiolamido]morphinan, 17-cyclopropylmethyl-7,8-didehydro-4,5α-epoxy-3,14β-dihydroxy-6β-[N-methyl-3-(3-methylphenyl)propiolamido]morphinan, 17-allyl-7,8-didehydro-4,5α-epoxy-3,14β-dihydroxy-6β-[N-methyl-3-(3-methylphenyl)propiolamido]morphinan, 17-methyl-7,8-didehydro-4,5α-epoxy-3,14β-dihydroxy-6β-[N-methyl-3-(3-methylphenyl)propiolamido]morphinan, 17-phenethyl-7,8-didehydro-4,5α-epoxy-3,14β-dihydroxy-6β-[N-methyl-3-(3-methylphenyl)propiolamido]morphinan, 17-butyl-4,5α-epoxy-3,14β-dihydroxy-6α-[N-methyl-trans-3-(3-furyl)acrylamido]morphinan, 17-butyl-4,5α-epoxy-3,14β-dihydroxy-6β-[N-methyl-trans-3-(3-furyl)acrylamido]morphinan, 17-cyclopropylmethyl-4,5α-epoxy-3,14β-dihydroxy-6α-[N-methyl-3-(4-methylphenyl)propiolamido]morphinan, 17-allyl-4,5α-epoxy-3,14β-dihydroxy-6α-[N-methyl-3-(4-methylphenyl)propiolamido]morphinan, 17-cyclopropylmethyl-4,5α-epoxy-3,14β-dihydroxy-6β-[N-methyl-3-(4-methylphenyl)propiolamido]morphinan, 17-allyl-4,5α-epoxy-3,14β-dihyroxy-6β-[N-methyl-3-(4-methylphenyl)propiolamido]morphinan, 17-cyclopropylmethyl-4,5α-epoxy-3,14β-dihydroxy-6α-[N-methyl-3-(3-methoxyphenyl)propiolamido]morphinan, 17-allyl-4,5α-epoxy-3,14β-dihydroxy-6α-[N-methyl-3-(3-methoxyphenyl)propiolamido]morphinan, 17-cyclopropylmethyl-4,5α- epoxy-3,14β-dihydroxy-6β-[N-methyl-3-(3-methoxyphenyl)propiolamido]morphinan, 17-allyl-4,5α-epoxy-3,14β-dihydroxy-6β-[N-methyl-3-(3-methoxyphenyl)propiolamido]morphinan, 17-cyclopropylmethyl-4,5α-epoxy-3,14β-dihydroxy-6α-(N-methyl-3-bromocinnamamido)morphinan, 17-allyl-4,5α-epoxy-3,14β-dihydroxy-6α-(N-methyl-3-bromocinnamamido)morphinan, 17-cyclopropylmethyl-4,5α-epoxy-3,14β-dihydroxy-6β-(N-methyl-3-bromocinnamamido)morphinan, 17-allyl-4,5α-epoxy-3,14β-dihydroxy-6β-(N-methyl-3-bromocinnamamido)morphinan, 17-cyclopropylmethyl-4,5α-epoxy-3,14β-dihydroxy-6α-(N-methyl-4-chlorocinnamamido)morphinan, 17-allyl-4,5α-epoxy-3,14β-dihydroxy-6α-(N-methyl-4-chlorocinnamamido)morphinan, 17-cyclopropylmethyl-4,5α-epoxy-3,14β-dihydroxy-6β-(N-methyl-4-chlorocinnamamido)morphinan, 17-allyl-4,5α-epoxy-3,14β-dihydroxy-6β-(N-methyl-4-chlorocinnamamido)morphinan, 17-cyclopropylmethyl-4,5α-epoxy-3,14β-dihydroxy-6α-[N-methyl-cis-3-(3-furyl)acrylamido]morphinan, 17-allyl-4,5α-epoxy-3,14β-dihydroxy-6α-[N-methyl-cis-3-(3-furyl)acrylamido]morphinan, 17-cyclopropylmethyl-4,5α-epoxy-3,14β-dihydroxy-6β-[N-methyl-cis-3-(3-furyl)acrylamido]morphinan, 17-allyl-4,5α-epoxy-3,14β-dihydroxy-6β-[N-methyl-cis-3-(3-furyl)acrylamido]morphinan, 17-cyclopropylmethyl-4,5α-epoxy-3,14β-dihydroxy-6α-[N-methyl-trans-3-(3-pyridyl)acrylamido]morphinan, 17-allyl-4,5α-epoxy-3,14β-dihydroxy-6α-[N-methyl-trans-3-(3-pyridyl)acrylamido]morphinan, 17-cyclopropylmethyl-4,5α-epoxy-3,14β-dihydroxy-6β-[N-methyl-trans-3-(3-pyridyl)acrylamido]morphinan, 17-allyl-4,5α-epoxy-3,14β-dihydroxy-6β-[N-methyl-trans-3-(3-pyridyl)acrylamido]morphinan, 17-cyclopropylmethyl-4,5α-epoxy-3,14β-dihydroxy-6α-[N-methyl-3-(2-furyl)propiolamido]morphinan, 17-allyl-4,5α-epoxy-3,14β-dihydroxy-6α-[N-methyl-3-(2-furyl)propiolamido]morphinan, 17-cyclopropylmethyl-4,5α-epoxy-3,14β-dihydroxy-6β-[N-methyl-3-(2-furyl)propiolamido]morphinan, 17-allyl-4,5α-epoxy-3,14β-dihydroxy-6β-[N-methyl-3-(2-furyl)propiolamido]morphinan, 17-cyclopropylmethyl-4,5α-epoxy-3,14β-dihydroxy-6α-[N-methyl-3-(4-methoxyphenyl)propiolamido]morphinan, 17-allyl-4,5α-epoxy-3,14β-dihydroxy-6α-[N-methyl-3-(4-methoxyphenyl)propiolamido]morphinan, 17-cyclopropylmethyl-4,5α-epoxy-3,14β-dihydroxy-6β-[N-methyl-3-(4-methoxyphenyl)propiolamido]morphinan, 17-allyl-4,5α-epoxy-3,14β-dihydroxy-6β-[N-methyl-3-(4-methoxyphenyl)propiolamido]morphinan, 17-cyclopropylmethyl-4,5α-epoxy-3,14β-dihydroxy-6α-[trans-3-(3-furyl)acryloylthio]morphinan, 17-allyl-4,5α-epoxy-3,14β-dihydroxy-6α-[trans-3-(3-furyl)acryloylthio]morphinan, 17-cyclopropylmethyl-4,5α-epoxy-3,14β-dihydroxy-6β-[trans-3-(3-furyl)acryloylthio]morphinan, 17-allyl-4,5α-epoxy-3,14β-dihydroxy-6β-[trans-3-(3-furyl)acryloylthio]morphinan, 17-cyclopropylmethyl-4,5α-epoxy-3,14β-dihydroxy-6α-(N-methyl-3-chlorocinnamamido)morphinan, 17-allyl-4,5α-epoxy-3,14β-dihydroxy-6α-(N-methyl-3-chlorocinnamamido)morphinan, 17-cyclopropylmethyl-4,5α-epoxy-3,14β-dihydroxy-6β-(N-methyl-3-chlorocinnamamido)morphinan, 17-allyl-4,5α-epoxy-3,14β-dihydroxy-6β-(N-methyl-3-chlorocinnamamido)morphinan, 17-cyclopropylmethyl-4,5α-epoxy-3,14β-dihydroxy-6α-(N-methyl-4-methylcinnamamido)morphinan, 17-allyl-4,5α-epoxy-3,14β-dihydroxy-6α-(N-methyl-4-methylcinnamamido)morphinan, 17-cyclopropylmethyl-4,5α-epoxy-3,14β-dihydroxy-6β-(N-methyl-4-methylcinnamamido)morphinan, 17-allyl-4,5α-epoxy-3,14β-dihydroxy-6β-(N-methyl-4-methylcinnamamido)morphinan, 17-cyclopropylmethyl-4,5α-epoxy-3,14β-dihydroxy-6α-[N-methyl-3-(3-furyl)propiolamido]morphinan, 17-allyl-4,5α-epoxy-3,14β-dihydroxy-6α-[N-methyl-3-(3-furyl)propiolamido]morphinan, 17-cyclopropylmethyl-4,5α-epoxy-3,14β-dihydroxy-6β-[N-methyl-3-(3-furyl)propiolamido]morphinan, 17-allyl-4,5α-epoxy-3,14β-dihydroxy-6β-[N-methyl-3-(3-furyl)propiolamido]morphinan, 17-cyclopropylmethyl-4,5α-epoxy-3,14β-dihydroxy-6α-(N-methyl-4-bromocinnamamido)morphinan, 17-allyl-4,5α-epoxy-3,14β-dihydroxy-6α-(N-methyl-4-bromocinnamamido)morphinan, 17-cyclopropylmethyl-4,5α-epoxy-3,14β-dihydroxy-6β-(N-methyl-4-bromocinnamamido)morphinan, 17-allyl-4,5α-epoxy-3,14β-dihydroxy-6β-(N-methyl-4-bromocinnamamido)morphinan, 17-cyclopropylmethyl-4,5α-epoxy-3,14β-dihydroxy-6α-[N-methyl-trans-3-(4-bromo-2-thienyl)acrylamido]morphinan, 17-allyl-4,5α-epoxy-3,14β-dihydroxy-6α-[N-methyl-trans-3-(4-bromo-2-thienyl)acrylamido]morphinan, 17-cyclopropylmethyl-4,5α-epoxy-3,14β-dihydroxy-6β-[N-methyl-trans-3-(4-bromo-2-thienyl)acrylamido]morphinan, 17-allyl-4,5α-epoxy-3,14β-dihydroxy-6β-[N-methyl-trans-3-(4-bromo-2-thienyl)acrylamido]morphinan, 17-cyclopropylmethyl-4,5α-epoxy-3,14β-dihydroxy-6α-(N-methyl-trans,trans-2,4-hexadienoamido)morphinan, 17-allyl-4,5α-epoxy-3,14β-dihydroxy-6α-(N-methyl-trans,trans-2,4-hexadienoamido)morphinan, 17-cyclopropylmethyl-4,5α-epoxy-3,14β-dihydroxy-6β-(N-methyl-trans,trans-2,4-hexadienoamido)morphinan, 17-allyl-4,5α-epoxy-3,14β-dihydroxy-6β-(N-methyl-trans,trans-2,4-hexadienoamido)morphinan, 17-cyclopropylmethyl-4,5α-epoxy-3,14β-dihydroxy-6α-[N-methyl-trans-3-(5-methyl-2-furyl)acrylamido]morphinan, 17-allyl-4,5α-epoxy-3,14β-dihydroxy-6α-[N-methyl-trans-3-(5-methyl-2-furyl)acrylamido]morphinan, 17-cyclopropylmethyl-4,5α-epoxy-3,14β-dihydroxy-6β-[N-methyl-trans-3-(5-methyl-2-furyl)acrylamido]morphinan, 17-allyl-4,5α-epoxy-3,14β-dihydroxy-6β-[N-methyl-trans-3-(5-methyl-2-furyl)acrylamido]morphinan, 17-cyclopropylmethyl-4,5α-epoxy-3,14β-dihydroxy-6α-[N-methyl-trans-3-(2-methyl-3-furyl)acrylamido]morphinan, 17-allyl-4,5α-epoxy-3,14β-dihydroxy-6α-[N-methyl-trans-3-(2-methyl-3-furyl)acrylamido]morphinan, 17-cyclopropylmethyl-4,5α-epoxy-3,14β-dihydroxy-6β-[N-methyl-trans-3-(2-methyl-3-furyl)acrylamido]morphinan, 17-allyl-4,5α-epoxy-3,14β-dihydroxy-6β-[N-methyl-trans-3-(2-methyl-3-furyl)acrylamido]morphinan, 17-cyclopropylmethyl-4,5α-epoxy-3,14β-dihydroxy-6α-[N-methyl-3-(4-chlorophenyl)propiolamido]morphinan, 17-allyl-4,5α-epoxy-3,14β-dihydroxy-6α-[N-methyl-3-(4-chlorophenyl)propiolamido]morphinan, 17-cyclopropylmethyl-4,5α-epoxy-3,14β-dihydroxy-6β-[N-methyl-3-(4-chlorophenyl)propiolamido]morphinan, 17-allyl-4,5α-epoxy-3,14β-dihydroxy-6β-[N-methyl-3-(4-chlorophenyl)

propiolamido]morphinan, 17-cyclopropylmethyl-4,5α-epoxy-3,14β-dihydroxy-6α-[N-methyl-trans-3-(5-methyl-2-thienyl)acrylamido]morphinan, 17-allyl-4,5α-epoxy-3,14β-dihydroxy-6α-[N-methyl-trans-3-(5-methyl-2-thienyl)acrylamido]morphinan, 17-cyclopropylmethyl-4,5α-epoxy-3,14β-dihydroxy-6β-[N-methyl-trans-3-(5-methyl-2-thienyl)acrylamido]morphinan, 17-allyl-4,5α-epoxy-3,14β-dihydroxy-6β-[N-methyl-trans-3-(5-methyl-2-thienyl)acrylamido]morphinan, 17-cyclopropylmethyl-4,5α-epoxy-3,14β-dihydroxy-6α-(N-ethyl-3-trifluoromethylcinnamamido)morphinan, 17-allyl-4,5α-epoxy-3,14β-dihydroxy-6α-(N-ethyl-3-trifluoromethylcinnamamido)morphinan, 17-cyclopropylmethyl-4,5α-epoxy-3,14β-dihydroxy-6β-(N-ethyl-3-trifluoromethylcinnamamido)morphinan, 17-allyl-4,5α-epoxy-3,14β-dihydroxy-6β-(N-ethyl-3-trifluoromethylcinnamamido)morphinan, 17-cyclopropylmethyl-4,5α-epoxy-3,14β-dihydroxy-6α-(N-isopropyl-3-trifluoromethylcinnamamido)morphinan, 17-allyl-4,5α-epoxy-3,14β-dihydroxy-6α-(N-isopropyl-3-trifluoromethylcinnamamido)morphinan, 17-cyclopropylmethyl-4,5α-epoxy-3,14β-dihydroxy-6β-(N-isopropyl-3-trifluoromethylcinnamamido)morphinan, 17-allyl-4,5α-epoxy-3,14β-dihydroxy-6β-(N-isopropyl-3-trifluoromethylcinnamamido)morphinan, 17-cyclopropylmethyl-4,5α-epoxy-3,14β-dihydroxy-6α-(N-butyl-3-trifluoromethylcinnamamido)morphinan, 17-allyl-4,5α-epoxy-3,14β-dihydroxy-6α-(N-butyl-3-trifluoromethylcinnamamido)morphinan, 17-cyclopropylmethyl-4,5α-epoxy-3,14β-dihydroxy-6β-(N-butyl-3-trifluoromethylcinnamamido)morphinan, 17-allyl-4,5α-epoxy-3,14β-dihydroxy-6β-(N-butyl-3-trifluoromethylcinnamamido)morphinan, 17-cyclopropylmethyl-4,5α-epoxy-3,14β-dihydroxy-6α-(N-methyl-3-trifluoromethoxycinnamamido)morphinan, 17-allyl-4,5α-epoxy-3,14β-dihydroxy-6α-(N-methyl-3-trifluoromethoxycinnamamido)morphinan, 17-cyclopropylmethyl-4,5α-epoxy-3,14β-dihydroxy-6β-(N-methyl-3-trifluoromethoxycinnamamido)morphinan, 17-allyl-4,5α-epoxy-3,14β-dihydroxy-6β-(N-methyl-3-trifluoromethoxycinnamamido)morphinan, 17-cyclopropylmethyl-4,5α-epoxy-3,14β-dihydroxy-6α-(N-methyl-3,4-difluorocinnamamido)morphinan, 17-allyl-4,5α-epoxy-3,14β-dihydroxy-6α-(N-methyl-3,4-difluorocinnamamido)morphinan, 17-cyclopropylmethyl-4,5α-epoxy-3,14β-dihydroxy-6β-(N-methyl-3,4-difluorocinnamamido)morphinan, 17-allyl-4,5α-epoxy-3,14β-dihydroxy-6β-(N-methyl-3,4-difluorocinnamamido)morphinan, 17-cyclopropylmethyl-4,5α-epoxy-3,14β-dihydroxy-6α-(N-methyl-γ-methylcinnamamido)morphinan, 17-allyl-4,5α-epoxy-3,14β-dihydroxy-6α-(N-methyl-γ-methylcinnamamido)morphinan, 17-cyclopropylmethyl-4,5α-epoxy-3,14β-dihydroxy-6β-(N-methyl-γ-methylcinnamamido)morphinan, 17-allyl-4,5α-epoxy-3,14β-dihydroxy-6β-(N-methyl-γ-methylcinnamamido)morphinan, 17-cyclopropylmethyl-4,5α-epoxy-3,14β-dihydroxy-6α-[N-methyl-3-(3,4-dimethylphenyl)propiolamido]morphinan, 17-allyl-4,5α-epoxy-3,14β-dihydroxy-6α-[N-methyl-3-(3,4-dimethylphenyl)propiolamido]morphinan, 17-cyclopropylmethyl-4,5α-epoxy-3,14β-dihydroxy-6β-[N-methyl-3-(3,4 dimethylphenyl)propiolamido]morphinan, 17-allyl-4,5α-epoxy-3,14β-dihydroxy-6β-[N-methyl-3-(3,4-dimethylphenyl)propiolamido]morphinan, 17-cyclopropylmethyl-4,5α-epoxy-3,14β-dihydroxy-7α-(N-methyl-3-trifluoromethylcinnamamido)morphinan, 17-allyl-4,5α-epoxy-3,14β-dihydroxy-7α-(N-methyl-3-trifluoromethylcinnamamido)morphinan, 17-methyl-4,5α-epoxy-3,14β-dihydroxy-7α-(N-methyl-3-trifluoromethylcinnamamido)morphinan, 17-phenethyl-4,5α-epoxy-3,14β-dihydroxy-7α-(N-methyl-3-trifluoromethylcinnamamido)morphinan, 17-cyclopropylmethyl-4,5α-epoxy-3,14β-dihydroxy-7α-[N-methyl-trans-3-(3-furyl)acrylamido]morphinan, 17-allyl-4,5α-epoxy-3,14β-dihydroxy-7α-[N-methyl-trans-3-(3-furyl)acrylamido]morphinan, 17-methyl-4,5α-epoxy-3,14β-dihydroxy-7α-[N-methyl-trans-3-(3-furyl)acrylamido]morphinan, 17-phenethyl-4,5α-epoxy-3,14β-dihydroxy-7α-[N-methyl-trans-3-(3-furyl)acrylamido]morphinan, 17-cyclopropylmethyl-4,5α-epoxy-3,14β-dihydroxy-7α-(N-methyl-3-methylcinnamamido)morphinan, 17-allyl-4,5α-epoxy-3,14β-dihydroxy-7α-(N-methyl-3-methylcinnamamido)morphinan, 17-methyl-4,5α-epoxy-3,14β-dihydroxy-7α-(N-methyl-3-methylcinnamamido)morphinan, 17-phenethyl-4,5α-epoxy-3,14β-dihydroxy-7α-(N-methyl-3-methylcinnamamido)morphinan, 17-cyclopropylmethyl-4,5α-epoxy-3,14β-dihydroxy-7α-[N-methyl-3-(4-trifluoromethylphenyl)propiolamido]morphinan, 17-allyl-4,5α-epoxy-3,14β-dihydroxy-7α-[N-methyl-3-(4-trifluoromethylphenyl)propiolamido]morphinan, 17-methyl-4,5α-epoxy-3,14β-dihydroxy-7α-[N-methyl-3-(4-trifluoromethylphenyl)propiolamido]morphinan, 17-phenethyl-4,5α-epoxy-3,14β-dihydroxy-7α-[N-methyl-3-(4-trifluoromethylphenyl)propiolamido]morphinan, 17-cyclopropylmethyl-4,5α-epoxy-3,14β-dihydroxy-7α-[N-methyl-3-(3-methylphenyl)propiolamido]morphinan, 17-allyl-4,5α-epoxy-3,14β-dihydroxy-7α-[N-methyl-3-(3-methylphenyl)propiolamido]morphinan, 17-methyl-4,5α-epoxy-3,14β-dihydroxy-7α-[N-methyl-3-(3-methylphenyl)propiolamido]morphinan, 17-phenethyl-4,5α-epoxy-3,14β-dihydroxy-7α-[N-methyl-3-(3-methylphenyl)propiolamido]morphinan, 17-cyclopropylmethyl-4,5α-epoxy-3,14β-dihydroxy-8α-(N-methyl-3-trifluoromethylcinnamamido)morphinan, 17-allyl-4,5α-epoxy-3,14β-dihydroxy-8α-(N-methyl-3-trifluoromethylcinnamamido)morphinan, 17-methyl-4,5α-epoxy-3,14β-dihydroxy-8α-(N-methyl-3-trifluoromethylcinnamamido)morphinan, 17-phenethyl-4,5α-epoxy-3,14β-dihydroxy-8α-(N-methyl-3-trifluoromethylcinnamamido)morphinan, 17-cyclopropylmethyl-4,5α-epoxy-3,14β-dihydroxy-8α-[N-methyl-trans-3-(3-furyl)acrylamido]morphinan, 17-allyl-4,5α-epoxy-3,14β-dihydroxy-8α-[N-methyl-trans-3-(3-furyl)acrylamido]morphinan, 17-methyl-4,5α-epoxy-3,14β-dihydroxy-8α-[N-methyl-trans-3-(3-furyl)acrylamido]morphinan, 17-phenethyl-4,5α-epoxy-3,14β-dihydroxy-8α-[N-methyl-trans-3-(3-furyl)acrylamido]morphinan, 17-cyclopropylmethyl-4,5α-epoxy-3,14β-dihydroxy-8α-(N-methyl-3-methylcinnamamido)morphinan, 17-allyl-4,5α-epoxy-3,14β-dihydroxy-8α-(N-methyl-3-methylcinnamamido)morphinan, 17-methyl-4,5α-epoxy-3,14β-dihydroxy-8α-(N-methyl-3-methylcinnamamido)morphinan, 17-phenethyl-4,5α-epoxy-3,14β-dihydroxy-8α-(N-methyl-3- methylcinnamamido)morphinan,
17-cyclopropylmethyl-4,5α-epoxy-3,14β-dihydroxy-8α-[N-methyl-3-(4-trifluoromethylphenyl)propiolamido]morphinan, 17-allyl-4,5α-epoxy-3,14β-dihydroxy-8α-[N-methyl-3-(4-trifluoromethylphenyl)propiolamido]morphinan, 17-methyl-4,5α-epoxy-3,14β-dihydroxy-8α-[N-methyl-3-(4-trifluoromethylphenyl)propiolamido]morphinan, 17-phenethyl-4,5α-epoxy-3,14β-dihydroxy-8α-[N-methyl-3-(4-trifluoromethylphenyl)propiolamido]morphinan, 17-cyclopropylmethyl-4,5α-epoxy-3,14β-dihydroxy-8α-[N-methyl-3-(3-methylphenyl)propiolamido]morphinan, 17-allyl-4,5α-epoxy-3,14β-dihydroxy-8α-[N-methyl-3-(3-methylphenyl)propiolamido]morphinan, 17-methyl-4,5α-epoxy-3,14β-dihydroxy-8α-[N-methyl-3-(3-methylphenyl)propiolamido]morphinan, 17-phenethyl-4,5α-epoxy-3,14β-dihydroxy-8α-[N-methyl-3-(3-methylphenyl)propiolamido]morphinan, 17-cyclopropylmethyl-4,5α-epoxy-3,14β-dihydroxy-1-nitro-6α-(N-methyl-3-trifluoromethylcinnamamido)morphinan, 17-allyl-4,5α-epoxy-3,14β-dihydroxy-1-nitro-6α-(N-methyl-3-trifluoromethylcinnamamido)morphinan, 17-methyl-4,5α-epoxy-3,14β-dihydroxy-1-nitro-6α-(N-methyl-3-trifluoromethylcinnamamido)morphinan, 17-phenethyl-4,5α-epoxy-3,14β-dihydroxy-1-nitro-6α-(N-methyl-3-trifluoromethylcinnamamido)morphinan, 17-cyclopropylmethyl-4,5α-epoxy-3,14β-dihydroxy-1-nitro-6α-[N-methyl-trans-3-(3-furyl)acrylamido]morphinan, 17-allyl-4,5α-epoxy-3,14β-dihydroxy-1-nitro-6α-[N-methyl-trans-3-(3-furyl)acrylamido]morphinan, 17-methyl-4,5α-epoxy-3,14β-dihydroxy-1-nitro-6α-[N-methyl-trans-3-(3-furyl)acrylamido]morphinan, 17-phenethyl-4,5α-epoxy-3,14β-dihydroxy-1-nitro-6α-[N-methyl-trans-3-(3-furyl)acrylamido]morphinan, 17-cyclopropylmethyl-4,5α-epoxy-3,14β-dihydroxy-1-nitro-6α-(N-methyl-3-methylcinnamamido)morphinan, 17-allyl-4,5α-epoxy-3,14β-dihydroxy-1-nitro-6α-(N-methyl-3-methylcinnamamido)morphinan, 17-methyl-4,5α-epoxy-3,14β-dihydroxy-1-nitro-6α-(N-methyl-3-methylcinnamamido)morphinan, 17-phenethyl-4,5α-epoxy-3,14β-dihydroxy-1-nitro-6α-(N-methyl-3-methylcinnamamido)morphinan,
17-cyclopropylmethyl-4,5α-epoxy-3,14β-dihydroxy-1-nitro-6α-[N-methyl-3-(4-trifluoromethylphenyl)propiolamido]morphinan, 17-allyl-4,5α-epoxy-3,14β-dihydroxy-1-nitro-6α-[N-methyl-3-(4-trifluoromethylphenyl)propiolamido]morphinan, 17-methyl-4,5α-epoxy-3,14β-dihydroxy-1-nitro-6α-[N-methyl-3-(4-trifluoromethylphenyl)propiolamido]morphinan, 17-phenethyl-4,5α-epoxy-3,14β-dihydroxy-1-nitro-6α-[N-methyl-3-(4-trifluoromethylphenyl)propiolamido]morphinan, 17-cyclopropylmethyl-4,5α-epoxy-3,14β-dihydroxy-1-nitro-6α-[N-methyl-3-(3-methylphenyl)propiolamido]morphinan, 17-allyl-4,5α-epoxy-3,14β-dihydroxy-1-nitro-6α-[N-methyl-3-(3-methylphenyl)propiolamido]morphinan, 17-methyl-4,5α-epoxy-3,14β-dihydroxy-1-nitro-6α-[N-methyl-3-(3-methylphenyl)propiolamido]morphinan, 17-phenethyl-4,5α-epoxy-3,14β-dihydroxy-1-nitro-6α-[N-methyl-3-(3-methylphenyl)propiolamido]morphinan, 17-cyclopropylmethyl-4,5α-epoxy-3,14β-dihydroxy-7α-methyl-6α-(N-methyl-3-trifluoromethylcinnamamido)morphinan, 17-allyl-4,5α-epoxy-3,14β-dihydroxy-7α-methyl-6α-(N-methyl-3-trifluoromethylcinnamamido)morphinan, 17-methyl-4,5α-epoxy-3,14β-dihydroxy-7α-methyl-6α-(N-methyl-3-trifluoromethylcinnamamido)morphinan, 17-phenethyl-4,5α-epoxy-3,14β-dihydroxy-7α-methyl-6α-(N-methyl-3-trifluoromethylcinnamamido)morphinan, 17-cyclopropylmethyl-4,5α-epoxy-3,14β-dihydroxy-7α-methyl-6α-[N-methyl-trans-3-(3-furyl)acrylamido]morphinan, 17-allyl-4,5α-epoxy-3,14β-dihydroxy-7α-methyl-6α-[N-methyl-trans-3-(3-furyl)acrylamido]morphinan, 17-methyl-4,5α-epoxy-3,14β-dihydroxy-7α-methyl-6α-[N-methyl-trans-3-(3-furyl)acrylamido]morphinan, 17-phenethyl-4,5α-epoxy-3,14β-dihydroxy-7α-methyl-6α-[N-methyl-trans-3-(3-furyl)acrylamido]morphinan, 17-cyclopropylmethyl-4,5α-epoxy-3,14β-dihydroxy-7α-methyl-6α-(N-methyl-3-methylcinnamamido)morphinan, 17-allyl-4,5α-epoxy-3,14β-dihydroxy-7α-methyl-6α-(N-methyl-3-methylcinnamamido)morphinan, 17-methyl-4,5α-epoxy-3,14β-dihydroxy-7α-methyl-6α-(N-methyl-3-methylcinnamamido)morphinan, 17-phenethyl-4,5α-epoxy-3,14β-dihydroxy-7α-methyl-6α-(N-methyl-3-methylcinnamamido)morphinan,
17-cyclopropylmethyl-4,5α-epoxy-3,14β-dihydroxy-7α-methyl-6α-[N-methyl-3-(4-trifluoromethylphenyl)propiolamido]-morphinan, 17-allyl-4,5α-epoxy-3,14β-dihydroxy-7α-methyl-6α-[N-methyl-3-(4-trifluoromethylphenyl)propiolamido]morphinan, 17-methyl-4,5α-epoxy-3,14β-dihydroxy-7α-methyl-6α-[N-methyl-3-(4-trifluoromethylphenyl)propiolamido]morphinan, 17-phenethyl-4,5α-epoxy-3,14β-dihydroxy-7α-methyl-6α-[N-methyl-3-(4-trifluoromethylphenyl)propiolamido]morphinan, 17-cyclopropylmethyl-4,5α-epoxy-3,14β-dihydroxy-7α-methyl-6α-[N-methyl-3-(3-methylphenyl)propiolamido]morphinan, 17-allyl-4,5α-epoxy-3,14β-dihydroxy-7α-methyl-6α-[N-methyl-3-(3-methylphenyl)propiolamido]morphinan, 17-methyl-4,5α-epoxy-3,14β-dihydroxy-7α-methyl-6α-[N-methyl-3-(3-methylphenyl)propiolamido]morphinan, 17-phenethyl-4,5α-epoxy-3,14β-dihydroxy-7α-methyl-6α-[N-methyl-3-(3-methylphenyl)propiolamido]morphinan, 17-cyclopropylmethyl-4,5α-epoxy-3,14β-dihydroxy-7β-methyl-6α-(N-methyl-3-trifluoromethylcinnamamido)morphinan, 17-allyl-4,5α-epoxy-3,14β-dihydroxy-7β-methyl-6α-(N-methyl-3 -trifluoromethylcinnamamido)morphinan, 17-methyl-4,5α-epoxy-3,14β-dihydroxy-7β-methyl-6α-(N-methyl-3-trifluoromethylcinnamamido)morphinan, 17-phenethyl-4,5α-epoxy-3,14β-dihydroxy-7β-methyl-6α-(N-methyl-3-trifluoromethylcinnamamido)morphinan, 17-cyclopropylmethyl-4,5α-epoxy-3,14β-dihydroxy-7β-methyl-6α-[N-methyl-trans-3-(3-furyl)acrylamido]morphinan, 17-allyl-4,5α-epoxy-3,14β-dihydroxy-7β-methyl-6α-[N-methyl-trans-3-(3-furyl)acrylamido]morphinan, 17-methyl-4,5α-epoxy-3,14β-dihydroxy-7β-methyl-6α-[N-methyl-trans-3-(3-furyl)acrylamido]morphinan, 17-phenethyl-4,5α-epoxy-3,14β-dihydroxy-7β-methyl-6α-[N-methyl-trans-3-(3-furyl)acrylamido]morphinan, 17-cyclopropylmethyl-4,5α-epoxy-3,14β-dihydroxy-7β-methyl-6α-(N-methyl-3-methylcinnamamido)morphinan, 17-allyl-4,5α-epoxy-3,14β-dihydroxy-7β-methyl-6α-(N-methyl-3-methylcinnamamido)morphinan, 17-methyl-4,5α-epoxy-3,14β-dihydroxy-7β-methyl-6α-(N-methyl-3-methylcinnamamido)morphinan, 17-phenethyl-4,5α-epoxy-3,14β-dihydroxy-7β-methyl-6α-(N-methyl-3- methylcinnamamido)morphinan, 17-cyclopropylmethyl-4,5α-epoxy-3,14β-dihydroxy-7β-methyl-6α-[N-methyl-3-(4-trifluoromethylphenyl)propiolamido]morphinan, 17-allyl-4,5α-epoxy-3,14β-dihydroxy-7β-methyl-6α-[N-methyl-3-(4-trifluoromethylphenyl)propiolamido]morphinan, 17-methyl-4,5α-epoxy-3,14β-dihydroxy-7β-methyl-6α-[N-methyl-3-(4-trifluoromethylphenyl)propiolamido]morphinan, 17-phenethyl-4,5α-epoxy-3,14β-dihydroxy-7β-methyl-6α-[N-methyl-3-(4-trifluoromethylphenyl)propiolamido]morphinan, 17-cyclopropylmethyl-4,5α-epoxy-3,14β-dihydroxy-7β-methyl-6α-[N-methyl-3-(3-methylphenyl)propiolamido]morphinan, 17-allyl-4,5α-epoxy-3,14β-dihydroxy-7β-methyl-6α-[N-methyl-3-(3-methylphenyl)propiolamido]morphinan, 17-methyl-4,5α-epoxy-3,14β-dihydroxy-7β-methyl-6α-[N-methyl-3-(3-methylphenyl)propiolamido]morphinan, 17-phenethyl-4,5α-epoxy-3,14β-dihydroxy-7β-methyl-6α-[N-methyl-3-(3-methylphenyl)propiolamido]morphinan, 17-cyclopropylmethyl-4,5α-epoxy-3,14β-dihydroxy-8β-methyl-6α-(N-methyl-3-trifluoromethylcinnamamido)morphinan, 17-allyl-4,5α-epoxy-3,14β-dihydroxy-8β-methyl-6α-(N-methyl-3-trifluoromethylcinnamamido)morphinan, 17-methyl-4,5α-epoxy-3,14β-dihydroxy-8β-methyl-6α-(N-methyl-3-trifluoromethylcinnamamido)morphinan, 17-phenethyl-4,5α-epoxy-3,14β-dihydroxy-8β-methyl-6α-(N-methyl-3-trifluoromethylcinnamamido]morphinan, 17-cyclopropylmethyl-4,5α-epoxy-3,14β-dihydroxy-8β-methyl-6α-[N-methyl-trans-3-(3-furyl)acrylamido]morphinan, 17-allyl-4,5α-epoxy-3,14β-dihydroxy-8β-methyl-6α-[N-methyl-trans-3-(3-furyl)acrylamido]morphinan, 17-methyl-4,5α-epoxy-3,14β-dihydroxy-8β-methyl-6α-[N-methyl-trans-3-(3-furyl)acrylamido]morphinan, 17-phenethyl-4,5α-epoxy-3,14β-dihydroxy-8β-methyl-6α-[N-methyl-trans-3-(3-furyl)acrylamido]morphinan, 17-cyclopropylmethyl-4,5α-epoxy-3,14β-dihydroxy-8β-methyl-6α-(N-methyl-3-methylcinnamamido)morphinan, 17-allyl-4,5α-epoxy-3,14β-dihydroxy-8β-methyl-6α-(N-methyl-3-methylcinnamamido)morphinan, 17-methyl-4,5α-epoxy-3,14β-dihydroxy-8β-methyl-6α-(N-methyl-3-methylcinnamamido)morphinan, 17-phenethyl-4,5α-epoxy-3,14β-dihydroxy-8β-methyl-6α-(N-methyl-3-methylcinnamamido)morphinan, 17-cyclopropylmethyl-4,5α-epoxy-3,14β-dihydroxy-8β-methyl-6α-[N-methyl-3-(4-trifluoromethylphenyl)propiolamido]morphinan, 17-allyl-4,5α-epoxy-3,14β-dihydroxy-8β-methyl-6α-[N-methyl-3-(4-trifluoromethylphenyl)propiolamido]morphinan, 17-methyl-4,5α-epoxy-3,14β-dihydroxy-8β-methyl-6α-[N-methyl-3-(4-trifluoromethylphenyl)propiolamido]morphinan, 17-phenethyl-4,5α-epoxy-3,14β-dihydroxy-8β-methyl-6α-[N-methyl-3-(4-trifluoromethylphenyl)propiolamido]morphinan, 17-cyclopropylmethyl-4,5α-epoxy-3,14β-dihydroxy-8β-methyl-6α-[N-methyl-3-(3-methylphenyl)propiolamido]morphinan, 17-allyl-4,5α-epoxy-3,14β-dihydroxy-8β-methyl-6α-[N-methyl-3-(3-methylphenyl)propiolamido]morphinan, 17-methyl-4,5α-epoxy-3,14β-dihydroxy-8β-methyl-6α-[N-methyl-3-(3-methylphenyl)propiolamido]morphinan, 17-phenethyl-4,5α-epoxy-3,14β-dihydroxy-8β-methyl-6α-[N-methyl-3-(3-methylphenyl)propiolamido]morphinan, 17-cyclopropylmethyl-4,5α-epoxy- 3,14β-dihydroxy-8β-ethyl-6α-(N-methyl-3-trifluoromethylcinnamamido)morphinan, 17-allyl-4,5α-epoxy-3,14β-dihydroxy-8β-ethyl-6α-(N-methyl-3-trifluoromethylcinnamamido)morphinan, 17-methyl-4,5α-epoxy-3,14β-dihydroxy-8β-ethyl-6α-(N-methyl-3-trifluoromethylcinnamamido)morphinan, 17-phenethyl-4,5α-epoxy-3,14β-dihydroxy-8β-ethyl-6α-(N-methyl-3-trifluoromethylcinnamamido)morphinan, 17-cyclopropylmethyl-4,5α-epoxy-8β-ethyl-3,14β-dihydroxy-6α-[N-methyl-trans-3-(3-furyl)acrylamido]morphinan, 17-allyl-4,5α-epoxy-8β-ethyl-3,14β-dihydroxy-6α-[N-methyl-trans-3-(3-furyl)acrylamido]morphinan, 17-methyl-4,5α-epoxy-8β-ethyl-3,14β-dihydroxy-6α-[N-methyl-trans-3-(3-furyl)acrylamido]morphinan, 17-phenethyl-4,5α-epoxy-8β-ethyl-3,14β-dihydroxy-6α-[N-methyl-trans-3-(3-furyl)acrylamido]morphinan, 17-cyclopropylmethyl-4,5α-epoxy-8β-ethyl-3,14β-dihydroxy-6α-(N-methyl-3-methylcinnamamido)morphinan, 17-allyl-4,5α-epoxy-8β-ethyl-3,14β-dihydroxy-6α-(N-methyl-3-methylcinnamamido)morphinan, 17-methyl-4,5α-epoxy-8β-ethyl-3,14β-dihydroxy-6α-(N-methyl-3-methylcinnamamido)morphinan, 17-phenethyl-4,5α-epoxy-8β-ethyl-3,14β-dihydroxy-6α-(N-methyl-3-methylcinnamamido)morphinan, 17-cyclopropylmethyl-4,5α-epoxy-8β-ethyl-3,14β-dihydroxy-6α-[N-methyl-3-(4-trifluoromethylphenyl)propiolamido]morphinan, 17-allyl-4,5α-epoxy-8β-ethyl-3,14β-dihydroxy-6α-[N-methyl-3-(4-trifluoromethylphenyl)propiolamido]morphinan, 17-methyl-4,5α-epoxy-8β-ethyl-3,14β-dihydroxy-6α-[N-methyl-3-(4-trifluoromethylphenyl)propiolamido]morphinan, 17-phenethyl-4,5α-epoxy-8β-ethyl-3,14β-dihydroxy-6α-[N-methyl-3-(4-trifluoromethylphenyl)propiolamido]morphinan, 17-cyclopropylmethyl-4,5α-epoxy-8β-ethyl-3,14β-dihydroxy-6α-[N-methyl-3-(3-methylphenyl)propiolamido]morphinan, 17-allyl-4,5α-epoxy-8β-ethyl-3,14β-dihydroxy-6α-[N-methyl-3-(3-methylphenyl)propiolamido]morphinan, 17-methyl-4,5α-epoxy-8β-ethyl-3,14β-dihydroxy-6α-[N-methyl-3-(3-methylphenyl)propiolamido]morphinan, 17-phenethyl-4,5α-epoxy-8β-ethyl-3,14β-dihydroxy-6α-[N-methyl-3-(3-methylphenyl)propiolamido]morphinan, 17-cyclopropylmethyl-4,5α-epoxy- 3,14β-dihydroxy-10-keto-6α-(N-methyl-3-trifluoromethylcinnamamido)morphinan, 17-allyl-4,5α-epoxy-3,14β-dihydroxy-10-keto-6α-(N-methyl-3-trifluoromethylcinnamamido)morphinan, 17-methyl-4,5α-epoxy-3,14β-dihydroxy-10-keto-6α-(N-methyl-3-trifluoromethylcinnamamido)morphinan, 17-phenethyl-4,5α-epoxy-3,14β-dihydroxy-10-keto-6α-(N-methyl-3-trifluoromethylcinnamamido)morphinan, 17-cyclopropylmethyl-4,5α-epoxy-3,14β-dihydroxy-10-keto-6α-[N-methyl-trans-3-(3-furyl)acrylamido]morphinan, 17-allyl-4,5α-epoxy-3,14β-dihydroxy-10-keto-6α-[N-methyl-trans-3-(3-furyl)acrylamido]morphinan, 17-methyl-4,5α-epoxy-3,14β-dihydroxy-10-keto-6α-[N-methyl-trans-3-(3-furyl)acrylamido]morphinan, 17-phenethyl-4,5α-epoxy-3,14β-dihydroxy-10-keto-6α-[N-methyl-trans-3-(3-furyl)acrylamido]morphinan, 17-cyclopropylmethyl-4,5α-epoxy-3,14β-dihydroxy-10-keto-6α-(N-methyl-3-methylcinnamamido)morphinan, 17-allyl-4,5α-epoxy-3,14β-dihydroxy-10-keto-6α-(N-methyl-3-methylcinnamamido)morphinan, 17-methyl-4,5α-epoxy-3,14β-dihydroxy-10-keto-6α-(N-methyl-3-methylcinnamamido)morphinan, 17-phenethyl-4,5α-epoxy-3,14β-dihydroxy-10-keto-6α-(N-methyl-3- methylcinnamamido)morphinan, 17-cyclopropylmethyl-4,5α-epoxy-3,14β-dihydroxy-10-keto-6α-[N-methyl-3-(4-trifluoromethylphenyl)propiolamido]morphinan, 17-allyl-4,5α-epoxy-3,14β-dihydroxy-10-keto-6α-[N-methyl-3-(4-trifluoromethylphenyl)propiolamido]morphinan, 17-methyl-4,5α-epoxy-3,14β-dihydroxy-10-keto-6α-[N-methyl-3-(4-trifluoromethylphenyl)propiolamido]morphinan, 17-phenethyl-4,5α-epoxy-3,14β-dihydroxy-10-keto-6α-[N-methyl-3-(4-trifluoromethylphenyl)propiolamido]morphinan, 17-cyclopropylmethyl-4,5α-epoxy-3,14β-dihydroxy-10-keto-6α-[N-methyl-3-(3-methylphenyl)propiolamido]morphinan, 17-allyl-4,5α-epoxy-3,14β-dihydroxy-10-keto-6α-[N-methyl-3-(3-methylphenyl)propiolamido]morphinan, 17-methyl-4,5α-epoxy-3,14β-dihydroxy-10-keto-6α-[N-methyl-3-(3-methylphenyl)propiolamido]morphinan, 17-phenethyl-4,5α-epoxy-3,14β-dihydroxy-10-keto-6α-[N-methyl-3-(3-methylphenyl)propiolamido]morphinan, 17-cyclopropylmethyl-4,5α-epoxy-3,14β,15β-trihydroxy-6α-(N-methyl-3-trifluoromethylcinnamamido)morphinan, 17-allyl-4,5α-epoxy-3,14β,15β-trihydroxy-6α-(N-methyl-3-trifluoromethylcinnamamido)morphinan, 17-methyl-4,5α-epoxy-3,14β,15β-trihydroxy-6α-(N-methyl-3-trifluoromethylcinnamamido)morphinan, 17-phenethyl-4,5α-epoxy-3,14β,15β-trihydroxy-6α-(N-methyl-3-trifluoromethylcinnamamido)morphinan, 17-cyclopropylmethyl-4,5α-epoxy-3,14β,15β-trihydroxy-6α-[N-methyl-trans-3-(3-furyl)acrylamido]morphinan, 17-allyl-4,5α-epoxy-3,14β,15β-trihydroxy-6α-[N-methyl-trans-3-(3-furyl)acrylamido]morphinan, 17-methyl-4,5α-epoxy-3,14β,15β-trihydroxy-6α-[N-methyl-trans-3-(3-furyl)acrylamido]morphinan, 17-phenethyl-4,5α-epoxy-3,14β,15β-trihydroxy-6α-[N-methyl-trans-3-(3-furyl)acrylamido]morphinan, 17-cyclopropylmethyl-4,5α-epoxy-3,14β,15β-trihydroxy-6α-(N-methyl-3-methylcinnamamido)morphinan, 17-allyl-4,5α-epoxy-3,14β,15β-trihydroxy-6α-(N-methyl-3-methylcinnamamido)morphinan, 17-methyl-4,5α-epoxy-3,14β,15β-trihydroxy-6α-(N-methyl-3-methylcinnamamido)morphinan, 17-phenethyl-4,5α-epoxy-3,14β,15β-trihydroxy-6α-(N-methyl-3-methylcinnamamido)morphinan, 17-cyclopropylmethyl-4,5α-epoxy-3,14β,15β-trihydroxy-6α-[N-methyl-3-(4-trifluoromethylphenyl)propiolamido]morphinan, 17-allyl-4,5α-epoxy-3,14β,15β-trihydroxy-6α-[N-methyl-3-(4-trifluoromethylphenyl)propiolamido]morphinan, 17-methyl-4,5α-epoxy-3,14β,15β-trihydroxy-6α-[N-methyl-3-(4-trifluoromethylphenyl)propiolamido]morphinan, 17-phenethyl-4,5α-epoxy-3,14β,15β-trihydroxy-6α-[N-methyl-3-(4-trifluoromethylphenyl)propiolamido]morphinan, 17-cyclopropylmethyl-4,5α-epoxy-3,14β,15β-trihydroxy-6α-[N-methyl-3-(3-methylphenyl)propiolamido]morphinan, 17-allyl-4,5α-epoxy-3,14β,15β-trihydroxy-6α-[N-methyl-3-(3-methylphenyl)propiolamido]morphinan, 17-methyl-4,5α-epoxy-3,14β,15β-trihydroxy-6α-[N-methyl-3-(3-methylphenyl)propiolamido]morphinan, 17-phenethyl-4,5α-epoxy-3,14β,15β-trihydroxy-6α-[N-methyl-3-(3-methylphenyl)propiolamido]morphinan, 17-cyclopropylmethyl-16-cyano-4,5α-epoxy-3,14β-dihydroxy-6α-(N-methyl-3-trifluoromethylcinnamamido)morphinan, 17-allyl-16-cyano-4,5α-epoxy-3,14β-dihydroxy-6α-(N-methyl-3-trifluoromethylcinnamamido)morphinan, 17-methyl-16-cyano-4,5α-epoxy-3,14β-dihydroxy-6α-(N-methyl-3-trifluoromethylcinnamamido)morphinan, 17-phenethyl-16-cyano-4,5α-epoxy-3,14β-dihydroxy-6α-(N-methyl-3-trifluoromethylcinnamamido)morphinan, 17-cyclopropylmethyl-16-cyano-4,5α-epoxy-3,14β-dihydroxy-6α-[N-methyl-trans-3-(3-furyl)acrylamido]morphinan, 17-allyl-16-cyano-4,5α-epoxy-3,14β-dihydroxy-6α-[N-methyl-trans-3-(3-furyl)acrylamido]morphinan, 17-methyl-16-cyano-4,5α-epoxy-3,14β-dihydroxy-6α-[N-methyl-trans-3-(3-furyl)acrylamido]morphinan, 17-phenethyl-16-cyano-4,5α-epoxy-3,14β-dihydroxy-6α-[N-methyl-trans-3-(3-furyl)acrylamido]morphinan, 17-cyclopropylmethyl-16-cyano-4,5α-epoxy-3,14β-dihydroxy-6α-(N-methyl-3-methylcinnamamido)morphinan, 17-allyl-16-cyano-4,5α-epoxy-3,14β-dihydroxy-6α-(N-methyl-3-methylcinnamamido)morphinan, 17-methyl-16-cyano-4,5α-epoxy-3,14β-dihydroxy-6α-(N-methyl-3-methylcinnamamido)morphinan, 17-phenethyl-16-cyano-4,5α-epoxy-3,14β-dihydroxy-6α-(N-methyl-3-methylcinnamamido)morphinan, 17-cyclopropylmethyl-16-cyano-4,5α-epoxy-3,14β-dihydroxy-6α-[N-methyl-3-(4-trifluoromethylphenyl)propiolamido]morphinan, 17-allyl-16-cyano-4,5α-epoxy-3,14β-dihydroxy-6α-[N-methyl-3-(4-trifluoromethylphenyl)propiolamido]morphinan, 17-methyl-16-cyano-4,5α-epoxy-3,14β-dihydroxy-6α-[N-methyl-3-(4-trifluoromethylphenyl)propiolamido]morphinan, 17-phenethyl-16-cyano-4,5α-epoxy-3,14β-dihydroxy-6α-[N-methyl-3-(4-trifluoromethylphenyl)propiolamido]morphinan, 17-cyclopropylmethyl-16-cyano-4,5α-epoxy-3,14β-dihydroxy-6α-[N-methyl-3-(3-methylphenyl)propiolamido]morphinan, 17-allyl-16-cyano-4,5α-epoxy-3,14β-dihydroxy-6α-[N-methyl-3-(3-methylphenyl)propiolamido]morphinan, 17-methyl-16-cyano-4,5α-epoxy-3,14β-dihydroxy-6α-[N-methyl-3-(3-methylphenyl)propiolamido]morphinan, 17-phenethyl-16-cyano-4,5α-epoxy-3,14β-dihydroxy-6α-[N-methyl-3-(3-methylphenyl)propiolamido]morphinan, 8-nor-17-cyclopropylmethyl-4,5α-epoxy-3,14β-dihydroxy-6α-(N-methyl-3-trifluoromethylcinnamamido)morphinan, 8-nor-17-allyl-4,5α-epoxy-3,14β-dihydroxy-6α-(N-methyl-3-trifluoromethylcinnamamido)morphinan, 8-nor-17-methyl-4,5α-epoxy-3,14β-dihydroxy-6α-(N-methyl-3-trifluoromethylcinnamamido)morphinan, 8-nor-17-phenethyl-4,5α-epoxy-3,14β-dihydroxy-6α-(N-methyl-3-trifluoromethylcinnamamido)morphinan, 8-nor-17-cyclopropylmethyl-4,5α-epoxy-3,14β-dihydroxy-6α-[N-methyl-trans-3-(3-furyl)acrylamido]morphinan, 8-nor-17-allyl-4,5α-epoxy-3,14β-dihydroxy-6α-[N-methyl-trans-3-(3-furyl)acrylamido]morphinan, 8-nor-17-methyl-4,5α-epoxy-3,14β-dihydroxy-6α-[N-methyl-trans-3-(3-furyl)acrylamido]morphinan, 8-nor-17-phenethyl-4,5α-epoxy-3,14β-dihydroxy-6α-[N-methyl-trans-3-(3-furyl)acrylamido]morphinan, 8-nor-17-cyclopropylmethyl-4,5α-epoxy-3,14β-dihydroxy-6α-(N-methyl-3-methylcinnamamido)morphinan, 8-nor-17-allyl-4,5α-epoxy-3,14β-dihydroxy-6α-(N-methyl-3-methylcinnamamido)morphinan, 8-nor-17-methyl-4,5α-epoxy-3,14β-dihydroxy-6α-(N-methyl-3-methylcinnamamido)morphinan, 8-nor-17-phenethyl-4,5α-epoxy-3,14β-dihydroxy-6α-(N-methyl-3- methylcinnamamido)morphinan, 8-nor-17-cyclopropylmethyl-4,5α-epoxy-3,14β-dihydroxy-6α-[N-methyl-3-(4-trifluoromethylphenyl)propiolamido]morphinan, 8-nor-17-allyl-4,5α-epoxy-3,14β-dihydroxy-6α-[N-methyl-3-(4-trifluoromethylphenyl)propiolamido]morphinan, 8-nor-17-methyl-4,5α-epoxy-3,14β-dihydroxy-6α-[N-methyl-3-(4-trifluoromethylphenyl)propiolamido]morphinan, 8-nor-17-phenethyl-4,5α-epoxy-3,14β-dihydroxy-6α-[N-methyl-3-(4-trifluoromethylphenyl)propiolamido]morphinan, 8-nor-17-cyclopropylmethyl-4,5α-epoxy-3,14β-dihydroxy-6α-[N-methyl-3-(3-methylphenyl)propiolamido]morphinan, 8-nor-17-allyl-4,5α-epoxy-3,14β-dihydroxy-6α-[N-methyl-3-(3-methylphenyl)propiolamido]morphinan, 8-nor-17-methyl-4,5α-epoxy-3,14β-dihydroxy-6α-[N-methyl-3-(3-methylphenyl)propiolamido]morphinan, 8-nor-17-phenethyl-4,5α-epoxy-3,14β-dihydroxy-6α-[N-methyl-3-(3-methylphenyl)propiolamido]morphinan, 8-homo-17-cyclopropylmethyl-4,5α-epoxy-3,14β-dihydroxy-6α-(N-methyl-3-trifluoromethylcinnamamido)morphinan, 8-homo-17-allyl-4,5α-epoxy-3,14β-dihydroxy-6α-(N-methyl-3-trifluoromethylcinnamamido)morphinan, 8-homo-17-methyl-4,5α-epoxy-3,14β-dihydroxy-6α-(N-methyl-3-trifluoromethylcinnamamido)morphinan, 8-homo-17-phenethyl-4,5α-epoxy-3,14β-dihydroxy-6α-(N-methyl-3-trifluoromethylcinnamamido)morphinan, 8-homo-17-cyclopropylmethyl-4,5α-epoxy-3,14β-dihydroxy-6α-[N-methyl-trans-3-(3-furyl)acrylamido]morphinan, 8-homo-17-allyl-4,5α-epoxy-3,14β-dihydroxy-6α-[N-methyl-trans-3-(3-furyl)acrylamido]morphinan, 8-homo-17-methyl-4,5α-epoxy-3,14β-dihydroxy-6α-[N-methyl-trans-3-(3-furyl)acrylamido]morphinan, 8-homo-17-phenethyl-4,5α-epoxy-3,14β-dihydroxy-6α-[N-methyl-trans-3-(3-furyl)acrylamido]morphinan, 8-homo-17-cyclopropylmethyl-4,5α-epoxy-3,14β-dihydroxy-6α-(N-methyl-3-methylcinnamamido)morphinan, 8-homo-17-allyl-4,5α-epoxy-3,14β-dihydroxy-6α-(N-methyl-3-methylcinnamamido)morphinan, 8-homo-17-methyl-4,5α-epoxy-3,14β-dihydroxy-6α-(N-methyl-3-methylcinnamamido)morphinan, 8-homo-17-phenethyl-4,5α-epoxy-3,14β-dihydroxy-6α-(N-methyl-3-methylcinnamamido)morphinan, 8-homo-17-cyclopropylmethyl-4,5α-epoxy-3,14β-dihydroxy-6α-[N-methyl-3-(4-trifluoromethylphenyl)propiolamido]morphinan, 8-homo-17-allyl-4,5α-epoxy-3,14β-dihydroxy-6α-[N-methyl-3-(4-trifluoromethylphenyl)propiolamido]morphinan, 8-homo-17-methyl-4,5α-epoxy-3,14β-dihydroxy-6α-[N-methyl-3-(4-trifluoromethylphenyl)propiolamido]morphinan, 8-homo-17-phenethyl-4,5α-epoxy-3,14β-dihydroxy-6α-[N-methyl-3-(4-trifluoromethylphenyl)propiolamido]morphinan, 8-homo-17-cyclopropylmethyl-4,5α-epoxy-3,14β-dihydroxy-6α-[N-methyl-3-(3-methylphenyl)propiolamido]morphinan, 8-homo-17-allyl-4,5α-epoxy-3,14β-dihydroxy-6α-[N-methyl-3-(3-methylphenyl)propiolamido]morphinan, 8-homo-17-methyl-4,5α-epoxy-3,14β-dihydroxy-6α-[N-methyl-3-(3-methylphenyl)propiolamido]morphinan, 8-homo-17-phenethyl-4,5α-epoxy-3,14β-dihydroxy-6α-[N-methyl-3-(3-methylphenyl)propiolamido]morphinan, 17-cyclopropylmethyl-4,5α-epoxy-3,14β-dihydroxy-7β-(N-methyl-3-trifluoromethylcinnamamido)morphinan, 17-allyl-4,5α-epoxy-3,14β-dihydroxy-7β-(N-methyl-3-trifluoromethylcinnamamido)morphinan, 17-methyl-4,5α-epoxy-3,14β-dihydroxy-7β-(N-methyl-3-trifluoromethylcinnamamido)morphinan, 17-phenethyl-4,5α-epoxy-3,14β-dihydroxy-7β-(N-methyl-3-trifluoromethylcinnamamido)morphinan, 17-cyclopropylmethyl-4,5α-epoxy-3,14β-dihydroxy-7β-[N-methyl-trans-3-(3-furyl)acrylamido]morphinan, 17-allyl-4,5α-epoxy-3,14β-dihydroxy-7β-[N-methyl-trans-3-(3-furyl)acrylamido]morphinan, 17-methyl-4,5α-epoxy-3,14β-dihydroxy-7β-[N-methyl-trans-3-(3-furyl)acrylamido]morphinan, 17-phenethyl-4,5α-epoxy-3,14β-dihydroxy-7β-[N-methyl-trans-3-(3-furyl)acrylamido]morphinan, 17-cyclopropylmethyl-4,5α-epoxy-3,14β-dihydroxy-7β-(N-methyl-3-methylcinnamamido)morphinan, 17-allyl-4,5α-epoxy-3,14β-dihydroxy-7β-(N-methyl-3-methylcinnamamido)morphinan, 17-methyl-4,5α-epoxy-3,14β-dihydroxy-7β-(N-methyl-3-methylcinnamamido)morphinan, 17-phenethyl-4,5α-epoxy-3,14β-dihydroxy-7β-(N-methyl-3-methylcinnamamido)morphinan, 17-cyclopropylmethyl-4,5α-epoxy-3,14β-dihydroxy-7β-[N-methyl-3-(4-trifluoromethylphenyl)propiolamido]morphinan, 17-allyl-4,5α-epoxy-3,14β-dihydroxy-7β-[N-methyl-3-(4-trifluoromethylphenyl)propiolamido]morphinan, 17-methyl-4,5α-epoxy-3,14β-dihydroxy-7β-[N-methyl-3-(4-trifluoromethylphenyl)propiolamido]morphinan, 17-phenethyl-4,5α-epoxy-3,14β-dihydroxy-7β-[N-methyl-3-(4-trifluoromethylphenyl)propiolamido]morphinan, 17-cyclopropylmethyl-4,5α-epoxy-3,14β-dihydroxy-7β-[N-methyl-3-(3-methylphenyl)propiolamido]morphinan, 17-allyl-4,5α-epoxy-3,14β-dihydroxy-7β-[N-methyl-3-(3-methylphenyl)propiolamido]morphinan, 17-methyl-4,5α-epoxy-3,14β-dihydroxy-7β-[N-methyl-3-(3-methylphenyl)propiolamido]morphinan, 17-phenethyl-4,5α-epoxy-3,14β-dihydroxy-7β-[N-methyl-3-(3-methylphenyl)propiolamido]morphinan, 17-cyclopropylmethyl-4,5α-epoxy-3,14β-dihydroxy-8β-(N-methyl-3-trifluoromethylcinnamamido)morphinan, 17-allyl-4,5α-epoxy-3,14β-dihydroxy-8β-(N-methyl-3-trifluoromethylcinnamamido)morphinan, 17-methyl-4,5α-epoxy-3,14β-dihydroxy-8β-(N-methyl-3-trifluoromethylcinnamamido)morphinan, 17-phenethyl-4,5α-epoxy-3,14β-dihydroxy-8β-(N-methyl-3-trifluoromethylcinnamamido)morphinan, 17-cyclopropylmethyl-4,5α-epoxy-3,14β-dihydroxy-8β-[N-methyl-trans-3-(3-furyl)acrylamido]-morphinan, 17-allyl-4,5α-epoxy-3,14β-dihydroxy-8β-[N-methyl-trans-3-(3-furyl)acrylamido]morphinan, 17-methyl-4,5α-epoxy-3,14β-dihydroxy-8β-[N-methyl-trans-3-(3-furyl)acrylamido]morphinan, 17-phenethyl-4,5α-epoxy-3,14β-dihydroxy-8β-[N-methyl-trans-3-(3-furyl)acrylamido]-morphinan, 17-cyclopropylmethyl-4,5α-epoxy-3,14β-dihydroxy-8β-(N-methyl-3-methylcinnamamido)morphinan, 17-allyl-4,5α-epoxy-3,14β-dihydroxy-8β-(N-methyl-3-methylcinnamamido)morphinan, 17-methyl-4,5α-epoxy-3,14β-dihydroxy-8β-(N-methyl-3-methylcinnamamido)morphinan, 17-phenethyl-4,5α-epoxy-3,14β-dihydroxy-8β-(N-methyl-3-methylcinnamamido)morphinan, 17-cyclopropylmethyl-4,5α-epoxy-3,14β-dihydroxy-8β-[N-methyl-3-(4-trifluoromethylphenyl)propiolamido]morphinan, 17-allyl-4,5α-epoxy-3,14β-dihydroxy-8β-[N-methyl-3-(4-trifluoromethylphenyl)

propiolamido]morphinan, 17-methyl-4,5α-epoxy-3,14β-dihydroxy-8β-[N-methyl-3-(4-trifluoromethylphenyl)propiolamido]morphinan, 17-phenethyl-4,5α-epoxy-3,14β-dihydroxy-8β-[N-methyl-3-(4-trifluoromethylphenyl)propiolamido]morphinan, 17-cyclopropylmethyl-4,5α-epoxy-3,14β-dihydroxy-8β-[N-methyl-3-(3-methylphenyl)propiolamido]morphinan, 17-allyl-4,5α-epoxy-3,14β-dihydroxy-8β-[N-methyl-3-(3-methylphenyl)propiolamido]morphinan, 17-methyl-4,5α-epoxy-3,14β-dihydroxy-8β-[N-methyl-3-(3-methylphenyl)propiolamido]morphinan, 17-phenethyl-4,5α-epoxy-3,14β-dihydroxy-8β-[N-methyl-3-(3-methylphenyl)propiolamido]morphinan, 17-cyclopropylmethyl-4,5α-epoxy-3,14β-dihydroxy-1-nitro-6β-(N-methyl-3-trifluoromethylcinnamamido)morphinan, 17-allyl-4,5α-epoxy-3,14β-dihydroxy-1-nitro-6β-(N-methyl-3-trifluoromethylcinnamamido)morphinan, 17-methyl-4,5α-epoxy-3,14β-dihydroxy-1-nitro-6β-(N-methyl-3-trifluoromethylcinnamamido)morphinan, 17-phenethyl-4,5α-epoxy-3,14β-dihydroxy-1-nitro-6β-(N-methyl-3-trifluoromethylcinnamamido)morphinan, 17-cyclopropylmethyl-4,5α-epoxy-3,14β-dihydroxy-1-nitro-6β-[N-methyl-trans-3-(3-furyl)acrylamido]morphinan, 17-allyl-4,5α-epoxy-3,14β-dihydroxy-1-nitro-6β-[N-methyl-trans-3-(3-furyl)acrylamido]morphinan, 17-methyl-4,5α-epoxy-3,14β-dihydroxy-1-nitro-6β-[N-methyl-trans-3-(3-furyl)acrylamido]morphinan, 17-phenethyl-4,5α-epoxy-3,14β-dihydroxy-1-nitro-6β-[N-methyl-trans-3-(3-furyl)acrylamido]morphinan, 17-cyclopropylmethyl-4,5α-epoxy-3,14β-dihydroxy-1-nitro-6β-(N-methyl-3-methylcinnamamido)morphinan, 17-allyl-4,5α-epoxy-3,14β-dihydroxy-1-nitro-6β-(N-methyl-3-methylcinnamamido)morphinan, 17-methyl-4,5α-epoxy-3,14β-dihydroxy-1-nitro-6β-(N-methyl-3-methylcinnamamido)morphinan, 17-phenethyl-4,5α-epoxy-3,14β-dihydroxy-1-nitro-6β-(N-methyl-3-methylcinnamamido)morphinan, 17-cyclopropylmethyl-4,5α-epoxy-3,14β-dihydroxy-1-nitro-6β-[N-methyl-3-(4-trifluoromethylphenyl)propiolamido]morphinan, 17-allyl-4,5α-epoxy-3,14β-dihydroxy-1-nitro-6β-[N-methyl-3-(4-trifluoromethylphenyl)propiolamido]morphinan, 17-methyl-4,5α-epoxy-3,14β-dihydroxy-1-nitro-6β-[N-methyl-3-(4-trifluoromethylphenyl)propiolamido]morphinan, 17-phenethyl-4,5α-epoxy-3,14β-dihydroxy-1-nitro-6β-[N-methyl-3-(4-trifluoromethylphenyl)propiolamido]morphinan, 17-cyclopropylmethyl-4,5α-epoxy-3,14β-dihydroxy-1-nitro-6β-[N-methyl-3-(3-methylphenyl)propiolamido]morphinan, 17-allyl-4,5α-epoxy-3,14β-dihydroxy-1-nitro-6β-[N-methyl-3-(3-methylphenyl)propiolamido]morphinan, 17-methyl-4,5α-epoxy-3,14β-dihydroxy-1-nitro-6β-[N-methyl-3-(3-methylphenyl)propiolamido]morphinan, 17-phenethyl-4,5α-epoxy-3,14β-dihydroxy-1-nitro-6β-[N-methyl-3-(3-methylphenyl)propiolamido]morphinan, 17-cyclopropylmethyl-4,5α-epoxy-3,14β-dihydroxy-7α-methyl-6β-(N-methyl-3-trifluoromethylcinnamamido)morphinan, 17-allyl-4,5α-epoxy-3,14β-dihydroxy-7α-methyl-6β-(N-methyl-3-trifluoromethylcinnamamido)morphinan, 17-methyl-4,5α-epoxy-3,14 -dihydroxy-7α-methyl-6β-(N-methyl-3-trifluoromethylcinnamamido)morphinan, 17-phenethyl-4,5α-epoxy-3,14β-dihydroxy-7α-methyl-6β-(N-methyl-3-trifluoromethylcinnamamido)morphinan, 17-cyclopropylmethyl-4,5α-epoxy-3,14β-dihydroxy-7α-methyl-6β-[N-methyl-trans-3-(3-furyl)acrylamido]morphinan, 17-allyl-4,5α-epoxy-3,14β-dihydroxy-7α-methyl-6β-[N-methyl-trans-3-(3-furyl)acrylamido]morphinan, 17-methyl-4,5α-epoxy-3,14β-dihydroxy-7α-methyl-6β-[N-methyl-trans-3-(3-furyl)acrylamido]morphinan, 17-phenethyl-4,5α-epoxy-3,14β-dihydroxy-7α-methyl-6β-[N-methyl-trans-3-(3-furyl)acrylamido]morphinan, 17-cyclopropylmethyl-4,5α-epoxy-3,14β-dihydroxy-7α-methyl-6β-(N-methyl-3-methylcinnamamido)morphinan, 17-allyl-4,5α-epoxy-3,14β-dihydroxy-7α-methyl-6β-(N-methyl-3-methylcinnamamido)morphinan, 17-methyl-4,5α-epoxy-3,14β-dihydroxy-7α-methyl-6β-(N-methyl-3-methylcinnamamido)morphinan, 17-phenethyl-4,5α-epoxy-3,14β-dihydroxy-7α-methyl-6)3-(N-methyl-3-methylcinnamamido)morphinan, 17-cyclopropylmethyl-4,5α-epoxy-3,14β-dihydroxy-7α-methyl-6β-[N-methyl-3-(4-trifluoromethylphenyl)propiolamido]morphinan, 17-allyl-4,5α-epoxy-3,14β-dihydroxy-7α-methyl-6β-[N-methyl-3-(4-trifluoromethylphenyl)propiolamido]morphinan, 17-methyl-4,5α-epoxy-3,14β-dihydroxy-7α-methyl-6β-[N-methyl-3-(4-trifluoromethylphenyl)propiolamido]morphinan, 17-phenethyl-4,5α-epoxy-3,14β-dihydroxy-7α-methyl-6β-[N-methyl-3-(4-trifluoromethylphenyl)propiolamido]morphinan, 17-cyclopropylmethyl-4,5α-epoxy-3,14β-dihydroxy-7α-methyl-6β-[N-methyl-3-(3-methylphenyl)propiolamido]morphinan, 17-allyl-4,5α-epoxy-3,14β-dihydroxy-7α-methyl-6β-[N-methyl-3-(3-methylphenyl)propiolamido]morphinan, 17-methyl-4,5α-epoxy-3,14β-dihydroxy-7α-methyl-6β-[N-methyl-3-(3-methylphenyl)propiolamido]morphinan, 17-phenethyl-4,5α-epoxy-3,14β-dihydroxy-7α-methyl-6)3-[N-methyl-3-(3-methylphenyl)propiolamido]morphinan, 17-cyclopropylmethyl-4,5α-epoxy-3,14β-dihydroxy-7β-methyl-6β-(N-methyl-3-trifluoromethylcinnamamido)morphinan, 17-allyl-4,5α-epoxy-3,14β-dihydroxy-7β-methyl-6β-(N-methyl-3-trifluoromethylcinnamamido)morphinan, 17-methyl-4,5α-epoxy-3,14β-dihydroxy-7β-methyl-6β-(N-methyl-3-trifluoromethylcinnamamido)morphinan, 17-phenethyl-4,5α-epoxy-3,14β-dihydroxy-7β-methyl-6β-(N-methyl-3-trifluoromethylcinnamamido)morphinan, 17-cyclopropylmethyl-4,5α-epoxy-3,14β-dihydroxy-7β-methyl-6β-[N-methyl-trans-3-(3-furyl)acrylamido]morphinan, 17-allyl-4,5α-epoxy-3,14β-dihydroxy-7β-methyl-6β-[N-methyl-trans-3-(3-furyl)acrylamido]morphinan, 17-methyl-4,5α-epoxy-3,14β-dihydroxy-7β-methyl-6β-[N-methyl-trans-3-(3-furyl)acrylamido]morphinan, 17-phenethyl-4,5α-epoxy-3,14β-dihydroxy-7β-methyl-6β-[N-methyl-trans-3-(3-furyl)acrylamido]morphinan, 17-cyclopropylmethyl-4,5α-epoxy-3,14β-dihydroxy-7β-methyl-6β-(N-methyl-3-methylcinnamamido)morphinan, 17-allyl-4,5α-epoxy-3,14β-dihydroxy-7β-methyl-6β-(N-methyl-3-methylcinnamamido)morphinan, 17-methyl-4,5α-epoxy-3,14β-dihydroxy-7β-methyl-6β-(N-methyl-3-methylcinnamamido)morphinan, 17-phenethyl-4,5α-epoxy-3,14β-dihydroxy-7β-methyl-6β-(N-methyl-3-methylcinnamamido)morphinan, 17-cyclopropylmethyl-4,5α-epoxy-3,14β-dihydroxy-7β-methyl-6β-[N-methyl-3-(4-trifluoromethylphenyl)propiolamido]morphinan, 17-allyl-4,5α-epoxy-3,14β-dihydroxy-7β-methyl-6β-[N-methyl-3-(4-trifluoromethylphenyl)propiolamido]morphinan, 17-methyl-4,5α-epoxy-3,14β-dihydroxy-7β-methyl-6β-[N-methyl-3-(4-trifluoromethylphenyl)propiolamido]morphinan, 17-phenethyl-4,5α-epoxy-3,14β-dihydroxy-7β-methyl-6β-[N-methyl-3-(4-trifluoromethylphenyl)propiolamido]morphinan, 17-cyclopropylmethyl-4,5α-epoxy-3,14β-dihydroxy-7β-methyl-6β-[N-methyl-3-(3-methylphenyl)propiolamido]morphinan, 17-allyl-4,5α-epoxy-3,14β-dihydroxy-7β-methyl-6β-[N-methyl-3-(3-methylphenyl)propiolamido]morphinan, 17-methyl-4,5α-epoxy-3,14β-dihydroxy-7β-methyl-6β-[N-methyl-3-(3-methylphenyl)propiolamido]morphinan, 17-phenethyl-4,5α-epoxy-3,14β-dihydroxy-7β-methyl-6β-[N-methyl-3-(3-methylphenyl)propiolamido]morphinan, 17-cyclopropylmethyl-4,5α-epoxy-3,14β-dihydroxy-8β-methyl-6β-(N-methyl-3-trifluoromethylcinnamamido)morphinan, 17-allyl-4,5α-epoxy-3,14β-dihydroxy-8β-methyl-6β-(N-methyl-3-trifluoromethylcinnamamido)morphinan, 17-methyl-4,5α-epoxy-3,14β-dihydroxy-8β-methyl-6β-(N-methyl-3-trifluoromethylcinnamamido)morphinan, 17-phenethyl-4,5α-epoxy-3,14β-dihydroxy-8β-methyl-6β-(N-methyl-3-trifluoromethylcinnamamido)morphinan, 17-cyclopropylmethyl-4,5α-epoxy-3,14β-dihydroxy-8β-methyl-6β-[N-methyl-trans-3-(3 -furyl)acrylamido]morphinan, 17-allyl-4,5α-epoxy-3,14β-dihydroxy-8β-methyl-6β-[N-methyl-trans-3-(3-furyl)acrylamido]morphinan, 17-methyl-4,5α-epoxy-3,14β-dihydroxy-8β-methyl-6β-[N-methyl-trans-3-(3-furyl)acrylamido]morphinan, 17-phenethyl-4,5α-epoxy-3,14β-dihydroxy-8β-methyl-6β-[N-methyl-trans-3-(3-furyl)acrylamido]morphinan, 17-cyclopropylmethyl-4,5α-epoxy-3,14β-dihydroxy-8β-methyl-6β-(N-methyl-3-methylcinnamamido)morphinan, 17-allyl-4,5α-epoxy-3,14β-dihydroxy-8β-methyl-6β-(N-methyl-3-methylcinnamamido)morphinan, 17-methyl-4,5α-epoxy-3,14β-dihydroxy-8β-methyl-6β-(N-methyl-3-methylcinnamamido)morphinan, 17-phenethyl-4,5α-epoxy-3,14β-dihydroxy-8β-methyl-6β-(N-methyl-3-methylcinnamamido)morphinan, 17-cyclopropylmethyl-4,5α-epoxy-3,14β-dihydroxy-8β-methyl-6β-[N-methyl-3-(4-trifluoromethylphenyl)propiolamido]morphinan, 17-allyl-4,5α-epoxy-3,14β-dihydroxy-8β-methyl-6β-[N-methyl-3-(4-trifluoromethylphenyl)propiolamido]morphinan, 17-methyl-4,5α-epoxy-3,14β-dihydroxy-8β-methyl-6β-[N-methyl-3-(4-trifluoromethylphenyl)propiolamido]morphinan, 17-phenethyl-4,5α-epoxy-3,14β-dihydroxy-8β-methyl-6β-[N-methyl-3-(4-trifluoromethylphenyl)propiolamido]morphinan, 17-cyclopropylmethyl-4,5α-epoxy-3,14β-dihydroxy-8β-methyl-6β-[N-methyl-3-(3-methylphenyl)propiolamido]morphinan, 17-allyl-4,5α-epoxy-3,14β-dihydroxy-8β-methyl-6β-[N-methyl-3-(3-methylphenyl)propiolamido]morphinan, 17-methyl-4,5α-epoxy-3,14β-dihydroxy-8β-methyl-6β-[N-methyl-3-(3-methylphenyl)propiolamido]morphinan, 17-phenethyl-4,5α-epoxy-3,14β-dihydroxy-8β-methyl-6β-[N-methyl-3-(3-methylphenyl)propiolamido]morphinan, 17-cyclopropylmethyl-4,5α-epoxy-3,14β-dihydroxy-8β-ethyl-6β-(N-methyl-3-trifluoromethylcinnamamido)morphinan, 17-allyl-4,5α-epoxy-3,14β-dihydroxy-8β-ethyl-6β-(N-methyl-3-trifluoromethylcinnamamido)morphinan, 17-methyl-4,5α-epoxy-3,14β-dihydroxy-8β-ethyl-6β-(N-methyl-3-trifluoromethylcinnamamido)morphinan, 17-phenethyl-4,5α-epoxy-3,14β-dihydroxy-8β-ethyl-6β-(N-methyl-3-trifluoromethylcinnamamido)morphinan, 17-cyclopropylmethyl-4,5α-epoxy-8β-ethyl-3,14β-dihydroxy-6β-[N-methyl-trans- 3-(3-furyl)acrylamido]morphinan, 17-allyl-4,5α-epoxy-8β-ethyl-3,14β-dihydroxy-6β-[N-methyl-trans-3-(3-furyl)acrylamido]morphinan, 17-methyl-4,5α-epoxy-8β-ethyl-3,14β-dihydroxy-6β-[N-methyl-trans-3-(3-furyl)acrylamido]morphinan, 17-phenethyl-4,5α-epoxy-8)-ethyl-3,14β-dihydroxy-6β-[N-methyl-trans-3-(3-furyl)acrylamido]morphinan, 17-cyclopropylmethyl-4,5α-epoxy-8β-ethyl-3,14β-dihydroxy-6β-(N-methyl-3-methylcinnamamido)morphinan, 17-allyl-4,5α-epoxy-8)-ethyl-3,14β-dihydroxy-6β-(N-methyl-3-methylcinnamamido)morphinan, 17-methyl-4,5α-epoxy-8β-ethyl-3,14β-dihydroxy-6β-(N-methyl-3-methylcinnamamido)morphinan, 17-phenethyl-4,5α-epoxy-8β-ethyl-3,14β-dihydroxy-6β-(N-methyl-3-methylcinnamamido)morphinan, 17-cyclopropylmethyl-4,5α-epoxy-8β-ethyl-3,14β-dihydroxy-6β-[N-methyl-3-(4-trifluoromethylphenyl)propiolamido]morphinan, 17-allyl-4,5α-epoxy-8β-ethyl-3,14β-dihydroxy-6β-[N-methyl-3-(4-trifluoromethylphenyl)propiolamido]morphinan, 17-methyl-4,5α-epoxy-8β-ethyl-3,14β-dihydroxy-6β-[N-methyl-3-(4-trifluoromethylphenyl)propiolamido]morphinan, 17-phenethyl-4,5α-epoxy-8β-ethyl-3,14β-dihydroxy-6β-[N-methyl-3-(4-trifluoromethylphenyl)propiolamido]morphinan, 17-cyclopropylmethyl-4,5α-epoxy-8β-ethyl-3,14β-dihydroxy-6β-[N-methyl-3-(3-methylphenyl)propiolamido]morphinan, 17-allyl-4,5α-epoxy-8β-ethyl-3,14β-dihydroxy-6β-[N-methyl-3-(3-methylphenyl)propiolamido]morphinan, 17-methyl-4,5α-epoxy-8β-ethyl-3,14β-dihydroxy-6β-[N-methyl-3-(3-methylphenyl)propiolamido]morphinan, 17-phenethyl-4,5α-epoxy-8β-ethyl-3,14β-dihydroxy-6β-[N-methyl-3-(3-methylphenyl)propiolamido]morphinan, 17-cyclopropylmethyl-4,5α-epoxy-3,14β-dihydroxy-10-keto-6β-(N-methyl-3-trifluoromethylcinnamamido)morphinan, 17-allyl-4,5α-epoxy-3,14β-dihydroxy-10-keto-6β-(N-methyl-3-trifluoromethylcinnamamido)morphinan, 17-methyl-4,55o-epoxy-3,14β-dihydroxy-10-keto-6β-(N-methyl-3-trifluoromethylcinnamamido)morphinan, 17-phenethyl-4,5α-epoxy-3,14β-dihydroxy-10-keto-6β-(N-methyl-3-trifluoromethylcinnamamido)morphinan, 17-cyclopropylmethyl-4,5α-epoxy-3,14β-dihydroxy- 10-keto-6β-[N-methyl-trans-3-(3-furyl)acrylamido]morphinan, 17-allyl-4,5α-epoxy-3,14β-dihydroxy-10-keto-6β-[N-methyl-trans-3-(3-furyl)acrylamido]morphinan, 17-methyl-4,5α-epoxy-3,14β-dihydroxy-10-keto-6β-[N-methyl-trans-3-(3-furyl)acrylamido]morphinan, 17-phenethyl-4,5α-epoxy-3,14β-dihydroxy-10-keto-6β-[N-methyl-trans-3-(3-furyl)acrylamido]morphinan, 17-cyclopropylmethyl-4,5α-epoxy-3,14β-dihydroxy-10-keto-6β-(N-methyl-3-methylcinnamamido)morphinan, 17-allyl-4,5α-epoxy-3,14β-dihydroxy-10-keto-6β-(N-methyl-3-methylcinnamamido)morphinan, 17-methyl-4,5α-epoxy-3,14β-dihydroxy-10-keto-6β-(N-methyl-3-methylcinnamamido)morphinan, 17-phenethyl-4,5α-epoxy-3,14β-dihydroxy-10-keto-6β-(N-methyl-3-methylcinnamamido)morphinan, 17-cyclopropylmethyl-4,5α-epoxy-3,14β-dihydroxy-10-keto-6β-[N-methyl-3-(4-trifluoromethylphenyl)propiolamido]morphinan, 17-allyl-4,5α-epoxy-3,14β-dihydroxy-10-keto-6β-[N-methyl-3-(4-trifluoromethylphenyl)propiolamido]morphinan, 17-methyl-4,5α-epoxy-3,14β-dihydroxy-10-keto-6β-[N-methyl-3-(4-trifluoromethylphenyl)propiolamido]morphinan, 17-phenethyl-4,5α-epoxy-3,14β-dihydroxy-10-keto-6β-[N-methyl-3-(4-trifluoromethylphenyl)propiolamido]morphinan, 17-cyclopropylmethyl-4,5α-epoxy-3,14β-dihydroxy-10-keto-6β-[N-methyl-3-(3-methylphenyl)propiolamido]morphinan, 17-allyl-4,5α-epoxy-3,14β-dihydroxy-10-keto-6β-[N-methyl-3-(3-methylphenyl)propiolamido]morphinan, 17-methyl-4,5α-epoxy-3,14β-dihydroxy-10-keto-6β-[N-methyl-3-(3-methylphenyl)propiolamido]morphinan, 17-phenethyl-4,5α-epoxy-3,14β-dihydroxy-10-keto-6β-[N-methyl-3-(3-methylphenyl)propiolamido]morphinan, 17-cyclopropylmethyl-4,5α-epoxy-3,14β,15β-trihydroxy-6β-(N-methyl-3-trifluoromethylcinnamamido)morphinan, 17-allyl-4,5α-epoxy-3,14β,15β-trihydroxy-6β-(N-methyl-3-trifluoromethylcinnamamido)morphinan, 17-methyl-4,5α-epoxy-3,14β,15β-trihydroxy-6β-(N-methyl-3-trifluoromethylcinnamamido)morphinan, 17-phenethyl-4,5α-epoxy-3,14β,15β-trihydroxy-6β-(N-methyl-3-trifluoromethylcinnamamido)morphinan, 17-cyclopropylmethyl-4,5α-epoxy-3,14β,15β-trihydroxy-6β-[N-methyl-trans-3-(3-furyl)acrylamido]morphinan, 17-allyl-4,5α-epoxy-3,14β,15β-trihydroxy-6β-[N-methyl-trans-3-(3-furyl)acrylamido]morphinan, 17-methyl-4,5α-epoxy-3,14β,15β-trihydroxy-6β-[N-methyl-trans-3-(3-furyl)acrylamido]morphinan, 17-phenethyl-4,5α-epoxy-3,14β,15β-trihydroxy-6β-[N-methyl-trans-3-(3-furyl)acrylamido]morphinan, 17-cyclopropylmethyl-4,5α-epoxy-3,14β,15β-trihydroxy-6β-(N-methyl-3-methylcinnamamido)morphinan, 17-allyl-4,5α-epoxy-3,14β,15β-trihydroxy-6β-(N-methyl-3-methylcinnamamido)morphinan, 17-methyl-4,5α-epoxy-3,14β,15β-trihydroxy-6β-(N-methyl-3-methylcinnamamido)morphinan, 17-phenethyl-4,5α-epoxy-3,14β,15β-trihydroxy-6β-(N-methyl-3-methylcinnamamido)morphinan, 17-cyclopropylmethyl-4,5α-epoxy-3,14β,15β-trihydroxy-6β-[N-methyl-3-(4-trifluoromethylphenyl)propiolamido]morphinan, 17-allyl-4,5α-epoxy-3,14β,15β-trihydroxy-6β-[N-methyl-3-(4-trifluoromethylphenyl)propiolamido]morphinan, 17-methyl-4,5α-epoxy-3,14β,15β-trihydroxy-6β-[N-methyl-3-(4-trifluoromethylphenyl)propiolamido]morphinan, 17-phenethyl-4,5α-epoxy-3,14β,15β-trihydroxy-6β-[N-methyl-3-(4-trifluoromethylphenyl)propiolamido]morphinan, 17-cyclopropylmethyl-4,5α-epoxy-3,14β,15β-trihydroxy-6β-[N-methyl-3-(3-methylphenyl)propiolamido]morphinan, 17-allyl-4,5α-epoxy-3,14β,15β-trihydroxy-6β-[N-methyl-3-(3-methylphenyl)propiolamido]morphinan, 17-methyl-4,5α-epoxy-3,14β,15β-trihydroxy-6β-[N-methyl-3-(3-methylphenyl)propiolamido]morphinan, 17-phenethyl-4,5α-epoxy-3,14β,15β-trihydroxy-6β-[N-methyl-3-(3-methylphenyl)propiolamido]morphinan, 17-cyclopropylmethyl-16-cyano-4,5α-epoxy-3,14β-dihydroxy-6β-(N-methyl-3-trifluoromethylcinnamamido)morphinan, 17-allyl-16-cyano-4,5α-epoxy-3,14β-dihydroxy-6β-(N-methyl-3-trifluoromethylcinnamamido)morphinan, 17-methyl-16-cyano-4,5α-epoxy-3,14β-dihydroxy-6β-(N-methyl-3-trifluoromethylcinnamamido)morphinan, 17-phenethyl-16-cyano-4,5α-epoxy-3,14β-dihydroxy-6β-(N-methyl-3-trifluoromethylcinnamamido)morphinan, 17-cyclopropylmethyl-16-cyano-4,5α-epoxy-3,14β-dihydroxy-6β-[N-methyl-trans-3-(3-furyl)acrylamido]morphinan, 17-allyl-16-cyano-4,5α-epoxy-3,14β-dihydroxy-6β-[N-methyl-trans-3-(3-furyl)acrylamido]morphinan, 17-methyl-16-cyano-4,5α-epoxy-3,14β-dihydroxy-6β-[N-methyl-trans-3-(3-furyl)acrylamido]morphinan, 17-phenethyl-16-cyano-4,5α-epoxy-3,14β-dihydroxy-6β-[N-methyl-trans-3-(3-furyl)acrylamido]morphinan, 17-cyclopropylmethyl-16-cyano-4,5α-epoxy-3,14β-dihydroxy-6β-(N-methyl-3-methylcinnamamido)morphinan, 17-allyl-16-cyano-4,5α-epoxy-3,14β-dihydroxy-6β-(N-methyl-3-methylcinnamamido)morphinan, 17-methyl-16-cyano-4,5α-epoxy-3,14β-dihydroxy-6β-(N-methyl-3-methylcinnamamido)morphinan, 17-phenethyl-16-cyano-4,5α-epoxy-3,14β-dihydroxy-6β-(N-methyl-3-methylcinnamamido)morphinan, 17-cyclopropylmethyl-16-cyano-4,5α-epoxy-3,14β-dihydroxy-6β-[N-methyl-3-(4-trifluoromethylphenyl)propiolamido]morphinan, 17-allyl-16-cyano-4,5α-epoxy-3,14β-dihydroxy-6β-[N-methyl-3-(4-trifluoromethylphenyl)propiolamido]morphinan, 17-methyl-16-cyano-4,5α-epoxy-3,14β-dihydroxy-6β-[N-methyl-3-(4-trifluoromethylphenyl)propiolamido]morphinan, 17-phenethyl-16-cyano-4,5α-epoxy-3,14β-dihydroxy-6β-[N-methyl-3-(4-trifluoromethylphenyl)propiolamido]morphinan, 17-cyclopropylmethyl-16-cyano-4,5α-epoxy-3,14β-dihydroxy-6β-[N-methyl-3-(3-methylphenyl)propiolamido]morphinan, 17-allyl-16-cyano-4,5α-epoxy-3,14β-dihydroxy-6β-[N-methyl-3-(3-methylphenyl)propiolamido]morphinan, 17-methyl-16-cyano-4,5α-epoxy-3,14β-dihydroxy-6β-[N-methyl-3-(3-methylphenyl)propiolamido]morphinan, 17-phenethyl-16-cyano-4,5α-epoxy-3,14β-dihydroxy-6β-[N-methyl-3-(3-methylphenyl)propiolamido]morphinan, 8-nor-17-cyclopropylmethyl-4,5α-epoxy-3,14β-dihydroxy-6β-(N-methyl-3-trifluoromethylcinnamamido)morphinan, 8-nor-17-allyl-4,5α-epoxy-3,14β-dihydroxy-6β-(N-methyl-3-trifluoromethylcinnamamido)morphinan, 8-nor-17-methyl-4,5α-epoxy-3,14β-dihydroxy-6β-(N-methyl-3-trifluoromethylcinnamamido)morphinan, 8-nor-17-phenethyl-4,5α-epoxy-3,14β-dihydroxy-6β-(N-methyl-3-trifluoromethylcinnamamido)morphinan, 8-nor-17-cyclopropylmethyl-4,5α-epoxy-3,14β-dihydroxy-6β-[N-methyl-trans-3-(3 -furyl)acrylamido]morphinan, 8-nor-17-allyl-4,5α-epoxy-3,14β-dihydroxy-6β-[N-methyl-trans-3-(3-furyl)acrylamido]morphinan, 8-nor-17-methyl-4,5α-epoxy-3,14A-dihydroxy-6β-[N-methyl-trans-3-(3-furyl)acrylamido]morphinan, 8-nor-17-phenethyl-4,5α-epoxy-3,14β-dihydroxy-6β-[N-methyl-trans-3-(3-furyl)acrylamido]morphinan, 8-nor-17-cyclopropylmethyl-4,5α-epoxy-3,14β-dihydroxy-6β-(N-methyl-3-methylcinnamamido)morphinan, 8-nor-17-allyl-4,5α-epoxy-3,14β-dihydroxy-6β-(N-methyl-3-methylcinnamamido)morphinan, 8-nor-17-methyl-4,5α-epoxy-3,14β-dihydroxy-6β-(N-methyl-3-methylcinnamamido)morphinan, 8-nor-17-phenethyl-4,5α-epoxy-3,14β-dihydroxy-6β-(N-methyl-3-methylcinnamamido)morphinan, 8-nor-17-cyclopropylmethyl-4,5α-epoxy-3,14β-dihydroxy-6β-[N-methyl-3-(4-trifluoromethylphenyl)propiolamido]morphinan, 8-nor-17-allyl-4,5α-epoxy-3,14β-dihydroxy-6β-[N-methyl-3-(4-trifluoromethylphenyl)propiolamido]morphinan, 8-nor-17-methyl-4,5α-epoxy-3,14β-dihydroxy-6β-[N-methyl-3-(4- trifluoromethylphenyl)propiolamido]morphinan, 8-nor-17-phenethyl-4,5α-epoxy-3,14β-dihydroxy-6β-[N-methyl-3-(4-trifluoromethylphenyl)propiolamido]morphinan, 8-nor-17-cyclopropylmethyl-4,5α-epoxy-3,14β-dihydroxy-6β-[N-methyl-3-(3-methylphenyl)propiolamido]morphinan, 8-nor-17-allyl-4,5α-epoxy-3,14β-dihydroxy-6β-[N-methyl-3-(3-methylphenyl)propiolamido]morphinan, 8-nor-17-methyl-4,5α-epoxy-3,14β-dihydroxy-6β-[N-methyl-3-(3-methylphenyl)propiolamido]morphinan, 8-nor-17-phenethyl-4,5α-epoxy-3,14β-dihydroxy-6β-[N-methyl-3-(3-methylphenyl)propiolamido]morphinan, 8-homo-17-cyclopropylmethyl-4,5α-epoxy-3,14β-dihydroxy-6β-(N-methyl-3-trifluoromethylcinnamamido)morphinan, 8-homo-17-allyl-4,5α-epoxy-3,14β-dihydroxy-6β-(N-methyl-3-trifluoromethylcinnamamido)morphinan, 8-homo-17-methyl-4,5α-epoxy-3,14β-dihydroxy-6β-(N-methyl-3-trifluoromethylcinnamamido)morphinan, 8-homo-17-phenethyl-4,5α-epoxy-3,14β-dihydroxy-6β-(N-methyl-3-trifluoromethylcinnamamido)morphinan, 8-homo-17-cyclopropylmethyl-4,5α-epoxy-3,14β-dihydroxy-6β-[N-methyl-trans-3-(3-furyl)acrylamido]morphinan, 8-homo-17-allyl-4,5α-epoxy-3,14β-dihydroxy-6β-[N-methyl-trans-3-(3-furyl)acrylamido]morphinan, 8-homo-17-methyl-4,5α-epoxy-3,14β-dihydroxy-6β-[N-methyl-trans-3-(3-furyl)acrylamido]morphinan, 8-homo-17-phenethyl-4,5α-epoxy-3,14β-dihydroxy-6β-[N-methyl-trans-3-(3-furyl)acrylamido]morphinan, 8-homo-17-cyclopropylmethyl-4,5α-epoxy-3,14β-dihydroxy-6β-(N-methyl-3-methylcinnamamido)morphinan, 8-homo-17-allyl-4,5α-epoxy-3,14β-dihydroxy-6β-(N-methyl-3-methylcinnamamido)morphinan, 8-homo-17-methyl-4,5α-epoxy-3,14β-dihydroxy-6β-(N-methyl-3-methylcinnamamido)morphinan, 8-homo-17-phenethyl-4,5α-epoxy-3,14β-dihydroxy-6β-(N-methyl-3-methylcinnamamido)morphinan, 8-homo-17-cyclopropylmethyl-4,5α-epoxy-3,14β-dihydroxy-6β-[N-methyl-3-(4-trifluoromethylphenyl)propiolamido]morphinan, 8-homo-17-allyl-4,5α-epoxy-3,14β-dihydroxy-6β-[N-methyl-3-(4-trifluoromethylphenyl)propiolamido]morphinan, 8-homo-17-methyl-4,5α-epoxy-3,14β-dihydroxy-6β-[N-methyl-3-(4-trifluoromethylphenyl)propiolamido]morphinan, 8-homo-17-phenethyl-4,5α-epoxy-3,14β-dihydroxy-6β-[N-methyl-3-(4-trifluoromethylphenyl)propiolamido]morphinan, 8-homo-17-cyclopropylmethyl-4,5α-epoxy-3,14β-dihydroxy-6β-[N-methyl-3-(3-methylphenyl)propiolamido]morphinan, 8-homo-17-allyl-4,5α-epoxy-3,14β-dihydroxy-6β-[N-methyl-3-(3-methylphenyl)propiolamido]morphinan, 8-homo-17-methyl-4,5α-epoxy-3,14β-dihydroxy-6β-[N-methyl-3-(3-methylphenyl)propiolamido]morphinan, 8-homo-17-phenethyl-4,5<-epoxy-3,14β-dihydroxy-6β-[N-methyl-3-(3-methylphenyl)propiolamido]morphinan, 17-cyclopropylmethyl-3,14β-dihydroxy-4,5α-epoxy-6β-(N-isopropylbenzylamino)morphinan, 17-cyclopropylmethyl-3,14β-dihydroxy-4,5α-epoxy-6α-(N-isopropylbenzylamino)morphinan, 17-allyl-3,14β-dihydroxy-4,5α-epoxy-6β-(N-isopropylbenzylamino)morphinan, 17-allyl-3,14β-dihydroxy-4,5α-epoxy-6α-(N-isopropylbenzylamino)morphinan, 17-cyclopropylmethyl-3,14β-dihydroxy-4,5α-epoxy-6β-(N-isobutylbenzylamino)morphinan, 17-cyclopropylmethyl-3,14β-dihydroxy-4,5α-epoxy-6α-(N-isobutylbenzylamino)morphinan, 17-allyl-3,14β-dihydroxy-4,5α-epoxy-6β-(N-isobutylbenzylamino)morphinan, 17-allyl-3,14β-dihydroxy-4,5α-epoxy-6α-(N-isobutylbenzylamino)morphinan, 17-cyclopropylmethyl-3,14β-dihydroxy-4,5α-epoxy-6β-(N-butylbenzylamino)morphinan, 17-cyclopropylmethyl-3,14β-dihydroxy-4,5α-epoxy-6α-(N-butylbenzylamino)morphinan, 17-allyl-3,14β-dihydroxy-4,5α-epoxy-6β-(N-butylbenzylamino)morphinan, 17-allyl-3,14β-dihydroxy-4,5α-epoxy-6α-(N-butylbenzylamino)morphinan, 17-cyclopropylmethyl-3,14β-dihydroxy-4,5α-epoxy-6β-(N-pentylbenzylamino)morphinan, 17-cyclopropylmethyl-3,14β-dihydroxy-4,5α-epoxy-6α-(N-pentylbenzylamino)morphinan, 17-allyl-3,14β-dihydroxy-4,5α-epoxy-6β-(N-pentylbenzylamino)morphinan, 17-allyl-3,14β-dihydroxy-4,5α-epoxy-6α-(N-pentylbenzylamino)morphinan, 17-cyclopropylmethyl-3,14β-dihydroxy-4,5α-epoxy-6β-(N-methyl-2,4,6-trichlorophenoxyacetamido)morphinan, 17-cyclopropylmethyl-3,14β-dihydroxy-4,5α-epoxy-6α-(N-methyl-2,4,6-trichlorophenoxyacetamido)morphinan, 17-allyl-3,14β-dihydroxy-4,5α-epoxy-6β-(N-methyl-2,4,6-trichlorophenoxyacetamido)morphinan, 17-allyl-3,14β-dihydroxy-4,5α-epoxy-6α-(N-methyl-2,4,6-trichlorophenoxyacetamido)morphinan, 17-cyclopropylmethyl-3,14β-dihydroxy-4,5α-epoxy-6β-(N-methyl-2,4,5-trichlorophenoxyacetamido)morphinan, 17-cyclopropylmethyl-3,14β-dihydroxy-4,5α-epoxy-6α-(N-methyl-2,4,5-trichlorophenoxyacetamido)morphinan, 17-allyl-3,14β-dihydroxy-4,5α-epoxy-6β-(N-methyl-2,4,5-trichlorophenoxyacetamido)morphinan, 17-allyl-3,14β-dihydroxy-4,5α-epoxy-6α-(N-methyl-2,4,5-trichlorophenoxyacetamido)morphinan, 17-cyclopropylmethyl-3,14β-dihydroxy-4,5α-epoxy-6β-(N-methyl-4-cyclohexylbutanoamido)morphinan, 17-cyclopropylmethyl-3,14β-dihydroxy-4,5α-epoxy-6α-(N-methyl-4-cyclohexylbutanoamido)morphinan, 17-allyl-3,14β-dihydroxy-4,5α-epoxy-6β-(N-methyl-4-cyclohexylbutanoamido)morphinan, 17-allyl-3,14β-dihydroxy-4,5α-epoxy-6α-(N-methyl-4-cyclohexylbutanoamido)morphinan, 17-cyclopropylmethyl-3,14β-dihydroxy-4,5α-epoxy-6β-(N-methyl-5-phenylpentanoamido)morphinan, 17-cyclopropylmethyl-3,14β-dihydroxy-4,5α-epoxy-6α-(N-methyl-5-phenylpentanoamido)morphinan, 17-allyl-3,14β-dihydroxy-4,5α-epoxy-6β-(N-methyl-5-phenylpentanoamido)morphinan, 17-allyl-3,14β-dihydroxy-4,5α-epoxy-6α-(N-methyl-5-phenylpentanoamido)morphinan, 17-cyclopropylmethyl-3,14β-dihydroxy-4,5α-epoxy-6β-(N-isobutyl-6-phenylhexanoamido)morphinan, 17-cyclopropylmethyl-3,14β-dihydroxy-4,5α-epoxy-6α-(N-isobutyl-6-phenylhexanoamido)morphinan, 17-allyl-3,14β-dihydroxy-4,5α-epoxy-6β-(N-isobutyl-6-phenylhexanoamido)morphinan, 17-allyl-3,14β-dihydroxy-4,5α-epoxy-6α-(N-isobutyl-6-phenylhexanoamido)morphinan, 17-cyclopropylmethyl-3,14β-dihydroxy-4,5α-epoxy-6β-(N-isobutyl-8-phenyloctanoamido)morphinan, 17-cyclopropylmethyl-3,14β-dihydroxy-4,5α-epoxy-6α-(N-isobutyl-8-phenyloctanoamido)morphinan, 17-allyl-3,14β-dihydroxy-4,5α-epoxy-6β-(N-isobutyl-8-phenyloctanoamido)morphinan, 17-allyl-3,14β-dihydroxy-4,5α-epoxy-6α-(N-isobutyl-8- phenyloctanoamido)morphinan,
17-cyclopropylmethyl-3,14β-dihydroxy-4,5α-epoxy-6β-(N-isobutyl-11-phenylundecanoamido)morphinan,
17-cyclopropylmethyl-3,14β-dihydroxy-4,5α-epoxy-6α-(N-isobutyl-11-phenylundecanoamido)morphinan,
17-allyl-3,14β-dihydroxy-4,5α-epoxy-6β-(N-isobutyl-11-phenylundecanoamido)morphinan, 17-allyl-3,14β-dihydroxy-4,5α-epoxy-6α-(N-isobutyl-11-phenylundecanoamido)morphinan,
17-cyclopropylmethyl-3,14β-dihydroxy-4,5α-epoxy-6β-(N-isobutyl-5-benzoylpentanoamido)morphinan,
17-cyclopropylmethyl-3,14β-dihydroxy-4,5α-epoxy-6α-(N-isobutyl-5-benzoylpentanoamido)morphinan,
17-allyl-3,14β-dihydroxy-4,5α-epoxy-6β-(N-isobutyl-5-benzoylpentanoamido)morphinan, 17-allyl-3,14β-dihydroxy-4,5α-epoxy-6α-(N-isobutyl-5-benzoylpentanoamido)morphinan,
17-cyclopropylmethyl-3,14β-dihydroxy-4,5α-epoxy-6β-(N-isobutyl-5-cyclohexylpentanoamido)morphinan, 17-cyclopropylmethyl-3,14β-dihydroxy-4,5α-epoxy-6α-(N-isobutyl-5-cyclohexylpentanoamido)morphinan, 17-allyl-3,14β-dihydroxy-4,5α-epoxy-6β-(N-isobutyl-5-cyclohexylpentanoamido)morphinan, 17-allyl-3,14β-dihydroxy-4,5α-epoxy-6α-(N-isobutyl-5-cyclohexylpentanoamido)morphinan, 17-isobutyl-3,14β-dihydroxy-4,5α-epoxy-6β-[N-methyl-3-(3-furan)acrylamido]morphinan, 17-isobutyl-3,14β-dihydroxy-4,5α-epoxy-6α-[N-methyl-3-(3-furan)acrylamido]morphinan, 17-cyclopropylmethyl-3,14β-dihydroxy-4,5α-epoxy-6β-(N-pentyl-6-phenylhexanoamido)morphinan, 17-cyclopropylmethyl-3,14β-dihydroxy-4,5α-epoxy-6α-N-pentyl-6-phenylhexanoamido)morphinan, 17-allyl-3,14β-dihydroxy-4,5α-epoxy-6β-(N-pentyl-6-phenylhexanoamido)morphinan, 17-allyl-3,14β-dihydroxy-4,5α-epoxy-6α-(N-pentyl-6-phenylhexanoamido)morphinan,
17-cyclopropylmethyl-3,14β-dihydroxy-4,5α-epoxy-6β-(N-isobutyl-N-6-phenylhexylamino)morphinan, 17-cyclopropylmethyl-3,14β-dihydroxy-4,5α-epoxy-6α-(N-isobutyl-N-6-phenylhexylamino)morphinan, 17-allyl-3,14β-dihydroxy-4,5α-epoxy-6β-(N-isobutyl-N-6-phenylhexylamino)morphinan, 17-allyl-3,14β-dihydroxy-4,5α-epoxy-6α-(N-isobutyl-N-6-phenylhexylamino)morphinan, 17-cyclopropylmethyl-4,5α-epoxy-3,14β-dihydroxy-6β,8β-bis[N-methyl-trans-3-(3-furan)acrylamido]morphinan, 17-allyl-4,5α-epoxy-3,14β-dihydroxy-6β,8β-bis[N-methyl-trans-3-(3-furan)acrylamido]morphinan, 17-methyl-4,5α-epoxy-3,14β-dihydroxy-6β,8β-bis[N-methyl-trans-3-(3-furan)acrylamido]morphinan, 17-phenethyl-4,5α-epoxy-3,14β-dihydroxy-6β,8β-bis[N-methyl-trans-3-(3-furan)acrylamido]morphinan,
17-cyclopropylmethyl-4,5α-epoxy-3,14β-dihydroxy-6α,8β-bis[N-methyl-trans-3-(3-furan)acrylamido]morphinan, 17-allyl-4,5α-epoxy-3,14β-dihydroxy-6α,8β-bis[N-methyl-trans-3-(3-furan)acrylamido]morphinan, 17-methyl-4,5α-epoxy-3,14β-dihydroxy-6α,8β-bis[N-methyl-trans-3-(3-furan)acrylamido]morphinan, 17-phenethyl-4,5α-epoxy-3,14β-dihydroxy-6α,8β-bis[N-methyl-trans-3-(3-furan)acrylamido]morphinan, 17-cyclopropylmethyl-4,5α-epoxy-3,14β-dihydroxy-6β,8α-bis[N-methyl-trans-3-(3-furan)acrylamido]morphinan, 17-allyl-4,5α-epoxy-3,14β-dihydroxy-6β,8α-bis[N-methyl-trans-3-(3-furan)acrylamido]morphinan, 17-methyl-4,5α-epoxy-3,14β-dihydroxy-6β,8α-bis[N-methyl-trans-3-(3-furan)acrylamido]morphinan, 17-phenethyl-4,5α-epoxy-3,14β-dihydroxy-6β,8α-bis[N-methyl-trans-3-(3-furan)acrylamido]morphinan,
17-cyclopropylmethyl-4,5α-epoxy-3,14β-dihydroxy-6α,8α-bis[N-methyl-trans-3-(3-furan)acrylamido]morphinan, 17-allyl-4,5α-epoxy-3,14β-dihydroxy-6α,8α-bis[N-methyl-trans-3-(3-furan)acrylamido]morphinan, 17-methyl-4,5α-epoxy-3,14β-dihydroxy-6α,8α-bis[N-methyl-trans-3-(3-furan)acrylamido]morphinan, 17-phenethyl-4,5α-epoxy-3,14β-dihydroxy-6α,8α-bis[N-methyl-trans-3-(3-furan)acrylamido]morphinan, 8-homo-17-cyclopropylmethyl-4,5α-epoxy-3,14β-dihydroxy-7β-[N-methyl-3-(4-trifluoromethylphenyl)propiolamido]morphinan, 8-homo-17-allyl-4,5α-epoxy-3,14β-dihydroxy-7β-[N-methyl-3-(4-trifluoromethylphenyl)propiolamido]morphinan, 8-homo-17-methyl-4,5α-epoxy-3,14β-dihydroxy-7β-[N-methyl-3-(4-trifluoromethylphenyl)propiolamido]morphinan, 8-homo-17-phenethyl-4,5α-epoxy-3,14β-dihydroxy-7β-[N-methyl-3-(4-trifluoromethylphenyl)propiolamido]morphinan, 8-homo-17-cyclopropylmethyl-4,5α-epoxy-3,14β-dihydroxy-7α-[N-methyl-3-(4-trifluoromethylphenyl)propiolamido]morphinan, 8-homo-17-allyl-4,5α-epoxy-3,14β-dihydroxy-7α-[N-methyl-3-(4-trifluoromethylphenyl)propiolamido]morphinan, 8-homo-17-methyl-4,5α-epoxy-3,14β-dihydroxy-7α-[N-methyl-3-(4-trifluoromethylphenyl)propiolamido]morphinan, 8-homo-17-phenethyl-4,5α-epoxy-3,14β-dihydroxy-7α-[N-methyl-3-(4-trifluoromethylphenyl)propiolamido]morphinan, 8-homo-17-cyclopropylmethyl-4,5α-epoxy-3,14β-dihydroxy-7β-[N-methyl-3-(3-methylphenyl)propiolamido]morphinan, 8-homo-17-allyl-4,5α-epoxy-3,14β-dihydroxy-7β-[N-methyl-3-(3-methylphenyl)propiolamido]morphinan, 8-homo-17-methyl-4,5α-epoxy-3,14β-dihydroxy-7β-[N-methyl-3-(3-methylphenyl)propiolamido]morphinan, 8-homo-17-phenethyl-4,5α-epoxy-3,14β-dihydroxy-7β-[N-methyl-3-(3-methylphenyl)propiolamido]morphinan, 8-homo-17-cyclopropylmethyl-4,5α-epoxy-3,14β-dihydroxy-7α-[N-methyl-3-(3-methylphenyl)propiolamido]morphinan, 8-homo-17-allyl-4,5α-epoxy-3,14β-dihydroxy-7α-[N-methyl-3-(3-methylphenyl)propiolamido]morphinan, 8-homo-17-methyl-4,5α-epoxy-3,14β-dihydroxy-7α-[N-methyl-3-(3-methylphenyl)propiolamido]morphinan, 8-homo-17-phenethyl-4,5α-epoxy-3,14β-dihydroxy-7α-[N-methyl-3-(3-methylphenyl)propiolamido]morphinan, 8-homo-17-cyclopropylmethyl-4,5α-epoxy-3,14β-dihydroxy-7β-(N-methyl-3-methylcinnamamido)morphinan, 8-homo-17-allyl-4,5α-epoxy-3,14β-dihydroxy-7β-(N-methyl-3-methylcinnamamido)morphinan, 8-homo-17-methyl-4,5α-epoxy-3,14β-dihydroxy-7β-(N-methyl-3-methylcinnamamido)morphinan, 8-homo-17-phenethyl-4,5α-epoxy-3,14β-dihydroxy-7β-(N-methyl-3-methylcinnamamido)morphinan, 8-homo-17-cyclopropylmethyl-4,5α-epoxy-3,14β-dihydroxy-7α-(N-methyl-3-methylcinnamamido)morphinan, 8-homo-17-allyl-4,5α-epoxy-3,14β-dihydroxy-7α-(N-methyl-3-methylcinnamamido)morphinan, 8-homo-17-methyl-4,5α-epoxy-3,14β-dihydroxy-7α-(N-methyl-3-methylcinnamamido)morphinan, 8-homo-17-phenethyl-4,5α-epoxy-3,14β-dihydroxy-7α-(N-methyl-3-methylcinnamamido)morphinan, 8-homo-17-cyclopropylmethyl-4,5α-epoxy-3,14β-dihydroxy- 7β-(N-methyl-3-trifluoromethylcinnamamido) morphinan, 8-homo-17-allyl-4,5α-epoxy-3,14β-dihydroxy-7β-(N-methyl-3-trifluoromethylcinnamamido)morphinan, 8-homo-17-methyl-4,5α-epoxy-3,14β-dihydroxy-7β-(N-methyl-3-trifluoromethylcinnamamido)morphinan, 8-homo-17-phenethyl-4,5α-epoxy-3,14β-dihydroxy-7β-(N-methyl-3-trifluoromethylcinnamamido)morphinan, 8-homo-17-cyclopropylmethyl-4,5α-epoxy-3,14β-dihydroxy-7α-(N-methyl-3-trifluoromethylcinnamamido)morphinan, 8-homo-17-allyl-4,5α-epoxy-3,14β-dihydroxy-7α-(N-methyl-3-trifluoromethylcinnamamido)morphinan, 8-homo-17-methyl-4,5α-epoxy-3,14β-dihydroxy-7α-(N-methyl-3-trifluoromethylcinnamamido)morphinan, 8-homo-17-phenethyl-4,5α-epoxy-3,14β-dihydroxy-7α-(N-methyl-3-trifluoromethylcinnamamido)morphinan, 8-homo-17-cyclopropylmethyl-4,5α-epoxy-3,14β-dihydroxy-7β-[N-methyl-trans-3-(3-furan)acrylamido]morphinan, 8-homo-17-allyl-4,5α-epoxy-3,14β-dihydroxy-7β-[N-methyl-trans-3-(3-furan)acrylamido]morphinan, 8-homo-17-methyl-4,5α-epoxy-3,14β-dihydroxy-7β-[N-methyl-trans-3-(3-furan)acrylamido]morphinan, 8-homo-17-phenethyl-4,5α-epoxy-3,14β-dihydroxy-7β-[N-methyl-trans-3-(3-furan)acrylamido]morphinan, 8-homo-17-cyclopropylmethyl-4,5α-epoxy-3,14β-dihydroxy-7α-[N-methyl-trans-3-(3-furan)acrylamido]morphinan, 8-homo-17-allyl-4,5α-epoxy-3,14β-dihydroxy-7α-[N-methyl-trans-3-(3-furan)acrylamido]morphinan, 8-homo-17-methyl-4,5α-epoxy-3,14β-dihydroxy-7α-[N-methyl-trans-3-(3-furan)acrylamido]morphinan, 8-homo-17-phenethyl-4,5α-epoxy-3,14β-dihydroxy-7α-[N-methyl-trans-3-(3-furan)acrylamido]morphinan, 17-methyl-4,5α-epoxy-3,14β-dihydroxy-6α-[N-methyl-3-(3,4-dimethylphenyl)propiolamido]morphinan, 17-phenethyl-4,5α-epoxy-3,14β-dihydroxy-6α-[N-methyl-3-(3,4-dimethylphenyl)propiolamido]morphinan, 17-cyclopropylmethyl-4,5α-epoxy-14β-acetoxy-3-hydroxy-6α-[N-methyl-3-(3,4-dimethylphenyl)propiolamido]morphinan, 17-allyl-4,5α-epoxy-14β-acetoxy-3-hydroxy-6α-[N-methyl-3-(3,4-dimethylphenyl)propiolamido]morphinan, 17-methyl-4,5α-epoxy-14β-acetoxy-3-hydroxy-6α-[N-methyl-3-(3,4-dimethylphenyl)propiolamido]morphinan, 17-phenethyl-4,5α-epoxy-14β-acetoxy-3-hydroxy-6α-[N-methyl-3-(3,4-dimethylphenyl)propiolamido]morphinan, 17-cyclopropylmethyl-4,5α-epoxy-14β-hydroxy-6α-[N-methyl-3-(3,4-dimethylphenyl)propiolamido]morphinan, 17-allyl-4,5α-epoxy-14β-hydroxy-6α-[N-methyl-3-(3,4-dimethylphenyl)propiolamido]morphinan, 17-methyl-4,5α-epoxy-14β-hydroxy-6α-[N-methyl-3-(3,4-dimethylphenyl)propiolamido]morphinan, 17-phenethyl-4,5α-epoxy-14β-hydroxy-6α-[N-methyl-3-(3,4-dimethylphenyl)propiolamido]morphinan, 17-cyclopropylmethyl-4,5α-epoxy-14β-acetoxy-6α-[N-methyl-3-(3,4-dimethylphenyl)propiolamido]morphinan, 17-allyl-4,5α-epoxy-14β-acetoxy-6α-[N-methyl-3-(3,4-dimethylphenyl)propiolamido]morphinan, 17-methyl-4,5α-epoxy-14β-acetoxy-6α-[N-methyl-3-(3,4-dimethylphenyl)propiolamido]morphinan, 17-phenethyl-4,5α-epoxy-14β-acetoxy-6α-[N-methyl-3-(3,4-dimethylphenyl)propiolamido]morphinan, 17-cyclopropylmethyl-4,5α-epoxy-14β-hydroxy-3-methoxy-6α-[N-methyl-3-(3,4-dimethylphenyl)propiolamido]morphinan, 17-allyl-4,5α-epoxy-14β-hydroxy-3-methoxy-6α-[N-methyl-3-(3,4-dimethylphenyl)propiolamido]morphinan, 17-methyl-4,5α-epoxy-14β-hydroxy-3-methoxy-6α-[N-methyl-3-(3,4-dimethylphenyl)propiolamido]morphinan, 17-phenethyl-4,5α-epoxy-14β-hydroxy-3-methoxy-6α-[N-methyl-3-(3,4-dimethylphenyl)propiolamido]morphinan, 17-cyclopropylmethyl-4,5α-epoxy-14β-acetoxy-3-methoxy-6α-[N-methyl-3-(3,4-dimethylphenyl)propiolamido]morphinan, 17-allyl-4,5α-epoxy-14β-acetoxy-3-methoxy-6α-[N-methyl-3-(3,4-dimethylphenyl)propiolamido]morphinan, 17-methyl-4,5α-epoxy-14β-acetoxy-3-methoxy-6α-[N-methyl-3-(3,4-dimethylphenyl)propiolamido]morphinan, 17-phenethyl-4,5α-epoxy-14β-acetoxy-3-methoxy-6α-[N-methyl-3-(3,4-dimethylphenyl)propiolamido]morphinan, 17-cyclopropylmethyl-4,5α-epoxy-14β-hydroxy-3-acetoxy-6α-[N-methyl-3-(3,4-dimethylphenyl)propiolamido]morphinan, 17-allyl-4,5α-epoxy-14β-hydroxy-3-acetoxy-6α-[N-methyl-3-(3,4-dimethylphenyl)propiolamido]morphinan, 17-methyl-4,5α-epoxy-14β-hydroxy-3-acetoxy-6α-[N-methyl-3-(3,4-dimethylphenyl)propiolamido]morphinan, 17-phenethyl-4,5α-epoxy-14β-hydroxy-3-acetoxy-6α-[N-methyl-3-(3,4-dimethylphenyl)propiolamido]morphinan, 17-cyclopropylmethyl-4,5α-epoxy-3,14β-diacetoxy-6α-[N-methyl-3-(3,4-dimethylphenyl)propiolamido]morphinan, 17-allyl-4,5α-epoxy-3,14β-diacetoxy-6α-[N-methyl-3-(3,4-dimethylphenyl)propiolamido]morphinan, 17-methyl-4,5α-epoxy-3,14β-diacetoxy-6α-[N-methyl-3-(3,4-dimethylphenyl)propiolamido]morphinan, 17-phenethyl-4,5α-epoxy-3,14β-diacetoxy-6α-[N-methyl-3-(3,4-dimethylphenyl)propiolamido]morphinan, 17-cyclopropylmethyl-4,5α-epoxy-3,14β-dihydroxy-6α-[N-isobutyl-3-(3,4-dimethylphenyl)propiolamido]morphinan, 17-allyl-4,5α-epoxy-3,14β-dihydroxy-6α-[N-isobutyl-3-(3,4-dimethylphenyl)propiolamido]morphinan, 17-methyl-4,5α-epoxy-3,14β-dihydroxy-6α-[N-isobutyl-3-(3,4-dimethylphenyl)propiolamido]morphinan, 17-phenethyl-4,5α-epoxy-3,14β-dihydroxy-6α-[N-isobutyl-3-(3,4-dimethylphenyl)propiolamido]morphinan, 17-cyclopropylmethyl-4,5α-epoxy-14β-acetoxy-3-hydroxy-6α-[N-isobutyl-3-(3,4-dimethylphenyl)propiolamido]morphinan, 17-allyl-4,5α-epoxy-14β-acetoxy-3-hydroxy-6α-[N-isobutyl-3-(3,4-dimethylphenyl)propiolamido]morphinan, 17-methyl-4,5α-epoxy-14β-acetoxy-3-hydroxy-6α-[N-isobutyl-3-(3,4-dimethylphenyl)propiolamido]morphinan, 17-phenethyl-4,5α-epoxy-14β-acetoxy-3-hydroxy-6α-[N-isobutyl-3-(3,4-dimethylphenyl)propiolamido]morphinan, 17-cyclopropylmethyl-4,5α-epoxy-14β-hydroxy-6α-[N-isobutyl-3-(3,4-dimethylphenyl)propiolamido]morphinan, 17-allyl-4,5α-epoxy-14β-hydroxy-6α-[N-isobutyl-3-(3,4-dimethylphenyl)propiolamido]morphinan, 17-methyl-4,5α-epoxy-14β-hydroxy-6α-[N-isobutyl-3-(3,4-dimethylphenyl)propiolamido]morphinan, 17-phenethyl-4,5α-epoxy-14β-hydroxy-6α-[N-isobutyl-3-(3,4-dimethylphenyl)propiolamido]morphinan, 17-cyclopropylmethyl-4,5α-epoxy-14β-acetoxy-6α-[N-isobutyl-3-(3,4-dimethylphenyl)propiolamido]morphinan, 17-allyl-4,5α-epoxy-14β-acetoxy-6α-[N-isobutyl-3-(3,4-dimethylphenyl)propiolamido]morphinan, 17-methyl-4,5α-epoxy-14β-acetoxy-6α-[N-isobutyl-3-(3,4-dimethylphenyl)propiolamido]morphinan, 17-phenethyl-4,5α-epoxy- 14β-acetoxy-6α-[N-isobutyl-3-(3,4-dimethylphenyl) propiolamido]morphinan, 17-cyclopropylmethyl-4,5α-epoxy-14β-hydroxy-3-methoxy-6α-[N-isobutyl-3-(3, 4-dimethylphenyl)propiolamido]morphinan, 17-allyl-4,5α-epoxy-14β-hydroxy-3-methoxy-6α-[N-isobutyl-3-(3,4-dimethylphenyl)propiolamido]morphinan, 17-methyl-4,5α-epoxy-14β-hydroxy-3-methoxy-6α-[N-isobutyl-3-(3,4-dimethylphenyl)propiolamido] morphinan, 17-phenethyl-4,5α-epoxy-14β-hydroxy-3-methoxy-6α-[N-isobutyl-3-(3,4-dimethylphenyl) propiolamido]morphinan, 17-cyclopropylmethyl-4,5α-epoxy-14β-acetoxy-3-methoxy-6α-[N-isobutyl-3-(3,4-dimethylphenyl)propiolamido]morphinan, 17-allyl-4, 5α-epoxy-14β-acetoxy-3-methoxy-6α-[N-isobutyl-3-(3,4-dimethylphenyl)propiolamido]morphinan, 17-methyl-4,5α-epoxy-14β-acetoxy-3-methoxy-6α-[N-isobutyl-3-(3,4-dimethylphenyl)propiolamido] morphinan, 17-phenethyl-4,5α-epoxy-14β-acetoxy-3-methoxy-6α-[N-isobutyl-3-(3,4-dimethylphenyl) propiolamido]morphinan, 17-cyclopropylmethyl-4,5α-epoxy-14β-hydroxy-3-acetoxy-6α-[N-isobutyl-3-(3,4-dimethylphenyl)propiolamido]morphinan, 17-allyl-4, 5α-epoxy-14β-hydroxy-3-acetoxy-6α-[N-isobutyl-3-(3,4-dimethylphenyl)propiolamido]morphinan, 17-methyl-4,5α-epoxy-14β-hydroxy-3-acetoxy-6α-[N-isobutyl-3-(3,4-dimethylphenyl)propiolamido] morphinan, 17-phenethyl-4,5α-epoxy-14β-hydroxy-3-acetoxy-6α-[N-isobutyl-3-(3,4-dimethylphenyl) propiolamido]morphinan, 17-cyclopropylmethyl-4,5α-epoxy-3,14β-diacetoxy-6α-[N-isobutyl-3-(3,4-dimethylphenyl)propiolamido]morphinan, 17-allyl-4,5 (5-epoxy-3,14β-diacetoxy-6α-[N-isobutyl-3-(3,4-dimethylphenyl)propiolamido]morphinan, 17-methyl-4,5α-epoxy-3,14β-diacetoxy-6α-[N-isobutyl-3-(3,4-dimethylphenyl)propiolamido]morphinan, 17-phenethyl-4,5α-epoxy-3,14β-diacetoxy-6α-[N-isobutyl-3-(3,4-dimethylphenyl)propiolamido] morphinan, 17-methyl-4,5α-epoxy-3,14β-dihydroxy-6β-[N-methyl-3-(3,4-dimethylphenyl)propiolamido] morphinan, 17-phenethyl-4,5α-epoxy-3,14β-dihydroxy-6β-[N-methyl-3-(3,4-dimethylphenyl) propiolamido]morphinan, 17-cyclopropylmethyl-4,5α-epoxy-14β-acetoxy-3-hydroxy-6β-[N-methyl-3-(3,4-dimethylphenyl)propiolamido]morphinan, 17-allyl-4, 5α-epoxy-14β-acetoxy-3-hydroxy-6β-[N-methyl-3-(3, 4-dimethylphenyl)propiolamido]morphinan, 17-methyl-4,5α-epoxy-14β-acetoxy-3-hydroxy-6β-[N-methyl-3-(3,4-dimethylphenyl)propiolamido] morphinan, 17-phenethyl-4,5α-epoxy-14β-acetoxy-3-hydroxy-6β-[N-methyl-3-(3,4-dimethylphenyl) propiolamido]morphinan, 17-cyclopropylmethyl-4,5α-epoxy-14β-hydroxy-6β-[N-methyl-3-(3,4-dimethylphenyl)propiolamido]morphinan, 17-allyl-4, 5α-epoxy-14β-hydroxy-6β-[N-methyl-3-(3,4-dimethylphenyl)propiolamido]morphinan, 17-methyl-4,5α-epoxy-14β-hydroxy-6β-[N-methyl-3-(3,4-dimethylphenyl)propiolamido]morphinan, 17-phenethyl-4,5α-epoxy-14β-hydroxy-6β-[N-methyl-3-(3,4-dimethylphenyl)propiolamido] morphinan, 17-cyclopropylmethyl-4,5α-epoxy-14β-acetoxy-6β-[N-methyl-3-(3,4-dimethylphenyl) propiolamido]morphinan, 17-allyl-4,5α-epoxy-14β-acetoxy-6β-[N-methyl-3-(3,4-dimethylphenyl) propiolamido]morphinan, 17-methyl-4,5α-epoxy-14β-acetoxy-6β-[N-methyl-3-(3,4-dimethylphenyl) propiolamido]morphinan, 17-phenethyl-4,5α-epoxy-14β-acetoxy-6β-[N-methyl-3-(3,4-dimethylphenyl) propiolamido]morphinan, 17-cyclopropylmethyl-4,5α-epoxy-14β-hydroxy-3-methoxy-6β-[N-methyl-3-(3,4-dimethylphenyl)propiolamido]morphinan, 17-allyl-4, 5α-epoxy-14β-hydroxy-3-methoxy-6β-[N-methyl-3-(3,4-dimethylphenyl)propiolamido]morphinan, 17-methyl-4,5α-epoxy-14β-hydroxy-3-methoxy-6β-[N-methyl-3-(3,4-dimethylphenyl)propiolamido] morphinan, 17-phenethyl-4,5α-epoxy-14β-hydroxy-3-methoxy-6)-[N-methyl-3-(3,4-dimethylphenyl) propiolamido]morphinan, 17-cyclopropylmethyl-4,5α-epoxy- 14β-acetoxy-3-methoxy-6β-[N-methyl-3-(3,4-dimethylphenyl)propiolamido]morphinan, 17-allyl-4, 5α-epoxy-14β-acetoxy-3-methoxy-6β-[N-methyl-3-(3,4-dimethylphenyl)propiolamido]morphinan, 17-methyl-4,5α-epoxy-14β-acetoxy-3-methoxy-6β-[N-methyl-3-(3,4-dimethylphenyl)propiolamido] morphinan, 17-phenethyl-4,5α-epoxy-14β-acetoxy-3-methoxy-6β-[N-methyl-3-(3,4-dimethylphenyl) propiolamido]morphinan, 17-cyclopropylmethyl-4,5α-epoxy-14β-hydroxy-3-acetoxy-6β-[N-methyl-3-(3,4-dimethylphenyl)propiolamido]morphinan, 17-allyl-4, 5α-epoxy-14β-hydroxy-3-acetoxy-6β-[N-methyl-3-(3, 4-dimethylphenyl)propiolamido]morphinan, 17-methyl-4,5α-epoxy-14β-hydroxy-3-acetoxy-6β-[N-methyl-3-(3,4-dimethylphenyl)propiolamido] morphinan, 17-phenethyl-4,5α-epoxy-14β-hydroxy-3-acetoxy-6β-[N-methyl-3-(3,4-dimethylphenyl) propiolamido]morphinan, 17-cyclopropylmethyl-4,5α-epoxy-3,14β-diacetoxy-6β-[N-methyl-3-(3,4-dimethylphenyl)propiolamido]morphinan, 17-allyl-4, 5α-epoxy-3,14β-diacetoxy-6β-[N-methyl-3-(3,4-dimethylphenyl)propiolamido]morphinan, 17-methyl-4,5α-epoxy-3,14β-diacetoxy-6β-[N-methyl-3-(3,4-dimethylphenyl)propiolamido]morphinan, 17-phenethyl-4,5α-epoxy-3,14β-diacetoxy-6β-[N-methyl-3-(3,4-dimethylphenyl)propiolamido] morphinan, 17-cyclopropylmethyl-4,5α-epoxy-3,14β-dihydroxy-6β-[N-isobutyl-3-(3,4-dimethylphenyl) propiolamido]morphinan, 17-allyl-4,5α-epoxy-3,14β-dihydroxy-6β-[N-isobutyl-3-(3,4-dimethylphenyl) propiolamido]morphinan, 17-methyl-4,5α-epoxy-3, 14β-dihydroxy-6β-[N-isobutyl-3-(3,4-dimethylphenyl)propiolamido]morphinan, 17-phenethyl-4,5α-epoxy-3,14β-dihydroxy-6β-[N-isobutyl-3-(3,4-dimethylphenyl)propiolamido] morphinan, 17-cyclopropylmethyl-4,5α-epoxy-14β-acetoxy-3-hydroxy-6β-[N-isobutyl-3-(3,4-dimethylphenyl)propiolamido]morphinan, 17-allyl-4, 5α-epoxy-14β-acetoxy-3-hydroxy-6β-[N-isobutyl-3-(3,4-dimethylphenyl)propiolamido]morphinan, 17-methyl-4,5α-epoxy-14)3-acetoxy-3-hydroxy-6β-[N-isobutyl-3-(3,4-dimethylphenyl)propiolamido] morphinan, 17-phenethyl-4,5α-epoxy-14β-acetoxy-3-hydroxy-6β-[N-isobutyl-3-(3,4-dimethylphenyl) propiolamido]morphinan, 17-cyclopropylmethyl-4,5α-epoxy- 14β-hydroxy-6β-[N-isobutyl-3-(3,4-dimethylphenyl)propiolamido]morphinan, 17-allyl-4, 5α-epoxy-14β-hydroxy-6β-[N-isobutyl-3-(3,4-dimethylphenyl)propiolamido]morphinan, 17-methyl-4,5α-epoxy-14β-hydroxy-6β-[N-isobutyl-3-(3,4-dimethylphenyl)propiolamido]morphinan, 17-phenethyl-4,5α-epoxy-14β-hydroxy-6β-[N-isobutyl-3-(3,4-dimethylphenyl)propiolamido] morphinan, 17-cyclopropylmethyl-4,5α-epoxy-14β-acetoxy-6β-[N-isobutyl-3-(3,4-dimethylphenyl) propiolamido]morphinan, 17-allyl-4,5α-epoxy-14β-acetoxy-6β-[N-isobutyl-3-(3,4-dimethylphenyl)

propiolamido]morphinan, 17-methyl-4,5α-epoxy-14β-acetoxy-6β-[N-isobutyl-3-(3,4-dimethylphenyl)propiolamido]morphinan, 17-phenethyl-4,5α-epoxy-14β-acetoxy-6β-[N-isobutyl-3-(3,4-dimethylphenyl)propiolamido]morphinan, 17-cyclopropylmethyl-4,5α-epoxy-14β-hydroxy-3-methoxy-6β-[N-isobutyl-3-(3,4-dimethylphenyl)propiolamido]morphinan, 17-allyl-4,5α-epoxy-14β-hydroxy-3-methoxy-6β-[N-isobutyl-3-(3,4-dimethylphenyl)propiolamido]morphinan, 17-methyl-4,5α-epoxy-14β-hydroxy-3-methoxy-6β-[N-isobutyl-3-(3,4-dimethylphenyl)propiolamido]morphinan, 17-phenethyl-4,5α-epoxy-14β-hydroxy-3-methoxy-6β-[N-isobutyl-3-(3,4-dimethylphenyl)propiolamido]morphinan, 17-cyclopropylmethyl-4,5α-epoxy-14β-acetoxy-3-methoxy-6β-[N-isobutyl-3-(3,4-dimethylphenyl)propiolamido]morphinan, 17-allyl-4,5α-epoxy-14β-acetoxy-3-methoxy-6β-[N-isobutyl-3-(3,4-dimethylphenyl)propiolamido]morphinan, 17-methyl-4,5α-epoxy-14β-acetoxy-3-methoxy-6,-[N-isobutyl-3-(3,4-dimethylphenyl)propiolamido]morphinan, 17-phenethyl-4,5α-epoxy-14β-acetoxy-3-methoxy-6β-[N-isobutyl-3-(3,4-dimethylphenyl)propiolamido]morphinan, 17-cyclopropylmethyl-4,5α-epoxy-14β-hydroxy-3-acetoxy-6β-[N-isobutyl-3-(3,4-dimethylphenyl)propiolamido]morphinan, 17-allyl-4,5α-epoxy-14β-hydroxy-3-acetoxy-6β-[N-isobutyl-3-(3,4-dimethylphenyl)propiolamido]morphinan, 17-methyl-4,5α-epoxy-14β-hydroxy-3-acetoxy-6β-[N-isobutyl-3-(3,4-dimethylphenyl)propiolamido]morphinan, 17-phenethyl-4,5α-epoxy-14β-hydroxy-3-acetoxy-6β-[N-isobutyl-3-(3,4-dimethylphenyl)propiolamido]morphinan, 17-cyclopropylmethyl-4,5α-epoxy- 3,14β-diacetoxy-6β-[N-isobutyl-3-(3,4-dimethylphenyl)propiolamido]morphinan, 17-allyl-4,5α-epoxy-3,14β-diacetoxy-6β-[N-isobutyl-3-(3,4-dimethylphenyl)propiolamido]morphinan, 17-methyl-4,5α-epoxy-3,14β-diacetoxy-6β-[N-isobutyl-3-(3,4-dimethylphenyl)propiolamido]morphinan, 17-phenethyl-4,5α-epoxy-3,14β-diacetoxy-6β-[N-isobutyl-3-(3,4-dimethylphenyl)propiolamido]morphinan, 17-methyl-4,5α-epoxy-3,14β-dihydroxy-6α-(N-methyl-3-trifluoromethoxycinnamamido)morphinan, 17-phenethyl-4,5α-epoxy-3,14β-dihydroxy-6α-(N-methyl-3-trifluoromethoxycinnamamido)morphinan, 17-cyclopropylmethyl-4,5α-epoxy-14β-acetoxy-3-hydroxy-6α-(N-methyl-3-trifluoromethoxycinnamamido)morphinan, 17-allyl-4,5α-epoxy-14β-acetoxy-3-hydroxy-6α-(N-methyl-3-trifluoromethoxycinnamamido)morphinan, 17-methyl-4,5α-epoxy-14β-acetoxy-3-hydroxy-6α-(N-methyl-3-trifluoromethoxycinnamamido)morphinan, 17-phenethyl-4,5α-epoxy-14β-acetoxy-3-hydroxy-6α-(N-methyl-3-trifluoromethoxycinnamamido)morphinan, 17-cyclopropylmethyl-4,5α-epoxy-14β-hydroxy-6α-(N-methyl-3-trifluoromethoxycinnamamido)morphinan, 17-allyl-4,5α-epoxy-14β-hydroxy-6α-(N-methyl-3-trifluoromethoxycinnamamido)morphinan, 17-methyl-4,5α-epoxy-14β-hydroxy-6α-(N-methyl-3-trifluoromethoxycinnamamido)morphinan, 17-phenethyl-4,5α-epoxy-14β-hydroxy-6α-(N-methyl-3-trifluoromethoxycinnamamido)morphinan, 17-cyclopropylmethyl-4,5α-epoxy-14β-acetoxy-6α-(N-methyl-3-trifluoromethoxycinnamamido) morphinan, 17-allyl-4,5α-epoxy-14β-acetoxy-6α-(N-methyl-3-trifluoromethoxycinnamamido)morphinan, 17-methyl-4,5α-epoxy-14β-acetoxy-6α-(N-methyl-3-trifluoromethoxycinnamamido)morphinan, 17-phenethyl-4,5α-epoxy-14β-acetoxy-6α-(N-methyl-3-trifluoromethoxycinnamamido)morphinan, 17-cyclopropylmethyl-4,5α-epoxy-14β-hydroxy-3-methoxy-6α-(N-methyl-3-trifluoromethoxycinnamamido)morphinan, 17-allyl-4,5α-epoxy-14β-hydroxy-3-methoxy-6α-(N-methyl-3-trifluoromethoxycinnamamido)morphinan, 17-methyl-4,5α-epoxy-14β-hydroxy-3-methoxy-6α-(N-methyl-3-trifluoromethoxycinnamamido)morphinan, 17-phenethyl-4,5α-epoxy-14β-hydroxy-3-methoxy-6α-(N-methyl-3 -trifluoromethoxycinnamamido)morphinan, 17-cyclopropylmethyl-4,5α-epoxy-14β-acetoxy-3-methoxy-6α-(N-methyl-3-trifluoromethoxycinnamamido)morphinan, 17-allyl-4,5α-epoxy-14β-acetoxy-3-methoxy-6α-(N-methyl-3-trifluoromethoxycinnamamido)morphinan, 17-methyl-4,5α-epoxy-14β-acetoxy-3-methoxy-6α-(N-methyl-3-trifluoromethoxycinnamamido)morphinan, 17-phenethyl-4,5α-epoxy-14β-acetoxy-3-methoxy-6α-(N-methyl-3-trifluoromethoxycinnamamido)morphinan, 17-cyclopropylmethyl-4,5α-epoxy-14β-hydroxy-3-acetoxy-6α-(N-methyl-3-trifluoromethoxycinnamamido)morphinan, 17-allyl-4,5α-epoxy-14β-hydroxy-3-acetoxy-6α-(N-methyl-3-trifluoromethoxycinnamamido)morphinan, 17-methyl-4,5α-epoxy-14β-hydroxy-3-acetoxy-6α-(N-methyl-3-trifluoromethoxycinnamamido)morphinan, 17-phenethyl-4,5α-epoxy-14β-hydroxy-3-acetoxy-6α-(N-methyl-3-trifluoromethoxycinnamamido)morphinan, 17-cyclopropylmethyl-4,5α-epoxy-3,14β-diacetoxy-6α-(N-methyl-3-trifluoromethoxycinnamamido)morphinan, 17-allyl-4,5α-epoxy-3,14β-diacetoxy-6α-(N-methyl-3-trifluoromethoxycinnamamido)morphinan, 17-methyl-4,5α-epoxy-3,14β-diacetoxy-6α-(N-methyl-3-trifluoromethoxycinnamamido)morphinan, 17-phenethyl-4,5α-epoxy-3,14β-diacetoxy-6α-(N-methyl-3-trifluoromethoxycinnamamido)morphinan, 17-cyclopropylmethyl-4,5α-epoxy-3,14β-dihydroxy-6α-(N-isobutyl-3-trifluoromethoxycinnamamido)morphinan, 17-allyl-4,5α-epoxy-3,14β-dihydroxy-6α-(N-isobutyl-3-trifluoromethoxycinnamamido)morphinan, 17-methyl-4,5α-epoxy-3,14β-dihydroxy-6α-(N-isobutyl-3-trifluoromethoxycinnamamido)morphinan, 17-phenethyl-4,5α-epoxy-3,14β-dihydroxy-6α-(N-isobutyl-3-trifluoromethoxycinnamamido)morphinan, 17-cyclopropylmethyl-4,5α-epoxy-14β-acetoxy-3-hydroxy-6α-(N-isobutyl-3-trifluoromethoxycinnamamido)morphinan, 17-allyl-4,5α-epoxy-14β-acetoxy-3-hydroxy-6α-(N-isobutyl-3-trifluoromethoxycinnamamido)morphinan, 17-methyl-4,5α-epoxy-14β-acetoxy-3-hydroxy-6α-(N-isobutyl-3-trifluoromethoxycinnamamido)morphinan, 17-phenethyl-4,5α-epoxy-14β-acetoxy-3-hydroxy-6α-(N-isobutyl-3-trifluoromethoxycinnamamido)morphinan, 17-cyclopropylmethyl-4,5α-epoxy-14β-hydroxy-6α-(N-isobutyl-3 -trifluoromethoxycinnamamido)morphinan, 17-allyl-5α-epoxy-14β-hydroxy-6α-(N-isobutyl-3-trifluoromethoxycinnamamido)morphinan, 17-methyl-4,5α-epoxy-14β-hydroxy-6α-(N-isobutyl-3-trifluoromethoxycinnamamido)morphinan, 17-phenethyl-4,5α-epoxy-14β-hydroxy-6α-(N-isobutyl-3-trifluoromethoxycinnamamido)morphinan, 17-cyclopropylmethyl-4,5α-epoxy-14β-acetoxy-6α-(N-isobutyl-3-trifluoromethoxycinnamamido)morphinan, 17-allyl-4,5α-epoxy-14β-acetoxy-6α-(N-isobutyl-3-trifluoromethoxycinnamamido)morphinan, 17-methyl-4,5α-epoxy-14β-acetoxy-6α-(N-isobutyl-3-trifluoromethoxycinnamamido)morphinan, 17-phenethyl-4,5α-epoxy-14β-acetoxy-6α-(N-isobutyl-3-trifluoromethoxycinnamamido)morphinan, 17-cyclopropylmethyl-4,5α-epoxy-14β-hydroxy-3-methoxy-6α-(N-isobutyl-3-trifluoromethoxycinnamamido)morphinan, 17-allyl-4,5α-epoxy-14β-hydroxy-3-methoxy-6α-(N-isobutyl-3-trifluoromethoxycinnamamido)morphinan, 17-methyl-4,5α-epoxy-14β-hydroxy-3-methoxy-6α-(N-isobutyl-3-trifluoromethoxycinnamamido)morphinan, 17-phenethyl-4,5α-epoxy-14β-hydroxy-3-methoxy-6α-(N-isobutyl-3-trifluoromethoxycinnamamido)morphinan, 17-cyclopropylmethyl-4,5α-epoxy-14β-acetoxy-3-methoxy-6α-(N-isobutyl-3-trifluoromethoxycinnamamido)morphinan, 17-allyl-4,5α-epoxy-14β-acetoxy-3-methoxy-6α-(N-isobutyl-3-trifluoromethoxycinnamamido)morphinan, 17-methyl-4,5α-epoxy-14β-acetoxy-3-methoxy-6α-(N-isobutyl-3-trifluoromethoxycinnamamido)morphinan, 17-phenethyl-4,5α-epoxy-14β-acetoxy-3-methoxy-6α-(N-isobutyl-3-trifluoromethoxycinnamamido)morphinan, 17-cyclopropylmethyl-4,5α-epoxy-14β-hydroxy-3-acetoxy-6α-(N-isobutyl-3-trifluoromethoxycinnamamido)morphinan, 17-allyl-4,5α-epoxy-14β-hydroxy-3-acetoxy-6α-(N-isobutyl-3-trifluoromethoxycinnamamido)morphinan, 17-methyl-4,5α-epoxy-14β-hydroxy-3-acetoxy-6α-(N-isobutyl-3-trifluoromethoxycinnamamido)morphinan, 17-phenethyl-4,5α-epoxy-14β-hydroxy-3-acetoxy-6α-(N-isobutyl-3-trifluoromethoxycinnamamido)morphinan, 17-cyclopropylmethyl-4,5α-epoxy-3,14β-diacetoxy-6α-(N-isobutyl-3-trifluoromethoxycinnamamido)morphinan, 17-allyl-4,5α-epoxy-3,14,-diacetoxy-6α-(N-isobutyl-3-trifluoromethoxycinnamamido)morphinan, 17-methyl-4,5α-epoxy-3,14β-diacetoxy-6α-(N-isobutyl-3-trifluoromethoxycinnamamido)morphinan, 17-phenethyl-4,5α-epoxy-3,14β-diacetoxy-6α-(N-isobutyl-3-trifluoromethoxycinnamamido)morphinan, 17-methyl-4,5α-epoxy-3,14β-dihydroxy-6β-(N-methyl-3-trifluoromethoxycinnamamido)morphinan, 17-phenethyl-4,5α-epoxy-3,14β-dihydroxy-6β-(N-methyl-3-trifluoromethoxycinnamamido)morphinan, 17-cyclopropylmethyl-4,5α-epoxy-14β-acetoxy-3-hydroxy-6β-(N-methyl-3-trifluoromethoxycinnamamido)morphinan, 17-allyl-4,5α-epoxy-14β-acetoxy-3-hydroxy-6β-(N-methyl-3-trifluoromethoxycinnamamido)morphinan, 17-methyl-4,5α-epoxy-14β-acetoxy-3-hydroxy-6β-(N-methyl-3-trifluoromethoxycinnamamido)morphinan, 17-phenethyl-4,5α-epoxy-14β-acetoxy-3-hydroxy-6β-(N-methyl-3-trifluoromethoxycinnamamido)morphinan, 17-cyclopropylmethyl-4,5α-epoxy-14β-hydroxy-6β-(N-methyl-3-trifluoromethoxycinnamamido)morphinan, 17-allyl-4,5α-epoxy-14β-hydroxy-6β-(N-methyl-3-trifluoromethoxycinnamamido)morphinan, 17-methyl-4,5α-epoxy-14β-hydroxy-6β-(N-methyl-3-trifluoromethoxycinnamamido)morphinan, 17-phenethyl-4,5α-epoxy-14β-hydroxy-6β-(N-methyl-3-trifluoromethoxycinnamamido)morphinan, 17-cyclopropylmethyl-4,5α-epoxy-14β-acetoxy-6β-(N-methyl-3-trifluoromethoxycinnamamido)morphinan, 17-allyl-4,5α-epoxy-14β-acetoxy-6β-(N-methyl-3-trifluoromethoxycinnamamido)morphinan, 17-methyl-4,5α-epoxy-14β-acetoxy-6β-(N-methyl-3-trifluoromethoxycinnamamido)morphinan, 17-phenethyl-4,5α-epoxy-14β-acetoxy-6β-(N-methyl-3-trifluoromethoxycinnamamido)morphinan, 17-cyclopropylmethyl-4,5α-epoxy-14β-hydroxy-3-methoxy-6β-(N-methyl-3-trifluoromethoxycinnamamido)morphinan, 17-allyl-4,5α-epoxy-14β-hydroxy-3-methoxy-6β-(N-methyl-3-trifluoromethoxycinnamamido)morphinan, 17-methyl-4,5α-epoxy-14β-hydroxy-3-methoxy-6β-(N-methyl-3-trifluoromethoxycinnamamido)morphinan, 17-phenethyl-4,5α-epoxy-14β-hydroxy-3-methoxy-6β-(N-methyl-3-trifluoromethoxycinnamamido)morphinan, 17-cyclopropylmethyl-4,5α-epoxy-14β-acetoxy-3-methoxy-6β-(N-methyl-3-trifluoromethoxycinnamamido)morphinan, 17-allyl-4,5α-epoxy-14β-acetoxy-3-methoxy-63-(N-methyl-3-trifluoromethoxycinnamamido)morphinan, 17-methyl-4,5α-epoxy-14β-acetoxy-3-methoxy-6β-(N-methyl-3-trifluoromethoxycinnamamido)morphinan, 17-phenethyl-4,5α-epoxy-14β-acetoxy-3-methoxy-6β-(N-methyl-3-trifluoromethoxycinnamamido)morphinan, 17-cyclopropylmethyl-4,5α-epoxy-14β-hydroxy-3-acetoxy-6β-(N-methyl-3-trifluoromnethoxycinnamamido)morphinan, 17-allyl-4,5α-epoxy-14β-hydroxy-3-acetoxy-6β-(N-methyl-3-trifluoromethoxycinnamnamido)morphinan, 17-methyl-4,5α-epoxy-14β-hydroxy-3-acetoxy-6β-(N-methyl-3-trifluoromethoxycinnamamido)morphinan, 17-phenethyl-4,5α-epoxy-14β-hydroxy-3-acetoxy-6β-(N-methyl-3-trifluoromethoxycinnamamido)morphinan, 17-cyclopropylmethyl-4,5βepoxy-3,14β-diacetoxy-6β-(N-methyl-3-trifluoromethoxycinnamamido)morphinan, 17-allyl-4,5α-epoxy-3,14β-diacetoxy-6β-(N-methyl-3-trifluoromethoxycinnamamido)morphinan, 17-methyl-4,5α-epoxy-3,14β-diacetoxy-6β-(N-methyl-3-trifluoromethoxycinnamamnido)morphinan, 17-phenethyl-4,5α-epoxy-3,14β-diacetoxy-6β-(N-methyl-3-trifluoromethoxycinnamnamido)morphinan, 17-cyclopropylmethyl-4,5α-epoxy-3,14β-dihydroxy-6β-(N-isobutyl-3-trifluoromethoxycinnamamnido)morphinan, 17-allyl-4,5α-epoxy-3,14β-dihydroxy-6β-(N-isobutyl-3-trifluoromethoxycinnamamido)morphinan, 17-methyl-4,5α-epoxy-3,14β-dihydroxy-6β-(N-isobutyl-3-trifluoromethoxycinnamamido)morphinan, 17-phenethyl-4,5α-epoxy-3,14β-dihydroxy-6β-(N-isobutyl-3-trifluoromethoxycinnamamido)morphinan, 17-cyclopropylmethyl-4,5α-epoxy-14β-acetoxy-3-hydroxy-6β-(N-isobutyl-3-trifluoromethoxycinnamamido)morphinan, 17-allyl-4,5α-epoxy-14β-acetoxy-3-hydroxy-6β-(N-isobutyl-3-trifluoromethoxycinnamamido)morphinan, 17-methyl-4,5α-epoxy-14β-acetoxy-3-hydroxy-6β-(N-isobutyl-3-trifluoromnethoxycinnamamido)morphinan, 17-phenethyl-4,5α-epoxy-14β-acetoxy-3-hydroxy-6β-(N-isobutyl-3-trifluoromethoxycinnamamido)morphinan, 17-cyclopropylmethyl-4,5α-epoxy-14β-hydroxy-6β-(N-isobutyl-3-trifluoromethoxycinnamamido)morphinan, 17-allyl-4,5α-epoxy-14β-hydroxy-6β-(N-isobutyl-3-trifluoromethoxycinnamnamido)morphinan, 17-methyl-4,5α-epoxy-14β-hydroxy-6β-(N-isobutyl-3-trifluoromethoxycinnamamido)morphinan, 17-phenethyl-4,5α-epoxy-14β-hydroxy-6β-(N-isobutyl-3-trifluoromethoxycinnamamido)morphinan, 17-cyclopropylmethyl-4,5α-epoxy-14β-acetoxy-6β-(N-isobutyl-3-trifluoromethoxycinnamamido)morphinan, 17-allyl-4,5α-epoxy-14β-acetoxy-6β-(N-isobutyl-3-trifluoromethoxycinnamamido)morphinan, 17-methyl-4,5α-epoxy-14β-acetoxy-6β-(N-isobutyl-3-trifluoromethoxycinnamamido)morphinan, 17-phenethyl-4,5α-epoxy-14β-acetoxy-6β-(N-isobutyl-3-trifluoromethoxycinnamamido)morphinan, 17-cyclopropylmethyl-4,5α-epoxy-14β-hydroxy-3-methoxy-6β-(N-isobutyl-3-trifluoromethoxycinnamamido)morphinan, 17-allyl-4,5α-epoxy-14β-hydroxy-3-methoxy-6β-(N-isobutyl-3-trifluoromethoxycinnamamido)morphinan, 17-methyl-4,5α-epoxy-14β-hydroxy-3-methoxy-6β-(N-isobutyl-3-trifluoromethoxycinnamamido)morphinan, 17-phenethyl-4,5α-epoxy-14β-hydroxy-3-methoxy-6β-(N-isobutyl-3-trifluoromethoxycinnamamido)morphinan, 17-cyclopropylmethyl-4,5α-epoxy-14β-acetoxy-3-methoxy-6β-(N-isobutyl-3-trifluoromethoxycinnamamido)morphinan, 17-allyl-4,5α-epoxy-14β-acetoxy-3-methoxy-6β-(N-isobutyl-3-trifluoromethoxycinnamamido)morphinan, 17-methyl-4,5α-epoxy-14β-acetoxy-3-methoxy-6β-(N-isobutyl-3-trifluoromethoxycinnamamido)morphinan, 17-phenethyl-4,5α-epoxy-14β-acetoxy-3-methoxy-6β-(N-isobutyl-3-trifluoromethoxycinnamamido)morphinan, 17-cyclopropylmethyl-4,5α-epoxy-14β-hydroxy-3-acetoxy-6β-(N-isobutyl-3-trifluoromethoxycinnamamido)morphinan, 17-allyl-4,5α-epoxy-14β-hydroxy-3-acetoxy-6β-(N-isobutyl-3-trifluoromethoxycinnamamido)morphinan, 17-methyl-4,5α-epoxy-14β-hydroxy-3-acetoxy-6β-(N-isobutyl-3-trifluoromethoxycinnamamido)morphinan, 17-phenethyl-4,5α-epoxy-14β-hydroxy-3-acetoxy-6β-(N hydroxy-6α-[N-isobutyl-trans-3-(4-bromo-2-thienyl) acrylamido]morphinan, 17-methyl-4,5α-epoxy-14β-hydroxy-6α-[N-isobutyl-trans-3-(4-bromo-2-thienyl) acrylamido]morphinan, 17-phenethyl-4,5α-epoxy-14β-hydroxy-6α-[N-isobutyl-trans-3-(4-bromo-2-thienyl)acrylamido]morphinan, 17-cyclopropylmethyl-4,5α-epoxy-14β-acetoxy-6α-[N-isobutyl-trans-3-(4-bromo-2-thienyl)acrylamido]morphinan, 17-allyl-4,5α-epoxy-14β-acetoxy-6α-[N-isobutyl-trans-3-(4-bromo-2-thienyl)acrylamido]morphinan, 17-methyl-4,5α-epoxy-14β-acetoxy-6α-[N-isobutyl-trans-3-(4-bromo-2-thienyl)acrylamido]morphinan, 17-phenethyl-4,5α-epoxy-14β-acetoxy-6α-[N-isobutyl-trans-3-(4-bromo-2-thienyl)acrylamido]morphinan, 17-cyclopropylmethyl-4,5α-epoxy-14β-hydroxy-3-methoxy-6α-[N-isobutyl-trans-3-(4-bromo-2-thienyl)acrylamido]morphinan, 17-allyl-4,5α-epoxy-14β-hydroxy-3-methoxy-6α-[N-isobutyl-trans-3-(4-bromo-2-thienyl)acrylamido]morphinan, 17-methyl-4,5α-epoxy-14β-hydroxy-3-methoxy-6α-[N-isobutyl-trans-3-(4-bromo-2-thienyl)acrylamido]morphinan, 17-phenethyl-4,5α-epoxy-14β-hydroxy-3-methoxy-6α-[N-isobutyl-trans-3-(4-bromo-2-thienyl) acrylamido]morphinan, 17-cyclopropylmethyl-4,5α-epoxy-14β-acetoxy-3-methoxy-6α-[N-isobutyl-trans-3-(4-bromo-2-thienyl)acrylamido]morphinan, 17-allyl-4,5α-epoxy-14)3-acetoxy-3-methoxy-6α-[N-isobutyl-trans-3-(4-bromo-2-thienyl)acrylamido]morphinan, 17-methyl-4,5α-epoxy-14β-acetoxy-3-methoxy-6α-[N-isobutyl-trans-3-(4-bromo-2-thienyl)acrylamido] morphinan, 17-phenethyl-4,5α-epoxy-14β-acetoxy-3-methoxy-6α-[N-isobutyl-trans-3-(4-bromo-2-thienyl) acrylamido]morphinan, 17-cyclopropylmethyl-4,5α-epoxy-14β-hydroxy-3-acetoxy-6α-[N-isobutyl-trans-3-(4-bromo-2-thienyl)acrylamido]morphinan, 17-allyl-4,5α-epoxy-14β-hydroxy-3-acetoxy-6α-[N-isobutyl-trans-3-(4-bromo-2-thienyl)acrylamido]morphinan, 17-methyl-4,5α-epoxy-14β-hydroxy-3-acetoxy-6α-[N-isobutyl-trans-3-(4-bromo-2-thienyl)acrylamido] morphinan, 17-phenethyl-4,5α-epoxy-14β-hydroxy-3-acetoxy-6α-[N-isobutyl-trans-3-(4-bromo-2-thienyl) acrylamido]morphinan, 17-cyclopropylmethyl-4,5α-epoxy-3,14β-diacetoxy-6α-[N-isobutyl-trans-3-(4-bromo-2-thienyl)acrylamido]morphinan, 17-allyl-4,5α-epoxy-3,14β-diacetoxy-6α-[N-isobutyl-trans-3-(4-bromo-2-thienyl)acrylamido]morphinan, 17-methyl-4,5α-epoxy-3,14β-diacetoxy-6α-[N-isobutyl-trans-3-(4-bromo-2-thienyl)acrylamido]morphinan, 17-phenethyl-4,5α-epoxy-3,14β-diacetoxy-6α-[N-isobutyl-trans-3-(4-bromo-2-thienyl)acrylamido] morphinan, 17-methyl-4,5α-epoxy-3,14β-dihydroxy-6β-[N-methyl-trans-3-(4-bromo-2-thienyl)acrylamido] morphinan, 17-phenethyl-4,5α-epoxy-3,14β-dihydroxy-6β-[N-methyl-trans-3-(4-bromo-2-thienyl) acrylamido]morphinan, 17-cyclopropylmethyl-4,5α-epoxy-14β-acetoxy-3-hydroxy-6β-[N-methyl-trans-3-(4-bromo-2-thienyl)acrylamido]morphinan, 17-allyl-4,5α-epoxy-14β-acetoxy-3-hydroxy-6β-[N-methyl-trans-3-(4-bromo-2-thienyl)acrylamido]morphinan, 17-methyl-4,5α-epoxy-14β-acetoxy-3-hydroxy-6β-[N-methyl-trans-3-(4-bromo-2-thienyl)acrylamido] morphinan, 17-phenethyl-4,5α-epoxy-14β-acetoxy-3-hydroxy-6β-[N-methyl-trans-3-(4-bromo-2-thienyl) acrylamido]morphinan, 17-cyclopropylmethyl-4,5α-epoxy-14β-hydroxy-6β-[N-methyl-trans-3-(4-bromo-2-thienyl)acrylamido]morphinan, 17-allyl-4,5α-epoxy-14β-hydroxy-6)-[N-methyl-trans-3-(4-bromo-2-thienyl)acrylamido]morphinan, 17-methyl-4,5α-epoxy-14β-hydroxy-6β-[N-methyl-trans-3-(4-bromo-2-thienyl)acrylamido]morphinan, 17-phenethyl-4,5α-epoxy-14β-hydroxy-6β-[N-methyl-trans-3-(4-bromo-2-thienyl)acrylamido]morphinan, 17-cyclopropylmethyl-4,5α-epoxy-14β-acetoxy-6β-[N-methyl-trans-3-(4-bromo-2-thienyl)acrylamido] morphinan, 17-allyl-4,5α-epoxy-14β-acetoxy-6β-[N-methyl-trans-3-(4-bromo-2-thienyl)acrylamido] morphinan, 17-methyl-4,5α-epoxy-14β-acetoxy-6β-[N-methyl-trans-3-(4-bromo-2-thienyl)acrylamido] morphinan, 17-phenethyl-4,5α-epoxy-14β-acetoxy-6β-[N-methyl-trans-3-(4-bromo-2-thienyl)acrylamido] morphinan, 17-cyclopropylmethyl-4,5α-epoxy-14β-hydroxy-3-methoxy-6β-[N-methyl-trans-3-(4-bromo-2-thienyl)acrylamido]morphinan, 17-allyl-4,5α-epoxy-14β-hydroxy-3-methoxy-6β-[N-methyl-trans-3-(4-bromo-2-thienyl)acrylamido]morphinan, 17-methyl-4,5α-epoxy-14β-hydroxy-3 -methoxy-6β-[N-methyl-trans-3-(4-bromo-2-thienyl)acrylamido]morphinan, 17-phenethyl-4,5α-epoxy-14β-hydroxy-3-methoxy-6β-[N-methyl-trans-3-(4-bromo-2-thienyl)acrylamido] morphinan, 17-cyclopropylmethyl-4,5α-epoxy-14β-acetoxy-3-methoxy-6β-[N-methyl-trans-3-(4-bromo-2-thienyl)acrylamido]morphinan, 17-allyl-4,5α-epoxy-14β-acetoxy-3-methoxy-6β-[N-methyl-trans-3-(4-bromo-2-thienyl)acrylamido]morphinan, 17-methyl-4,5α-epoxy-14β-acetoxy-3-methoxy-6β-[N-methyl-trans-3-(4-bromo-2-thienyl)acrylamido]morphinan, 17-phenethyl-4,5α-epoxy-14β-acetoxy-3-methoxy-6β-[N-methyl-trans-3-(4-bromo-2-thienyl)acrylamido] morphinan, 17-cyclopropylmethyl-4,5α-epoxy-14β-hydroxy-3-acetoxy-6β-[N-methyl-trans-3-(4-bromo-2-thienyl)acrylamido]morphinan, 17-allyl-4,5α-epoxy-14β-hydroxy-3-acetoxy-6β-[N-methyl-trans-3-(4-bromo-2-thienyl)acrylamido]morphinan, 17-methyl-4,5α-epoxy-14β-hydroxy-3-acetoxy-6β-[N-methyl-trans-3-(4-bromo-2-thienyl)acrylamido]morphinan, 17-phenethyl-4,5α-epoxy-14β-hydroxy-3-acetoxy-6β-[N-methyl-trans-3-(4-bromo-2-thienyl)acrylamido] morphinan, 17-cyclopropylmethyl-4,5α-epoxy-3,14β-diacetoxy-6β-[N-methyl-trans-3-(4-bromo-2-thienyl) acrylamido]morphinan, 17-allyl-4,5α-epoxy-3,14β-diacetoxy-6β-[N-methyl-trans-3-(4-bromo-2-thienyl) acrylamido]morphinan, 17-methyl-4,5α-epoxy-3,14β-diacetoxy-6β-[N-methyl-trans-3-(4-bromo-2-thienyl) acrylamido]morphinan, 17-phenethyl-4,5α-epoxy-3,14β-diacetoxy-6β-[N-methyl-trans-3-(4-bromo-2-thienyl)acrylamido]morphinan, 17-cyclopropylmethyl-4,5α-epoxy-3,14β-dihydroxy-6β-[N-isobutyl-trans-3-(4-bromo-2-thienyl)acrylamido]morphinan, 17-allyl-4,5α-epoxy-3,14β-dihydroxy-6β-[N-isobutyl-trans-3-(4-bromo-2-thienyl)acrylamido]morphinan, 17-methyl-4,5α-epoxy-3,14β-dihydroxy-6β-[N-isobutyl-trans-3-(4-bromo-2-thienyl)acrylamido]morphinan, 17-phenethyl-4,5α-epoxy-3,14β-dihydroxy-6β-[N-isobutyl-trans-3-(4-bromo-2-thienyl)acrylamido] morphinan, 17-cyclopropylmethyl-4,5α-epoxy-14β-acetoxy-3-hydroxy-6β-[N-isobutyl-trans-3-(4-bromo-2-thienyl)acrylamido]morphinan, 17-allyl-4,5α-epoxy-14β-acetoxy-3-hydroxy-6β-[N-isobutyl-trans-3-(4-bromo-2-thienyl)acrylamido]morphinan, 17-methyl-4,5α-epoxy-14β-acetoxy-3-hydroxy-6β-[N-isobutyl-trans-3-(4-bromo-2-thienyl)acrylamido]morphinan, 17-phenethyl-4,5α-epoxy-14β-acetoxy-3-hydroxy-6β-[N-isobutyl-trans-3-(4-bromo-2-thienyl)acrylamido] morphinan, 17-cyclopropylmethyl-4,5α-epoxy-14β- hydroxy-6β-[N-isobutyl-trans-3-(4-bromo-2-thienyl) acrylamido]morphinan, 17-allyl-4,5α-epoxy-14β-hydroxy-6β-[N-isobutyl-trans-3-(4-bromo-2-thienyl) acrylamido]morphinan, 17-methyl-4,5α-epoxy-14β-hydroxy-6β-[N-isobutyl-trans-3-(4-bromo-2-thienyl) acrylamido]morphinan, 17-phenethyl-4,5α-epoxy-14β-hydroxy-6β-[N-isobutyl-trans-3-(4-bromo-2-thienyl)acrylamido]morphinan, 17-cyclopropylmethyl-4,5α-epoxy-14β-acetoxy-6β-[N-isobutyl-trans-3-(4-bromo-2-thienyl)acrylamido]morphinan, 17-allyl-4,5α-epoxy-14β-acetoxy-6β-[N-isobutyl-trans-3-(4-bromo-2-thienyl)acrylamido]morphinan, 17-methyl-4,5α-epoxy-14β-acetoxy-6β-[N-isobutyl-trans-3-(4-bromo-2-thienyl)acrylamido]morphinan, 17-phenethyl-4,5α-epoxy-14β-acetoxy-6β-[N-isobutyl-trans-3-(4-bromo-2-thienyl)acrylamido] morphinan, 17-cyclopropylmethyl-4,5α-epoxy-14β-hydroxy-3-methoxy-6β-[N-isobutyl-trans-3-(4-bromo-2-thienyl)acrylamido]morphinan, 17-allyl-4,5α-epoxy-14β-hydroxy-3-methoxy-6β-[N-isobutyl-trans-3-(4-bromo-2-thienyl)acrylamido]morphinan, 17-methyl-4,5α-epoxy-14β-hydroxy-3-methoxy-6β-[N-isobutyl-trans-3-(4-bromo-2-thienyl)acrylamido]morphinan, 17-phenethyl-4,5α-epoxy-14β-hydroxy-3-methoxy-6β-[N-isobutyl-trans-3-(4-bromo-2-thienyl) acrylamido]morphinan, 17-cyclopropylmethyl-4,5α-epoxy-14β-acetoxy-3-methoxy-6β-[N-isobutyl-trans-3-(4-bromo-2-thienyl)acrylamido]morphinan, 17-allyl-4,5α-epoxy-14β-acetoxy-3-methoxy-6β-[N-isobutyl-trans-3-(4-bromo-2-thienyl)acrylamido]morphinan, 17-methyl-4,5α-epoxy-14β-acetoxy-3-methoxy-6β-[N-isobutyl-trans-3-(4-bromo-2-thienyl)acrylamido] morphinan, 17-phenethyl-4,5α-epoxy-14β-acetoxy-3-methoxy-6β-[N-isobutyl-trans-3-(4-bromo-2-thienyl) acrylamido]morphinan, 17-cyclopropylmethyl-4,5α-epoxy-14β-hydroxy-3-acetoxy-6β-[N-isobutyl-trans-3-(4-bromo-2-thienyl)acrylamido]morphinan, 17-allyl-4,5α-epoxy- 14β-hydroxy-3-acetoxy-6β-[N-isobutyl-trans-3-(4-bromo-2-thienyl)acrylamido]morphinan, 17-methyl-4,5α-epoxy-14β-hydroxy-3-acetoxy-6β-[N-isobutyl-trans-3-(4-bromo-2-thienyl)acrylamido] morphinan, 17-phenethyl-4,5α-epoxy-14β-hydroxy-3-acetoxy-6β-[N-isobutyl-trans-3-(4-bromo-2-thienyl) acrylamido]morphinan, 17-cyclopropylmethyl-4,5α-epoxy-3,14β-diacetoxy-6β-[N-isobutyl-trans-3-(4-bromo-2-thienyl)acrylamido]morphinan, 17-allyl-4,5α-epoxy-3,14β-diacetoxy-6β-[N-isobutyl-trans-3-(4-bromo-2-thienyl)acrylamido]morphinan, 17-methyl-4,5α-epoxy-3,14β-diacetoxy-6β-[N-isobutyl-trans-3-(4-bromo-2-thienyl)acrylamido]morphinan, 17-phenethyl-4,5α-epoxy-3,14β-diacetoxy-6β-[N-isobutyl-trans-3-(4-bromo-2-thienyl)acrylamido] morphinan, 17-cyclopropylmethyl-4,5α-epoxy-3-hydroxy-6α-[N-methyl-3-(3,4-dimethylphenyl) propiolamido]morphinan, 17-allyl-4,5α-epoxy-3-hydroxy-6α-[N-methyl-3-(3,4-dimethylphenyl) propiolamido]morphinan, 17-methyl-4,5α-epoxy-3-hydroxy-6α-[N-methyl-3-(3,4-dimethylphenyl) propiolamido]morphinan, 17-phenethyl-4,5α-epoxy-3-hydroxy-6α-[N-methyl-3-(3,4-dimethylphenyl) propiolamido]morphinan, 17-cyclopropylmethyl-4,5α-epoxy-3-hydroxy-14β-nitro-6α-[N-methyl-3-(3,4-dimethylphenyl)propiolamido]morphinan, 17-allyl-4,5α-epoxy-3-hydroxy-14β-nitro-6α-[N-methyl-3-(3,4-dimethylphenyl)propiolamido]morphinan, 17-methyl-4,5α-epoxy-3-hydroxy-14β-nitro-6α-[N-methyl-3-(3,4-dimethylphenyl)propiolamido]morphinan, 17-phenethyl-4,5α-epoxy-3-hydroxy-14β-nitro-6α-[N-methyl-3-(3,4-dimethylphenyl)propiolamido] morphinan, 17-cyclopropylmethyl-4,5α-epoxy-3-hydroxy-14β-dimethylamino-6α-[N-methyl-3-(3,4-dimethylphenyl)propiolamido]morphinan, 17-allyl-4,5α-epoxy-3-hydroxy-14β-dimethylamino-6α-[N-methyl-3-(3,4-dimethylphenyl)propiolamido] morphinan, 17-methyl-4,5α-epoxy-3-hydroxy-14β-dimethylamino-6α-[N-methyl-3-(3,4-dimethylphenyl) propiolamido]morphinan, 17-phenethyl-4,5α-epoxy-3-hydroxy-14β-dimethylamino-6α-[N-methyl-3-(3,4-dimethylphenyl)propiolamido]morphinan, 17-cyclopropylmethyl-4,5α-epoxy-3-hydroxy-14β-methyl-6α-[N-methyl-3-(3,4-dimethylphenyl) propiolamido]morphinan, 17-allyl-4,5α-epoxy-3-hydroxy-14β-methyl-6α-[N-methyl-3-(3,4-dimethylphenyl)propiolamido]morphinan, 14β,17-dimethyl-4,5α-epoxy-3-hydroxy-6α-[N-methyl-3-(3,4-dimethylphenyl)propiolamido]morphinan, 17-phenethyl-4,5α-epoxy-3-hydroxy-14β-methyl-6α-[N-methyl-3-(3,4-dimethylphenyl)propiolamido] morphinan, 17-cyclopropylmethyl-3,14β-dihydroxy-6α-[N-methyl-3-(3,4-dimethylphenyl)propiolamido] morphinan, 17-allyl-3,14β-dihydroxy-6α-[N-methyl-3-(3,4-dimethylphenyl)propiolamido]morphinan, 17-methyl-3,14β-dihydroxy-6α-[N-methyl-3-(3,4-dimethylphenyl)propiolamido]morphinan, 17-phenethyl-3,14β-dihydroxy-6α-[N-methyl-3-(3,4-dimethylphenyl)propiolamido]morphinan, 17-cyclopropylmethyl-3,14β-dihydroxy-4-methoxy-6α-[N-methyl-3-(3,4-dimethylphenyl)propiolamido] morphinan, 17-allyl-3,14β-dihydroxy-4-methoxy-6α-[N-methyl-3-(3,4-dimethylphenyl)propiolamido] morphinan, 17-methyl-3,14β-dihydroxy-4-methoxy-6α-[N-methyl-3-(3,4-dimethylphenyl)propiolamido] morphinan, 17-phenethyl-3,14β-dihydroxy-4-methoxy-6α-[N-methyl-3-(3,4-dimethylphenyl) propiolamido]morphinan, 17-cyclopropylmethyl-4,5α-epoxy-3,14β-dihydroxy-5β-methyl-6α-[N-methyl-3-(3,4-dimethylphenyl)propiolamido]morphinan, 17-allyl-4,5α-epoxy-3,14β-dihydroxy-51-methyl-6α-[N-methyl-3-(3,4-dimethylphenyl)propiolamido] morphinan, 5β,17-dimethyl-4,5α-epoxy-3,14β-dihydroxy-6α-[N-methyl-3-(3,4-dimethylphenyl) propiolamido]morphinan, 17-phenethyl-4,5α-epoxy-3, 14β-dihydroxy-5β-methyl-6α-[N-methyl-3-(3,4-dimethylphenyl)propiolamido]morphinan, 17-cyclopropylmethyl-7,8-didehydro-4,5α-epoxy-3, 14β-dihydroxy-6α-[N-methyl-3-(3,4-dimethylphenyl) propiolamido]morphinan, 17-allyl-7,8-didehydro-4, 5α-epoxy-3,14β-dihydroxy-6α-[N-methyl-3-(3,4-dimethylphenyl)propiolamido]morphinan, 17-methyl-7,8-didehydro-4,5α-epoxy-3,14β-dihydroxy-6α-[N-methyl-3-(3,4-dimethylphenyl)propiolamido] morphinan, 17-phenethyl-7,8-didehydro-4,5α-epoxy-3,14β-dihydroxy-6α-[N-methyl-3-(3,4-dimethylphenyl)propiolamido]morphinan, 17-cyclopropylmethyl-4,5α-epoxy-3-hydroxy-6β-[N-methyl-3-(3,4-dimethylphenyl)propiolamido] morphinan, 17-allyl-4,5α-epoxy-3-hydroxy-6β-[N-methyl-3-(3,4-dimethylphenyl)propiolamido] morphinan, 17-methyl-4,5α-epoxy-3-hydroxy-6β-[N-methyl-3-(3,4-dimethylphenyl)propiolamido] morphinan, 17-phenethyl-4,5α-epoxy-3-hydroxy-6β-[N-methyl-3-(3,4-dimethylphenyl)propiolamido] morphinan, 17-cyclopropylmethyl-4,5α-epoxy-3-hydroxy-14β-nitro-6β-[N-methyl-3-(3,4- dimethylphenyl)propiolamido]morphinan, 17-allyl-4,5α-epoxy-3-hydroxy-14β-nitro-6β-[N-methyl-3-(3,4-dimethylphenyl)propiolamido]morphinan, 17-methyl-4,5α-epoxy-3-hydroxy-14β-nitro-6β-[N-methyl-3-(3,4-dimethylphenyl)propiolamido]morphinan, 17-phenethyl-4,5α-epoxy-3-hydroxy-14β-nitro-6β-[N-methyl-3-(3,4-dimethylphenyl)propiolamido]morphinan, 17-cyclopropylmethyl-4,5α-epoxy-3-hydroxy-14β-dimethylamino-6β-[N-methyl-3-(3,4-dimethylphenyl)propiolamido]morphinan, 17-allyl-4,5α-epoxy-3-hydroxy-14β-dimethylamino-6β-[N-methyl-3-(3,4-dimethylphenyl)propiolamido]morphinan, 17-methyl-4,5α-epoxy-3-hydroxy-14β-dimethylamino-6β-[N-methyl-3-(3,4-dimethylphenyl)propiolamido]morphinan, 17-phenethyl-4,5α-epoxy-3-hydroxy-14β-dimethylamino-6β-[N-methyl-3-(3,4-dimethylphenyl)propiolamido]morphinan, 17-cyclopropylmethyl-4,5α-epoxy-3-hydroxy-14β-methyl-6β-[N-methyl-3-(3,4-dimethylphenyl)propiolamido]morphinan, 17-allyl-4,5α-epoxy-3-hydroxy-14β-methyl-6β-[N-methyl-3-(3,4-dimethylphenyl)propiolamido]morphinan, 14β17-dimethyl-4,5α-epoxy-3-hydroxy-6β-[N-methyl-3-(3,4-dimethylphenyl)propiolamido]morphinan, 17-phenethyl-4,5α-epoxy-3-hydroxy-14β-methyl-6β-[N-methyl-3-(3,4-dimethylphenyl)propiolamido]morphinan, 17-cyclopropylmethyl-3,14β-dihydroxy-6β-[N-methyl-3-(3,4-dimethylphenyl)propiolamido]morphinan, 17-allyl-3,14β-dihydroxy-6β-[N-methyl-3-(3,4-dimethylphenyl)propiolamido]morphinan, 17-methyl-3,14β-dihydroxy-6β-[N-methyl-3-(3,4-dimethylphenyl)propiolamido]morphinan, 17-phenethyl-3,14β-dihydroxy-6β-[N-methyl-3-(3,4-dimethylphenyl)propiolamido]morphinan, 17-cyclopropylmethyl-3,14β-dihydroxy-4-methoxy-6β-[N-methyl-3-(3,4-dimethylphenyl)propiolamido]morphinan, 17-allyl-3,14β-dihydroxy-4-methoxy-6β-[N-methyl-3-(3,4-dimethylphenyl)propiolamido]morphinan, 17-methyl-3,14β-dihydroxy-4-methoxy-6β-[N-methyl-3-(3,4-dimethylphenyl)propiolamido]morphinan, 17-phenethyl-3,14β-dihydroxy-4-methoxy-6β-[N-methyl-3-(3,4-dimethylphenyl)propiolamido]morphinan, 17-cyclopropylmethyl-4,5α-epoxy-3,14β-dihydroxy-5β-methyl-6β-[N-methyl-3-(3,4-dimethylphenyl)propiolamido]morphinan, 17-allyl-4,5α-epoxy-3,14β-dihydroxy-5β-methyl-6β-[N-methyl-3-(3,4-dimethylphenyl)propiolamido]morphinan, 5β,17-dimethyl-4,5α-epoxy-3,14β-dihydroxy-6β-[N-methyl-3-(3,4-dimethylphenyl)propiolamido]morphinan, 17-phenethyl-4,5α-epoxy-3,14β-dihydroxy-5β-methyl-6β-[N-methyl-3-(3,4-dimethylphenyl)propiolamido]morphinan, 17-cyclopropylmethyl-7,8-didehydro-4,5α-epoxy-3,14β-dihydroxy-6β-[N-methyl-3-(3,4-dimethylphenyl)propiolamido]morphinan, 17-allyl-7,8-didehydro-4,5α-epoxy-3,14β-dihydroxy-6β-[N-methyl-3-(3,4-dimethylphenyl)propiolamido]morphinan, 17-methyl-7,8-didehydro-4,5α-epoxy-3,14β-dihydroxy-6β-[N-methyl-3-(3,4-dimethylphenyl)propiolamido]morphinan, 17-phenethyl-7,8-didehydro-4,5α-epoxy-3,14β-dihydroxy-6β-[N-methyl-3-(3,4-dimethylphenyl)propiolamido]morphinan, 17-cyclopropylmethyl-4,5α-epoxy-3-hydroxy-6α-(N-methyl-3-trifluoromethoxycinnamamido)morphinan, 17-allyl-4,5α-epoxy-3-hydroxy-6α-(N-methyl-3-trifluoromethoxycinnamamido)morphinan, 17-methyl-4,5α-epoxy-3-hydroxy-6α-(N-methyl-3-trifluoromethoxycinnamamido)morphinan, 17-phenethyl-4,5α-epoxy-3-hydroxy-6α-(N-methyl-3-trifluoromethoxycinnamamido)morphinan, 17-cyclopropylmethyl-4,5α-epoxy-3-hydroxy-14β-nitro-6α-(N-methyl-3-trifluoromethoxycinnamamido)morphinan, 17-allyl-4,5α-epoxy-3-hydroxy-14β-nitro-6α-(N-methyl-3-trifluoromethoxycinnamamido)morphinan, 17-methyl-4,5α-epoxy-3-hydroxy-14β-nitro-6α-(N-methyl-3-trifluoromethoxycinnamamido)morphinan, 17-phenethyl-4,5α-epoxy-3-hydroxy-14β-nitro-6α-(N-methyl-3-trifluoromethoxycinnamamido)morphinan, 17-cyclopropylmethyl-4,5α-epoxy-3-hydroxy-14β-dimethylamino-6α-(N-methyl-3-trifluoromethoxycinnamamido)morphinan, 17-allyl-4,5α-epoxy-3-hydroxy-14β-dimethylamino-6α-(N-methyl-3-trifluoromethoxycinnamamido)morphinan, 17-methyl-4,5α-epoxy-3-hydroxy-14β-dimethylamino-6α-(N-methyl-3-trifluoromethoxycinnamamido)morphinan, 17-phenethyl-4,5α-epoxy-3-hydroxy-14β-dimethylamino-6α-(N-methyl-3-trifluoromethoxycinnamamido)morphinan, 17-cyclopropylmethyl-4,5α-epoxy-3-hydroxy-14β-methyl-6α-(N-methyl-3-trifluoromethoxycinnamamido)morphinan, 17-allyl-4,5α-epoxy-3-hydroxy-14β-methyl-6α-(N-methyl-3-trifluoromethoxycinnamamido)morphinan, 14β,17-dimethyl-4,5α-epoxy-3-hydroxy-6α-(N-methyl-3-trifluoromethoxycinnamamido)morphinan, 17-phenethyl-4,5α-epoxy-3-hydroxy-14β-methyl-6α-(N-methyl-3-trifluoromethoxycinnamamido)morphinan, 17-cyclopropylmethyl-3,14β-dihydroxy-6α-(N-methyl-3-trifluoromethoxycinnamamido)morphinan, 17-allyl-3,14β-dihydroxy-6α-(N-methyl-3-trifluoromethoxycinnamamido)morphinan, 17-methyl-3,14β-dihydroxy-6α-(N-methyl-3-trifluoromethoxycinnamamido)morphinan, 17-phenethyl-3,14β-dihydroxy-6α-(N-methyl-3-trifluoromethoxycinnamamido)morphinan, 17-cyclopropylmethyl-3,14β-dihydroxy-4-methoxy-6α-(N-methyl-3-trifluoromethoxycinnamamido)morphinan, 17-allyl-3,14β-dihydroxy-4-methoxy-6α-(N-methyl-3-trifluoromethoxycinnamamido)morphinan, 17-methyl-3,14β-dihydroxy-4-methoxy-6α-(N-methyl-3-trifluoromethoxycinnamamido)morphinan, 17-phenethyl-3,14β-dihydroxy-4-methoxy-6α-(N-methyl-3-trifluoromethoxycinnamamido)morphinan, 17-cyclopropylmethyl-4,5α-epoxy-3,14β-dihydroxy-5β-methyl-6α-(N-methyl-3-trifluoromethoxycinnamamido)morphinan, 17-allyl-4,5α-epoxy-3,14β-dihydroxy-5β-methyl-6α-(N-methyl-3-trifluoromethoxycinnamamido)morphinan, 5β,17-dimethyl-4,5α-epoxy-3,14β-dihydroxy-6α-(N-methyl-3-trifluoromethoxycinnamamido)morphinan, 17-phenethyl-4,5α-epoxy-3,14β-dihydroxy-5β-methyl-6α-(N-methyl-3-trifluoromethoxycinnamamido)morphinan, 17-cyclopropylmethyl-7,8-didehydro-4,5α-epoxy-3,14β-dihydroxy-6α-(N-methyl-3-trifluoromethoxycinnamamido)morphinan, 17-allyl-7,8-didehydro-4,5α-epoxy-3,14β-dihydroxy-6α-(N-methyl-3-trifluoromethoxycinnamamido)morphinan, 17-methyl-7,8-didehydro-4,5α-epoxy-3,14β-dihydroxy-6α-(N-methyl-3-trifluoromethoxycinnamamido)morphinan, 17-phenethyl-7,8-didehydro-4,5α-epoxy-3,14β- dihydroxy-6α-(N-methyl-3-trifluoromethoxycinnamamido)morphinan, 17-cyclopropylmethyl-4,5α-epoxy-3-hydroxy-6β-(N-methyl-3-trifluoromethoxycinnamamido)morphinan, 17-allyl-4,5α-epoxy-3-hydroxy-6β-(N-methyl-3-trifluoromethoxycinnamamido)morphinan, 17-methyl-4,5α-epoxy-3-hydroxy-6β-(N-methyl-3-trifluoromethoxycinnamamido)morphinan, 17-phenethyl-4,5α-epoxy-3-hydroxy-6β-(N-methyl-3-trifluoromethoxycinnamamido)morphinan, 17-cyclopropylmethyl-4,5α-epoxy-3-hydroxy-14β-nitro-6β-(N-methyl-3-trifluoromethoxycinnamamido)morphinan, 17-allyl-4,5α-epoxy-3-hydroxy-14β-nitro-6β-(N-methyl-3-trifluoromethoxycinnamamido)morphinan, 17-methyl-4,5α-epoxy-3-hydroxy-14β-nitro-6β-(N-methyl-3-trifluoromethoxycinnamamido)morphinan, 17-phenethyl-4,5α-epoxy-3-hydroxy-14β-nitro-6β-(N-methyl-3-trifluoromethoxycinnamamido)morphinan, 17-cyclopropylmethyl-4,5α-epoxy-3-hydroxy-14β-dimethylamino-6β-(N-methyl-3-trifluoromethoxycinnamamido)morphinan, 17-allyl-4,5α-epoxy-3-hydroxy-14β-dimethylamino-6β-(N-methyl-3-trifluoromethoxycinnamamido)morphinan, 17-methyl-4,5α-epoxy-3-hydroxy-14β-dimethylamino-6β-(N-methyl-3-trifluoromethoxycinnamamido)morphinan, 17-phenethyl-4,5α-epoxy-3-hydroxy-14β-dimethylamino-6β-(N-methyl-3-trifluoromethoxycinnamamido)morphinan, 17-cyclopropylmethyl-4,5α-epoxy-3-hydroxy-14β-methyl-6β-(N-methyl-3-trifluoromethoxycinnamamido)morphinan, 17-allyl-4,5α-epoxy-3-hydroxy-14β-methyl-6β-(N-methyl-3-trifluoromethoxycinnamamido)morphinan, 14β,17-dimethyl-4,5α-epoxy-3-hydroxy-6β-(N-methyl-3-trifluoromethoxycinnamamido)morphinan, 17-phenethyl-4,5α-epoxy-3-hydroxy-14β-methyl-6β-(N-methyl-3-trifluoromethoxycinnamamido)morphinan, 17-cyclopropylmethyl-3,14β-dihydroxy-6β-(N-methyl-3-trifluoromethoxycinnamamido)morphinan, 17-allyl-3,14β-dihydroxy-6β-(N-methyl-3-trifluoromethoxycinnamamido)morphinan, 17-methyl-3,14 -dihydroxy-6β-(N-methyl-3-trifluoromethoxycinnamamido)morphinan, 17-phenethyl-3,14β-dihydroxy-6β-(N-methyl-3-trifluoromethoxycinnamamido)morphinan, 17-cyclopropylmethyl-3,14β-dihydroxy-4-methoxy-6β-(N-methyl-3-trifluoromethoxycinnamamido)morphinan, 17-allyl-3,14β-dihydroxy-4-methoxy-6β-(N-methyl-3-trifluoromethoxycinnamamido)morphinan, 17-methyl-3,14β-dihydroxy-4-methoxy-6β-(N-methyl-3-trifluoromethoxycinnamamido)morphinan, 17-phenethyl-3,14β-dihydroxy-4-methoxy-6β-(N-methyl-3-trifluoromethoxycinnamamido)morphinan, 17-cyclopropylmethyl-4,5α-epoxy-3,14β-dihydroxy-5β-methyl-6β-(N-methyl-3-trifluoromethoxycinnamamido)morphinan, 17-allyl-4,5α-epoxy-3,14β-dihydroxy-5β-methyl-6β-(N-methyl-3-trifluoromethoxycinnamamido)morphinan, 5β,17-dimethyl-4,5α-epoxy-3,14β-dihydroxy-6β-(N-methyl-3-trifluoromethoxycinnamamido)morphinan, 17-phenethyl-4,5α-epoxy-3,14β-dihydroxy-5β-methyl-6β-(N-methyl-3-trifluoromethoxycinnamamido)morphinan, 17-cyclopropylmethyl-7,8-didehydro-4,5α-epoxy-3,14β-dihydroxy-6β-(N-methyl-3-trifluoromethoxycinnamamido)morphinan, 17-allyl-7,8-didehydro-4,5α-epoxy-3,14β-dihydroxy-6β-(N-methyl-3-trifluoromethoxycinnamamido)morphinan, 17-methyl-7,8-didehydro-4,5α-epoxy-3,14β-dihydroxy-6β-(N-methyl-3-trifluoromethoxycinnamamido)morphinan, 17-phenethyl-7,8-didehydro-4,5α-epoxy-3,14β-dihydroxy-6β-(N-methyl-3-trifluoromethoxycinnamamido)morphinan, 17-cyclopropylmethyl-4,5α-epoxy-3-hydroxy-6α-[N-methyl-trans-3-(4-bromo-2-thienyl)acrylamido]morphinan, 17-allyl-4,5α-epoxy-3-hydroxy-6α-[N-methyl-trans-3-(4-bromo-2-thienyl)acrylamido]morphinan, 17-methyl-4,5α-epoxy-3-hydroxy-6α-[N-methyl-trans-3-(4-bromo-2-thienyl)acrylamido]morphinan, 17-phenethyl-4,5α-epoxy-3-hydroxy-6α-[N-methyl-trans-3-(4-bromo-2-thienyl)acrylamido]morphinan, 17-cyclopropylmethyl-4,5α-epoxy-3-hydroxy-14β-nitro-6α-[N-methyl-trans-3-(4-bromo-2-thienyl)acrylamido]morphinan, 17-allyl-4,5α-epoxy-3-hydroxy-14β-nitro-6α-[N-methyl-trans-3-(4-bromo-2-thienyl)acrylamido]morphinan, 17-methyl-4,5α-epoxy-3-hydroxy-14β-nitro-6α-[N-methyl-trans-3-(4-bromo-2-thienyl)acrylamido]morphinan, 17-phenethyl-4,5α-epoxy-3-hydroxy-14β-nitro-6α-[N-methyl-trans-3-(4-bromo-2-thienyl)acrylamido]morphinan, 17-cyclopropylmethyl-4,5α-epoxy-3-hydroxy-14β-dimethylamino-6α-[N-methyl-trans-3-(4-bromo-2-thienyl)acrylamido]morphinan, 17-allyl-4,5α-epoxy-3-hydroxy-14β-dimethylamino-6α-[N-methyl-trans-3-(4-bromo-2 -thienyl)acrylamido]morphinan, 17-methyl-4,5α-epoxy-3-hydroxy-14β-dimethylamino-6α-[N-methyl-trans-3-(4-bromo-2-thienyl)acrylamido]morphinan, 17-phenethyl-4,5α-epoxy-3-hydroxy-14β-dimethylamino-6α-[N-methyl-trans-3-(4-bromo-2-thienyl)acrylamido]morphinan, 17-cyclopropylmethyl-4,5α-epoxy-3-hydroxy-14β-methyl-6α-[N-methyl-trans-3-(4-bromo-2-thienyl)acrylamido]morphinan, 17-allyl-4,5α-epoxy-3-hydroxy-14β-methyl-6α-[N-methyl-trans-3-(4-bromo-2-thienyl)acrylamido]morphinan, 14β,17-dimethyl-4,5α-epoxy-3-hydroxy-6α-[N-methyl-trans-3-(4-bromo-2-thienyl)acrylamido]morphinan, 17-phenethyl-4,5α-epoxy-3-hydroxy-14β-methyl-6α-[N-methyl-trans-3-(4-bromo-2-thienyl)acrylamido]morphinan, 17-cyclopropylmethyl-trans-3,14β-dihydroxy-6α-[N-methyl-trans-3-(4-bromo-2-thienyl)acrylamido]morphinan, 17-allyl-trans-3,14β-dihydroxy-6α-[N-methyl-trans-3-(4-bromo-2-thienyl)acrylamido]morphinan, 17-methyl-trans-3,14β-dihydroxy-6α-[N-methyl-trans-3-(4-bromo-2-thienyl)acrylamido]morphinan, 17-phenethyl-trans-3,14β-dihydroxy-6α-[N-methyl-trans-3-(4-bromo-2-thienyl)acrylamido]morphinan, 17-cyclopropylmethyl-trans-3,14β-dihydroxy-4-methoxy-6α-[N-methyl-trans-3-(4-bromo-2-thienyl)acrylamido]morphinan, 17-allyl-trans-3,14β-dihydroxy-4-methoxy-6α-[N-methyl-trans-3-(4-bromo-2-thienyl)acrylamido]morphinan, 17-methyl-trans-3,14β-dihydroxy-4-methoxy-6α-[N-methyl-trans-3-(4-bromo-2-thienyl)acrylamido]morphinan, 17-phenethyl-trans-3,14β-dihydroxy-4-methoxy-6α-[N-methyl-trans-3-(4-bromo-2-thienyl)acrylamido]morphinan, 17-cyclopropylmethyl-4,5α-epoxy-3,14β-dihydroxy-5β-methyl-6α-[N-methyl-trans-3-(4-bromo-2-thienyl)acrylamido]morphinan, 17-allyl-4,5α-epoxy-3,14β-dihydroxy-5β-methyl-6α-[N-methyl-trans-3-(4-bromo-2-thienyl)acrylamido]

morphinan, 5β,17-dimethyl-4,5α-epoxy-3,14β-dihydroxy-6α-[N-methyl-trans-3-(4-bromo-2-thienyl)acrylamido]morphinan, 17-phenethyl-4,5α-epoxy-3,14β-dihydroxy-5β-methyl-6α-[N-methyl-trans-3-(4-bromo-2-thienyl)acrylamido]morphinan, 17-cyclopropylmethyl-7,8-didehydro-4,5α-epoxy-3,14β-dihydroxy-6α-[N-methyl-trans-3-(4-bromo-2-thienyl)acrylamido]morphinan, 17-allyl-7,8-didehydro-4,5α-epoxy-3,14β-dihydroxy-6α-[N-methyl-trans-3-(4-bromo-2-thienyl)acrylamido]morphinan, 17-methyl-7,8-didehydro-4,5α-epoxy-3,14β-dihydroxy-6α-[N-methyl-trans-3-(4-bromo-2-thienyl)acrylamido]morphinan, 17-phenethyl-7,8-didehydro-4,5α-epoxy-3,14,-dihydroxy-6α-[N-methyl-trans-3-(4-bromo-2-thienyl)acrylamido]morphinan, 17-cyclopropylmethyl-4,5α-epoxy-3-hydroxy-6β-[N-methyl-trans-3-(4-bromo-2-thienyl)acrylamido]morphinan, 17-allyl-4,5α-epoxy-3-hydroxy-6β-[N-methyl-trans-3-(4-bromo-2-thienyl)acrylamido]morphinan, 17-methyl-4,5α-epoxy-3-hydroxy-6β-[N-methyl-trans-3-(4-bromo-2-thienyl)acrylamido]morphinan, 17-phenethyl-4,5α-epoxy-3-hydroxy-6β-[N-methyl-trans-3-(4-bromo-2-thienyl)acrylamido]morphinan, 17-cyclopropylmethyl-4,5α-epoxy-3-hydroxy-14β-nitro-6β-[N-methyl-trans-3-(4-bromo-2-thienyl)acrylamido]morphinan, 17-allyl-4,5α-epoxy-3-hydroxy-14β-nitro-6β-[N-methyl-trans-3-(4-bromo-2-thienyl)acrylamido]morphinan, 17-methyl-4,5α-epoxy-3-hydroxy-14β-nitro-6β-[N-methyl-trans-3-(4-bromo-2-thienyl)acrylamido]morphinan, 17-phenethyl-4,5α-epoxy-3-hydroxy-14β-nitro-6β-[N-methyl-trans-3-(4-bromo-2-thienyl)acrylamido]morphinan, 17-cyclopropylmethyl-4,5α-epoxy-3-hydroxy-14β-dimethylamino-6β-[N-methyl-trans-3-(4-bromo-2-thienyl)acrylamido]morphinan, 17-allyl-4,5α-epoxy-3-hydroxy-14β-dimethylamino-6β-[N-methyl-trans-3-(4-bromo-2-thienyl)acrylamido]morphinan, 17-methyl-4,5α-epoxy-3-hydroxy-14β-dimethylamino-6β-[N-methyl-trans-3-(4-bromo-2-thienyl)acrylamido]morphinan, 17-phenethyl-4,5α-epoxy-3-hydroxy-14β-dimethylamino-6β-[N-methyl-trans-3-(4-bromo-2-thienyl)acrylamido]morphinan, 17-cyclopropylmethyl-4,5α-epoxy-3-hydroxy-14β-methyl-6β-[N-methyl-trans-3-(4-bromo-2-thienyl)acrylamido]morphinan, 17-allyl-4,5α-epoxy-3-hydroxy-14β-methyl-6β-[N-methyl-trans-3-(4-bromo-2-thienyl)acrylamido]morphinan, 14,β17-dimethyl-4,5α-epoxy-3-hydroxy-6β-[N-methyl-trans-3-(4-bromo-2-thienyl)acrylamido]morphinan, 17-phenethyl-4,5α-epoxy-3-hydroxy-14β-methyl-6β-[N-methyl-trans-3-(4-bromo-2-thienyl)acrylamido]morphinan, 17-cyclopropylmethyl-trans-3,14β-dihydroxy-6β-[N-methyl-trans-3-(4-bromo-2-thienyl)acrylamido]morphinan, 17-allyl-trans-3,14β-dihydroxy-6β-[N-methyl-trans-3-(4-bromo-2-thienyl)acrylamido]morphinan, 17-methyl-trans-3,14β-dihydroxy-6β-[N-methyl-trans-3-(4-bromo-2-thienyl)acrylamido]morphinan, 17-phenethyl-trans-3,14β-dihydroxy-6β-[N-methyl-trans-3-(4-bromo-2-thienyl)acrylamido]morphinan, 17-cyclopropylmethyl-trans-3,14β-dihydroxy-4-methoxy-6β-[N-methyl-trans-3-(4-bromo-2-thienyl)acrylamido]morphinan, 17-allyl-trans-3,14β-dihydroxy-4-methoxy-6β-[N-methyl-trans-3-(4-bromo-2-thienyl)acrylamido]morphinan, 17-methyl-trans-3,14β-dihydroxy-4-methoxy-6β-[N-methyl-trans-3-(4-bromo-2-thienyl)acrylamido]morphinan, 17-phenethyl-trans-3,14β-dihydroxy-4-methoxy-6β-[N-methyl-trans-3-(4-bromo-2-thienyl)acrylamido]morphinan, 17-cyclopropylmethyl-4,5α-epoxy-3,14β-dihydroxy-5β-methyl-6β-[N-methyl-trans-3-(4-bromo-2-thienyl)acrylamido]morphinan, 17-allyl-4,5α-epoxy-3,14β-dihydroxy-5β-methyl-6β-[N-methyl-trans-3-(4-bromo-2-thienyl)acrylamido]morphinan, 5β,17-dimethyl-4,5α-epoxy-3,14β-dihydroxy-6β-[N-methyl-trans-3-(4-bromo-2-thienyl)acrylamido)morphinan, 17-phenethyl-4,5α-epoxy-3,14β-dihydroxy-5β-methyl-6β-[N-methyl-trans-3-(4-bromo-2-thienyl)acrylamido]morphinan, 17-cyclopropylmethyl-7,8-didehydro-4,5α-epoxy-3,14β-dihydroxy-6β-[N-methyl-trans-3-(4-bromo-2-thienyl)acrylamido]morphinan, 17-allyl-7,8-didehydro-4,5α-epoxy-3,14β-dihydroxy-6β-[N-methyl-trans-3-(4-bromo-2-thienyl)acrylamido]morphinan, 17-methyl-7,8-didehydro-4,5α-epoxy-3,14β-dihydroxy-6β-[N-methyl-trans-3-(4-bromo-2-thienyl)acrylamido]morphinan, 17-phenethyl-7,8-didehydro-4,5α-epoxy-3,14β-dihydroxy-6β-[N-methyl-trans-3-(4-bromo-2-thienyl)acrylamido]morphinan, 17-cyclopropylmethyl-4,5α-epoxy-3,14β-dihydroxy-7α-(N-methyl-3-trifluoromethoxycinnamamido)morphinan, 17-allyl-4,5α-epoxy-3,14β-dihydroxy-7α-(N-methyl-3-trifluoromethoxycinnamamido)morphinan, 17-methyl-4,5α-epoxy-3,14β-dihydroxy-7α-(N-methyl-3-trifluoromethoxycinnamamido)morphinan, 17-phenethyl-4,5α-epoxy-3,14β-dihydroxy-7α-(N-methyl-3-trifluoromethoxycinnamamido)morphinan, 17-cyclopropylmethyl- 4,5α-epoxy-3,14β-dihydroxy-8α-(N-methyl-3-trifluoromethoxycinnamamido)morphinan, 17-allyl-4,5α-epoxy-3,14β-dihydroxy-8α-(N-methyl-3-trifluoromethoxycinnamamido)morphinan, 17-methyl-4,5α-epoxy-3,14β-dihydroxy-8α-(N-methyl-3-trifluoromethoxycinnamamido)morphinan, 17-phenethyl-4,5α-epoxy-3,14β-dihydroxy-8α-(N-methyl-3-trifluoromethoxycinnamamido)morphinan, 17-cyclopropylmethyl-4,5α-epoxy-3,14β-dihydroxy-1-nitro-6α-(N-methyl-3-trifluoromethoxycinnamamido)morphinan, 17-allyl-4,5α-epoxy-3,14β-dihydroxy-1-nitro-6α-(N-methyl-3-trifluoromethoxycinnamamido)morphinan, 17-methyl-4,5α-epoxy-3,14β-dihydroxy-1-nitro-6α-(N-methyl-3-trifluoromethoxycinnamamido)morphinan, 17-phenethyl-4,5α-epoxy-3,14β-dihydroxy-1-nitro-6α-(N-methyl-3-trifluoromethoxycinnamamido)morphinan, 17-cyclopropylmethyl-4,5α-epoxy-3,14β-dihydroxy-7α-methyl-6α-(N-methyl-3-trifluoromethoxycinnamamido)morphinan, 17-allyl-4,5α-epoxy-3,14β-dihydroxy-7α-methyl-6α-(N-methyl-3-trifluoromethoxycinnamamido)morphinan, 17-methyl-4,5α-epoxy-3,14β-dihydroxy-7α-methyl-6α-(N-methyl-3-trifluoromethoxycinnamamido)morphinan, 17-phenethyl-4,5α-epoxy-3,14β-dihydroxy-7α-methyl-6α-(N-methyl-3-trifluoromethoxycinnamamido)morphinan, 17-cyclopropylmethyl-4,5α-epoxy-3,14β-dihydroxy-7β-methyl-6α-(N-methyl-3-trifluoromethoxycinnamamido)morphinan, 17-allyl-4,5α-epoxy-3,14β-dihydroxy-7β-methyl-6α-(N-methyl-3-trifluoromethoxycinnamamido)morphinan, 17-methyl-4,5α-epoxy-3,14β-dihydroxy-7β-methyl-6α-(N-methyl-3-trifluoromethoxycinnamamido)morphinan, 17-phenethyl-4,5α-epoxy-3,14β-dihydroxy-7β-methyl-6α-(N-methyl-3- trifluoromethoxycinnamamido)morphinan, 17-cyclopropylmethyl-4,5α-epoxy-3,14β-dihydroxy-8β-methyl-6α-(N-methyl-3-trifluoromethoxycinnamamido)morphinan, 17-allyl-4,5α-epoxy-3,14β-dihydroxy-8β-methyl-6α-(N-methyl-3-trifluoromethoxycinnamamido)morphinan, 17-methyl-4,5α-epoxy-3,14β-dihydroxy-8β-methyl-6α-(N-methyl-3-trifluoromethoxycinnamamido)morphinan, 17-phenethyl-4,5α-epoxy-3,14β-dihydroxy-8β-methyl-6α-(N-methyl-3-trifluoromethoxycinnamamido)morphinan, 17-cyclopropylmethyl-4,5α-epoxy-3,14β-dihydroxy-8β-ethyl-6α-(N-methyl-3-trifluoromethoxycinnamamido)morphinan, 17-allyl-4,5α-epoxy-3,14β-dihydroxy-8β-ethyl-6α-(N-methyl-3-trifluoromethoxycinnamamido)morphinan, 17-methyl-4,5α-epoxy-3,14β-dihydroxy-8β-ethyl-6α-(N-methyl-3-trifluoromethoxycinnamamido)morphinan, 17-phenethyl-4,5α-epoxy-3,14β-dihydroxy-8β-ethyl-6α-(N-methyl-3-trifluoromethoxycinnamamido)morphinan, 17-cyclopropylmethyl-4,5α-epoxy-3,14β-dihydroxy-7α-[N-methyl-3-(3,4-dimethylphenyl)propiolamido]morphinan, 17-allyl-4,5α-epoxy-3,14β-dihydroxy-7α-[N-methyl-3-(3,4-dimethylphenyl)propiolamido]morphinan, 17-methyl-4,5α-epoxy-3,14β-dihydroxy-7α-[N-methyl-3-(3,4-dimethylphenyl)propiolamido]morphinan, 17-phenethyl-4,5α-epoxy-3,14β-dihydroxy-7α-[N-methyl-3-(3,4-dimethylphenyl)propiolamido]morphinan, 17-cyclopropylmethyl-4,5α-epoxy-3,14β-dihydroxy-8α-[N-methyl-3-(3,4-dimethylphenyl)propiolamido]morphinan, 17-allyl-4,5α-epoxy-3,14β-dihydroxy-8α-[N-methyl-3-(3,4-dimethylphenyl)propiolamido]morphinan, 17-methyl-4,5α-epoxy-3,14β-dihydroxy-8α-[N-methyl-3-(3,4-dimethylphenyl)propiolamido]morphinan, 17-phenethyl-4,5α-epoxy-3,14β-dihydroxy-8α-[N-methyl-3-(3,4-dimethylphenyl)propiolamido]morphinan, 17-cyclopropylmethyl-4,5α-epoxy-3,14β-dihydroxy-1-nitro-6α-[N-methyl-3-(3,4-dimethylphenyl)propiolamido]morphinan, 17-allyl-4,5α-epoxy-3,14β-dihydroxy-1-nitro-6α-[N-methyl-3-(3,4-dimethylphenyl)propiolamido]morphinan, 17-methyl-4,5α-epoxy-3,14β-dihydroxy-1-nitro-6α-[N-methyl-3-(3,4-dimethylphenyl)propiolamido]morphinan, 17-phenethyl-4,5α-epoxy-3,14β-dihydroxy-1-nitro-6α-[N-methyl-3-(3,4-dimethylphenyl)propiolamido]morphinan, 17-cyclopropylmethyl-4,5α-epoxy-3,14β-dihydroxy-7α-methyl-6α-[N-methyl-3-(3,4-dimethylphenyl)propiolamido]morphinan, 17-allyl-4,5α-epoxy-3,14β-dihydroxy-7α-methyl-6α-[N-methyl-3-(3,4-dimethylphenyl)propiolamido]morphinan, 17-methyl-4,5α-epoxy-3,14β-dihydroxy-7α-methyl-6α-[N-methyl-3-(3,4-dimethylphenyl)propiolamido]morphinan, 17-phenethyl-4,5α-epoxy-3,14β-dihydroxy-7α-methyl-6α-[N-methyl-3-(3,4-dimethylphenyl)propiolamido]morphinan, 17-cyclopropylmethyl-4,5α-epoxy-3,14β-dihydroxy-7β-methyl-6α-[N-methyl-3-(3,4-dimethylphenyl)propiolamido]morphinan, 17-allyl-4,5α-epoxy-3,14β-dihydroxy-7β-methyl-6α-[N-methyl-3-(3,4-dimethylphenyl)propiolamido]morphinan, 17-methyl-4,5α-epoxy-3,14β-dihydroxy-7β-methyl-6α-[N-methyl-3-(3,4-dimethylphenyl)propiolamido]morphinan, 17-phenethyl-4,5α-epoxy-3,14β-dihydroxy-7β-methyl-6α-[N-methyl-3-(3,4-dimethylphenyl)propiolamido]morphinan, 17-cyclopropylmethyl-4,5α-epoxy-3,14β-dihydroxy-8β-methyl-6α-[N-methyl-3-(3,4-dimethylphenyl)propiolamido]morphinan, 17-allyl-4,5α-epoxy-3,14β-dihydroxy-8β-methyl-6α-[N-methyl-3-(3,4-dimethylphenyl)propiolamido]morphinan, 17-methyl-4,5α-epoxy-3,14β-dihydroxy-8β-methyl-6α-[N-methyl-3-(3,4-dimethylphenyl)propiolamido]morphinan, 17-phenethyl-4,5α-epoxy-3,14β-dihydroxy-8β-methyl-6α-[N-methyl-3-(3,4-dimethylphenyl)propiolamido]morphinan, 17-cyclopropylmethyl-4,5α-epoxy-8β-ethyl-3,14β-dihydroxy-6α-[N-methyl-3-(3,4-dimethylphenyl)propiolamido]morphinan, 17-allyl-4,5α-epoxy-8β-ethyl-3,14β-dihydroxy-6α-[N-methyl-3-(3,4-dimethylphenyl)propiolamido]morphinan, 17-methyl-4,5α-epoxy-8β-ethyl-3,14β-dihydroxy-6α-[N-methyl-3-(3,4-dimethylphenyl)propiolamido]morphinan, 17-phenethyl-4,5α-epoxy-8β-ethyl-3,14β-dihydroxy-6α-[N-methyl-3-(3,4-dimethylphenyl)propiolamido]morphinan, 17-cyclopropylmethyl-4,5α-epoxy-3,14β-dihydroxy-7β-(N-methyl-3-trifluoromethoxycinnamamido)morphinan, 17-allyl-4,5α-epoxy-3,14β-dihydroxy-7β-(N-methyl-3-trifluoromethoxycinnamamido)morphinan, 17-methyl-4,5α-epoxy-3,14β-dihydroxy-7β-(N-methyl-3-trifluoromethoxycinnamamido)morphinan, 17-phenethyl-4,5α-epoxy-3,14β-dihydroxy-7β-(N-methyl-3-trifluoromethoxycinnamamido)morphinan, 17-cyclopropylmethyl-4,5α-epoxy-3,14β-dihydroxy-8β-(N-methyl-3-trifluoromethoxycinnamamido)morphinan, 17-allyl-4,5α-epoxy-3,14β-dihydroxy-8β-(N-methyl-3-trifluoromethoxycinnamamido)morphinan, 17-methyl-4,5α-epoxy-3,14β-dihydroxy-8β-(N-methyl-3-trifluoromethoxycinnamamido)morphinan, 17-phenethyl-4,5α-epoxy-3,14β-dihydroxy-8β-(N-methyl-3-trifluoromethoxycinnamamido)morphinan, 17-cyclopropylmethyl-4,5α-epoxy-3,14β-dihydroxy-1-nitro-6β-(N-methyl-3-trifluoromethoxycinnamamido)morphinan, 17-allyl-4,5α-epoxy-3,14β-dihydroxy-1-nitro-6β-(N-methyl-3-trifluoromethoxycinnamamido)morphinan, 17-methyl-4,5α-epoxy-3,14β-dihydroxy-1-nitro-6β-(N-methyl-3-trifluoromethoxycinnamamido)morphinan, 17-phenethyl-4,5α-epoxy-3,14β-dihydroxy-1-nitro-6β-(N-methyl-3-trifluoromethoxycinnamamido)morphinan, 17-cyclopropylmethyl-4,5α-epoxy-3,14β-dihydroxy-7α-methyl-6β-(N-methyl-3-trifluoromethoxycinnamamido)morphinan, 17-allyl-4,5α-epoxy-3,14β-dihydroxy-7α-methyl-6β-(N-methyl-3-trifluoromethoxycinnamamido)morphinan, 17-methyl-4,5α-epoxy-3,14β-dihydroxy-7α-methyl-6β-(N-methyl-3-trifluoromethoxycinnamamido)morphinan, 17-phenethyl-4,5α-epoxy-3,14β-dihydroxy-7α-methyl-6β-(N-methyl-3-trifluoromethoxycinnamamido)morphinan, 17-cyclopropylmethyl-4,5α-epoxy-3,14β-dihydroxy-7β-methyl-6β-(N-methyl-3-trifluoromethoxycinnamamido)morphinan, 17-allyl-4,5α-epoxy-3,14β-dihydroxy-7β-methyl-6β-(N-methyl-3-trifluoromethoxycinnamamido)morphinan, 17-methyl-4,5α-epoxy-3,14β-dihydroxy-7β-methyl-6β-(N-methyl-3-trifluoromethoxycinnamamido)morphinan, 17-phenethyl-4,5α-epoxy-3,14β-dihydroxy-7β-methyl-6β-(N-methyl-3-trifluoromethoxycinnamamido)morphinan, 17-cyclopropylmethyl-4,5α-epoxy-3,14β-dihydroxy- 8β-methyl-6β-(N-methyl-3-trifluoromethoxycinnamamido)morphinan, 17-allyl-4,5α-epoxy-3,14β-dihydroxy-8β-methyl-6β-(N-methyl-3-trifluoromethoxycinnamamido)morphinan, 17-methyl-4,5α-epoxy-3,14β-dihydroxy-8β-methyl-6β-(N-methyl-3-trifluoromethoxycinnamamido)morphinan, 17-phenethyl-4,5α-epoxy-3,14β-dihydroxy-8β-methyl-6β-(N-methyl-3-trifluoromethoxycinnamamido)morphinan, 17-cyclopropylmethyl-4,5α-epoxy-3,14β-dihydroxy-8β-ethyl-6β-(N-methyl-3-trifluoromethoxycinnamamido)morphinan, 17-allyl-4,5α-epoxy-3,14β-dihydroxy-8β-ethyl-6β-(N-methyl-3-trifluoromethoxycinnamamido)morphinan, 17-methyl-4,5α-epoxy-3,14β-dihydroxy-8β-ethyl-6β-(N-methyl-3-trifluoromethoxycinnamamido)morphinan, 17-phenethyl-4,5α-epoxy-3,14β-dihydroxy-8β-ethyl-6β-(N-methyl-3-trifluoromethoxycinnamamido)morphinan, 17-cyclopropylmethyl-4,5α-epoxy-3,14β-dihydroxy-7β-[N-methyl-3-(3,4-dimethylphenyl)propiolamido]morphinan, 17-allyl-4,5α-epoxy-3,14β-dihydroxy-7β-[N-methyl-3-(3,4-dimethylphenyl)propiolamido]morphinan, 17-methyl-4,5α-epoxy-3,14,-dihydroxy-7β-[N-methyl-3-(3,4-dimethylphenyl)propiolamido]morphinan, 17-phenethyl-4,5α-epoxy-3,14β-dihydroxy-7β-[N-methyl-3-(3,4-dimethylphenyl)propiolamido]morphinan, 17-cyclopropylmethyl-4,5α-epoxy-3,14β-dihydroxy-8β-[N-methyl-3-(3,4-dimethylphenyl)propiolamido]morphinan, 17-allyl-4,5α-epoxy-3,14β-dihydroxy-8β-[N-methyl-3-(3,4-dimethylphenyl)propiolamido]morphinan, 17-methyl-4,5α-epoxy-3,14β-dihydroxy-8β-[N-methyl-3-(3,4-dimethylphenyl)propiolamido]morphinan, 17-phenethyl-4,5α-epoxy-3,14β-dihydroxy-8β-[N-methyl-3-(3,4-dimethylphenyl)propiolamido]morphinan, 17-cyclopropylmethyl-4,5α-epoxy-3,14β-dihydroxy-1-nitro-6β-[N-methyl-3-(3,4-dimethylphenyl)propiolamido]morphinan, 17-allyl-4,5α-epoxy-3,14β-dihydroxy-1-nitro-6β-[N-methyl-3-(3,4-dimethylphenyl)propiolamido]morphinan, 17-methyl-4,5α-epoxy-3,14β-dihydroxy-1-nitro-6β-[N-methyl-3-(3,4-dimethylphenyl)propiolamido]morphinan, 17-phenethyl-4,5α-epoxy-3,14β-dihydroxy-1-nitro-6β-[N-methyl-3-(3,4-dimethylphenyl)propiolamido]morphinan, 17-cyclopropylmethyl-4,5α-epoxy-3,14β-dihydroxy-7α-methyl-6β-[N-methyl-3-(3,4-dimethylphenyl)propiolamido]morphinan, 17-allyl-4,5α-epoxy-3,14β-dihydroxy-7α-methyl-6β-[N-methyl-3-(3,4-dimethylphenyl)propiolamido]morphinan, 17-methyl-4,5α-epoxy-3,14β-dihydroxy-7α-methyl-6β-[N-methyl-3-(3,4-dimethylphenyl)propiolamido]morphinan, 17-phenethyl-4,5α-epoxy-3,14β-dihydroxy-7α-methyl-6β-(N-methyl-3-(3,4-dimethylphenyl)propiolamido]morphinan, 17-cyclopropylmethyl-4,5α-epoxy-3,14β-dihydroxy-7β-methyl-6β-[N-methyl-3-(3,4-dimethylphenyl)propiolamido]morphinan, 17-allyl-4,5α-epoxy-3,14β-dihydroxy-7β-methyl-6β-[N-methyl-3-(3,4-dimethylphenyl)propiolamido]morphinan, 17-methyl-4,5α-epoxy-3,14β-dihydroxy-7β-methyl-6β-[N-methyl-3-(3,4-dimethylphenyl)propiolamido]morphinan, 17-phenethyl-4,5α-epoxy-3,14β-dihydroxy-7β-methyl-6β-[N-methyl-3-(3,4-dimethylphenyl)propiolamido]morphinan, 17-cyclopropylmethyl-4,5α-epoxy-3,14)-dihydroxy-8β-methyl-6)3-[N-methyl-3-(3,4-dimethylphenyl)propiolamido]morphinan, 17-allyl-4,5α-epoxy-3,14β-dihydroxy-8β-methyl-6β-[N-methyl-3-(3,4-dimethylphenyl)propiolamido]morphinan, 17-methyl-4,5α-epoxy-3,14β-dihydroxy-8β-methyl-6β-[N-methyl-3-(3,4-dimethylphenyl)propiolamido]morphinan, 17-phenethyl-4,5α-epoxy-3,14β-dihydroxy-8β-methyl-6β-[N-methyl-3-(3,4-dimethylphenyl)propiolamido]morphinan, 17-cyclopropylmethyl-4,5α-epoxy-8β-ethyl-3,14β-dihydroxy-6β-[N-methyl-3-(3,4-dimethylphenyl)propiolamido]morphinan, 17-allyl-4,5α-epoxy-8β-ethyl-3,14β-dihydroxy-6β-[N-methyl-3-(3,4-dimethylphenyl)propiolamido]morphinan, 17-methyl-4,5α-epoxy-8β-ethyl-3,14β-dihydroxy-6β-[N-methyl-3-(3,4-dimethylphenyl)propiolamido]morphinan, 17-phenethyl-4,5α-epoxy-8β-ethyl-3,14β-dihydroxy-6β-[N-methyl-3-(3,4-dimethylphenyl)propiolamido]morphinan, 17-cyclopropylmethyl-4,5α-epoxy-3,14β-dihydroxy-10-keto-6α-(N-methyl-3-trifluoromethoxycinnamamido)morphinan, 17-allyl-4,5α-epoxy-3,14β-dihydroxy-10-keto-6α-(N-methyl-3-trifluoromethoxycinnamamido)morphinan, 17-methyl-4,5α-epoxy-3,14β-dihydroxy-10-keto-6α-(N-methyl-3-trifluoromethoxycinnamamido)morphinan, 17-phenethyl-4,5α-epoxy-3,14β-dihydroxy-10-keto-6α-(N-methyl-3-trifluoromethoxycinnamamido)morphinan, 17-cyclopropylmethyl-4,5α-epoxy-3,14β,15β-trihydroxy-6α-(N-methyl-3-trifluoromethoxycinnamamido)morphinan, 17-allyl-4,5α-epoxy-3,14β,15β-trihydroxy-6α-(N-methyl-3-trifluoromethoxycinnamamido)morphinan, 17-methyl-4,5α-epoxy-3,14β,15β-trihydroxy-6α-(N-methyl-3-trifluoromethoxycinnamamido)morphinan, 17-phenethyl-4,5α-epoxy-3,14β,15β-trihydroxy-6α-(N-methyl-3-trifluoromethoxycinnamamido)morphinan, 17-cyclopropylmethyl-16-cyano-4,5α-epoxy-3,14β-dihydroxy-6α-(N-methyl-3-trifluoromethoxycinnamamido)morphinan, 17-allyl-16-cyano-4,5α-epoxy-3,14β-dihydroxy-6α-(N-methyl-3-trifluoromethoxycinnamamido)morphinan, 17-methyl-16-cyano-4,5α-epoxy-3,14β-dihydroxy-6α-(N-methyl-3-trifluoromethoxycinnamamido)morphinan, 17-phenethyl-16-cyano-4,5α-epoxy-3,14β-dihydroxy-6α-(N-methyl-3-trifluoromethoxycinnamamido)morphinan, 8-nor-17-cyclopropylmethyl-4,5α-epoxy-3,14β-dihydroxy-6α-(N-methyl-3-trifluoromethoxycinnamamido)morphinan, 8-nor-17-allyl-4,5α-epoxy-3,14β-dihydroxy-6α-(N-methyl-3-trifluoromethoxycinnamamido)morphinan, 8-nor-17-methyl-4,5α-epoxy-3,14β-dihydroxy-6α-(N-methyl-3-trifluoromethoxycinnamamido)morphinan, 8-nor-17-phenethyl-4,5α-epoxy-3,14β-dihydroxy-6α-(N-methyl-3-trifluoromethoxycinnamamido)morphinan, 8-homo-17-cyclopropylmethyl-4,5o&-epoxy-3,14β-dihydroxy-6α-(N-methyl-3-trifluoromethoxycinnamamido)morphinan, 8-homo-17-allyl-4,5α-epoxy-3,14β-dihydroxy-6α-(N-methyl-3-trifluoromethoxycinnamamido)morphinan, 8-homo-17-methyl-4,5α-epoxy-3,14β-dihydroxy-6α-(N-methyl-3-trifluoromethoxycinnamamido)morphinan, 8-homo-17-phenethyl-4,5α-epoxy-3,14β-dihydroxy-6α-(N-methyl-3-trifluoromethoxycinnamamido)morphinan, 8-homo-17-cyclopropylmethyl-4,5α-epoxy-3,14β-dihydroxy-7α-(N-methyl-3-trifluoromethoxycinnamamido)morphinan, 8-homo-17-allyl-4,5α-epoxy-3,14β-dihydroxy-7α-(N-methyl- 3-trifluoromethoxycinnamamido)morphinan, 8-homo-17-methyl-4,5α-epoxy-3,14β-dihydroxy-7α-(N-methyl-3-trifluoromethoxycinnamamido)morphinan, 8-homo-17-phenethyl-4,5α-epoxy-3,14β-dihydroxy-7α-(N-methyl-3-trifluoromethoxycinnamamido) morphinan, 17-cyclopropylmethyl-4,5α-epoxy-3,14β-dihydroxy-10-keto-6α-[N-methyl-3-(3,4-dimethylphenyl)propiolamido]morphinan, 17-allyl-4,5α-epoxy-3,14β-dihydroxy-10-keto-6α-[N-methyl-3-(3,4-dimethylphenyl)propiolamido]morphinan, 17-methyl-4,5α-epoxy-3,14β-dihydroxy-10-keto-6α-[N-methyl-3-(3,4-dimethylphenyl)propiolamido] morphinan, 17-phenethyl-4,5α-epoxy-3,14β-dihydroxy-10-keto-6α-[N-methyl-3-(3,4-dimethylphenyl)propiolamido]morphinan, 17-cyclopropylmethyl-4,5α-epoxy-3,14β,15β-trihydroxy-6α-[N-methyl-3-(3,4-dimethylphenyl)propiolamido]morphinan, 17-allyl-4,5α-epoxy-3,14β,15β-trihydroxy-6α-[N-methyl-3-(3,4-dimethylphenyl)propiolamido]morphinan, 17-methyl-4,5α-epoxy-3,14β,15β-trihydroxy-6α-[N-methyl-3-(3,4-dimethylphenyl)propiolamido]morphinan, 17-phenethyl-4,5α-epoxy-3,14β,15β-trihydroxy-6α-[N-methyl-3-(3,4-dimethylphenyl)propiolamido] morphinan, 17-cyclopropylmethyl-16-cyano-4,5α-epoxy-3,14β-dihydroxy-6α-[N-methyl-3-(3,4-dimethylphenyl)propiolamido]morphinan, 17-allyl-16-cyano-4,5α-epoxy-3,14β-dihydroxy-6α-[N-methyl-3-(3,4-dimethylphenyl)propiolamido]morphinan, 17-methyl-16-cyano-4,5α-epoxy-3,14β-dihydroxy-6α-[N-methyl-3-(3,4-dimethylphenyl)propiolamido]morphinan, 17-phenethyl-16-cyano-4,5α-epoxy-3,14β-dihydroxy-6α-[N-methyl-3-(3,4-dimethylphenyl)propiolamido]morphinan, 8-nor-17-cyclopropylmethyl-4,5α-epoxy-3,14β-dihydroxy-6α-[N-methyl-3-(3,4-dimethylphenyl)propiolamido]morphinan, 8-nor-17-allyl-4,5α-epoxy-3,14β-dihydroxy-6α-[N-methyl-3-(3,4-dimethylphenyl)propiolamido]morphinan, 8-nor-17-methyl-4,5α-epoxy-3,14β-dihydroxy-6α-[N-methyl-3-(3,4-dimethylphenyl)propiolamido]morphinan, 8-nor-17-phenethyl-4,5α-epoxy-3,14β-dihydroxy-6α-[N-methyl-3-(3,4-dimethylphenyl)propiolamido] morphinan, 8-homo-17-cyclopropylmethyl-4,5α-epoxy-3,14β-dihydroxy-6α-[N-methyl-3-(3,4-dimethylphenyl)propiolamido]morphinan, 8-homo-17-allyl-4,5α-epoxy-3,14β-dihydroxy-6α-[N-methyl-3-(3,4-dimethylphenyl)propiolamido]morphinan, 8-homo-17-methyl-4,5α-epoxy-3,14β-dihydroxy-6α-[N-methyl-3-(3,4-dimethylphenyl)propiolamido] morphinan, 8-homo-17-phenethyl-4,5α-epoxy-3,14β-dihydroxy-6α-[N-methyl-3-(3,4-dimethylphenyl)propiolamido]morphinan, 8-homo-17-cyclopropylmethyl-4,5α-epoxy-3,14β-dihydroxy-7α-[N-methyl-3-(3,4-dimethylphenyl)propiolamido] morphinan, 8-homo-17-allyl-4,5α-epoxy-3,14β-dihydroxy-7α-[N-methyl-3-(3,4-dimethylphenyl)propiolamido]morphinan, 8-homo-17-methyl-4,5α-epoxy-3,14β-dihydroxy-7α-[N-methyl-3-(3,4-dimethylphenyl)propiolamido]morphinan, 8-homo-17-phenethyl-4,5α-epoxy-3,14β-dihydroxy-7α-[N-methyl-3-(3,4-dimethylphenyl)propiolamido] morphinan, 17-cyclopropylmethyl-4,5α-epoxy-3,14β-dihydroxy-10-keto-6β-(N-methyl-3-trifluoromethoxycinnamamido)morphinan, 17-allyl-4,5α-epoxy-3,14β-dihydroxy-10-keto-6β-(N-methyl-3-trifluoromethoxycinnamamido)morphinan, 17-methyl-4,5α-epoxy-3,14β-dihydroxy-10-keto-6β-(N-methyl-3-trifluoromethoxycinnamamido)morphinan, 17-phenethyl-4,5α-epoxy-3,14β-dihydroxy-10-keto-6β-(N-methyl-3-trifluoromethoxycinnamamido) morphinan, 17-cyclopropylmethyl-4,5α-epoxy-3,14β,15β-trihydroxy-6β-(N-methyl-3-trifluoromethoxycinnamamido)morphinan, 17-allyl-4,5α-epoxy-3,14β,15β-trihydroxy-6β-(N-methyl-3-trifluoromethoxycinnamamido)morphinan, 17-methyl-4,5α-epoxy-3,14β,15β-trihydroxy-6β-(N-methyl-3-trifluoromethoxycinnamamido)morphinan, 17-phenethyl-4,5α-epoxy-3,14β,15β-trihydroxy-6β-(N-methyl-3-trifluoromethoxycinnamamido) morphinan, 17-cyclopropylmethyl-16-cyano-4,5α-epoxy-3,14β-dihydroxy-6β-(N-methyl-3-trifluoromethoxycinnamamido)morphinan, 17-allyl-16-cyano-4,5α-epoxy-3,14β-dihydroxy-6β-(N-methyl-3-trifluoromethoxycinnamamido)morphinan, 17-methyl-16-cyano-4,5α-epoxy-3,14β-dihydroxy-6β-(N-methyl-3-trifluoromethoxycinnamamido) morphinan, 17-phenethyl-16-cyano-4,5α-epoxy-3,14β-dihydroxy-6β-(N-methyl-3-trifluoromethoxycinnamamido)morphinan, 8-nor-17-cyclopropylmethyl-4,5α-epoxy-3,14β-dihydroxy-6β-(N-methyl-3-trifluoromethoxycinnamamido) morphinan, 8-nor-17-allyl-4,5α-epoxy-3,14β-dihydroxy-6β-(N-methyl-3-trifluoromethoxycinnamamido)morphinan, 8-nor-17-methyl-4,5α-epoxy-3,14β-dihydroxy-6β-(N-methyl-3-trifluoromethoxycinnamamido)morphinan, 8-nor-17-phenethyl-4,5α-epoxy-3,14β-dihydroxy-6β-(N-methyl-3-trifluoromethoxycinnamamido)morphinan, 8-homo-17-cyclopropylmethyl-4,5α-epoxy-3,14β-dihydroxy-6β-(N-methyl-3-trifluoromethoxycinnamamido)morphinan, 8-homo-17-allyl-4,5α-epoxy-3,14β-dihydroxy-6β-(N-methyl-3-trifluoromethoxycinnamamido)morphinan, 8-homo-17-methyl-4,5α-epoxy-3,14β-dihydroxy-6β-(N-methyl-3-trifluoromethoxycinnamamido)morphinan, 8-homo-17-phenethyl-4,5α-epoxy-3,14β-dihydroxy-6β-(N-methyl-3-trifluoromethoxycinnamamido) morphinan, 8-homo-17-cyclopropylmethyl-4,5α-epoxy-3,14β-dihydroxy-7β-(N-methyl-3-trifluoromethoxycinnamamido)morphinan, 8-homo-17-allyl-4,5α-epoxy-3,14β-dihydroxy-7β-(N-methyl-3-trifluoromethoxycinnamamido)morphinan, 8-homo-17-methyl-4,5α-epoxy-3,14β-dihydroxy-7β-(N-methyl-3-trifluoromethoxycinnamamido)morphinan, 8-homo-17-phenethyl-4,5α-epoxy-3,14β-dihydroxy-7β-(N-methyl-3-trifluoromethoxycinnamamido) morphinan, 17-cyclopropylmethyl-4,5α-epoxy-3,14β-dihydroxy-10-keto-6β-[N-methyl-3-(3,4-dimethylphenyl)propiolamido]morphinan, 17-allyl-4,5α-epoxy-3,14β-dihydroxy-10-keto-6β-[N-methyl-3-(3,4-dimethylphenyl)propiolamido]morphinan, 17-methyl-4,5α-epoxy-3,14β-dihydroxy-10-keto-6β-[N-methyl-3-(3,4-dimethylphenyl)propiolamido] morphinan, 17-phenethyl-4,5α-epoxy-3,14β-dihydroxy-10-keto-6β-[N-methyl-3-(3,4-dimethylphenyl)propiolamido]morphinan, 17-cyclopropylmethyl-4,5α-epoxy-3,14β,15β-trihydroxy-6β-[N-methyl-3-(3,4-dimethylphenyl)propiolamido]morphinan, 17-allyl-4,5α-epoxy-3,14β,15β-trihydroxy-6β-[N-methyl-3-(3,4-dimethylphenyl)propiolamido]morphinan, 17-methyl-4,5α-epoxy-3,14β,15β-trihydroxy-6β-[N-methyl-3-(3,4-dimethylphenyl)propiolamido]morphinan, 17-phenethyl-4,5α-epoxy-3,14β,15β-trihydroxy-6β-[N-methyl-3-(3,4-dimethylphenyl)propiolamido]morphinan, 17-cyclopropylmethyl-16-cyano-4,5α-epoxy-3,14β-dihydroxy-6β-[N-methyl-3-(3,4-dimethylphenyl)propiolamido]morphinan, 17-allyl-16-cyano-4,5α-epoxy-3,14β-dihydroxy-6β-[N-methyl-3-(3,4-dimethylphenyl)propiolamido]morphinan, 17-methyl-16-cyano-4,5α-epoxy-3,14β-dihydroxy-6β-[N-methyl-3-(3,4-dimethylphenyl)propiolamido]morphinan, 17-phenethyl-16-cyano-4,5α-epoxy-3,14β-dihydroxy-6β-[N-methyl-3-(3,4-dimethylphenyl)propiolamido]morphinan, 8-nor-17-cyclopropylmethyl-4,5α-epoxy-3,14β-dihydroxy-6β-[N-methyl-3-(3,4-dimethylphenyl)propiolamido]morphinan, 8-nor-17-allyl-4,5α-epoxy-3,14β-dihydroxy-6β-[N-methyl-3-(3,4-dimethylphenyl)propiolamido]morphinan, 8-nor-17-methyl-4,5α-epoxy-3,14β-dihydroxy-6β-[N-methyl-3-(3,4-dimethylphenyl)propiolamido]morphinan, 8-nor-17-phenethyl-4,5α-epoxy-3,14β-dihydroxy-6β-[N-methyl-3-(3,4-dimethylphenyl)propiolamido]morphinan, 8-homo-17-cyclopropylmethyl-4,5α-epoxy-3,14β-dihydroxy-6β-[N-methyl-3-(3,4-dimethylphenyl)propiolamido]morphinan, 8-homo-17-allyl-4,5α-epoxy-3,14β-dihydroxy-6β-[N-methyl-3-(3,4-dimethylphenyl)propiolamido]morphinan, 8-homo-17-methyl-4,5α-epoxy-3,14β-dihydroxy-6β-[N-methyl-3-(3,4-dimethylphenyl)propiolamido]morphinan , 8 -homo-17-phenethyl-4,5α-epoxy-3,14β-dihydroxy-6β-[N-methyl-3-(3,4-dimethylphenyl)propiolamido]morphinan, 8-homo-17-cyclopropylmethyl-4,5α-epoxy-3,14β-dihydroxy-7β-[N-methyl-3-(3,4-dimethylphenyl)propiolamido]morphinan, 8-homo-17-allyl-4,5α-epoxy-3,14β-dihydroxy-7β-[N-methyl-3-(3,4-dimethylphenyl)propiolamido]morphinan, 8-homo-17-methyl-4,5α-epoxy-3,14β-dihydroxy-7β-[N-methyl-3-(3,4-dimethylphenyl)propiolamido]morphinan, 8-homo-17-phenethyl-4,5α-epoxy-3,14β-dihydroxy-7β-[N-methyl-3-(3,4-dimethylphenyl)propiolamido]morphinan, 17-cyclopropylmethyl-4,5α-epoxy-3,14β-dihydroxy-7α-[N-methyl-trans-3-(4-bromo-2-thienyl)acrylamido]morphinan, 17-allyl-4,5α-epoxy-3,14β-dihydroxy-7α-[N-methyl-trans-3-(4-bromo-2-thienyl)acrylamido]morphinan, 17-methyl-4,5α-epoxy-3,14β-dihydroxy-7α-[N-methyl-trans-3-(4-bromo-2-thienyl)acrylamido]morphinan, 17-phenethyl-4,5α-epoxy-3,14β-dihydroxy-7α-[N-methyl-trans-3-(4-bromo-2-thienyl)acrylamido]morphinan, 5α-epoxy-3,14β-dihydroxy-7α-methyl-6β-[N-methyl-trans-3-(4-bromo-2-thienyl)acrylamido]morphinan, 17-methyl-4,5α-epoxy-3,14β-dihydroxy-7α-methyl-6β-[N-methyl-trans-3-(4-bromo-2-thienyl)acrylamido]morphinan, 17-phenethyl-4,5α-epoxy-3,14β-dihydroxy-7α-methyl-6β-[N-methyl-trans-3-(4-bromo-2-thienyl)acrylamido]morphinan, 17-cyclopropylmethyl-4,5α-epoxy-3,14β-dihydroxy-7β-methyl-6β-[N-methyl-trans-3-(4-bromo-2-thienyl)acrylamido]morphinan, 17-allyl-4,5α-epoxy-3,14β-dihydroxy-7β-methyl-6β-[N-methyl-trans-3-(4-bromo-2-thienyl)acrylamido]morphinan, 17-methyl-4,5α-epoxy-3,14β-dihydroxy-7β-methyl-6β-[N-methyl-trans-3-(4-bromo-2-thienyl)acrylamido]morphinan, 17-phenethyl-4,5α-epoxy-3,14β-dihydroxy-7β-methyl-6β-[N-methyl-trans-3-(4-bromo-2-thienyl)acrylamido]morphinan, 17-cyclopropylmethyl-4,5α-epoxy-3,14β-dihydroxy-8β-methyl-6β-[N-methyl-trans-3-(4-bromo-2-thienyl)acrylamido]morphinan, 17-allyl-4,5α-epoxy-3,14β-dihydroxy-8β-methyl-6β-[N-methyl-trans-3-(4-bromo-2-thienyl)acrylamido]morphinan, 17-methyl-4,5α-epoxy-3,14β-dihydroxy-8β-methyl-6β-[N-methyl-trans-3-(4-bromo-2-thienyl)acrylamido]morphinan, 17-phenethyl-4,5α-epoxy-3,14β-dihydroxy-8β-methyl-6β-[N-methyl-trans-3-(4-bromo-2-thienyl)acrylamido]morphinan, 17-cyclopropylmethyl-4,5α-epoxy-8β-ethyl-trans-3,14β-dihydroxy-6β-[N-methyl-trans-3-(4-bromo-2-thienyl)acrylamido]morphinan, 17-allyl-4,5α-epoxy-8β-ethyl-trans-3,14β-dihydroxy-6β-[N-methyl-trans-3-(4-bromo-2-thienyl)acrylamido]morphinan, 17-methyl-4,5α-epoxy-8β-ethyl-trans-3,14β-dihydroxy-6β-[N-methyl-trans-3-(4-bromo-2-thienyl)acrylamido]morphinan, 17-phenethyl-4,5α-epoxy-8β-ethyl-trans-3,14β-dihydroxy-6β-[N-methyl-trans-3-(4-bromo-2-thienyl)acrylamido]morphinan, 17-cyclopropylmethyl-4,5α-epoxy-3,14β-dihydroxy-10-keto-6α-[N-methyl-trans-3-(4-bromo-2-thienyl)acrylamido]morphinan, 17-allyl-4,5α-epoxy-3,14β-dihydroxy-10-keto-6α-[N-methyl-trans-3-(4-bromo-2-thienyl)acrylamido]morphinan, 17-methyl-4,5α-epoxy-3,14β-dihydroxy-10-keto-6α-[N-methyl-trans-3-(4-bromo-2-thienyl)acrylamido]morphinan, 17-phenethyl-4,5α-epoxy-3,14β-dihydroxy-10-keto-6α-[N-methyl-trans-3-(4-bromo-2-thienyl)acrylamido]morphinan, 17-cyclopropylmethyl-4,5α-epoxy-3,14β,15β-trihydroxy-6α-[N-methyl-trans-3-(4-bromo-2-thienyl)acrylamido]morphinan, 17-allyl-4,5α-epoxy-3,14β,15β-trihydroxy-6α-[N-methyl-trans-3-(4-bromo-2-thienyl)acrylamido]morphinan, 17-methyl-4,5α-epoxy-3,14β,15β-trihydroxy-6α-[N-methyl-trans-3-(4-bromo-2-thienyl)acrylamido]morphinan, 17-phenethyl-4,5α-epoxy-3,14β,15β-trihydroxy-6α-[N-methyl-trans-3-(4-bromo-2-thienyl)acrylamido]morphinan, 17-cyclopropylmethyl-16-cyano-4,5α-epoxy-3,14β-dihydroxy-6α-[N-methyl-trans-3-(4-bromo-2-thienyl)acrylamido]morphinan, 17-allyl-16-cyano-4,5α-epoxy-3,14β-dihydroxy-6α-[N-methyl-trans-3-(4-bromo-2-thienyl)acrylamido]morphinan, 17-methyl-16-cyano-4,5α-epoxy-3,14β-dihydroxy-6α-[N-methyl-trans-3-(4-bromo-2-thienyl)acrylamido]morphinan, 17-phenethyl-16-cyano-4,5α-epoxy-3,14β-dihydroxy-6α-[N-methyl-trans-3-(4-bromo-2-thienyl)acrylamido]morphinan, 8-nor-17-cyclopropylmethyl-4,5α-epoxy-3,14β-dihydroxy-6α-[N-methyl-trans-3-(4-bromo-2-thienyl)acrylamido]morphinan, 8-nor-17-allyl-4,5α-epoxy-3,14β-dihydroxy-6α-[N-methyl-trans-3-(4-bromo-2-thienyl)acrylamido]morphinan, 8-nor-17-methyl-4,5α-epoxy-3,14β-dihydroxy-6α-[N-methyl-trans-3-(4-bromo-2-thienyl)acrylamido]morphinan, 8-nor-17-phenethyl-4,5α-epoxy-3,14β-dihydroxy-6α-[N-methyl-trans-3-(4-bromo-2-thienyl)acrylamido]morphinan, 8-homo-17-cyclopropylmethyl-4,5α-epoxy-3,14β-dihydroxy-6α-[N-methyl-trans-3-(4-bromo-2-thienyl)acrylamido]morphinan, 8-homo-17-allyl-4,5α-epoxy-3,14β-dihydroxy-6α-[N-methyl-trans-3-(4-bromo-2-thienyl)acrylamido]morphinan, 8-homo-17-methyl-4,5α-epoxy-3,14β-dihydroxy-6α-[N-methyl-trans-3-(4-bromo-2-thienyl)acrylamido]morphinan, 8-homo-17-phenethyl-4,5α-epoxy-3,14β-dihydroxy-6α-[N-methyl-trans-3-(4-bromo-2-thienyl)acrylamido]morphinan, 8-homo-17-cyclopropylmethyl-4,5α-epoxy-3,14β-dihydroxy-7α-[N-methyl-trans-3-(4-bromo-2-thienyl)acrylamido]morphinan, 8-homo-17-allyl-4,5α-epoxy-3,14β-dihydroxy-7α-[N-methyl-trans-3-(4-bromo-2-thienyl)acrylamido]morphinan, 8-homo-17-methyl-4,5α-epoxy-3,14β-dihydroxy-7α-[N-methyl-trans-3-(4-bromo-2-thienyl)acrylamido]morphinan, 8-homo-17-phenethyl-4,5α-epoxy-3,14β-dihydroxy-7α-[N-methyl-trans-3-(4-bromo-2-thienyl)acrylamido]morphinan, 17-cyclopropylmethyl-16-cyano-4,5α-epoxy-3,14β-dihydroxy-6β-[N-methyl-trans-3-(4-bromo-2-thienyl)acrylamido]morphinan, 17-allyl-16-cyano-4,5α-epoxy-3,14β-dihydroxy-6β-[N-methyl-trans-3-(4-bromo-2-thienyl)acrylamido]morphinan, 17-methyl-16-cyano-4,5α-epoxy-3,14β-dihydroxy-6β-[N-methyl-trans-3-(4-bromo-2-thienyl)acrylamido]morphinan, 17-phenethyl-16-cyano-4,5α-epoxy-3,14β-dihydroxy-6β-[N-methyl-trans-3-(4-bromo-2-thienyl)acrylamido]morphinan, 8-nor-17-cyclopropylmethyl-4,5α-epoxy-3,14β-dihydroxy-6β-[N-methyl-trans-3-(4-bromo-2-thienyl)acrylamido]morphinan, 8-nor-17-allyl-4,5α-epoxy-3,14β-dihydroxy-6β-[N-methyl-trans-3-(4-bromo-2-thienyl)acrylamido]morphinan, 8-nor-17-methyl-4,5α-epoxy-3,14β-dihydroxy-6β-[N-methyl-trans-3-(4-bromo-2-thienyl)acrylamido]morphinan, 8-nor-17-phenethyl-4,5α-epoxy-3,14β-dihydroxy-6β-[N-methyl-trans-3-(4-bromo-2-thienyl)acrylamido]morphinan, 8-homo-17-cyclopropylmethyl-4,5α-epoxy-3,14β-dihydroxy-6β-[N-methyl-trans-3-(4-bromo-2-thienyl)acrylamido]morphinan, 8-homo-17-allyl-4,5α-epoxy-3,14β-dihydroxy-6β-[N-methyl-trans-3-(4-bromo-2-thienyl)acrylamido]morphinan, 8-homo-17-methyl-4,5α-epoxy-3,14β-dihydroxy-6β-

[N-methyl-trans-3-(4-bromo-2-thienyl)acrylamido]
morphinan, 8-homo-17-phenethyl-4,5α-epoxy-3,14β-
dihydroxy-6β-[N-methyl-trans-3-(4-bromo-2-thienyl)
acrylamido]morphinan, 8-homo-17-
cyclopropylmethyl-4,5α-epoxy-3,14β-dihydroxy-7β-
[N-methyl-trans-3-(4-bromo-2-thienyl)acrylamido]
morphinan, 8-homo-17-allyl-4,5α-epoxy-3,14β-
dihydroxy-7β-[N-methyl-trans-3-(4-bromo-2-thienyl)
acrylamido]morphinan, 8-homo-17-methyl-4,5α-
epoxy-3,14β-dihydroxy-7β-[N-methyl-trans-3-(4-
bromo-2-thienyl)acrylamido]morphinan, 8-homo-17-
phenethyl-4,5α-epoxy-3,14β-dihydroxy-7β-[N-
methyl-trans-3-(4-bromo-2-thienyl)acrylamido]
morphinan, but the present invention is not limited to
these compounds.

Furthermore, the compound of the present invention
includes the (+) form, (−) form and (±) form.

The compound of general formula (I-B), one of the
preferable modes of the present invention, can specifically
be obtained by the following procedure.

The compound indicated with general formula (I-B),
which is a preferable mode of the present invention, wherein
A' is —XC(=Y)—, —XC(=Y)Z—, or —XSO$_2$— (where
X represents NR$^{12}$ or O, Y represents O or S, and Z
represents O, NH or S, and R$^{12}$ is the same as previously
defined), can specifically be obtained with the following
procedure.

In general, as shown in Chart 1, said compound can be
obtained by condensing the carboxylic acid derivative represented with general formula (III) (wherein B and R$^{11'}$ are
the same as previously defined), the formic acid derivative
represented with general formula (IV) (wherein Z, B and
R$^{11'}$ are the same as previously defined), the isocyanic acid
or isothiocyanic acid derivative represented with general
formula (V) (wherein B and R$^{11'}$ are the same as previously
defined), or the sulfonic acid derivative represented with
general formula (VI) (wherein B and R$^{11'}$ are the same as
previously defined) and so forth with the 6-amino form or
6-hydroxy form represented with general formula (II)
(wherein R$^1$, R$^{2'}$ R$^{4'}$ R$^{5'}$, R$^{6'}$ and R$^{10'}$ are the same as
previously defined, and E represents NHR$^{12}$ (wherein R$^{12}$ is
the same as previously defined) or OH).

Chart 1

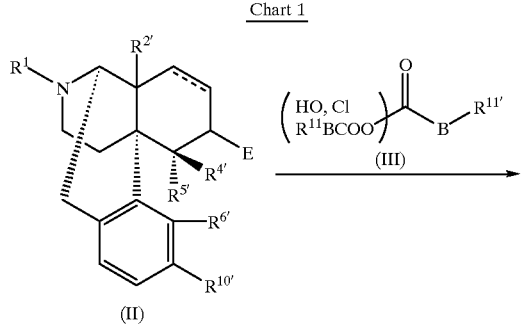

(II)

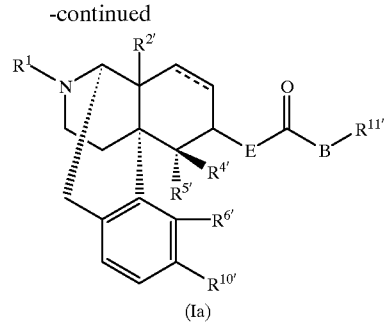

(Ia)

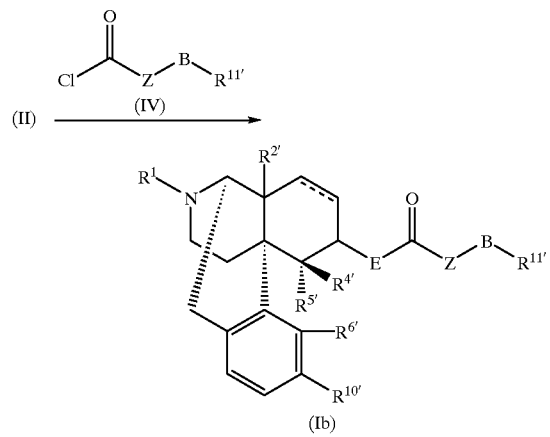

(Ib)

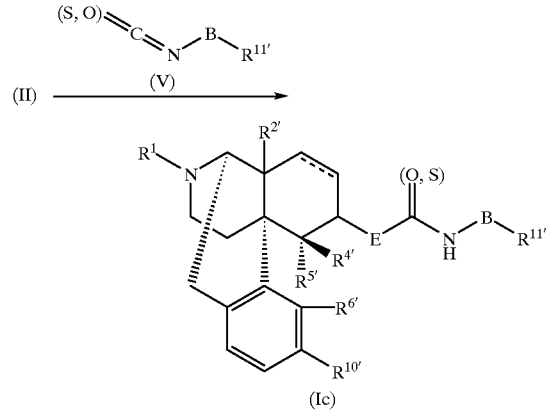

(Ic)

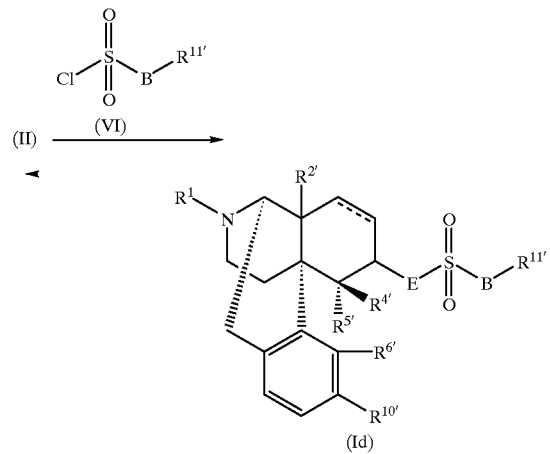

(Id)

The 6-amino form and 6-hydroxy form used in this condensation can specifically be obtained by the following process.

As shown in Chart 2, the 6α-amino form represented with general formula (IIaα1) (wherein $R^1$, $R^{2'}$, $R^{4'}$, $R^{5'}$, $R^{6'}$ and $R^{10'}$ are the same as previously defined, and $R^{12'}$ represents a straight chain or branched chain alkyl group having 1–5 carbon atoms or an aryl group having 6–12 carbon atoms) is obtained by mixing in solvent the 6-keto form represented with general formula (VIIa) (wherein $R^1$, $R^{2'}$, $R^{4'}$, $R^{5'}$, $R^{6'}$ and $R^{10'}$ are the same as previously defined) and the primary amine represented with general formula (VIII) (wherein $R^{12'}$ is the same as previously defined) followed either by the addition of a suitable amount of acid and hydrogenation in the presence of a metal catalyst, or reduction with a metal hydride reducing agent in the presence of acid. The hydrogenation reaction is preferable for obtaining the α-amino form with high selectivity. However, although the ratio varies according to the substrate, both the α form and β form are obtained simultaneously in the case of reduction by metal hydride reducing agent, and is preferable in that a compound having the desired stereochemistry can be obtained by using ordinary separation and purification methods. In addition, this is also useful as a process for obtaining the amino form with a substrate having functional groups such as olefins and so forth that end up reacting under conditions of hydrogenation. In the case of reduction by a hydrogenation reaction, 1–30 equivalents, and preferably 1–10 equivalents, of amine is used. Although any solvent can be used for the solvent provided it is inactive under conditions of hydrogenation, examples of which include alcohol solvents such as methanol and ethanol, ether solvents such as THF, ether, DME and dioxane, and aromatic hydrocarbon solvents such as benzene and toluene, alcohol solvents are used preferably and methanol is used particularly preferably. Although any acid can be used for the acid provided that it normally forms a salt with an amine, examples of which include inorganic acids such as hydrochloric acid, hydrobromic acid, sulfuric acid and phosphoric acid, sulfonic acids such as methanesulfonic acid and p-toluenesulfonic acid, and organic acids such as benzoic acid, acetic acid and oxalic acid, hydrochloric acid, sulfuric acid and methanesulfonic acid are used preferably. Satisfactory results are usually obtained by using hydrochloric acid in an amount that is 1 equivalent less than the total amount of base. These acids can be added to the reaction system by first converting the substrate and reaction agents into salts. Although all metal catalysts can be used that are normally used in hydrogenation reactions, examples of which include platinum catalysts such as platinum oxide and platinum hydroxide, palladium catalysts such as palladium hydroxide and palladium—carbon, and nickel catalysts such as Raney nickel, a platinum catalyst, and particularly platinum oxide, is used preferably. Although the reaction can be carried out at a reaction temperature from −30° C. to 80° C., and preferably from −10° C. to 50° C., and hydrogen pressure from 1 to 100 atmospheres, and preferably from 1 to 30 atmospheres, favorable results are usually obtained at room temperature and normal pressure.

When reducing with a metal hydride, the amount of amine used is from 1 to 30 equivalents, and preferably from 1 to 15 equivalents. Although examples of solvents used include alcohol solvents such as methanol and ethanol, ether solvents such as THF, ether, DME and dioxane, and aromatic hydrocarbon solvents such as benzene and toluene, alcohol solvents are used preferably, while methanol is used particularly preferably. Although any acid can be used for the acid present in the reaction provided it normally forms a salt with amines, examples of which include inorganic acids such as hydrochloric acid, hydrobromic acid, sulfuric acid and phosphoric acid, sulfonic acids such as methanesulfonic acid and p-toluenesulfonic acid, and organic acids such as benzoic acid, acetic acid and oxalic acid, hydrochloric acid, sulfuric acid, methanesulfonic acid and so forth are used preferably. In addition, these acids can be added to the reaction system by first converting the substrate and reaction agents into salts. Metal hydride reducing agents that can be used to carry out the reaction are those which are relatively stable under conditions in which acid is present, examples of which include sodium borohydride, sodium cyanoborohydride, zinc borohydride, sodium triacetoxyborohydride, tetramethylammonium triacetoxyborohydride and borane-pyridine, with sodium cyanoborohydride being used particularly preferably. Although the reaction can be carried out at a reaction temperature from −30° C. to 100° C., and preferably from −10° C. to 50° C., satisfactory results are usually obtained at room temperature.

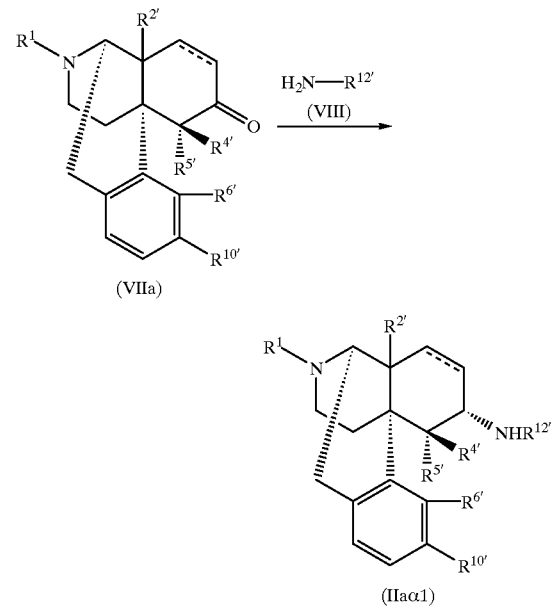

Chart 2

As shown in Chart 3, the 6β-amino form represented with general formula (IIaβ2) (wherein $R^1$, $R^{2'}$, $R^{4'}$, $R^{5'}$, $R^{6'}$, $R^{10'}$ and $R^{12'}$ are the same as previously defined) can be obtained from the 6-keto form represented with general formula (VIIb) (wherein $R^1$, $R^{2'}$, $R^{4'}$, $R^{5'}$, $R^{6'}$ and $R^{10'}$ are the same as previously defined) with the three steps described below.

In the first step, the ketone form is reacted with a secondary amine form having at least one benzyl substituent group represented with general formula (IX) (wherein $R^{12'}$ is the same as previously defined) in the presence of acid to obtain the iminium intermediate represented with general formula (X) (wherein $R^1$, $R^{2'}$, $R^{4'}$, $R^{5'}$, $R^{6'}$, $R^{10'}$ and $R^{12'}$ are the same as previously defined). It is desirable that the reaction be allowed to proceed while removing the water formed either by azeotropic distillation or using a dehydrating agent. 1–30 equivalents, and preferably 1–10 equivalents, of the secondary amine are used. Although any acid can be used for the acid present in the reaction provided it normally forms a salt with amines, examples of which include inorganic acids such as hydrochloric acid, hydrobromic acid, sulfuric acid and phosphoric acid, sulfonic acids such as methanesulfonic acid and p-toluenesulfonic acid, and organic acids such as benzoic acid, acetic acid and oxalic acid, hydrochloric acid, sulfuric acid, methanesulfonic acid and benzoic acid are used preferably, while hydrochloric acid and benzoic acid are used particularly preferably. Processes are preferably carried out wherein these acids are added to the reaction system are first converting the substrate and reaction agents into salts. Moreover, in the case of carrying out the reaction in the presence of weak acid, preferable results may be obtained by adding strong acid to the reaction system as an acid catalyst, examples of which include inorganic acids such as hydrochloric acid, hydrobromic acid, sulfuric acid and phosphoric acid, and sulfonic acids such as methanesulfonic acid and p-toluenesulfonic acid, with p-toluenesulfonic acid and so forth being particularly preferable. Examples of reaction solvents that can be used include ether solvents such as THF, ether, DME and dioxane, halogen solvents such as dichloromethane and chloroform, aromatic hydrocarbon solvents such as benzene, toluene and xylene, ester solvents such as ethyl acetate and methyl acetate, as well as mixed solvents of these. When using an ordinary Dean-Stark water separator for the purpose of removing water, solvents having excellent azeotropic efficiency and water separation efficiency, examples of which include aromatic hydrocarbon solvents such as benzene and toluene, are used preferably. At this time, the mixing in of an amount of a solvent such as ethyl acetate or THF to an extent which does not decrease water separation efficiency for the purpose of lowering the azeotropic temperature may yield more favorable results.

Although the reaction temperature is considered to be from 40° C. to 200° C., and preferably from 50° C. to 150° C., satisfactory results are obtained from 50° C. to 130° C. In addition, it has also been a found that a new process is effective wherein water is continuously removed by filling a continuous Soxhlet extractor with a dehydrating agent. Although any of the solvents mentioned above can be used for the solvent in this case, ether solvents, ester solvents and aromatic hydrocarbon solvents are used preferably, while THF, DME, ethyl acetate, benzene and toluene are used particularly preferably. Although examples of dehydrating agents include molecular sieves as well as inorganic dehydrating agents such as anhydrous calcium sulfate, anhydrous copper sulfate, anhydrous sodium sulfate, anhydrous magnesium sulfate and calcium chloride, molecular sieves are used particularly preferably. The amount used is from 1 to 100 times, and preferably from 1 to 30 times as converted from their water retention and the theoretical amount of water formed. Although the reaction temperature is considered to be from 40° C. to 200° C., and preferably from 50° C. to 150° C., satisfactory results are obtained from 50° C. to 120° C. In addition, the reaction can also be carried out by directly adding the dehydrating agent to the reaction system. Examples of dehydrating agents include molecular sieves, inorganic dehydrating agents such as anhydrous calcium sulfate, anhydrous copper sulfate, anhydrous sodium sulfate, anhydrous magnesium sulfate and calcium chloride, and titanic compounds having dehydrating properties such as tetraisopropoxy titanium and titanium tetrachloride. In this case as well, the amount used is from 1 to 100 times, and preferably from 1 to 30 times as converted from their water retention and theoretical amount of water formed. Although the reaction temperature is considered to be from −80° C. to 100° C., satisfactory results are obtained from −30° C. to 50° C.

In the second step, the product of the first step is converted to the 6-N-alkyl-N-benzylamino form represented with general formula (XI) (wherein $R^1, R^{2'}, R^{4'}, R^{5'}, R^{6'}, R^{10'}$ and $R^{12'}$ are the same as previously defined) by reducing with a metal hydride reducing agent without isolating the iminium salt. Although the solvent used in the first step may continue to be used for the solvent of this reaction, favorable results are obtained by adding alcohol solvents such as methanol and ethanol, particularly preferably methanol. The reaction may naturally also be carried out by distilling off the reaction solvent in the first step and using only alcohol solvents such as methanol or ethanol. Metal hydride reducing agents that can be used to carry out the reaction are those which are relatively stable under conditions in which acid is present, examples of which include sodium borohydride, sodium cyanoborohydride, zinc borohydride, sodium triacetoxyborohydride, tetramethylammonium triacetoxyborohydride and borane-pyridine, with sodium cyanoborohydride being used particularly preferably. The reaction temperature is from −20° C. to 150° C., and preferably 0° C. to 120° C. The 6-N-alkyl-N-benzylamino form obtained here represented with general formula (XI) (wherein $R^1, R^{2'}, R^{4'}, R^{5'}, R^{6'}, R^{10'}$ and $R^{12'}$ are the same as previously defined) can also be obtained by carrying out the reductive amination process using a metal hydride reducing agent of Chart 2 while using a secondary amine. Moreover, if these processes are carried out using corresponding secondary amines, the compound of general formula (I-B) can also be obtained wherein A is —$NR^{12'}$—.

In the third step, a benzyl group is removed under hydrogenolytic conditions to form the 6β-amino form (IIaβ2). In this step, good results are obtained by either first converting the substrate to a salt using an inorganic acid such as hydrochloric acid, hydrobromic acid, sulfuric acid and phosphoric acid, a sulfonic acid such as methanesulfonic acid, p-toluenesulfonic acid and camphasulfonic acid, or an organic acid such as benzoic acid, acetic acid, oxalic acid and phthalic acid, and preferably hydrochloric acid or phthalic acid, or carrying out the reaction by adding suitable amounts of these acids. Since there are cases in which the resulting secondary amine salt can be purified as a crystal depending on the acid, selection of the acid is important. For example, in the case of a compound wherein $R^1$ is a cyclopropylmethyl group, $R^{2'}$, and $R^{10'}$ are hydroxy groups, $R^{12'}$ is a methyl group, $R^{5'}$ and $R^{6'}$ are collectively —O—, and $R^{4'}$ is a hydrogen atom, a crystalline salt that can be easily purified is obtained when phthalic acid is used for the acid. Although any solvent can be used for the reaction solvent provided it is inactive under conditions of hydrogenation, examples of which include alcohol solvents such as methanol and ethanol, ether solvents such as THF, ether, DME and dioxane, and aromatic hydrocarbon solvents such as benzene and toluene, alcohol solvents are used preferably and methanol is used particularly preferably. Although all metal catalysts can be used that are normally used in hydrogenation reactions, examples of which include platinum catalysts such as platinum oxide and platinum hydroxide, palladium catalysts such as palladium hydroxide and palladium—carbon, and nickel catalysts such as Raney nickel, a palladium catalyst, and particularly palladium—carbon, is used preferably. Although the reaction can be carried out at a reaction temperature from −30° C. to 80° C., and preferably from −10° C. to 50° C., and hydrogen pressure from 1 to 100 atmospheres, and preferably from 1 to 30 atmospheres, favorable results are usually obtained at room temperature and normal pressure.

Chart 3

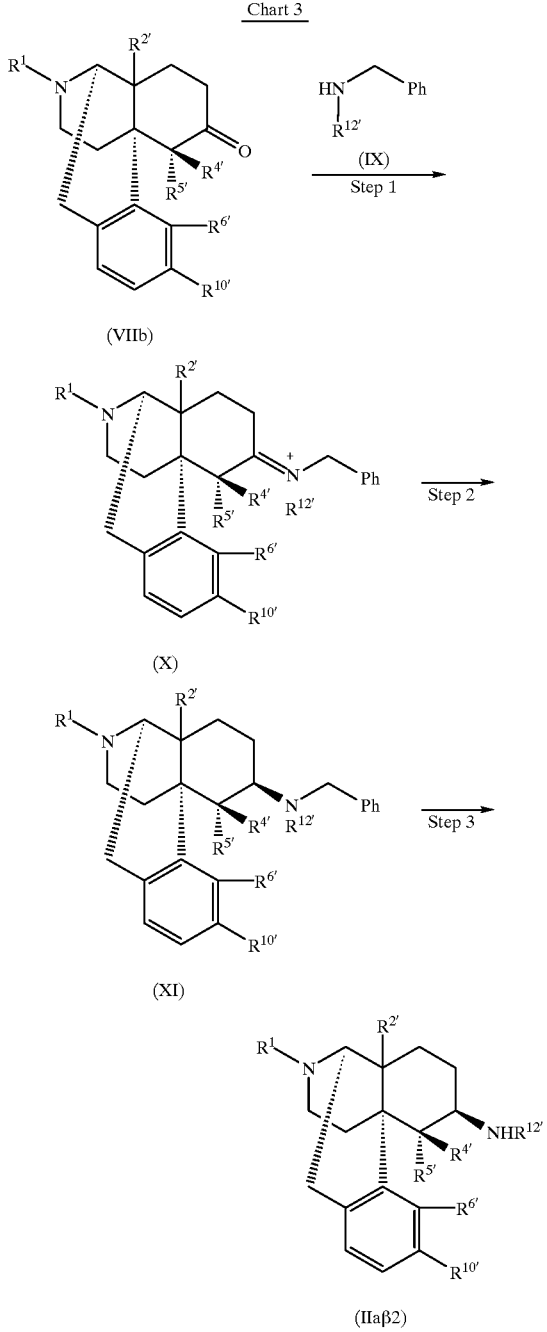

In addition, in the reductive amination reaction shown in Chart 2, a primary amino form can be obtained by using ammonium acetate instead of primary amine or using dibenzylamine in the process shown in Chart 3, or reducing with borane or under hydrogenation conditions after converting ketone into an oxime using the process described in the literature (J. Med. Chem., 27, 1727 (1984)). This primary amino form can be converted to a secondary amino form by going through two steps consisting of acylation and reduction, and this is useful as a different route for obtaining the secondary amino form. As shown in Chart 4, the 6α-hydroxy form represented with general formula (IIbα) (wherein $R^1$, $R^{2'}$, $R^{4'}$, $R^{5'}$, $R^{6'}$ and $R^{10'}$ are the same as previously defined) is obtained by either reducing the 6-keto form represented with general formula (VIIa) (wherein $R^1$, $R^{2'}$, $R^{4'}$, $R^{5'}$, $R^{6'}$ and $R^{10'}$ are the same as previously defined) with a metal hydride reducing agent or hydrogenating in the presence of acid and metal catalyst. Although examples of metal hydride reducing agents that are used include sodium borohydride, sodium cyanoborohydride, zinc borohydride, sodium triacetoxyborohydride, L-selectride and lithium aluminum hydride, sufficiently satisfactory results are obtained with sodium borohydride. Although examples of solvents that are used include alcohol solvents such as methanol and ethanol, and ether solvents such as THF, ether, DME and dioxane, alcohol solvents are used preferably and methanol is used particularly preferably. In the case of hydrogenation, although examples of solvents used preferably for the reaction solvent include alcohol solvents such as methanol and ethanol, and ether solvents such as THF, ether and dioxane, alcohol solvents are used preferably, while methanol is used particularly preferably. Although examples of the acid present include inorganic acids such as hydrochloric acid, hydrobromic acid, sulfuric acid and phosphoric acid, sulfonic acids such as methanesulfonic acid and p-toluenesulfonic acid, and organic acids such as benzoic acid, acetic acid and oxalic acid, hydrochloric acid is used preferably. Although all metal catalysts can be used that are normally used in hydrogenation reactions, examples of which include platinum catalysts such as platinum oxide and platinum hydroxide, palladium catalysts such as palladium hydroxide and palladium—carbon, and nickel catalysts such as Raney nickel, a platinum catalyst, and particularly platinum oxide, is used preferably. Although the reaction can be carried out at a reaction temperature from −30° C. to 80° C., and preferably from −10° C. to 50° C., and hydrogen pressure from 1 to 100 atmospheres, and preferably from 1 to 30 atmospheres, favorable results are usually obtained at room temperature and normal pressure.

Chart 4

As shown in Chart 5, the 6β-hydroxy form represented with general formula (IIbβ) (wherein $R^1$, $R^{2'}$, $R^{4'}$, $R^{5'}$, $R^{6'}$ and $R^{10'}$ are the same as previously defined) can be obtained by reacting the 6-keto form represented with general formula (VIIa) (wherein $R^1$, $R^{2'}$, $R^{4'}$, $R^{5'}$, $R^{6'}$ and $R^{10'}$ are the same as previously defined) with formamizine-sulfinic acid in the presence of base. Preferable examples of bases used include inorganic bases such as sodium hydroxide, potassium hydroxide, potassium carbonate and sodium bicarbonate, while sodium hydroxide is used particularly preferably. Although examples of reaction solvents used include water, alcohol solvents such as methanol and ethanol, and aprotic dipolar solvents such as DMF and DMSO, satisfactory results are usually obtained by using water. Although the reaction temperature is considered to be from 0° C. to 150° C., a temperature from 60° C. to 100° C. is preferable.

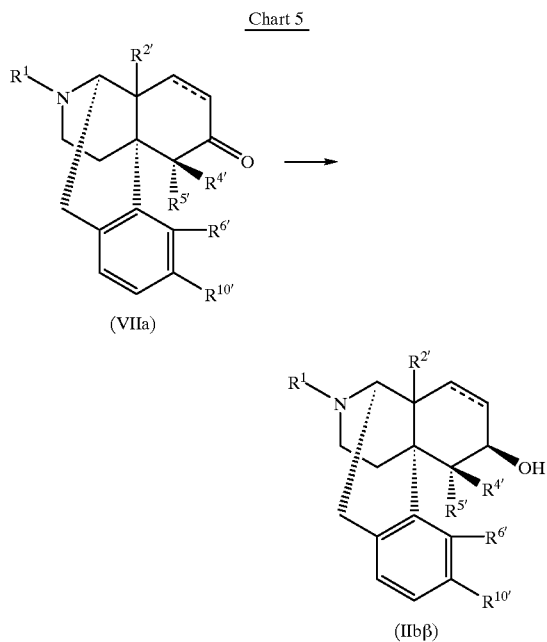

Chart 5

(VIIa)

(IIbβ)

Among the 6-amino forms or 6-hydroxy forms synthesized as shown above, the compound wherein $R^{10'}$ is a hydrogen atom in particular is obtained using a process similar to Charts 2, 3, 4 and 5 and using the 3-dehydroxy-6-keto form represented with general formula (VIIe) (wherein $R^1$, $R^{2'}$, $R^{4'}$, $R^{5'}$ and $R^{6'}$ are the same as previously defined, but excluding the case wherein $R^{6'}$ is a hydroxy group) for the starting material, which is obtained by using as substrate the 3-hydroxy-6-keto form represented with general formula (VIIc) (wherein $R^1$, $R^{2'}$, $R^{4'}$, $R^{5'}$ and $R^{6'}$ are the same as previously defined, but excluding the case wherein $R^{6'}$ is a hydroxy group) according to the scheme shown in Chart 6. In addition, the intermediate wherein $R^{10'}$ is a siloxy group is obtained using a process similar to Charts 2, 3, 4 and 5 and using for the starting material the 3-siloxy-6-keto form represented with general formula (VIIf) (wherein $R^1$, $R^{2'}$, $R^{4'}$, $R^{5'}$ and $R^{6'}$ are the same as previously defined, the case wherein $R^{6'}$ is a hydroxy group is excluded, and G represents an alkylsilyl group) which is obtained from the 3-hydroxy-6-keto form (VIIc) according to the scheme shown in Chart 7.

Namely, as shown in Chart 6, in the first step for obtaining the 3-dehydroxy-6-keto form represented with general formula (VIIe) (wherein $R^1$, $R^{2'}$, $R^{4'}$, $R^{5'}$ and $R^{6'}$ are the same as previously defined, but excluding the case wherein $R^{6'}$ is a hydroxy group), trifluoromethanesulfonic anhydride is allowed to act on phenolic hydroxyl groups in the presence of base to obtain the trifrate form represented with general formula (VIId) (wherein $R^1$, $R^{2'}$, $R^{4'}$, $R^{5'}$ and $R^{6'}$ are the same as previously defined, but excluding the case wherein $R^{6'}$ is a hydroxy group). Although examples of reaction solvents that can be considered include halogen solvents such as dichloromethane and chloroform, ether solvents such as THF, ether, DME and dioxane, and amines having large steric hindrance that can be used as solvents such as 2,6-lutidine and diisopropyl ethyl amine, halogen solvents are used preferably, while dichloromethane is used particularly preferably. Although examples of coexisting bases include tertiary amines such as triethyl amine, diisopropyl ethyl amine and proton sponge®, as well as pyridine, 2,6-lutidine and imidazole, 2,6-lutidine is used preferably. Although the reaction can be carried out at a temperature from −30° C. to 50° C., satisfactory results are usually obtained at a temperature from 0° C. to room temperature.

In the second step, the trifrate form is reduced with formic acid in the presence of phosphine ligand and base using a palladium catalyst. Although examples of solvents that are used include amines that can be used as solvents such as triethyl amine and diisopropyl ethyl amine, ether solvents such as THF, ether, DME and dioxane, aromatic hydrocarbon solvents such as toluene and benzene, alcohol solvents such as methanol and ethanol, and aprotic dipolar solvents such as DMF and DMSO, DMF is used particularly preferably. Although examples of palladium catalysts that are frequently used include zero-valency complexes such as tetrakis(triphenylphosphine)palladium and bis(benzylidenacetone)palladium, and bivalent complexes such as palladium acetate and palladium chloride, palladium acetate is used normally. Although examples of phosphine ligands used include monodentate phosphines such as trimethylphosphine, triethylphosphine, triphenylphosphine and tris(o-tolu)phosphine, and bidentate phosphines such as bis(diphenylphosphino)methane, 1,2-bis-(diphenylphosphino)ethane, 1,3-bis-(diphenylphosphino)propane and 1,1'-bis-diphenylphosphino ferrocene, 1,1'-bis-diphenylphosphino ferrocene is used particularly preferably. Although examples of coexisting bases include amines such as triethyl amine and diisopropyl ethyl amine, and inorganic salts such as silver carbonate, sodium acetate and potassium acetate, triethyl amine is used preferably. Although the reaction can be carried out at a temperature from 0° C. to 150° C., satisfactory results are usually obtained from room temperature to 80° C.

Chart 6

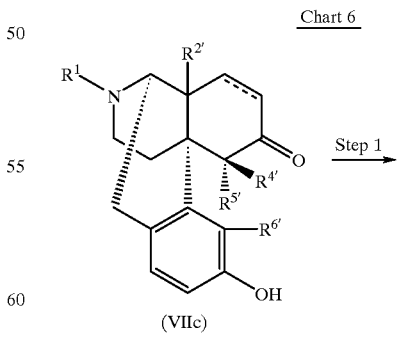

(VIIc)

Step 1

Chart 7

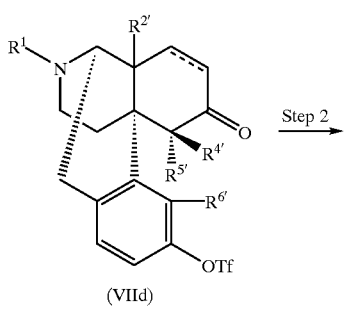

(VIId)

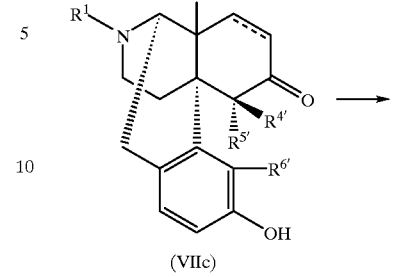

(VIIc)

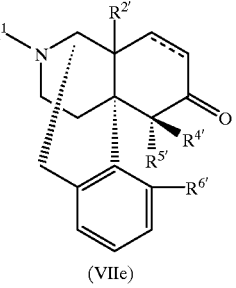

(VIIe)

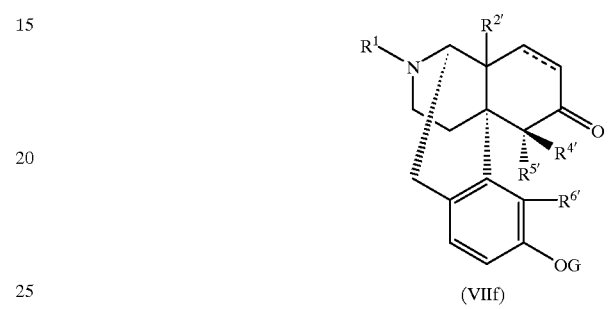

(VIIf)

As shown in Chart 7, in order to obtain the 3-siloxy-6-keto form represented with general formula (VIIf) (wherein $R^1$, $R^{2'}$, $R^{4'}$, $R^{5'}$ and $R^{6'}$ are the same as previously defined, the case wherein $R^{6'}$ is a hydroxy group is excluded, and G represents an alkylsilyl group), the 3-hydroxy-6-keto form represented with general formula (VIIc) (wherein $R^1$, $R^{2'}$, $R^{4'}$, $R^{5'}$ and $R^{6'}$ are the same as previously defined) should be reacted with silylchloride in the presence of base. Although examples of silyl chlorides include trimethylsilyl chloride, triphenylsilyl chloride, t-butyldimethylsilyl chloride and diphenylmethylsilyl chloride, t-butyldimethylsilyl chloride is used preferably. Although examples of bases that are used include tertiary amines such as triethyl amine, diisopropylethyl amine and proton sponge®, as well as pyridine, dimethylaminopyridine and imidazole, imidazole is used preferably. Although examples of reaction solvents include halogen solvents such as dichloromethane, chloroform, carbon tetrachloride and 1,2-dichloroethane, ether solvents such as ether, THF, DME and dioxane, and pyridine, dichloromethane is used preferably. The reaction can be carried out at a temperature from −80° C. to 100° C., and particularly preferably results are obtained in the vicinity of 0° C. to room temperature. Although the reaction can be carried out for 5 to 300 minutes, with respect to compounds wherein lines parallel to the solid and broken lines are single bonds and $R^{5'}$ and $R^{6'}$ collectively are —O— in particular, since there are cases in which the 6th position ketone group also ends up being enolsilylated as the reaction time is prolonged, a reaction time of 5 to 60 minutes is preferable.

As shown in Chart 8, compounds wherein X is $NR^{12'}$ can be obtained by condensing the 6-amino form obtained in the processes shown in Charts 2 and 3 and represented with general formula (IIa) (wherein $R^1$, $R^{2'}$, $R^{4'}$, $R^{5'}$, $R^{6'}$, $R^{10'}$ and $R^{12'}$ are the same as previously defined) with the carboxylic acid and carboxylic acid derivative represented with general formula (III) (wherein B and $R^{11'}$ are the same as previously defined), the formic acid derivative represented with general formula (IV) (wherein Z, B and $R^{11'}$ are the same as previously defined), the isocyanic acid and isothiocyanic acid derivative represented with general formula (V) (wherein B and $R^{11'}$ are the same as previously defined), or the sulfonic acid derivative represented with general formula (VI) (wherein B and $R^{11'}$ are the same as previously defined). Condensation with carboxylic acid derivative can be performed either by reacting the 6-amino form with acid chloride or acid anhydride that reacts in the presence of base, or by reacting with the carboxylic acid itself using N,N'-dicyclohexylcarbodiimide (DCC), 1,1'-carbonyldiimidazole or bis-(2-oxo-3-oxazolidinyl)phosphinic chloride (BOPCl). From 1 to 20 equivalents, and preferably from 1 to 5 equivalents, of acid chloride or acid anhydride are used. Although examples of reaction solvents that are used include halogen solvents such as dichloromethane, chloroform, carbon tetrachloride and 1,2-dichloroethane, ether solvents such as ether, THF, DME and dioxane, pyridine, water or a mixed solvent of the above, chloroform or a mixed solvent of THF and water is used particularly preferably when using acid chloride, while pyridine is used particularly preferably as both base and solvent in the case of using acid anhydride.

Although examples of bases that are used include tertiary amines such as triethyl amine, diisopropylethyl amine and proton sponge, organic bases such as pyridine, dimethylaminopyridine and imidazole, and inorganic bases such as potassium carbonate, sodium carbonate, sodium bicarbonate, sodium hydroxide and potassium hydroxide, satisfactory results are usually obtained using from 1 to 20 equivalents, and preferably from 1 to 5 equivalents, of triethyl amine when using chloroform as the solvent, and from 1 to 20 equivalents, and preferably from 1 to 5 equivalents, of potassium carbonate, sodium carbonate or sodium bicarbonate in the case of using a mixed solvent of THF and water. The reaction can be carried out over a range of −80° C. to 100° C., and particularly preferable results are obtained from 0° C. to room temperature. In the case of using DCC for the condensing agent, from 1 to 20 equivalents, and preferably from 1 to 5 equivalents, are used. Although examples of reaction solvents used include halogen solvents such as dichloromethane, chloroform, carbon tetrachloride and 1,2-dichloroethane, and ether solvents such as ether, THF, DME and dioxane, dichloromethane and chloroform are used particularly preferably. Although examples of bases present in the reaction include tertiary amines such as triethyl amine, diisopropylethyl amine and proton sponge, and organic bases such as pyridine, dimethylaminopyridine and imidazole, from 0.01 to 2 equivalents of dimethylaminopyridine is used particularly preferably. Although the reaction can be carried out over a range of −80° C. to 100° C., particularly preferable results are obtained in the vicinity of 0° C. to room temperature. In the case of using 1,1'-carbonyldiimidazole for the condensing agent, from 1 to 20 equivalents, and preferably from 1 to 5 equivalents, are used. Although examples of reaction solvents that are used include ether solvents such as ether, THF, DME and dioxane, and halogen solvents such as dichloromethane, chloroform, carbon tetrachloride and 1,2-dichloroethane, THF is used particularly preferably. Although the reaction can be carried out over a range of −20° C. to 120° C., a temperature in the vicinity of room temperature to 100° C. is particularly preferable. In the case of using BOPCl for the condensing agent, from 1 to 20 equivalents, and preferably from 1 to 5 equivalents, are used. Although examples of reaction solvents that are used include halogen solvents such as dichloromethane, chloroform, carbon tetrachloride and 1,2-dichloroethane, and ether solvents such as ether, THF, DME and dioxane, dichloromethane and chloroform are used preferably. Although examples of base present in the reaction include tertiary amines such as triethyl amine, diisopropylethyl amine, proton sponge and N-ethylpiperidine, and organic bases such as pyridine, dimethylaminopyridine and imidazole, from 1 to 20 equivalents, and preferably from 1 to 5 equivalents of N-ethylpiperidine is used particularly preferably. Although the reaction can be carried out over a range of −80° C. to 100° C., particularly preferable results are obtained at a temperature from 0° C. to 50° C.

Condensation with formic acid can be performed by reacting the 6-amino form with from 1 to 20 equivalents, and preferably from 1 to 5 equivalents, of corresponding acid chloride in the presence of base. Although examples of reaction solvents that are used include halogen solvents such as dichloromethane, chloroform, carbon tetrachloride and 1,2-dichloroethane, ether solvents such as ether, THF, DME and dioxane, pyridine, water, as well as mixed solvents of these, chloroform or a mixed solvent of THF and water is used particularly preferably. Although examples of bases that are used include tertiary amines such as triethyl amine, diisopropylethyl amine and proton sponge, organic bases such as pyridine, dimethylaminopyridine and imidazole, and inorganic bases such as potassium carbonate, sodium carbonate and sodium bicarbonate, satisfactory results are usually obtained by using from 1 to 20 equivalents, and preferably from 1 to 5 equivalents, of triethyl amine when using chloroform for the solvent, and from 1 to 20 equivalents, and preferably from 1 to 5 equivalents, or potassium carbonate, sodium carbonate or sodium bicarbonate in the case of a mixed solvent of THF and water. Although the reaction can be carried out over a range of −80° C. to 100° C., particularly preferable results are obtained in the vicinity of 0° C. to room temperature.

Condensation with isocyanic acid or isothiocyanic acid derivative can be performed by allowing from 1 to 20 equivalents, and preferably from 1 to 5 equivalents, of the corresponding isocyanate to act on the 6-amino form. Although examples of reaction solvents that are used include halogen solvents such as dichloromethane, chloroform, carbon tetrachloride and 1,2-dichloroethane, and ether solvents such as ether, THF, DME and dioxane, chloroform is used particularly preferably. Although the reaction can be carried out over a range of −80° C. to 100° C., particularly preferable results are obtained in the vicinity of 0° C. to room temperature.

Condensation with sulfonic acid derivative can be performed by allowing from 1 to 20 equivalents, and preferably from 1 to 5 equivalents, of the corresponding sulfonyl chloride to act on the 6-amino form. Although examples of bases that are used include tertiary amines such as triethyl amine, diisopropylethyl amine and proton sponge, as well as pyridine, dimethylaminopyridine and imidazole, while examples of reaction solvents that are used include halogen solvents such as dichloromethane, chloroform, carbon tetrachloride and 1,2-dichloroethane, ether solvents such as ether, THF, DME and dioxane, as well as pyridine, pyridine is used particularly preferably as both base and solvent. Although the reaction can be carried out over a range of −80° C. to 100° C., particularly preferable results are obtained in the vicinity of 0° C. to room temperature.

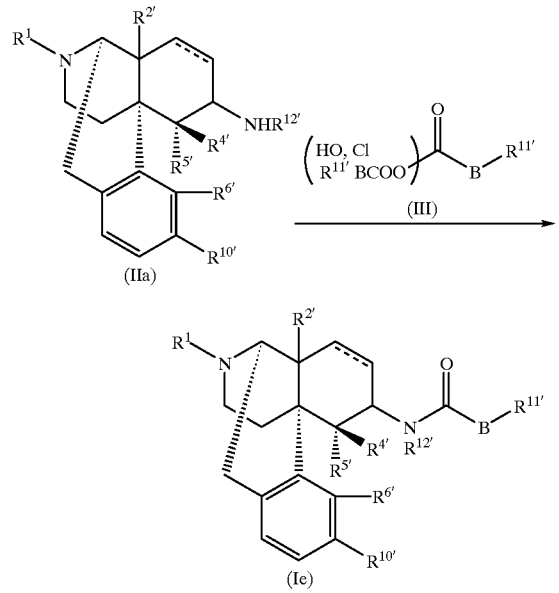

Chart 8

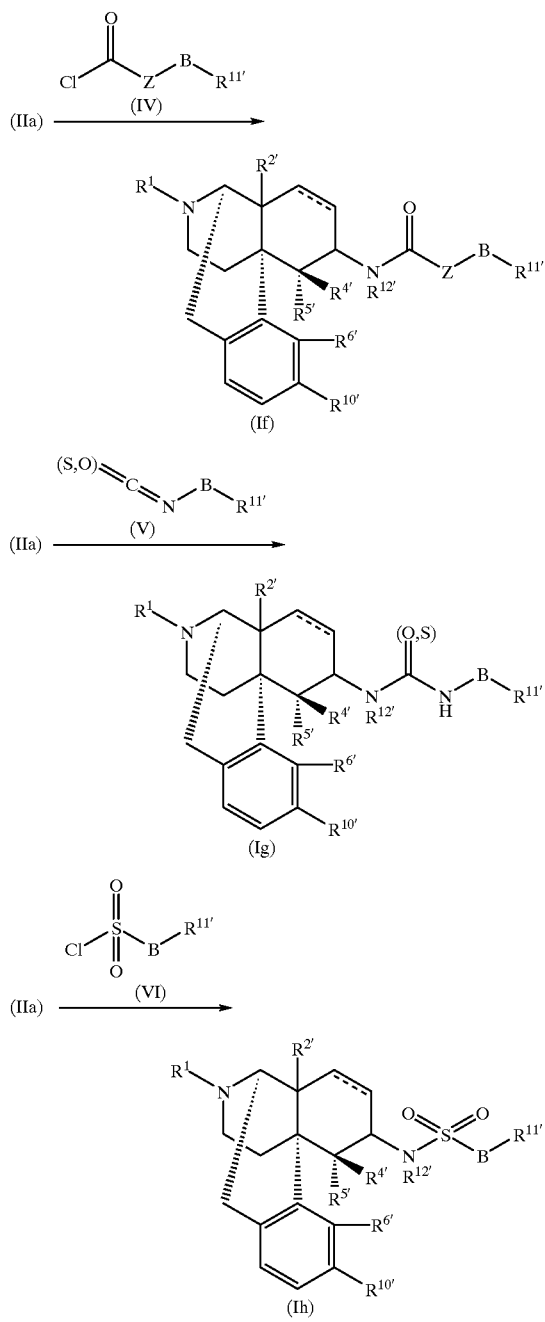

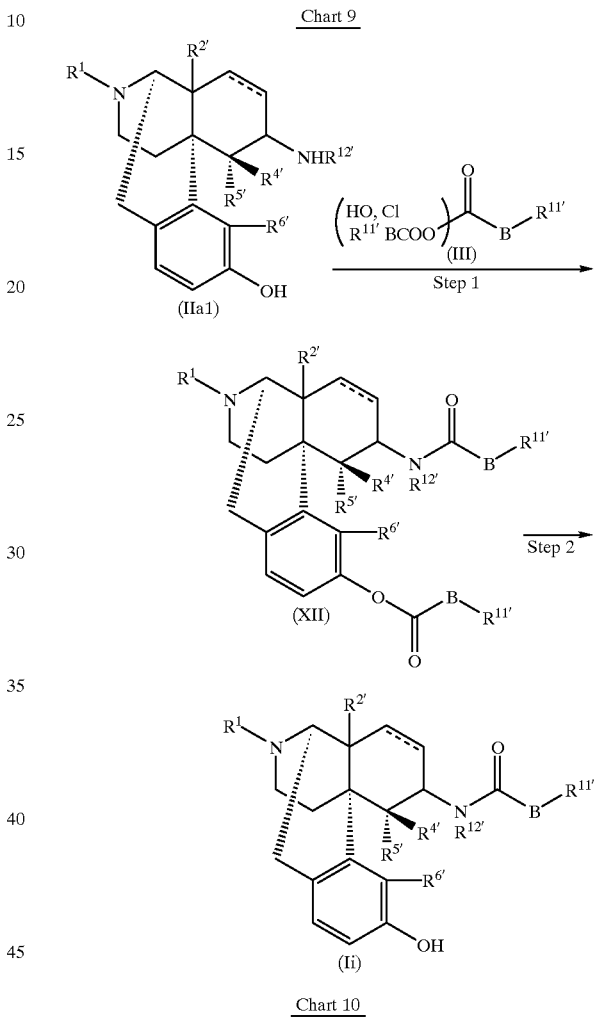

carbonate, sodium carbonate, sodium bicarbonate, sodium hydroxide and potassium hydroxide, normally from 1 to 20 equivalents, and preferably from 1 to 10 equivalents, of potassium carbonate or sodium hydroxide are used. Although the reaction can be carried out over a range of −80° C. to 100° C., particularly preferably results are obtained at a temperature of from 0° C. to 50° C.

Since there are cases in which phenolic hydroxyl groups may react at the same time, particularly in the case of compounds wherein $R^{10'}$ is a hydroxy group, in the case of carboxylic acid derivatives, formic acid derivatives, and isocyanic acid or isothiocyanic acid derivatives, after performing the first step in the same manner as Chart 8, the target compound can be obtained by performing alkaline treatment for the second step as shown in Charts 9 through 11. Although examples of reaction solvents used in the second step include water, alcohol solvents such as methanol and ethanol, ether solvents such as ether, THF, DME and dioxane, or mixed solvents of these, when solubility is insufficient, halogen solvents such as dichloromethane and chloroform can be suitably added. Although examples of bases used include inorganic bases such as potassium

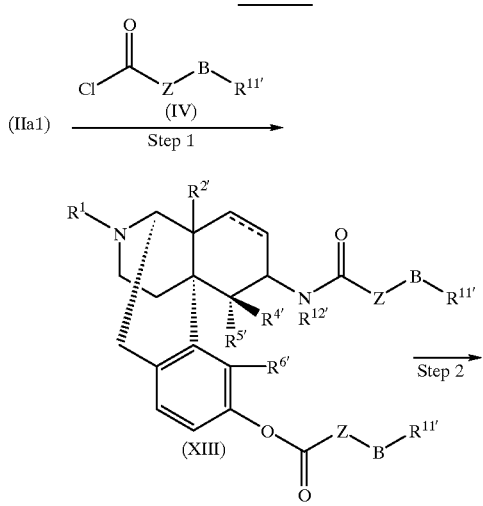

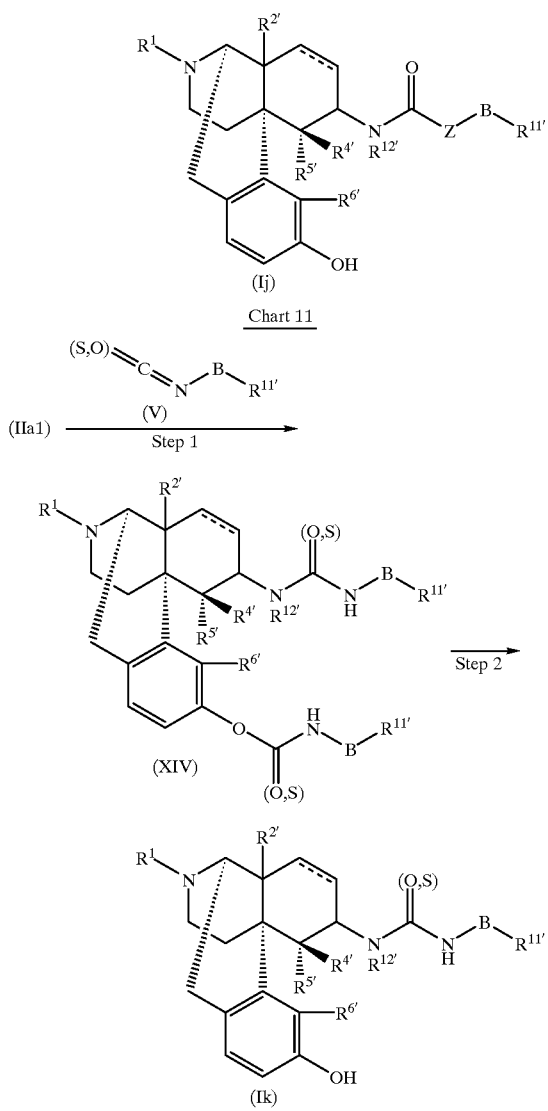

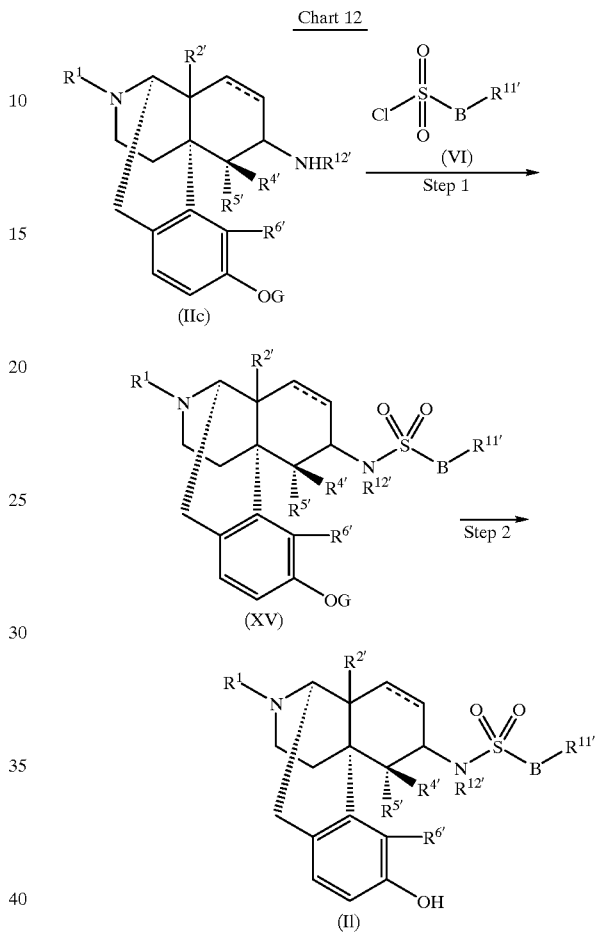

When condensing a compound wherein $R^{10'}$ is a hydroxy group with a sulfonic acid derivative, preferable results are obtained by using the 3-siloxy-6-amino form represented with general formula (IIc) (wherein $R^1, R^{2'}, R^{4'}, R^{5'}, R^{6'}, R^{12'}$ and G are the same as previously defined) in which phenolic hydroxyl groups have been protected in advance with silylether as shown in Chart 12. The following process can naturally also be applied to condensation with carboxylic acid derivatives, formic acid derivatives, and isocyanic acid or isothiocyanic acid derivatives. Namely, after performing the first step in the same manner as Chart 8, the silyl group is removed. Although a quaternary ammonium salt such as tetrabutylammonium fluoride, tetrabutylammonium chloride or pyridinium hydrofluoride, or acid such as acetic acid, hydrochloric acid, sulfuric acid or hydrofluoric acid is used for removal of the silyl group in the second step, normally from 1 to 20 equivalents, and preferably from 1 to 5 equivalents, of tetrabutylammonium fluoride are used. Although examples of solvents used include ether solvents such as THF, ether, DME and dioxane, halogen solvents such as dichloromethane and chloroform, and acetonitrile, THF is used particularly preferably. Although the reaction can be performed at a temperature from −20° C. to 100° C., satisfactory results are usually obtained at room temperature.

In addition, the 6-amino form represented with general formula (Im) in which A' is —$NR^{12'}$— (wherein $R^1, R^{2'}, R^{4'}, R^{5'}, B, R^{6'}, R^{10'}, R^{11'}$ and $R^{12'}$ are the same as previously defined) is obtained by reducing the amido form represented with general formula (Ie') (wherein $R^1, R^{2'}, R^{4'}, R^{5'}, R^{6'}, R^{10'}, R^{11'}, R^{12'}$ and B are the same as previously defined) using metal hydride catalyst as shown in Chart 13. Examples of reducing agents used include metal hydride compounds having powerful reducing ability such as lithium aluminum hydride, diisobutyl aluminum hydride, aluminum hydride, lithium borohydride and diborane, with from 1 to 20 equivalents, and preferably from 1 to 5 equivalents, of diborane used particularly preferably. Although examples of solvents used preferably when using lithium aluminum hydride, lithium borohydride or diborane include ether solvents such as THF, DME, ether and dioxane, THF is used particularly preferably. When using diisobutyl aluminum hydride or aluminum hydride, aromatic hydrocarbon solvents such as benzene and toluene are used preferably. Although the reaction can be carried out over a range of −40° C. to 100° C., a temperature in the vicinity of 0° C. to room temperature is particularly preferable.

Chart 13

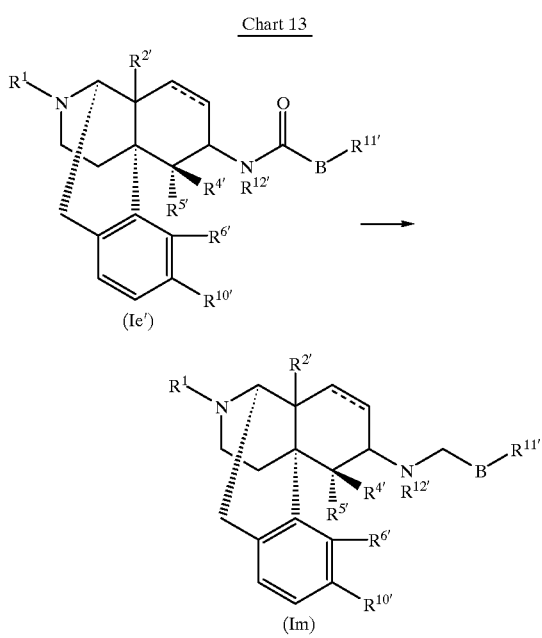

Compounds in which X is O can be obtained by condensing the 6-hydroxy form obtained in Charts 4 and 5 and represented with general formula (IIb) (wherein $R^1$, $R^{2'}$, $R^{4'}$, $R^{5'}$, $R^{6'}$ and $R^{10'}$ are the same as previously defined) with carboxylic acid derivative (III), formic acid derivative (IV), isocyanic acid or isothiocyanic acid derivative (V) or sulfonic acid derivative (VI) as shown in Chart 14.

Condensation with carboxylic acid derivatives can be performed by reacting the 6-hydroxy form with from 1 to 20 equivalents, and preferably from 1 to 5 equivalents, of the corresponding acid chloride or acid anhydride in the presence of base. Although examples of reaction solvents that can be used include halogen solvents such as dichloromethane, chloroform, carbon tetrachloride and 1,2-dichloroethane, ether solvents such as ether, THF, DME and dioxane, and pyridine, chloroform is used particularly preferably when using an acid chloride, while pyridine is used particularly preferably as both base and solvent when using an acid anhydride. Although examples of bases used include tertiary amines such as triethyl amine, diisopropylethyl amine and proton sponge, as well as pyridine, dimethylaminopyridine and imidazole, satisfactory results are usually obtained by combining the use of from 1 to 20 equivalents, and preferably from 1 to 5 equivalents, of diisopropylethyl amine and dimethylaminopyridine. Although the reaction can be carried out over a range of −80° C. to 100° C., particularly preferable results are obtained at a temperature in the vicinity of room temperature to 80° C.

Condensation with formic acid derivatives can be performed by reacting the 6-hydroxy form with from 1 to 20 equivalents, and preferably from 1 to 5 equivalents, of the corresponding acid chloride in the presence of base. Although examples of reaction solvents used include halogen solvents such as dichloromethane, chloroform, carbon tetrachloride and 1,2-dichloroethane, and ether solvents such as ether, THF, DME and dioxane, chloroform and carbon tetrachloride are used particularly preferably. Although examples of bases used include tertiary amines such as triethyl amine, diisopropylethyl amine and proton sponge, as well as pyridine, dimethylaminopyridine and imidazole, satisfactory results are usually obtained by combining the use of from 1 to 20 equivalents, and preferably from 1 to 5 equivalents, of diisopropylethyl amine and dimethylaminopyridine. Although the reaction can be carried out over a range of −80° C. to 100° C., particularly preferable results are obtained at a temperature in the vicinity of room temperature to 80° C.

Condensation with isocyanic acid or isothiocyanic acid derivatives can be performed by allowing from 1 to 20 equivalents, and preferably from 1 to 5 equivalents, of the corresponding isocyanate to act on the 6-hydroxy form. Although examples of reaction solvents used include halogen solvents such as dichloromethane, chloroform, carbon tetrachloride and 1,2-dichloroethane, and ether solvents such as ether, THF, DME and dioxane, chloroform is used particularly preferably. Although the reaction can be carried out over a range of −80° C. to 100° C., particularly referable results are obtained at a temperature in the vicinity of room temperature to 80° C.

Condensation with sulfonic acid derivatives can be performed by allowing from 1 to 20 equivalents, and preferably from 1 to 5 equivalents, of the corresponding sulfonyl chloride to act on the 6-hydroxy form in the presence of base. Although examples of bases that are used include tertiary amines such as triethyl amine, diisopropylethyl amine and proton sponge, as well as pyridine, dimethylaminopyridine and imidazole, while examples of reaction solvents that are used include halogen solvents such as dichloromethane, chloroform, carbon tetrachloride and 1,2-dichloroethane, ether solvents such as ether, THF, DME and dioxane, as well as pyridine, pyridine is used particularly preferably as both base and solvent. Although the reaction can be carried out over a range of −80° C. to 100° C., particularly preferable results are obtained in the vicinity of room temperature to 80° C.

Chart 14

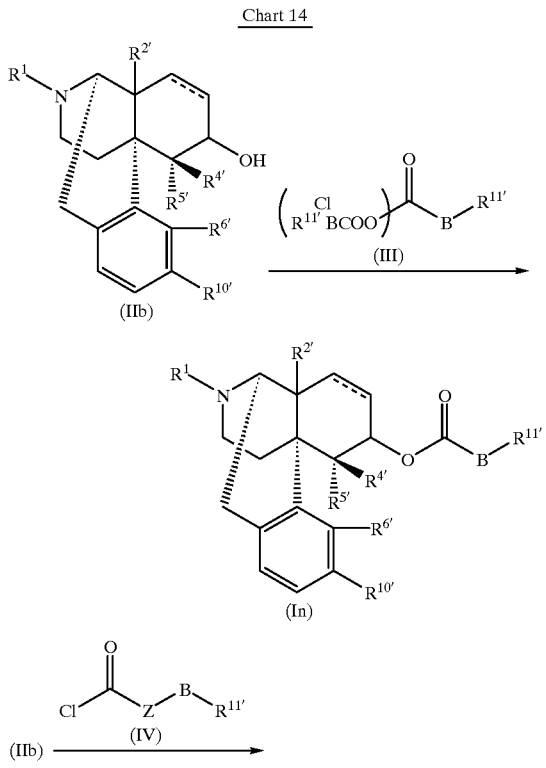

145

-continued

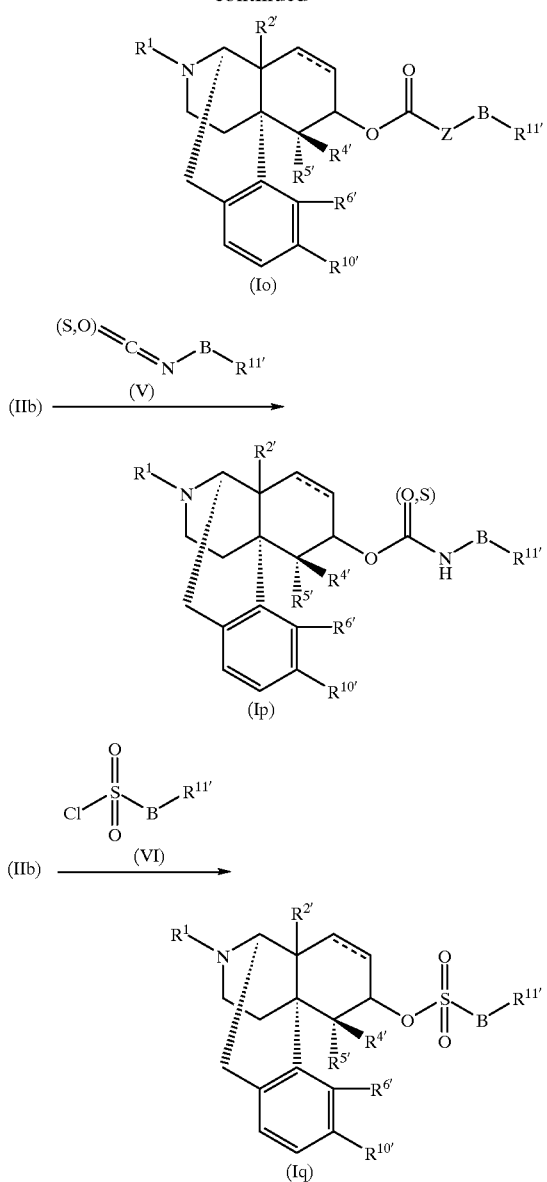

146

C. to 50° C. However, since solvolysis may also proceed at the 6th position, this can be accommodated by either lowering the reaction temperature or shortening reaction time.

Chart 15

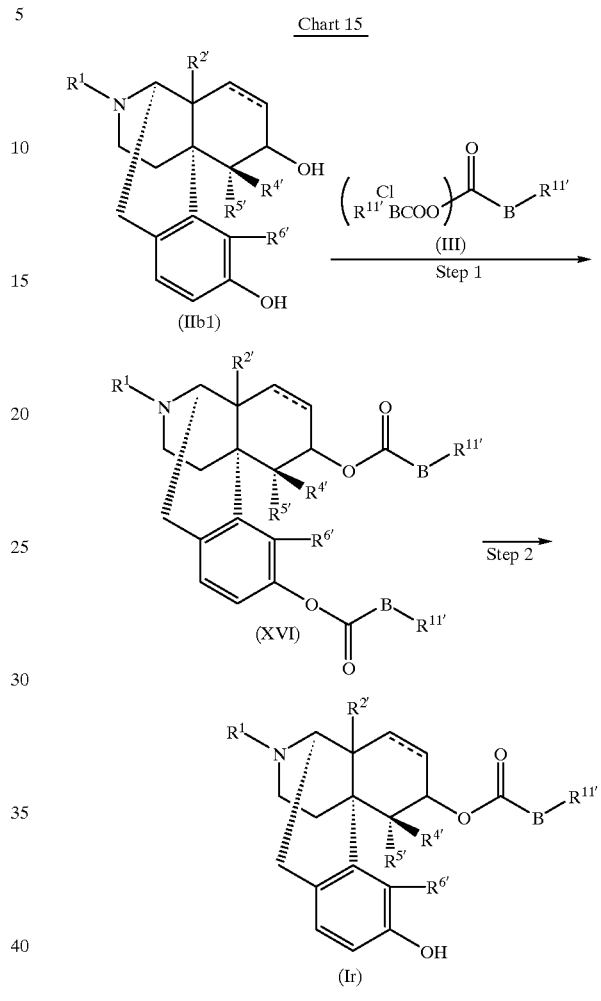

Since there are cases in which phenolic hydroxyl groups react at the same time, particularly in the case of compounds wherein $R^{10'}$ is a hydroxy group, in the case of carboxylic acid derivatives, formic acid derivatives, and isocyanic acid or isothiocyanic acid derivatives, after performing the condensation reaction of the first step in the same manner as Chart 14, the target compound can be obtained by performing alkaline treatment for the second step as shown in Charts 15 through 17. Although examples of reaction solvents used in the second step include water, and alcohol solvents such as methanol and ethanol, when solubility is insufficient, halogen solvents such as dichloromethane and chloroform can be suitably added. Although examples of bases used include inorganic bases such as potassium carbonate, sodium carbonate, sodium bicarbonate, potassium carbonate is normally used preferably. Although the reaction can be carried out over a range of –80° C. to 100° C., particularly preferably results are obtained at a temperature of from –20°

Chart 16

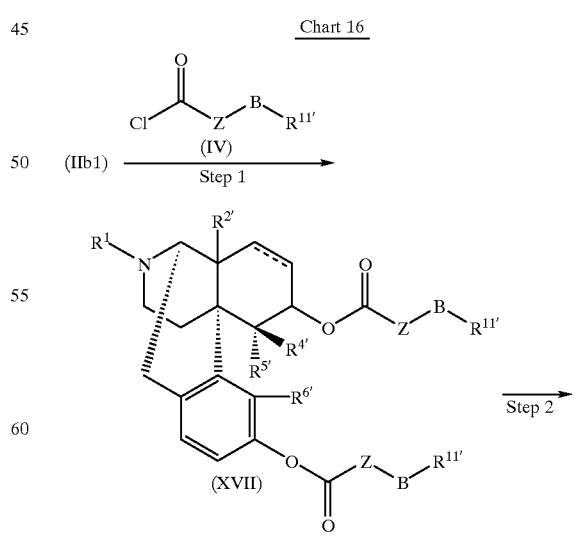

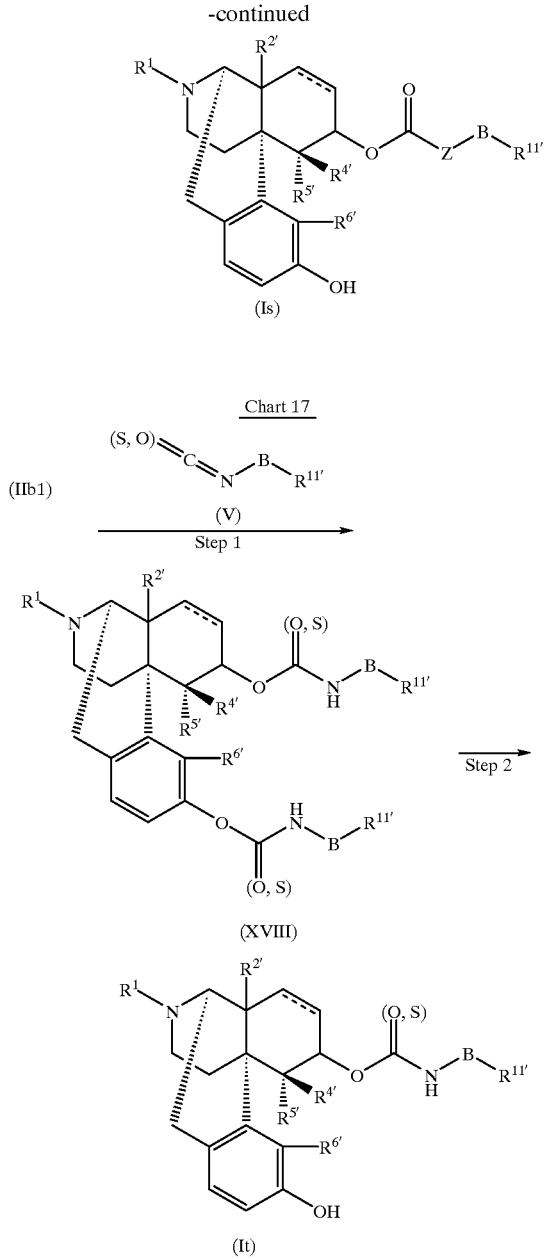

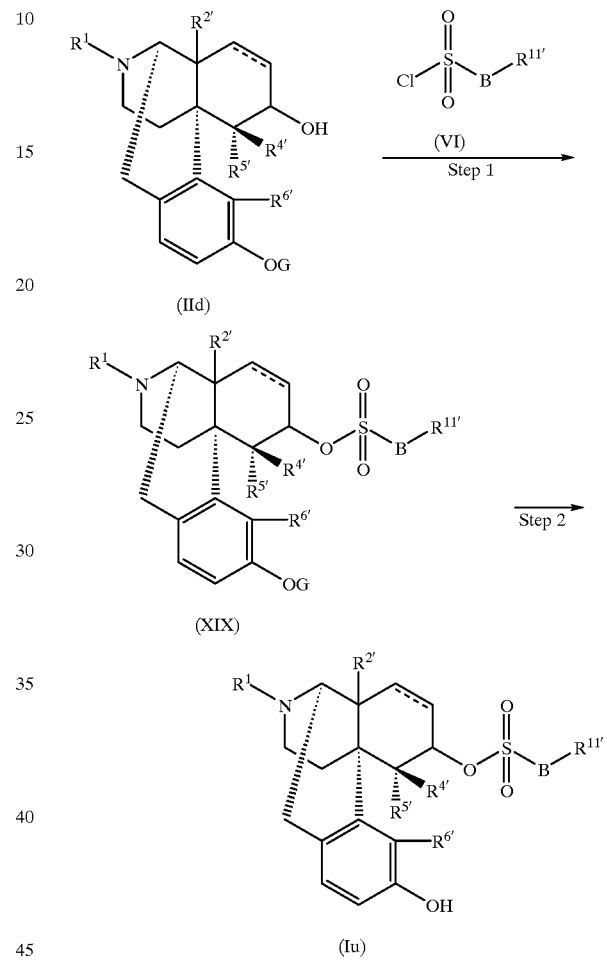

ride are used. Although examples of solvents used include ether solvents such as THF, DME and dioxane, acetonitrile, and halogen solvents such as dichloromethane and chloroform, THF is used particularly preferably. Although the reaction can be performed at a temperature from −20° C. to 100° C., satisfactory results are usually obtained at room temperature.

In the case of condensation with a sulfonic acid derivative, preferable results are obtained by using the 3-siloxy-6-hydroxy form represented with general formula (IId) (wherein $R^1$, $R^{2'}$, $R^{4'}$, $R^{5'}$, $R^{6'}$ and G are the same as previously defined) in which phenolic hydroxyl groups have been protected in advance with silylether and so forth as shown in Chart 18. This process can naturally also be carried out in the same manner for condensation with carboxylic acid derivatives, formic acid derivatives, and isocyanic acid or isothiocyanic acid derivatives. After performing the first step of condensation in the same manner as Chart 14, the silyl group is removed in the second step. Although a quaternary ammonium salt such as tetrabutylammonium fluoride, tetrabutylammonium chloride or pyridinium hydrofluoride, or acid such as acetic acid, hydrochloric acid, sulfuric acid or hydrofluoric acid is used for removal of the silyl group, normally from 1 to 20 equivalents, and preferably from 1 to 5 equivalents, of tetrabutylammonium fluo- The free base obtained in the above steps can specifically be converted into a salt with a pharmacologically acceptable acid using the process indicated below. Namely, after dissolving or suspending the resulting free base in solvent and adding acid, either the precipitated solid or crystal is obtained by filtration, or in the case of not precipitating, the resulting salt is settled by addition of solvent of lower polarity or substituted with a solvent of lower polarity followed by obtaining by filtration. Alternatively, after forming the salt as described above, the salt can be obtained by concentration. However, in the case organic solvent remains in these processes, the residual solvent can also be removed under reduced pressure after freeze-drying as an aqueous solution. Although examples of solvents used for dissolution or suspension include water, alcohol solvents such as methanol, ethanol and isopropyl alcohol, halogen solvents such as dichloromethane and chloroform, ether solvents such as ether, THF, DME and dioxane, ester solvents such as ethyl acetate and methyl acetate, or mixed solvents of these, methanol, ethanol, isopropyl alcohol, ethyl acetate, chloroform, chloroform-methanol, water-methanol and water-ethanol are used preferably. Preferable examples of solvents used for precipitating the solid include ether and ethyl acetate. Although it is desirable to add acid to match the equivalent as much as possible, in cases in which the resulting salt is washed and the excess acid can be removed, from 1 to 10 equivalents may be used. In addition, the acid may be added directly or added after suitably dissolving in the above-mentioned solvents. For example, hydrochloric acid can be added in the form of concentrated hydrochloric acid, a 1 N aqueous solution, a saturated methanol solution or a saturated ethyl acetate solution, while tartaric acid can be added in the form of a solid, aqueous solution or methanol solution. During salt formation, since the temperature of the system may rise due to the heat of neutralization, there are cases in which preferable results are obtained by cooling with a water bath or ice bath.

As a result of both in vitro and in vivo pharmacological studies, the compounds of the present invention represented with general formula (I) were found to possess strong analgesic activity, diuretic activity, antitussive activity as an opioid κ-agonist. It thus became clear that said compounds can be expected to be useful analgesics, diuretics and antitussives. In addition, based on their properties of being κ-agonists, they can also be used as hypotensives and sedatives. Moreover, it was also found that selective agonists for δ receptors are also included in the compounds of the present invention, thus suggesting their possible use as immunostimulator and anti-HIV drugs. On the other hand, since these compounds also demonstrate excellent defensive effects against cerebral nerve cell necrosis, they can also be used as cerebro-neuroprotective agents for prevention and treatment of ischemic brain damage and dementia based on damage to cerebral nerve cells.

More specifically, the compounds of the present invention are useful in pharmaceutical fields as preventive and therapeutic agents for post-operative pain, carcinomatous pain and other broad-ranging, general pain, hypertension, edema and promotion of urination during gestosis, various types of respiratory diseases such as colds, acute bronchitis, chronic bronchitis, bronchiectasis, pneumonia, pulmonary tuberculosis, silicosis and silicotic tuberculosis, lung cancer, upper respiratory tract diseases (pharyngitis, laryngitis, nasal catarrh), asthmatic bronchitis, bronchial asthma, infantile asthma, (chronic) pulmonary emphysema, pneumoconiosis, fibroid lung, silicosis, pulmonary suppuration, pleurisy, tonsillitis, tussive urticaria and pertussis, suppression of coughing during bronchography and accompanying bronchoscopic examinations, and as preventive and therapeutic agent for cerebrovascular diseases such as cerebral hemorrhage, stroke, cerebral infarction and subarachnoid hemorrhage; as preventive and therapeutic agents for sequela based on these cerebral nerve cell disorders (consciousness disorders, motor paralysis, language disorders, sensory disorders, mental disorders and memory disorders); as preventive and therapeutic agents for neural diseases such as hypoxia, hypoglycemia, cerebral palsy, cerebral ischemic stroke and Huntington's chorea; as preventive and therapeutic agents for cerebroneural function diseases such as senile dementia, Alzheimer's dementia, amnesia and cerebroneural disorders; suppression of activated oxygen disorders; and as preventive and therapeutic agents for degenerative nerve diseases such as epilepsy, depression and Parkinson's disease.

When the analgesic, diuretic, antitussive or cerebro-neuroprotective agents of the present invention is used clinically, it may be in the form of a free base or its salt. In addition, it may also be suitably mixed with stabilizers, buffers, diluents, isotonics, antiseptics and other vehicles. Examples of administrative forms include injection preparations; oral preparations such as tablets, capsules, granules, powders and syrups; transrectal administration by suppositories; or local administration by ointments, creams and compresses. It is desirable that the analgesic, diuretic, antitussive and cerebro-neuroprotective agents of the present invention contain from 1% to 90% by weight, and preferably from 30% to 70% by weight, of the above-mentioned active ingredients. Although the dose should be suitably selected according to symptoms, age, body weight and administration method, the normal adult dose is from 0.0001 mg to 1 g per day as the amount of active ingredient in the case of injection preparations, and from 0.005 mg to 10 g in the case of oral preparations, each administered in a single dosing or divided among several dosings.

EXAMPLES

Although the following provides an explanation of the present invention in the form of the specific examples described below, the present invention is not limited to these examples.

Reference Example 1

N-Acetylbenzylamine 10 g of benzylamine was dissolved in 200 ml of methylene chloride followed by the addition of 26 ml of triethylamine and dropwise addition of 7.3 ml of acetyl chloride at 0° C. After stirring for 1 hour at room temperature, 2 ml of methanol was added to the reaction system at 0° C. followed by 120 ml of water and separation of the phases. The aqueous layer was extracted with 100 ml of chloroform, and the resulting organic layer was concentrated after drying with anhydrous sodium sulfate to obtain 8.55 g of the target compound (yield: 61%).

NMR (90 MHz, CDCl$_3$)

δ 1.9 (3H, s), 4.3 (2H, d, J=4.8 Hz), 6.8 (1H, br s), 7.3 (5H, s).

IR (liquid film method)

υ 3296, 1649, 1543, 1499, 1377, 1359, 1284, 1077, 1033 cm$^{-1}$

Reference Example 2

N-Benzylethylamine 2.96 g of the N-acetylbenzylamine obtained in reference example 1 was dissolved in 45 ml of anhydrous tetrahydrofuran followed by the addition of 1.73 g of lithium aluminum hydride at 0° C. After stirring for 2 hours at room temperature, the reaction mixture was refluxed while heating for 2 hours. After cooling the reaction mixture to 0° C., 22.8 g of sodium fluoride was added followed by dropwise addition of 91 ml of 10% aqueous tetrahydrofuran and stirred for 1 hour at room temperature. The precipitate was removed using Celite and the filtrate was concentrated to obtain 2.5 g of the target compound in liquid form (yield: 93%).

NMR (90 MHz, CDCl$_3$)

δ 1.10 (3H, t, J=7.3 Hz), 1.4 (1H, brs), 2.65 (2H, q, J=7.3 Hz), 3.75 (2H, s), 7.15–7.4 (5H, m).

Reference Example 3

3-tert-butyldimethylsilyloxy-17-cyclopropylmethyl-4,5α-epoxy-14β-hydroxy-6-oxomorphinan 2

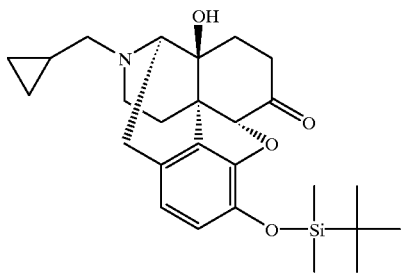

3.49 g of naltrexone hydrochloride was suspended in 10.5 ml of N,N-dimethylformamide. After adding 3.46 g of imidazole, 3.48 g of tert-butyldimethylchlorosilane was added followed by stirring for 35 minutes at room temperature. 30 ml of water and 50 ml of diethyl ether were added to the reaction system followed by separation. The aqueous layer was extracted twice with 30 ml of diethyl ether. The combined extracts were dried over anhydrous sodium sulfate and concentrated. The resulting residue was recrystallized from ethanol to obtain 3.2 g of the target compound (yield: 76%).

NMR (90 MHz, CDCl$_3$)

δ 0.0–1.2 (5H, m), 0.2 (3H, s), 0.3 (3H, s), 1.0 (9H, s), 1.3–2.0 (3H, m), 2.0–3.2 (8H, m), 2.4 (2H, d, J=4.4 Hz), 4.60 (1H, s), 6.5 (1H, d, J=6.4 Hz), 6.6 (1H, d, J=6.4 Hz).

Reference Example 4

3-Dehydroxynaltrexone 3

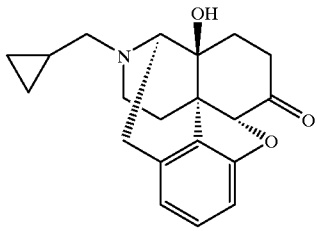

Naltrexone (5 g) was dissolved in dichloromethane (50 ml) followed by the addition of 2,6-lutidine (2.56 ml) and anhydrous trifluoromethanesulfonic acid (2.96 ml) at 0° C. After reacting for 15 minutes at the same temperature, distilled water (40 ml) and saturated aqueous sodium bicarbonate (20 ml) were added followed by extraction with chloroform (20+30 ml). After washing with saturated brine, the extracts was dried with anhydrous sodium sulfate and the solvent was distilled off. Ether (20 ml) was added and the precipitating solid was filtered out using Celite followed by initial purification with silica gel column chromatography (Merk 7734, 300 g; chloroform→1% methanol/chloroform).

The initially purified product was dissolved in anhydrous DMF (25 ml) and reacted with triethylamine (5.9 ml), palladium acetate (0.06 g), DPPF (0.16 g) and formic acid (1.1 ml) for 15 minutes at 60° C. After distilling off the solvent, saturated aqueous sodium bicarbonate (20 ml) and distilled water (10 ml) were added followed by extraction with chloroform (30 ml×2). After washing with saturated brine and drying with anhydrous sodium sulfate, the solvent was distilled off and the resulting black oily substance was purified with silica gel column chromatography (Merk 7734, 300 g; chloroform) to obtain the target compound (3.32 g, yield: 62%).

NMR (400 MHz, CDCl$_3$)

δ 0.26 (2H, m), 0.57 (2H, m), 0.88 (1H, m), 1.54 (1H, dd, J=12.7, 2.0 Hz), 1.63 (1H, dt, J=14.7, 3.9 Hz), 1.89 (1H, m), 2.13 (1H, dt, J=12.7, 3.9 Hz), 2.31 (1H, dt, J=14.7, 2.9 Hz), 2.42 (3H, m), 2.63 (1H, dd, J=18.6, 5.7 Hz), 2.70 (1H, dd, J=12.7, 4.9 Hz), 3.04 (1H, dt, J=14.7, 4.9 Hz), 3.11 (1H, d, J=19.5 Hz), 3.21 (1H, d, J=5.9 Hz), 4.65 (1H, s), 5.0–5.5 (1H, br), 6.69 (1H, d, J=6.8 Hz), 6.75 (1H, d, J=6.8 Hz), 7.07 (1H, t, J=6.8 Hz).

IR (neat)

υ 3406, 1729, 1630, 1607, 1458, 1052, 938, 781 cm$^1$

Mass (EI)

m/z 325 (M+).

Example 1

17-Cyclopropylmethyl-4,5α-epoxy-3,14β-dihydroxy-6α-methylaminomorphinan 4

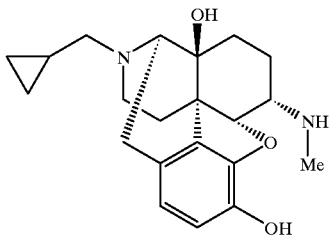

Naltrexone (1.0 g) and methylamine hydrochloride (0.99 g, 5 equivalents) were dissolved in methanol (15 ml) followed by stirring for 20 minutes at room temperature. This reaction solution was added to platinum oxide (0.05 g, 5 w %) in methanol (10 ml) activated in advance in a hydrogen atmosphere followed by hydrogenation for 4 hours at room temperature and atmospheric pressure. The catalyst was removed by Celite filtration and the solvent was distilled off. After adding saturated aqueous sodium bicarbonate (20 ml) and extracting with chloroform (20 ml×2), the extract was washed with saturated brine and dried with anhydrous sodium sulfate, and the solvent was distilled off. The resulting dark reddish-violet oily substance was dissolved in chloroform (2 ml) followed by addition of ethyl acetate (4 ml) to obtain the target compound (0.83 g, yield: 79%) by crystallization. A portion of this compound was removed and various spectra were measured in the form of a hydrochloride.

mp 270° C. (decomposition)

NMR (500 MHz, DMSO-d$_6$)

δ 0.40 (1H, m), 0.48 (1H, m), 0.61 (1H, m), 0.69 (1H, m), 0.95 (1H, m), 1.08 (1H, m), 1.47 (1H, m), 1.70 (1H, d, J=13.2 Hz), 1.81 (1H, m), 1.92 (1H, m), 2.49 (1H, m), 2.68 (3H, s), 2.72 (1H, m), 3.00 (1H, m), 3.08 (2H, m), 3.26 (2H, m), 3.57 (1H, m), 4.01 (3H, m), 4.97 (1H, brs), 6.50 (1H, s), 6.65 (1H, d, J=8.3 Hz), 6.78 (1H, d, J=8.3 Hz), 9.20 (2H, m).

IR (KBr)
υ 3200, 1510, 1464, 1238, 1116, 982, 859 cm$^{-1}$.
Mass (EI)
m/z 356 (M+) (measured in the free form)
Elementary Analysis: As $C_{21}H_{28}N_2O_3 \cdot 2HCl \cdot 0.2H_2O$
Calculated values: C 58.25; H 7.08; N 6.47; Cl 16.38
Measured values: C 58.35; H 7.20; N 6.44; Cl 16.14

Example 2

17-Cyclopropylmethyl-4,5α-epoxy-3,14β-dihydroxy-6α-isobutylaminomorphinan 5 was obtained by following the procedure of example 1 but using isobutylamine instead of methylamine.

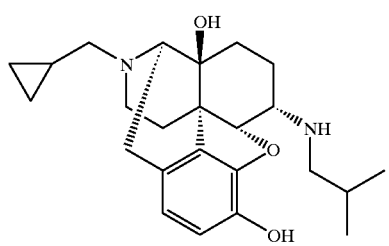

5

NMR (500 MHz, CDCl$_3$)
δ 0.22 (2H, m), 0.53 (2H, m), 0.84 (1H, m), 0.92 (1H, m), 0.94 (3H, d, J=6.7 Hz), 0.95 (3H, d, J=6.1 Hz), 1.40 (1H, dd, J=14.7, 10.4 Hz), 1.57 (1H, m), 1.68 (2H, m), 1.83 (1H, m), 2.30 (4H, m), 2.55 (2H, m), 2.63 (2H, m), 3.00 (1H, d, J=18.3 Hz), 3.06 (1H, d, J=6.7 Hz), 3.18 (1H, dt, J=13.4, 3.7 Hz), 4.3–5.2 (3H, br), 4.66 (1H, d, J=3.7 Hz), 6.46 (1H, d, J=7.9 Hz), 6.64 (1H, d, J=7.9 Hz).
IR (neat)
υ 3350, 1609, 1460, 1249, 1118, 913 cm$^{-1}$
Mass (EI)
m/z 398 (M+).

Example 3

17-Cyclopropylmethyl-14β-hydroxy-4,5α-epoxy-6α-methylaminomorphinan 6 (yield: 75%) was obtained by following the procedure of example 1 but using 3-dehydroxynaltrexone 3 instead of naltrexone hydrochloride.

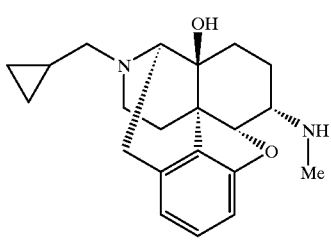

6

NMR (500 MHz, CDCl$_3$)
δ 0.13 (2H, m), 0.54 (2H, m), 0.75 (1H, m), 0.86 (1H, m), 1.40 (1H, dd, J=14.7, 5.5 Hz), 1.57 (1H, m), 1.63 (1H, m), 1.72 (2H, m), 2.25 (2H, m), 2.36 (2H, m), 2.52 (3H, s), 2.65 (2H, m), 3.08 (3H, m), 4.70 (1H, dd, J=3.7, 1.8 Hz), 4.9–5.1 (1H, br), 6.56 (1H, d, J=7.9 Hz), 6.61 (1H, d, J=7.3 Hz), 7.04 (1H, t, J=7.9 Hz).

IR (neat)
υ 3372, 1605, 1560, 1543, 1458, 1104, 864 cm$^{-1}$
Mass (EI)
m/z 340 (M+).

Example 3

3-tert-butyldimethylsilyloxy-17-cyclopropylmethyl-4,5α-epoxy-14β-hydroxy-6α-methylaminomorphinan 7 (yield: 50%) was obtained by following the procedure of example 1 but using 3-tert-butyldimethylsilyloxy-17-cyclopropylmethyl-4,5α-epoxy-14β-hydroxy-6-oxomorphinan 2 instead of Naltrexone hydrochloride.

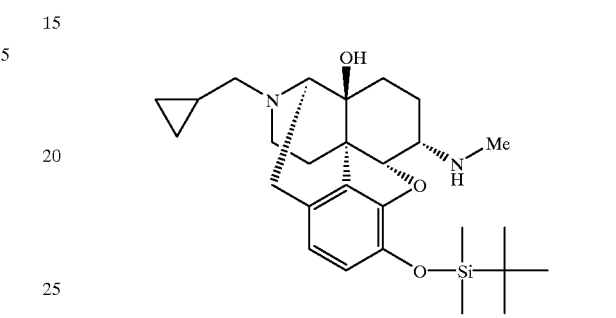

7

NMR (90 MHz, CDCl$_3$)
δ 0.0–1.2 (5H, m), 0.19 (3H, s), 0.2 (3H, s), 1.0 (9H, s), 1.3–1.9 (4H, m), 2.2–2.8 (7H, m), 2.56 (3H, s), 3.0 (1H, d, J=7.6 Hz), 3.0–3.3 (2H, m), 4.75 (1H, d, J=3.6 Hz), 6.5 (1H, d, J=7.2 Hz), 6.63 (1H, d, J=7.2 Hz).

Example 4

6β-(N-Benzyl)methylamino-17-cyclopropylmethyl-4,5α-epoxy-3,14β-dihydroxymorphinan 8

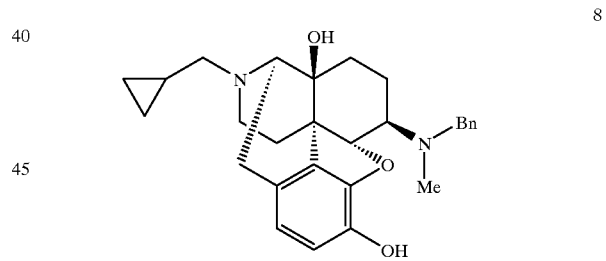

8

10.1 g of Naltrexone hydrochloride was separated with 150 ml of a 4:1 solution of chloroform and methanol and 150 ml of saturated aqueous sodium bicarbonate. The aqueous layer was extracted twice with 100 ml of a 4:1 solution of chloroform and methanol. The resulting organic layer was dried with anhydrous sodium sulfate followed by the addition of 3.26 g of benzoic acid and concentration after completely dissolving. After adequately drying the residue with a vacuum pump, the residue was suspended in 400 ml of benzene. After adding 5.2 ml of benzylmethylamine, 4.9 g of benzoic acid and 0.23 g of p-toluenesulfonic acid, the resulting mixture was stirred for 18 hours in a 110° C. oil bath while boiling off the water. After distilling off 330 ml of benzene at atmospheric pressure, 330 ml of ethanol and 4 g of molecular sieves 4A were added to the reaction mixture followed by cooling to 0° C. Next, 2.52 g of sodium cyanoborohydride was added followed by stirring for 2 hours at room temperature. After adding 200 ml of methanol to the reaction system, the molecular sieves was filtered out and the filtrate was concentrated. 200 ml of chloroform and 150 ml of saturated aqueous sodium bicarbonate were added to the resulting residue and the resulting precipitate was filtered followed by separation. The aqueous layer was extracted twice with 100 ml of chloroform, and the organic layer was concentrated after drying with anhydrous sodium sulfate. The resulting crude product was purified with silica gel column chromatography (480 g ammonia saturated ammonium chloroform/chloroform=2/1) to obtain 10.87 g of the oily target compound (yield: 91%). This was then recrystallized from methanol.

mp 71–80° C. (decomposition)

NMR (400 MHz, CDCl$_3$)

δ 0.09–0.13 (2H, m), 0.49–0.55 (2H, m), 0.79–0.88 (1H, m), 1.25–1.35 (1H, m), 1.43–1.49 (1H, m), 1.59–1.66 (2H, m), 1.87–2.00 (1H, m), 2.11 (1H, dt, J=3.4, 11.7 Hz), 2.19–2.27 (1H, m), 2.34 (3H, s), 2.35 (2H, d, J=6.8 Hz), 2.50–2.59 (1H, m), 2.56 (1H, dd, J=5.4, 18.1 Hz), 2.62 (1H, dd, J=4.4, 11.7 Hz), 2.99 (1H, d, J=18.1 Hz), 3.04 (1H, d, J=5.4 Hz), 3.53 (1H, d, J=13.2 Hz), 3.82 (1H, d, J=13.7 Hz), 4.68 (1H, d, J=8.3 Hz), 6.51 (1H, d, J=8.3 Hz), 6.65 (1H, d, J=8.3 Hz), 7.20–7.35 (5H, m).

IR (KBr)

υ 3428, 3220, 1638, 1615, 1502, 1458, 1375, 1330, 1238, 1147, 1116, 1033, 990, 917, 857, 735 cm$^{-1}$

Mass (EI)

m/z 446 (M+), 355, 286, 160.

Elementary Analysis: As $C_{28}H_{34}N_2O_3 \cdot 0.5H_2O$

Calculated values: C, 73.82; H, 7.74; N, 6.15.

Measured values: C, 73.94; H, 7.79; N, 6.08.

Example 5

17-Cyclopropylmethyl-4,5α-epoxy-6β-(N-benzyl) ethylamino-3,14β-dihydroxymorphinan 9 (yield: 46%) was obtained by following the procedure of example 4 but using benzylethylamine instead of benzylmethylamine.

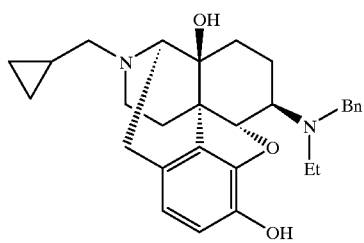

NMR (400 MHz, CDCl$_3$)

δ 0.05–0.18 (2H, m), 0.46–0.58 (2H, m), 0.77–0.89 (1H, m), 1.03 (3H, t, J=7.1 Hz), 1.22–1.33 (1H, m), 1.41–1.48 (1H, m), 1.55–1.65 (2H, m), 1.86–1.99 (1H, m), 2.11 (1H, dt, J=3.9, 12.2 Hz), 2.20 (1H, dt, J=4.9, 12.2 Hz), 2.33 (1H, dd, J=6.8, 12.7 Hz), 2.36 (1H, dd, J=6.8, 12.7 Hz), 2.50–2.75 (5H, m), 2.98 (1H, d, J=18.6 Hz), 3.03 (1H, d, J=5.9 Hz), 3.56 (1H, d, J=14.4 Hz), 3.87 (1H, d, J=14.4 Hz), 4.59 (1H, d, J=7.8 Hz), 4.85 (2H, brs), 6.50 (1H, d, J=7.8 Hz), 6.63 (1H, d, J=7.8 Hz), 7.18–7.32 (3H, m), 7.40 (2H, d, J=6.8 Hz).

Mass (EI)

m/z 460 M+

Example 6

17-Cyclopropylmethyl-4,5α-epoxy-3,14β-dihydroxy-6β-methylaminomorphinan 10

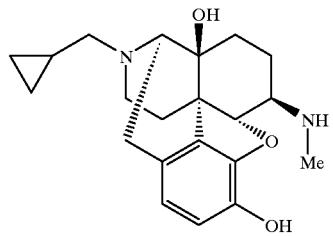

12.65 g of 6β-(N-benzyl)methylamino-17-cyclopropylmethyl-4,5α-epoxy-3,14β-dihydroxymorphinan 8•2 hydrochloride (converted to a hydrochloride by established methods) was dissolved in 250 ml of methanol followed by the addition of 2.53 g of 5% palladium—carbon and stirring for 4 hours in a hydrogen atmosphere. After removing the catalyst using Celite, the filtrate was concentrated. 100 ml of a 4:1 solution of chloroform and ethanol and 100 ml of saturated aqueous sodium bicarbonate were added to the resulting residue to separate, and the aqueous layer was then extracted twice with 100 ml of a 4:1 solution of chloroform and ethanol. After drying the organic layer with anhydrous sodium sulfate, the dried organic layer was concentrated to obtain 8.00 g of crude product. This was then recrystallized from methanol to obtain 5.84 g of the target compound (yield: 67%).

NMR (400 MHz, CDCl$_3$)

δ 0.10–0.14 (2H, m), 0.50–0.55 (2H, m), 0.79–0.86 (1H, m), 1.38 (1H, dt, J=2.9 Hz, 12.8 Hz), 1.41–1.48 (1H, m), 1.58–1.72 (2H, m), 1.78–1.91 (1H, m), 2.08–2.25 (2H, m), 2.36 (1H, d, J=6.6 Hz), 2.45 (3H, s), 2.49–2.65 (3H, m), 3.00 (1H, d, J=18.3 Hz), 3.05 (1H, d, J=5.9 Hz), 4.48 (1H, d, J=7.7 Hz), 6.54 (1H, d, J=8.1 Hz), 6.66 (1H, d, J=8.1 Hz).

IR (KBr)

υ 3380, 2926, 1638, 1607, 1462, 1255, 1180, 795 cm$^{-1}$.

Mass (EI)

m/e 356 M+

Elementary Analysis: $C_{21}H_{28}O_3N_2$

Calculated values: C, 70.76; H, 7.92; N, 7.86.

Measured values: C, 70.51; H, 7.94; N, 7.84.

Example 7

17-Cyclopropylmethyl-4,5α-epoxy-6β-ethylamino-3,14β-dihydroxymorphinan 11 (yield: 95%) was obtained by following the procedure of example 6 but using 6β-(N-benzyl)ethylamino-17-cyclopropylmethyl-4,5α-epoxy-3,14β-dihydroxymorphinan 9•2 hydrochloride for the starting material instead of 6β-(N-benzyl)methylamino-17-cyclopropylmethyl-4,5α-epoxy-3,14β-dihydroxymorphinan 8•2 hydrochloride.

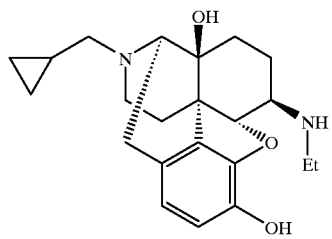

NMR (500 MHz, CDCl₃+D2O)

δ 0.08–0.17 (2H, m), 0.49–0.56 (2H, m), 0.78–0.87 (1H, m), 1.16 (3H, t, J=7.1 Hz), 1.37 (1H, dt, J=2.9, 13.2 Hz), 1.40–1.45 (1H, m), 1.57–1.61 (1H, m), 1.66–1.71 (1H, m), 1.83 (1H, dq, J=2.9, 13.2 Hz), 2.13 (1H, dt, J=12.1, 3.3 Hz), 2.20 (1H, dt, J=12.1, 4.8 Hz), 2.34 (1H, dd, J=12.8, 6.6 Hz), 2.37 (1H, dd, J=12.8, 6.6 Hz), 2.52–2.69 (4H, m), 2.80 (1H, dq, J=11.4, 7.0 Hz), 3.00 (1H, d, J=18.3 Hz), 3.05 (1H, d, J=5.9 Hz), 4.46 (1H, d, J=7.7 Hz), 6.54 (1H, d, J=8.1 Hz), 6.67 (1H, d, J=8.1 Hz).

Mass (EI)

m/e 370 M+

Reference Example 6

17-Allyl-3,14β-dihydroxy-4,5α-epoxy-6α-methylamino-morphinan 12

17-Allyl-3,14β-dihydroxy-4,5α-epoxy-6β-methylamino-morphinan 13

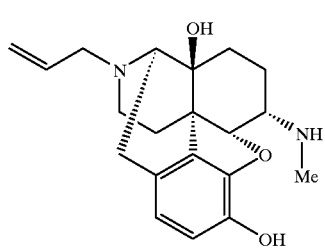

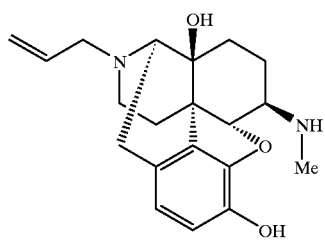

Naloxone hydrochloride (3.0 g), methylamine hydrochloride (5.57 g) and sodium cyanoborohydride (0.33 g) were suspended in anhydrous methanol (40 ml) and stirred for 17 hours at room temperature. After addition of concentrated hydrochloric acid (1.0 ml) and removal of solvent by distillation, distilled water (50 ml) was added followed by washing with chloroform (20 ml). Saturated aqueous sodium bicarbonate (10 ml) was added to make the solution basic followed by extraction with chloroform (30 ml×3). After drying with anhydrous magnesium sulfate, the solvent was distilled off. The resulting crude product was purified with silica gel column chromatography (Merk 7734 100 g; ethyl acetate/methanol/aqueous ammonia=90/10/1→80/20/2) to obtain the target compound in the form of a pure fraction (12 0.4 g, 12%; 13 0.8 g, 24%).

Compound 12

NMR (400 MHz, CDCl₃)

δ 0.87 (1H, m), 1.39 (1H, m), 1.66 (3H, m), 2,19 (1H, dt, J=12.2, 4.9 hz), 2.29(1H, dt, J=12.7, 3.4 Hz), 2.55 (3H, m), 2.59 (3H, s), 2.90 (1H, d, J=6.4 Hz), 3.09 (2H, m), 3.18 (1H, m), 4.76 (1H, d, J=3.4 Hz), 4.7–4.9 (1H, br), 5.17 (2H, m), 5.80 (1H, m), 6.50 (1H, d, J=7.8 Hz), 6.69 (1H, d, J=7.8 Hz).

IR (neat)

υ 3400, 1618, 1450, 1386, 1160, 1067, 750 cm⁻¹.

Mass (EI)

m/z 342 (M+).

Compound 13

NMR (500 MHz, CDCl₃)

δ 1.42 (2H, m), 1.61 (2H, m), 1.91 (1H, dq, J=12.8, 3.1 Hz), 2.16 (2H, m), 2.47 (3H, s), 2.56 (3H, m), 2.87 (1H, d, J=5.5 Hz), 3.03 (1H, d, J=18.3 Hz), 3.11 (2H, d, J=6.7 Hz), 4.51 (1H, d, J=7.9 Hz), 4.7–5.2 (3H, br), 5.18 (2H, m), 5.79 (1H, m), 6.55 (1H, d, J=7.9 Hz), 6.64 (1H, d, J=7.9 Hz).

IR (neat)

υ 3400, 1560, 1543, 1458, 1255, 1036, 731 cm⁻¹.

Mass (EI)

m/z 342 (M+).

Reference Example 7

17-Cyclopropylmethyl-7,8-didehydro-4,5α-epoxy-14β-hydroxy-3-methoxy-6α-(N-methylamino)morphinan (yield: 40%) 14, and 17-cyclopropylmethyl-4,5α-epoxy-14β-hydroxy-3-methoxy-6β-(N-methylamino)morphinan (yield: 23%) 15 were obtained by following the procedure of reference example 6 but using 17-cyclopropylmethyl -7,8-didehydro-4,5α-epoxy-14β-hydroxy-3-methoxymorphinan-6-one instead of naloxone hydrochloride.

Compound 14

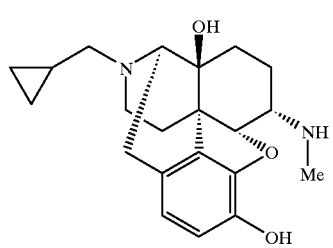

NMR (500 MHz, CDCl₃)

δ 0.13–0.18 (2H, m), 0.53–0.59 (2H, m), 0.88 (1H, m), 1.78 (1H, d, J=7.8 Hz), 2.38 (2H, d, J=7.8 Hz), 2.40 (1H, d, J=6.3 Hz), 2.44 (1H, dd, J=12.7, 6.3 Hz), 2.50 (1H, dd, J=18.6, 6.8 Hz), 2.58 (3H, s), 2.72 (1H, d, J=7.8 Hz), 3.08 (1H, d, J=18.6 Hz), 3.35 (1H, d, J=6.8 Hz), 3.65 (1H, m), 3.84 (3H, s), 4.97 (1H, br), 4.99 (1H, dd, J=5.9, 1.5 Hz), 5.54 (1H, dd, J=9.8, 2.9 Hz), 5.88 (1H, dt, J=9.8, 1.5 Hz), 6.51 (1H, d, J=7.8 Hz), 6.63 (1H, d, J=7.8 Hz).

IR (neat)

υ 3342, 2938, 1508, 1456, 1284, 1205, 1123, 1054, 1017, 748 cm⁻¹

Mass (EI)

m/z 368 (M+).

Compound 15

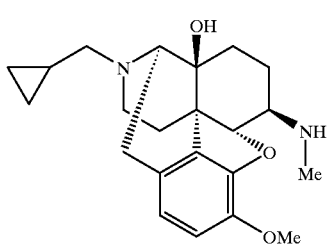

mp 121.5–123.5° C. (ethylacetate-ether)
NMR (400 MHz, CDCl₃)

δ 0.09–0.16 (2H, m), 0.50–0.56 (2H, m), 0.84 (1H, m), 1.36 (1H, td, J=12.7, 3.9 Hz), 1.44 (1H, dd, J=12.7, 2.4 Hz), 1.61 (1H, dt, J=13.2, 3.4 Hz), 1.66–1.83 (2H, m), 2.10 (1H, td, J=12.2, 3.9 Hz), 2.23 (1H, td, J=12.2, 4.9 Hz), 2.36 (2H, dd, J=6.4, 1.5 Hz), 2.43 (1H, m), 2.48 (3H, s), 2.57–2.66 (2H, m), 3.03 (1H, d, J=18.6 Hz), 3.08 (1H, d, J=5.9 Hz), 3.87 (3H, s), 4.45 (1H, d, J=6.8 Hz), 6.61 (1H, d, J=8.3 Hz), 6.72 (1H, d, J=8.3 Hz).

IR (KBr)
υ 3390, 3344, 2944, 2802, 1632, 1611, 1504, 1446, 1282, 1263, 1044, 980, 901 cm⁻¹

Mass (EI)
m/z 370 (M+).

Reference Example 8

3-tert-butyldimethylsilyloxy-17-cyclopropylmethyl-4,5α-epoxy-14β-hydroxy-6α-(N-methyl-3,4-dichlorophenylmethanesulfonamido)morphinan 16

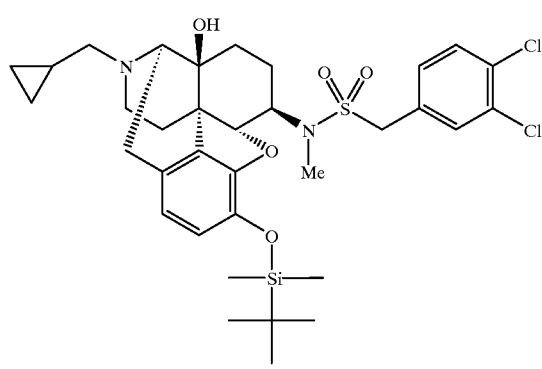

203.9 mg of 3-tert-butyldimethylsilyloxy-17-cyclopropylmethyl-4,5α-epoxy-14β-hydroxy-6α-methylaminomorphinan 7 obtained in reference example 5 was dissolved in 3 ml of pyridine followed by the addition of 124 mg of 3,4-dichlorophenylmethanesufonylchloride and stirring for 30 minutes at room temperature. After concentrating the reaction system, 3 ml of saturated aqueous sodium bicarbonate and 3 ml of chloroform were added to separate layers, after which the aqueous layer was extracted twice with 3 ml of chloroform. After drying with anhydrous sodium sulfate, the organic layer was concentrated to obtain the oily crude product. This was then purified with silica gel column chromatography (30 g benzene/ethyl acetate=5/1) to obtain 235.4 mg of the target compound (yield: 78%).

NMR (500 MHz, CDCl₃)

δ 0.09–0.16 (2H, m), 0.15 (3H, s), 0.21 (3H, s), 0.51–0.57 (2H, m), 0.80–0.89 (1H, m), 0.97 (9H, s), 1.21–1.30 (2H, m), 1.42–1.49 (2H, m), 1.71 (1H, dt, J=14.7, 9.5 Hz), 2.15 (1H, dt, J=12.5, 5.1 Hz), 2.22 (1H, dt, J=12.5, 3.7 Hz), 2.30 (1H, dd, J=12.8, 6.6 Hz), 2.35 (1H, dd, J=12.8, 6.6 Hz), 2.56 (1H, dd, J=18.7, 7.0 Hz), 2.60–2.65 (1H, m), 2.89 (3H, s), 3.01 (1H, d, J=18.7 Hz), 3.05 (1H, d, J=7.0 Hz), 4.16 (1H, d, J=13.9 Hz), 4.19 (1H, d, J=13.9 Hz), 4.22–4.28 (1Hm), 4.41 (1H, d, J=3.3 Hz), 4.90 (1H, brs), 6.48 (1H, d, J=8.1 Hz), 6.62 (1H, d, J=8.1 Hz), 7.31 (1H, dd, J=8.1, 2.2 Hz), 7.46 (1H, d, J=8.1 Hz), 7.53 (1H, d, J=2.2 Hz).

Mass (EI)
m/z 692 M+

Reference Example 9

3-tert-butyldimethylsilyloxy-17-cyclopropylmethyl-4,5α-epoxy-14β-hydroxy-6α-(N-methylphenylmethanesulfonamido)morphinan 17 (yield: 50%) was obtained by following the procedure of reference example 8 but using phenylmethanesulfonylchloride instead of 3,4-dichlorophenylmethanesulfonylchloride.

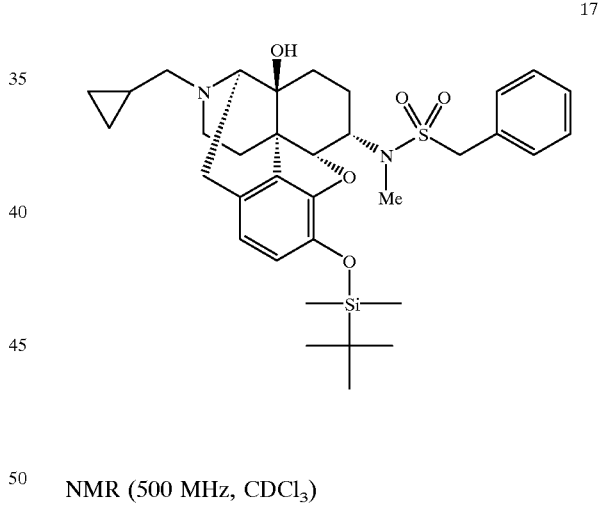

NMR (500 MHz, CDCl₃)

δ 0.08–0.13 (2H, m), 0.14 (3H, s), 0.20 (3H, s), 0.50–0.55 (2H, m), 0.79–0.87 (1H, m), 0.97 (9H, s), 1.10–1.22 (2H, m), 1.37–1.43 (2H, m), 1.64 (1H, dt, J=15.0, 9.5 Hz), 2.12 (1H, dt, J=12.5, 5.1 Hz), 2.20 (1H, dt, J=12.5, 3.3 Hz), 2.29 (1H, dd, J=12.5, 6.6 Hz), 2.33 (1H, dd, J=12.5, 6.6 Hz), 2.54 (1H, dd, J=18.7, 7.0 Hz), 2.59–2.63 (1H, m), 2.83 (3H, s), 2.99 (1H, d, J=18.7 Hz), 3.02 (1H, d, J=7.0 Hz), 4.19–4.24 (1H, m), 4.24 (1H, d, J=13.9 Hz), 4.28 (1H, d, J=13.9 Hz), 4.34 (1H, d, J=2.9 Hz), 4.88 (1H, brs), 6.46 (1H, d, J=8.1 Hz), 6.61 (1H, d, J=8.1 Hz), 7.32–7.40 (3H, m), 7.42–7.47 (2H, m).

Mass (EI)
m/z 624 M+

Reference Example 10

5β-Methylnaltrexone-O-methyloxime(17-cyclopropylmethyl-3,14β-dihydroxy-4,5α-epoxy-5β-methyl-6-methoxyiminomorphinan) 18

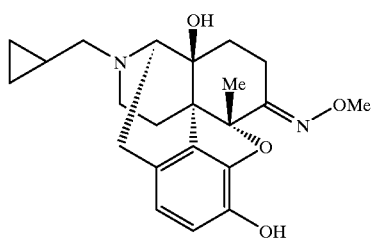

18

109.3 mg of 5β-methylnaltrexone (0.326 mmol) and 37.2 mg of methoxyamine hydrochloride (0.445 mmol) were dissolved in 1.6 ml of methanol followed by the addition of 0.17 ml of 10% aqueous sodium hydroxide to this solution and refluxing while heating. After 8.5 hours part way through the refluxing period, a solution of 36.1 mg (0.432 mmol) of methoxyamine hydrochloride in 0.5 ml of methanol was added and refluxing was continued until a total of 23 hours had elapsed. After allowing the reaction solution to cool to room temperature by standing, 5 ml of water and 1 ml of saturated aqueous sodium bicarbonate were added followed by extraction with 2×5 ml of chloroform. The organic layers were combined and dried with anhydrous sodium sulfate followed by concentration to obtain 107.4 mg of the unpurified target compound. This unpurified compound was used in the following reaction without being purified.

NMR (400 MHz, CDCl$_3$)

δ 0.13 (2H, m), 0.53 (2H, m), 0.84 (1H, m), 1.37 (1H, m), 1.43 (1H, dd, J=14.1, 3.4 Hz), 1.62 (1H, m), 1.71 (3H, s), 2.23–2.30 (3H, m), 2.30 (1H, br s, OH), 2.37 (2H, d, J=6.5 Hz), 2.55 (1H, dd, J=18.3, 6.1 Hz), 2.71 (1H, m), 3.00 (1H, d, J=18.3 Hz), 3.04 (1H, d, J=6.1 Hz), 3.14 (1H, ddd, J=14.7, 3.2, 3.2 Hz), 3.80 (3H, s), 4.95 (1H, br s, OH), 6.55 (1H, d, J=8.0 Hz), 6.70 (1H, d, J=8.0 Hz).

IR (KBr)

υ 3380, 1638, 1620, 1510, 1460, 1377, 1336, 1241, 1118, 1038, 953, 866, 752 cm$^{-1}$.

Mass (EI)

m/z 384 (M+).

Reference Example 11

17-Cyclopropylmethyl-3,14β-dihydroxy-4,5α-epoxy-5β-methyl-6α-aminomorphinan 19

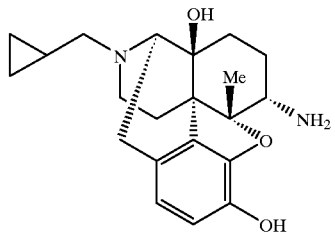

19

101.0 mg (approximately 0.26 mmol) of the unpurified 5β-methylnaltrexone-O-methyloxime 18 obtained in reference example 10 was dissolved in 2.5 ml of anhydrous THF in the presence of argon gas followed by cooling to 0° C. After adding 1.31 ml of an anhydrous THF solution of 1.0 M borane.THF complex to this solution, the solution was refluxed for 18.5 hours while heating. After cooling the reaction solution to 0° C. and slowly adding 10 ml of 2 N hydrochloric acid, the solution was again refluxed for 40 minutes while heating. The reaction solution was cooled to 0° C. followed by the addition of 4 ml of 5 N aqueous ammonia and 2 ml of saturated aqueous sodium bicarbonate, and extraction with 3×5 ml of chloroform-methanol (4:1). The organic layers were combined and dried with anhydrous sodium sulfate followed by concentration to obtain 89.6 mg of the unpurified target compound. This unpurified compound was then used in the following reaction without being purified.

NMR (400 MHz, CDCl$_3$)

δ 0.12 (2H, m), 0.53 (2H, m), 0.83 (1H, m), 1.37–1.84 (5H, m), 1.63 (3H, s), 2.15–2.28 (2H, m), 2.33 (2H, d, J=5.7 Hz), 2.60 (1H, dd, J=18.5, 6.3 Hz), 2.67 (1H, m), 2.99 (1H, d, J=18.5 Hz), 3.00 (3H, br s, OH, NH2), 3.02 (1H, d, J=6.3 Hz), 3.14 (1H, dd, J=8.8, 3.8 Hz), 4.90 (1H, br s, OH), 6.49 (1H, d, J=8.0 Hz), 6.63 (1H, d, J=8.0 Hz).

IR (KBr)

υ 3376, 3082, 1611, 1502, 1460, 1379, 1332, 1245, 1122, 1038, 944, 868, 803 cm$^{-1}$.

Mass (EI)

m/z 356 (M+).

Example 8

6β-(N-Benzyl)methylamino-17-cyclopropylmethyl-4,5α-epoxy-3,14β-dihydroxymorphinan 8

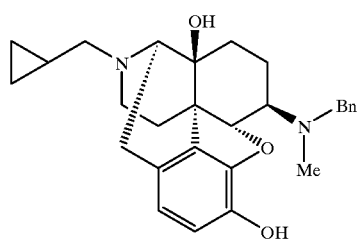

8

50.08 g (0.108 mol) of naltrexone benzoate was suspended in THF (350 ml) followed by the addition of 19.61 g (0.162 mol) of benzylmethylamine. A Soxhlet extractor containing molecular sieves 4A (50 g) was attached followed by refluxing for 23 hours while heating. After adding methanol (200 ml) to the reaction system, 10.2 g (0.162 mol) of sodium cyanoborohydride was dissolved in methanol (50 ml) and added to the reaction mixture followed by stirring for 30 minutes. After stirring, the solvent was distilled off and ethylacetate (400 ml) and 1% aqueous sodium bicarbonate (400 ml) were added to the residue to separate layers. The aqueous layer was re-extracted with ethylacetate (80 ml). The resulting organic layer was washed with saturated brine (250 ml) and concentrated after drying. Methanol (240 ml) was added to the resulting residue to recrystallize and obtain 42.68 g of the target substance (yield: 88%). The data of this compound is the same as that shown in example 4.

Example 9

An isomer mixture of 17-cyclopropylmethyl-4,5α-epoxy-3-hydroxy-6β-methylaminomorphinan 20 and 17-cyclopropylmethyl-4,5α-epoxy-3-hydroxy-6α-methylaminomorphinan 21 (20:21=approximately 2:1, 44%) was obtained by following the procedure of example 8 but using 14-dehydroxynaltrexone instead of naltrexone benzoate.

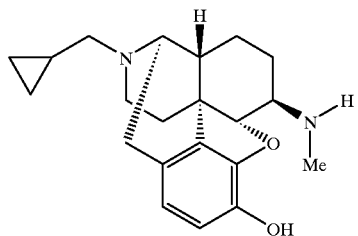

20

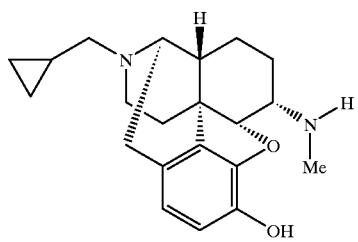

21

Mixture of Compound 20 and Compound 21

NMR (400 MHz, CDCl$_3$)

δ 0.08–0.17 (2H, m), 0.49–0.55 (2H, m), 0.8–2.5 (12H), 2.42 (2.1H, s), 2.54 (0.9H, s), 2.7–2.9 (2H), 3.36 (0.7H, m), 3.41 (0.3H, m), 4.36 (0.7H, d, J=7.3 Hz), 4.78 (0.3H, d, J=2.9 Hz), 6.48–6.56 (1H, m), 6.64–6.68 (1H, m).

IR (neat)

υ 2932, 1609, 1454, 1325, 1259, 911, 731 cm$^{-1}$

Mass (EI)

m/z 340 (M+).

Example 10

17-Cyclopropylmethyl-4,5α-epoxy-3,14β-dihydroxy-6β-methylaminomorphinan 10.phthalate

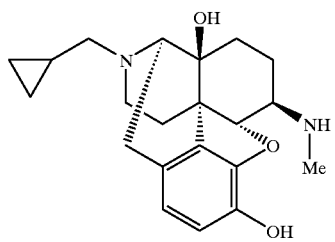

10

42.58 g (0.0953 mol) of 6β-(N-benzyl)methylamino-17-cyclopropylmethyl-4,5α-epoxy-3,14β-dihydroxymorphinan 8 and 17.42 g (0.105 mol) of phthalic acid were dissolved in 500 ml of methanol followed by the addition of 12.7 g of 10% palladium—carbon and stirring for 12 hours in a hydrogen atmosphere. After the atmospheric hydrogen was replaced to nitrogen, 300 ml of methanol was added followed by refluxing while heating. After dissolving the precipitated crystals, the catalyst was filtered out during heating using Celite. After distilling off 200 ml of filtrate by atmospheric pressure condensation, the remaining filtrate was allowed to stand undisturbed to recrystallize and obtain 26.82 g of the target compound (yield: 54%).

mp 151–164° C. (decomposition)

NMR (400 MHz, D20)

δ 0.40–0.50 (2H, m), 0.73 (1H, m), 0.82 (1H, m), 1.08 (1H, m), 1.56 (1H, m), 1.67 (1H, m), 1.85 (1H, m), 1.89–2.02 (2H, m), 2.52 (1H, ddd, J=13.2, 13.2, 4.9 Hz), 2.75 (1H, ddd, J=12.9, 12.9, 4.2 Hz), 2.78 (3H, s), 2.93–3.04 (2H, m), 3.16–3.25 (2H, m), 3.32–3.43 (2H, m), 4.07 (1H, br d, J=5.9 Hz), 4.99 (1H, d, J=7.3 Hz), 6.85 (1H, d, J=8.0 Hz), 6.90 (1H, d, J=8.0 Hz), 7.34–7.39 (2H, m), 7.43–7.48 (2H, m).

IR (KBr)

υ 3388, 3032, 1605, 1557, 1510, 1460, 1367, 1330, 1243, 1168, 1120, 1035, 992, 936, 859, 770 cm$^{-1}$.

Mass (FAB)

m/z 357 ((M+H)+).

Elementary Analysis: As C$_{21}$H$_{28}$N$_2$O$_3$•C$_8$H$_6$O$_4$•0.8H$_2$O

Calcd.: C, 64.86; H, 6.68; N, 5.22.

Found.: C, 64.93; H, 6.61; N, 5.23.

Example 11

17-Cyclopropylmethyl-4,5α-epoxy-3,14β-dihydroxy-6α-(N-methyl-3,4-dichlorophenylacetoamido)morphinan•hydrochloride 1

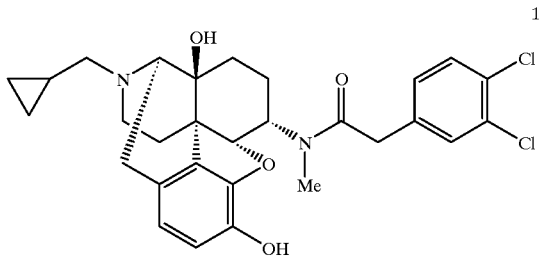

8.9 g of 17-cyclopropylmethyl-4,5α-epoxy-3,14β-dihydroxy-6α-methylaminomorphinan 4 obtained in example 1 was dissolved in 180 ml of chloroform. After adding 10.4 ml of triethylamine, 10.4 ml of 3,4-dichlorophenylacetyl chloride (obtained by converting commercially available carboxylic acid into an acid chloride by established methods) was added dropwise at 0° C. After completion of dropwise addition, the reaction solution was stirred for 1 hour at room temperature followed by the addition of 150 ml of saturated aqueous sodium bicarbonate to the reaction system to separate. The aqueous layer was then extracted twice with 100 ml of chloroform. After drying with anhydrous sodium sulfate, the organic layer was concentrated. The resulting residue was dissolved in a mixed solvent of 140 ml of methanol and 14 ml of chloroform followed by the addition of 1.7 g of potassium carbonate at room temperature and stirring for 30 minutes. 100 ml of water and 350 ml of chloroform were then added to the reaction solution to separate layers, and the aqueous layer was extracted twice with 80 ml of chloroform. After drying with anhydrous sodium sulfate, the resulting organic layer was concentrated. The resulting residue was recrystallized from a 2:1 mixture of ethylacetate and methanol to obtain 8.15 g of the free base form. This was then dissolved in a mixed solvent of chloroform and methanol followed by concentration after adjusting to pH 3 by addition of methanol solution of hydrochloride. This solution was re-precipitated from chloroform, methanol and ether to obtain 8.44 g of the target compound (yield: 58%).

mp 252–254° C.

NMR (400 MHz, DMSO-$d_6$)

δ 0.43 (2H, m), 0.65 (2H, m), 1.05 (1H, m), 1.16 (1.5H, m), 1.37 (1H, m), 1.58 (2H, m), 1.92 (1H, m), 2.43 (1H, m), 2.68 (1H, m), 2.81 (0.5H, s), 2.96 (2.5H, s), 3.05 (2.5H, m), 3.30 (2H, m), 3.85 (3H, m), 4.48 (0.2H, m), 4.62 (0.8H, d, J=3.9 Hz), 4.75 (0.2H, m), 4.96 (0.8H, m), 6.21 (0.8H, m), 6.46 (0.2H, m), 6.58 (1H, d, J=8.3 Hz), 6.72 (1H, d, J=8.3 Hz), 7.25 (1H, m), 7.55 (2H, m), 8.80 (1H, brs), 9.32 (1H, brs)

IR (KBr)

υ 3370, 1620, 1510, 1473, 1120, 1035, $cm^{-1}$.

Mass (FAB)

m/z 543 (M+H)+

Elementary Analysis: As $C_{29}H_{32}N_2O_4Cl_2$•HCl•$0.5H_2O$

Calcd.: C, 59.14; H, 5.82; N, 4.75; Cl, 18.06

Found.: C, 59.34; H, 5.78; N, 4.78; Cl, 17.78

Examples 12–40

17-Cyclopropylmethyl-4,5α-epoxy-3,14β-dihydroxy-6α-(N-methyl-3-phenylpropionamido)morphinan•tartrate 22 (yield: 84%), 17-cyclopropylmethyl-3,14β-dihydroxy-4,5α-epoxy-6α-(N-methylphenylacetamido)morphinan•hydrochloride 23 (yield: 70%), 17-cyclopropylmethyl-3,14β-dihydroxy-4,5α-epoxy-6α-(N-methylcinnamamido)morphinan•hydrochloride 24 (yield: 74%), 17-cyclopropylmethyl-3,14β-dihydroxy-4,5α-epoxy-6α-(N-methylacetamido)morphinan•hydrochloride 25 (yield: 93%), 17-cyclopropylmethyl-3,14β-dihydroxy-4,5α-epoxy-6α-(N-methyl-3-bromophenylacetamido)morphinan•hydrobromate 26 (yield: 85%), 17-cyclopropylmethyl-3,14β-dihydroxy-4,5α-epoxy-6α-(N-methyl-3,4-dichlorobenzamido)morphinan•hydrochloride 27 (yield: 58%), 17-cyclopropylmethyl-3,14β-dihydroxy-4,5α-epoxy-6α-(N-methyl-4-bromophenylacetamido)morphinan•hydrobromide 28 (yield: 73%), 17-cyclopropylmethyl-4,5α-epoxy-3,14β-dihydroxy-6α-[(R)-N-methyl-2-phenylpropionamido]morphinan•hydrochloride 29 (yield: 52%), 17-cyclopropylmethyl-3,14β-dihydroxy-4,5α-epoxy-6α-[(R)-N-methylmethoxyphenylacetamido]morphinan•hydrochloride 30 (yield: 98%), 17-cyclopropylmethyl-3,14β-dihydroxy-4,5α-epoxy-6α-[(S)-N-methylmethoxyphenylacetamido]morphinan•hydrochloride 31 (yield: 70%), 17-cyclopropylmethyl-4,5α-epoxy-3,14β-dihydroxy-6α-[(S)-N-methyl-2-phenylpropionamido]morphinan•tartrate 32 (yield: 85%), 17-cyclopropylmethyl-3,14β-dihydroxy-4,5α-epoxy-6α-(N-methylcyclohexylcarboxyamido)morphinan•hydrochloride 33 (yield: 58%), 17-cyclopropylmethyl-3,14β-dihydroxy-4,5α-epoxy-6α-(N-methylbenzamido)morphinan•hydrochloride 34 (yield: 52%), 17-cyclopropylmethyl-3,14β-dihydroxy-4,5α-epoxy-6α-(N-methyl-4-phenylbutyramido)morphinan•hydrochloride 35 (yield: 80%), 17-cyclopropylmethyl-3,14β-dihydroxy-4,5α-epoxy-6α-(N-methyl-6-phenylhexanamido)morphinan•hydrochloride 36 (yield: 63%), 17-cyclopropylmethyl-3,14β-dihydroxy-4,5α-epoxy-6α-(N-methyl-3-fluorophenylacetamido)morphinan•hydrochloride 37 (yield: 57%), 17-cyclopropylmethyl-3,14β-dihydroxy-4,5α-epoxy-6α-(N-methylphenoxyacetamido)morphinan•hydrochloride 38 (yield: 86%), 17-cyclopropylmethyl-3,14β-dihydroxy-4,5α-epoxy-6α-(N-methylhexanamido)morphinan•tartrate 39 (yield: 68%), 17-cyclopropylmethyl-3,14β-dihydroxy-4,5α-epoxy-6α-(N-methylheptanamido)morphinan•tartrate 40 (yield: 81%), 17-cyclopropylmethyl-3,14β-dihydroxy-4,5α-epoxy-6α-[N-methyl-3-(3-pyridyl)propionamido]morphinan•tartrate 41 (yield: 65%), 17-cyclopropylmethyl-3,14β-dihydroxy-4,5α-epoxy-6α-(N-methylbenzyloxycarbamido)morphinan•tartrate 42 (yield: 61%), 17-cyclopropylmethyl-3,14β-dihydroxy-4,5α-epoxy-6α-(N-methyl-4-nitrobenzyloxycarbamido)morphinan•hydrochloride 43 (yield: 68%), 17-cyclopropylmethyl-4,5α-epoxy-3,14β-dihydroxy-6α-[N-methyl-(3-pyridyl)methyloxycarbamido]morphinan•tartrate 44 (yield: 31%), 17-cyclopropylmethyl-4,5α-epoxy-3,14β-dihydroxy-6α-(N-methylthiophenoxyacetamido)morphinan•tartrate 45 (yield: 50%), 17-cyclopropylmethyl-3,14β-dihydroxy-4,5α-epoxy-6α-(N-methylheptanamido)morphinan•hydrochloride 46 (yield: 62%), 17-cyclopropylmethyl-4,5α-epoxy-3,14β-dihydroxy-6α-(N-methylbutyroxycarbamido)morphinan•tartrate 47 (yield: 70%), 17-cyclopropylmethyl-4,5α-epoxy-3,14β-dihydroxy-6α-(N-methyl-3-cyclopentylpropionamido)morphinan•tartrate 48 (yield: 84%), 17-cyclopropylmethyl-4,5α-epoxy-3,14β-dihydroxy- 6α-(N-methyl-2-methoxyethoxycarbamido) morphinan•tartrate 49 (yield: 70%), and 17-cyclopropylmethyl-4,5α-epoxy-3,14β-dihydroxy-6α-(N-methyl-trans-3-cyclohexylacrylamido) morphinan•hydrochloride 50 (yield: 72%) were obtained by following the procedure of example 11, but using 3-phenylpropionyl chloride, phenylacetyl chloride, trans-cinnamoyl chloride, acetyl chloride, 3-bromophenylacetyl chloride, 3,4-dichlorobenzoyl chloride, 4-bromophenylacetyl chloride, R-(−)-2-phenylpropionyl chloride, R-(−)-methoxyphenylacetyl chloride, S-(+)-methoxyphenylacetyl chloride, S-(+)-2-phenylpropionyl chloride, cyclohexanecarbonyl chloride, benzoyl chloride, 4-phenylbutanoyl chloride, 6-phenylhexanoyl chloride, 3-fluorophenylacetyl chloride, phenoxyacetyl chloride, hexanoyl chloride, heptanoyl chloride, 3-(3-pyridyl)propionyl chloride, benzyl chloroformate, 4-nitrobenzyl chloroformate, 3-pyridylmethyl chloroformate, thiophenoxyacetyl chloride, heptanoyl chloride, butyl chloroformate, 3-cyclopentylpropionyl chloride, 2-methoxyethyl chloroformate and trans-3-cyclohexylacryloyl chloride instead of 3,4-dichlorophenylacetyl chloride.

Compound 22

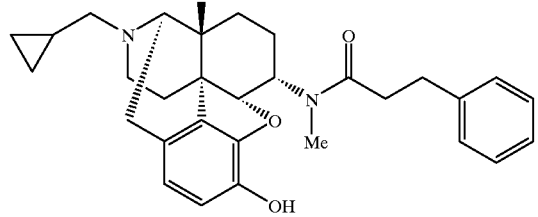

mp >203° C. (decomposition)

NMR (500 MHz, DMSO-$d_6$)

δ 0.13–0.27 (2H, m), 0.47–0.59 (2H, m), 0.80–0.95 (1H, m), 1.06–1.57 (5H, m), 1.68–1.79 (1H, m), 1.95–2.33 (2H, m), 2.57–2.89 (6H, m), 2.88 (2.1H, s), 3.17 (0.9H, s), 3.00–3.53 (3H, m), 3.45 (3H, brs), 4.09 (1H, s), 4.29–4.36 (0.3H, m), 4.54 (0.7H, d, J=3.7 Hz). 4.54–4.59 (0.3H, m), 4.92 (0.7H, m), 6.51 (0.7H, d, J=8.0 Hz), 6.49–6.52 (0.3H, m), 6.62 (1H, d, J=8.0 Hz), 7.05–7.31 (5H, m), 9.10 (1H, brs).

IR (KBr)

υ 3420, 1605, 1460, 1174, 1120, 1073, 1036 cm$^{-1}$.

Mass (EI)

m/z=488 M+.

Elementary Analysis: As $C_{30}H_{36}N_2O_4 \cdot 0.5C_4H_6O_6 \cdot 0.2H_2O$

Calcd.: C, 67.75; H, 7.00; N, 4.94.

Found.: C, 67.79; H, 7.09; N, 5.04.

Compound 23

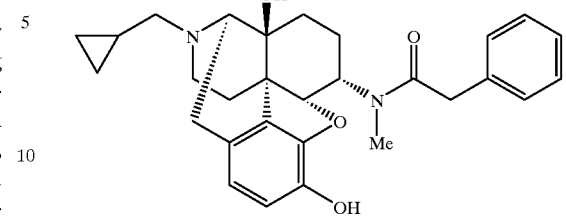

mp 253.0–257.0° C. (decomposition, ether)

NMR (400 MHz, DMSO-$d_6$)

δ 0.40 (1H, m), 0.47 (1H, m), 0.60 (1H, m), 0.69 (1H, m), 1.05 (1H, m), 1.09 (1H, m), 1.34 (1H, m), 1.47 (1H, m), 1.56 (1H, dd, J=14.7, 9.3 Hz), 1.61 (1H, d, J=13.7 Hz), 1.91 (1H, m), 2.36~2.52 (2H, m), 2.69 (1H, m), 2.80 (0.8H, s), 2.93 (1H, m), 2.95 (2.2H, s), 3.15 (1H, d, J=12.2 Hz), 3.09 (1H, dd, J=19.8, 7.1 Hz), 3.76 (2H, s), 3.89 (1H, br s), 4.27 (0.27H, s), 4.51 (0.27H, m), 4.63 (0.73H, d, J=3.4 Hz), 5.00 (0.73H, dt, J=13.7, 3.4 Hz), 6.20 (0.73H, brs), 6.40 (0.27H, m), 6.58 (1H, d, J=8.3 Hz), 6.72 (1H, dd, J=8.3, 2.0 Hz), 7.22~7.29 (2H, m), 7.30~7.38 (3H, m), 8.80 (1H, br s), 9.29 (1H, d, J=5.9 Hz).

IR (KBr)

υ 3400, 3100, 2952, 1620, 1508, 1475, 1319, 1120, 1036, 806 cm$^{-1}$.

Mass (FAB)

m/z 475 (M+H)+.

Elementary Analysis: As $C_{29}H_{35}N_2O_4Cl \cdot 0.3H_2O$

Calcd.: C, 67.44; H, 6.95; N, 5.43; Cl, 6.86.

Found.: C, 67.45; H, 7.15; N, 5.40; Cl, 6.99.

Compound 24

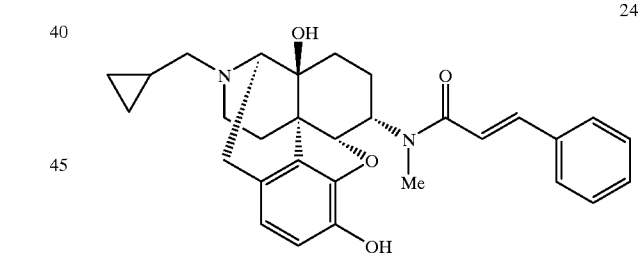

mp 254–257° C.

NMR (400 MHz, DMSO-$d_6$)

δ 0.21 (2H, m), 0.52 (2H, m), 0.91 (1H, m), 1.20 (1.5H, m), 1.48 (3H, m), 1.78 (1H, m), 2.26 (2.5H, m), 2.58 (1H, m), 2.73 (2H, m), 2.91 (0.5H, s), 3.06 (1H, m), 3.09 (2.5H, m), 3.20–3.90 (4H, br), 4.03 (1H, s), 4.5–5.1 (2H, m), 6.52 (1H, d, J=7.9 Hz), 6.62 (1H, d, J=7.9 Hz), 7.09 (0.2H, d, J=15.9 Hz), 7.23 (0.8H, d, J=15.9 Hz), 7.40–7.60 (4H, m), 7.60–7.80 (2H, m), 8.80–9.20 (1H, br).

IR (KBr)

υ 3400, 1644, 1593, 1317, 1118, 1038, 768 cm$^{-1}$.

Mass (FAB)

m/z 487 (M+H)

Elementary Analysis: As $C_{32}H_{37}N_2O_7 \cdot 0.8H_2O$

Calcd.: C, 66.72; H, 6.75; N, 4.86

Found.: C, 66.56; H, 6.74; N, 5.08

Compound 25

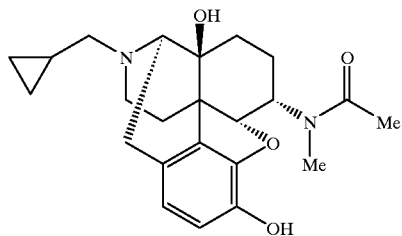

mp >300.0° C. (decomposition, ether)
NMR (400 MHz, DMSO-$d_6$)
δ 0.40 (1H, m), 0.48 (1H, m), 0.61 (1H, m), 0.69 (1H, m), 1.05 (1H, m), 1.13 (1H, m), 1.33 (1H, m), 1.55 (1H, dd, J=15.3, 9.8 Hz), 1.59 (1H, d, J=14.0 Hz),1.92 (1H, dt, J=15.3, 9.5 Hz), 2.05 (2.5H, s), 2.13 (0.5H, s), 2.43 (1H, dt, J=13.4, 4.9 Hz), 2.69 (1H, m), 2.77 (0.5H, s), 2.89 (2.5H, s), 2.94 (1H, dd, J=13.1, 7.0 Hz), 3.03 (1H, br d, J=10.3 Hz), 3.09 (1H, dd, J=20.1, 7.3 Hz), 3.24~3.38 (2H, m), 3.91 (1H, d, J=6.7 Hz), 4.37 (0.17H, br d, J=12.2 Hz), 4.61 (0.83H, d, J=4.3 Hz), 4.81 (0.17H, d, J=4.3 Hz), 4.94 (0.83H, dt, J=14.0, 3.7 Hz), 6.26 (0.83H, s), 6.46 (0.17H, s), 6.58 (1H, d, J=8.2 Hz), 6.73 (1H, dd, J=8.2, 1.8 Hz), 8.82 (1H, br s), 9.31 (1H, s).
IR (KBr)
υ 3400, 3100, 2866, 1618, 1500, 1301, 1172, 1120, 1038, 920 cm$^{-1}$.
Mass (FAB)
m/z 399 (M+H)+.
Elementary Analysis: As $C_{23}H_{30}N_2O_4$•1.12HCl•0.5$H_2O$
Calcd.: C, 61.61; H, 7.22; N, 6.25; Cl, 8.86.
Found.: C, 61.43; H, 7.21; N, 6.33; Cl, 9.00.

Compound 26

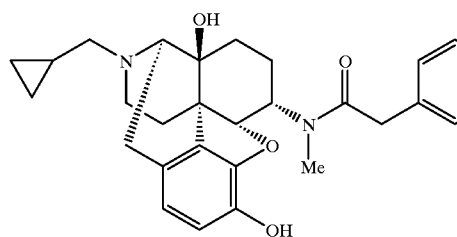

mp 200.0–205.0° C. (decomposition, ether)
NMR (400 MHz, DMSO-$d_6$)
δ 0.40 (1H, m), 0.46 (1H, m), 0.60 (1H, m), 0.68 (1H, m), 1.03 (1H, m), 1.15 (1H, m), 1.36 (1H, m), 1.53~1.65 (2H, m), 1.87 (1H, m), 2.41 (1H, m), 2.68 (1H, m), 2.80 (0.4H, s), 2.96 (2.6H, s), 2.87~3.12 (3H, m), 3.20~3.35 (2H, m), 3.79 (2H, s), 3.85 (1H, m), 4.63 (0.87H, d, J=3.4 Hz), 4.65 (0.13H, m), 4.97 (1H, dt, J=13.7, 3.4 Hz), 6.13 (0.87H, s), 6.22 (0.13H, s), 6.59 (1H, d, J=8.3 Hz), 6.71 (1H, d, J=8.3 Hz), 7.25 (1H, d, J=7.8 Hz), 7.29 (1H, t, J=7.8 Hz), 7.45 (1H, d, J=7.8 Hz), 7.46 (1H, s), 8.76 (1H, br s), 9.29 (1H, s).
IR (KBr)
υ 3400, 2952, 1626, 1506, 1407, 1319, 1120, 1036, 919, 772, 748 cm$^{-1}$
Mass (FAB)
m/z 553 (M+H)+.
Elementary Analysis: As $C_{29}H_{34}N_2O_4Br_2$•0.4$H_2O$
Calcd.: C, 54.29; H, 5.48; N, 4.37; Br, 24.91.
Found.: C, 54.04; H, 5.63; N, 4.34; Br, 25.19.

Compound 27

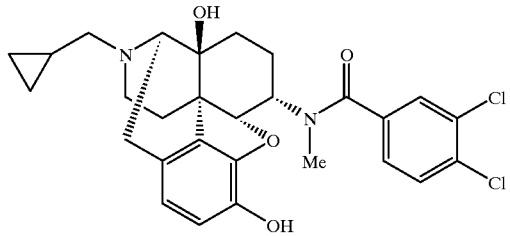

mp 230° C. (decomposition)
NMR (500 MHz, DMSO-$d_6$)
δ 0.32–0.74 (4H, m), 0.93–1.11 (1H, m), 1.12–1.42 (2H, m), 1.45–1.78 (3H, m), 1.94–2.22 (1H, m), 2.65–2.76 (1H, m), 2.86 (2.4H, s), 2.91–3.15 (3.6H, m), 3.20–3.40 (2H, m), 3.79 (0.2H, m), 3.94 (0.8H, m), 4.24 (0.2H, m), 4.62 (0.2H, m), 4.85 (0.8H, m), 4.98 (0.8H, m), 5.97 (0.2H, br s), 6.35 (0.8H, br s), 6.59 (1H, d, J=7.9 Hz), 6.73 (1H, d, J=7.9 Hz), 7.40–7.50 (1H, m), 7.69–7.79 (2H, m), 8.66 (0.2H, br s), 8.88 (0.8H, br s), 9.31 (0.8H, br s), 9.38 (0.2H, br s).
IR (KBr)
υ 3152, 1626, 1508, 1473, 1408, 1379, 1315, 1033 cm$^{-1}$.
Mass (FAB)
m/z 529 ((M+H)+).
Elementary Analysis: As $C_{28}H_{30}N_2O_4Cl_2$•HCl•0.2$H_2O$
Calcd.: C, 59.05; H, 5.56; N, 4.92; Cl, 18.67.
Found.: C, 58.93; H, 5.68; N, 4.90; Cl 18.54.

Compound 28

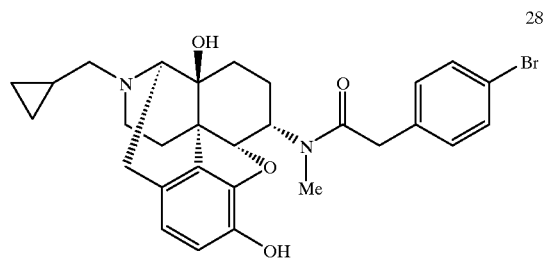

mp 210° C. (decomposition)
NMR (500 MHz, DMSO-$d_6$)
δ 0.45 (2H, m), 0.64 (2H, m), 1.07 (1H, m), 1.15 (2H, m), 1.35 (1H, m), 1.58 (2H, m), 1.90 (1H, m), 2.42 (1H, m), 2.67 (1H, m), 2.80 (0.5H, s), 2.92 (1H, m), 2.95 (2.5H, s), 3.10 (2H, m), 3.31 (1H, m), 3.80 (3H, m), 4.4–5.0 (2H, m), 6.14 (0.8H, brs), 6.23 (0.2H, brs), 6.59 (1H, d, J=8.6 Hz), 6.72 (1H, d, J=8.6 Hz), 7.21 (2H, m), 7.52 (2H, m), 8.76 (1H, brs), 9.0–9.5 (1H, br).
IR (KBr)
υ 3320, 1620, 1466, 1321, 1120, 803 cm$^{-1}$.
Mass (FAB)
m/z 553 (M+H)
Elementary Analysis: As $C_{29}H_{33}N_2O_4Br$•HBr•0.5$H_2O$
Calcd.: C, 54.14; H, 5.48; N, 4.35; Br, 24.84
Found.: C, 53.90; H, 5.42; N, 4.30; Br, 25.21

Compound 29

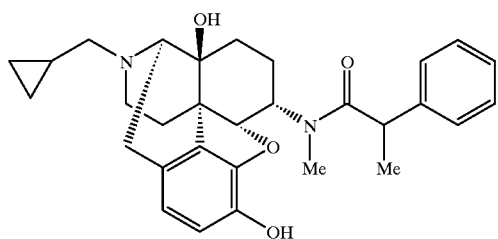

mp >203° C. (decomposition)
NMR (400 MHz, DMSO-$d_6$)
δ 0.35–0.75 (4H, m), 1.07–1.15 (3H, m), 1.33 (3H, d, J=6.8 Hz), 1.40–1.67 (2H, m), 1.84–2.15 (1.4H, m), 2.43–2.75 (0.6H, m), 2.80 (0.9H, s), 2.81 (2.1H, s), 2.90–3.15 (3H, m), 3.20–3.50 (3H, m), 3.85–3.95 (1H, m), 4.12–4.28 (1H, m), 4.53–4.70 (1.3H, m), 4.95–5.05 (0.7H, m), 6.25 (0.7H, brs), 6.40–6.60 (1.3H, m), 6.66 (0.3H, d, J=8.3 Hz), 6.71 (0.7H, d, J=7.8 Hz), 7.18–7.42 (5H, m), 8.80–8.95 (1H, brs), 9.21 (0.3H, s), 9.30 (0.7H, s).
IR (KBr)
υ 3420, 1620, 1508, 1460, 1120, 1067, 1036, 704 $cm^{-1}$
Mass (FAB)
m/z 489 (M+H)+.
Elementary Analysis: As $C_{30}H_{36}N_2O_4 \cdot HCl \cdot 0.3H_2O$
Calcd.: C, 67.92; H, 7.14; N, 5.28; Cl, 6.68.
Found.: C, 68.05; H, 7.21; N, 5.39; Cl, 6.31.

Compound 30

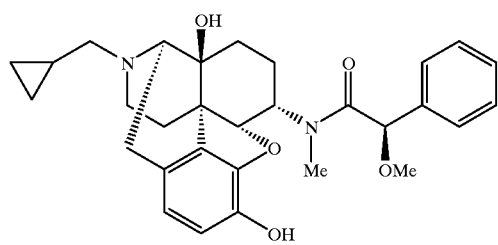

mp 207.0–211.0° C. (decomposition, ether)
NMR (400 MHz, DMSO-$d_6$)
δ 0.39 (1H, m), 0.47 (1H, m), 0.61 (1H m), 0.68 (1H, m), 1.07 (1H, m), 1.22 (1H, m), 1.39 (1H, m), 1.50 (1H, dd, J=15.1, 9.3 Hz), 1.63 (1H, d, J=11.2 Hz), 1.90 (1H, m), 2.30 (0.15H, dt, J=13.2, 4.9 Hz), 2.47 (0.85H, dt, J=13.2, 4.9 Hz), 2.64 (1H, m), 2.81 (0.45H, s), 2.88 (2.55H, s), 2.95~3.10 (3H, m), 3.20~3.35 (2H, m), 3.30 (0.45H, s), 3.40 (2.55H, s), 3.78 (0.15H, br s), 3.92 (0.85H, d, J=6.8 Hz), 4.64 (0.15H, br d, J=12.7 Hz), 4.69 (1H, d, J=3.4 Hz), 4.95 (0.85H, br d, J=13.7 Hz), 5.26 (0.85H, s), 5.35 (0.15H, s), 6.28 (0.85H, s), 6.54 (0.15H, d, J=8.3 Hz), 6.57 (0.85H, d, J=8.3 Hz), 6.63 (0.15H, s), 6.69 (0.15H, d, J=8.3 Hz), 6.72 (0.85H, d, J=8.3 Hz), 7.31~7.46 (5H, m), 8.86 (0.85H, br s), 8.92 (0.15H, br s), 9.27 (0.15H, s), 9.34 (0.85H, s).
IR (KBr)
υ 3400, 1638, 1460, 1321, 1120, 1035, 600, 418 $cm^{-1}$
Mass (FAB)
m/z 505 (M+H)+.
Elementary Analysis: As $C_{30}H_{37}N_2O_5Cl \cdot 0.4H_2O$
Calcd.: C, 65.72; H, 6.95; N, 5.11; Cl, 6.47.
Found.: C, 65.77; H, 7.14; N, 5.23; Cl, 6.41.

Compound 31

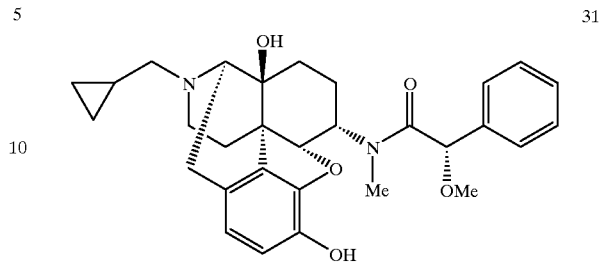

mp 270.0–275.0° C. (decomposition, ether)
NMR (400 MHz, DMSO-$d_6$)
δ 0.40 (1H, m), 0.48 (1H, m), 0.62 (1H, m), 0.69 (1H, m), 1.07 (1H, m), 1.11 (1H, m), 1.35 (1H, m), 1.50 (1H, t, J=14.5 Hz), 1.57 (1H, t, J=15.6 Hz), 1.86 (0.22H, m), 1.97 (0.78H, m), 2.44 (1H, dt, J=13.2, 4.4 Hz), 2.66 (1H, m), 2.80 (0.66H, s), 2.88 (2.34H, s), 2.96~3.12 (3H, m), 3.24~3.37 (2H, m), 3.30 (2.34H, s), 3.38 (0.66H, s), 3.92 (1H, d, J=5.9 Hz), 4.27 (0.22H, d, J=1.5 Hz), 4.56 (0.78H, d, J=3.4 Hz), 4.75 (0.22H, m), 5.07 (0.78H, br d, J=13.7 Hz), 5.19 (0.78H, s), 5.24 (0.22H, s), 6.31 (0.78H, s), 6.50 (0.22H, s), 6.56 (1H, d, J=8.3 Hz), 6.71 (1H, d, J=8.3 Hz), 7.34~7.43 (5H, m), 8.85 (1H, br s), 9.27 (0.78H, s), 9.30 (0.22H, s).
IR (KBr)
υ 3500, 3100, 2942, 2346, 1638, 1508 1475, 1319, 1176, 1120, 1036, 905 $cm^{-1}$.
Mass (FAB)
m/z 505 (M+H)+.
Elementary Analysis: As $C_{30}H_{37}N_2O_5Cl \cdot 0.3H_2O$
Calcd.: C, 65.93; H, 6.94; N, 5.13; Cl, 6.49.
Found.: C, 65.89; H, 7.02; N, 5.12; Cl, 6.53.

Compound 32

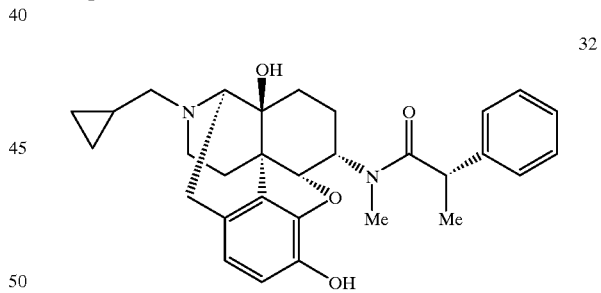

mp 162–165° C.
NMR (400 MHz, DMSO-$d_6$)
δ 0.21 (2H, m), 0.53 (2H, m), 0.91 (1H, m), 1.09 (1H, m), 1.28 (3H, d, J=6.4 Hz), 1.3–1.5 (3.3H, m), 1.75 (0.7H, m), 2.2–2.3 (2H, m), 2.4–2.8 (4H, m), 2.78 (1H, s), 2.84 (2H, s), 3.0–3.3 (2H, m), 4.04 (1H, s), 4.0–4.1 (1H, m), 4.4–5.1 (2H, m), 6.47 (1H, m), 6.59 (1H, m), 7.2–7.4 (5H, m).
IR (KBr)
υ 3400, 1620, 1462, 1120, 1067, 702 $cm^{-1}$.
Mass (FAB)
m/z 489 (M+H)
Elementary Analysis: As $C_{32}H_{39}N_2O_7 \cdot 0.4H_2O$
Calcd.: C, 67.33; H, 7.03; N, 4.91
Found.: C, 67.28; H, 7.26; N, 4.90

Compound 33

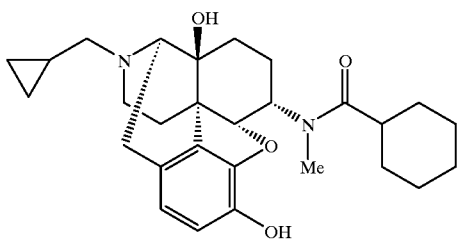

mp >260° C. (decomposition, methanol-ether)
NMR (400 MHz, CD₃OD; data only for major amide form (approximately 90%))

δ 0.49 (2H, m), 0.73 (1H, m), 0.83 (11, m), 1.08 (1H, m), 1.22–1.57 (7H, m), 1.62–1.98 (8H, m), 2.57–2.74 (2H, m), 2.83–3.02 (2H, m), 3.04–3.20 (2H, m), 3.06 (3H, s), 3.22–3.39 (2H, m), 3.97 (1H, m), 4.74 (1H, m), 5.08 (1H, ddd, J=14.7, 3.9, 3.9 Hz), 6.67 (1H, d, J=8.3 Hz), 6.75 (1H, d, J=8.3 Hz).

IR (KBr)
υ 3366, 1607, 1510, 1473, 1319, 1197, 1118, 1038, 907, 804 cm⁻¹.

Mass (FAB)
m/z 467 ((M+H)+).
Elementary Analysis: As C₂₈H₃₈N₂O₄•HCl
Calcd.: C, 66.85; H, 7.81; N 5.57; Cl, 7.05.
Found.: C, 66.87; H, 7.90; N, 5.53; Cl, 7.03.

Compound 34

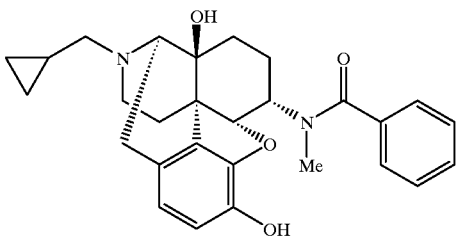

mp 235° C. (decomposition)
NMR (500 MHz, DMSO-d₆)

δ 0.35–0.76 (4H, m), 0.96–1.14 (1H, m), 1.16–1.42 (2H, m), 1.43–1.82 (3H, m), 1.96–2.20 (1H, m), 2.58–2.77 (1H, m), 2.78–3.07 (6H, m), 3.20–3.35 (2H, m), 3.79 (0.2H, m), 3.96 (0.8H, m), 4.35 (0.2H, m), 4.58 (0.2H, m), 4.87 (0.8H, m), 5.01 (0.8H, m), 5.95 (0.2H, br s), 6.38 (0.8H, br s), 6.59 (1H, d, J=7.3 Hz), 6.73 (1H, d, J=7.3 Hz), 7.40–7.50 (5H, m), 8.63 (0.2H, br s), 8.88 (0.8H, br s), 9.31 (0.8H, br s), 9.38 (0.2H, br s).

IR (KBr)
υ 3270, 3072, 1613, 1506, 1475, 1321, 1120, 1069, 905, 806, 710 cm⁻¹

Mass (FAB)
m/z 461 ((M+H)+).
Elementary Analysis: As C₂₈H₃₂N₂O₄•HCl•0.7H₂O
Calcd.: C, 65.99; H, 6.80; N, 5.49; Cl, 6.96.
Found.: C, 65.97; H, 6.86; N, 5.55; Cl, 6.94.

Compound 35

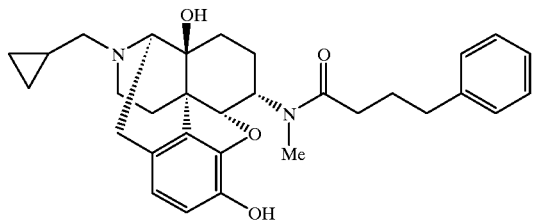

mp 235° C. (decomposition)
NMR (400 MHz, DMSO-d₆)

δ 0.40 (1H, m), 0.47 (1H, m), 0.61 (1H, m), 0.68 (1H, m), 1.01–1.09 (2H, m), 1.36 (1H, m), 1.50–1.64 (2H, m), 1.80–1.98 (3H, m), 2.34–2.46 (3H, m), 2.60–2.75 (3H, m), 2.80 (0.6H, s), 2.85 (2.4H, s), 2.88–3.14 (3H, m), 3.22–3.35 (2H, m), 3.90 (1H, m), 4.41 (0.2H, m), 4.61 (0.8H, d, J=3.9 Hz), 4.68 (0.2H, m), 4.97 (0.8H, m), 6.24 (0.8H, br s), 6.46 (0.2H, br s), 6.58 (1H, d, J=8.1 Hz), 6.75 (1H, m), 7.16–7.26 (3H, m), 7.30 (2H, m), 8.82 (1H, br s), 9.30 (0.8H, s), 9.33 (0.2H, s).

IR (KBr)
υ 3068, 1618, 1508, 1475, 1369, 1317, 1118, 1036, 919, 806, 750, 704 cm⁻¹.

Mass (FAB)
m/z 503 ((M+H)+).
Elementary Analysis: As C₃₁H₃₈N₂O₄•HCl
Calcd.: C, 69.06; H, 7.29; N, 5.19; Cl, 6.58.
Found.: C, 69.05; H, 7.43; N, 5.27; Cl, 6.43.

Compound 36

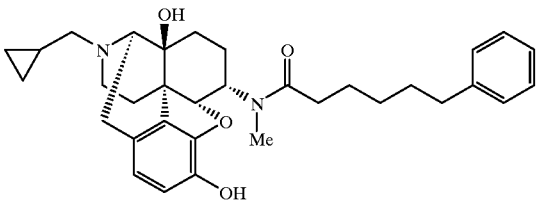

mp 225° C. (decomposition)
NMR (400 MHz, DMSO-d₆)

δ 0.40 (1H, m), 0.47 (1H, m), 0.61 (1H, m), 0.68 (1H, m), 1.01–1.20 (2H, m), 1.25–1.37 (3H, m), 1.50–1.64 (6H, m), 1.91 (1H, m), 2.33 (2H, t, J=7.1 Hz), 2.42 (1H, m), 2.58 (2H, t, J=7.5 Hz), 2.68 (1H, m), 2.78 (0.6H, s), 2.87 (2.4H, s), 2.93 (1H, m), 2.99–3.14 (2H, m), 3.24–3.35 (2H, m), 3.89 (1H, m), 4.42 (0.2H, m), 4.59 (0.8H, d, J=3.4 Hz), 4.76 (0.2H, m), 4.96 (0.8H, m), 6.22 (0.8H, s), 6.44 (0.2H, s), 6.58 (1H, d, J=7.8 Hz), 6.72 (1H, d, J=7.8 Hz), 7.16–7.23 (3H, m), 7.24–7.30 (2H, m), 8.81 (1H, br S), 9.29 (0.8H, s), 9.31 (0.2H, s).

IR (KBr)
υ 3086, 1618, 1508, 1460, 1315, 1174, 1120, 1038, 748, 700 cm⁻¹.

Mass (FAB)
m/z 531 ((M+H)+).
Elementary Analysis: As C₃₃H₄₂N₂O₄•HCl
Calcd.: C, 69.88; H, 7.64; N, 4.94; Cl, 6.25.
Found.: C, 69.70; H, 7.64; N, 4.98; Cl, 6.25.

Compound 37

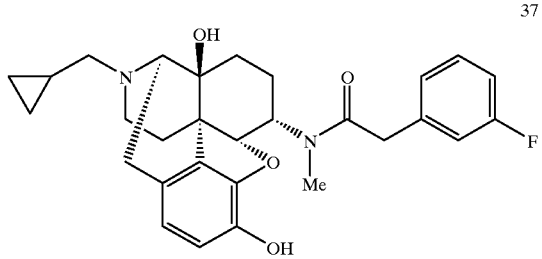

mp 225° C. (decomposition)
NMR (400 MHz, DMSO-$d_6$)
δ 0.40 (1H, m), 0.47 (1H, m), 0.61 (1H, m), 0.69 (1H, m), 1.01–1.20 (2H, m), 1.35 (1H, m), 1.50–1.64 (2H, m), 1.90 (1H, m), 2.41 (1H, m), 2.67 (1H, m), 2.70 (0.6H, s), 2.95 (2.4H, s), 2.89–3.13 (3H, m), 3.23–3.35 (2H, m), 3.80 (1.6H, s), 3.85–3.94 (1.4H, m), 4.47 (0.2H, m), 4.51 (0.2H, m), 4.63 (0.8H, d, J=3.9 Hz), 4.98 (0.8H, m), 6.20 (0.8H, s), 6.43 (0.2H, br S), 6.58 (1H, d, J=8.3 Hz), 6.72 (1H, d, J=8.3 Hz), 7.05–7.15 (3H, m), 7.35 (1H, m), 8.80 (1H, br s), 9.30 (0.2H, s), 9.31 (0.8H, s).
IR (KBr)
δ 3120, 1620, 1510, 1460, 1321, 1118, 777, 683, 518 cm$^{-1}$.
Mass (FAB)
m/z 493 ((M+H)+).
Elementary Analysis: As $C_{29}H_{33}N_2O_4F•HCl$
Calcd.: C, 65.83; H, 6.48; N, 5.29; Cl, 6.70; F, 3.59.
Found.: C, 65.69; H, 6.59; N, 5.44; Cl, 6.43; F, 3.60.

Compound 38

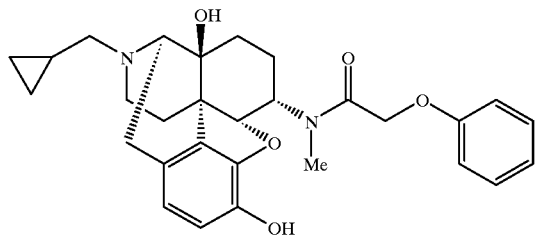

mp 198.0–206.0° C. (decomposition, diethylether)
NMR (400 MHz, DMSO-$d_6$)
δ 0.10–0.30 (2H, m), 0.44–0.63 (2H, m), 0.83–0.99 (1H, m), 0.90–1.28 (1H, m), 1.28–1.39 (1H, m), 1.39–1.57 (2H, m), 1.66–1.84 (1H, m), 2.12–2.38 (2H, m), 2.41–2.65 (2H, m), 2.65–2.80 (2H, m), 2.84 (0.6H, s), 2.95 (2.4H, s), 3.00–3.13 (1H, m), 3.20–3.34 (1H, m), 2.50–4.25 (3H, br s), 4.05 (1H, s), 4.38 (0.2H, dt J=11.2, 3.4 Hz), 4.54 (0.8H, d, J=3.4 Hz), 4.85 (2H, s), 4.76– 4.96 (1H, m), 6.51 (1H, d, J=7.8 Hz), 6.64 (1H, d, J=8.3 Hz), 6.86–7.02 (3H, m), 7.22–7.37 (2H, m), 8.65–9.60 (1H, br s).
IR (KBr)
υ 1601, 1562, 1497, 1460, 1321, 1236, 1120, 1067, 919, 758 cm$^{-1}$
Mass (FAB)
m/z 491 ((M+H)).
Elementary Analysis: As $C_{31}H_{37}N_2O_5•0.8H_2O$
Calcd.: C, 64.19; H, 6.70; N, 4.83
Found: C, 64.16; H, 6.64; N, 4.89

Compound 39

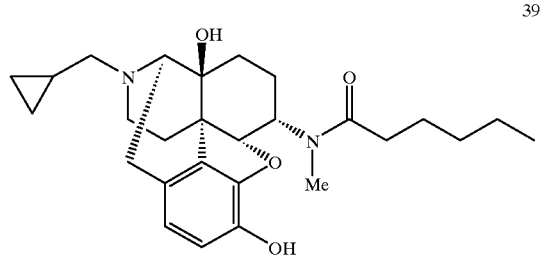

mp 205–207° C.
NMR (400 MHz, DMSO-$d_6$)
δ 0.18–0.30 (2H, m), 0.47–0.60 (2H, m), 0.82–0.97 (4H, m), 1.13 (1H, m), 1.24–1.38 (5H, m), 1.38–1.60 (4H, m), 1.75 (1H, m), 2.20–2.40 (4H, m), 2.57 (1H, m), 2.70–2.79 (3H, m), 2.80 (0.6H, s), 2.88 (2.4H, s), 3.00–3.63 (5H, m), 4.10 (1H, s), 4.36 (0.2H, m), 4.53 (0.8H, d, J=3.4 Hz), 4.62 (0.2H, m), 4.95 (0.8H, m), 6.52 (1H, d, J=8.3 Hz), 6.63 (1H, d, J=8.3 Hz), 9.10 (1H, br s).
IR (KBr)
υ 3230, 1609, 1460, 1317, 1122 cm$^{-1}$.
Mass (FAB)
m/z 455 ((M+H)+).
Elementary Analysis: As $C_{27}H_{38}N_2O_4•0.5C_4H_6O_6•0.5H_2O$
Calcd.: C, 64.66; H, 7.86; N, 5.20.
Found.: C, 64.54; H, 7.76; N, 5.31.

Compound 40

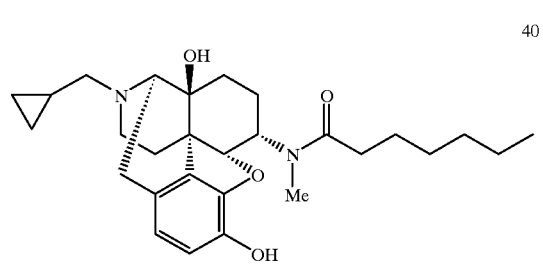

mp 210–212° C. (decomposition)
NMR (500 MHz, DMSO-$d_6$)
δ 0.25–0.35 (2H, m), 0.45–0.57 (2H, m), 0.84–0.96 (4H, m), 1.11 (1H, m), 1.21–1.35 (8H, m), 1.39–1.580 (4H, m), 1.72 (1H, m), 2.15–2.25 (2H, m), 2.27–2.35 (2H, m), 2.51 (1H, m), 2.65–2.76 (2H, m), 2.79 (0.6H, s), 2.88 (2.4H, s), 2.95–3.80 (5H, m), 4.03 (1H, s), 4.34 (0.2H, m), 4.51 (0.8H, d, J=3.4 Hz), 4.61 (0.2H, m), 4.89 (0.8H, m), 6.50 (1H, d, J=8.3 Hz), 6.62 (1H, d, J=8.3 Hz), 9.20 (1H, br s).
IR (KBr)
υ 3180, 1607, 1460, 1359, 1317, 1122 cm$^{-1}$.
Mass (FAB)
m/z 469 ((M+H)+).
Elementary Analysis: As $C_{28}H_{40}N_2O_4•0.5C_4H_6O_6$
Calcd.: C, 66.27; H, 7.97; N, 5.15.
Found.: C, 66.38; H, 8.14; N, 5.33.

Compound 41

41 mp 195–210° C.
NMR (400 MHz, DMSO-$d_6$)
δ 0.15–0.28 (2H, m), 0.47–0.60 (2H, m), 0.92 (1H, m), 1.12 (1H, m), 1.24 (1H, m), 1.40–1.55 (2H, m), 1.73 (1H, m), 2.20–2.35 (2H, m), 2.55 (1H, m), 2.60–2.92 (9H, m), 3.05 (1H, m), 3.15–3.95 (5.7H, m), 4.10 (1.7H, s), 4.32 (0.2H, m), 4.54 (0.8H, d, J=3.4 Hz), 4.61 (0.2H, m), 4.90 (0.8H, m), 6.52 (1H, d, J=8.3 Hz), 6.63 (1H, d, J=8.3 Hz), 7.33 (1H, m), 7.71 (1H, m), 8.40 (1H, m), 8.50 (1H, m), 9.08 (1.7H, br s).
IR (KBr)
υ 3220, 1607, 1460, 1311, 1120 cm$^{-1}$.
Mass (FAB)
m/z 490 ((M+H)+).
Elementary Analysis: As $C_{29}H_{35}N_3O_4 \cdot 0.85C_4H_6O_6 \cdot 0.3H_2O$
Calcd.: C, 62.50; H, 6.59; N, 6.75.
Found.: C, 62.33; H, 6.77; N, 6.78.

Compound 42

42 mp 254.0–259.0° C. (decomposition, ether)
NMR (400 MHz, DMSO-$d_6$)
δ 0.40 (1H, m), 0.47 (1H, m), 0.60 (1H, m), 0.69 (1H, m), 1.06 (1H, m), 1.40–1.64 (3H, m), 1.90 (1H, m), 2.44 (1H, m), 2.69 (1H, m), 2.85 (3H, s), 2.92 (1H, m), 3.03 (1H, m), 3.09 (1H, dd, J=20.0, 6.4 Hz), 3.23–3.38 (3H, m), 3.89 (1H, br d, J=5.4 Hz), 4.59, 4.63, 4.67 (2H, each br s), 5.13–5.23 (2H, m), 6.23 (1H, s), 6.58 (1H, d, J=8.1 Hz), 6.71 (1H, d, J=8.1 Hz), 7.35 (1H, m), 7.39, 7.40 (4H, each s), 8.80 (1H, br s), 9.29 (1H, br s).
IR (KBr)
υ 3500, 3100, 2850, 1663, 1470, 1350, 1317, 1156, 1120, 1035 cm$^{-1}$.
Mass (FAB)
m/z 491 (M+H)+.
Elementary Analysis: As $C_{29}H_{35}N_2O_5Cl \cdot 0.2H_2O$
Calcd.: C, 65.64; H, 6.72; N, 5.28; Cl, 6.68.
Found.: C, 65.66; H, 6.71; N, 5.30; Cl, 6.70.

Compound 43

43 mp 198.0–206.0° C. (decomposition, diethylether)
NMR (400 MHz, DMSO-$d_6$)
δ 0.31–0.43 (1H, m), 0.43–0.57 (1H, m), 0.57–0.65 (1H, m), 0.65–0.77 (1H, m), 1.00–1.25 (2H, m), 1.38–1.70 (3H, m), 1.87–2.09 (1H, m), 2.35–2.50 (1H, m), 2.60–2.79 (1H, m), 2.89–3.18 (3H, m), 2.87 (1.4H, s), 2.90 (1.6H, s), 3.18–3.38(2H, m), 3.95 (1H, br s), 4.57–4.80 (2H, m), 5.29 (1.2H, s), 5.22–5.40 (0.8H, m), 6.35 (0.6H, brs), 6.45 (0.4H, br s), 6.59 (1H, d, J=7.8 Hz), 6.74 (1H, dd, J=8.3, 2.0 Hz), 7.60–7.74 (2H, m), 8.20–8.36 (2H, m), 8.87 (1H, br s), 9.34 (0.4H, s), 9.35 (0.6H, s).
IR (KBr)
υ 1686, 1638, 1560, 1543, 1522, 1460, 1346, 1120, 1035 cm$^{-1}$.
Mass (FAB)
m/z 536 ((M+H)+).
Elementary Analysis: As $C_{29}H_{34}N_3O_7Cl \cdot 0.3H_2O$
Calcd.: C, 60.21; H, 6.20; N, 7.26; Cl, 6.13.
Found.: C, 60.29; H, 6.18; N, 7.16; Cl, 6.24.

Compound 44

44 mp >130° C. (decomposition)
NMR (400 MHz, DMSO-$d_6$)
δ 0.15–0.30 (2H, m), 0.45–0.60 (2H, m), 0.85–0.98 (1H, m), 1.05–1.20 (1H, m), 1.30–1.53 (3H, m), 1.68–1.82 (1H, m), 2.10–2.40 (2H, m), 2.45–2.90 (4H, m), 2.85 (3H, s), 3.00–3.18 (1H, m), 3.21–3.42 (1H, m), 4.11 (2H, s), 4.49–4.62 (2H, m), 5.10–5.30 (2H, m), 6.51 (1H, d, J=8.0 Hz), 6.62 (1H, d, J=8.0 Hz), 7.39–7.48 (1H, m), 7.81 (1H, d, J=7.3 Hz), 8.55 (1H, d, J=3.4 Hz), 8.62 (1H, s), 9.00 (2H, brs).
IR (KBr)
υ 3312, 1692, 1603, 1406, 1350, 1311, 1267, 1122, 1069, 1035 cm$^{-1}$
Mass (EI)
m/z 492 (M+H)+.
Elementary Analysis: As $C_{28}H_{33}N_3O_5 \cdot C_4H_6N_6 \cdot 0.3H_2O$
Calcd.: C, 59.40; H, 6.17; N, 6.50.
Found.: C, 59.39; H, 6.27; N, 6.52.

Compound 45

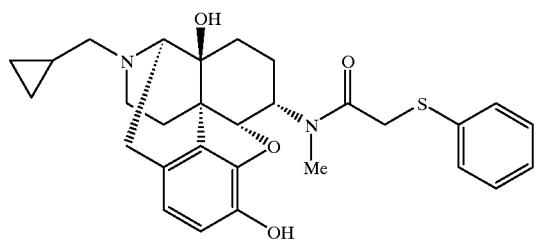

mp 197.0° C. (decomposition, diethylether)
NMR (400 MHz, DMSO-$d_6$)
δ 0.10–0.30 (2H, m), 0.44–0.63 (2H, m), 0.83–0.99 (1H, m), 1.00–1.20 (1H, m), 1.20–1.35 (1H, m), 1.35–1.57 (2H, m), 1.66–1.84 (1H, m), 2.10–2.34 (2H, m), 2.39–2.62 (2H, m), 2.62–2.79 (2H, m), 2.82 (0.6H, s), 2.99 (2.4H, s), 3.00–3.13 (1H, m), 3.20–3.34 (1H, m), 2.00–3.98 (3H, br s), 4.05 (1H, s), 3.95–4.13 (2H, m), 4.41 (0.2H, br d, J=12.2 Hz), 4.52 (0.8H, d, J=3.7 Hz), 4.80–4.90 (1H, m), 6.51 (1H, d, J=8.6 Hz), 6.63 (1H, d, J=7.9 Hz), 7.15–7.27 (1H, m), 7.27–7.38 (2H, m), 7.38–7.46 (2H, m), 8.65–9.50 (1H, br s).
IR (KBr)
υ 3430, 1618, 1508, 1460, 1400, 1120, 1036, 917, 746, 692 cm$^{-1}$.
Mass (FAB)
m/z 507 ((M+H)+).
Elementary Analysis: As $C_{31}H_{37}N_2O_7S$•0.5$H_2O$
Calcd.: C, 63.03; H, 6.48; N, 4.74; S, 5.43
Found.: C, 63.14; H, 6.51; N, 4.65; S, 5.33

Compound 46

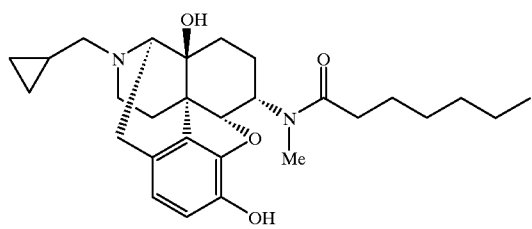

mp >230° C. (decomposition)
NMR (400 MHz, $CD_3OD$)
δ 0.50 (2H, m), 0.73 (1H, m), 0.92 (3H, t, J=6.8 Hz), 1.09 (1H, m), 1.28–1.55 (8H, m), 1.59–1.79 (4H, m), 1.93 (1H, m), 2.38–2.56 (2H, m), 2.64 (1H, m), 2.84–3.05 (2H, m), 2.93 (0.45H, s), 3.02 (2.55H, s), 3.05–3.22 (2H, m), 3.23–3.40 (2H, m), 3.98 (1H, m), 4.57 (0.15H, m), 4.76 (1H, br d, J=2.9 Hz), 5.09 (0.85H, ddd, J=13.7, 3.9, 3.9 Hz), 6.67 (0.85H, d, J=8.3 Hz), 6.68 (0.15H, d, J=8.3 Hz), 6.75 (0.85H, d, J=8.3 Hz), 6.76 (0.15H, d, J=8.3 Hz).
IR (KBr)
υ 3400, 3158, 1624, 1508, 1468, 1317, 1174, 1120, 1038, 907, 808 cm$^{-1}$.
Mass (FAB)
m/z 469 ((M+H)+).
Elementary Analysis: As $C_{28}H_{40}N_2O_4$•HCl•0.2$H_2O$
Calcd.: C, 66.11; H, 8.20; N, 5.51; Cl, 6.97
Found.: C, 66.02; H, 8.07; N, 5.64; Cl, 7.02. .

Compound 47

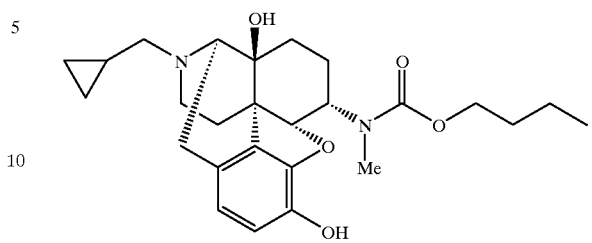

mp 169–170° C. (ethylacetate-methanol)
NMR (400 MHz, DMSO-$d_6$)
δ 0.18 (2H, m), 0.44–0.56 (2H, m), 0.84–0.96 (4H, m), 1.10 (1H, m), 1.30–1.53 (5H, m), 1.53–1.62 (2H, m), 1.73 (1H, m), 2.12–2.38 (2H, m), 2.41–2.57 (2H, m), 2.63–2.75 (2H, m), 2.80 (3H, s), 3.04 (1H, d, J=18.6 Hz), 3.24 (1H, m), 3.45 (3H, br s, 3×OH), 3.95–4.15 (2H, m), 4.04 (1H, s), 4.48 (1H, m), 4.56 (1H, m), 6.50 (1H, d, J=7.8 Hz), 6.61 (1H, d, J=7.8 Hz), 9.05 (1H, br s, NH+).
IR (KBr)
υ 3366, 1678, 1613, 1462, 1406, 1350, 1317, 1176, 1122, 1069, 1035, 861, 808 cm$^{-1}$.
Mass (FAB)
m/z 457 ((M+H)+).
Elementary Analysis: As $C_{26}H_{36}N_2O_5$•0.5$C_4H_6O_6$•0.5$H_2O$
Calcd.: C, 62.21; H, 7.46; N, 5.18.
Found.: C, 62.40; H, 7.15; N, 5.23.

Compound 48

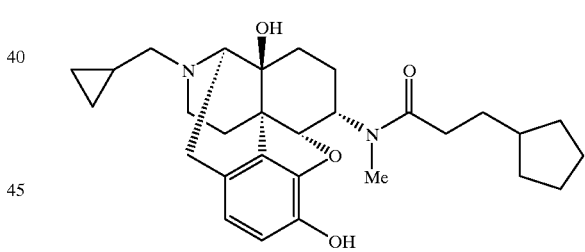

mp 200–212° C. (decomposition)
NMR (400 MHz, DMSO-$d_6$)
δ 0.19 (2H, m), 0.45–0.57 (2H, m), 0.90 (1H, m), 1.03–1.18 (3H, m), 1.27 (1H, m), 1.34–1.63 (8H, m), 1.66–1.82 (4H, m), 2.16–2.56 (6H, m) 2.63–2.77 (2H, m), 2.79 (0.6H, s), 2.89 (2.4H, s), 3.03 (1H, br d, J=18.6 Hz), 3.25 (1H, m), 3.45 (3H, br s, 3×OH), 4.03 (1H, s), 4.35 (0.2H, m), 4.52 (0.8H, d, J=3.4 Hz), 4.59 (0.2H, m), 4.88 (0.8H, dt, J=14.1, 3.9 Hz), 6.50 (1H, d, J=8.3 Hz), 6.62 (0.8H, d, J=8.3 Hz), 6.63 (0.2H, d, J=8.3 Hz), 9.06 (1H, br s, NH+).
IR (KBr)
υ 3316, 1719, 1603, 1462, 1408, 1361, 1321, 1172, 1122, 1071, 1038, 917, 808 cm$^{-1}$.
Mass (FAB)
m/z 481 ((M+H)+).
Elementary Analysis: As $C_{29}H_{40}N_2O_4$•0.5$C_4H_6O_6$•0.2$H_2O$ Calcd.: C, 66.57; H, 7.82; N, 5.01.

Found.: C, 66.63; H, 7.83; N, 5.06.

Compound 49

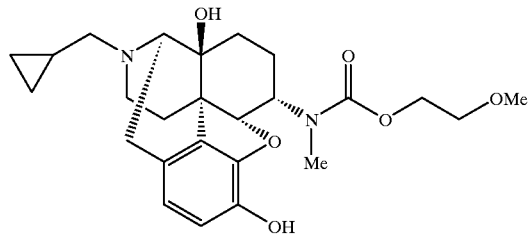

mp >132° C. (decomposition)

NMR (400 MHz, DMSO-$d_6$)

δ 0.20 (2H, m), 0.48–0.58 (2H, m), 0.91 (1H, m), 1.10 (1H, m), 1.22–1.54 (3H, m), 1.73 (1H, m), 2.06–2.34 (2H, m), 2.45–2.62 (2H, m), 2.65–2.78 (2H, m), 2.81 (3H, s), 3.06 (1H, br d, J=18.6 Hz), 3.27 (1H, m), 3.29 (3H, br s), 3.50 (3.2H, br s, 3.1×OH+0.1×COOH), 3.52–3.59 (2H, m), 4.06 (1.1H, s), 4.07–4.30 (2H, m), 4.40–4.64 (2H, m), 6.51 (1H, d, J=8.0 Hz), 6.62 (1H, d, J=8.0 Hz), 9.06 (1H, brs, NH+).

IR (KBr)

υ 3342, 1686, 1609, 1462, 1406, 1346, 1317, 1249, 1176, 1120, 1069, 1036, 924, 903, 806 cm$^{-1}$.

Mass (FAB)

m/z 459 ((M+H)+).

Elementary Analysis: As $C_{25}H_{34}N_2O_6 \cdot 0.55 C_4H_6O_6 \cdot 0.9H_2O$

Calcd.: C, 58.62; H, 7.07; N, 5.03.

Found.: C, 58.67; H, 7.06; N, 4.91.

Compound 50

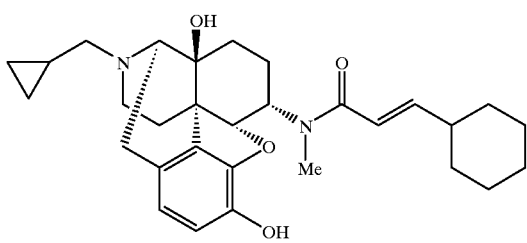

mp 260.0° C. (decomposition)

NMR (400 MHz, DMSO-$d_6$)

δ 0.08–0.32 (2H, m), 0.40–0.64 (2H, m), 0.80–1.00 (1H, m), 1.00–1.38 (7H, m), 1.38–1.83 (6H, m), 2.05–2.38 (3H, m), 2.40–2.65 (2H, m), 2.65–2.81 (3H, m), 2.83 (0.9H, s), 2.95 (2.1H, s), 2.98–3.15 (1H, m), 3.15–3.44 (1H, m), 4.47 (0.3H, m), 4.56 (0.3H, m), 4.58 (0.7H, d, J=3.4 Hz), 4.90 (0.7H, m), 3.50–6.20 (5H, br s), 6.29 (0.3H, d, J=15.1 Hz), 6.37 (0.7H, d, J=14.7 Hz), 6.51 (1H, d, J=8.3 Hz), 6.57–6.74 (2H, m).

IR (KBr)

υ 3420, 1651, 1599, 1450, 1408, 1321, 1120, 1036, 922, 441 cm$^{-1}$.

Mass (FAB)

m/z 493 ((M+H)+).

Elementary Analysis: As $C_{30}H_{43}N_2O_8Pl \cdot 1.3H_2O$

Calcd.: C, 58.68; H, 7.48; N, 4.56; P, 5.04.

Found.: C, 58.60; H, 7.44; N, 4.61; P, 5.12.

Embodiments 41–44

17-cyclopropylmethyl-4,5α-epoxy-3,14β-dihydroxy-6α-(N-isobutyl-3,4-dichlorophenylacetoamido) morphinan•hydrochloride 51 (yield: 78%), 17-cyclopropylmethyl-4,5α-epoxy-3,14β-dihydroxy-6α-(3,4-dichlorophenylacetoamido)morphinan•hydrochloride 52 (yield: 92%), 17-cyclopropylmethyl-4,5α-epoxy-3,14β-dihydroxy-6β-(N-methyl-3,4-dichlorophenylacetoamido) morphinan•hydrochloride 53 (yield: 51%), and 17-cyclopropylmethyl-4,5α-epoxy-3,14β-dihydroxy-6β-(N-ethyl-3,4-dichlorophenylacetoamido) morphinan•hydrochloride 54 (yield: 56%) were obtained by following the procedure of example 11 but using 17-cyclopropylmethyl-4,5α-epoxy-3,14β-dihydroxy-6α-isobutylaminomorphinan 5, 17-cyclopropylmethyl-4,5α-epoxy-3,14β-dihydroxy-6α-aminomorphinan (J. B. Jiang, R. N. Hanson, P. S. Portoghese, and A. E. Takemori, J. Med. Chem., 20, 1100 (1977).), 17-cyclopropylmethyl-4,5α-epoxy-3,14β-dihydroxy-6β-methylaminomorphinan 10, and 17-cyclopropylmethyl-4,5α-epoxy-3,14β-dihydroxy-6β-ethylaminomorphinan 11 instead of the starting material 17-cyclopropylmethyl-4,5α-epoxy-3,14β-dihydroxy-6α-methylaminomorphinan 4.

Compound 51

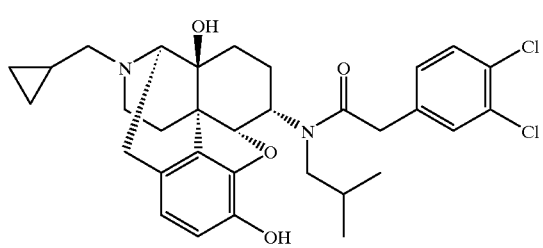

mp 185–188° C.

NMR (400 MHz, DMSO-$d_6$)

δ 0.40 (1H, m), 0.48 (1H, m), 0.61 (1H, m), 0.72 (4H, m), 0.88 (4H, m), 1.06 (2H, m), 1.57 (3H, m), 1.90 (2H, m), 2.42 (1H, m), 2.68 (1H, m), 3.00 (3H, m), 3.36 (2H, m), 3.45 (1H, m), 3.86 (3H, m), 4.4–5.1 (2H, m), 6.19 (0.7H, s), 6.50 (0.3H, s), 6.58 (1H, m), 6.73 (1H, d, J=7.8 Hz), 7.27 (1H, m), 7.52 (1H, d, J=4.4 Hz), 7.59 (1H, t, J=8.3 Hz), 8.82 (1H, brs), 9.26 (0.7H, s), 9.30 (0.3H, s).

IR (KBr)

υ 3370, 1620, 1510, 1468, 1120, 1035 cm$^{-1}$.

Mass (FAB)

m/z 585 (M+H)

Elementary Analysis: As $C_{32}H_{38}N_2O_4Cl_2 \cdot HCl \cdot 0.2H_2O$

Calcd.: C, 61.43; H, 6.35; N, 4.48; Cl, 17.00.

Found.: C, 61.44; H, 6.42; N, 4.45; Cl, 16.82.

Compound 52

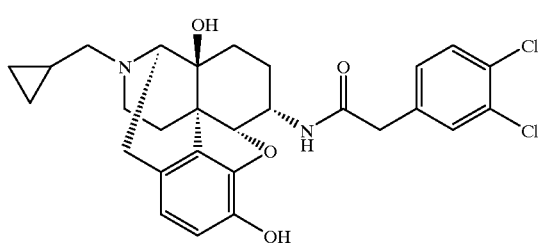

mp 212.0–215.0° C. (decomposition, ether)
NMR (400 MHz, DMSO-$d_6$)
δ 0.39 (1H, m), 0.47 (1H, m), 0.60 (1H, m), 0.68 (1H, m), 0.97 (1H, m), 1.05 (1H, m), 1.40 (2H, dd, J=14.7, 9.8 Hz), 1.60 (1H, d, J=10.7 Hz), 1.84 (1H, dt, J=15.1, 9.3 Hz), 2.44 (1H, dt, J=13.2, 4.9 Hz), 2.70 (1H, br q, J=12.7 Hz), 2.94 (1H, m), 3.04 (2H, dd, J=19.5, 6.8 Hz), 3.25~3.35 (2H, m), 3.55 (2H, s), 3.89 (1H, d, J=6.8 Hz), 4.38 (1H, m), 4.59 (1H, d, J=3.4 Hz), 6.25 (1H, s), 6.56 (1H, d, J=8.3 Hz), 6.73 (1H, d, J=8.3 Hz), 7.29 (1H, dd, J=8.3, 2.0 Hz), 7.56 (1H, d, J=2.0 Hz), 7.57 (1H, d, J=8.3 Hz), 8.14 (1H, d, J=8.3 Hz), 8.83 (1H, br s), 9.28 (1H, s).
IR (KBr)
υ 3400, 2942, 1651, 1510, 1460, 1236, 1120, 1035, 903, 787 $cm^{-1}$.
Mass (FAB)
m/z 529 (M+H)+.
Elementary Analysis: As $C_{28}H_{31}N_2O_4Cl_3$•0.3$H_2O$
Calcd.: C, 58.86; H, 5.58; N, 4.90; Cl, 18.62.
Found.: C, 58.99; H, 5.79; N, 4.93; Cl, 18.61.

Compound 53

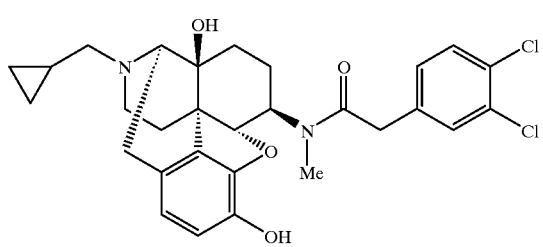

mp 194–196° C. (decomposition)
NMR (400 MHz, $CDCl_3$+D20, Data for free base)
δ 0.09–0.17 (2H, m), 0.49–0.57 (2H, m), 0.78–0.89 (2H, m), 1.05 (0.7H, dt, J=13.2, 3.4 Hz), 1.42–1.51 (0.3H, m), 1.49 (2H, brd, J=13.2 Hz), 1.97–2.29 (3H, m), 2.36 (2H, d, J=6.4 Hz), 2.56–2.69 (2H, m), 2.92 (2.1H, s), 2.99 (0.9H, s), 3.00–3.08 (2H, m), 3.48 (0.7H, d, J=15.6 Hz), 3.49–3.56 (1H, m), 3.66 (0.7H, d, J=15.6 Hz), 3.70 (0.6H, s), 4.55 (0.3H, d, J=8.3 Hz), 4.58 (0.7H, d, J=8.3 Hz), 6.57 (0.3H, d, J=8.3 Hz), 6.73 (0.3H, d, J=8.3 Hz), 6.78–6.82 (1.4H, m), 6.83 (0.7H, d, J=8.3 Hz), 7.11 (0.3H, dd, J=8.3, 2.5 Hz), 7.23 (0.7H, d, J=8.3 Hz), 7.36 (0.3H, d, J=2.0 Hz), 7.39 (0.3H, d, J=8.3 Hz).
IR (KBr)
υ 3420, 1620, 1321, 1127, 1035 $cm^{1}$.
Mass (FAB)
m/z 543 (M+H)+.
Elementary Analysis: As $C_{29}H_{32}N_2O_4Cl_2$•HCl•0.7$H_2O$
Calcd.: C, 58.78; H, 5.85; N, 4.73; Cl, 17.95.
Found.: C, 58.72; H, 5.86; N, 4.71; Cl, 18.03.

Compound 54

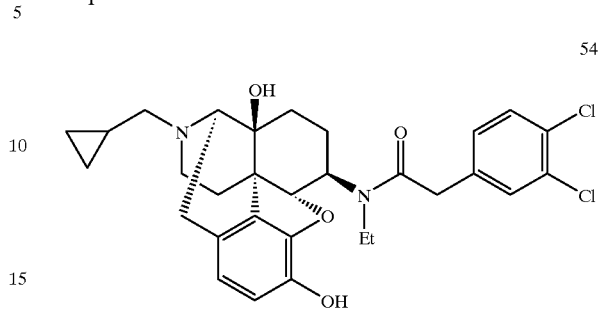

mp 184–187° C. (decomposition)
NMR (500 MHz, DMSO-$d_6$)
δ 0.35–0.75 (4H, m), 1.00–1.53 (4H, m), 1.09 (2.25H, t, J=6.8 Hz), 1.15 (0.75H, t, J=6.8 Hz), 1.60–1.75 (1H, m), 1.93–2.10 (1H, m), 2.38–2.50 (1H, m), 2.80–2.93 (1H, m), 2.96–3.08 (2H, m), 3.15–3.35 (3H, m), 3.40–3.60 (2H, m), 3.56 (2.25H, s), 3.76 (0.75H, s), 3.76–3.87 (1H, m), 4.76 (0.75H, brd, J=7.9 Hz), 5.07 (0.25H, brd, J=7.9 Hz), 6.08 (0.25H, brs), 6.45 (0.75H, brs), 6.63 (0.25H, d, J=7.9 Hz), 6.71 (0.25H, d, J=7.9 Hz), 6.72 (0.75H, d, J=8.1 Hz), 6.80 (0.75 H, d, J=8.1 Hz), 6.98 (0.75H, dd, J=8.3, 2.0 Hz), 7.03 (0.75H, d, J=2.0 Hz), 7.24 (0.25H, dd, J=8.3, 2.0 Hz), 7.51 (0.75H, d, J=8.3 Hz), 7.53 (0.25H, d, J=2.0 Hz), 7.57 (0.25H, d, J=8.3 Hz), 8.80 (1H, brs) 9.31 (0.25H, s), 9.65 (0.75H, s).
IR (KBr)
υ 3420, 1626, 1508, 1319, 1127, 1033 $cm^{-1}$.
Mass (FAB)
m/z 557 (M+H)+.
Elementary Analysis: As $C_{30}H_{34}N_2O_4Cl_2$•HCl•0.3$H_2O$
Calcd.: C, 60.12; H, 5.99; N, 4.67; Cl, 17.74.
Found.: C, 60.14; H, 6.17; N, 4.70; Cl, 17.70.

Examples 45–63

17-cyclopropylmethyl-3,14β-dihydroxy-4,5α-epoxy-6β-(N-methylphenylacetamido)morphinan•hydrochloride 55 (yield: 57%), 17-cyclopropylmethyl-3,14β-dihydroxy-4,5α-epoxy-6β-(N-methylbenzyloxycarbamido)morphinan•hydrochloride 56 (yield: 43%), 17-cyclopropylmethyl-3,14β-dihydroxy-4,5α-epoxy-6β-(N-methyl-3-phenylpropionamido)morphinan•hydrochloride 57 (yield: 84%), 17-cyclopropylmethyl-3,14β-dihydroxy-4,5α-epoxy-6β-(N-methylphenoxyacetamido)morphinan•tartrate 58 (yield: 75%), 17-cyclopropylmethyl-3,14β-dihydroxy-4,5α-epoxy-6β-(N-methylbutyroxycarbamido)morphinan•tartrate 59 (yield: 81%), 17-cyclopropylmethyl-3,14β-dihydroxy-4,5α-epoxy-6β-(N-methyl-3-trifluoromethylcinnamamido)morphinan•tartrate 60 (yield: 84%), 17-cyclopropylmethyl-3,14β-dihydroxy-4,5α-epoxy-6β-[N-methyl-trans-3-(3-furyl)acrylamido]morphinan•tartrate 61 (yield: 91%), 17-cyclopropylmethyl-3,14β-dihydroxy-4,5α-epoxy-6β-(N-methylhexanamido)morphinan•tartrate 62 (yield: 43%), 17-cyclopropylmethyl-3,14β-dihydroxy-4,5α-epoxy-6β-(N-methyl-3-methoxycinnamamido)morphinan•tartrate 63 (yield: 88%), 17-cyclopropylmethyl-3,14β-dihydroxy-4,5α-epoxy-6β-(N-methyl-3-cyclopentylpropionamido)morphinan•tartrate 64 (yield: 39%), 17-cyclopropylmethyl- 3,14β-dihydroxy-4,5α-epoxy-6β-(N-methylthiophenoxyacetamido)morphinan•tartrate 65 (yield: 75%), 17-cyclopropylmethyl-3,14β-dihydroxy-4,5α-epoxy-6β-(N-methyl-2-naphthamido)morphinan•hydrochloride 66 (yield: 95%), 17-cyclopropylmethyl-3,14β-dihydroxy-4,5α-epoxy-6β-(N-methyl-2-methoxyethoxycarbamido)morphinan•tartrate 67 (yield: 63%), 17-cyclopropylmethyl-3,14β-dihydroxy-4,5α-epoxy-6β-(N-methyl-3-cyclohexylacrylamido)morphinan•tartrate 68 (yield: 77%), 17-cyclopropylmethyl-3,14β-dihydroxy-4,5α-epoxy-6β-(N-methyl-3-methylcinnamamido)morphinan•hydrochloride 69 (yield: 87%), 17-cyclopropylmethyl-3,14β-dihydroxy-4,5α-epoxy-6β-[N-methyl-trans-3-(2-furyl)acrylamido]morphinan•hydrochloride 70 (yield: 80%), 17-cyclopropylmethyl-3,14β-dihydroxy-4,5α-epoxy-6β-[N-methyl-trans-3-(3-thienyl)acrylamido]morphinan•methanesulfonate 71 (yield: 88%), 17-cyclopropylmethyl-3,14β-dihydroxy-4,5α-epoxy-6β-(N-methyl-2-trifluoromethylcinnamamido)morphinan•hydrochloride 72 (yield: 93%), and 17-cyclopropylmethyl-3,14β-dihydroxy-4,5α-epoxy-6β-(N-methyl-4-trifluoromethylcinnamamido)morphinan•tartrate 73 (yield: 84%) were obtained by following the procedure of example 11 but using 17-cyclopropylmethyl-4,5α-epoxy-3,14β-dihydroxy-6β-methylaminomorphinan 10 instead of the starting material 17-cyclopropylmethyl-4,5α-epoxy-3,14β-dihydroxy-6α-methylaminomorphinan 4, and using phenylacetyl chloride, benzyl chloroformate, 3-phenylpropionyl chloride, phenoxyacetyl chloride, butyl chloroformate, 3-trifluoromethylcinnamoyl chloride, trans-3-(3-furyl)acryloyl chloride, hexanoyl chloride, 3-methoxycinnamoyl chloride, 3-cyclopentylpropionyl chloride, thiophenoxyacetyl chloride, 2-naphthoyl chloride, 2-methoxyethyl chloroformate, trans-3-cyclohexylacryloyl chloride, 3-methylcinnamoyl chloride, trans-3-(2-furyl)acryloyl chloride, trans-3-(3-thienyl)acryloyl chloride, 2-trifluoromethylcinnamoyl chloride and 4-trifluoromethylcinnamoyl chloride instead of 3,4-dichlorophenylacetyl chloride.

Compound 55

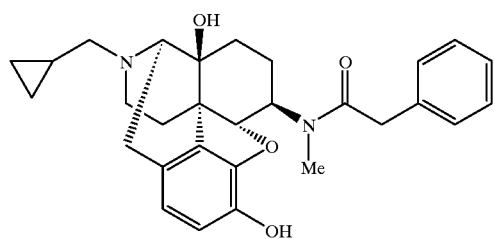

55 mp 205–207° C.
NMR (500 MHz, DMSO-$d_6$)
δ 0.40 (1H, m), 0.50 (1H, m), 0.57 (1H, m), 0.67 (1H, m), 0.81 (1H, m), 1.00–1.08 (2H, m), 1.37–1.56 (2H, m), 1.97 (1H, m), 2.42–2.53 (2H, m), 2.83 (3H, s), 2.85 (1H, m), 2.45–3.07 (3H, m), 3.25–3.37 (2H, m), 3.46–3.57 (2H, m), 3.81 (0.8H, m), 4.04 (0.2H, m), 4.81 (0.8H, m), 4.88 (0.2H, m), 6.31 (0.2H, br s), 6.42 (0.8H, br s), 6.63 (0.2H, d, J=8.1 Hz), 6.70 (0.2H, d, J=8.1 Hz), 6.75 (0.8H, d, J=8.1 Hz), 6.77–6.80 (1.4H, m), 6.84 (0.8H, d, J=8.1 Hz), 7.12–7.33 (3.6H, m), 8.80 (1H, br s), 9.27 (0.2H, s), 9.65 (0.8H, s).

IR (KBr)
υ 3400, 1620, 1502, 1460, 1321, 1125, 1033, 920, 859, 748, 719 cm$^{-1}$
Mass (FAB)
m/z 475 ((M+H)+).
Elementary Analysis: As $C_{29}H_{34}N_2O_4 \cdot HCl \cdot 0.5H_2O$
Calcd.: C, 66.98; H, 6.98; N, 5.38; Cl, 6.82.
Found.: C, 67.25; H, 7.05; N, 5.40; Cl, 6.43.

Compound 56

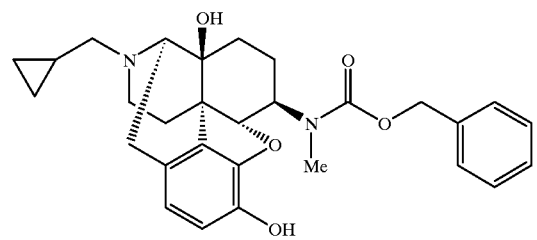

56 mp 189.0–192.0° C. (decomposition, diethylether)
NMR (400 MHz, DMSO-$d_6$)
δ 0.31–0.47 (1H, m), 0.47–0.56 (1H, m), 0.56–0.63 (1H, m), 0.63–0.76 (1H, m), 1.00–1.14 (1H, m), 1.20–1.52 (3H, m), 1.63–1.82 (1H, m), 2.03–2.22 (1H, m), 2.34–2.59 (1H, m), 2.80–2.90 (1H, m), 2.90 (1.7H, s), 2.93 (1.3H, s), 2.98–3.17 (2H, m), 3.22–3.40 (2H, m), 3.60–3.72 (0.6H, m), 3.72–3.80 (0.4H, m), 3.84 (1H, d, J=4.9 Hz), 4.83 (1H, brt), 4.98 (0.4H, d, J=13.2 Hz), 5.04 (1H, d, J=12.7 Hz), 5.09 (0.6H, d, J=13.2 Hz), 6.42 (1H, brs), 6.72 (0.6H, d, J=8.3 Hz), 6.77 (0.4H, d, J=7.8 Hz), 7.37 (5H, s), 7.16–7.45 (2H, m), 8.83 (1H, brs), 9.32 (0.4H, s), 9.45 (0.6H, s).

IR (KBr)
υ 1678, 1560, 1543, 1460, 1315, 1152, 1033 cm$^{-1}$.
Mass (FAB)
m/z 491 ((M+H)+).
Elementary Analysis: As $C_{29}H_{35}N_2O_5Cl$
Calcd.: C, 66.09; H, 6.69; N, 5.31; Cl, 6.73
Found.: C, 66.10; H, 6.64; N, 5.18; Cl, 6.56

Compound 57

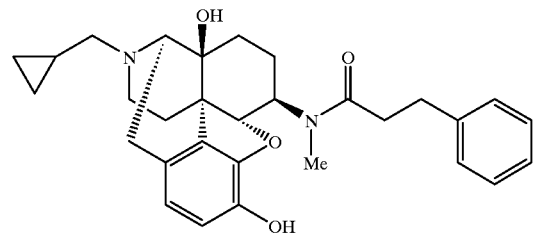

57 mp 207.0° C. (decomposition)
NMR (400 MHz, DMSO-$d_6$)
δ 0.31–0.47 (1H, m), 0.47–0.55 (1H, m), 0.55–0.63 (1H, m), 0.63–0.75 (1H, m), 0.99–1.13 (1H, m), 1.13–1.50 (3H, m), 1.60–1.78 (1H, m), 1.98–2.16 (1H, m), 2.28–2.52 (3H, m), 2.52–2.95 (4H, m), 2.83 (2.4H, s), 2.96 (0.6H, s), 2.95–3.16 (2H, m), 3.22–3.35 (2H, m), 3.36–3.53 (1H, m), 3.83 (1H, m), 4.79 (0.8H, d, J=7.8 Hz), 4.85 (0.2H, d, J=8.3 Hz), 6.38 (0.2H, m), 6.46

(0.8H, m), 6.60–6.80 (2H, m), 7.02–7.32 (5H, m), 8.82 (1H, br s), 9.29 (0.2H, s), 9.56 (0.8H, s).
IR (KBr)
υ 3416, 1622, 1502, 1454, 1410, 1383, 1321, 1125 cm$^{-1}$.
Mass (FAB)
m/z 489 (M+).
Elementary Analysis: As $C_{30}H_{37}N_2O_4Cl_1 \cdot 0.2H_2O$
Calcd.: C, 67.92; H, 7.11; N, 5.28; Cl, 6.68
Found.: C, 67.96; H, 7.06; N, 5.27; Cl, 6.85

Compound 58

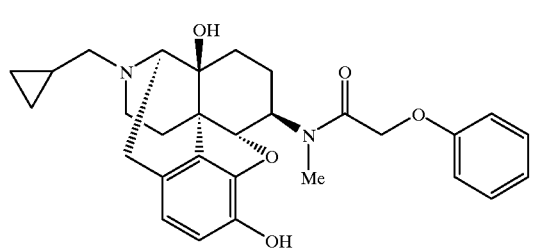

mp 150–200° C. (decomposition)
NMR (500 MHz, DMSO-$d_6$)
δ 0.21 (2H, m), 0.46–0.58 (2H, m), 0.90 (1H, m), 1.15–1.46 (3H, m), 1.57 (1H, m), 2.03–2.17 (2H, m), 2.28 (1H, m), 2.58–2.78 (3H, m), 2.82 (2.4H, S), 3.00 (0.6H, s), 3.08 (1H, d, J=18.9 Hz), 3.24 (1H, m), 3.45 (1H, m), 3.50 (3H, br s, 3×OH), 4.00–4.05 (1H, m), 4.04 (1H, s), 4.63–4.82 (3H, m), 6.54–6.67 (2H, m), 6.78–6.95 (3H, m), 7.18–7.29 (2H, m), 9.34 (1H, br s, NH+).
IR (KBr)
υ 3390, 1638, 1601, 1497, 1323, 1241, 1118, 1064, 1035, 922, 859 cm$^{-1}$.
Mass (FAB)
m/z 491 ((M+H)+).
Elementary Analysis: As $C_{29}H_{34}N_2O_5 \cdot 0.5C_4H_6O_6 \cdot 1.1H_2O$
Calcd.: C, 63.60; H, 6.75; N, 4.78.
Found.: C, 63.69; H, 6.63; N, 4.72.

Compound 59

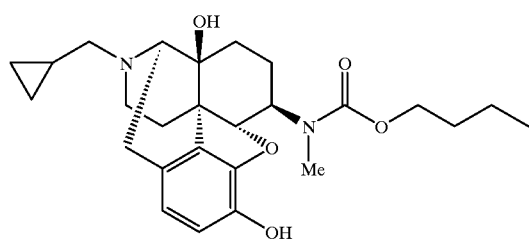

mp 110–150° C. (decomposition)
NMR (400 MHz, DMSO-$d_6$)
δ 0.20 (2H, m), 0.45–0.56 (2H, m), 0.76–0.96 (4H, m), 1.14–1.40 (5H, m), 1.40–1.60 (3H, m), 2.01–2.15 (2H, m), 2.25 (1H, m), 2.55–2.77 (3H, m), 2.82 (3H, s), 3.06 (1H, d, J=18.6 Hz), 3.23 (1H, m), 3.53 (3H, br s, 3×OH), 3.53–3.68 (2H, m), 3.84–3.98 (2H, m), 4.01 (1H, s), 4.67 (1H, m), 6.55 (1H, d, J=8.1 Hz), 6.61 (1H, d, J=8.1 Hz), 9.10 (1H, br s, NH+).

IR (KBr)
υ 3420, 1678, 1607, 1460, 1408, 1359, 1315, 1164, 1122, 1067, 1035, 922, 861 cm$^{-1}$.
Mass (FAB)
m/z 457 ((M+H)+).
Elementary Analysis: As $C_{26}H_{36}N_2O_5 \cdot 0.5C_4H_6O_6 \cdot 0.5H_2O$
Calcd.: C, 62.21; H, 7.46; N, 5.18.
Found.: C, 62.21; H, 7.59; N, 5.33.

Compound 60

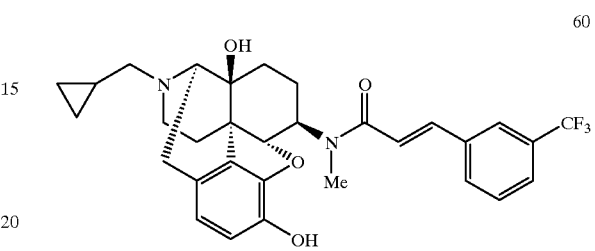

mp 156–159° C.
NMR (400 MHz, DMSO-$d_6$)
δ 0.21 (2H, m), 0.52 (2H, m), 0.91 (1H, m), 1.2–1.5 (3H, m), 1.57 (1H, d, J=13.2 Hz), 2.12 (2H, m), 2.29 (1H, m), 2.49 (1H, m), 2.6–2.8 (3H, m), 2.90 (2H, s), 3.08 (1H, d, J=18.6 Hz), 3.17 (1H, s), 3.26 (1H, m), 3.67 (0.7H, m), 4.02 (1H, s), 4.21 (0.3H, m), 4.68 (0.7H, d, J=7.8 Hz), 4.79 (0.3H, d, J=8.3 Hz), 6.6–6.8 (2.6H, m), 7.37 (1H, dd, J=7.3, 16.1 Hz), 7.5–7.8 (3.8H, m), 8.02 (0.3H, d, J=7.8 Hz), 8.14 (0.3H, s).
IR (KBr)
δ 3350, 1649, 1601, 1336, 1168, 1127 cm$^{-1}$.
Mass (FAB)
m/z 555 (M+H)
Elementary Analysis: As $C_{31}H_{33}N_2O_4F_3 \cdot 0.5(C_4H_6O_6) \cdot 0.3H_2O$
Calcd.: C, 62.41; H, 5.81; N, 4.41; F, 8.98
Found.: C, 62.32; H, 5.99; N, 4.48; F, 8.88

Compound 61

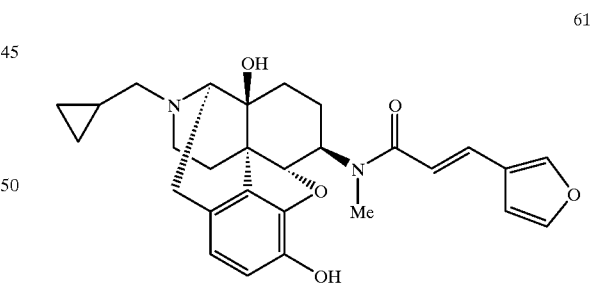

mp 168–172° C.
NMR (400 MHz, DMSO-$d_6$)
δ 0.20 (2H, brs), 0.52 (2H, m), 0.90 (1H, m), 1.2–1.4 (3H, m), 1.56 (1H, d, J=13.2 Hz), 2.12 (2H, m), 2.24 (1H, m), 2.47 (1H, m), 2.5–2.8 (3H, m), 2.86 (2H, s), 3.08 (1H, d, J=19.6 Hz), 3.10 (1H, s), 3.22 (1H, m), 3.60 (0.7H, m), 4.00 (1H, s), 4.19 (0.3H, m), 4.66 (0.7H, d, J=8.3 Hz), 4.76 (0.3H, d, J=8.3 Hz), 6.39 (0.7H, d, J=15.6 Hz), 6.5–6.7 (2H, m), 6.74 (0.7H, d, J=8.3 Hz), 6.89 (0.3H, d, J=15.1 Hz), 7.00 (0.3H, s), 7.21 (0.7H, d, J=15.6 Hz), 7.36 (0.3H, d, J=15.1 Hz), 7.66 (0.7H, s), 7.72 (0.3H, s), 7.92 (0.7H, s), 8.03 (0.3H, s).

IR (KBr)
υ 3370, 1651, 1599, 1323, 1158, 1114 cm$^{-1}$.
Mass (FAB)
m/z 477 (M+H)
Elementary Analysis: As $C_{28}H_{32}N_2O_5 \cdot 0.5(C_4H_6O_6) \cdot 0.2H_2O$
Calcd.: C, 64.90; H, 6.43; N, 5.04.
Found.: C, 64.79; H, 6.59; N, 5.01.

Compound 62

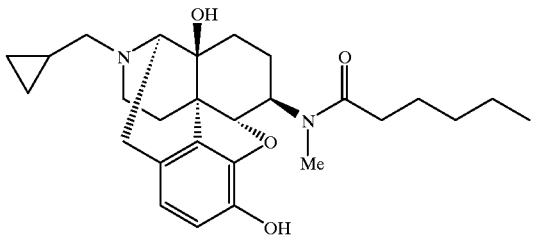

62 mp 150–158° C. (decomposition)
NMR (400 MHz, DMSO-d$_6$)
δ 0.23 (2H, m), 0.48–0.59 (2H, m), 0.79 (2.1H, br t, J=6.8 Hz), 0.88 (0.9H, br t, J=6.8 Hz), 0.92 (1H, m), 1.11–1.22 (3H, m), 1.23–1.51 (6H, m), 1.58 (1H, m), 1.98–2.33 (5H, m), 2.52 (1H, m), 2.67–2.82 (3H, m), 2.77 (2.1H, s), 2.93 (0.9H, s), 3.11 (1H, br d, J=19.1 Hz), 3.33 (1H, m), 3.48 (1H, m), 3.50 (5H, br s, 5×OH), 4.08 (2H, s), 4.60 (0.7H, d, J=8.3 Hz), 4.72 (0.3H, d, J=8.3 Hz), 6.56 (0.3H, d, J=7.8 Hz), 6.60 (0.7H, d, J=7.8 Hz), 6.62 (0.3H, d, J=7.8 Hz), 6.67 (0.7H, d, J=7.8 Hz), 9.26 (1H, br s, NH+).
IR (KBr)
ν 3314, 1719, 1618, 1460, 1412, 1311, 1267, 1120, 1069, 1035, 922, 859 cm$^{-1}$.
Mass (FAB)
m/z 455 ((M+H)+).
Elementary Analysis: As $C_{27}H_{38}N_2O_4 \cdot C_4H_6O_6 \cdot 1.0H_2O$
Calcd.: C, 59.79; H, 7.45; N, 4.50.
Found.: C, 59.59; H, 7.46; N, 4.67.

Compound 63

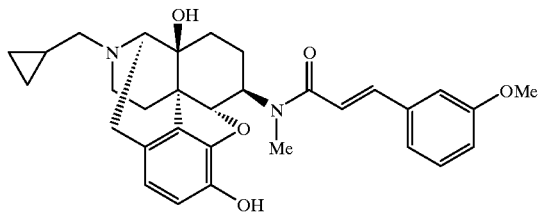

63 mp 160° C. (decomposition)
NMR (400 MHz, DMSO-d$_6$)
δ 0.15–0.35 (2H, m), 0.45–0.65 (2H, m), 0.85–1.05 (1H, m), 1.20–1.50 (3H, m), 1.52–1.70 (1H, m), 2.00–2.25 (2H, m), 2.25–2.42 (1H, m), 2.63–2.77 (3H, m), 2.90 (1.8H, s), 2.90–4.20 (3H, br s), 3.05–3.22 (1H, m), 3.15 (1.2H, s), 3.22–3.42 (1H, m), 3.50–3.74 (1.6H, m), 3.77 (1.8H, s), 3.80 (1.2H, s), 4.00 (1H, s), 4.20 (0.4H, br s), 4.71 (0.6H, d, J=7.8 Hz), 4.80 (0.4H, d, J=8.3 Hz), 6.55–6.71 (2.6H, m), 6.92 (0.6H, dd, J=8.3, 2.5 Hz), 6.95–7.03 (1H, m), 7.10 (0.6H, d, J=7.3 Hz), 7.17 (0.4H, d, J=15.1 Hz), 7.23–7.35 (2.4H, m), 7.42 (0.4H, d, J=15.6 Hz), 9.07 (0.4H, br s), 9.37 (0.6H, br s).
IR (KBr)
υ 3390, 1642, 1599, 1460, 1408, 1313, 1272, 1127, 1035, 787, 683 cm$^{-1}$.
Mass (FAB)
m/z 517 ((M+H)+).
Elementary Analysis: As $C_{33}H_{39}N_2O_8 \cdot 0.7H_2O$
Calcd.: C, 65.59; H, 6.74; N, 4.64
Found.: C, 65.46; H, 6.78; N, 4.70

Compound 64

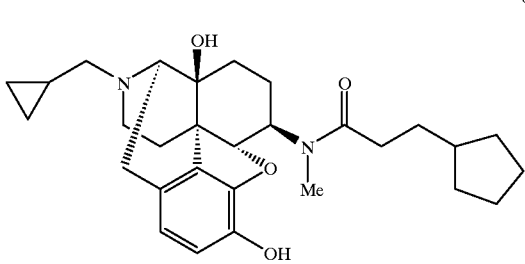

64 mp 145–160° C. (decomposition)
NMR (400 MHz, DMSO-d$_6$)
δ 0.23 (2H, m), 0.48–0.59 (2H, m), 0.82–1.12 (3H, m), 1.14–1.78 (13H, m), 2.00–2.33 (5H, m), 2.52 (1H, m), 2.66–2.81 (3H, m), 2.76 (2.4H, s), 2.93 (0.6H, s), 3.11 (1H, br d, J=18.6 Hz), 3.31 (1H, m), 3.46 (1H, m), 3.50 (5H, br s, 5×OH), 4.07 (2H, s), 4.61 (0.8H, d, J=7.8 Hz), 4.71 (0.2H, d, J=7.8 Hz), 6.56 (0.2H, d, J=8.0 Hz), 6.59 (0.8H, d, J=8.0 Hz), 6.61 (0.2H, d, J=8.0 Hz), 6.66 (0.8H, d, J=8.0 Hz), 9.25 (1H, br s, NH+).
IR (KBr)
υ 3398, 1721, 1620, 1456, 1408, 1325, 1243, 1125, 1071, 1035, 922, 859 cm$^{-1}$.
Mass (FAB)
m/z 481 ((M+H)+).
Elementary Analysis: As $C_{29}H_{40}N_2O_4 \cdot C_4H_6O_6 \cdot 0.3H_2O$
Calcd.: C, 62.31; H, 7.38; N, 4.40.
Found.: C, 62.18; H, 7.65; D, 4.57.

Compound 65

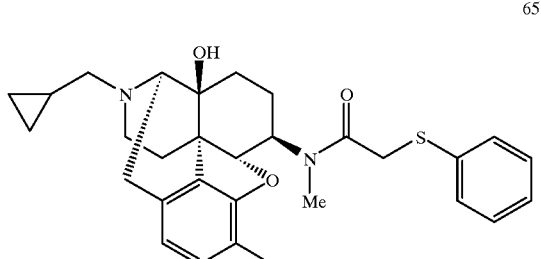

65 mp 145.0° C. (decomposition)
NMR (400 MHz, DMSO-d$_6$)
δ 0.15–0.30 (2H, m), 0.43–0.60 (2H, m), 0.83–0.98 (1H, m), 1.13–1.26 (1H, m), 1.26–1.41 (2H, m), 1.43–1.62 (1H, m), 1.97–2.19 (2H, m), 2.19–2.33 (1H, m), 2.40–2.55 (1H, m), 2.55–2.78 (3H, m), 2.80 (2.4H, s), 3.03 (0.6H, s), 3.05 (1H, br d, J=13.4 Hz), 3.22 (1H, br s), 2.90–4.30 (3H, br s), 3.42–3.52 (1H, m), 3.74 (0.8H, d, J=14.0 Hz), 3.91 (0.8H, d, J=14.7 Hz), 3.96 (0.2H, d, J=14.6 Hz), 4.02 (0.2H, d, J=14.6 Hz), 4.04 (1H, s), 4.61 (0.8H, d, J=7.9 Hz), 4.73 (0.2H, d, J=7.9 Hz), 6.55 (0.2H, d, J=7.9 Hz), 6.59–6.67 (1H, m), 6.71 (0.8H, d, J=7.9 Hz), 7.08–7.26 (4.2H, m), 7.30 (0.4H, t), 7.35–7.42 (0.4H, m), 9.10–9.60 (1H, br s).

IR (KBr)
υ 3380, 1620, 1508, 1408, 1313, 1267, 1122, 1035, 690 cm$^{-1}$.

Mass (FAB)
m/z 507 ((M+H)+).

Elementary Analysis: As $C_{31.4}H_{37.6}N_2O_{7.6}S1.0·0.6H_2O$
Calcd.: C, 62.08; H, 6.44; N, 4.61; S, 5.28.
Found.: C, 61.84; H, 6.60; N, 4.67; S, 5.35.

Compound 66

66 mp 220° C. (decomposition)
NMR (400 MHz, DMSO-d$_6$)
δ 0.34 (1H, m), 0.47 (1H, m), 0.54 (1H, m), 0.62 (1H, m), 0.87 (1H, m), 0.99 (1H, m), 1.28 (1H, m), 1.4–1.6 (2H, m), 2.17 (1H, m), 2.34 (1H, m), 2.52 (1H, m), 2.7–2.9 (2H, m), 3.01 (1H, m), 3.10 (2H, s), 3.2–3.4 (3.7H, m), 3.70 (0.7H, m), 3.87 (0.3H, m), 4.15 (0.3H, m), 5.00 (0.7H, d, J=7.8 Hz), 5.06 (0.3H, m), 6.37 (0.3H, m), 6.39 (0.7H, d, J=7.8 Hz), 6.58 (0.7H, d, J=8.3 Hz), 6.71 (0.3H, m), 7.6–8.0 (7H, m).

IR (KBr)
υ 3400, 1620, 1319, 1176, 1120, 1035 cm$^{-1}$.

Mass (FAB)
m/z 511 (M+H)

Elementary Analysis: As $C_{32}H_{34}N_2O_4·HCl·0.4H_2O$
Calcd.: C, 69.34; H, 6.51; N, 5.05; Cl, 6.40
Found.: C, 69.13; H, 6.86; N, 4.96; Cl, 6.73

Compound 67

67 mp >130° C. (decomposition)
NMR (400 MHz, DMSO-d$_6$)
δ 0.23 (2H, m), 0.48–0.58 (2H, m), 0.92 (1H, m), 1.23–1.38 (3H, m), 1.58 (1H, m), 2.02–2.18 (2H, m), 2.27 (1H, m), 2.52 (1H, m), 2.66–2.79 (3H, m), 2.81–2.87 (3H, m), 3.08 (1H, br d, J=18.6 Hz), 3.14 (1.5H, br s), 3,28 (1.5H, br s), 3.30 (1H, m), 3.42–3.57 (2H, m), 3.50 (4H, br s, 3.5×OH+0.5×COOH), 3.61 (1H, m), 4.02–4.13 (2H, m), 4.05 (1.5H, s), 4.69 (1H, m), 6.56 (1H, d, J=8.3 Hz), 6.63 (1H, m), 9.15 (1H, br s, NH+).

IR (KBr)
υ 3424, 1686, 1609, 1460, 1410, 1313, 1251, 1123, 1066, 1033, 922, 905, 859 cm$^{-1}$.

Mass (FAB)
m/z 459 ((M+H)+).

Elementary Analysis: As $C_{25}H_{34}N_2O_6·0.75C_4H_6O_6·0.8H_2O$
Calcd.: C, 57.44; H, 6.90; N, 4.78.
Found.: C, 57.41; H, 6.89; N, 4.71.

Compound 68

68 mp 154.0° C. (decomposition)
NMR (500 MHz, DMSO-d$_6$)
δ 0.16–0.32 (2H, m), 0.42–0.62 (2H, m), 0.82–1.02 (2H, m), 1.02–1.42 (7H, m), 1.42–1.80 (6H, m), 1.88–2.33 (4H, m), 2.42–2.58 (1H, m), 2.58–2.87 (3H, m), 2.60–5.10 (3H, br s), 2.81 (2.1H, s), 3.01 (0.9H, s), 3.09 (1H, br d, J=18.3 Hz), 3.28 (1H, br s), 3.60 (0.7H, m), 4.05 (1H, s), 4.11 (0.3H, m), 4.61 (0.7H, d, J=7.9 Hz), 4.73 (0.3H, d, J=8.5 Hz), 5.93 (0.7H, d, J=15.3 Hz), 6.33 (0.7H, d, J=15.3 Hz), 6.34 (0.3H, d, J=15.3 Hz), 6.52–6.62 (1.6H, m), 6.66 (0.7H, d, J=8.5 Hz), 8.60–9.60 (1H, br s).

IR (KBr)
υ 3322, 1651, 1601, 1504, 1450, 1410, 1311, 1267, 1216, 1129, 681 cm$^{-1}$.

Mass (FAB)
m/z 493 ((M+H)+).

Elementary Analysis: As $C_{32.8}H_{44.2}N_2O_{8.2}·0.8H_2O$
Calcd.: C, 64.36; H, 7.54; N, 4.58
Found.: C, 64.37; H, 7.67; N, 4.58

Compound 69

69 mp 245° C. (decomposition)
NMR (400 MHz, DMSO-d$_6$)
δ 0.42 (1H, m), 0.50 (1H, m), 0.59 (1H, m), 0.69 (1H, m), 1.07 (1H, m), 1.2–1.5 (3H, m), 1.72 (1H, d, J=13.7), 2.12 (1H, m), 2.34 (3H, s), 2.4–2.6 (2H, m), 2.88 (1H, m), 2.92 (2H, s), 3.0–3.1 (2H, m), 3.18 (1H, s), 3.3–3.4 (2H, m), 3.66 (0.7H, m), 3.83 (1H, m), 4.20 (0.3H, m), 4.83 (0.7H, d, J=7.8 Hz), 4.90 (0.3H, d, J=8.3 Hz), 6.6–6.8 (2H, m), 6.85 (0.7H, d, J=8.3 Hz), 7.1–7.3 (4.4H, m), 7.41 (0.3H, d, J=15.1 Hz), 7.48 (0.3H, d, J=7.3 Hz), 7.54 (0.3H, brs).
IR (KBr)
υ 3390, 1647, 1605, 1323, 1127, 1035 cm$^{-1}$.
Mass (FAB)
m/z 501 (M+H)
Elementary Analysis: As $C_{31}H_{36}N_2O_4 \cdot HCl \cdot 0.8H_2O$
Calcd.: C, 67.51; H, 7.06; N, 5.08; Cl, 6.43.
Found.: C, 67.35; H, 7.05; N, 5.17; Cl, 6.53.
Compound 70

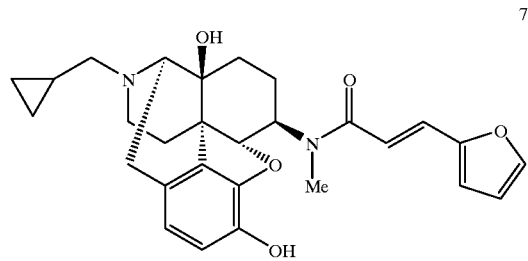

mp 200° C. (decomposition)
NMR (400 MHz, DMSO-$d_6$)
δ 0.42 (1H, m), 0.53 (1H, m), 0.61 (1H, m), 0.69 (1H, m), 1.08 (1H, m), 1.28 (0.5H, m), 1.3–1.5 (2.5H, m), 1.74 (1H, m), 2.15 (1H, m), 2.4–2.6 (2.5H, m), 2.8–2.9 (1.5H, m), 2.93 (1.5H, s), 3.0–3.1 (2H, m), 3.16 (1.5H, s), 3.3–3.4 (2H, m), 3.61 (0.5H, m), 3.85 (1H, brs), 4.20 (0.5H, m), 4.85 (0.5H, d, J=7.3 Hz), 4.91 (0.5H, d, J=7.8 Hz), 6.4–6.7 (3.5H, m), 6.8–6.9 (1.5H, m), 7.14 (0.5H, d, J=15.1 Hz), 7.28 (0.5H, d, J=15.6 Hz), 7.68 (0.5H, s), 7.80 (0.5H, s).
IR (KBr)
υ 3390, 1647, 1597, 1321, 1127, 1017 cm$^{-1}$.
Mass (FAB)
m/z 477 (M+H)
Elementary Analysis: As $C_{28}H_{32}N_2O_5 \cdot HCl \cdot 0.6H_2O$
Calcd.: C, 64.20; H, 6.58; N, 5.35; Cl, 6.77.
Found.: C, 64.21; H, 6.84; N, 5.38; Cl, 6.69.
Compound 71

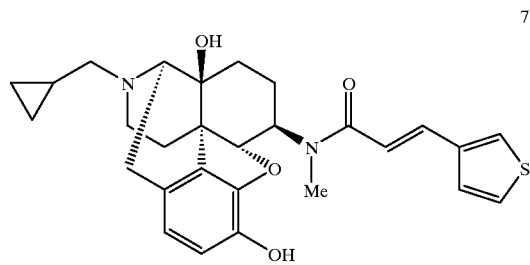

mp 235° C. (decomposition)
NMR (400 MHz, DMSO-$d_6$)
δ 0.42 (1H, m), 0.51 (1H, m), 0.60 (1H, m), 0.68 (1H, m), 1.08 (1H, m), 1.2–1.5 (3H, m), 1.72 (1H, d, J=12.2 Hz), 2.12 (1H, m), 2.34 (3H, s), 2.4–2.5 (2H, m), 2.86 (1H, m), 2.91 (2H, s), 3.0–3.1 (2H, m), 3.15 (1H, s), 3.3–3.5 (2H, m), 3.61 (0.7H, m), 3.82 (1H, brs), 4.19 (0.3H, m), 4.81 (0.7H, d, J=7.8 Hz), 4.89 (0.3H, d, J=8.3 Hz), 6.46 (0.7H, d, J=15.6 Hz), 6.6–6.7 (1.3H, m), 6.85 (0.7H, d, J=7.8 Hz), 7.00 (0.3H, d, J=15.1 Hz), 7.26 (0.7H, d, J=4.9 Hz), 7.31 (0.7H, d, J=15.6 Hz), 7.46 (0.3H, d, J=15.1 Hz), 7.5–7.7 (2H, m), 7.87 (0.3H, s).
IR (KBr)
υ 3410, 1642, 1595, 1323, 1127, 1035, 859 cm$^{-1}$.
Mass (FAB)
m/z 493 (M+H)
Elementary Analysis: As $C_{28}H_{32}N_2O_4S \cdot CH_3SO_3H \cdot 0.2H_2O$
Calcd.: C, 58.80; H, 6.19; N, 4.73; S, 10.83
Found.: C, 58.60; H, 6.42; N, 4.72; S, 10.82
Compound 72

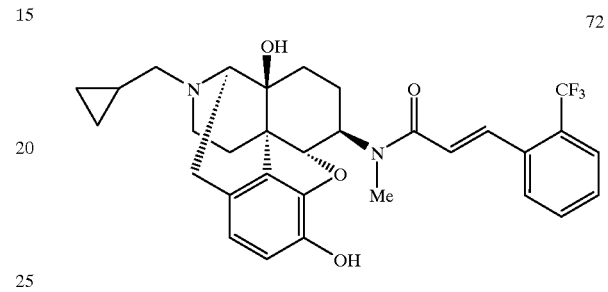

mp 196–199° C•8
NMR (400 MHz, DMSO-$d_6$)
δ 0.41 (1H, m), 0,53 (1H, m), 0.59 (1H, m), 0.67 (1H, m), 1.09 (1H, m), 1.3–1.5 (3H, m), 1.73 (1H, d, J=13.2 Hz), 2.20 (1H, m), 2.4–2.6 (2H, m), 2.88 (1H, m), 2.97 (2H, s), 3.0–3.1 (2H, m), 3.23 (1H, s), 3.3–3.4 (2H, m), 3.68 (0.7H, m), 3.87 (1H, brs), 4.18 (0.3H, m), 4.88 (0.7H, d, J=7.8 Hz), 4.97 (0.3H, d, J=8.3 Hz), 6.6–6.9 (2.7H, m), 7.28 (0.3H, d, J=15.1 Hz), 7.5–7.7 (1.7H, m), 7.7–7.9 (3H, m), 8.14 (0.3H, d, J=7.8 Hz).
IR (KBr)
υ 3400, 1649, 1605, 1460, 1317, 1125, 1036 cm$^{-1}$.
Mass (FAB)
m/z 555 (M+H)
Elementary Analysis: As $C_{31}H_{33}N_2O_4F_3 \cdot 1.1HCl \cdot 0.4H_2O$
Calcd.: C, 61.86; H, 5.84; N, 4.65; F, 9.47; Cl, 6.48
Found.: C, 61.88; H, 5.94; N, 4.67; F, 9.47; Cl, 6.44
Compound 73

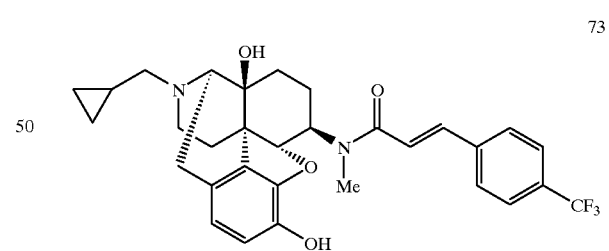

mp 167–170° C.
NMR (400 MHz, DMSO-$d_6$)
δ 0.21 (2H, m), 0.52 (2H, m),0.91 (1H, m), 1.2–1.4 (3H, m), 1.58 (1H, m), 2.1–2.2 (2H, m), 2.30 (1H, m), 2.49 (1H, m), 2.6–2.8 (3H, m), 2.90 (2H, s), 3.18 (1H, d, J=18.6 Hz), 3.16 (1H, s), 3.24 (1H, m), 3.65 (0.7H, m), 4.03 (1H, s), 4.20 (0.3H, m), 4.68 (0.7H, d, J=8.3 Hz), 4.79 (0.3H, d, J=7.8 Hz), 6.5–6.7 (1.3H, m), 6.8–6.9 (1.4H, m), 7.34 (1H, d, J=15.6 Hz), 7.51 (0.3H, d, J=15.6 Hz), 7.7–7.8 (3.7H, m), 7.94 (0.3H, d, J=8.3 Hz).

IR (KBr)
υ 3400, 1649, 1601, 1325, 1168, 1114 cm$^{-1}$.
Mass (FAB)
m/z 555 (M+H)
Elementary Analysis: As $C_{31}H_{33}N_2O_4F_3 \cdot 0.5(C_4H_6O_6) \cdot 0.3H_2O$
Calcd.: C, 62.41; H, 5.81; N, 4.41; F, 8.98
Found.: C, 62.36; H, 5.80; N, 4.41; F, 8.98

Example 64

17-cyclopropylmethyl-14β-hydroxy-4,5α-epoxy-6α-(N-methylbenzyloxycarbamido)morphinan•phosphate 74 (yield: 82%) was obtained by following the procedure of example 11 but using 17-cyclopropylmethyl-4,5α-epoxy-14β-hydroxy-6α-methylaminomorphinan 6 instead of the starting material 17-cyclopropylmethyl-4,5α-epoxy-3,14β-dihydroxy-6α-methylaminomorphinan 4, and using benzyl chloroformate instead of 3,4-dichlorophenylacetyl chloride.

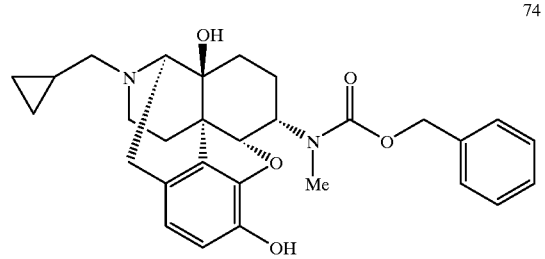

74 mp 122–125° C.
NMR (400 MHz, DMSO-d$_6$)
δ 0.23 (2H, m), 0.54 (2H, m), 0.93 (1H, m), 1.06 (1H, m), 1.3–1.5 (3H, m), 1.75 (1H, m), 2.2–2.3 (2H, m), 2.5–2.7 (2H, m), 2.80 (3H, s), 2.7–2.9 (2H, m), 3.18 (1H, d, J=19.5 Hz), 3.35 (1H, m), 4.59 (2H, m), 5.1–5.2 (2H, m), 6.60 (1H, d, J=7.3 Hz), 6.70 (1H, d, J=7.3 Hz), 7.10 (1H, t, J=7.3 Hz), 7.3–7.4 (5H, m).
IR (KBr)
υ 3400, 1692, 1462, 1350, 1245, 1120 cm$^{-1}$.
Mass (FAB)
m/z 474 (M+H)
Elementary Analysis: As $C_{29}H_{34}N_2O_4 \cdot H_3PO_4 \cdot 0.7H_2O$
Calcd.: C, 59.52; H, 6.61; N, 4.78; P, 5.29
Found.: C, 59.51; H, 6.56; N, 4.78; P, 5.60

Example 65

17-Cyclopropylmethyl-7,8-didehydro-4,5α-epoxy-14β-hydroxy-3-methoxy-6α-[N-methyl-trans-3-(3-furyl)acrylamido]morphinan 75

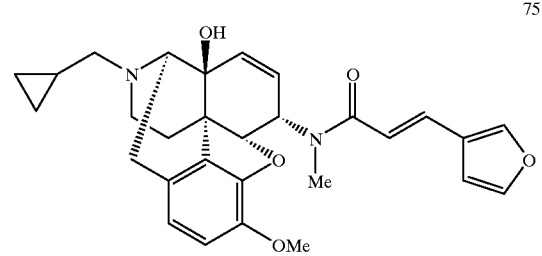

75

540 mg of 17-cyclopropylmethyl-7,8-didehydro-4,5α-epoxy-14β-hydroxy-3-methoxy-6α-(N-methylamino) morphinan 14 and 0.31 ml of triethylamine was dissolved in 10 ml of chloroform followed by addition of 250 mg of trans-3-(3-furyl)acryloyl chloride and stirring for 30 minutes at room temperature. The resulting solution was neutralized by addition of saturated aqueous sodium bicarbonate followed by extraction with chloroform. The organic layer was washed with saturated brine, dried and concentrated. The resulting residue was separated and purified by column chromatography [silica gel; chloroform—chloroform:methanol (100:1)] to obtain 610 mg of crude crystal. This was then recrystallized from dichloromethane-ether to obtain 580 mg of the target compound (yield: 81%).
mp 199–201° C.
NMR (400 MHz, CDCl$_3$)
δ 0.19 (2H, m) 0.60 (2H, m), 0.93 (1H, m), 1.58 (1H, m), 1.74 (1H, m), 2.27–2.64 (4H, m), 2.78 (1H, m), 3.00 (3H, s), 3.09 (1H, d, J=18.6 Hz), 3.40 (1H, m), 3.82 (3H, s), 4.97 (1H, br s, OH), 5.14 (1H, d, J=6.8 Hz), 5.70–5.77 (2H, m), 5.83 (1H, m), 6.56 (1H, d, J=8.3 Hz), 6.61 (1H, d, J=1.5 Hz), 6.66 (1H, d, J=15.3 Hz), 6.67 (1H, d, J=8.3 Hz), 7.42 (1H, br s), 7.63 (1H, d, J=15.3 Hz), 7.65 (1H, br s).
IR (KBr)
υ 3338, 1659, 1638, 1404, 1282, 1205, 1160, 1122, 1054, 1017, 980, 808 cm$^{-1}$.
Mass (EI)
m/z 488 (M+).

Example 66

17-Cyclopropylmethyl-7,8-didehydro-4,5α-epoxy-3,14β-dihydroxy-6α-[N-methyl-trans-3-(3-furyl)acrylamido]morphinan•hydrochloride 76

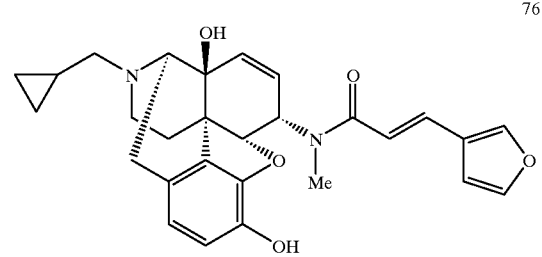

76

300 mg of 17-cyclopropylmethyl-7,8-didehydro-4,5α-epoxy-14β-hydroxy-3-methoxy-6α-[N-methyl-trans-3-(3-furyl)acrylamido]morphinan 75 was dissolved in 5 ml of anhydrous dichloromethane and cooled to 0° C. 3.7 ml of a dichloromethane solution of boron tribromide (1.0 M) was then added followed by stirring for 2 hours (at room temperature.). The reaction solution was cooled to 0° C. followed by addition of 6 ml of 28% aqueous ammonia:water (1:4). After stirring for 30 minutes at 0° C., the reaction solution was extracted with chloroform and methanol (3:1). The organic layer was washed with saturated brine, dried and concentrated, and the resulting residue was purified with column chromatography [silica gel; chloroform—chloroform:methanol:28% aqueous ammonia (100:2:0.2)] to obtain 350 mg of crude crystal. This was then recrystallized from dichloromethane, methanol and ethyl acetate to obtain 265 mg of a free base of the target compound. 238 mg of the resulting crystal was dissolved in 5 ml of methanol and concentrated after adding of an excess amount of methanol solution of hydrochloride. The residue was recrystallized from methanol to obtain 159.3 mg of the target compound (yield: 57%).

mp 251° C. (decomposition)
NMR (400 MHz, DMSO-$d_6$)
δ 0.43 (1H, m), 0.53 (1H, m), 0.62 (1H, m), 0.72 (1H, m), 1.07 (1H, m), 1.69–1.82 (1H, m), 2.54–3.02 (4H, m), 2.91 (3H, s), 3.08–3.18 (1H, m), 3.30–3.44 (2H, m), 4.07 (0.3H, m), 4.12 (0.7H, m), 4.94 (0.7H, d, J=6.8 Hz), 5.21 (0.3H, d, J=7.3 Hz), 5.49 (0.7H, m), 5.76 (0.3H, m), 5.83– 5.94 (2H, m), 6.52–6.57 (1H, m), 6.69–6.76 (1.6H, m), 6.95 (0.7H, d, J=15.3 Hz), 7.05 (0.7H, d, J=2.0 Hz), 7.31 (0.3H, br s, OH), 7.46 (0.7H, br s, OH), 7.51 (1H, d, J=15.3 Hz), 7.70 (0.3H, br s), 7.74 (0.7H, br s), 8.09 (1H, br s), 8.90–9.06 (1H, m, NH+), 9.33 (0.3H, br s, OH), 9.34 (0.7H, br s, OH).
IR (KBr)
υ 3422, 3190, 1653, 1600, 1504, 1473, 1406, 1321, 1160, 1118, 1023, 949, 870, 799 $cm^{-1}$.
Mass (FAB)
m/z 475 ((M+H)+).
Elementary Analysis: As $C_{28}H_{30}N_2O_5 \cdot HCl$
Calcd.: C, 65.81; H, 6.11; Cl, 6.94; N, 5.48.
Found.: C, 65.62; H, 6.19; Cl, 6.82; N, 5.61.

Example 67

17-Cyclopropylmethyl-3,14β-dihydroxy-4,5α-epoxy-5β-methyl-6α-[trans-3-(3-furyl)acrylamido]morphinan•0.5 tartrate 77 (yield: 40%) was obtained by following the procedure of example 11 but using 17-cyclopropylmethyl-3,14-dihydroxy-4,5α-epoxy-5β-methyl-6α-aminomorphinan 19 instead of the starting material of 17-cyclopropylmethyl-4,5α-epoxy-3,14β-dihydroxy-6α-methylaminomorphinan 4, and using trans-3-(3-furyl)acryloyl chloride instead of 3,4-dichlorophenylacetyl chloride.

77

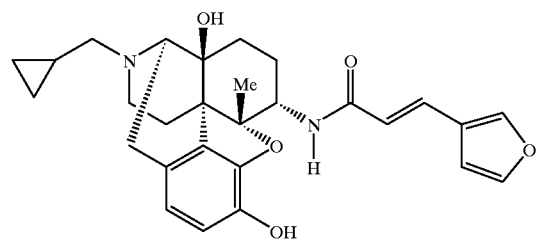

mp >170° C. (decomposition)
NMR (400 MHz, DMSO-$d_6$)
δ 0.31 (2H, m), 0.53 (2H, m), 0.81–0.97 (2H, m), 1.33–1.52 (3H, m), 1.39 (3H, s), 1.70 (1H, m), 2.21–2.33 (2H, m), 2.41–2.83 (4H, m), 3.06 (1H, br d, J=18.6 Hz), 3.25 (1H, m), 3.48 (3H, br s, 3OH), 4.03 (1H, s), 4.27 (1H, m), 6.49 (1H, d, J=8.3 Hz), 6.54 (1H, d, J=15.6 Hz), 6.61 (1H, d, J=8.3 Hz), 6.71 (1H, d, J=1.5 Hz), 7.34 (1H, d, J=15.3 Hz), 7.46 (1H, d, J=9.3 Hz), 7.73 (1H, br s), 8.01 (1H, s), 8.85 (1H, br s, NH+).
IR (KBr)
υ 3398, 1665, 1611, 1508, 1462, 1352, 1245, 1158, 1123, 1062, 870, 803 $cm^{-1}$.
Mass (FAB)
m/z 477 ((M+H)+).
Elementary Analysis: As $C_{28}H_{32}N_2O_5 \cdot 0.5C_4H_6O_6 \cdot 1.0H_2O$
Calcd.: C, 63.26; H, 6.55; N, 4.92.
Found.: C, 63.33; H, 6.43; N, 4.79.

Example 68

17-Cyclopropylmethyl-3,14β-dihydroxy-4,5α-epoxy-6β-[N-methyl-trans-3-(3-furyl)acrylamido]morphinan•hydrochloride 78

78

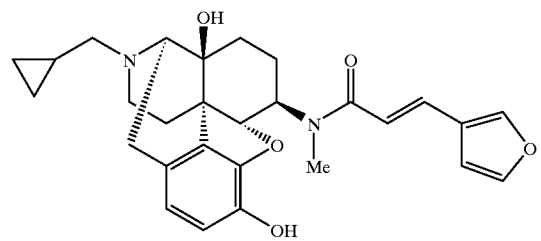

21.12 g (0.0404 mol) of 17-cyclopropylmethyl-4,5α-epoxy-3,14β-dihydroxy-6β-(N-methylamino)morphinan•phthalate 10 was dissolved in 110 ml of water. After adding 110 ml of THF and 8.75 g (0.0808 mol) of sodium carbonate, the atmosphere of reaction system was replaced to argon. Then, 6.96 g of trans-3-(3-furyl)acryloyl chloride (0.04444 mol) was dissolved in 40 ml of THF and added dropwise. After stirring for 30 minutes, 40 ml of methanol and 54 ml of 3 N aqueous sodium hydroxide were added and stirred for 1 hour. 350 ml of ethyl acetate and 250 ml of saturated aqueous sodium bicarbonate were added to the reaction solution to separate, and the aqueous layer was re-extracted with 100 ml of ethyl acetate. After washing with 200 ml of saturated brine, the resulting organic layer was dried with sodium sulfate and concentrated. The residue was dissolved in 630 ml of ethyl acetate while heating, and after dissolving, 150 ml was distilled off while heating. The resulting solution was allowed to stand and recrystallized to obtain 15.47 g of the free base of the target compound. 9.03 g of this free base was suspended in 90 ml of ethanol. After then adding 18.7 ml of 1 N aqueous hydrochloric acid, the resulting solution was concentrated and dried to obtain 9.72 g of the target compound (yield: 80%).
mp 187° C. (decomposition)
NMR (400 MHz, DMSO-$d_6$)
δ 0.42 (1H, m), 0.51 (1H, m), 0.60 (1H, m), 0.68 (1H, m), 1.07 (1H, m), 1.26 (0.4H, m), 1.32–1.50 (3.6H, m), 1.73 (1H, br d, J=13.7 Hz), 2.13 (1H, m), 2.40–2.60 (3H, m), 2.88 (1H, m), 2.92 (1.8H, s), 3.06 (1H, br d, J=13.18 Hz), 3.16 (1.2H, s), 3.59 (0.6H, m), 3.86 (1H, m), 4.19 (0.4H, m), 4.86 (0.6H, d, J=7.8 Hz), 4.92 (0.4H, d, J=7.8 Hz), 6.35 (0.6H, d, J=15.6 Hz), 6.40 (0.4H, br s), 6.50 (0.6H, br s), 6.62 (0.6H, s), 6.64 (0.4H, d, J=8.3 Hz), 6.71 (1H, d, J=8.3 Hz), 6.85 (0.6H, d, J=8.3 Hz), 6.90 (0.4H, d, J=15.1 Hz), 6.99 (0.4H, s), 7.22 (0.6H, d, J=15.6 Hz), 7.36 (0.4H, d, J=15.1 Hz), 7.66 (0.6H, s), 7.72 (0.4H, s), 7.92 (0.6H, s), 8.03 (0.4H, s), 8.85 (1H, br s), 9.28 (0.4H, s), 9.68 (0.6H, s).
IR (KBr)
υ 3376, 1653, 1506, 1599, 1410, 1323, 1158, 1127, 1033, 872, 799 $cm^{-1}$.
Mass (FAB)
m/z 477 (M+H)
Elementary Analysis: As $C_{28}H_{32}N_2O_5 \cdot HCl \cdot 0.2H_2O$
Calcd.: C, 65.10; H, 6.52; N, 5.42; Cl, 6.86.
Found.: C, 65.11; H, 6.63; N, 5.60; Cl, 6.80.

Examples 69–71

17-Cyclopropylmethyl-3,14β-dihydroxy-4,5α-epoxy-6β-[trans-3-(3-furyl)acrylamido]morphinan•hydrochloride 79, 17-cyclopropylmethyl-3-hydroxy-4,5α-epoxy-6β-[N-methyl-trans-3-(3-furyl)acrylamido]morphinan•hydrochloride 80, and 17-cyclopropylmethyl-3-hydroxy-4,5α-epoxy-6α-[N-methyl-trans-3-(3-furyl)acrylamido]morphinan•hydrochloride 81 were obtained by following the procedure of example 68 but using 17-cyclopropylmethyl-4,5α-epoxy-3,14β-dihydroxy-6β-aminomorphinan (J. B. Jiang, R. N. Hanson, P. S. Portoghese and A. E. Takemori, J. Med. Chem., 20, 1100 (1977)), 17-cyclopropylmethyl-3-hydroxy-4,5α-epoxy-6β-methylaminomorphinan 20, and 17-cyclopropylmethyl-3-hydroxy-4,5α-epoxy-6α-methylaminomorphinan 21 instead of 17-cyclopropylmethyl-4,5α-epoxy-3,14β-dihydroxy-6β-(N-methylamino)morphinan 10.phthalate.

Compound 79

79

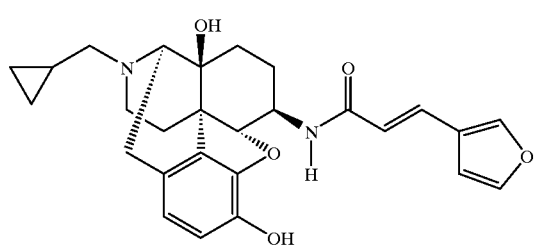

mp 240° C. (decomposition)
NMR (400 MHz, DMSO-d$_6$)
δ 0.41 (1H, m), 0.52 (1H, m), 0.59 (1H, m), 0.67 (1H, m), 1.07 (1H, m), 1.32–1.49 (2H, m), 1.57 (1H, m), 1.68–1.83 (2H, m), 2.37–2.47 (2H, m), 2.86 (1H, m), 2.98–3.12 (2H, m), 3.27–3.39 (2H, m), 3.52 (1H, m), 3.86 (1H, br d, J=4.9 Hz), 4.60 (1H, d, J=7.8 Hz), 6.23 (1H, br s), 6.33 (1H, d, J=15.6 Hz), 6.65 (1H, d, J=7.8 Hz), 6.72 (1H, d, J=7.8 Hz), 6.73 (1H, br s), 7.32 (1H, d, J=15.6 Hz), 7.74 (1H, br s), 8.01 (1H, s), 8.40 (1H, d, J=7.8 Hz), 8.86 (1H, m, NH+), 9.36 (1H, s, OH).
IR (KBr)
υ 3376, 3244, 1663, 1620, 1560, 1508, 1460, 1377, 1340, 1241, 1156, 1127, 1035, 980, 872, 795 cm$^{-1}$.
Mass (FAB)
m/z 463 ((M+H)+).
Elementary Analysis: As C$_{27}$H$_{30}$N$_2$O$_5$•HCl•0.2H$_2$O
Calcd.: C, 64.52; H, 6.30; Cl, 7.05; N, 5.57
Found.: C, 64.50; H, 6.39; Cl, 7.00; N, 5.53

Compound 80

80

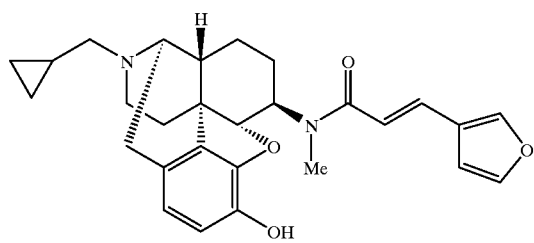

mp 225–230° C. (decomposition)
NMR (400 MHz, DMSO-d$_6$)
δ 0.38 (1H, m), 0.51 (1H, m), 0.63 (2H, m), 0.97 (1H, m), 1.21 (1H, m), 1.40–1.72 (3.8H, m), 2.29 (1H, m), 2.40–2.52 (1.2H, m), 2.57 (0.2H, m), 2.70 (0.8H, m), 2.80–2.96 (1.2H, m), 2.89 (2.4H, s), 3.00–3.18 (1.6H, m), 3.14 (0.6H, s), 3.18–3.35 (2.2H, m), 3.48 (0.8H, m), 3.95–4.10 (1.2H, m), 4.65–4.95 (1H, m), 6.27–8.32 (7H, m).
IR (KBr)
υ 3370, 1651, 1593, 1321, 1156, 872 cm$^{-1}$.
Mass (FAB)
m/z 461 (M+H)
Elementary Analysis: As C$_{28}$H$_{32}$N$_2$O$_4$•1.7HCl•0.5H$_2$O
Calcd.: C, 63.27; H, 6.58; N, 5.27; Cl, 11.34
Found.: C, 63.24; H, 6.60; N, 5.09; Cl, 11.55

Compound 81

81

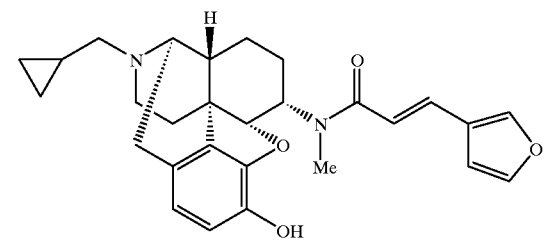

mp 210–215° C. (decomposition)
NMR (400 MHz, DMSO-d$_6$)
δ 0.38 (1H, m), 0.48 (1H, m), 0.65 (2H, m), 0.98 (1H, m), 1.16 (2H, m), 1.32 (1H, m), 1.62–1.90 (2H, m), 2.23 (1H, m), 2.68 (0.7H, m), 2.8–3.4 (7.2H, m), 3.04 (2.1H, s), 4.01–4.10 (1H, m), 4.52–4.81 (2H, m), 6.6–8.3 (7H, m).
IR (KBr)
υ 3380, 1651, 1591, 1323, 1160, 872 cm$^{-1}$.
Mass (FAB)
m/z 461 (M+H)
Elementary Analysis: As C$_{28}$H$_{32}$N$_2$O$_4$•1.4HCl•0.5H$_2$O
Calcd.: C, 64.60; H, 6.66; N, 5.38; Cl, 9.53
Found.: C, 64.78; H, 6.82; N, 5.01; Cl, 9.29

Example 72

17-cyclopropylmethyl-3,14β-dihydroxy-4,5α-epoxy-6β-[N-methyl-trans-3-(2-thienyl)acrylamido]morphinan•tartrate 82 (yield: 84%) was obtained by following the procedure of example 68 but using trans-3-(2-thienyl)acryloyl chloride instead of trans-3-(3-furyl)acryloyl chloride.

82

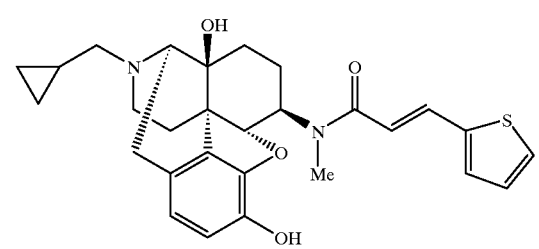

mp 178–181° C.
NMR (400 MHz, DMSO-d$_6$)
δ 0.22 (2H, brs), 0.53 (2H, m), 0.91 (1H, m), 1.2–1.4 (3H, m), 1.58 (1H, d, J=10.4 Hz), 2.14 (2H, m), 2.27 (1H, m), 2.50 (1H, m), 2.6–2.8 (3H, m), 2.88 (1.8H, s), 3.08 (1H, d, J=17.1 Hz), 3.11 (1.2H, s), 3.24 (1H, m), 3.59 (0.6H, m), 4.02 (1H, s), 4.20 (0.4H, m), 4.66 (0.6H, d, J=8.6 Hz), 4.76 (0.4H, d, J=8.6 Hz), 6.42 (0.6H, d, J=15.3 Hz), 6.48 (0.4H, d, J=12.2 Hz), 6.57 (1H, d, J=7.9 Hz), 6.75 (0.6H, d, J=7.9 Hz), 6.85 (0.4H, d, J=15.3 Hz), 7.07 (0.6H, t, J=3.7 Hz), 7.12 (0.4H, t, J=4.9 Hz), 7.32 (0.6H, d, J=3.1 Hz), 7.45–7.48 (1H, m), 7.58–7.67 (1.4H, m).

IR (KBr)

υ 3350, 1636, 1590, 1460, 1035 cm$^{-1}$.

Mass (FAB)

m/z 493 (M+H)

Elementary Analysis: As $C_{28}H_{32}N_2O_4S \cdot 0.5(C_4H_6O_6) \cdot 0.5H_2O$ Calcd.: C, 62.48; H, 6.29; N, 4.86; S, 5.56

Found.: C, 62.32; H, 6.36; N, 4.92; S, 5.57

Example 73

17-Cyclopropylmethyl-3,14β-dihydroxy-4,5α-epoxy-6α-(N-methyl-3-nitrophenylacetamido)morphinan•hydrochloride 83

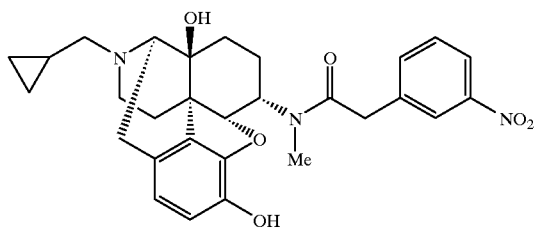

83

567.1 mg (1.59 mmol) of 17-cyclopropylmethyl-3,14β-dihydroxy-4,5α-epoxy-6α-methylaminomorphinan 4 and 577.9 mg (3.19 mmol) of 3-nitrophenylacetic acid were dissolved in 18 ml of chloroform followed by the addition of 657.0 mg (3.18 mmol) of dicyclohexylcarbodiimide and 10.0 mg (0.082 mmol) of 4-(N,N-dimethylamino)pyridine to this solution and stirring for 1 hour at room temperature. The solid that formed in the reaction solution was filtered out, the residue was washed with chloroform, and the filtrate and washing were combined and concentrated. The resulting solid was dissolved in a mixed solution of methanol and chloroform (4:1) followed by the addition of 445 mg (3.22 mmol) of potassium carbonate and stirring for 2 hours at room temperature. 15 ml of water was added to the reaction solution followed by extraction with chloroform (3×15 ml). The organic layers were then combined and concentrated to obtain 2.27 g of solid. This solid was then purified with column chromatography [silica gel 80 g; chloroform-methanol (40:1→20:1)] to obtain 717.4 mg of the free base of the target compound (yield: 87%). This crystal was then dissolved in methanol followed by addition of methanol solution saturated with hydrogen chloride gas. The precipitated crystal was then filtered to obtain 300.5 mg of the target compound (yield: 34%). In addition, the crystal resulting from concentration of this filtrate was then recrystallized from methanol to further obtain 354.0 mg of the target compound (yield: 40%). Both of these compounds were then combined to obtain 654.5 mg of the target compound (yield: 74%).

mp >210° C. (decomposition, methanol)

NMR (400 MHz, DMSO-d$_6$)

δ 0.39 (1H, m), 0.47 (1H, m), 0.61 (1H, m), 0.68 (1H, m), 1.06 (1H, m), 1.17 (1H, m), 1.37 (1H, m), 1.50–1.64 (2H, m), 1.94 (1H, m), 2.43 (1H, m), 2.68 (1H, m), 2.82 (0.6H, s), 2.90–3.14 (3H, m), 3.00 (2.4H, s), 3.22–3.38 (2H, m), 3.90–4.10 (3H, m), 4.54 (0.2H, m), 4.63 (0.8H, d, J=3.3 Hz), 4.82 (0.2H, m), 4.98 (0.8H, m), 6.28 (1H, br s, OH), 6.58 (1H, d, J=7.8 Hz), 6.75 (1H, d, J=7.8 Hz), 7.62 (0.8H, dd, J=7.8, 7.8 Hz), 7.65 (0.2H, dd, J=7.8, 7.8 Hz), 7.71 (0.8H, d, J=7.8 Hz), 7.75 (0.2H, d, J=7.8 Hz), 8.13 (1H, d, J=7.8 Hz), 8.14 (1H, br s), 8.84 (1H, m, NH+), 9.36 (1H, s, OH).

IR (KBr)

υ 3388, 1618, 1528, 1466, 1352, 1321, 1120, 1036, 920, 806 cm$^{-1}$.

Mass (FAB)

m/z 520 ((M+H)+).

Elementary Analysis: As $C_{29}H_{33}N_3O_6 \cdot HCl$

Calcd.: C, 62.64; H, 6.16; N, 7.56; Cl, 6.38.

Found.: C, 62.25; H, 6.39; N, 7.68; Cl, 6.20.

Examples 74–88

17-cyclopropylmethyl-3,14β-dihydroxy-4,5α-epoxy-6α-(N-methyl-3-phenylpropiolamido)morphinan•hydrochloride 84 (yield: 16%), 17-cyclopropylmethyl-3,14β-dihydroxy-4,5α-epoxy-6α-((N-methylcyclohexylacetamido)morphinan•hydrochloride 85 (yield: 55%), 17-cyclopropylmethyl-3,14β-dihydroxy-4,5α-epoxy-6α-(N-methyl-3,4-dichlorocinnamamido)morphinan•hydrochloride 86 (yield: 78%), 17-cyclopropylmethyl-3,14β-dihydroxy-4,5α-epoxy-6α-(N-methyl-4-nitrophenylacetamido)morphinan•hydrochloride 87 (yield: 83%), 17-cyclopropylmethyl-3,14β-dihydroxy-4,5α-epoxy-6α-(N-methyl-2-bromophenylacetamido)morphinan•hydrochloride 88 (yield: 81%), 17-cyclopropylmethyl-3,14β-dihydroxy-4,5α-epoxy-6α-[N-methyl-trans-3-(3-furyl)acrylamido]morphinan•tartrate 89 (yield: 39%), 17-cyclopropylmethyl-3,14β-dihydroxy-4,5α-epoxy-6α-(N-methyl-4-pyridylacetamido)morphinan•2 hydrochloride 90 (yield: 83%), 17-cyclopropylmethyl-3,14β-dihydroxy-4,5α-epoxy-6α-[N-methyl-trans-3-(3-thienyl)acrylamido]morphinan•tartrate 91 (yield: 40%), 17-cyclopropylmethyl-3,14β-dihydroxy-4,5α-epoxy-6α-(N-methyl-2-pyridylacetamido)morphinan•2 hydrochloride 92 (yield: 82%), 17-cyclopropylmethyl-3,14β-dihydroxy-4,5α-epoxy-6α-(N-methyl-3-pyridylacetamido)morphinan•hydrochloride 93 (yield: 92%), 17-cyclopropylmethyl-3,14β-dihydroxy-4,5α-epoxy-6α-(N-methyl-3-cyclohexylpropionamido)morphinan•hydrochloride 94 (yield: 45%), 17-cyclopropylmethyl-3,14β-dihydroxy-4,5α-epoxy-6α-(N-methyl-trans-2-hexenamido)morphinan•tartrate 95 (yield: 46%), 17-cyclopropylmethyl-3,14β-dihydroxy-4,5α-epoxy-6α-(N-methyl-3-fluorocinnamamido)morphinan•tartrate 96 (yield: 79%), 17-cyclopropylmethyl-3,14β-dihydroxy-4,5α-epoxy-6α-(N-methyl-3-nitrocinnamamido)morphinan•phosphate 97 (yield: 40%) and 17-cyclopropylmethyl-3,14β-dihydroxy-4,5α-epoxy-6α-(N-methylbenzoylacetamido)morphinan•tartrate 98 (yield: 37%) were obtained by following the procedure of example 73 but using phenylpropiolic acid, cyclohexylacetic acid, trans-3,4-dichlorocinnamic acid, 4-nitrophenylacetic acid, 2-bromophenylacetic acid, trans-3-(3-furyl)acrylic acid, 4-pyridylacetic acid, trans-3-(3-thienyl)acrylic acid, 2-pyridylacetic acid, 3-pyridylacetic acid, 3-cyclohexylpropionic acid, trans-2-hexenoic acid, 3-fluorocinnamic acid, 3-nitrocinnamic acid and benzoylacetic acid instead of 3-nitrophenylacetic acid.

Compound 84

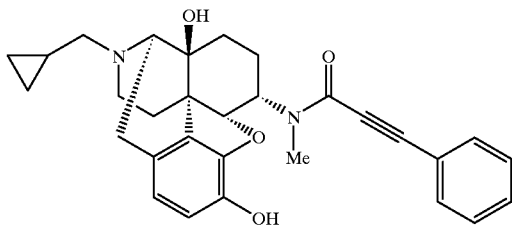

mp 206.0–209.0° C. (decomposition, ether)
NMR (400 MHz, DMSO-$d_6$)
δ 0.41 (1H, m), 0.49 (1H, m), 0.62 (1H, m), 0.69 (1H, m), 1.08 (1H, m), 1.19 (0.5H, m), 1.27 (0.5H, m), 1.45~1.72 (3H, m), 1.95 (0.5H, m), 2.02 (0.5H, m), 2.48 (1H, m), 2.71 (1H, m), 2.92 (1.5H, s), 2.94~3.06 (2H, m), 3.12 (1H, dd, J=19.5, 6.7 Hz), 3.24 (1.5H, s), 3.27~3.38 (2H, m), 3.95 (1H, dd, J=15.6, 6.7 Hz), 4.71 (0.5H, d, J=3.7 Hz), 4.81 (0.5H, d, J=3.7 Hz), 4.92 (0.5H, br d, J=13.4 Hz), 5.09 (0.5H, br d, J=13.4 Hz), 6.32 (0.5H, s), 6.42 (0.5H, s), 6.61 (0.5H, d, J=7.9 Hz), 6.62 (0.5H, d, J=7.9 Hz), 6.74 (0.5H, d, J=7.9 Hz), 6.75 (0.5H, d, J=7.9 Hz), 7.49 (1H, t, J=7.3 Hz), 7.52~7.57 (2H, m), 7.66 (1H, d, J=8.5 Hz), 7.72 (1H, d, J=7.3 Hz), 8.85 (0.5H, br s), 8.93 (0.5H, br s), 9.37 (1H, s).

IR (KBr)
υ 3400, 2952, 2216, 1613, 1493, 1377, 1321, 1120, 1036, 692 cm$^{-1}$.

Mass (FAB)
m/z 485 (M+H)+.

Elementary Analysis: As $C_{30}H_{32}N_2O_4 \cdot 1.5HCl \cdot 0.8H_2O$
Calcd.: C, 66.61; H, 6.48; N, 5.18; Cl, 7.54.
Found.: C, 66.42; H, 6.55; N, 5.19; Cl, 7.72.

Compound 85

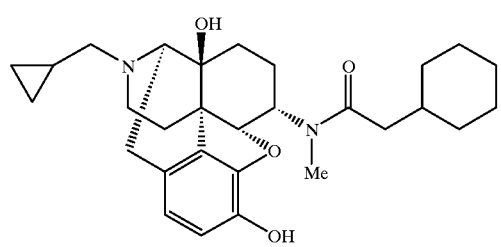

mp 245.0–248.0° C. (decomposition, ether)
NMR (400 MHz, DMSO-$d_6$)
δ 0.40 (1H, m), 0.47 (1H, m), 0.61 (1H, m), 0.68 (1H, m), 0.93~1.35 (8H, m), 1.53~1.74 (8H, m), 1.90 (1H, m), 2.22 (2H, dd, J=6.8, 2.4 Hz), 2.39~2.54 (2H, m), 2.69 (1H, m), 2.79 (0.6H, s), 2.88 (2.4H, s), 2.92 (1H, m), 3.03 (1H, br d, J=13.2 Hz), 3.09 (1H, dd, J=20.4, 7.6 Hz), 3.39 (1H, m), 3.87 (1H, d, J=6.4 Hz), 4.48 (0.2H, m), 4.60 (0.8H, d, J=3.9 Hz), 4.73 (0.2H, br s), 4.98 (0.8H, dt, J=14.2, 3.9 Hz), 6.16 (0.8H, s), 6.38 (0.2H, s), 6.58 (0.8H, d, J=8.3 Hz), 6.59 (0.2H, d, J=7.8 Hz), 6.71 (0.8H, d, J=7.8 Hz), 6.72 (0.2H, d, J=8.3 Hz), 8.79 (1H, br s), 9.28 (0.8H, s), 9.31 (0.2H, s).

IR (KBr)
υ 3400, 2928, 2856, 1615, 1508, 1317, 1120, 804 cm$^{-1}$.

Mass (FAB)
m/z 481 (M+H)+.

Elementary Analysis: As $C_{29}H_{41}N_2O_4Cl \cdot 0.4H_2O$
Calcd.: C, 66.43; H, 8.04; N, 5.34; Cl, 6.76.
Found.: C, 66.33; H, 7.81; N, 5.35; Cl, 6.97.

Compound 86

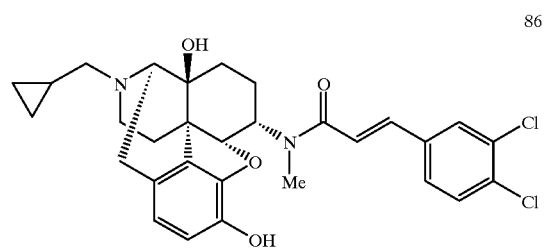

mp 249–258° C. (decomposition, methanol)
NMR (400 MHz, DMSO-$d_6$)
δ 0.31–0.43 (1H, m), 0.43–0.54 (1H, m), 0.54–0.66 (1H, m), 0.66–0.76 (1H, m), 0.99–1.12 (1H, m), 1.12–1.33 (1H, m), 1.33–1.50 (1H, m), 1.50–1.70 (2H, m), 1.86–2.03 (1H, m), 2.40–2.50 (1H, m), 2.61–2.78 (1H, m), 2.87–2.99 (1H, m), 2.90 (0.6H, s), 2.99–3.19 (2H, m), 3.09 (2.4H, s), 3.19–3.39 (2H, m), 3.92 (1H, br d, J=5.9 Hz), 4.63 (0.2H, m), 4.73 (0.8H, d, J=3.9 Hz), 4.92 (0.2H, brs), 5.04 (0.8H, dt, J=14.2, 4.0 Hz), 6.27 (0.8H, br s), 6.46 (0.2H, br s), 6.60 (1H, d, J=7.8 Hz), 6.73 (1H, d, J=7.8 Hz), 7.32 (0.2H, d, J=15.1 Hz), 7.38 (0.8H, d, J=15.1 Hz), 7.47 (0.2H, d, J=15.1 Hz), 7.49 (0.8H, d, J=15.1 Hz), 7.64–7.73 (1H, m), 7.75 (1H, dd, J=8.3, 2.0 Hz), 8.04 (0.2H, s), 8.13 (0.8H, d, J=2.0 Hz), 8.82 (1H, br s), 9.31 (0.8H, s), 9.34 (0.2H, s).

IR (KBr)
υ 1649, 1599, 1510, 1475, 1377, 1317, 1120, 1033 cm$^{-1}$.

Mass (FAB)
m/z 555 ((M+H)+).

Elementary Analysis: As $C_{30}H_{33}N_2O_4Cl_3$
Calcd.: C, 60.87; H, 5.62; N, 4.73; Cl, 17.97
Found.: C, 60.87; H, 5.82; N, 4.73; Cl, 17.75

Compound 87

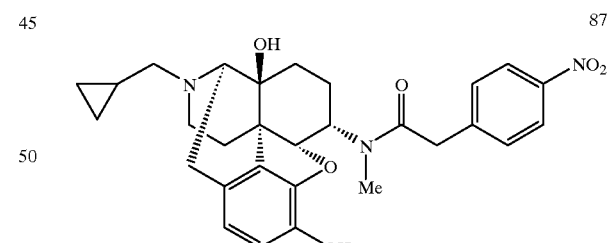

mp >190° C. (decomposition)
NMR (400 MHz, DMSO-$d_6$)
δ 0.39 (1H, m), 0.47 (1H, m), 0.61 (1H, m), 0.68 (1H, m), 1.05 (1H, m), 1.18 (1H, m), 1.37 (1H, m), 1.46–1.63 (2H, m), 1.93 (1H, m), 2.43 (1H, m), 2.67 (1H, m), 2.82 (0.6H, s), 2.90–3.14 (3H, m), 2.98 (2.4H, s), 3.21–3.39 (2H, m), 3.88–4.07 (3H, m), 4.50 (0.2H, m), 4.60–4.67 (1H, m), 4.98 (0.8H, m), 6.27 (0.8H, br s, OH), 6.58 (1H, d, J=7.8 Hz), 6.59 (0.2H, br s, OH), 6.74 (1H, d, J=7.8 Hz), 7.53 (1.6H, d, J=8.8 Hz), 7.58 (0.4H, d, J=8.8 Hz), 8.20 (1.6H, d, J=8.8 Hz), 8.23 (0.4H, d, J=8.8 Hz), 8.83 (1H, m, NH+), 9.34 (1H, br s, OH).

IR (KBr)

υ 3358, 1611, 1520, 1468, 1346, 1323, 1118, 1035, 919, 820 cm$^{-1}$.

Mass (FAB)

m/z 520 ((M+H)+).

Elementary Analysis: As $C_{29}H_{33}N_3O_6 \cdot HCl0.7H_2O$

Calcd.: C, 61.25; H, 6.27; N, 7.39; Cl, 6.23.

Found.: C, 61.24; H, 6.38; N, 7.18; Cl, 6.37.

Compound 88

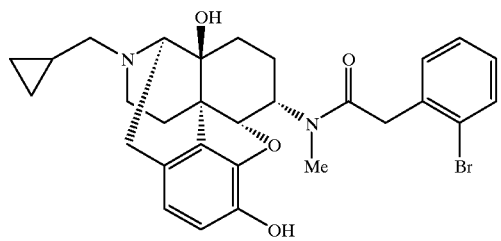

88 mp 230° C. (decomposition)

NMR (400 MHz, DMSO-d$_6$)

δ 0.40 (1H, m), 0.46 (1H, m), 0.60 (1H, m), 0.68 (1H, m), 1.05 (1H, m), 1.18 (1H, m), 1.38 (1H, m), 1.50–1.64 (2H, m), 1.93 (1H, m), 2.42 (1H, m), 2.69 (1H, m), 2.84 (0.6H, s), 2.94 (1H, m), 3.01 (2.4H, s), 3.02–3.14 (2H, m), 3.21–3.33 (2H, m), 3.82–3.97 (3H, m), 4.57 (0.2H, m), 4.61 (0.8H, d, J=3.7 Hz), 4.84 (0.2H, m), 4.98 (0.8H, m), 6.24 (0.8H, br s), 6.46 (0.2H, br s), 6.58 (1H, d, J=7.9 Hz), 6.75 (1H, d, J=7.9 Hz), 7.21 (1H, m), 7.30–7.38 (2H, m), 7.60 (1H, m), 8.82 (1H, br s), 9.34 (0.8H, s), 9.35 (0.2H, s).

IR (KBr)

υ 3120, 1620, 1508, 1473, 1377, 1317, 1118, 1027, 752 cm$^{-1}$.

Mass (FAB)

m/z 553 ((M+H)+).

Elementary Analysis: As $C_{29}H_{33}N_2O_4Br \cdot HCl \cdot 0.4H_2O$

Calcd.: C, 58.33; H, 5.87; N, 4.69; Cl, 5.94; Br, 13.38.

Found.: C, 58.52; H, 5.76; N, 4.77; Cl, 6.07; Br, 13.03.

Compound 89

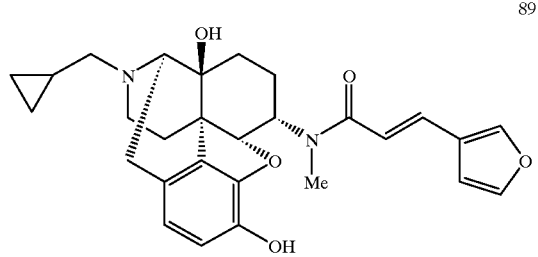

89 mp 243.0–254.0° C. (decomposition, diethylether)

NMR (400 MHz, DMSO-d$_6$)

δ 0.10–0.30 (2H, m), 0.44–0.63 (2H, m), 0.83–0.99 (1H, m), 0.90–1.30 (1H, m), 1.30–1.42 (1H, m), 1.42–1.60 (2H, m), 1.69–1.83 (1H, m), 2.12–2.41 (2H, m), 2.41–2.65 (2H, m), 2.65–2.82 (2H, m), 2.82–2.98 (1H, m), 3.05 (3H, s), 3.05–3.16 (1H, m), 3.16–3.39 (1H, m), 2.80–3.80 (1H, br s), 4.07 (1H, s), 4.55 (0.2H, m), 4.63 (0.8H, d, J=2.9 Hz), 4.68 (0.2H, br s), 4.96 (0.8H, dt, J=13.6, 4.0 Hz), 6.52 (1H, d, J=8.3 Hz), 6.63 (1H, d, J=7.8 Hz), 6.72–6.87 (0.4H, m), 6.96 (0.8H, d, J=15.1 Hz), 7.01 (0.8H, s), 7.43 (1H, d, J=15.1 Hz), 7.72 (0.8H, s), 7.70–7.78 (1H, m), 8.80–9.60 (1H, br s).

IR (KBr)

υ 1651, 1597, 1510, 1460, 1377, 1160, 1120, 1038, 801 cm$^{-1}$.

Mass (FAB)

m/z 477 ((M+H)+).

Elementary Analysis: As $C_{30}H_{35}N_2O_8 \cdot 0.8H_2O$

Calcd.: C, 63.66; H, 6.52; N, 4.95

Found.: C, 63.42; H, 6.50; N, 4.87

Compound 90

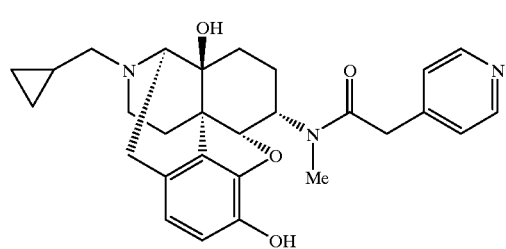

90 mp 200° C. (decomposition)

NMR (400 MHz, DMSO-d$_6$)

δ 0.40 (1H, m), 0.47 (1H, m), 0.61 (1H, m), 0.68 (1H, m), 1.06 (1H, m), 1.18 (1H, m), 1.38 (1H, m), 1.50–1.64 (2H, m), 1.95 (1H, m), 2.42 (1H, m), 2.67 (1H, m), 2.83 (0.6H, s), 3.00 (2.4H, s), 2.90–3.13 (3H, m), 3.23–3.36 (2H, m), 3.50–4.30 (4H, m), 4.51 (0.2H, m), 4.62 (0.8H, d, J=3.9 Hz), 4.89 (0.2H, m), 4.97 (0.8H, m), 6.32 (1H, br s), 6.59 (1H, d, J=8.3 Hz), 6.75 (1H, d, J=8.3 Hz), 7.81 (2H, d, J=6.8 Hz), 8.79 (2H, d, J=6.8 Hz), 8.85 (1H, br s), 9.38 (1H, br s).

IR (KBr)

υ 3390, 1620, 1510, 1460, 1321, 1120, 803 cm$^{-1}$.

Mass (EI)

m/z 475 (M+).

Elementary Analysis: As $C_{28}H_{33}N_3O_4 \cdot 1.8HCl \cdot 0.4H_2O$

Calcd.: C, 61.32; H, 6.54; N, 7.66; Cl, 11.64.

Found.: C, 61.23; H, 6.68; N, 7.55; Cl, 11.59.

Compound 91

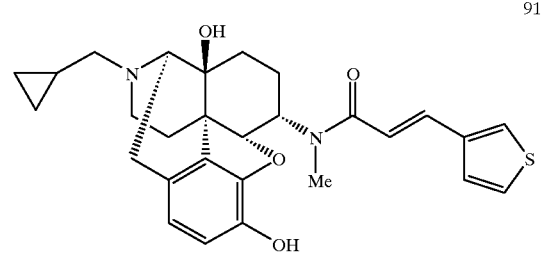

91 mp 249.0–250.0° C. (decomposition, methanol)

NMR (400 MHz, DMSO-d$_6$)

δ 0.10–0.30 (2H, m), 0.44–0.63 (2H, m), 0.83–0.99 (1H, m), 1.10–1.32 (2H, m), 1.32–1.42 (1H, m), 1.42–1.67 (3H, m), 1.69–1.86 (1H, m), 2.18–2.41 (2H, m), 2.41–2.66 (2H, m), 2.66–2.84 (2H, m), 2.84–2.96 (1H, m), 3.06 (3H, s), 3.05–3.16 (1H, m), 3.30 (1H, br s), 4.06 (1H, s), 4.59 (0.2H, m), 4.64 (0.8H, d, J=2.9 Hz), 4.65 (0.2H, brs), 4.97 (0.8H, dt, J=13.7, 2.5 Hz), 6.52 (1H, d, J=7.8 Hz), 6.63 (1H, d, J=8.3 Hz), 6.91 (0.2H, m), 7.07 (0.8H, d, J=15.1 Hz), 7.41–7.50 (0.2H, m), 7.53 (1H, d, J=15.1 Hz), 7.61 (1.8H, s), 7.89 (1H, s), 8.52–9.48 (1H, br s).
IR (KBr)
υ 1638, 1597, 1508, 1460, 1402, 1321, 1118, 1069, 1038, 789 cm$^{-1}$.
Mass (FAB)
m/z 493 ((M+H)+).
Elementary Analysis: As $C_{30}H_{35}N_2O_7S \cdot 1.2H_2O$
Calcd.: C, 61.14; H, 6.40; N, 4.75; S, 5.44
Found.: C, 61.20; H, 6.39; N, 4.69; S, 5.29

Compound 92

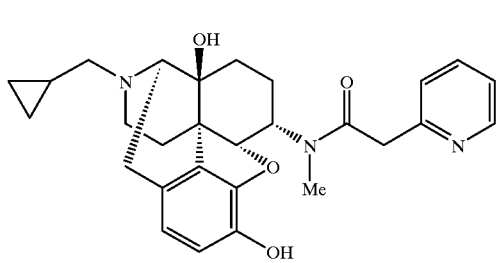

mp 190° C. (decomposition)
NMR (400 MHz, DMSO-d$_6$)
υ 0.40 (1H, m), 0.47 (1H, m), 0.61 (1H, m), 0.68 (1H, m), 1.06 (1H, m), 1.20 (1H, m), 1.38 (1H, m), 1.48–1.64 (2H, m), 1.95 (1H, m),2.41 (1H, m), 2.67 (1H, m), 2.83 (0.6H, s), 3.02 (2.4H, s), 2.90–3.15 (3H, m), 3.22–3.36 (2H, m), 3.40–3.85 (1H, br), 3.93–4.40 (3H, m), 4.58 (0.2H, m), 4.60 (0.8H, d, J=3.9 Hz), 4.97 (1H, m), 6.32 (1H, br s), 6.59 (1H, d, J=8.3 Hz), 6.76 (1H, d, J=8.3 Hz), 7.74–7.83 (2H, m), 8.36 (1H, m), 8.79 (1H, br d, J=3.9 Hz), 8.94 (1H, brs), 9.40 (1H, br s).
IR (KBr)
υ 3380, 1638, 1508, 1460, 1321, 1120, 768 cm$^{-1}$.
Mass (FAB)
m/z 476 ((M+H)+).
Elementary Analysis: As $C_{28}H_{33}N_3O_4 \cdot 0.8HCl \cdot 0.6H_2O$
Calcd.: C, 60.92; H, 6.57; N, 7.61; Cl, 11.56.
Found.: C, 60.91; H, 6.82; N, 7.47; Cl, 11.52.

Compound 93

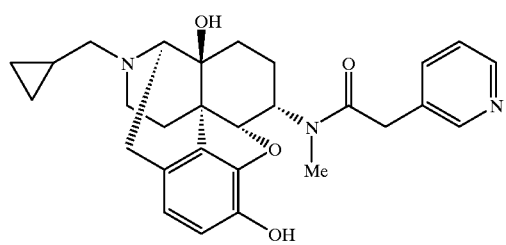

mp 195° C. (decomposition)
NMR (400 MHz, DMSO-d$_6$)
δ 0.40 (1H, m), 0.47 (1H, m), 0.61 (1H, m), 0.68 (1H, m), 1.08 (1H, m), 1.19 (1H, m), 1.38 (1H, m), 1.48–1.64 (2H, m), 1.95 (1H, m), 2.42 (1H, m), 2.65 (1H, m), 2.83 (0.6H, s), 3.02 (2.4H, s), 2.88–3.15 (3H, m), 3.22–3.36 (2H, m), 3.45–3.80 (1H, br), 3.95–4.23 (3H, m), 4.60 (1H, m), 4.97 (1H, m), 6.32 (1H, br s), 6.59 (1H, m), 6.77 (1H, m), 7.91 (1H, m), 8.32 (1H, m), 8.74–8.82 (2H, m), 8.94 (1H, br s), 9.38 (1H, br s).
IR (KBr)
υ 3410, 1626, 1475, 1321, 1120, 1036, 919, 806, 683 cm$^{-1}$.
Mass (FAB)
m/z 476 ((M+H)+).
Elementary Analysis: As $C_{28}H_{33}N_3O_4 \cdot 1.8HCl \cdot 0.75H_2O$
Calcd.: C, 60.63; H, 6.60; N, 7.57; Cl, 11.50.
Found.: C, 61.01; H, 6.82; N, 7.17; Cl, 11.49.

Compound 94

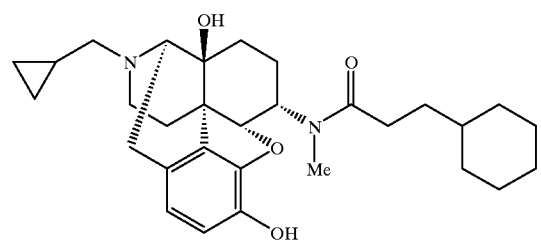

mp >265° C. (decomposition)
NMR (400 MHz, CD$_3$OD)
δ 0.49 (2H, m), 0.73 (1H, m), 0.83 (1H, m), 0.90–1.03 (2H, m), 1.09 (1H, m), 1.15–1.41 (5H, m), 1.43–1.58 (3H, m), 1.63–1.83 (7H, m), 1.92 (1H, m), 2.38–2.52 (2H, m), 2.64 (1H, m), 2.84–3.05 (2H, m), 2.93 (0.6H, s), 3.02 (2.4H, s), 3.05–3.21 (2H, m), 3.23–3.40 (2H, m), 3.98 (1H, m), 4.57 (0.2H, m), 4.75 (1H, br d, J=3.4 Hz), 5.08 (0.8H, ddd, J=13.7, 3.9, 3.9 Hz), 6.67 (0.8H, d, J=8.3 Hz), 6.69 (0.2H, d, J=8.3 Hz), 6.75 (0.8H, d, J=8.3 Hz), 6.76 (0.2H, d, J=8.3 Hz).
IR (KBr)
υ 3342, 3140, 1622, 1508, 1470, 1317, 1172, 1118, 1038, 920, 907, 806 cm$^{-1}$.
Mass (FAB)
m/z 495 ((M+H)+).
Elementary Analysis: As $C_{30}H_{42}N_2O_4 \cdot HCl \cdot 0.18H_2O$
Calcd.: C, 67.43; H, 8.18; N, 5.24; Cl, 6.63.
Found.: C, 67.80; H, 8.01; N, 4.84; Cl, 6.69.

Compound 95

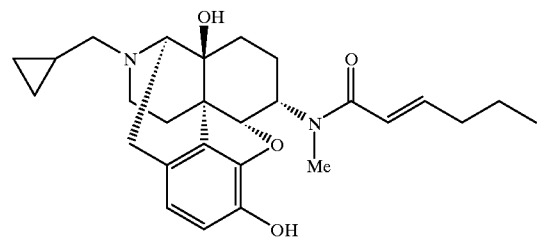

mp 230–240° C. (decomposition)
NMR (400 MHz, DMSO-d$_6$)
δ 0.19 (2H, m), 0.45–0.58 (2H, m), 0.90 (1H, m), 0.91 (3H, t, J=7.3 Hz), 1.07–1.37 (2H, m), 1.38–1.55 (4H, m), 1.73 (1H, m), 2.13–2.27 (4H, m), 2.42–2.58 (2H, m), 2.62–2.78 (2H, m), 2.84 (0.6H, s), 2.95 (2.4H, s), 3.03 (1H, br d, J=19.0 Hz), 3.23 (1H, m), 3.50 (3H, br s, 3×OH), 4.02 (1H, s), 4.45 (0.2H, m), 4.56 (0.2H, m), 4.58 (0.8H, d, J=3.4 Hz), 4.90 (0.8H, m), 6.34 (0.2H, d, J=15.1 Hz), 6.45 (0.8H, d, J=15.1 Hz), 6.50 (1H, d, J=8.0 Hz), 6.61 (1H, d, J=8.0 Hz), 6.65–6.73 (1H, m), 9.06 (1H, br s, NH+).
IR (KBr)
υ 3386, 1657, 1591, 1462, 1408, 1359, 1315, 1170, 1122, 1069, 1038, 980, 920, 810 cm$^{-1}$.
Mass (FAB)
m/z 453 ((M+H)+).
Elementary Analysis: As C$_{27}$H$_{36}$N$_2$O$_4$•0.5C$_4$H$_6$O$_6$•0.2H$_2$O
Calcd.: C, 65.57; H, 7.48; N, 5.27.
Found.: C, 65.54; H, 7.35; N, 5.37.

Compound 96

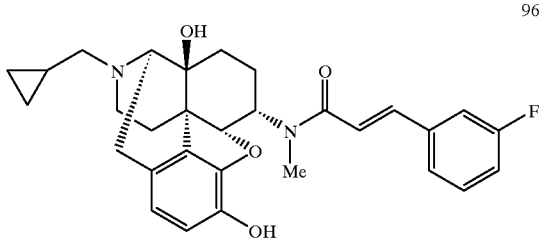

mp 225° C. (decomposition)
NMR (400 MHz, DMSO-d$_6$)
δ 0.10–0.23 (2H, m), 0.43–0.60 (2H, m), 0.82–0.98 (1H, m), 1.12–1.60 (4H, m), 1.68–1.82 (1H, m), 2.18–2.40 (2H, m), 2.62–2.80 (2H, m), 2.83–4.00 (10H, m), 4.04 (1H, s), 4.52–4.60 (0.3H, m), 4.65 (0.7H, d, J=3.4 Hz), 4.75 (0.3H, br s), 4.92–5.02 (0.7H, m), 6.51 (1H, d, J=7.8 Hz), 6.62 (1H, d, J=7.8 Hz), 7.10–7.26 (1H, m), 7.31 (1H, d, J=15.6 Hz), 7.40–7.57 (3H, m), 7.67 (1H, d, J=10.3 Hz), 9.07 (1H, br s).
IR (KBr)
υ 3400, 1644, 1586, 1462, 1408, 1359, 1315, 1120, 789 cm$^{-1}$.
Mass (FAB)
m/z 505 ((M+H)+).
Elementary Analysis: As C$_{30}$H$_{33}$N$_2$O$_4$F•0.5C$_4$H$_6$O$_6$
Calcd.: C, 66.31; H, 6.26; N, 4.83; F, 3.28.
Found.: C, 66.43; H, 6.37; N, 4.87; F, 3.27.

Compound 97

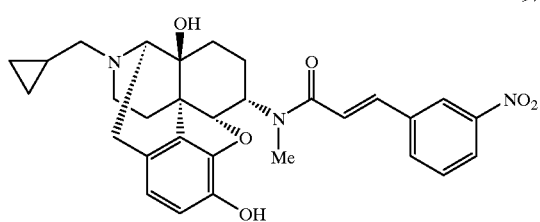

mp 185–200° C.
NMR (400 MHz, DMSO-d$_6$)
δ 0.10–0.30 (2H, m), 0.45–0.62 (2H, m), 0.82–1.00 (1H, m), 1.10–1.60 (4H, m), 1.70–1.85 (1H, m), 2.20–2.35 (2H, m), 2.55–2.90 (5H, m), 2.92 (0.6H, s), 2.97–3.10 (1H, m), 3.12 (2.4H, s), 3.23–3.37 (1H, m), 3.50–5.75 (4H, br), 4.55 (0.2H, m), 4.66 (0.8H, d, J=3.4 Hz), 4.78 (0.2H, m), 4.98 (0.8H, m), 6.53 (1H, d, J=8.1 Hz), 6.64 (1H, d, J=8.1 Hz). 7.29 (0.2H, d, J=15.1 Hz), 7.48 (0.8H, d, J=15.4 Hz), 7.58 (0.2H, d, J=15.1 Hz), 7.63 (0.8H, d, J=15.4 Hz), 7.71 (1H, t, J=8.1 Hz), 8.10–8.27 (2H, m), 8.50 (0.2H, s), 8.61 (0.8H, s).
IR (KBr)
υ 3398, 3360, 3216, 3094, 1649, 1591, 1531, 1350, 1120, 1036, 973, 812, 741
Mass (FAB)
m/z 532 ((M+H)+).
Elementary Analysis: As C$_{30}$H$_{33}$N$_3$O$_6$•H$_3$PO$_4$•1.6H$_2$O
Calcd.: C, 54.73; H, 6.00; N 6.38; P, 4.70.
Found.: C, 54.66; H, 5.85; N, 6.28; P, 4.45.

Compound 98

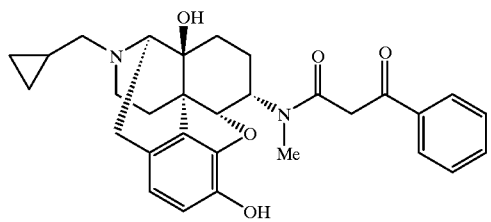

mp >176° C. (decomposition)
NMR (400 MHz, DMSO-d$_6$)
δ 0.14–0.24 (2H, m), 0.43–0.57 (2H, m), 0.81–0.95 (1H, m), 1.10–1.58 (4H, m), 1.74 (1H, m), 2.16–2.31 (2H, m), 2.40–2.56 (2H, m), 2.62–2.78 (2H, m), 2.84 (0.27H, s), 2.94 (1.71H, s), 2.99–3.08 (1H, m), 3.04 (1.02H, s), 3.25 (1H, m), 3.50 (3H, br s, 3×OH), 4.03 (1H, s), 4.15–4.25 (0.15H, m), 4.20 (0.51H, d, J=16.6 Hz), 4.29 (0.51H, d, J=16.6 Hz), 4.29 (0.09H, d, J=16.6 Hz), 4.36 (0.09H, d, J=16.6 Hz), 4.52 (0.51H, d, J=3.9 Hz), 4.63 (0.34H, d, J=3.9 Hz), 4.72 (0.06H, m), 4.77 (0.09H, m), 4.91 (0.51H, ddd, J=13.7, 3.9, 3.9 Hz), 4.98 (0.34H, ddd, J=13.7, 3.9, 3.9 Hz), 5.97 (0.06H, s), 6.18 (0.34H, s), 6.50–6.56 (1H, m), 6.61–6.67 (1H, m), 7.45–8.02 (5H, m), 9.10 (1H, br s, NH+), 15.84 (0.34H, s), 15.92 (0.06H, s).
IR (KBr)
υ 3400, 1688, 1611, 1464, 1359, 1323, 1214, 1172, 1120, 1069, 1038, 919, 806 cm$^{-1}$.
Mass (FAB)
m/z 503 ((M+H)+).
Elementary Analysis: As C$_{30}$H$_{34}$N$_2$O$_5$•0.5C$_4$H$_6$O$_6$•0.7H$_2$O
Calcd.: C, 65.12; H, 6.56; M, 4.75.
Found.: C, 65.15; H, 6.43; N, 4.74.

Examples 89–94

17-cyclopropylmethyl-3,14β-dihydroxy-4,5α-epoxy-6β-(N-methylcinnararido)morphinan•hydrochloride 99 (yield: 46%), 17-cyclopropylmethyl-3,14β-dihydroxy-4,5α-epoxy-6β-(N-methyl-trans-2-hexenamido)morphinan•tartrate 100 (yield: 52%), 17-cyclopropylmethyl-3,14β-dihydroxy-4,5α-epoxy-6β-(N-methyl-3-phenylpropiolamido)morphinan•hydrochloride 101 (yield: 49%), 17-cyclopropylmethyl-3,14β-dihydroxy-4,5α-epoxy-6β-(N-methyl-3-fluorocinnamamido)morphinan•tartrate 102 (yield: 81%), 17-cyclopropylmethyl-3,14β-dihydroxy-4,5α-epoxy-6β-(N-methylbenzoylacetamido)morphinan•tartrate 103 (yield: 52%) and 17-cyclopropylmethyl-3,14β-dihydroxy-4,5α-epoxy-6β-(N-methyl-3-nitrocinnamamido)morphinan•tartrate 104 (yield: 47%) were obtained by following the procedure of example 73 but using 17-cyclopropylmethyl-4,5α-epoxy-3,14β-dihydroxy-6β-methylaminomorphinan 10 instead of the starting material of 17-cyclopropylmethyl-4,5α-epoxy-3,14β-dihydroxy-6α-methylaminomorphinan 4, and using cinnamic acid, trans-2-hexenoic acid, phenylpropiolic acid, 3-fluorocinnamic acid, benzoylacetic acid and 3-nitrocinnamic acid instead of 3-nitrophenylacetic acid.

Compound 99

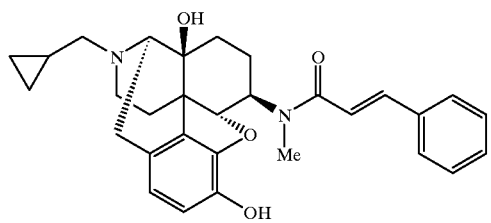

mp 225° C. (decomposition)
NMR (400 MHz, DMSO-$d_6$)
δ 0.42 (1H, m), 0.50 (1H, m), 0.59 (1H, m), 0.68 (1H, m), 1.07 (1H, m), 1.20–1.50 (3.5SH, m), 1.72 (1H, m), 2.13 (1H, m), 2.40–2.60 (2.5H, m), 2.87 (1H, m), 2.92 (2H, s), 3.06 (2H, m), 3.19 (1H, s), 3.32 (2H, m), 3.6–4.3 (2H, m), 4.85 (0.7H, m), 4.92 (0.3H, m), 6.30 (1H, m), 6.68 (2H, m), 6.88 (0.5H, d, J=8.3 Hz), 7.30–7.50 (5H, m), 7.71 (0.5H, d, J=6.4 Hz), 8.79 (1H, m), 9.29 (0.3H, s), 9.70 (0.7H, s).
IR (KBr)
υ 3380, 1642, 1599, 1499, 1321, 1127, 768 cm$^{-1}$.
Mass (FAB)
m/z 487 (M+H)
Elementary Analysis: As $C_{30}H_{34}N_2O_4 \cdot HCl \cdot 0.3H_2O$
Calcd.: C, 68.18; H, 6.79; N, 5.30; Cl, 6.71
Found.: C, 68.06; H, 7.11; N, 5.46; Cl, 6.37

Compound 100

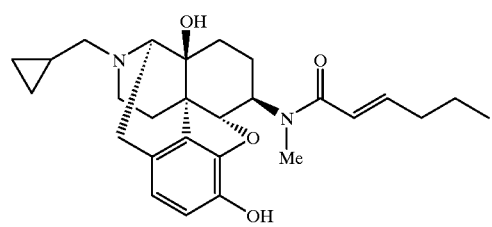

mp >145° C. (decomposition)
NMR (400 MHz, DMSO-$d_6$)
δ 0.25 (2H, m), 0.48–0.59 (2H, m), 0.79 (2.1H, t, J=7.3 Hz), 0.90 (0.9H, t, J=7.3 Hz), 0.92 (1H, m), 1.20–1.48 (5H, m), 1.58 (1H, m), 1.91–2.20 (4H, m), 2.29 (1H, m), 2.53 (1H, m), 2.67–2.85 (3H, m), 2.81 (2.1H, s), 3.01 (0.9H, s), 3.11 (1H, br d, J=18.6 Hz), 3.31 (1H, m), 3.45 (4.2H, br s, 3.6×OH+0.6×COOH), 3.57 (1H, m), 4.06 (1.6H, s), 4.62 (0.7H, d, J=7.8 Hz), 4.74 (0.3H, d, J=7.8 Hz), 6.05 (0.7H, d, J=15.1 Hz), 6.35–6.44 (1.0H, m), 6.54–6.71 (2.3H, m), 9.26 (1H, br s, NH+).
IR (KBr)
υ 3396, 1736, 1655, 1601, 1460, 1410, 1319, 1123, 1067, 1035, 922, 859 cm$^{-1}$.
Mass (FAB)
m/z 453 ((M+H)+).
Elementary Analysis: As $C_{27}H_{36}N_2O_4 \cdot 0.8C_4H_6O_6 \cdot 1.1H_2O$ Calcd.: C, 61.22; H, 7.32; N, 4.73.
Found.: C, 61.13; H, 7.23; N, 4.82.

Compound 101

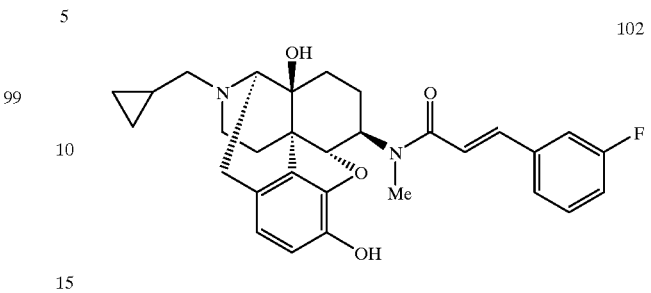

mp 208.0–225.0° C. (decomposition, ether)
NMR (400 MHz, DMSO-$d_6$) (data for 0.5 tartrate)
δ 0.25 (2H, br s), 0.54 (2H, m), 0.93 (1H, m), 1.27~1.47 (3H, m), 1.66 (1H, m), 1.88~5.20 (3H, br OH×2), 2.08~2.19 (2H, m), 2.30 (1H, m), 2.44~2.53 (2H, m), 2.58~2.80 (3H, m), 2.93 (2.1H, s), 3.12 (1H, m), 3.17 (0.9H, s), 3.27 (1H, br s), 4.00 (1H, s), 4.06 (0.3H, m), 4.20 (0.7H, m), 4.73 (0.7H, d, J=8.3 Hz), 4.82 (0.3H, d, J=8.3 Hz), 6.55~6.67 (2H, m), 7.19 (1.55H, d, J=7.3 Hz), 7.37 (1.55H, t, J=7.3 Hz), 7.45~7.56 (1.40H, m), 7.60 (0.5H, d, J=6.8 Hz), 9.15 (1H, br s).
IR (KBr) (Data for free base)
υ 3218, 2218, 1618, 1458 cm$^{-1}$.
Mass (FAB)
m/z 485 (M+H)+.
Elementary Analysis: As $C_{30}H_{33}N_2O_4Cl \cdot 0.7H_2O$
Calcd.: C, 67.52; H, 6.50; N, 5.25; Cl, 6.64.
Found.: C, 67.43; H, 6.65; N, 5.25; Cl, 6.67.

Compound 102

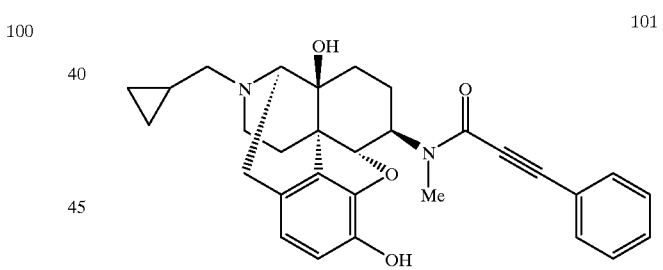

mp 145–153° C.
NMR (400 MHz, DMSO-$d_6$)
δ 0.20–0.32 (2H, m), 0.46–0.62 (2H, m), 0.88–1.00 (1H, m), 1.20–1.50 (3H, m), 1.55–1.65 (1H, m), 2.00–2.40 (3H, m), 2.42–2.60 (2H, m), 2.70–2.88 (3H, m), 2.90 (2.1H, s), 3.15 (0.9H, m), 3.05–4.00 (7H, m), 4.11 (2H, s), 4.71 (0.7H, d, J=8.1 Hz), 4.81 (0.3H, d, J=8.1 Hz), 6.58–6.68 (3H, m), 7.14–7.68 (5H, m), 9.15 (0.3H, br s), 9.45 (0.7H, br s).
IR (KBr)
υ 3320, 1731, 1647, 1586, 1412, 1311, 1270, 1127, 1077, 1033, 980, 859, 789, 677 cm$^{-1}$
Mass (FAB)
m/z 505 ((M+H)+).
Elementary Analysis: As $C_{30}H_{33}N_2O_4F \cdot C_4H_6O_6 \cdot H_2O$
Calcd.: C, 60.71; H, 6.14; N, 4.16; F, 2.82.
Found.: C, 60.63; H, 6.22; N, 4.07; F, 2.81.

Compound 103

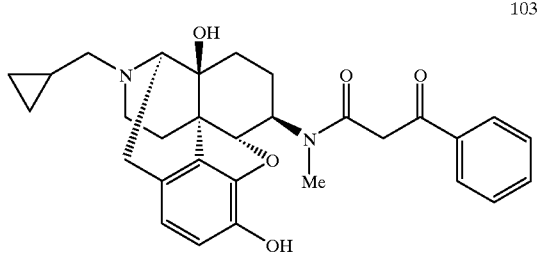

mp >161° C. (decomposition)
NMR (400 MHz, DMSO-$d_6$)
δ 0.17–0.27 (2H, m), 0.45–0.58 (2H, m), 0.89(1H, m), 1.16–1.44 (3H, m), 1.50–1.61 (1H, m), 2.02–2.18 (2H, m), 2.28 (1H, m), 2.43 (1H, m), 2.53–2.78 (3H, m), 2.81 (1.68H, s), 2.93 (0.18H, s), 2.98 (0.72H, s), 3.04 (1H, br d, J=19.1 Hz), 3.10 (0.42H, s), 3.17–3.28 (1H, m), 3.35 (1H, m), 3.50 (3H, br s, 3×OH), 3.98–4.37 (1.4H, m), 4.04 (1H, s), 4.67 (0.8H, d, J=7.8 Hz), 4.76 (0.14H, d, J=8.3 Hz), 4.77 (0.06H, d, J=8.3 Hz), 5.62 (0.06H, s), 6.12 (0.24H, s), 6.52 (0.56H, d, J=8.3 Hz), 6.52–6.78 (0.88H, m), 6.61 (0.56H, d, J=8.3 Hz), 7.41–7.96 (5H, m), 9.02–9.60 (1H, m, NH+), 15.50 (0.06H, s), 15.76 (0.24H, s).
IR (KBr)
υ 3390, 1686, 1626, 1452, 1323, 1278, 1125, 1035, 926, 859 $cm^{-1}$.
Mass (FAB)
m/z 503 ((M+H)+).
Elementary Analysis: As $C_{30}H_{34}N_2O_5 \cdot 0.5C_4H_6O_6 \cdot 1.2H_2O$
Calcd.: C, 64.14; H, 6.63; N, 4.67.
Found.: C, 64.20; H, 6.57; N, 4.61.
Compound 104

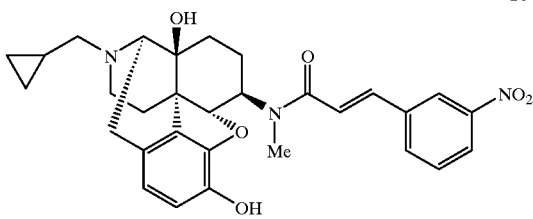

mp 161–164° C.
NMR (400 MHz, DMSO-$d_6$)
δ 0.18–0.30 (2H, m), 0.46–0.60 (2H, m), 0.85–0.97 (1H, m), 1.22–1.50 (3H, m), 1.53–1.62 (1H, m), 2.03–2.21 (2H, m), 2.23–2.35 (1H, m), 2.50–2.90 (4H, m), 2.91 (2.1H, s), 3.18 (0.9H, s), 3.10–4.20 (3H, m), 4.05 (1H, s), 4.67 (0.7H, d, J=8.3 Hz), 4.81 (0.3H, d, J=8.3 Hz), 6.58 (0.3H, d, J=7.8 Hz), 6.63 (1H, d, J=7.8 Hz), 6.73 (0.7H, d, J=7.8 Hz), 6.84 (0.7H, d, J=15.6 Hz), 7.42 (0.3H, d, J=15.9 Hz), 7.45 (0.7H, d, J=15.6 Hz), 7.57 (0.3H, d, J=15.6 Hz), 7.66 (0.7H, dd, J=8.3, 7.8 Hz), 7.71 (0.3H, dd, 8.3, 7.8 Hz), 7.93 (0.7H, d, J=7.8 Hz), 8.15–8.27 (2H, m), 8.60 (0.3H, s), 9.12 (0.3H, br s), 9.28 (0.7H, br s).
IR (KBr)
υ 3380, 1649, 1601, 1531, 1352, 1127, 1035, 922, 859, 810, 743 $cm^{-1}$.

Mass (FAB)
m/z 532 ((M+H)+).
Elementary Analysis: As $C_{30}H_{33}N_3O_6 \cdot 0.5C_4H_6O_6 \cdot 2.2H_2O$
Calcd.: C, 59.47; H, 6.30; N, 6.50.
Found.: C, 59.42; H, 5.96; N, 6.25.

Example 95

17-cyclopropylmethyl-3,14β-dihydroxy-4,5α-epoxy-6α-(N-methyl-3,4-difluorophenylacetamido)morphinan•hydrochloride 105

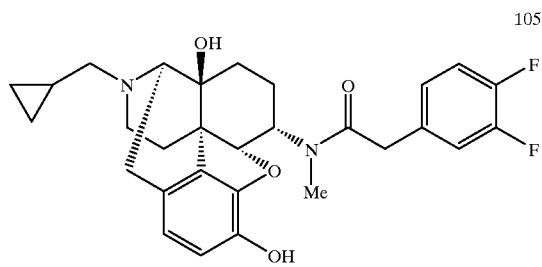

128 mg of 3,4-difluorophenylacetic acid and 131 mg of carbonyl diimidazole were dissolved in 2.5 ml of anhydrous tetrahydrofuran. After refluxing while heating for 30 minutes, the solution was cooled to room temperature. A solution of 200 mg of 17-cyclopropylmethyl-4,5α-epoxy-3,14β-dihydroxy-6α-methylaminomorphinan 4 dissolved in 13 ml of anhydrous tetrahydrofuran was added to the reaction solution followed by refluxing while heating for 1 hour. After cooling to room temperature, the reaction solution was concentrated and the resulting residue was dissolved in 16 ml of methanol and stirred for 1 hour following the addition of 1 ml of 1 N aqueous sodium hydroxide. The reaction system was then concentrated followed by the addition of 40 ml of ethylacetate to the residue and sequential washing with 25 ml of water and 25 ml of saturated brine. After drying with anhydrous sodium sulfate, the organic layer was concentrated to obtain 439 mg of crude product. This was then recrystallized from ethylacetate to obtain 190 mg of the free base of the target compound. The mother liquor was then purified with silica gel column chromatography (25 g chloroform/methanol=19/1) to obtain 177 mg of the free base of the target compound. The free base obtained in this manner was then dissolved in a mixed solvent of chloroform and methanol, and this solution was concentrated after adding methanol solution of hydrochloride to adjust to pH 4. The residue was re-precipitated with ether and filtered to obtain 176 mg of the target compound (yield: 57%).
mp 194–208° C. (decomposition, diethylether)
NMR (400 MHz, DMSO-$d_6$)
δ 0.31–0.43 (1H, m), 0.43–0.53 (1H, m), 0.53–0.64 (1H, m), 0.64–0.76 (1H, m), 0.99–1.12 (1H, m), 1.12–1.28 (1H, m), 1.28–1.45 (1H, m), 1.45–1.67 (2H, m), 1.86–2.03 (1H, m), 2.35–2.50 (1H, m), 2.59–2.77 (1H, m), 2.80 (0.6H, s), 2.88–3.18 (3H, m), 2.96 (2.4H, s), 3.18–3.39 (2H, m), 3.78 (1.6H, s), 3.88 (0.4H, s), 3.91 (1H, d, J=6.8 Hz), 4.49 (0.2H, m), 4.62 (1H, d, J=3.4 Hz), 4.97 (0.8H, dt, J=14.2, 3.4 Hz), 6.25 (0.8H, br s), 6.56 (0.2H, br s), 6.58 (1H, d, J=7.8 Hz), 6.73 (1H, d, J=7.8 Hz), 7.03–7.18 (1H, m), 7.25–7.45 (2H, m), 8.82 (1H, br s), 9.32 (1H, s).

IR (KBr)

υ 1620, 1560, 1520, 1460, 1278, 1172, 1120, 1036, 774 cm⁻¹.

Mass (FAB)

m/z 511 ((M+H)+).

Elementary Analysis: As C$_{29}$H$_{33}$N$_2$O$_4$ClF$_2$•0.7H$_2$O•0.25AcOEt

Calcd.: C, 61.95; H, 6.31; N, 4.82; Cl, 6.09; F, 6.53

Found.: C, 61.91; H, 6.47; N, 4.81; Cl, 6.04; F, 6.53

Examples 96–98

17-cyclopropylmethyl-3,14β-dihydroxy-4,5α-epoxy-6α-(N-methyl-4-benzo[b]thienylacetamido)morphinan•hydrochloride 106 (yield: 74%), 17-cyclopropylmethyl-3,14β-dihydroxy-4,5α-epoxy-6α-(N-methyl-3-benzo[b]thienylacetamido)morphinan•hydrochloride 107 (yield: 71%) and 17-cyclopropylmethyl-3,14β-dihydroxy-4,5α-epoxy-6α-(N-methyl-3-trifluoromethylphenylacetamido)morphinan•hydrochloride 108 (yield: 78%) were obtained by following the procedure of example 95 but using 4-benzo[b]thienylacetic acid, 3-benzo[b]thienylacetic acid and 3-trifluoromethylphenylacetic acid instead of 3,4-difluorophenylacetic acid.

Compound 106

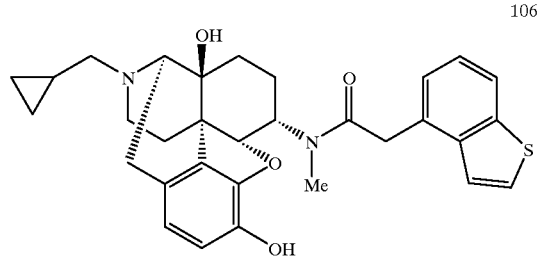

mp 207.0–215.0° C. (decomposition, diethylether)

NMR (400 MHz, DMSO-d$_6$)

δ 0.31–0.42 (1H, m), 0.42–0.53 (1H, m), 0.53–0.65 (1H, m), 0.65–0.74 (1H, m), 1.00–1.11 (1H, m), 1.11–1.29 (1H, m), 1.29–1.48 (1H, m), 1.55 (1H, dd, J=15.1, 9.3 Hz), 1.61 (1H, br d, J=12.2 Hz), 1.88–2.00 (1H, m), 2.42 (1H, dq, J=13.2, 4.9 Hz), 2.60–2.75 (1H, m), 2.81 (0.6H, s), 2.89–2.99 (1H, m), 3.02 (2.4H, s), 3.01–3.15 (2H, m), 3.19–3.32 (2H, m), 3.90 (1H, d, J=6.7 Hz), 4.11 (1.6H, s), 4.20 (0.4H, s), 4.51 (0.2H, br s), 4.63 (0.8H, d, J=3.9 Hz), 4.66 (0.2H, br s), 5.00 (0.8H, dt, J=13.7, 3.4 Hz), 6.22 (0.8H, br s), 6.49 (0.2H, br s), 6.58 (1H, d, J=8.3 Hz), 6.74 (1H, d, J=8.3 Hz), 7.22 (1H, d, J=6.8 Hz), 7.36 (0.8H, t, J=7.6 Hz), 7.35–7.40 (0.2H, m), 7.52 (0.8H, d, J=4.9 Hz), 7.64 (0.2H, d, J=5.9 Hz), 7.76 (0.8H, d, J=5.4 Hz), 7.77 (0.2H, d, J=5.9 Hz), 7.90 (0.8H, d, J=8.3 Hz), 7.92 (0.2H, m), 8.82 (1H, br s), 9.29 (0.2H, s), 9.32 (0.8H, s).

IR (KBr)

υ 1620, 1543, 1508, 1460, 1321, 1120, 1036, 764 cm⁻¹.

Mass (FAB)

m/z 531 ((M+H)+).

Elementary Analysis: As C$_{31}$H$_{35}$N$_2$O$_4$ClS•0.7H$_2$O

Calcd.: C, 64.22; H, 6.33; N, 4.83; Cl, 6.12; S, 5.53

Found.: C, 64.13; H, 6.43; N, 4.79; Cl, 6.43; S, 5.24

Compound 107

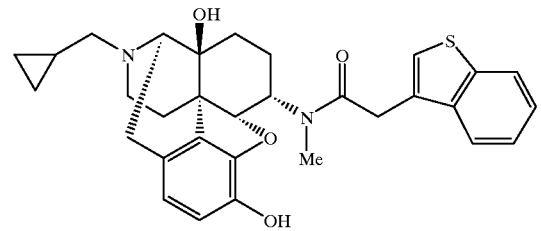

mp 239–250° C. (decomposition, ethylacetate)

NMR (400 MHz, DMSO-d$_6$)

δ 0.31–0.43 (1H, m), 0.43–0.53 (1H, m), 0.53–0.63 (1H, m), 0.63–0.74 (1H, m), 0.98–1.12 (1H, m), 1.12–1.31 (1H, m), 1.31–1.47 (1H, m), 1.47–1.69 (2H, m), 1.82–2.07 (1H, m), 2.29–2.49 (1H, m), 2.59–2.77 (1H, m), 2.81 (0.6H, s), 2.84–2.98 (1H, m), 3.03 (2.4H, s), 2.98–3.18 (2H, m), 3.18–3.42 (2H, m), 3.81–3.96 (1H, m), 4.00 (1.6H, s), 4.02–4.27 (0.4H, m), 4.32–4.43 (0.2H, m), 4.66 (0.8H, d, J=3.4 Hz), 4.66–4.74 (0.2H, m), 5.00 (1H, dt, J=14.2, 3.3 Hz), 6.22 (0.8H, brs), 6.59 (1H, d, J=7.8 Hz), 6.73 (1H, d, J=8.3 Hz), 7.31–7.48 (2H, m), 7.52 (0.8H, s), 7.64 (0.2H, brs), 7.81 (0.8H, d, J=7.3 Hz), 7.91–8.04 (1.2H, m), 8.81 (1H, br s), 9.28 (0.2H, s), 9.33 (0.8H, s).

IR (KBr)

υ 1620, 1510, 1460, 1321, 1120, 1038 cm⁻¹.

Mass (FAB)

m/z 531 ((M+H)+).

Elementary Analysis: As C$_{31}$H$_{35}$N$_2$O$_4$ClS•0.5H$_2$O

Calcd.: C, 64.62; H, 6.29; N, 4.86; Cl, 6.15; S, 5.57

Found.: C, 64.62; H, 6.50; N, 5.00; Cl, 6.08; S, 5.62

Compound 108

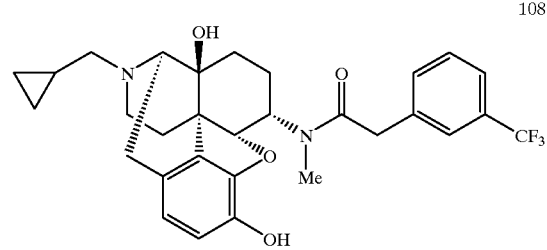

mp 192.0–200.0° C. (decomposition, ethylacetate)

NMR (400 MHz, DMSO-d$_6$)

δ 0.31–0.42 (1H, m), 0.42–0.53 (1H, m), 0.53–0.62 (1H, m), 0.62–0.77 (1H, m), 0.96–1.12 (1H, m), 1.12–1.31 (1H, m), 1.31–1.47 (1H, m), 1.47–1.69 (2H, m), 1.82–2.04 (1H, m), 2.30–2.49 (1H, m), 2.59–2.78 (1H, m), 2.81 (0.4H, s), 2.86–3.18 (3H, m), 2.99 (2.6H, s), 3.18–3.40 (2H, m), 3.90 (2H, s), 3.90–4.1 (1H, m), 4.53 (0.2H, m), 4.62 (0.8H, d, J=3.9 Hz), 4.77 (0.2H, br s), 4.98 (0.8H, dt, J=13.7, 3.9 Hz), 6.24 (1H, br s), 6.58 (1H, d, J=7.8 Hz), 6.74 (1H, d, J=8.3 Hz), 7.49–7.68 (4H, m), 8.82 (1H, br s), 9.33 (1H, s).

IR (KBr)

υ 1620, 1508, 1460, 1334, 1166, 1120, 1077, 1036, 801, 702 cm⁻¹.

Mass (FAB)

m/z 543 ((M+H)+).

Elementary Analysis: As $C_{30}H_{34}N_2O_4ClF_3 \cdot 0.5H_2O$
Calcd.: C, 61.27; H, 6.00; N, 4.76; Cl, 6.02; F, 9.69
Found.: C, 61.37; H, 6.08; N, 4.75; Cl, 5.89; F, 9.92

Examples 99–110

17-cyclopropylmethyl-3,14β-dihydroxy-4,5α-epoxy-6β-(N-methyl-4-chlorophenylacetamido)morphinan•hydrochloride 109 (yield: 78%), 17-cyclopropylmethyl-3,14β-dihydroxy-4,5α-epoxy-6β-(N-methyl-3-chlorophenylacetamido)morphinan•hydrochloride 110 (yield: 84%), 17-cyclopropylmethyl-3,14β-dihydroxy-4,5α-epoxy-6β-(N-methyl-1-naphthylacetamido)morphinan•hydrochloride 111 (yield: 61%), 17-cyclopropylmethyl-3,14β-dihydroxy-4,5α-epoxy-6β-(N-methyl-2-naphthylacetamido)morphinan•hydrochloride 112 (yield: 63%), 17-cyclopropylmethyl-3,14β-dihydroxy-4,5α-epoxy-6β-(N-methyl-3-thienylacetamido)morphinan•hydrochloride 113 (yield: 61%), 17-cyclopropylmethyl-3,14β-dihydroxy-4,5α-epoxy-6β-(N-methyl-3,4-methylenedioxyphenylacetamido)morphinan•hydrochloride 114 (yield: 45%), 17-cyclopropylmethyl-3,14β-dihydroxy-4,5α-epoxy-6β-(N-methyl-3-benzo[b]thienylacetamido)morphinan•hydrochloride 115 (yield: 55%), 17-cyclopropylmethyl-3,14β-dihydroxy-4,5α-epoxy-6β-(N-methyl-3-trifluoromethylphenylacetamido)morphinan•hydrochloride 116 (yield: 57%), 17-cyclopropylmethyl-3,14β-dihydroxy-4,5α-epoxy-6β-(N-methyl-9-fluorenamido)morphinan•hydrochloride 117 (yield: 65%), 17-cyclopropylmethyl-3,14β-dihydroxy-4,5α-epoxy-6β-(N-methyl-2,3,4,5,6-pentafluorophenylacetamido)morphinan•hydrochloride 118 (yield: 68%), 17-cyclopropylmethyl-3,14β-dihydroxy-4,5α-epoxy-6β-[N-methyl-3-(5-chlorobenzo[b]thienyl)acetamido]morphinan•hydrochloride 119 (yield: 83%) and 17-cyclopropylmethyl-3,14β-dihydroxy-4,5α-epoxy-6β-(N-methyl-4-benzo[b]thienylacetamido)morphinan•hydrochloride 120 (yield: 76%) were obtained by following the procedure of example 95 but using 17-cyclopropylmethyl-4,5α-epoxy-3,14β-dihydroxy-6β-methylaminomorphinan 10 instead of the starting material of 17-cyclopropylmethyl-4,5α-epoxy-3,14β-dihydroxy-6α-methylaminomorphinan 4, and using 4-chlorophenylacetic acid, 3-chlorophenylacetic acid, 1-naphthylacetic acid, 2-naphthylacetic acid, 3-thienylacetic acid, 3,4-methylenedioxyphenylacetic acid, 3-benzo[b]thienylacetic acid, 3-trifluoromethylphenylacetic acid, 9-fluorenecarboxylic acid, 2,3,4,5,6-pentafluorophenylacetic acid, 3-(5-chlorobenzo[b]thienyl)acetic acid and 4-benzo[b]thienylacetic acid instead of 3,4-difluorophenylacetic acid.

Compound 109

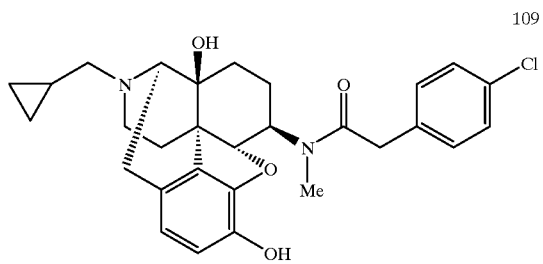

mp 201.0–205.0° C. (decomposition, methanol)
NMR (400 MHz, CD$_3$OD)

δ 0.31–0.58 (2H, m), 0.61–0.75 (1H, m), 0.75–0.87 (1H, m), 0.87–1.00 (1H, m), 1.00–1.12 (1H, m), 1.12–1.27 (1H, m), 1.35–1.82 (3H, m), 2.06 (1H, dq, J=13.4, 2.7 Hz), 2.42–2.73 (2H, m), 2.73–2.88 (1H, m), 2.92 (2.5H,s), 3.07 (0.5H, s), 2.97–3.20 (3H, m), 3.68 (2H, dd, J=28.8, 15.6 Hz), 3.51–4.38 (2H, m), 4.75 (1H, d, J=8.3 Hz), 6.82 (2H, d, J=8.8 Hz), 6.87 (1H, d, J=7.8 Hz), 7.18 (2H, d, J=8.8 Hz), 7.22 (1H, m).
IR (KBr)
υ 1626, 1493, 1460, 1321, 1125, 1035, 924, 808 cm$^{-1}$.
Mass (FAB)
m/z 509 ((M+H)+).
Elementary Analysis: As $C_{29}H_{34}N_2O_4Cl_3 \cdot 0.6H_2O$
Calcd.: C, 62.61; H, 6.38; N, 5.04; Cl, 12.74
Found.: C, 62.56; H, 6.49; N, 5.02; Cl, 12.64

Compound 110

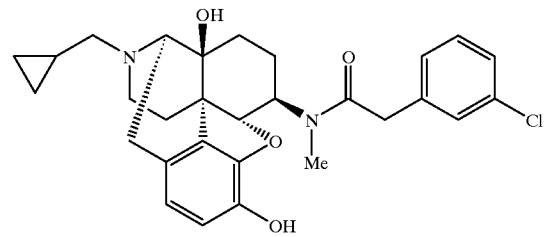

mp 200.0–209.0° C. (decomposition, methanol)
NMR (400 MHz, CD$_3$OD)

δ 0.31–0.58 (2H, m), 0.61–0.75 (1H, m), 0.75–0.89 (2H, m), 0.96–1.24 (2H, m), 1.34–1.82 (3H, m), 2.03 (1H, dq, J=13.2, 2.9 Hz), 2.42–2.73 (2H, m), 2.73–2.88 (1H, m), 2.91 (2.5H, s), 3.09 (0.5H, s), 2.97–3.20 (3H, m), 3.54–3.65 (1H$_1$, m), 3.68 (2H, s), 3.73–4.97 (1H, m), 4.75 (1H, d, J=8.3 Hz), 6.62–7.39 (6H, m).
IR (KBr)
υ 1620, 1502, 1460, 1321, 1125, 1035, 924, 808 cm$^{-1}$.
Mass (FAB)
m/z 509 ((M+H)+).
Elementary Analysis: As $C_{29}H_{34}N_2O_4Cl_3 \cdot 0.3H_2O$
Calcd.: C, 63.22; H, 6.33; N, 5.08; Cl, 12.87
Found.: C, 63.20; H, 6.50; N, 5.03; Cl, 12.69

Compound 111

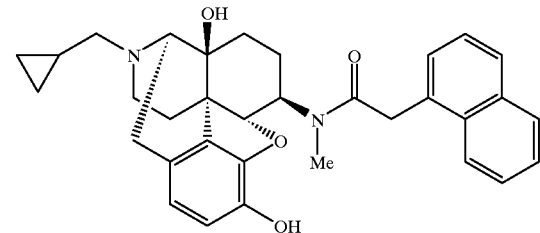

mp 210.0–215.0° C. (decomposition, diethylether)
NMR (400 MHz, CD$_3$OD)

δ 0.31–0.60 (3H, m), 0.61–0.91 (3H, m), 0.91–1.18 (1H, m), 1.31 (1H, brd, J=14.2 Hz), 1.43–1.81 (2H, m), 1.89 (1H, dq, J=13.2, 2.9 Hz), 2.42–2.73 (2H, m), 2.73–3.00 (2H, m), 2.92 (2.6H, s), 3.15 (0.4H, s), 3.00–3.19 (2H, m), 3.54–3.85 (2H, m), 3.99 (1H, d, J=16.1 Hz), 4.23 (1H, d, J=16.1 Hz), 4.75 (1H, d, J=8.3 Hz), 6.80 (1H, d, J=8.30 Hz), 6.90 (1H, d, J=7.82 Hz), 7.00 (1H, d, J=6.84 Hz), 7.27 (1H, t, J=7.6 Hz), 7.31–7.59 (2H, m), 7.70 (2H, t, J=8.30 Hz), 7.80 (1H, d, J=8.3 Hz).
IR (KBr)
υ 1620, 1510, 1502, 1460, 1402, 1321, 1125, 1035, 924, 797 cm$^{-1}$.
Mass (FAB)
m/z 525 ((M+H)+).
Elementary Analysis: As $C_{33}H_{37}N_2O_4Cl \cdot 0.3H_2O$
Calcd.: C, 69.96; H, 6.69; N, 4.94; Cl, 6.26
Found.: C, 70.04; H, 6.68; N, 5.03; Cl, 6.20
Compound 112

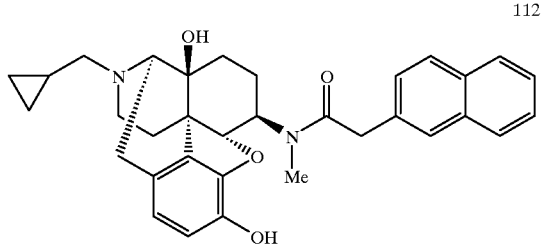

112 mp 207.0–214.0° C. (decomposition, diethylether)
NMR (400 MHz, CD$_3$OD)
δ 0.35–0.58 (3H, m), 0.61–0.91 (3H, m), 0.91–1.18 (1H, m), 1.23 (1H, brd, J=14.2 Hz), 1.39–1.81 (2H, m), 1.89 (1H, dq, J=13.2, 2.9 Hz), 2.42–2.76 (2H, m), 2.76–3.02 (2H, m), 2.92 (2.6H, s), 3.10 (0.4H, s), 3.02–3.20 (2H, m), 3.60–3.82 (2H, m), 3.86 (1H, d, J=21.5 Hz), 3.95 (1H, d, J=18.1 Hz), 4.75 (1H, d, J=8.3 Hz), 6.87–7.00 (2H, m), 7.00–7.13 (2H, m), 7.35–7.49 (2H, m), 7.49–7.58 (1H, m), 7.70 (1H, d, J=8.3 Hz), 7.73–7.80 (1H, m).
IR (KBr)
υ 1620, 1504, 1460, 1408, 1321, 1125, 1035, 859, 803, 748 cm$^{-1}$.
Mass (FAB)
m/z 525 ((M+H)+).
Elementary Analysis: As $C_{33}H_{37}N_2O_4Cl$
Calcd.: C, 70.64; H, 6.65; N, 4.99; Cl, 6.32
Found.: C, 70.39; H, 6.75; N, 5.05; Cl, 6.00
Compound 113

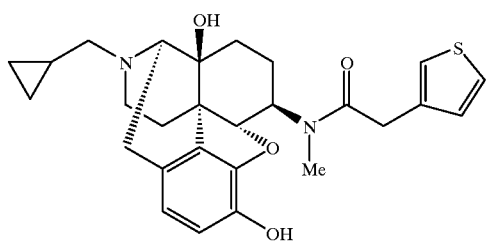

113 mp 208.0–219.0° C. (decomposition, diethylether)
NMR (400 MHz, DMSO-d$_6$)
δ 0.31–0.45 (1H, m), 0.45–0.53 (1H, m), 0.53–0.63 (1H, m), 0.63–0.78 (1H, m), 0.84–1.30 (3H, m), 1.30–1.80 (2H, m), 1.90–2.14 (1H, m), 2.30–2.61 (3H, m), 2.83 (2.4H, s), 3.00 (0.6H, s), 2.75–2.91 (1H, m), 2.91–3.17 (3H, m), 3.40–3.57 (2H, m), 3.57–3.72 (1H, m), 3.72–3.88 (1H, m), 4.81 (0.8H, d, J=8.3 Hz), 4.87 (0.2H, d, J=8.3 Hz), 6.30 (0.2H, s), 6.40 (0.8H, s), 6.62 (1H, d, J=4.9 Hz), 6.72 (1H, s), 6.73 (1H, d, J=8.3 Hz), 6.82 (1H, d, J=8.3 Hz), 7.38 (0.8H, dd, J=4.9, 2.9 Hz), 7.47 (0.2H, dd, J=4.9, 2.9 Hz), 8.80 (1H, br s), 9.28 (0.2H, s), 9.65 (0.8H, s).
IR (KBr)
υ 1620, 1508, 1460, 1321, 1125, 1035, 922, 859 cm$^{-1}$.
Mass (FAB)
m/z 481 ((M+H)+).
Elementary Analysis: As $C_{27}H_{33}N_2O_4ClS \cdot 0.05H_2O$
Calcd.: C, 61.64; H, 6.51; N, 5.32; Cl, 6.74; S, 6.10
Found.: C, 61.77; H, 6.50; N, 5.19; Cl, 6.65; S, 5.83
Compound 114

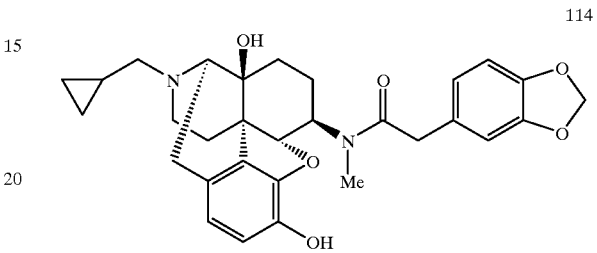

114 mp 203.0–208.0° C. (decomposition, ethylacetate, diethylether)
NMR (400 MHz, DMSO-d$_6$)
δ 0.31–0.45 (1H, m), 0.45–0.54 (1H, m), 0.54–0.63 (1H, m), 0.63–0.73 (1H, m), 0.85–0.99 (1H, m), 0.99–1.10 (1H, m), 1.10–1.29 (1H, m), 1.32–1.80 (3H, m), 1.92–2.13 (1H, m), 2.36–2.55 (2H, m), 2.72–2.92 (1H, m), 2.82 (2.4H, s), 2.99 (0.6H, s), 2.92–3.13 (2H, m), 3.25–3.41 (1H, m), 3.44 (2H, s), 3.48–3.70 (1H, m), 3.82 (1H, br d, J=4.9 Hz), 4.81 (0.8H, d, J=8.3 Hz), 4.87 (0.2H, d, J=8.3 Hz), 5.93 (1.6H, d, J=0.98 Hz), 5.98 (0.4H, s), 6.23 (1H, dd, J=1.3, 8.1 Hz), 6.34 (1H, s), 6.40 (1H, br s), 6.58–6.90 (3H, m), 8.80 (1H, brs), 9.26 (0.2H, s), 9.63 (0.8H, s).
IR (KBr)
υ 1620, 1504, 1491, 1323, 1249, 1125, 1036 cm$^{-1}$.
Mass (FAB)
m/z 519 ((M+H)+).
Elementary Analysis: As $C_{30}H_{35}N_2O_6Cl \cdot 0.4H_2O$
Calcd.: C, 64.08; H, 6.41; N, 4.98; Cl, 6.31
Found.: C, 64.00; H, 6.43; N, 5.01; Cl, 6.27
Compound 115

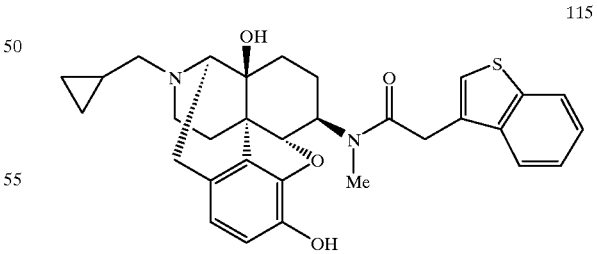

115 mp 215.0–225.0° C. (decomposition, ethylacetate, diethylether)
NMR (400 MHz, DMSO-d$_6$)
δ 0.31–0.45 (1H, m), 0.45–0.53 (1H, m), 0.53–0.62 (1H, m), 0.62–0.73 (1H, m), 0.79–0.89 (1H, m), 0.89–1.12 (2H, m), 1.34–1.60 (2H, m), 1.98–2.07 (1H, m), 2.39–2.55 (2H, m), 2.73–2.98 (1H, m), 2.85 (2.4H, s), 3.07 (0.6H, s), 2.98–3.13 (2H, m), 3.17–3.39 (2H, m), 3.50–3.61 (1H, m), 3.68 (1H, d, J=16.1 Hz), 3.78 (1H, br d, J=3.9 Hz), 3.88 (1H, d, J=16.1 Hz), 4.83 (0.8H, d, J=8.3 Hz), 4.90 (0.2H, d, J=8.3 Hz), 6.29 (0.2H, s), 6.35 (0.8H, s), 6.03 (0.2H, d, J=8.3 Hz), 6.70 (0.2H, d, J=8.3 Hz), 6.74 (0.8H, d, J=8.3 Hz), 6.82 (0.8H, d, J=8.3 Hz), 7.08 (0.8H, s), 7.21–7.42 (2.8H, m), 7.48 (0.2H, s), 7.77–7.82 (0.2H, m), 7.92 (0.8H, d, J=7.8 Hz), 7.97–8.02 (0.2H, m), 8.78 (1H, br s), 9.28 (0.2H, s), 9.68 (0.8H, s).

IR (KBr)

υ 1626, 1502, 1460, 1319, 1125, 1035 cm$^{-1}$.

Mass (FAB)

m/z 531 ((M+H)+).

Elementary Analysis: As $C_{31}H_{35}N_2O_4ClS \cdot 0.4H_2O$

Calcd.: C, 64.83; H, 6.28; N, 4.88; Cl, 6.17; S, 5.58

Found.: C, 64.85; H, 6.42; N, 4.89; Cl, 6.15; S, 5.53

Compound 116

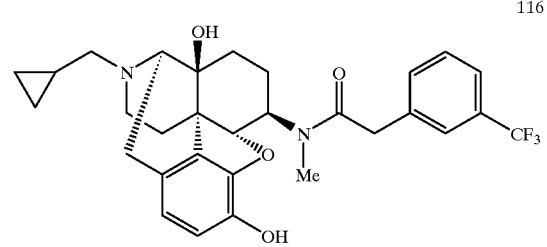

mp 195.0–203.0° C. (decomposition, methanol)

NMR (400 MHz, DMSO-d$_6$)

δ 0.31–0.45 (1H, m), 0.45–0.53 (1H, m), 0.53–0.63 (1H, m), 0.63–0.77 (1H, m), 0.96–1.12 (2H, m), 1.12–1.30 (1H, m), 1.30–1.80 (3H, m), 2.06 (1H, br q, J=13.2 Hz), 2.39–2.59 (2H, m), 2.85 (2.4H, s), 3.05 (0.6H, s), 2.71–2.92 (1H, m), 2.92–3.12 (2H, m), 3.41–3.58 (1H, m), 3.68 (1H, d, J=3.4 Hz), 3.58–3.77 (1H, m), 3.77–4.10 (2H, m), 4.84 (0.8H, br d, J=5.4 Hz), 4.88 (0.2H, br d, J=5.4 Hz), 6.30 (0.2H, br s), 6.42 (0.8H, br s), 6.62 (0.2H, d, J=8.3 Hz), 6.69 (0.2H, d, J=8.3 Hz), 6.72 (0.8H, d, J=8.3 Hz), 6.81 (0.8H, d, J=8.3 Hz), 7.13 (0.8H, s), 7.17 (0.2H, d, J=6.8 Hz), 7.22–7.28 (0.2H, m), 7.30 (0.8H, d, J=7.8 Hz), 7.48 (1H, t, J=7.8 Hz), 7.52–7.63 (1H, m), 8.80 (1H, br s), 9.25 (0.2H, s), 9.64 (0.8H, s).

IR (KBr)

υ 1628, 1508, 1460, 1334, 1166, 1127, 1077, 1035, 922, 704 cm$^{-1}$.

Mass (FAB)

m/z 543 ((M+H)+).

Elementary Analysis: As $C_{30}H_{34}N_2O_4ClF_3$

Calcd.: C, 62.23; H, 5.92; N, 4.84; Cl, 6.12; F, 9.84

Found.: C, 62.19; H, 6.04; N, 4.82; Cl, 5.76; F, 9.87

Compound 117

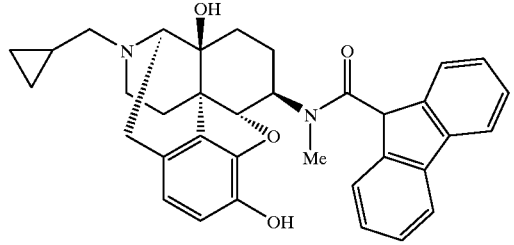

mp 215.0–224.0° C. (decomposition, ethylacetate)

NMR (400 MHz, DMSO-d$_6$)

δ 0.31–0.47 (1H, m), 0.47–0.57 (1H, m), 0.57–0.64 (1H, m), 0.64–0.77 (1H, m), 0.98–1.13 (1H, m), 1.20–1.60 (2H, m), 1.60–1.92 (2H, m), 2.31–2.70 (2H, m), 2.79–2.91 (1H, m), 2.97 (2.1H, s), 2.99–3.15 (2H, m), 3.36 (0.9H, s), 3.37–3.60 (2H, m), 3.81 (0.3H, br d, J=5.2 Hz), 3.89 (0.7H, br d, J=5.2 Hz), 3.72–3.93 (0.3H, m), 4.12–4.29 (0.7H, m), 4.90–5.02 (0.3H, m), 5.04 (0.7H, d, J=7.3 Hz), 5.09 (0.7H, s), 5.38 (0.3H, m), 6.17 (0.3H, br s), 6.46 (0.7H, br s), 6.61 (1H, s), 6.55–6.78 (1H, m), 7.08–7.52 (6H, m), 7.64 (1H, d, J=7.3 Hz), 7.84 (1H, dd, J=7.8, 4.4 Hz), 7.91 (1H, d, J=7.3 Hz), 8.77 (0.3H, br s), 8.83 (0.7H, br s), 9.24 (0.3H, s), 9.26 (0.7H, s).

IR (KBr)

υ 1620, 1510, 1460, 748 cm$^{-1}$.

Mass (FAB)

m/z 549 ((M+H)+).

Elementary Analysis: As $C_{35}H_{37}N_2O_4Cl \cdot 0.6H_2O$

Calcd.: C, 70.54; H, 6.46; N, 4.70; Cl, 5.95

Found.: C, 70.77; H, 6.54; N, 4.71; Cl, 5.58

Compound 118

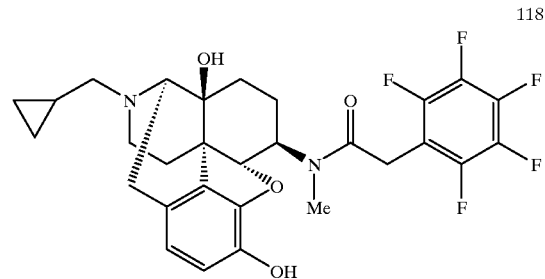

mp 208.0–214.0° C. (decomposition, methanol)

NMR (400 MHz, DMSO-d$_6$)

δ 0.31–0.47 (1H, m), 0.47–0.56 (1H, m), 0.56–0.63 (1H, m), 0.63–0.77 (1H, m), 1.00–1.13 (1H, m), 1.20–1.65 (3H, m), 1.74 (1H, br t, J=13.4 Hz), 2.16 (1H, br q, J=12.7 Hz), 2.39–2.62 (2H, m), 2.89 (2.4H, s), 2.76–2.96 (1H, m), 2.96–3.12 (2H, m), 3.17 (0.6H, s), 3.20–3.45 (2H, m), 3.62–3.75 (1H, m), 3.75–3.98 (3H, m), 4.85 (0.8H, d, J=7.8 Hz), 4.94 (0.2H, d, J=7.8 Hz), 6.38 (0.2H, br s), 6.52 (0.8H, brs), 6.62 (0.2H, d, J=8.3 Hz), 6.68 (1H, d, J=8.3 Hz), 6.74 (0.8H, d, J=7.8 Hz), 8.85 (1H, br s), 9.27 (0.2H, s), 9.41 (0.8H, s).

IR (KBr)

υ 1638, 1510, 1315, 1127, 1009, 919, 859 cm$^{-1}$.

Mass (FAB)

m/z 565 ((M+H)+).

Elementary Analysis: As $C_{29}H_{30}N_2O_4ClF \cdot 0.2H_2O$
Calcd.: C, 57.61; H, 5.07; N, 4.63; Cl, 5.86; F, 15.71
Found.: C, 57.60; H, 5.36; N, 4.74; Cl, 5.94; F, 15.51
Compound 119

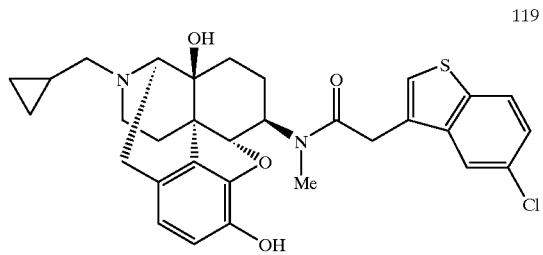

119 mp 210.0–219.0° C. (decomposition, diethylether)
NMR (400 MHz, DMSO-$d_6$)

δ 0.31–0.45 (1H, m), 0.45–0.54 (1H, m), 0.54–0.62 (1H, m), 0.62–0.73 (1H, m), 1.00–1.12 (1H, m), 1.19–1.57 (3H, m), 1.61–1.78 (1H, m), 2.00–2.18 (1H, m), 2.40–2.60 (2H, m), 2.73–2.92 (1H, m), 2.87 (2.4H, s), 3.09 (0.6H, s), 2.92–3.13 (2H, m), 3.23–3.41 (2H, m), 3.59–3.69 (0.8H, m), 3.76 (0.8H, d, J=16.5 Hz), 3.80–3.90 (1H, m), 3.89 (0.8H, d, J=16.5 Hz), 3.95 (0.4H, s), 4.00–4.12 (0.2H, m), 4.88 (0.8H, d, J=7.9 Hz), 4.90 (0.2H, d, J=7.9 Hz), 6.35 (0.2H, br s), 6.47 (0.8H, br s), 6.63 (0.2H, d, J=7.9 Hz), 6.69 (1H, d, J=8.5 Hz), 6.78 (0.8H, d, J=7.9 Hz), 7.23 (0.8H, s), 7.36 (0.8H, dd, J=8.6, 1.8 Hz), 7.40 (0.2H, dd, J=8.6, 1.8 Hz), 7.60 (0.2H, s), 7.66 (0.8H, d, J=1.8 Hz), 7.86 (0.2H, d, J=1.8 Hz), 7.97 (0.8H, d, J=8.6 Hz), 8.01 (0.2H, d, J=8.5 Hz), 8.82 (1H, br s), 9.25 (0.2H, s), 9.60 (0.8H, s).

IR (KBr)
υ 1628, 1508, 1427, 1321, 1127, 1079, 1035, 859, 835 cm$^{-1}$.

Mass (FAB)
m/z 565 ((M+H)+).

Elementary Analysis: As $C_{31}H_{34}N_2O_4Cl_2S \cdot 0.3H_2O$
Calcd.: C, 61.34; H, 5.75; N, 4.62; Cl, 11.68; S, 5.28
Found.: C, 61.40; H, 5.81; N, 4.63; Cl, 11.38; S, 5.20
Compound 120

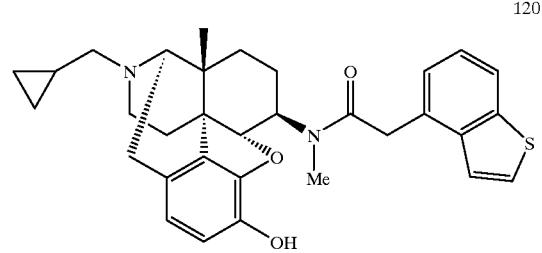

120 mp 219.0–226.0° C. (decomposition, diethylether)
NMR (400 MHz, DMSO-$d_6$)

δ 0.31–0.45 (1H, m), 0.45–0.53 (1H, m), 0.53–0.62 (2H, m), 0.62–0.73 (1H, m), 0.77–0.92 (1H, m), 0.97–1.12 (1H, m), 1.43 (1H, d, J=12.2 Hz), 1.47 (1H, d, J=10.3 Hz), 1.91 (1H, br q, J=13.2 Hz), 2.48 (2H, d, J=8.6 Hz), 2.77–2.89 (1H, m), 2.83 (2.4H, s), 2.92 (1H, dd, J=19.5, 6.1 Hz), 3.06 (0.6H, s), 2.99–3.11 (1H, m), 3.25–3.39 (1H, m), 3.51–3.61 (1H, m), 3.78 (1H, d, J=5.4 Hz), 3.85 (1H, d, J=15.4 Hz), 3.89 (1H, d, J=15.4 Hz), 4.83 (0.8H, d, J=8.3 Hz), 4.91 (0.2H, d, J=8.3 Hz), 6.31 (0.2H, br s), 6.37 (0.8H, br s), 6.63 (0.2H, d, J=8.3 Hz), 6.70 (0.2H, dd, J=7.8, 2.0 Hz), 6.77 (0.8H, d, J=8.3 Hz), 6.80–6.90 (1.8H, m), 6.98 (1H, d, J=5.4 Hz), 7.18 (0.8H, t, J=7.8 Hz), 7.31 (0.2H, t, J=7.8 Hz), 7.36 (0.8H, s), 7.50 (0.2H, d, J=4.9 Hz), 7.60 (0.8H, d, J=5.4 Hz), 7.73 (0.2H, d, J=5.9 Hz), 7.82 (0.8H, d, J=8.3 Hz), 7.88 (0.2H, d, J=7.8 Hz), 8.78 (1H, br s), 9.25 (0.2H, s), 9.66 (0.8H, s).

IR (KBr)
υ 1620, 1543, 1516, 1460, 1125, 1033, 766 cm$^{-1}$.

Mass (FAB)
m/z 531 ((M+H)+).

Elementary Analysis: As $C_{31}H_{35}N_2O_4ClS \cdot 0.4H_2O$
Calcd.: C, 64.83; H, 6.28; N, 4.88; Cl, 6.17; S 5.58
Found.: C, 65.03; H, 6.49; N, 4.78; Cl, 6.03; S, 5.19

Examples 111–113

17-Cyclopropylmethyl-3,14β-dihydroxy-4,5α-epoxy-6β-(3,4-dichlorophenylacetamido)morphinan•hydrochloride 121 (yield: 54%) and 17-allyl-3,14β-dihydroxy-4,5α-epoxy-6α-(N-methyl-3,4-dichlorophenylacetamido)morphinan•hydrochloride 122 (yield: 63%), 17-allyl-3,14β-dihydroxy-4,5α-epoxy-6β-(N-methyl-3,4-dichlorophenylacetamido)morphinan•hydrochloride 123 (yield: 76%) were obtained by following the procedure of example 95 but using 17-cyclopropylmethyl-4,5α-epoxy-3,14β-dihydroxy-6β-aminomorphinan (J. B. Jiang, R. N. Hanson, P. S. Portoghese and A. E. Takemori, J. Med. Chem., 20, 1100 (1977)), 17-allyl-4,5α-epoxy-3,14β-dihydroxy-6α-methylaminomorphinan 12 and 17-allyl-4,5α-epoxy-3,14β-dihydroxy-6β-methylaminomorphinan 13 instead of the starting material of 17-cyclopropylmethyl-4,5α-epoxy-3,14β-dihydroxy-6α-methylaminomorphinan 4, and using 3,4-dichlorophenylacetic acid instead of 3,4-difluorophenylacetic acid.

Compound 121

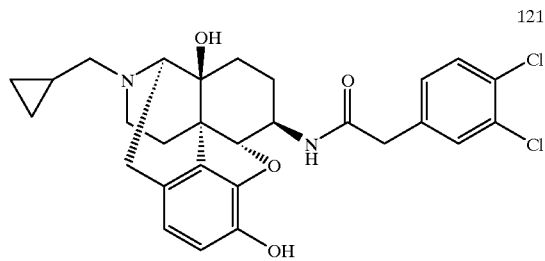

121 mp 245.0–254.0° C. (decomposition, methanol)
NMR (400 MHz, DMSO-$d_6$)

δ 0.31–0.46 (1H, m), 0.46–0.53 (1H, m), 0.53–0.63 (1H, m), 0.63–0.75 (1H, m), 0.98–1.12 (1H, m), 1.21–1.39 (1H, m), 1.39–1.57 (2H, m), 1.57–1.80 (2H, m), 2.28–2.48 (2H, m), 2.77–2.92 (1H, m), 3.02 (1H, brd, J=6.4 Hz), 3.07 (1H, br d, J=5.9 Hz), 3.19–3.41 (3H, m), 3.45 (1H, d, J=14.7 Hz), 3.50 (1H, d, J=14.7 Hz), 3.82 (1H, br s), 4.58 (1H, d, J=7.8 Hz), 6.17 (1H, br s), 6.63 (1H, d, J=7.8 Hz), 6.71 (1H, d, J=8.3 Hz), 7.25 (1H, dd, J=8.3, 2.0 Hz), 7.53 (1H, d, J=2.0 Hz), 7.57 (1H, d, J=8.3 Hz), 8.45 (1H, br s), 8.82 (1H, br s), 9.34 (1H, d, J=1.5 Hz).

IR (KBr)
υ 1655, 1545, 1508, 1461, 1128, 1034, 922 cm$^{-1}$.

Mass (FAB)

m/z 529 ((M+H)+).
Elementary Analysis: As $C_{28}H_{31}N_2O_4Cl_3 \cdot 0.4H_2O$
Calcd.: C, 58.67; H, 5.59; N, 4.89; Cl, 18.56
Found.: C, 58.70; H, 5.65; N, 4.88; Cl, 18.63
Compound 122

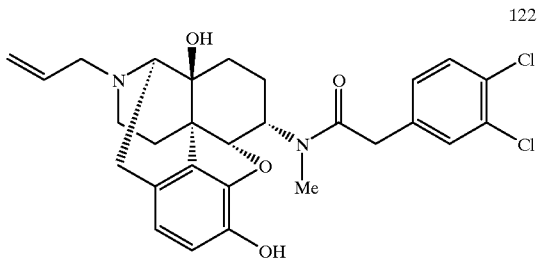

mp 214–216° C.
NMR (400 MHz, DMSO-$d_6$)

δ 1.16 (1H, m), 1.34 (1H, m), 1.51 (1H, m), 1.62 (1H, m), 1.86 (1H, m), 2.41 (1H, m), 2.72 (1H, m), 2.80 (0.5H, s), 2.95 (2.5H, s), 3.0–3.3 (2H, m), 3.40 (1H, m), 3.52 (1H, m), 3.88 (3H, m), 4.45 (0.2H, m), 4.61 (0.8H, d, J=3.9 Hz), 4.73 (0.2H, m), 4.95 (0.8H, m), 5.57 (2H, m), 5.89 (1H, m), 6.14 (0.8H, brs), 6.48 (0.2H, brs), 6.59 (1H, d, J=8.3 Hz), 6.72 (1H, d, J=8.3 Hz), 7.23 (1H, m), 7.52 (1H, d, J=2.0 Hz), 7.58 (1H, m), 9.12 (1H, brs), 9.32 (1H, s).

IR (KBr)
υ 3300, 1624, 1473, 1118, 1035, 804 cm$^{-1}$.
Mass (FAB)
m/z 529 (M+H)
Elementary Analysis: As $C_{28}H_{30}N_2O_4Cl_2 \cdot HCl \cdot 0.4H_2O$
Calcd.: C, 58.68; H, 5.59; N, 4.89; Cl, 18.56
Found.: C, 58.77; H, 5.66; N, 4.87; Cl, 18.29
Compound 123

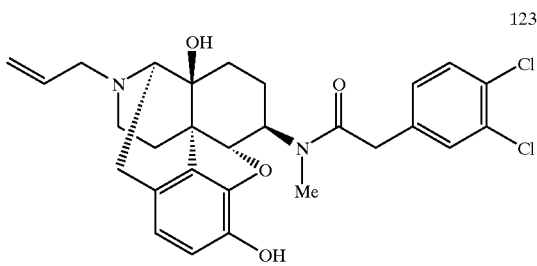

mp 185° C. (decomposition)
NMR (500 MHz, DMSO-$d_6$)

δ 1.15–1.39 (2H, m), 1.44 (0.2H, brd, J=9.2 Hz), 1.51 (0.8H, brd, J=9.8 Hz), 1.61–1.68 (1H, m), 2.00–2.11 (1H, m), 2.44–2.57 (2H, m), 2.83 (2.4H, s), 2.90–3.00 (1H, m), 3.02 (0.6H, s), 3.07–3.15 (1H, m), 3.35–3.39 (0.2H, m), 3.37 (0.8H, d, J=6.7 Hz), 3.43–3.55 (2H, m), 3.57 (1.6H, d, J=3.1 Hz), 3.70–3.79 (1.4H, m), 3.88–4.05 (1H, m), 4.80–4.88 (1H, m), 5.52 (1H, brd, J=11.0 Hz), 5.62 (1H, d, J=7.1 Hz), 5.83–5.96 (1H, m), 6.10–6.38 (1H, m), 6.64 (0.2H, d, J=8.2 Hz), 6.69 (0.2H, d, J=8.2 Hz), 6.73 (0.8H, d, J=8.2 Hz), 6.80 (0.8H, d, J=8.2 Hz), 6.99 (0.8H, dd, J=8.6, 1.8 Hz), 7.10 (0.8H, d, J=1.8 Hz), 7.19–7.23 (0.2H, m), 7.47–7.50 (0.2H, m), 7.50 (0.8H, d, J=8.5 Hz), 7.55 (0.2H, d, J=8.6 Hz), 9.18 (1H, brs), 9.25 (0.2H, s), 9.63 (0.8H, s).

IR (KBr)
υ 3380, 1620, 1502, 1475, 1321, 1125, 1033 cm$^{-1}$.
Mass (EI)
m/z 528 (M+).
Elementary Analysis: As $C_{28}H_{30}N_2O_4Cl_2 \cdot HCl \cdot H_2O$
Calcd.: C, 57.59; H, 5.70; N, 4.80; Cl, 18.21
Found.: C, 57.93; H, 5.80; N, 4.82; Cl, 17.85

Example 114

17-Cyclopropylmethyl-3,14β-dihydroxy-4,5α-epoxy-6β-[N-methyl-3-(3-trifluoromethylphenyl)propiolamido]morphinan•hydrochloride 124

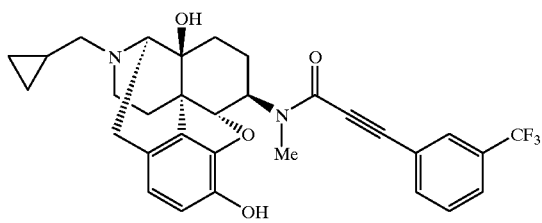

400 mg (1.12 mmol) of 17-cyclopropylmethyl-4,5α-epoxy-3,14β-dihydroxy-6β-methylaminomorphinan 10 and 360 mg (1.68 mmol) of 3-(3-trifluoromethylphenyl)propiolic acid were dissolved in 12 ml of chloroform followed by sequential addition of 0.40 ml (2.91 mmol) of N-ethylpiperidine and 428 mg (1.68 mmol) of bis-(2-oxo-3-oxazolidinyl)phosphinic chloride and stirring for 12 hours at room temperature. Then, 15 ml of 1 N aqueous sodium hydroxide were added to separate layers, and the organic layer was washed with 10 ml each of water and saturated brine, dried and concentrated. The residue was dissolved in 10 ml of methanol followed by the addition of 2 ml of 1 N aqueous sodium hydroxide and stirring for 3 hours. 30 ml of ethylacetate were then added to separate layers, and the resulting organic layer was washed with 20 ml of saturated brine, dried and concentrated. The residue was purified with silica gel column chromatography (Merk 9385, 30 g, chloroform/methanol=30/1) to obtain 562.8 mg of the free base of the target compound. This was then re-precipitated from hexane and ethylacetate, and the resulting solid was dissolved in ethylacetate. An excess amount of ethylacetate solution of hydrochloride solution was added followed by stirring and filtration of the resulting precipitate to obtain 274 mg of the target compound (yield: 42%).

mp >195° C. (decomposition)
NMR (400 MHz, DMSO-$d_6$)

δ 0.42 (1H, m), 0.52 (1H, m), 0.59 (1H, m), 0.67 (1H, m), 1.07 (1H, m), 1.29–1.51 (3H, m), 1.73–1.83 (1H, m), 2.09–2.26 (1H, m), 2.40–2.58 (2H, m), 2.86 (1H, m), 2.98 (2.4H, s), 3.02–3.11 (2H, m), 3.31 (0.6H, s), 3.30–3.38 (2H, m), 3.87 (1H, br d, J=5.9 Hz), 4.13 (1H, m), 4.89 (0.8H, d, J=8.3 Hz), 4.96 (0.2H, d, J=8.3 Hz), 6.40 (0.2H, s, OH), 6.46 (0.8H, d, J=7.3 Hz), 6.53 (0.8H, s, OH), 6.60 (0.8H, d, J=7.3 Hz), 6.66 (0.2H, d, J=7.3 Hz), 6.72 (0.2H, d, J=7.3 Hz), 7.47 (0.8H, br s), 7.57 (0.8H, d, J=7.8 Hz), 7.63 (0.8H, dd, J=7.8, 7.8 Hz), 7.73 (0.2H, dd, J=7.8, 7.8 Hz), 7.83 (0.8H, d, J=7.8 Hz), 7.90 (0.2H, d, J=7.8 Hz), 7.97 (0.2H, d, J=7.8 Hz), 8.06 (0.2H, br s), 8.81 (1H, m, NH+), 9.30 (0.8H, s, OH), 9.31 (0.2H, s, OH).

IR (KBr)
υ 3400, 2224, 1620, 1439, 1334, 1170, 1127, 1073, 1035, 924, 806 cm$^{-1}$.

Mass (FAB)
m/z 553 ((M+H)+).
Elementary Analysis: As $C_{31}H_{31}F_3N_2O_4 \cdot HCl \cdot 0.5H_2O$
Calcd.: C, 62.26; H, 5.56; Cl, 5.93; F, 9.53; N, 4.68
Found.: C, 62.25; H, 5.64; Cl, 5.78; F, 9.49; N, 4.73

Example 115

17-cyclopropylmethyl-3,14β-dihydroxy-4,5α-epoxy-6α-[N-methyl-3-(3-trifluoromethylphenyl)propiolamido]morphinan•hydrochloride 125 was obtained by following the procedure of example 114 but using 17-cyclopropylmethyl-4,5α-epoxy-3,14β-dihydroxy-6α-methylaminomorphinan 4 instead of 17-cyclopropylmethyl-4,5α-epoxy-3,14β-dihydroxy-6β-methylaminomorphinan 10.

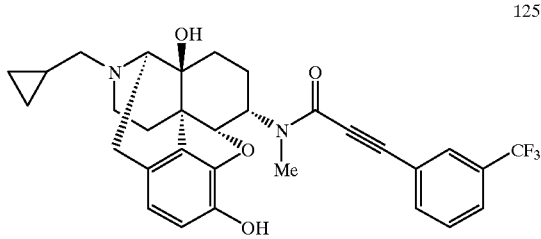

125 mp >190° C. (decomposition)
NMR (400 MHz, DMSO-$d_6$)
δ 0.41 (1H, m), 0.48 (1H, m), 0.62 (1H, m), 0.68 (1H, m), 1.07 (1H, m), 1.14–1.33 (1H, m), 1.48–1.70 (3H, m), 1.92–2.07 (1H,m), 2.47 (1H, m), 2.70 (1H, m), 2.92–3.15 (3H, m), 2.93 (1.2H, s), 3.22–3.38 (2H, m), 3.26 (1.8H, s), 3.96 (1H, m), 4.72 (0.6H, d, J=3.4 Hz), 4.85 (0.4H, d, J=3.4 Hz), 4.92 (0.6H, ddd, J=14.2, 3.9, 3.9 Hz), 5.07 (0.4H, ddd, J=13.2, 3.9, 3.9 Hz), 6.34 (0.6H, s, OH), 6.43 (0.4H, s, OH), 6.61 (0.6H, d, J=7.8 Hz), 6.61 (0.4H, J=7.3 Hz), 6.75 (0.6H, d, J=7.8 Hz), 6.75 (0.4H, d, J=7.3 Hz), 7.73 (0.6H, dd, J=7.8, 7.3 Hz), 7.82 (0.4H, dd, J=7.8, 7.3 Hz), 7.91 (0.6H, d, J=7.3 Hz), 7.92 (0.6H, d, J=7.3 Hz), 7.98 (0.6H, d, J=7.8 Hz), 8.06 (0.6H, br s), 8.06 (0.4H, d, J=7.8 Hz), 8.08 (0.4H, br s), 8.82–8.94 (1H, m, NH+), 9.38 (0.4H, s, OH), 9.38 (0.6H, s, OH).
IR (KBr)
υ 3400, 2220, 1611, 1460, 1334, 1172, 1122, 1071, 1036, 922, 806 cm$^{-1}$.
Mass (FAB)
m/z 553 ((M+H)+).
Elementary Analysis: As $C_{31}H_{31}F_3N_2O_4 \cdot HCl \cdot 0.6H_2O$
Calcd.: C, 62.07; H, 5.58; Cl, 5.91; F, 9.50; N, 4.67
Found.: C, 61.96; H, 5.64; Cl, 6.06; F, 9.47; N, 4.69

Example 116

17-Cyclopropylmethyl-3,14β-dihydroxy-4,5α-epoxy-6α-[N-methyl-3-(4-trifluoromethylphenyl)propiolamido]morphinan•0.5 tartrate 126 was obtained by following the procedure of example 114 but using 17-cyclopropylmethyl-4,5α-epoxy-3,14β-dihydroxy-6α-methylaminomorphinan 4 instead of 17-cyclopropylmethyl-4,5α-epoxy-3,14β-dihydroxy-6β-methylaminomorphinan 10, and using 3-(4-trifluoromethylphenyl)propiolic acid instead of 3-(3-trifluoromethylphenyl)propiolic acid.

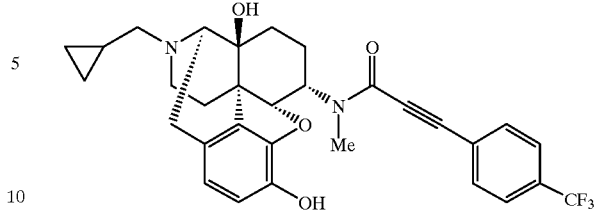

126 mp 197.0° C. (decomposition)
NMR (400 MHz, DMSO-$d_6$)
δ 0.10–0.30 (2H, m), 0.44–0.63 (2H, m), 0.83–0.99 (1H, m), 1.10–1.35 (1H, m), 1.40–1.60 (3H, m), 1.70–1.88 (1H, m), 2.15–2.34 (2H, m), 2.39–2.62 (2H, m), 2.62–2.84 (2H, m), 2.93 (1.5H, s), 3.00–3.13 (1H, m), 3.25 (1.5H, s), 3.20–3.34 (1H, m), 2.40–4.40 (3H, br s), 4.10 (1H, s), 4.62 (0.5H, br d, J=3.4 Hz), 4.70 (0.5H, br d, J=2.9 Hz), 4.85 (0.5H, ddd, J=14.2, 3.9, 3.9 Hz), 5.03 (0.5H, ddd, J=13.2, 3.9, 3.9 Hz), 6.53 (1H, d, J=8.3 Hz), 6.64 (0.5H, d, J=7.8 Hz), 6.65 (0.5H, d, J=8.3 Hz), 7.85 (1H, d, J=8.3 Hz), 7.89 (1H, d, J=8.3 Hz), 7.90 (1H, d, J=8.3 Hz), 7.93 (1H, d, J=8.3 Hz), 8.80–9.60 (1H, br s).
IR (KBr)
υ 3416, 2222, 1609, 1508, 1406, 1325, 1125, 1067 cm$^{-1}$.
Mass (FAB)
m/z 553 ((M+H)+).
Elementary Analysis: As $C_{31}H_{31}F_3N_2O_4 \cdot 0.5C_4H_6O_6 \cdot 0.5H_2O$
Calcd.: C, 62.26; H, 5.54; F, 8.95; N, 4.40
Found.: C, 62.14; H, 5.58; F, 8.91; N, 4.43

Example 17

17-Cyclopropylmethyl-3,14β-dihydroxy-4,5α-epoxy-6β-[N-methyl-3-(4-trifluoromethylphenyl)propiolamido]morphinan•hydrochloride 127 was obtained by following the procedure of example 114 but using 3-(4-trifluoromethylphenyl)propiolic acid instead of 3-(3-trifluoromethylphenyl)propiolic acid.

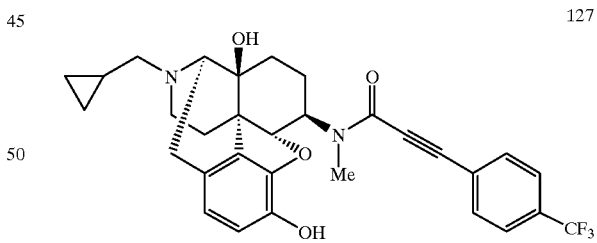

127 mp 197.0° C. (decomposition)
NMR (400 MHz, DMSO-$d_6$)
δ 0.35–0.46 (1H, m), 0.46–0.56 (1H, m), 0.56–0.64 (1H, m), 0.64–0.75 (1H, m), 1.01–1.15 (1H, m), 1.27–1.37 (0.6H, m), 1.37–1.52 (2.4H, m), 1.70–1.85 (1H, m), 2.05–2.30 (1H, m), 2.36–2.62 (2H, m), 2.80–2.92 (1H, m), 2.99 (2.4H, s), 3.00–3.16 (2H, m), 3.32 (0.6H, s), 3.30–3.40 (2H, m), 3.86 (1H, br d, J=4.4 Hz), 4.05–4.18 (1H, m), 4.90 (0.8H, d, J=8.3 Hz), 4.97 (0.2H, d, J=8.8 Hz), 6.43 (0.2H, s), 6.55 (0.8H, s), 6.57 (0.8H, d, J=7.8 Hz), 6.66 (1H, d, J=8.3 Hz), 6.72 (0.2H, d, J=7.8 Hz), 7.43 (1.6H, d, J=7.8 Hz), 7.74 (1.6H, d, J=8.3 Hz), 7.85 (0.4H, d, J=8.8 Hz), 7.89 (0.4H, d, J=8.8 Hz), 8.83 (1H, br s), 9.32 (0.2H, s), 9.35 (0.8H, s).

IR (KBr)

υ 3416, 2224, 1618, 1508, 1408, 1325, 1172, 1127, 1067 cm$^{-1}$.

Mass (FAB)

m/z 553 ((M+H)+).

Elementary Analysis: As $C_{31}H_{31}F_3N_2O_4 \cdot HCl \cdot 0.6H_2O$

Calcd.: C, 62.07; H, 5.58; Cl, 5.91; F, 9.50; N, 4.67

Found.: C, 62.14; H, 5.62; Cl, 5.90; F, 9.29; N, 4.62

Example 118

17-cyclopropylmethyl-4,5α-epoxy-3,14β-dihydroxy-6α-(N-methyl-3,4-dichlorophenylmethanesulfonamido)morphinan•tartrate 128

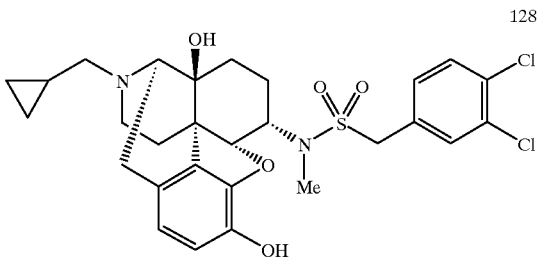

227 mg of 3-tert-butyldimethylsilyloxy-17-cyclopropylmethyl-4,5α-epoxy-14β-hydroxy-6α-(N-methyl-3,4-dichlorophenylmethanesulfonamido)morphinan 16 obtained in reference example 8 was dissolved in 4.5 ml of tetrahydrofuran followed by the addition of 0.39 ml of tetrabutylammonium fluoride and stirring for 30 minutes. 15 ml of ethylacetate and 10 ml of saturated aqueous ammonium chloride were added to separate layers, and the aqueous layer was extracted twice with 10 ml of ethylacetate. The resulting organic layer was concentrated after drying with anhydrous sodium sulfate, and the residue was purified with silica gel column chromatography (25 g chloroform/methanol=20/1) to obtain the crude compound. This was then recrystallized from ethylacetate and methanol to obtain 158 mg of the free base of the target compound. This was dissolved in a mixed solvent of chloroform and methanol, completely dissolved by addition of 20.4 mg of tartaric acid and concentrated. This residue was re-precipitated from methanol and ether followed by filtration to obtain 105 mg of the target compound (yield: 49%).

mp >149° C. (decomposition)

NMR (400 MHz, DMSO-d$_6$)

δ 0.13–0.22 (2H, m), 0.47–0.58 (2H, m), 0.82–0.92 (1H, m), 0.98–1.11 (1H, m), 1.18–1.27 (1H, m), 1.35–1.48 (2H, m), 1.55–1.67 (1H, m), 2.07–2.26 (2H, m), 2.48–2.60 (1H, m), 2.60–2.73 (2H, m), 2.83 (3H, s), 3.01 (1H, brd, J=8.6 Hz), 2.90–4.00 (5H, m, 3×OH), 3.98–4.07 (1H, m), 4.11 (1H, s), 4.35 (1H, d, J=3.4 Hz), 4.49 (1H, d, J=13.7 Hz), 4.53 (1H, d, J=13.7 Hz), 6.49 (1H, d, J=8.3 Hz), 6.61 (1H, d, J=8.3 Hz), 7.44 (1H, dd, J=2.0, 8.3 Hz), 7.67 (1H, d, J=8.3 Hz), 7.71 (1H, d, J=2.0 Hz), 9.08 (1H, brs).

IR (KBr)

υ 3410, 1607, 1470, 1323, 1122, 1035, 959, 917 cm$^{-1}$.

Mass (FAB)

m/z 579 (M+H)+.

Elementary Analysis: As $C_{28}H_{32}N_2O_5Cl_2S \cdot 0.65C_4H_6N_6 \cdot 0.4H_2O$ Calcd.: C, 53.71; H, 5.41; N, 4.09; Cl, 10.36; S, 4.69

Found.: C, 53.79; H, 5.50; N, 4.12; Cl, 10.09; S, 4.58

Example 119

17-Cyclopropylmethyl-4,5α-epoxy-3,14β-dihydroxy-6α-(N-methylphenylmethanesulfonamido)morphinan•tartrate 129 (yield: 87%) was obtained by following the procedure of example 118 but using 3-tert-butyldimethylsilyloxy-17-cyclopropylmethyl-4,5α-epoxy-14β-hydroxy-6α-(N-methylphenylmethanesulfonamido)morphinan 17 instead of the starting material of 3-tert-butyldimethylsilyloxy-17-cyclopropylmethyl-4,5α-epoxy-14β-hydroxy-6α-(N-methyl-3,4-dichlorophenylmethanesulfonamido)morphinan 16.

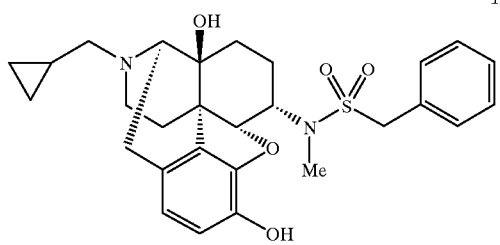

mp >147° C. (decomposition)

NMR (400 MHz, DMSO-d$_6$)

δ 0.13–0.22 (2H, m), 0.45–0.58 (2H, m), 0.82–1.07 (2H, m), 1.09–1.19 (1H, m), 1.33–1.42 (2H, m), 1.50–1.62 (1H, m), 2.07–2.27 (2H, m), 2.40–2.72 (3H, m), 2.79 (3H, s), 2.99 (1H, brd, J=9.0 Hz), 2.95–4.15 (5H, m, 3×OH), 3.98–4.07 (1H, m), 4.10 (1H, s), 4.34 (1H, d, J=3.4 Hz), 4.40 (1H, d, J=13.9 Hz), 4.45 (1H, d, J=13.9 Hz), 6.47 (1H, d, J=8.0 Hz), 6.61 (1H, d, J=8.0 Hz), 7.31–7.46 (5H, m), 9.10 (1H, brs).

IR (KBr)

υ 3420, 1603, 1460, 1321, 1122, 1069, 1036, 959, 917 cm$^{-1}$.

Mass (FAB)

m/z 511 (M+H)+.

Elementary Analysis: As $C_{28}H_{34}N_2O_5S \cdot 0.5C_4H_6N_6 \cdot H_2O$

Calcd.: C, 59.67; H, 6.51; N, 4.64; S, 5.31

Found.: C, 59.50; H, 6.47; N, 4.68; S, 5.21

Example 120

17-cyclopropylmethyl-4,5α-epoxy-3,14β-dihydroxy-6α-(3-phenylpropionyloxy)morphinanan•tartrate 130

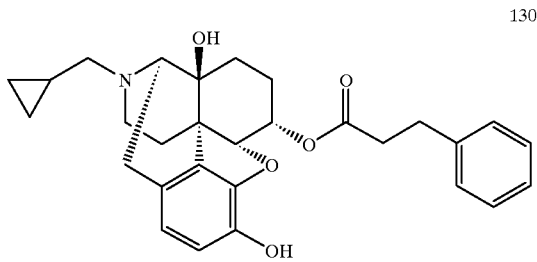

148 mg of 17-cyclopropylmethyl-4,5α-epoxy-3,6a,14β-trihydroxymorphinan (N. Chatterjie, C. E. Inturrisi, H. B. Dayton and H. Blumberg, J. Med. Chem., 18, 490 (1975); H. C. Brown and S. Krishnamurthy, J. Am. Chem. Soc., 94, 7159 (1972)) was dissolved in 0.9 ml of carbon tetrachloride and 0.3 ml of methylene chloride followed by the addition of 0.225 ml diisopropylethylamine and 26 mg of 4-dimethylaminopyridine, and the dropwise addition of 0.13 ml of 3-phenylpropionyl chloride at 0° C. After stirring for 20 hours at room temperature, 2 ml of saturated aqueous sodium bicarbonate was added to the reaction system to separate layers, and the aqueous layer was extracted twice with chloroform. The organic layer was concentrated after drying with anhydrous sodium sulfate. The resulting residue was dissolved in a mixed solvent of chloroform and methanol followed by the addition of 30 mg of potassium carbonate and stirring for 1 hour. Water was then added to the reaction mixture to separate layer, and the aqueous layer was extracted twice with chloroform. The resulting organic layer was concentrated after drying with anhydrous sodium sulfate, and the residue was purified with silica gel column chromatography (15 g chloroform/methanol=20/1) to obtain 95.3 mg of the free base of the target compound. This was then dissolved in methanol, completely dissolved by addition of 15 mg of tartaric acid and concentrated. The residue was re-precipitated from ether followed by filtration to obtain 103 mg of the target compound (yield: 43%).

mp >110° C. (decomposition)

NMR (500 MHz, DMSO-$d_6$)

δ 0.18–0.28 (2H, m), 0.47–0.60 (2H, m), 0.83–0.95 (1H, m), 1.19–1.28 (1H, m), 1.32–1.49 (3H, m), 1.74–1.82 (1H, m), 2.19–2.29 (2H, m), 2.40–2.47 (2H, m), 2.55–2.80 (6H, m), 3.08 (1H, brd, J=18.9 Hz), 3.28 (1H, brs), 3.36 (5H, m), 4.10 (2H, s), 4.64 (1H, d, J=4.9 Hz), 5.27–5.31 (1H, m), 6.51 (1H, d, J=8.2 Hz), 6.63 (1H, d, J=8.2 Hz), 7.13–7.19 (3H, m), 7.22–7.28 (2H, m), 9.10 (1H, brs).

IR (KBr)

υ 3400, 1719, 1460, 1307, 1267, 1122, 1069, 1036 cm$^{-1}$.

Mass (FAB)

m/z 476 (M+H)+.

Elementary Analysis: As $C_{29}H_{33}NO_5$•0.95$C_4H_6O_6$•1/6$C_4H_{10}O$•1/6$C_2H_6O$•0.4$H_2O$ Calcd.: C, 62.91; H, 6.59; N, 2.17

Found.: C, 62.92; H, 6.56; N, 2.32

Example 121

17-Cyclopropylmethyl-3,14β-dihydroxy-4,5α-epoxy-6α-[N-methyl-N'-(3,4-dichlorophenyl)ureido]morphinan•hydrochloride 131

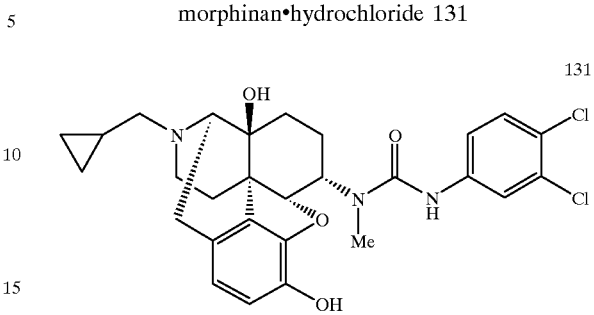

17-Cyclopropylmethyl-3,14β-dihydroxy-4,5α-epoxy-6α-methylaminomorphinan 4 (0.20 g) was dissolved in chloroform (5 ml) followed by the addition of 3,4-dichlorophenylisocyanate (0.26 g, 2.5 equivalents) and reacting for 5 minutes at room temperature. The precipitated solid was filtered out and dissolved in chloroform (8 ml) and methanol (10 ml) followed by the addition of 3 N aqueous sodium hydroxide to carry out hydrolysis for 5 minutes at room temperature. The solvent was distilled off followed by addition of saturated aqueous sodium bicarbonate (10 ml) and distilled water (4 ml), extraction with chloroform and methanol (12/2+10/2 ml), and drying with anhydrous sodium sulfate. After purifying with silica gel column chromatography (Merk 9385, 20 g; chloroform→3% methanol/chloroform), the residue was again dissolved in chloroform and methanol (5/0.5 ml) followed by addition of methanol solution of hydrochloric acid to obtain the target compound (0.23 g, 70%) in the form of its hydrochloride.

mp 210° C. (decomposition)

NMR (400 MHz, DMSO-$d_6$)

δ 0.41 (1H, m), 0.44 (1H, m), 0.62 (1H, m), 0.68 (1H, m), 1.0–1.2 (2H, m), 1.40 (1H, m), 1.60 (2H, m), 1.94 (1H, m), 2.4–2.5 (1H, m), 2.68 (1H, m), 2.92 (3H, s), 2.9–3.2 (3H, m), 3.3–3.4 (2H, m), 3.91 (1H, d, J=6.8 Hz), 4.74 (1H, d, J=3.9 Hz), 4.81 (1H, dt, J=13.7, 3.9 Hz), 6.34 (1H, s), 6.59 (1H, d, J=7.8 Hz), 6.73 (1H, d, J=7.8 Hz), 7.49 (1H, d, J=8.8 Hz), 7.55 (1H, dd, J=9.3, 2.4 Hz), 7.94 (1H, d, J=2.4 Hz), 8.73 (1H, s), 8.82 (1H, brs), 9.32 (1H, s).

IR (KBr)

υ 3300, 1638, 1510, 1477, 1120, 1040 cm$^{-1}$.

Mass (FAB)

m/z 544 (M+H)

Elementary Analysis: As $C_{28}H_{31}N_3O_4Cl_2$•HCl•0.4$H_2O$

Calcd.: C 57.18; H 5.62; N 7.14; Cl 18.08

Found.: C 57.32; H 5.83; N 7.04; Cl 17.85

Examples 122–124

17-Cyclopropylmethyl-3,14β-dihydroxy-4,5α-epoxy-6α-(N-methyl-N'-benzylureido)morphinan•tartrate 132 (yield: 65%), 17-cyclopropylmethyl-3,14β-dihydroxy-4,5α-epoxy-6α-(N-methyl-N'-benzylthioureido)morphinan•tartrate 133 (yield: 88%) and 17-cyclopropylmethyl-3,14β-dihydroxy-4,5α-epoxy-6β-(N-methyl-N'-benzylthioureido)morphinan•tartrate 134 (yield: 74%) were obtained by following the procedure of example 121 but using benzylisocyanate and benzylisothiocyanate instead of 3,4-dichlorophenylisocyanate, and using 17-cyclopropylmethyl- 3,14β-dihydroxy-4,5α-epoxy-6β-methylaminomorphinan 10 instead of 17-cyclopropylmethyl-3,14β-dihydroxy-4,5α-epoxy-6α-methylaminomorphinan 4.

Compound 132

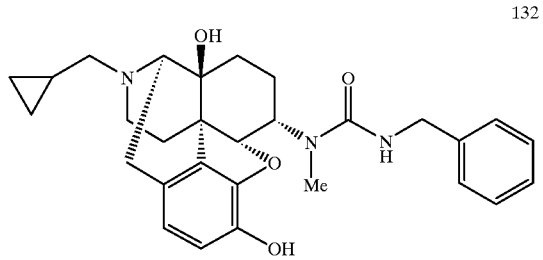

mp 202–205° C. (decomposition, methanol-ethylacetate)
NMR (400 MHz, DMSO-$d_6$)
δ 0.28 (2H, m), 0.52 (2H, m), 0.89 (1H, m), 1.10 (1H, m), 1.24 (1H, m), 1.38–1.53 (2H, m), 1.73 (1H, m), 2.15–2.30 (2H, m), 2.62–2.76 (2H, m), 2.78 (3H, s), 3.04 (1H, br d, J=18.6 Hz), 3.24 (1H, m), 3.39–3.52 (2H, m), 3.53 (3H, br s, 3×OH), 3.99 (1H, s), 4.28 (2H, d, J=5.9 Hz), 4.53 (1H, d, J=3.4 Hz), 4.70 (1H, m), 6.49 (1H, d, J=8.1 Hz), 6.61 (1H, d, J=8.1 Hz), 6.89 (1H, t, J=5.9 Hz, NH), 7.18–7.34 (5H, m), 9.03 (1H, br s, NH+).
IR (KBr)
υ 3422, 3204, 1630, 1615, 1589, 1535, 1468, 1359, 1319, 1123, 903, 735 cm$^{-1}$.
Mass (FAB)
m/z 490 ((M+H)+).
Elementary Analysis: As $C_{29}H_{35}N_3O_4$•0.5$C_4H_6O_6$
Calcd.: C, 65.94; H, 6.78; N, 7.44
Found.: C, 65.95; H, 6.74; N, 7.47

Compound 133

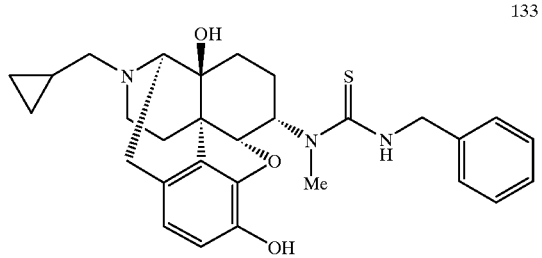

mp 155–195° C. (decomposition)
NMR (500 MHz, DMSO-$d_6$)
δ 0.29 (2H, m), 0.52 (2H, m), 0.90 (1H, m), 1.18 (1H, m), 1.35 (1H, m), 1.43 (1H, br d, J=9.1 Hz), 1.50 (1H, dd, T=14.6, 9.1 Hz), 1.77 (1H, m), 2.18–2.28 (2H, m), 2.42–2.57 (2H, m), 2.66–2.78 (2H, m), 2.95 (3H, s), 3.04 (1H, br d, J=18.9 Hz), 3.23 (1H, m), 3.48 (3H, br s, 3×OH), 4.01 (1H, s), 4.80 (1H, d, J=3.6 Hz), 4.82 (1H, dd, J=15.3, 6.1 Hz), 4.89 (1H, dd, J=15.3, 6.1 Hz), 5.81 (1H, m), 6.51 (1H, d, J=7.9 Hz), 6.62 (1H, d, J=7.9 Hz), 7.23 (1H, m), 7.28–7.33 (4H, m), 8.01 (1H, dd, J=6.1, 6.1 Hz, NH), 9.03 (1H, br s, NH+).
IR (KBr)
υ 3374, 1605, 1535, 1460, 1381, 1330, 1243, 1176, 1118, 1067, 1036, 907, 698 cm$^{-1}$.
Mass (FAB)
m/z 506 ((M+H)+).
Elementary Analysis: As $C_{29}H_{35}N_3O_3S$•0.5$C_4H_6O_6$•0.3$H_2O$•0.15$CH_3COOC_2H_5$
Calcd.: C, 63.33; H, 6.69; N, 7.01; S, 5.35
Found.: C, 63.44; H, 6.56; N, 6.90; S, 5.35

Compound 134

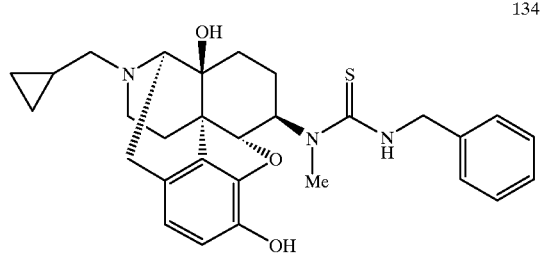

mp 160–180° C. (decomposition)
NMR (400 MHz, DMSO-$d_6$)
δ 0.22 (2H, m), 0.47–0.58 (2H, m), 0.91 (1H, m), 1.27–1.47 (3H, m), 1.55 (1H, m), 1.94 (1H, m), 2.12 (1H, m), 2.28 (1H, m), 2.43–2.78 (5H, m), 3.07 (1H, m), 3.08 (3H, s), 3.26 (1H, m), 3.50 (3.6H, br s, 3.3×OH+0.3×COOH), 4.01 (1.3H, s), 4.60 (1H, dd, J=15.3, 4.9 Hz), 4.74 (1H, d, J=8.3 Hz), 4.93 (1H, dd, J=15.3, 5.9 Hz), 6.55 (1H, d, J=8.3 Hz), 6.60 (1H, d, J=8.3 Hz), 7.19–7.34 (5H, m), 7.95 (1H, dd, J=5.9, 4.9 Hz, NH), 9.11 (1H, br s, NH+).
IR (KBr)
υ 3352, 1721, 1605, 1531, 1456, 1330, 1238, 1125, 1067, 1033, 915, 859 cm$^{-1}$.
Mass (FAB)
m/z 506 ((M+H)+).
Elementary Analysis: As $C_{29}H_{35}N_3O_3S$•0.65$C_4H_6O_6$•0.4$H_2O$
Calcd.: C, 62.18; H, 6.56; N, 6.88; S, 5.25
Found.: C, 62.09; H, 6.74; N, 6.83; S, 5.21

Example 125

17-Cyclopropylmethyl-3,14β-dihydroxy-4,5α-epoxy-6α-[N-methyl-N-2-(3,4-dichlorophenyl)ethylamino]morphinan•1.8 hydrochloride 135

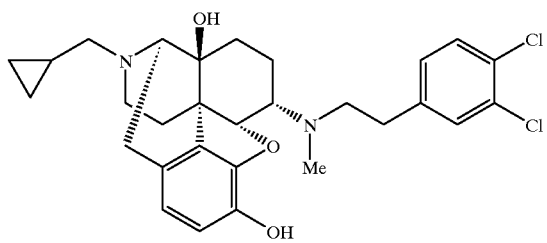

234.5 mg (0.431 mmol) of 17-cyclopropylmethyl-3,14β-dihydroxy-4,5α-epoxy-6α-(N-methyl-3,4-dichlorophenylacetamido)morphinan (free base of 1) was dissolved in 5.0 ml of anhydrous THF under argon atmosphere followed by the dropwise addition of 1.1 ml (2.2 mmol) of a 2.0 M anhydrous THF solution of borane-dimethylsulfide complex at 0° C. and refluxing for 1.5 hours. This reaction solution was cooled to 0° C. followed by the addition of 2 ml of 6 N hydrochloric acid and again refluxing for 1 hour. The reaction solution was again cooled to 0° C. and 25 ml of saturated aqueous sodium bicarbonate was added to make the solution basic. The solution was then extracted with chloroform and methanol (4:1) (3×20 ml), and the organic layers were combined, dried and concentrated to obtain 281 mg of an oily substance. This oily substance was purified with column chromatography [silica gel 25 g; chloroform-methanol (50:1→40:1)] to obtain 191.0 mg of the free base of the target compound. This free base was dissolved in methanol followed by the addition of a methanol solution of hydrogen chloride and concentration. The resulting hydrochloride was purified with Sephadex gel column chromatography [methanol] to obtain 193.3 mg of the target compound (yield: 74%).

mp >205° C. (decomposition)

NMR (400 MHz, CDCl$_3$; data for free base)

δ 0.13 (2H, m), 0.53 (2H, m), 0.85 (1H, m), 1.00 (1H, m), 1.49 (1H, dd, J=15.1, 8.8 Hz), 1.53–1.62 (2H, m), 1.71 (1H, ddd, J=15.1, 9.5, 9.5 Hz), 2.0–3.1 (1H, br s, OH), 2.15–2.40 (4H, m), 2.51 (3H, s), 2.55–2.67 (2H, m), 2.72–2.85 (3H, m), 2.89 (1H, m), 2.98–3.10 (3H, m), 4.78 (1H, dd, J=3.0, 2.0 Hz), 4.98 (1H, br s, OH), 6.50 (1H, d, J=8.1 Hz), 6.68 (1H, d, J=8.1 Hz), 7.03 (1H, dd, J=8.3, 2.0 Hz), 7.28 (1H, d, J=2.0 Hz), 7.33 (1H, d, J=8.3 Hz).

IR (KBr)

υ 3422, 1638, 1620, 1508, 1470, 1390, 1323, 1241, 1172, 1122, 1035, 982, 919, 886 cm$^{-1}$.

Mass (FAB)

m/z 529 ((M+H)+).

Elementary Analysis: As C$_{29}$H$_{34}$Cl$_2$N$_2$O$_3$•1.8HCl•0.4H$_2$O

Calcd.: C, 57.83; H, 6.12; N, 4.65; Cl, 22.37

Found.: C, 57.73; H, 6.31; N, 4.60; Cl, 22.38

Example 126

17-Cyclopropylmethyl-3,14β-dihydroxy-4,5α-epoxy-6β-[N-methyl-N-2-(3,4-dichlorophenyl)ethylamino] morphinan•1.9 hydrochloride 136 (yield: 65%) was obtained by following the procedure of example 125 but using 17-cyclopropylmethyl-3,14β-dihydroxy-4,5α-epoxy-6β-(N-methyl-3,4-dichlorophenylacetamido)morphinan (free base of 53) instead of the starting material of 17-cyclopropylmethyl-3,14β-dihydroxy-4,5α-epoxy-6α-(N-methyl-3,4-dichlorophenylacetamido)morphinan (free base of 1).

Compound 136

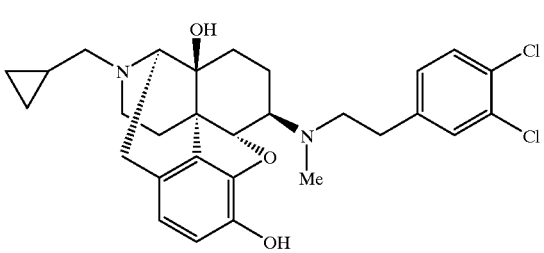

136 mp >185° C. (decomposition)

NMR (400 MHz, CDCl$_3$; data of free base);

δ 0.12 (2H, m), 0.52 (2H, m), 0.83 (1H, m), 1.29 (1H, ddd, J=13.2, 13.2, 2.9 Hz), 1.44 (1H, m), 1.51 (1H, m), 1.61 (1H, ddd, J=13.2, 2.9, 2.9 Hz), 1.86 (1H, m), 2.0–3.8 (2H, br s, 2×OH), 2.11 (1H, ddd, 11.7, 11.7, 3.4 Hz), 2.21 (1H, ddd, J=12.2, 12.2, 4.9 Hz), 2.33–2.38 (2H, m), 2.41 (3H, s), 2.47–2.56 (2H, m), 2.57–2.75 (4H, m), 2.81 (1H, m), 2.97–3.06 (2H, m), 4.56 (1H, d, J=8.3 Hz), 6.56 (1H, d, J=8.1 Hz), 6.71 (1H, d, J=8.1 Hz), 7.01 (1H, dd, J=8.3, 2.0 Hz), 7.29 (1H, d, J=2.0 Hz), 7.30 (1H, d, J=8.3 Hz).

IR (KBr)

υ 3250, 1638, 1618, 1473, 1398, 1330, 1241, 1218, 1116, 1035, 982, 919, 855, 756 cm$^{-1}$.

Mass (FAB)

m/z 529 ((M+H)+).

Elementary Analysis: As C$_{29}$H$_{34}$Cl$_2$N$_2$O$_3$•1.9HCl•0.5H$_2$O

Calcd.: C, 57.31; H, 6.12; N, 4.61; Cl, 22.75

Found.: C, 57.40; H, 6.22; N, 4.55; Cl, 22.54

Example 127

17-cyclopropylmethyl-3,14β-dihydroxy-4,5α-epoxy-6α-(N-methyl-4-aminophenylacetamido) morphinanan•1.6 hydrochloride 137

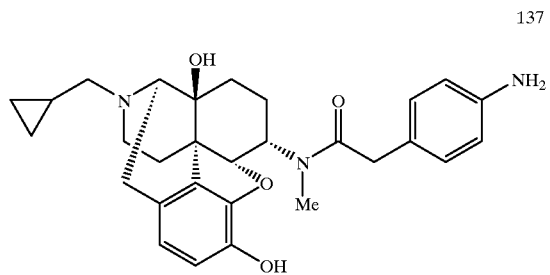

137

156.8 mg (0.282 mmol) of 17-cyclopropylmethyl-3,14β-dihydroxy-4,5α-epoxy-6α-(N-methyl-4-nitrophenylacetamido)morphinan•hydrochloride 87 was dissolved in 2.1 ml of methanol followed by the addition of roughly 0.2 ml of a saturated methanol solution of hydrogen chloride gas and 5.3 mg of platinum oxide, and stirring for 2.5 hours at room temperature in a hydrogen atmosphere (1 atm). The reaction mixture was filtered by passing through Celite, and the filtration residue was washed with methanol. The filtrate and washing were combined and concentrated to obtain 166 mg of crude product. This crude product was purified twice with Sephadex column chromatography [methanol] to obtain 108.2 mg of the target compound (yield: 68%).

mp >200° C. (decomposition)

NMR (400 MHz, DMSO-d$_6$)

δ 0.39 (1H, m), 0.47 (1H, m), 0.62 (1H, m), 0.69 (1H, m), 1.00–1.23 (2H, m), 1.34 (1H, m), 1.45–1.63 (2H, m), 1.94 (1H, m), 2.44 (1H, m), 2.68 (1H, m), 2.78 (0.9H, s), 2.92–3.13 (3H, m), 2.93 (2.1H, s), 3.21–3.43 (2H, m), 3.67–3.82 (2H, m), 3.92–3.98 (1H, m), 4.38 (0.3H, m), 4.57 (0.3H, m), 4.61 (0.7H, d, J=3.4 Hz), 4.98 (0.7H, m), 6.29 (0.7H, br s, OH), 6.57 (1H, d, J=8.3 Hz), 6.63 (0.3H, br s, OH), 6.72 (0.3H, d, J=8.3 Hz), 6.74 (0.7H, d, J=8.3 Hz), 6.97 (0.6H, d, J=8.3 Hz) 7.00 (1.4H, d, J=8.3 Hz), 7.16 (1.4H, d, J=8.3 Hz), 7.20 (0.6H, d, J=8.3 Hz), 8.53 (2.8H, br s, NH3+), 8.84 (0.8H, m, NH+), 9.30 (0.3H, br s, OH), 9.33 (0.7H, br s, OH).

IR (KBr)

υ 3370, 1620, 1510, 1466, 1321, 1120, 1038, 919, 804 cm$^{-1}$.

Mass (FAB)

m/z 490 ((M+H)+).

Elementary Analysis: As $C_{29}H_{35}N_3O_4 \cdot 1.6HCl \cdot 0.8H_2O$

Calcd.: C, 61.94; H, 6.85; N, 7.47; Cl, 10.09.

Found.: C, 62.09; H, 7.02; N, 7.15; Cl, 9.93.

Example 128

17-Cyclopropylmethyl-3,14β-dihydroxy-4,5α-epoxy-6α-(N-methyl-3-aminophenylacetamido)morphinan•1.1 tartrate 138 (yield: 90%) was obtained by following the procedure of example 127 but using 17-cyclopropylmethyl-3,14β-dihydroxy-4,5α-epoxy-6α-(N-methyl-3-nitrophenylacetamido)morphinan•hydrochloride 83 instead of the starting material of 17-cyclopropylmethyl-3,14β-dihydroxy-4,5α-epoxy-6α-(N-methyl-4-nitrophenylacetamido)morphinan•hydrochloride 87.

138

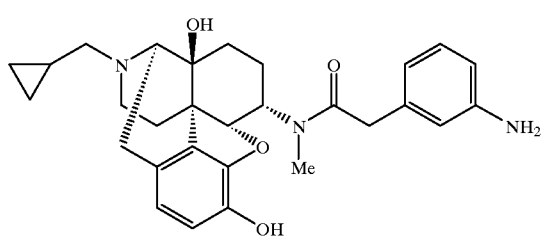

mp >160° C. (decomposition)

NMR (400 MHz, DMSO-d$_6$)

δ 0.23 (2H, m), 0.53 (2H, m), 0.92 (1H, m), 1.18–1.32 (2H, m), 1.48–1.53 (2H, m), 1.74 (1H, m), 2.14–2.38 (2H, m), 2.54 (1H, m), 2.63–2.84 (2H, m), 2.79 (0.9H, s), 2.90 (2.1H, s), 3.08 (1H, m), 3.26–3.41 (2H, m), 3.51–3.63 (3H, m), 3.60 (7H, br s, 4×OH, NH3+), 4.09 (0.3H, m), 4.11 (2H, s), 4.47 (0.3H, m), 4.56 (0.7H, d, J=3.4 Hz), 4.95 (0.7H, m), 6.37–6.56 (3H, m), 6.58–6.64 (1H, m), 6.62–7.00 (1H, m), 9.10 (1H, br s, NH+).

IR (KBr)

υ3312, 1736, 1719, 1609, 1510, 1460, 1402, 1309, 1267, 1120, 1069, 1038, 919, 774, 687 cm$^{-1}$.

Mass (FAB)

m/z 490 ((M+H)+).

Elementary Analysis: As $C_{29}H_{35}N_3O_4 \cdot 1.1C_4H_6O_6 \cdot 1.8H_2O \cdot 0.5CH_3COOC_2H_5$ Calcd.: C, 58.15; H, 6.78; N, 5.75

Found.: C, 58.18; H, 6.76; N, 5.65

Example 129

17-Cyclopropylmethyl-3-acetoxy-4,5α-epoxy-14β-hydroxy-6α-(N-methyl-3,4-dichlorophenylacetamido)morphinan•hydrochloride 139

139

152 mg of 17-cyclopropylmethyl-4,5α-epoxy-3,14β-dihydroxy-6α-(N-methyl-3,4-dichlorophenylacetamido) morphinan•hydrochloride 1 obtained in example 11 was dissolved in 2.3 ml of pyridine followed by the addition of 0.04 ml of acetic anhydride and stirring for 30 minutes. After concentrating the reaction solvent and removing the pyridine by azeotrope with toluene, the residue was washed with ether to obtain 148 mg of the target compound (yield: 91%).

mp >187° C. (decomposition)

NMR (400 MHz, CDCl$_3$)

δ 0.35–0.58 (1.3H, m), 0.63–0.94 (2.7H, m),1.25–1.75 (5H, m), 2.26 (2.1H, s), 2.27 (0.9H, s), 2.47–2.70 (2H, m), 2.83 (0.9H, s), 2.85 (2.1H, s), 2.90–3.26 (4H, m), 3.27–3.60 (2H, m), 3.69 (1.4H, s), 3.71 (0.6H, s), 4.35–4.60 (1.3H, m), 4.75–4.83 (0.3H, m), 4.86 (0.7H, d, J=2.9 Hz), 5.18–5.28 (0.7H, m), 6.70 (1H, d, J=8.4 Hz), 6.72 (1H, brs), 6.87–6.93 (1H, m), 7.09 (0.7H, dd, J=8.3, 2.0 Hz), 7.30 (0.3H, dd, J=8.3, 2.0 Hz), 7.35 (0.7H, d, J=2.0 Hz), 7.40 (0.7H, d, J=8.3 Hz), 7.48 (0.3H, d, J=2.0 Hz), 7.56 (0.3H, d, J=8.3 Hz), 9.40–9.70 (1H, m).

IR (KBr)

υ 3380, 1765, 1636, 1626, 1475, 1458, 1224, 1201, 1122, 1036 cm$^{-1}$.

Mass (FAB)

m/z 585 (M+H)+.

Elementary Analysis: As $C_{31}H_{34}N_2O_5Cl_2 \cdot HCl$

Calcd.: C, 59.86; H, 5.67; N, 4.50; Cl, 17.10

Found.: C, 59.71; H, 5.70; N, 4.55; Cl, 16.95

Examples 130–131

17-Cyclopropylmethyl-3-acetoxy-14β-hydroxy-4,5α-epoxy-6β-(N-methylcinnamamido)morphinan•tartrate 140 (yield: 70%) and 17-cyclopropylmethyl-3-acetoxy-14β-hydroxy-4,5α-epoxy-6β-(N-methyl-3-trifluoromethylcinnamamido)morphinan•tartrate 141 (yield: 56%) were obtained by following the procedure of example 129 but using 17-cyclopropylmethyl-3,14β-dihydroxy-4,5α-epoxy-6β-(N-methylcinnamamido)morphinan•tartrate 99 and 17-cyclopropylmethyl-3,14β-dihydroxy-4,5α-epoxy-6β-(N-methyl-3-trifluoromethylcinnamamido) morphinan•tartrate 60 instead of 17-cyclopropylmethyl-4,5α-epoxy-3,14β-dihydroxy-6α-(N-methyl-3,4-dichlorophenylacetamido)morphinan•hydrochloride 1.

Compound 140

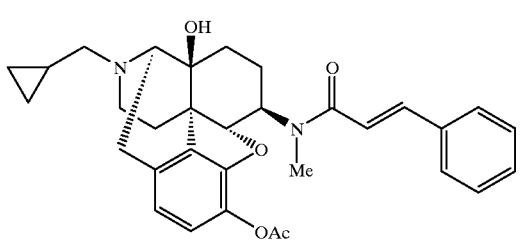

mp 142–146° C. (decomposition, ethylacetate)
PNMR (400 MHz, DMSO-$d_6$)

δ 0.23 (2H, br s), 0.54 (2H, m), 0.92 (1H, m), 1.30 (1H, m), 1.38–1.50 (2H, m), 1.60 (1H, m), 1.85 (1.73H, s), 2.09–2.26 (2H, m), 2.21 (1.27H, s), 2.33 (1H, m), 2.60–4.40 (5H, br OH×5), 2.69 (1H, m), 2.78 (2H, m), 2.90 (1.73H, s), 3.13 (1.27H, s), 3.30 (1H, m), 3.33 (1H, m), 3.72 (1H, m), 3.89 (1H, m), 4.13 (2H, s), 4.78 (0.67H, d, J=7.8 Hz), 5.00 (0.33H, d, J=8.3 Hz), 6.72–7.72 (9H, m).

IR (KBr)

υ 3350, 1760, 1640, 1600, 1493, 1309, 1189 cm$^{-1}$.

Mass (FAB)

m/z 529 (M+H)+.

Elementary Analysis: As $C_{36}H_{42}N_2O_{11}$

Calcd.: C, 63.71; H, 6.24; N, 4.13.

Found.: C, 63.51; H, 6.37; N, 4.10.

Compound 141

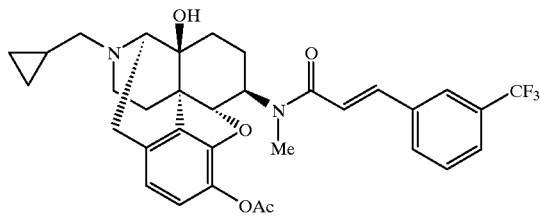

mp 125–128° C.
NMR (400 MHz, DMSO-$d_6$)

δ 0.22 (2H, brs), 0.53 (2H, m), 0.91 (1H, m), 1.3–1.7 (4H, m), 1.76 (2H, br s), 2.1–2.2 (2H, m), 2.21 (1H, s), 2.35 (1H, m) 2.46 (1H, m), 2.6–2.8 (3H, m), 2.91 (2H, s), 3.15 (1H, s), 3.2–3.9 (3H, m), 4.12 (1.4H, s), 4.75 (0.7H, d, J=7.3 Hz), 5.00 (0.3H, d, J=8.3 Hz), 6.7–7.9 (2.7H, m), 7.36 (0.3H, d, J=15.6 Hz), 7.5–7.7 (2H, m), 7.71 (1H, d, J=7.3 Hz), 7.80 (0.7H, d, J=7.8 Hz), 7.92 (0.7H, s), 8.01 (0.3H, d, J=7.8 Hz), 8.14 (0. 3H, s).

IR(KBr)

υ 3400, 1765, 1648, 1605, 1336, 1127 cm$^{-1}$.

Mass (FAB)

m/z 597 (M+H).

Elementary Analysis: As $C_{33}H_{35}N_2O_5F_3$·0.70($C_4H_6O_6$)·1.0$H_2O$

Calcd.: C, 59.74; H, 5.77; N, 3.89; F, 7.92.

Found.: C, 59.83; H, 5.82; N, 3.88; F, 7.88.

Example 132

17-cyclopropylmethyl-4,5α-epoxy-14β-hydroxy-3-methoxy-6α-(N-methyl-3,4-dichlorophenylacetamido)morphinan•tartrate 142

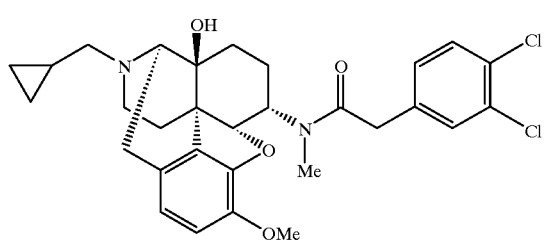

245 mg of 17-cyclopropylmethyl-4,5α-epoxy-3,14β-dihydroxy-6α-(N-methyl-3,4-dichlorophenylacetamido) morphinan (free base of 1) obtained in example 11 was dissolved in 3.5 ml of chloroform followed by the addition of an excess amount of diazomethane and stirring for 1 hour. After concentrating the reaction system, the residue was purified with silica gel column chromatography (20 g hexane/ethylacetate/methanol/aqueous ammonia=5/3/0.2/0.04) to obtain the free base of the target compound. After dissolving this in methanol, 11 mg of tartaric acid was added to completely dissolve followed by concentration. The residue was re-precipitated from ether followed by filtration to obtain 83 mg of the target compound (yield: 30%).

mp >115° C. (decomposition)

NMR (400 MHz, DMSO-$d_6$+D20)

δ 0.15–0.33 (2H, m), 0.48–0.63 (2H, m), 0.87–1.00 (1H, m), 1.05–1.55 (4H, m), 1.69–1.85 (1H, m), 2.20–2.45 (2H, m), 2.55–2.95 (3H, m), 2.79 (0.9H, s), 2.94 (2.1H, s), 3.08–3.22 (1H, m), 3.30–3.58 (2H, m), 3.78 (3H, s), 3.77 (1H, d, J=16.1 Hz), 3.84 (1H, d, J=16.1 Hz), 4.09 (2H, s), 4.38–4.45 (0.3H, m), 4.55–4.63 (0.3H, m), 4.60 (0.7H, d, J=3.4 Hz), 4.88–4.96 (0.7H, m), 6.68 (0.7H, d, J=8.3 Hz), 6.64–6.70 (0.3H, m), 6.86 (0.7H, d, J=8.3 Hz), 6.82–6.88 (0.3H, m), 7.24 (0.7H, dd, J=8.3, 2.0 Hz), 7.24–7.30 (0.3H, m), 7.52 (0.7H, d, J=2.0 Hz), 7.52–7.56 (0.3H, m), 7.57 (0.7H, d, J=8.3 Hz), 7.60 (0.3H, d, J=8.3 Hz).

IR (KBr)

υ 3324, 1628, 1402, 1309, 1267, 1131 cm$^{-1}$.

Mass (EI)

m/z=556 M+.

Elementary Analysis: As $C_{30}H_{34}N_2O_4Cl_2$·0.87$C_4H_6O_6$·0.7$H_2O$

Calcd.: C 57.39; H 5.80; N 4.00; Cl 10.12

Found.: C 57.35; H 5.91; N 4.09; Cl 10.19

Example 133

14β-Acetoxy-17-cyclopropylmethyl-4,5α-epoxy-3-hydroxy-6α-(N-methyl-3,4-dichlorophenylacetamido)morphinan•hydrochloride 143

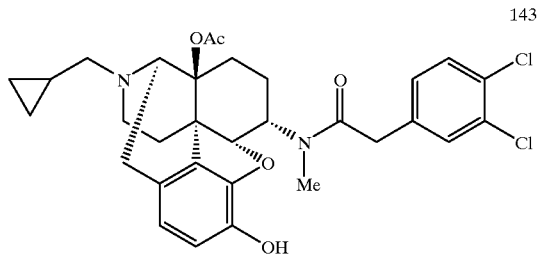

443 mg of 17-cyclopropylmethyl-4,5α-epoxy-3,14β-dihydroxy-6α-(N-methyl-3,4-dichlorophenylacetamido) morphinan (free base of 1) obtained in example 11 was dissolved in acetic anhydride followed by stirring for 1 hour at 160° C. with an oil bath. After concentrating the reaction solvent, the acetic anhydride was completely removed by azeotrope with toluene. The residue was dissolved in 10 ml of methanol followed by the addition of 14 ml of 4% aqueous sulfuric acid and stirring for 18 hours. 10 ml of aqueous ammonia and 30 ml of chloroform were then added to the system to separate, and the aqueous layer was extracted twice with 15 ml of chloroform. The organic layer was concentrated after drying with anhydrous sodium sulfate and the residue was purified with silica gel column chromatography (45 g, chloroform/ethylacetate=2/1). This was then recrystallized from chloroform and methanol followed by derivation of the crystals into hydrochloride with methanol solution of hydrochloride to obtain 299 mg of the target compound (yield: 59%).

mp >190° C. (decomposition)
NMR (400 MHz, DMSO-$d_6$)
δ 0.35–0.73 (4H, m), 0.90–1.03 (1H, m), 1.05–1.75 (4H, m), 2.17 (2.25H, s), 2.24 (0.75H, s),2.30–2.62 (2H, m), 2.65–2.83 (1H, m), 2.80 (0.75H, s), 2.96 (2.25H, s), 2.90–3.15 (2H, m), 3.18–3.52 (3H, m), 3.79 (0.75H, d, J=16.1 Hz), 3.84 (0.75H, d, J=16.1 Hz), 3.93–4.07 (0.5H, m), 4.55–4.60 (0.25H, m), 4.72 (0.75H, d, J=3.4 Hz), 4.77–4.85 (1H, m), 5.26 (1H, d, J=6.4 Hz), 6.50 (0.25H, d, J=8.3 Hz), 6.61 (0.75H, d, J=8.3 Hz), 6.77 (1H, d, J=8.3 Hz), 7.19–7.25 (0.25H, m), 7.24 (0.75H, dd, J=8.3, 2.0 Hz), 7.49 (0.25H, d, J=2.0 Hz), 7.52 (0.75H, d, J=2.0 Hz), 7.58 (0.75H, d, J=8.3 Hz), 7.60 (0.25H, d, J=8.3 Hz), 9.20–9.47 (1H, m), 9.42 (0.25H, s), 9.43 (0.75H, s).
IR (KBr)
υ 3420, 1744, 1626, 1473, 1406, 1371, 1321, 1214, 1116, 1035 cm$^{-1}$.
Mass (EI)
m/z 584 M+.
Elementary Analysis: As $C_{31}H_{34}N_2O_5Cl_2$•HCl•$0.2H_2O$
Calcd.: C, 59.52; H, 5.70; N, 4.48; Cl, 17.00.
Found.: C, 59.40; H, 5.90; N, 4.56; Cl, 17.12.

Example 134

17-Cyclopropylmethyl-3-hydroxy-14β-acetoxy-4,5α-epoxy-6β-(N-methylcinnamamido)morphinan•tartrate 144 (yield: 48%) was obtained by following the procedure of example 133 but using 17-cyclopropylmethyl-3,14β-dihydroxy-4,5α-epoxy-6β-(N-methylcinnamamido) morphinan (free base of 99) instead of 17-cyclopropylmethyl-4,5α-epoxy-3,14β-dihydroxy-6α-(N-methyl-3,4-dichlorophenylacetamido)morphinan (free base of 1).

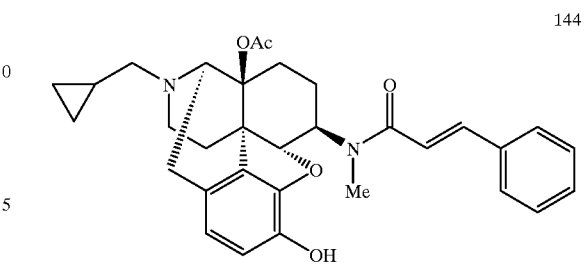

mp 154–157° C.
NMR (400 MHz, DMSO-$d_6$)
δ 0.06 (2H, m), 0.42 (2H, d, J=8.3 Hz), 0.72 (1H, m), 1.2–1.4 (3H, m), 1.93 (1H, m), 2.05 (1H, m), 2.11 (3H, s), 2.24 (1H, m), 2.37 (2H, m), 2.43 (1H, m), 2.62 (1H, m), 2.89 (2H, s), 3.03 (1H, d, J=18.1 Hz), 3.15 (1H, s), 3.2–3.4 (1H, m), 3.69 (0.7H, m), 4.15 (0.3H, m), 4.28 (1H, s), 4.70 (0.7H, d, J=7.8 Hz), 4.82 (0.3H, d, J=8.3 Hz), 6.5–6.8 (3H, m), 7.1–7.5 (5.3H, m), 7.71 (0.7H, d, J=6.3 Hz).
IR (KBr)
υ 3390, 1738, 1647, 1590, 1408, 1122 cm$^{-1}$.
Mass (FAB)
m/z 529 (M+H).
Elementary Analysis: As $C_{32}H_{36}N_2O_5$•$0.5(C_4H_6O_6)$•$1.0H_2O$
Calcd.: C, 65.68; H, 6.65; N, 4.50.
Found.: C, 65.85; H, 6.66; N, 4.43.

Example 135

17-Cyclopropylmethyl-3,14β-dihydroxy-4,5α-epoxy-6β-(N-methyl-3-aminocinnamamido)morphinan•hydrochloride 145

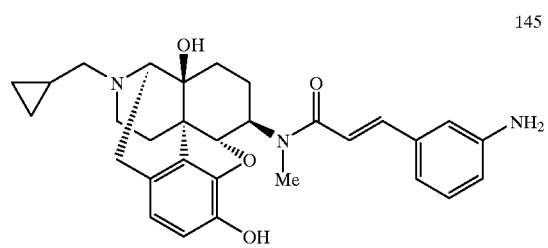

360 mg of 17-cyclopropylmethyl-3,14β-dihydroxy-4,5α-epoxy-6β-(N-methyl-3-nitrocinnamamido)morphinan (free base of 104) and 1.07 g of stannic chloride dihydrate was dissolved in 7.5 ml of ethanol followed by heating to 70° C. and stirring for 2 hours. After cooling the reaction mixture to room temperature, 2 N aqueous sodium hydroxide was added while cooling with ice to neutralize followed by extraction with dichloromethane. The organic layers were combined and washed with saturated brine. After drying and concentrating, the organic substances were removed by chromatographic filtration [silica gel; chloroform:methanol (9:1)]. The resulting crude target compound was converted into a dihydrochloride to obtain 310 mg.

Mass (FAB)
m/z 502 ((M+H)+).

Example 136

17-Cyclopropylmethyl-3,14β-dihydroxy-4,5α-epoxy-6β-(N-methyl-3-isothiocyanatocinnamamido)morphinanan•methanesulfonate 146

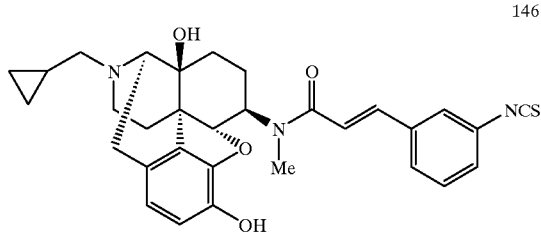

146

300 mg of 17-cyclopropylmethyl-3,14β-dihydroxy-4,5α-epoxy-6β-(N-methyl-3-aminocinnamamido)morphinan•hydrochloride 145 obtained in example 135 was dissolved in 9 ml of water and cooled with ice. 40 μl of thiophosgene dissolved in 2 ml of chloroform was added dropwise followed by stirring for 5 hours at warming to room temperature. Saturated aqueous sodium bicarbonate was then added to neutralize while cooling with ice followed by extraction with chloroform. The organic layers were combined and washed with saturated brine followed by drying and concentrating. The resulting residue was purified with column chromatography [silica gel; chloroform:methanol (97.5:2.5)], to obtain 208 mg of the resulting target compound after converting a methanesulfonate from (yield: 52% 2 steps).

mp 170° C. (decomposition)
NMR (500 MHz, DMSO-$d_6$)
δ 0.42 (1H, m), 0.49 (1H, m), 0.60 (1H, m), 0.69 (1H, m), 1.07 (1H, m), 1.27–1.58 (3H, m), 1.72 (1H, m), 2.11 (1H, m), 2.31 (3H, s), 2.43–2.52 (2H, m), 2.86 (1H, m), 2.92 (2.1H, s), 3.02–3.14 (2H, m), 3.18 (0.9H, s), 3.30–3.38 (2H, m), 3.70 (0.7H, m), 3.83 (1H, m), 4.19 (0.3H, m), 4.80 (0.7H, d, J=8.3 Hz), 4.90 (0.3H, d, J=8.3 Hz), 6.14 (0.3H, br s), 6.22 (0.7H, br s), 6.65–6.84 (2.1H, m), 6.88 (0.7H, d, J=7.8 Hz), 7.29 (1H, d, J=15.6 Hz), 7.40–7.50 (3.6H, m), 7.69 (0.3H, d, J=7.8 Hz), 7.91 (0.3H, s), 8.74 (1H, br s), 9.30 (0.3H, br s), 9.54 (0.7H, br s).

IR (KBr)
υ 3380, 3210, 2124, 1649, 1599, 1197, 1060, 785 cm$^{-1}$.
Mass (FAB)
m/z 544 ((M+H)+).
Elementary Analysis: As $C_{31}H_{33}N_3O_4S \cdot CH_3SO_3H \cdot H_2O$
Calcd.: C, 58.43; H, 5.98; N, 6.39; S, 9.75
Found.: C, 58.67; H, 6.15; N, 6.11; S, 9.78

Example 137

17-Cyclopropylmethyl-3,14β-dihydroxy-4,5α-epoxy-6α-(N-methyl-3-aminocinnamamido)morphinan•hydrochloride 147 was obtained by following the procedure of example 135 but using 17-cyclopropylmethyl-3,14β-dihydroxy-4,5α-epoxy-6α-(N-methyl-3-nitrocinnamamido)morphinan (free base of 97) instead of 17-cyclopropylmethyl-3,14β-dihydroxy-4,5α-epoxy-6β-(N-methyl-3-nitrocinnamamido)morphinan (free base of 104).

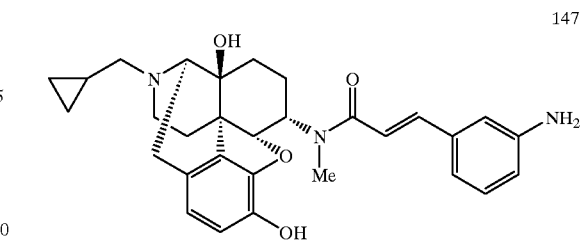

147

Mass (FAB)
m/z 502 ((M+H)+).

Examples 138–139

17-Cyclopropylmethyl-3,14β-dihydroxy-4,5α-epoxy-6α-(N-methyl-3-isothiocyanatocinnamamido)morphinan•methanesulfonate (yield: 32% 2 steps) 148 and 17-cyclopropylmethyl-3,14β-dihydroxy-4,5α-epoxy-6α-(N-methyl-3-isothiocyanatophenylacetamido)morphinanan•methanesulfonate 149 (yield: 78%) were obtained by following the procedure of example 136 but using 17-cyclopropylmethyl-3,14β-dihydroxy-4,5α-epoxy-6α-(N-methyl-3-aminocinnamamido)morphinan•hydrochloride 147 and 17-cyclopropylmethyl-3,14β-dihydroxy-4,5α-epoxy-6α-(N-methyl-3-aminophenylacetamido)morphinan•hydrochloride 138 instead of 17-cyclopropylmethyl-3,14β-dihydroxy-4,5α-epoxy-6β-(N-methyl-3-aminocinnamamido)morphinan•hydrochloride 145.

Compound 148

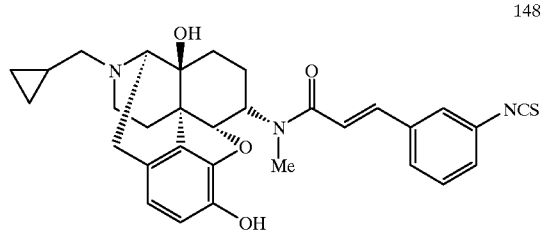

148 mp 160° C. (decomposition)
NMR (500 MHz, DMSO-$d_6$)
δ 0.41 (1H, m), 0.48 (1H, m), 0.62 (1H, m), 0.70 (1H, m), 1.05 (1H, m), 1.20 (1H, m), 1.40–1.67 (3H, m), 1.93 (1H, m), 2.31 (3.3H, s), 2.47 (1H, m), 2.71 (1H, m), 2.91 (0.6H, s), 2.93 (1H, m), 3.01–3.15 (2H, m), 3.10 (2.4H, s), 3.25–3.38 (2H, m), 3.89 (1H, br d, J=5.9 Hz), 4.58 (0.2H, m), 4.73 (0.8H, d, J=3.4 Hz), 4.94 (0.2H, br s), 5.04 (0.8H, m), 6.20 (0.8H, s), 6.25 (0.2H, br s), 6.61 (1H, d, J=7.8 Hz), 6.72 (1H, d, J=7.8 Hz), 7.22 (0.2H, d, J=14.1 Hz), 7.37 (0.8H, d, J=15.6 Hz), 7.42–7.54 (3H, m), 7.68 (0.2H, d, J=7.3 Hz), 7.71 (0.8H, d, J=7.3 Hz), 7.77 (0.2H, s), 7.93 (0.8H, s), 8.77 (1H, br s), 9.30 (1H, br s).

IR (KBr)
υ 3340, 3200, 2112, 1649, 1599, 1508, 1460, 1210, 1195, 1118, 1060, 1038, 785 cm$^{-1}$.
Mass (FAB)
m/z 544 ((M+H)+).
Elementary Analysis: As $C_{31}H_{33}N_3O_4S \cdot 1.1CH_3SO_3H \cdot H_2O$
Calcd.: C 57.77; H 5.95; N 6.29; S 10.09
Found.: C 57.72; H 6.04; N 6.22; S 10.22

Compound 149

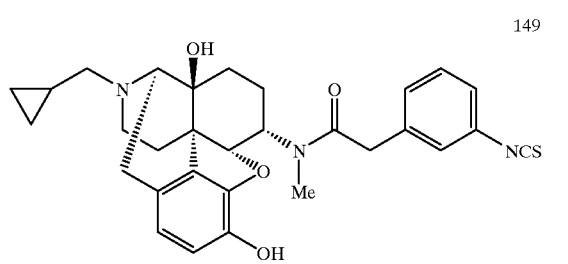

mp >155° C. (decomposition)

NMR (500 MHz, DMSO-$d_6$)

δ 0.38 (1H, m), 0.46 (1H, m), 0.61 (1H, m), 0.70 (1H, m), 1.04 (1H, m), 1.15 (1H, m), 1.36 (1H, m), 1.55 (1H, m), 1.62 (1H, m), 1.89 (1H, m), 2.30 (3H, s), 2.42 (1H, m), 2.71 (1H, m), 2.93 (1H, m), 2.96 (3H, s), 3.03 (1H, m), 3.10 (1H, m), 3.23–3.37 (2H, m), 3.73–3.90 (3H, m), 4.44 (0.1H, m). 4.63 (0.9H, d, J=3.7 Hz), 4.71 (0.1H, m), 4.98 (0.9H, ddd, J=14.3, 4.0, 4.0 Hz), 6.12 (0.9H, s, OH), 6.23 (0.1H, s, OH), 6.59 (1H, d, J=8.3 Hz), 6.71 (1H, d, J=8.3 Hz), 7.01–7.44 (4H, m), 8.75 (1H, m, NH+)., 9.27 (1H, s, OH).

IR (KBr)

υ 3258, 2122, 1736, 1625, 1613, 1460, 1402, 1323, 1207, 1160, 1120, 919, 775 cm$^{-1}$.

Mass (FAB)

m/z 532 ((M+H)+).

Elementary Analysis: As $C_{30}H_{33}N_3O_4S \cdot CH_3SO_3H \cdot 0.9H_2O$

Calcd.: C 57.82; H 6.07; N 6.52; S 9.96

Found.: C 58.21; H 6.22; N 6.40; S 9.58

Examples 140 to 152

The procedure of Example 68 was repeated, except that 4-phenylbutanoyl chloride, 3-bromocinnamoyl chloride, 4-chlorocinnamoyl chloride, trans-3-(3-pyridyl)acryloyl chloride, 3-chlorocinnamoyl chloride, 4-methylcinnamoyl chloride, 4-bromocinnamoyl chloride, trans-3-(4-bromo-2-thienyl)acryloyl chloride, trans-3-(5-methyl-2-furyl)acryloyl chloride, trans-3-(2-methyl-3-furyl)acryloyl chloride, trans-3-(5-methyl-2-thienyl)acryloyl chloride, 3-trifluoromethoxycinnamoyl chloride and γ-methylcinnamoyl chloride were used instead of trans-3-(3-furyl)acryloyl chloride, thereby preparing 17-cyclopropylmethyl-4,5α-epoxy-3,14β-dihydroxy-6β-(N-methyl-4-phenylbutanoylamido)morphinan tartrate 150 (yield: 77%), 17-cyclopropylmethyl-3,14β-dihydroxy-4,5α-epoxy-6β-(N-methyl-3-bromocinnamamido)morphinan hydrobromide 151 (yield: 86%), 17-cyclopropylmethyl-3,14β-dihydroxy-4,5α-epoxy-6β-(N-methyl-4-chlorocinnamamido)morphinan hydrochloride 152 (yield: 65%), 17-cyclopropylmethyl-3,14β-dihydroxy-4,5α-epoxy-6β-[N-methyl-trans-3-(3-pyridyl)acrylamido]morphinan tartrate 153 (yield: 86%), 17-cyclopropylmethyl-3,14β-dihydroxy-4,5α-epoxy-6β-(N-methyl-3-chlorocinnamamido)morphinan hydrochloride 154 (yield: 80%), 17-cyclopropylmethyl-3,14β-dihydroxy-4,5α-epoxy-6β-(N-methyl-4-methylcinnamamido)morphinan hydrochloride 155 (yield: 57%), 17-cyclopropylmethyl-3,14β-dihydroxy-4,5α-epoxy-6β-(N-methyl-4-bromocinnamamido)morphinan hydrobromide 156 (yield: 93%), 17-cyclopropylmethyl-3,14β-dihydroxy-4,5α-epoxy-6β-[N-methyl-trans-3-(4-bromo-2-thienyl)acrylamido]morphinan hydrobromide 157 (yield: 84%), 17-cyclopropylmethyl-3,14β-dihydroxy-4,5α-epoxy-6β-[N-methyl-trans-3-(5-methyl-2-furyl)acrylamido]morphinan hydrochloride 158 (yield: 67%), 17-cyclopropylmethyl-3,14β-dihydroxy-4,5α-epoxy-6β-[N-methyl-trans-3-(2-methyl-3-furyl)acrylamido]morphinan hydrochloride 159 (yield: 46%), 17-cyclopropylmethyl-3,14β-dihydroxy-4,5α-epoxy-6β-[N-methyl-trans-3-(5-methyl-2-thienyl)acrylamido]morphinan tartrate 160 (yield: 75%), 17-cyclopropylmethyl-3,14β-dihydroxy-4,5α-epoxy-6β-(N-methyl-3-trifluoromethoxycinnamamido)morphinan tartrate 161 (yield: 49%) and 17-cyclopropylmethyl-3,14β-dihydroxy-4,5α-epoxy-6β-(N-methyl-γ-methylcinnamamido)morphinan tartrate 162 (yield: 78%).

Compound 150

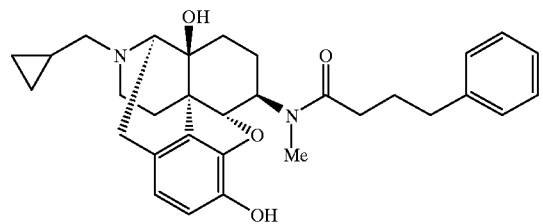

m.p. 134–135° C. (decomp.)

NMR (400 MHz, DMSO-$d_6$)

δ 0.18–0.28 (2H, m), 0.45–0.60 (2H, m), 0.87–0.96 (1H, m), 1.13–1.40 (3H, m), 1.52–1.82 (3H, m), 1.98–2.21 (3H, m), 2.22–2.35 (2H, m), 2.39–2.62 (3H, m), 2.65–2.80 (3H, m), 2.78 (2.1H, s), 2.90 (0.9H, s), 3.05–3.17 (1H, m), 3.25–3.35 (1H, m), 3.41–3.50 (1H, m), 4.02 (1.5H, s), 4.61 (0.7H, d, J=8.3 Hz), 4.71 (0.3H, d, J=8.3 Hz), 6.56 (0.3H, d, J=7.8 Hz), 6.61 (0.3H, d, J=7.8 Hz), 6.62 (0.7H, d, J=8.3 Hz), 6.71 (0.7H, d, J=8.3 Hz), 7.07–7.32 (5H, m). 9.35 (1H, brs).

IR (KBr)

ν 3320, 1650, 1609, 1313, 1125, 1067, 1035, 859 cm$^{-1}$.

Mass (FAB)

m/z 503 (M+H)$^+$.

Elementary analysis for $C_{31}H_{38}N_2O_4 \cdot 0.75C_4H_6O_6 \cdot 0.6H_2O$

Calculated: C, 65.23; H, 7.04; N, 4.47.

Found: C, 65.14; H, 7.04; N, 4.56.

Compound 151

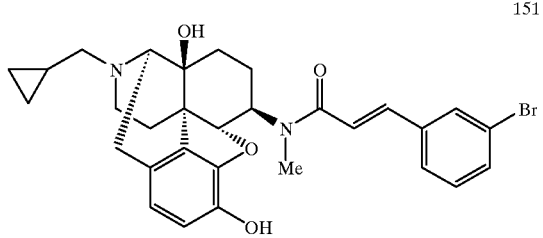

m.p.: 275–285° C. (decomp.)
NMR (400 MHz, DMSO-$d_6$)
δ 0.41 (1H, m), 0.51 (1H, m), 0.60 (1H, m), 0.69 (1H, m), 1.06 (1H, m), 1.29 (0.3H, m), 1.35–1.55 (2.7H, m), 1.73 (1H, d, J=13.2 Hz), 2.12 (1H, m), 2.40–2.60 (2H, m), 2.88 (1H, m), 2.93 (2H, s), 3.05–3.15 (2H, m), 3.19 (1H, s), 3.35–3.40 (2H, m), 3.66 (0.7H, m), 3.85 (1H, m), 4.20 (0.3H, m), 4.82 (0.7H, d, J=8.3 Hz), 4.91 (0.3H, d, J=8.3 Hz), 6.16 (0.3H, s), 6.24 (0.7H, s), 6.60–6.75 (2H, m), 6.88 (0.7H, d, J=8.3 Hz), 7.25–7.60 (4H, m), 7.65 (0.7H, s), 7.70 (0.3H, d, J=7.8 Hz), 8.03 (0.3H, s), 8.75 (1H, br s), 9.28 (0.3H, s), 9.53 (0.7H s).
IR (KBr)
ν 3400, 3200, 1649, 1605, 1323, 1033, 859 cm$^{-1}$.
Mass (FAB)
m/z 565 (M+H)
Elementary analysis for $C_{30}H_{33}N_2O_4Br·HBr·0.1H_2O$
Calculated: C, 55.59; H, 5.32; N, 4.32; Br, 24.65
Found: C, 55.74; H, 5.38; N, 4.40; Br, 24.40

Compound 152

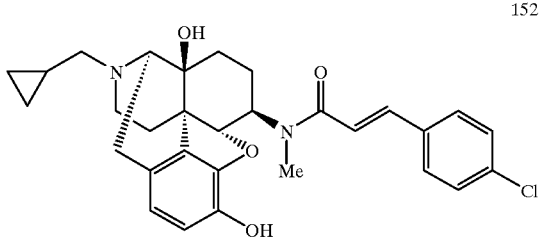

m.p. 234–244° C. (decomp.)
NMR (400 MHz, DMSO-$d_6$)
δ 0.41 (1H, m), 0.52 (1H, m), 0.60 (1H, m), 0.68 (1H, m), 1.08 (1H, m), 1.27 (0.3H, m), 1.35–1.50 (2.7H, m), 1.73 (1H, d, J=14.2 Hz), 2.18 (1H, m), 2.40–2.65 (2H, m), 2.90 (1H, m), 2.94 (2H, s), 3.05–3.15 (2H, m), 3.20 (1H, s), 3.30–3.40 (2H, m), 3.62 (0.7H, m), 3.86 (1H, m), 4.21 (0.3H, m), 4.87 (0.7H, d, J=8.3 Hz), 4.94 (0.3H, d, J=8.3 Hz), 6.44 (0.3H, s), 6.53 (0.7H, s), 6.65–6.75 (2H, m), 6.92 (0.7H, d, J=8.3 Hz), 7.20–7.30 (1H, m), 7.40–7.55 (3.6H, m), 7.76 (0.7H, d, J=8.8 Hz), 8.86 (1H, br s), 9.30 (0.3H, s), 9.74 (0.7H, s).
IR (KBr)
ν 3400, 3200, 1649, 1603, 1323, 1033, 824 cm$^{-1}$.
Mass (FAB)
m/z 521 (M+H)
Elementary analysis for $C_{30}H_{33}N_2O_4Cl·HCl·0.2H_2O$
Calculated: C, 64.22; H, 6.18; N, 4.99; Cl, 12.64
Found: C, 64.20; H, 6.26; N, 5.07; Cl, 12.66

Compound 153

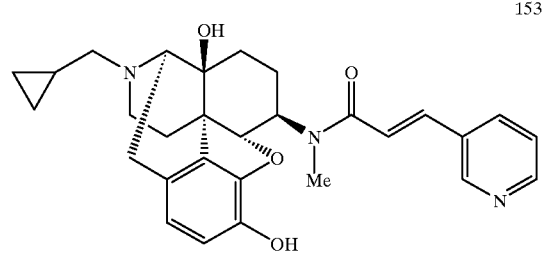

m.p. 170–174° C.
NMR (400 MHz, DMSO-$d_6$)
δ 0.25–0.30 (2H, m), 0.50–0.60 (2H, m), 0.94 (1H, m), 1.25–1.50 (3H, m), 1.60 (1H, m), 2.10–2.25 (2H, m), 2.34 (1H, m), 2.57 (1H, m), 2.75–2.85 (3H, m), 2.91 (2H, s), 3.12 (0.7H, m), 3.16 (1H, s), 3.37 (1H, m), 3.50 (0.3H, s), 3.68 (0.7H, m), 4.09 (2H, s), 4.20 (0.3H, m), 4.70 (0.7H, d, J=7.8 Hz), 4.82 (0.3H, d, J=8.3 Hz), 6.60–6.80 (2.7H, m), 7.30–7.50 (2.3H, m), 7.88 (0.7H, d, J=7.8 Hz), 8.18 (0.3H, d, J=8.3 Hz), 8.50–8.55 (1H, m), 8.63 (0.7H, s), 8.88 (0.3H, s).
IR (KBr)
ν 3300, 1649, 1599, 1311, 1127, 1069 cm$^{-1}$.
Mass (FAB)
m/z 488 (M+H)
Elementary analysis for $C_{29}H_{33}N_3O_4·C_4H_6O_6·0.7H_2O$
Calculated: C, 60.95; H, 6.26; N, 6.46
Found: C, 60.94; H, 6.35; N, 6.39

Compound 154

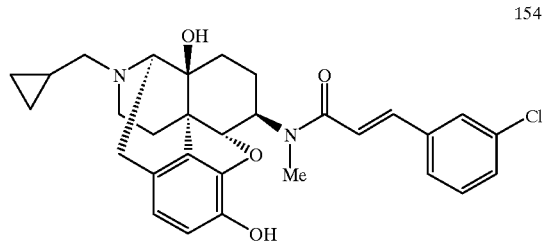

m.p. 234–240° C. (decomp.)
NMR (400 MHz, DMSO-$d_6$)
δ 0.41 (1H, m), 0.52 (1H, m), 0.60 (1H, m), 0.68 (1H, m), 1.07 (1H, m), 1.29 (0.3H, m), 1.35–1.55 (2.7H, m), 1.73 (1H, d, J=13.2 Hz), 2.18 (1H, m), 2.45–2.60 (2H, m), 2.88 (1H, m), 2.94 (2H, s), 3.05–3.10 (2H, m), 3.20 (1H, s), 3.30–3.40 (2H, m), 3.65 (0.7H, m), 3.85 (1H, m), 4.21 (0.3H, m), 4.86 (0.7H, d, J=8.3 Hz), 4.93 (0.3H, d, J=8.8 Hz), 6.36 (0.3H, s), 6.47 (0.7H, s), 6.65–6.75 (2H, m), 6.86 (0.7H, d, J=8.3 Hz), 7.28 (1H, m), 7.35–7.45 (3H, m), 7.52 (0.7H, s), 7.66 (0.3H, m), 7.89 (0.3H, s), 8.83 (1H, br s), 9.30 (0.3H, s), 9.58 (0.7H, s).
IR (KBr)
ν 3400, 3100, 1649, 1605, 1323, 1127, 1033, 922, 859, 795 cm$^{-1}$.
Mass (FAB)
m/z 521 (M+H)
Elementary analysis for $C_{30}H_{33}N_2O_4Cl·HCl·0.1H_2O$
Calculated: C, 64.42; H, 6.16; N, 5.01; Cl, 12.68
Found: C, 64.37; H, 6.20; N, 5.05; Cl, 12.65

Compound 155

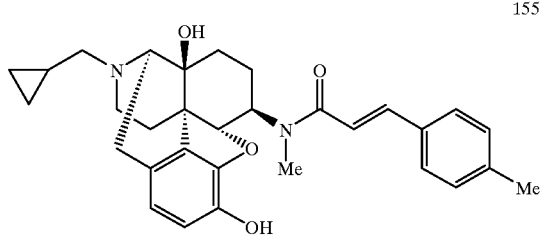

m.p. 245–255° C. (decomp.)
NMR (400 MHz, DMSO-$d_6$)

δ 0.41 (1H, m), 0.52 (1H, m), 0.60 (1H, m), 0.68 (1H, m) 1.08 (1H, m), 1.28 (0.3H, m), 1.30–1.50 (2.7H, m), 1.73 (1H, d, J=13.2 Hz), 2.18 (1H, m), 2.31 (2H, s), 2.33 (1H, s), 2.40–2.60 (2H, m), 2.89 (1H, m) 2.94 (2H, s), 3.00–3.10 (2H, m), 3.20 (1H, s), 3.25–3.35 (2H, m), 3.62 (0.7H, m), 3.86 (1H, m), 4.22 (0.3H, m), 4.88 (0.7H, d, J=7.8 Hz), 4.94 (0.3H, d, J=8.3 Hz), 6.45 (0.3H, s), 6.55–6.65 (1.7H, m), 6.72 (1H, m), 6.89 (0.7H, d, J=8.3 Hz), 7.10–7.25 (3H, m), 7.35–7.45 (1.6H, m), 7.60 (0.7H, d, J=7.8 Hz), 8.86 (1H, br s), 9.30 (0.3H, s), 9.71 (0.7H, s).

IR (KBr)

ν 3400, 3200, 1647, 1597, 1325, 1127, 816 cm$^{-1}$.

Mass (FAB)

m/z 501 (M+H)

Elementary analysis for $C_{31}H_{36}N_2O_4 \cdot HCl \cdot 0.7H_2O$

Calculated: C, 67.73; H, 7.04; N, 5.09; Cl, 6.45

Found: C, 67.73; H, 7.04; N, 5.12; Cl, 6.42

Compound 156

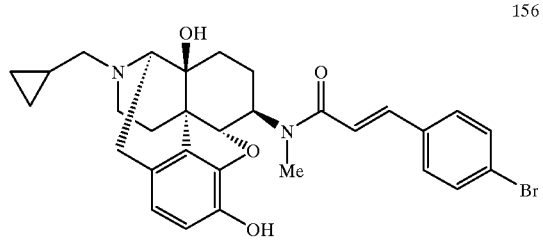

m.p. 233–239° C. (decomp.)
NMR (400 MHz, DMSO-$d_6$)

δ 0.42 (1H, m), 0.51 (1H, m), 0.60 (1H, m), 0.69 (1H, m), 1.08 (1H, m), 1.29 (0.3H, m), 1.35–1.50 (2.7H, m), 1.72 (1H, m), 2.13 (1H, m), 2.45–2.55 (2H, m), 2.88 (1H, m), 2.92 (2H, s), 3.00–3.10 (2H, m), 3.18 (1H, s), 3.30–3.40 (2H, m), 3.64 (0.7H, m), 3.85 (1H, m), 4.20 (0.3H, m), 4.82 (0.7H, d, J=7.8 Hz), 4.90 (0.3H, d, J=8.3 Hz), 6.15 (0.3H, s), 6.23 (0.7H, s), 6.65–6.75 (2H, m), 6.88 (0.7H, d, J=8.3 Hz), 7.25 (1H, m), 7.40–7.45 (1.6H, m), 7.55–7.65 (2H, m), 7.69 (0.7H, d, J=8.8 Hz), 8.75 (1H, br s), 9.28 (0.3H, s), 9.63 (0.7H, s).

IR (KBr)

ν 3300, 1649, 1591, 1321, 1127, 826 cm$^{-1}$.

Mass (FAB)

m/z 565 (M+H)

Elementary analysis for $C_{30}H_{33}N_2O_4Br \cdot HBr \cdot 0.5H_2O \cdot 0.2AcOEt$ Calculated: C, 54.96; H, 5.48; N, 4.16; Br, 23.74

Found: C, 54.93; H, 5.68; N, 4.27; Br, 23.67

Compound 157

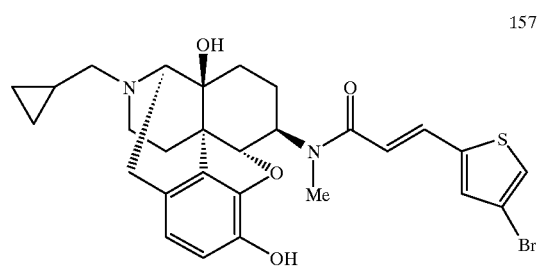

m.p. 247–258° C. (decomp.)
NMR (400 MHz, DMSO-$d_6$)

δ 0.42 (1H, m), 0.51 (1H, m), 0.60 (1H, m), 0.69 (1H, m), 1.07 (1H, m), 1.28 (0.4H, m), 1.45–1.55 (2.6H, m), 1.73 (1H, d, J=13.2 Hz), 2.10 (1H, m), 2.45–2.60 (2H, m), 2.88 (1H, m), 2.92 (1.8H, s), 3.05–3.10 (2H, m), 3.15 (1.2H, s), 3.30–3.40 (2H, m), 3.59 (0.6H, m), 3.85 (1H, m), 4.19 (0.4H, m), 4.79 (0.6H, d, J=8.3 Hz), 4.88 (0.4H, d, J=8.3 Hz), 6.16 (0.4H, s), 6.24 (0.6H, s), 6.41 (0.6H, d, J=15.1 Hz), 6.65–6.75 (1.4H, m), 6.81 (0.6H, d, J=8.3 Hz), 6.96 (0.4H, d, J=15.1 Hz), 7.33 (0.6H, s), 7.41 (0.6H, d, J=15.1 Hz), 7.53 (0.4H, d, J=15.1 Hz), 7.58 (0.4H, s), 7.71 (0.6H, s), 7.78 (0.4H, s), 8.75 (1H, br s), 9.27 (0.4H, s), 9.45 (0.6H, s).

IR (KBr)

ν 3400, 3200, 1638, 1597, 1319, 1125, 1033, 859 cm$^{-1}$.

Mass (FAB)

m/z 571 (M+H)

Elementary analysis for $C_{28}H_{31}N_2O_4SBr \cdot HBr \cdot 0.6H_2O$

Calculated: C, 50.71; H, 5.05; N, 4.22; S, 4.83; Br, 24.10

Found: C, 50.70; H, 5.11; N, 4.18; S, 4.78; Br, 24.16

Compound 158

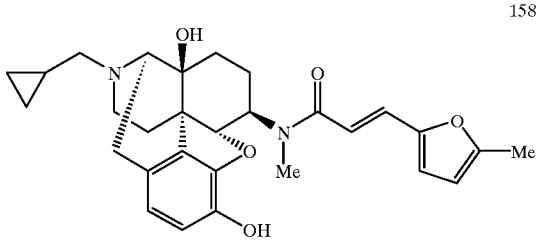

m.p. 245–255° C. (decomp.)
NMR (400 MHz, DMSO-$d_6$)

δ 0.41 (1H, m), 0.52 (1H, m), 0.59 (1H, m), 0.68 (1H, m), 1.09 (1H, m), 1.26 (0.4H, m), 1.35–1.50 (2.6H, m), 1.74 (1H, m), 2.14 (1H, m), 2.32 (1.8H, s), 2.34 (1.2H, s), 2.40–2.60 (2H, m), 2.89 (1H, m), 2.93 (1.8H, s), 3.05–3.15 (2H, m), 3.15 (1.2H, s), 3.25–3.40 (2H, m), 3.61 (0.6H, m), 3.87 (1H, m), 4.22 (0.4H, m), 4.85 (0.6H, d, J=8.3 Hz), 4.90 (0.4H, d, J=8.3 Hz), 6.15 (0.6H, d, J=2.4 Hz), 6.24 (0.4H, d, J=2.4 Hz), 6.48 (0.6H, s), 6.48 (0.4H, s), 6.55–6.60 (1H, m), 6.64 (0.6H, d, J=7.8 Hz), 6.70–6.75 (1.8H, m), 6.82 (0.6H, d, J=7.8 Hz), 7.08 (0.6H, d, J=15.1 Hz), 7.21 (0.4H, d, J=15.1 Hz), 8.87 (1H, br s), 9.31 (0.4H, s), 9.37 (0.6H, s).

IR (KBr)

ν 3400, 3200, 1647, 1578, 1410, 1321, 1025, 859 cm$^{-1}$.

Mass (FAB)

m/z 491 (M+H)
Elementary analysis for $C_{29}H_{34}N_2O_5 \cdot HCl \cdot 0.5H_2O$
Calculated: C, 64.98; H, 6.77; N, 5.22; Cl, 6.61
Found: C, 65.09; H, 6.74; N, 5.16; Cl, 6.62
Compound 159

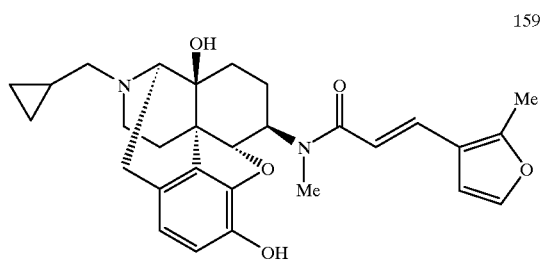

m.p. 215–225° C. (decomp.)
NMR (400 MHz, DMSO-$d_6$)
δ 0.41 (1H, m), 0.52 (1H, m), 0.59 (1H, m), 0.68 (1H, m), 1.08 (1H, m), 1.25–1.50 (3H, m), 1.75 (1H, d, J=13.2 Hz), 2.18 (1H, m), 2.30 (1.8H, s), 2.36 (1.2H, s), 2.40–2.65 (2H, m), 2.91 (1H, m), 2.93 (1.8H, s), 3.00–3.15 (2H, m), 3.17 (1.2H, s), 3.25–3.40 (2H, m), 3.57 (0.6H, m), 3.88 (1H, m), 4.20 (0.4H, m), 4.88 (0.6H, d, J=8.3 Hz), 4.94 (0.4H, d, J=8.3 Hz), 6.26 (0.6H, d, J=15.1 Hz), 6.50 (0.4H, s), 6.53 (0.6H, s), 6.61 (0.6H, s), 6.64 (0.4H, d, J=7.8 Hz), 6.70–6.85 (2H, m), 6.91 (0.4H, s), 7.17 (0.6H, d, J=15.1 Hz), 7.32 (0.4H, d, J=15.1 Hz), 7.50 (0.6H, s), 7.57 (0.4H, s), 8.89 (1H, br s), 9.32 (0.4H, s), 9.70 (0.6H, s).
IR (KBr)
ν 3400, 3200, 1649, 1591, 1321, 1125, 859 cm$^{-1}$.
Mass (EI)
m/z 490 (M$^+$)
Elementary analysis for $C_{29}H_{34}N_2O_5 \cdot HCl \cdot 0.6H_2O$
Calculated: C, 64.76; H, 6.78; N, 5.21; Cl, 6.59
Found: C, 64.70; H, 6.97; N, 5.11; Cl, 6.62
Compound 160

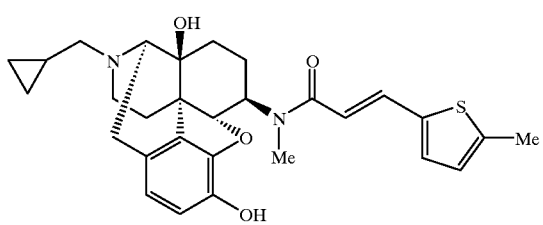

m.p. 174–176° C.
NMR (400 MHz, DMSO-$d_6$)
δ 0.22 (2H, m), 0.53 (2H, m), 0.91 (1H, m), 1.25–1.45 (3H, m), 1.58 (1H, m), 2.00–2.20 (2H, m), 2.28 (1H, m), 2.44 (1.8H, s), 2.47 (1.2H, s), 2.50 (1H, m), 2.60–2.80 (3H, m), 2.87 (1.8H, s), 3.08 (1.2H, s), 3.12 (1H, m), 3.46 (1H, m), 3.57 (0.6H, m), 4.03 (1H, s), 4.18 (0.4H, m), 4.65 (0.6H, d, J=8.1 Hz), 4.75 (0.4H, d, J=8.1 Hz), 6.25 (0.6H, d, J=15.0 Hz), 6.55–6.80 (3.4H, m), 7.10 (0.6H, d, J=3.3 Hz), 7.25 (0.4H, d, J=3.7 Hz), 7.36 (0.6H, d, J=15.0 Hz), 7.51 (0.4H, d, J=14.7 Hz).
IR (KBr)
ν 3400, 1630, 1593, 1315, 1127 cm$^{-1}$.
Mass (FAB)

m/z 507 (M+H)
Elementary analysis for $C_{29}H_{34}N_2O_4S \cdot 0.5C_4H_6O_6 \cdot 0.6H_2O$
Calculated: C, 62.84; H, 6.50; N, 4.73; S, 5.41
Found: C, 62.96; H, 6.46; N, 4.76; S, 5.32
Compound 161

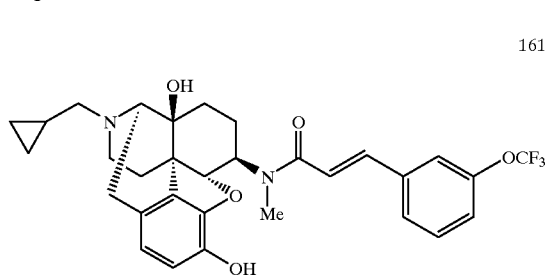

m.p. 152–155° C.
NMR (400 MHz, DMSO-$d_6$)
δ 0.23 (2H, m), 0.52 (2H, m), 0.91 (1H, m), 1.25–1.45 (3H, m), 1.59 (1H, m), 2.05–2.20 (2H, m), 2.31 (1H, m), 2.53 (1H, m), 2.65–2.80 (3H, m), 2.90 (2H, s), 3.11 (1H, d, J=18.6 Hz), 3.16 (1H, s), 3.41 (1H, m), 3.63 (0.7H, m), 4.06 (1H, s), 4.20 (0.3H, m), 4.70 (0.7H, d, J=8.3 Hz), 4.80 (0.3H, d, J=8.3 Hz), 6.55–6.75 (2.7H, m), 7.30–7.55 (4.7H, m), 7.74 (0.3H, d, J=7.8 Hz), 7.81 (0.3H, s).
IR (KBr)
ν 3350, 1649, 1603, 1261, 1216, 1127 cm$^{-1}$.
Mass (FAB)
m/z 571 (M+H)
Elementary analysis for $C_{31}H_{33}N_2O_5F_3 \cdot 0.5C_4H_6O_6 \cdot 1.3H_2O$
Calculated: C, 59.24; H, 5.82; N, 4.19; F, 8.52
Found: C, 59.43; H, 5.66; N, 4.13; F, 8.45
Compound 162

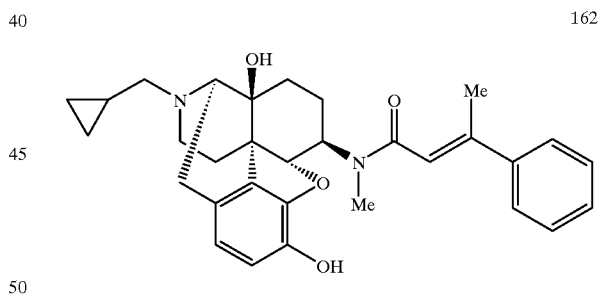

m.p. 255–260° C. (decomp.)
NMR (500 MHz, CD$_3$OD)
δ 0.41 (2H, m), 0.69 (1H, m), 0.74 (1H, m), 1.08 (1H, m), 1.45–1.60 (3H, m), 1.79 (1H, d, J=13.7 Hz), 2.08 (2.4H, s), 2.25 (0.6H, s), 2.31 (1H, m), 2.55–2.65 (2H, m), 2.80 (1H, m), 3.02 (1H, m), 3.04 (2.4H, s), 3.13 (1H, m), 3.15 (0.6H, s), 3.25–3.35 (2H, m), 3.78 (0.8H, m), 3.85 (1H, m), 4.20 (0.2H, m), 4.35 (1H, s), 4.78 (0.8H, d, J=8.3 Hz), 4.97 (0.2H, d, J=8.3 Hz), 6.27 (0.8H, s), 6.40 (0.2H, s), 6.65–6.75 (2H, m), 7.20–7.40 (4.8H, m), 7.52 (0.2H, d, J=7.3 Hz).
IR (KBr)
ν 3350, 1603, 1313, 1129, 1035, 859 cm$^{-1}$.
Mass (FAB)
m/z 501 (M+H)
Elementary analysis for $C_{31}H_{36}N_2O_4 \cdot 0.5C_4H_6O_6 \cdot 0.4H_2O$ Calculated: C, 68.00; H, 6.88; N, 4.80.
Found: C, 67.99; H, 6.84; N, 4.76.

Example 153

The procedure of Example 68 was repeated, except that 17-butyl-4,5α-epoxy-3,14β-dihydroxy-6β-(N-methylamino)morphinan was used instead of 17-cyclopropylmethyl-4,5α-epoxy-3,14β-dihydroxy-6β-(N-methylamino)morphinan 10 phthalate, thereby preparing 17-butyl-3,14β-dihydroxy-4,5α-epoxy-6β-[N-methyl-trans-3-(3-furyl)acrylamido]morphinan tartrate 163 (yield: 80%).

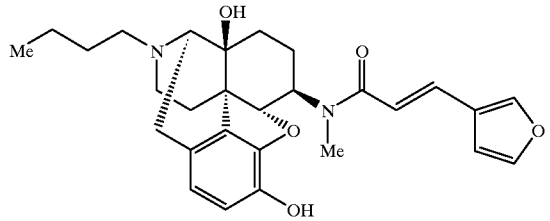

163 m.p. 161.0–165.0° C. (decomp., ethyl acetate)
NMR (400 MHz, DMSO-$d_6$) (as 1/2 tartrate)
δ 0.91 (3H, t, J=7.3 Hz), 1.20–1.60 (8H, m), 2.02–2.18 (2H, m), 2.27 (1H, m), 2.47–2.78 (4H, m), 2.86 (2.1H, s), 2.97–3.09 (2H, m), 3.10 (0.9H, s), 3.59 (0.7H, m), 4.06 (1H, s), 4.18 (0.3H, m), 4.66 (0.7H, d, J=7.8 Hz), 4.76 (0.3H, d, J=8.3 Hz), 6.40 (0.7H, d, J=15.1 Hz), 6.57 (0.3H, d, J=7.8 Hz), 6.61 (0.7H, d, J=7.8 Hz), 6.64 (0.3H, d, J=7.8 Hz), 6.64 (0.7H, d, J=2.0 Hz), 6.75 (0.7H, d, J=7.8 Hz), 6.90 (0.3H, d, J=15.1 Hz), 7.00 (0.3H, d, J=1.0 Hz), 7.22 (0.7H, d, J=15.1 Hz), 7.36 (0.3H, d, J=15.1 Hz), 7.67 (0.7H, s), 7.72 (0.3H, s), 7.92 (0.7H, s), 8.03 (0.3H, s), 9.10 (0.3H, br s), 9.50 (0.7H, br s).
IR (KBr) (as free base)
ν 3400, 1649, 1601, 1408, 1377, 1323, 1125 $cm^{-1}$.
Mass (FAB)
m/z 479 (M+H)$^+$.
Elementary analysis for $C_{30}H_{37}N_2O_8 \cdot 1.0H_2O$
Calculated: C, 63.03; H, 6.88; N, 4.90.
Found: C, 62.23; H, 6.84; N, 4.80.

Examples 154 to 157

The procedure of Example 11 was repeated, except that 17-cyclopropylmethyl-4,5α-epoxy-3,14β-dihydroxy-6β-(N-ethylamino)morphinan 11, 17-cyclopropylmethyl-4,5α-epoxy-3,14β-dihydroxy-6β-(N-isopropylamino)morphinan, 17-cyclopropylmethyl-4,5α-epoxy-3,14β-dihydroxy-6β-(N-isobutylamino)morphinan and 17-cyclopropylmethyl-4,5α-epoxy-3,14β-dihydroxy-6β-(N-butylamino)morphinan were used instead of 17-cyclopropylmethyl-4,5α-epoxy-3,14β-dihydroxy-6α-(N-methylamino)morphinan 4 and, further, 3-trifluoromethylcinnamoyl chloride was used instead of 3,4-dichlorophenylacetyl chloride, thereby preparing 17-cyclopropylmethyl-3,14β-dihydroxy-4,5α-epoxy-6β-(N-ethyl-3-trifluoromethylcinnamamido)morphinan 0.5 tartrate 164 (87%), 17-cyclopropylmethyl-3,14β-dihydroxy-4,5α-epoxy-6β-(N-isopropyl-3-trifluoromethylcinnamamido)morphinan hydrochloride 165 (21%), 17-cyclopropylmethyl-3,14β-dihydroxy-4,5α-epoxy-6β-(N-isobutyl-3-trifluoromethylcinnamamido) morphinan 0.5 tartrate 166 (81%) and 17-cyclopropylmethyl-3,14β-dihydroxy-4,5α-epoxy-6β-(N-butyl-3-trifluoromethylcinnamamido)morphinan tartrate 167 (78%).

Compound 164

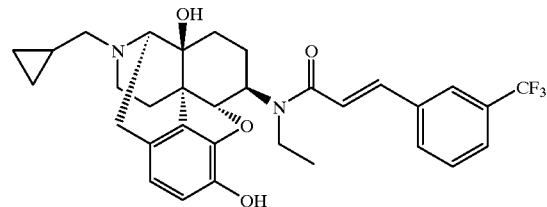

164 m.p. >200° C. (decomp.)
NMR (400 MHz, DMSO-$d_6$)
δ 0.22 (2H, m), 0.53 (2H, m), 0.91 (1H, m), 1.19 (1.5H, t, J=6.8 Hz), 1.21 (1.5H, t, J=6.8 Hz), 1.27–1.62 (4H, m), 2.04–2.38 (3H, m), 2.48 (1H, m), 2.55–2.80 (3H, m), 3.09 (1H, m), 3.14–3.34 (2H, m), 3.50–3.75 (2H, m), 3.55 (3H, br s, 3×OH), 4.03 (1H, s), 4.60 (0.5H, br d, J=6.3 Hz), 4.99 (0.5H, m), 6.57 (0.5H, d, J=8.1 Hz), 6.61 (0.5H, d, J=8.1 Hz), 6.63 (0.5H, d, J=8.1 Hz), 6.70 (0.5H, J=8.1 Hz), 6.75 (0.5H, br d, J=15.6 Hz), 7.26 (0.5H, d, J=15.6 Hz), 7.37 (0.5H, br d, J=15.6 Hz), 7.57 (0.5H, d, J=15.6 Hz), 7.58–7.83 (3H, m), 8.03 (0.5H, d, J=7.8 Hz) 8.12 (0.5H, br s), 9.33 (1H, m, NH+).
IR (KBr)
ν 3386, 1649, 1595, 1506, 1433, 1328, 1243, 1168, 1118, 1073, 982, 920, 859, 804 $cm^{-1}$.
Mass (FAB)
m/z 569 ((M+H)$^+$).
Elementary analysis for $C_{32}H_{35}F_3N_2O_4 \cdot 0.5C_4H_6O_6 \cdot 0.3H_2O$
Calculated: C, 62.92; H, 5.99; F, 8.78; N, 4.32.
Found: C, 62.89; H, 6.05; F, 8,84; N, 4.29.

Compound 165

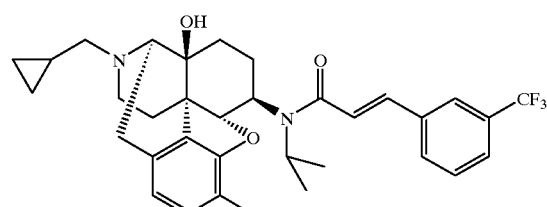

165 m.p. >200° C. (decomp.)
NMR (400 MHz, DMSO-$d_6$)
δ 0.42 (1H, m), 0.52 (1H, m), 0.61 (1H, m), 0.68 (1H, m), 1.02 (1.5H, br d, J=5.8 Hz), 1.04–1.13 (2H, m), 1.17 (1.5H, br d, J=5.8 Hz), 1.36–1.48 (2H, m), 1.43 (1.5H, d, J=6.8 Hz), 1.51 (1.5H, d, J=6.8 Hz), 1.73 (1H, m), 2.10–2.60 (3H, m), 2.82–2.95 (2H, m), 2.98–3.12 (2H, m), 3.25–3.42 (2H, m), 3.55 (0.5H, m), 3.85 (1H, d, J=4.9 Hz), 4.48 (0.5H, m), 4.80 (0.5H, d, J=8.3 Hz), 5.34 (0.5H, m), 6.01 (0.5H, s, OH), 6.51 (0.5H, s, OH), 6.64 (0.5H, d, J=15.6 Hz), 6.66 (0.5H, d, J=8.3 Hz), 6.68 (0.5H, d, J=8.3 Hz), 6.75 (0.5H, d, J=8.3 Hz), 6.82 (0.5H, d, J=8.3 Hz), 7.28 (0.5H, d, J=15.6 Hz), 7.42–7.78 (4H, m), 8.02 (0.5H, d, J=7.8 Hz), 8.14 (1H, brs), 8.84 (1H, m, NH+), 9.29 (0.5H, s, OH), 9.65 (0.5H, s).

IR (KBr)
v 3362, 1651, 1605, 1510, 1462, 1439, 1334, 1201, 1168, 1125, 1033, 980, 917, 857, 806 cm$^{-1}$.
Mass (FAB)
m/z 583 ((M+H)$^+$).
Elementary analysis for $C_{33}H_{37}F_3N_2O_4$•HCl•0.7H$_2$O
Calculated: C, 62.74; H, 6.29; Cl, 5.61; F, 9.02; N, 4.43.
Found: C, 62.76; H, 6.29; Cl, 5.50; F, 9.28; N, 4.45.
Compound 166

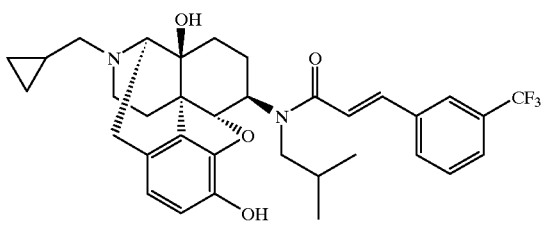

166 m.p. >140° C. (decomp.)
NMR (400 MHz, DMSO-d$_6$)
δ 0.31 (2H, m), 0.53 (2H, m), 0.81–0.98 (7H, m), 1.27–1.61 (4H, m), 1.78–2.34 (3H, m), 2.42–2.80 (4H, m), 3.00–3.15 (2H, m), 3.20–3.44 (3H, m), 3.50 (3H, br s, OH), 3.70 (1H, m), 4.03 (1H, s), 4.55 (0.5H, m), 5.22 (0.5H, m), 6.57 (0.5H, d, J=7.8 Hz), 6.58 (0.5H, d, J=7.8 Hz), 6.64 (0.5H, d, J=7.8 Hz), 6.65 (0.5H, d, J=7.8 Hz), 6.78 (0.5H, m), 7.31 (0.5H, m), 7.31 (0.5H, d, J=15.1 Hz), 7.55–7.82 (3H, m), 7.57 (0.5H, d, J=15.1 Hz), 8.05 (0.5H, d, J=8.3 Hz), 8.06 (0.5H, br s), 9.25 (1H, m, NH+).
IR (KBr)
v 3358, 1649, 1603, 1504, 1460, 1334, 1232, 1168, 1125, 1071, 1035, 984, 924, 859, 801 cm$^{-1}$.
Mass (FAB)
m/z 597 ((M+H)$^+$).
Elementary analysis for $C_{34}H_{39}F_3N_2O_4$•0.5$C_4H_6O_6$
Calculated: C, 64.37; H, 6.30; F, 8.48; N, 4.17.
Found: C, 64.21; H, 6.40; F, 8.47; N, 4.21.
Compound 167

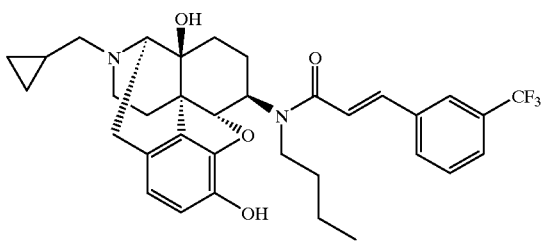

167 m.p. >130° C. (decomp.)
NMR (400 MHz, DMSO-d$_6$)
δ 0.27 (2H, m), 0.53 (2H, m), 0.92 (1.5H, t, J=7.8 Hz), 0.93 (1H, m) 0.94 (1.5H, t, J=7.8 Hz), 1.28–1.63 (7H, m), 2.03–2.38 (2H, m), 2.54 (1H, m), 2.67–2.85 (3H, m), 3.07–3.18 (2H, m), 3.30–3.53 (4H, m), 3.50 (5H, br s, OH), 3.68 (1H, m), 4.10 (2H, s), 4.61 (0.5H, m), 5.05 (0.5H, m), 6.58 (0.5H, d, J=8.3 Hz), 6.62 (0.5H, d, J=8.3 Hz), 6.65 (0.5H, d, J=8.3 Hz), 6.70 (0.5H, d, J=8.3 Hz), 6.75 (0.5H, br d, J=15.6 Hz), 7.24 (0.5H, d, J=15.6 Hz), 7.35 (0.5H, br d, J=15.6 Hz), 7.57 (0.5H, d, J=15.6 Hz), 7.58–7.82 (3H, m), 8.03 (0.5H, d, J=7.8 Hz), 8.07 (0.5H, br s), 9.32 (1H, m, NH).
IR (KBr)
v 3316, 1731, 1649, 1593, 1506, 1459, 1334, 1251, 1199, 1170, 1122, 1075, 1035, 980, 922, 859, 803 cm$^{-1}$.
Mass (FAB)
m/z 597 ((M+H)$^+$).
Elementary analysis for $C_{34}H_{39}F_3N_2O_4$•$C_4H_6O_6$
Calculated: C, 61.12; H, 6.07; F, 7.63; N, 3.75.
Found: C, 60.88; H, 6.20; F, 7.73; N, 3.74.

Example 158

The procedure of Example 11 was repeated, except that 17-cyclopropylmethyl-4,5α-epoxy-3,14β-dihydroxy-6β-(N-isobutylamino)morphinan was used instead of 17-cyclopropylmethyl-4,5α-epoxy-3,14β-dihydroxy-6α-(N-methylamino)morphinan 4, thereby preparing 17-cyclopropylmethyl-3,14β-dihydroxy-4,5α-epoxy-6β-(N-isobutyl-3,4-dichlorophenylacetamido)morphinan 0.8 tartrate 168 (48%).

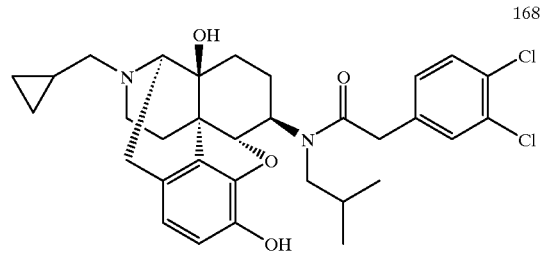

168 m.p. >238° C. (decomp.)
NMR (400 MHz, DMSO-d$_6$)
δ 0.22 (2H, m), 0.52 (2H, m), 0.82–0.94 (7H, m), 1.12–1.38 (3H, m), 1.53 (1H, m), 1.73–2.34 (4H, m), 2.54 (1H, m), 2.61–2.82 (4H, m), 3.05–3.20 (2H, m), 3.22–3.35 (2H, m), 3.50–3.77 (2H, m), 3.55 (4.2H, s, OH), 4.08 (1.6H, s), 4.56 (0.6H, d, J=8.0 Hz), 5.16 (0.4H, d, J=7.7 Hz), 6.56 (0.4H, d, J=8.1 Hz), 6.64 (0.4H, d, J=8.1 Hz), 6.66 (0.6H, d, J=8.1 Hz), 6.73 (0.6H, d, J=8.1 Hz), 6.95 (0.6H, br d, J=8.4 Hz), 7.00 (0.6H, br s), 7.23 (0.4H, dd, J=8.4, 1.8 Hz), 7.51 (0.6H, d, J=8.1 Hz), 7.52 (0.4H, br s), 7.58 (0.4H, d, J=8.1 Hz), 9.46 (1H, m, NH$^+$).
IR (KBr)
v 3322, 1636, 1510, 1473, 1460, 1388, 1309, 1241, 1135, 1033 cm$^{-1}$.
Mass (FAB)
m/z 585 ((M+H)$^+$).
Elementary analysis for $C_{32}H_{38}Cl_2N_2O_4$•0.8$C_4H_6O_6$•0.5H$_2$O
Calculated: C, 59.16; H, 6.18; Cl, 9.92; N, 3.92.
Found: C, 69.15; H, 6.18; Cl, 9.88; N, 3.89.

Example 159

The procedure of Example 11 was repeated, except that 17-cyclopropylmethyl-4,5α-epoxy-14β-hydroxy-3-methoxy-6β-mercaptomorphinan(K. Kanematsu, T. Toshiyasu, M. Yoshida., Chem., Pharm. Bull., 38, 1141, (1990)) was used instead of 17-cyclopropylmethyl-4,5α-epoxy-3,14β-dihydroxy-6α-(N-methylamino)morphinan 4 and trans-3-(3-furyl)acryloyl chloride was used instead of 3,4-dichlorophenylacetyl chloride, thereby preparing 17-cyclopropylmethyl-4,5α-epoxy-14β-hydroxy-3-methoxy-6β-[trans-3-(3-furyl)acryloylthio]morphinan 169 (yield: 59%).

169

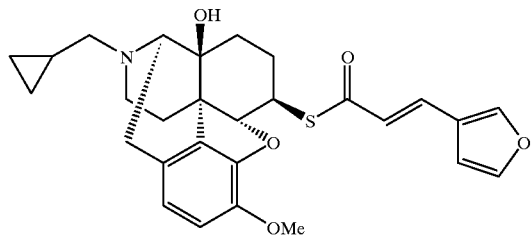

NMR (400 MHz, DMSO-d₆)

δ 0.08–0.18 (2H, m), 0.50–0.58 (2H, m), 0.78–0.90 (1H, m), 1.43–1.67 (4H, m), 1.78–1.86 (1H, m), 2.05–2.18 (2H, m), 2.24 (1H, dt, J=4.9,12.2 Hz), 2.37 (2H, d, J=6.3 Hz), 2.60–2.70 (2H, m), 3.04 (1H, d, J=19.0 Hz), 3.08 (1H, d, J=6.4 Hz), 3.44–3.54 (1H, m), 3.84 (3H, s), 4.55 (1H, d, J=8.8 Hz), 5.10 (1H, brs), 6.42 (1H, d, J=15.6 Hz), 6.58 (1H, d, J=1.5 Hz), 6.64 (1H, d, J=8.3 Hz), 6.73 (1H, d, J=8.3 Hz), 7.43 (1H, brs), 7.46 (1H, d, J=15.6 Hz), 7.68 (1H, s).

Mass (EI)

m/z 493 (M)⁺

Example 160

The procedure of Example 66 was repeated, except that 17-cyclopropylmethyl-4,5α-epoxy-14β-hydroxy-3-methoxy-6β-[trans-3-(3-furyl)acryloylthio]morphinan 169 was used instead of 17-cyclopropylmethyl-7,8-didehydro-4,5α-epoxy-14β-hydroxy-3-methoxy-6α-[N-methyl-trans-3-(3-furyl)acrylamido]morphinan 75, thereby preparing 17-cyclopropylmethyl-4,5α-epoxy-3,14β-dihydroxy-6β-[trans-3-(3 -furyl)acryloylthio]morphinan 0.5 tartrate 170 (yield: 63%).

170

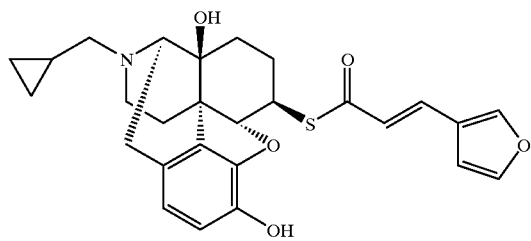

m.p. 225° C. (decomp.)

NMR (400 MHz, DMSO-d₆)

δ 0.15–0.24 (2H, m), 0.45–0.57 (2H, m), 0.84–0.93 (1H, m), 1.23–1.43 (2H, m), 1.52–1.67 (2H, m), 1.92–2.29 (3H, m), 2.40–2.52 (1H, m), 2.53–2.78 (3H, m), 3.08 (1H, d, J=19.1 Hz), 3.19–3.30 (1H, m), 4.01 (1H, s), 4.52 (1H, d, J=8.8 Hz), 6.60 (1H, d, J=7.8 Hz), 6.64 (1H, d, J=7.8 Hz), 6.74 (1H, d, J=15.6 Hz), 7.01 (1H, d, J=1.5 Hz), 7.50 (1H, d, J=15.6 Hz), 7.76 (1H, brs), 8.18 (1H, s), 9.18 (1H, brs).

IR (KBr)

ν 3402, 3222, 1665, 1649, 1613, 1578, 1315, 1040, 859, 795, 673 cm⁻¹.

Mass (FAB)

m/z 480 (M+H)⁺.

Elementary analysis for C₂₇H₂₉NO₅S•0.5C₄H₆O₆•0.3H₂O

Calculated: C, 62.19; H, 5.87; N, 2.50; S, 5.73.

Found: C, 62.21; H, 5.86; N, 2.57; S, 5.65.

Examples 161–172

The procedure of Example 114 was repeated, except that 3-(4-methylphenyl)propiolic acid, 3-(3-methylphenyl)propiolic acid, 3-(3-methoxyphenyl)propiolic acid, cis-3-(3-furyl)acrylic acid, 3-(2-furyl)propiolic acid, 3-(4-methoxyphenyl)propiolic acid, 3-(3-furyl)propiolic acid, 2,4-hexadienoic acid, 3,4-dichlorocinnamic acid, 3-(4-chlorophenyl)propiolic acid, 3,4-difluorocinnamic acid and 3-(3,4-dimethylphenyl)propiolic acid were used instead of 3-(3-trifluoromethylphenyl)propiolic acid, thereby preparing 17-cyclopropylmethyl-3,14β-dihydroxy-4,5α-epoxy-6β-[N-methyl-3-(4-methylphenyl)propiolamido]morphinan hydrochloride 171 (yield: 37%), 17-cyclopropylmethyl-3,14β-dihydroxy-4,5α-epoxy-6β-[N-methyl-3-(3-methylphenyl)propiolamido]morphinan hydrochloride 172 (yield: 54%), 17-cyclopropylmethyl-3,14β-dihydroxy-4,5α-epoxy-6β-[N-methyl-3-(3-methoxyphenyl)propiolamido]morphinan tartrate 173 (yield 34%), 17-cyclopropylmethyl-3,14β-dihydroxy-4,5α-epoxy-6β-[N-methyl-cis-3-(3-furyl)acrylamido]morphinan tartrate 174 (yield: 28%), 17-cyclopropylmethyl-3,14β-dihydroxy-4,5α-epoxy-6β-[N-methyl-3-(2-furyl)propiolamido]morphinan hydrochloride 175 (yield: 68%), 17-cyclopropylmethyl-3,14β-dihydroxy-4,5α-epoxy-6β-[N-methyl-3-(4-methoxyphenyl)propiolamido]morphinan hydrochloride 176 (yield: 87%), 17-cyclopropylmethyl-3,14β-dihydroxy-4,5α-epoxy-6β-[N-methyl-(3-furyl)propiolamido]morphinan tartrate 177 (yield: 98%), 17-cyclopropylmethyl-3,14β-dihydroxy-4,5α-epoxy-6β-(N-methyl-trans,trans-2,4-hexadienoylamino)morphinan tartrate 178 (yield: 89%), 17-cyclopropylmethyl-3,14β-dihydroxy-4,5α-epoxy-6β-(N-methyl-3,4-dichlorocinnamamido)morphinan hydrochloride 179 (yield: 96%), 17-cyclopropylmethyl-3,14β-dihydroxy-4,5α-epoxy-6β-[N-methyl-3-(4-chlorophenyl)propiolamido]morphinan hydrochloride 180 (yield: 44%), 17-cyclopropylmethyl-3,14β-dihydroxy-4,5α-epoxy-6β-(N-methyl-3,4-difluorocinnamamido)morphinan tartrate 181 (yield: 75%) and 17-cyclopropylmethyl-3,14β-dihydroxy-4,5α-epoxy-6β-[N-methyl-3-(3,4-dimethylphenyl)propiolamido]morphinan hydrochloride 182 (yield: 82%).

Compound 171

171

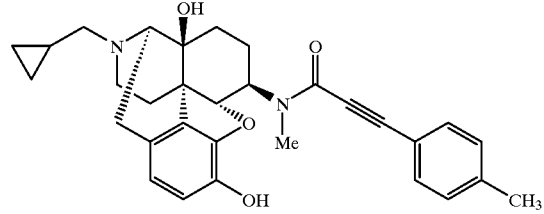

m.p. 205.0–207.0° C.

NMR (400 MHz, DMSO-d₆)

δ 0.32–0.46 (1H, m), 0.46–0.56 (1H, m), 0.56–0.63 (1H, m), 0.64–0.74 (1H, m), 1.00–1.13 (1H, m), 1.21–1.34

(0.6H, m), 1.34–1.52 (2.4H, m), 1.70–1.85 (1H, m), 2.05–2.30 (1H, m), 2.33 (2.4H, s), 2.36 (0.6H, s), 2.38–2.62 (2H, m), 2.80–2.92 (1H, m), 2.97 (2.4H, s), 2.99–3.18 (2H, m), 3.30 (0.6H, s), 3.22–3.43 (2H, m),. 3.86 (1H, m), 4.04–4.13 (0.2H, m), 4.13–4.25 (0.8H, m), 4.91 (0.8H, d, J=8.3 Hz), 4.96 (0.2H, d, J=8.3 Hz), 6.48 (0.2H, br s), 6.60 (0.8H, br s), 6.64 (0.8H, d, J=7.8 Hz), 6.65 (0.2H, d, J=8.3 Hz), 6.68 (0.8H, d, J=7.8 Hz), 6.72 (0.2H, d, J=8.3 Hz), 7.07 (1.6H, d, J=7.8 Hz), 7.17 (1.6H, d, J=7.8 Hz), 7.29 (0.4H, d, J=8.3 Hz), 7.53 (0.4H, d, J=7.8 Hz), 8.85 (1H, br s), 9.32 (0.2H, s), 9.35 (0.8H, s).

IR (KBr)

ν 3410, 2216, 1607, 1510, 1460, 1410, 1377, 1319, 1127, 1035, 818 cm$^{-1}$.

Mass (FAB)

m/z 499 ((M+H)$^+$).

Elementary analysis for $C_{31}H_{35}N_2O_4Cl_1 \cdot 0.5H_2O$

Calculated: C, 68.43; H, 6.67; N, 5.15; Cl, 6.52

Found: C, 68.42; H, 6.83; N, 5.14; Cl, 6.46

Compound 172

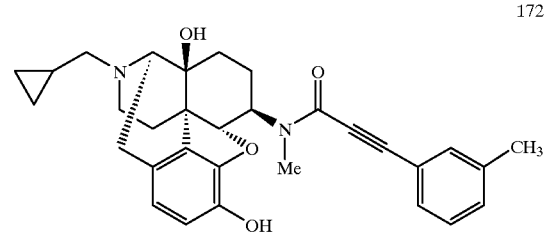

172 m.p. 182.0–183.0° C.

NMR (400 MHz, DMSO-d$_6$)

δ 0.33–0.47 (1H, m), 0.47–0.56 (1H, m), 0.56–0.64 (1H, m), 0.64–0.76 (1H, m), 1.00–1.15 (1H, m), 1.21–1.36 (0.6H, m), 1.36–1.55 (2.4H, m), 1.70–1.87 (1H, m), 2.05–2.28 (1H, m), 2.29 (2.4H, s), 2.34 (0.6H, s), 2.48–2.63 (2H, m), 2.78–2.93 (1H, m), 2.98 (2.4H, s), 2.99–3.18 (2H, m), 3.30 (0.6H, s), 3.21–3.43 (2H, m), 3.80–3.93 (1H, m), 4.02–4.14 (0.2H, m), 4.14–4.26 (0.8H, m), 4.91 (0.8H, d, J=7.8 Hz), 4.96 (0.2H, d, J=8.3 Hz), 6.45 (0.2H, br s), 6.58 (0.8H, br s), 6.63 (0.8H, d, J=8.3 Hz), 6.65 (0.2H, d, J=8.3 Hz), 6.69 (0.8H, d, J=8.3 Hz), 6.72 (0.2H, d, J=8.3 Hz), 6.92 (0.8H, s), 7.05 (0.8H, d, J=6.8 Hz), 7.20–7.32 (1.6H, m), 7.32–7.40 (0.4H, m), 7.40–7.51 (0.4H, m), 8.85 (1H, br s), 9.33 (0.2H, s), 9.36 (0.8H, s).

IR (KBr)

ν 3410, 2218, 1613, 1508, 1460, 1410, 1377, 1321, 1125, 1033, 930, 789, 690 cm$^{-1}$.

Mass (FAB)

m/z 499 ((M+H)$^+$).

Elementary analysis for $C_{31}H_{35}N_2O_4Cl_1 \cdot 0.4H_2O$

Calculated: C, 68.66; H, 6.65; N, 5.17; Cl, 6.54

Found: C, 68.86; H, 6.75; N, 5.22; Cl, 6.48

Compound 173

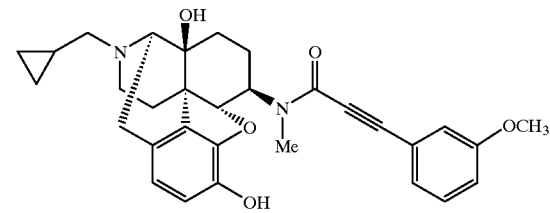

173 m.p. 154.0–156.0° C. (decomp., ethyl acetate)

NMR (400 MHz, DMSO-d$_6$)

δ 0.17–0.30 (2H, m), 0.50–0.62 (2H, m), 0.91 (1H, m), 1.18 (0.4H, m), 1.26 (0.6H, m), 1.42–1.59 (3H, m), 1.80 (1H, m), 2.17–2.34 (2H, m), 2.40–2.62 (2H, m), 2.64–2.82 (2H, m), 2.80–3.98 (3H, br), 2.92 (1.8H, s), 3.04 (0.6H, m), 3.08 (0.4H, m), 3.20–3.36 (1H, m), 3.24 (1.2H, s), 3.80 (1.2H, s), 3.82 (1.8H, s), 4.09 (1H, s), 4.62 (0.4H, d, J=3.4 Hz), 4.70 (0.6H, d, J=3.4 Hz), 4.84 (0.4H, dt, J=14.2, 3.4 Hz), 5.05 (0.6H, dt, J=13.7, 3.4 Hz), 6.53 (1H, d, J=8.3 Hz), 6.64 (0.4H, d, J=8.3 Hz), 6.65 (0.6H, d, J=8.3 Hz), 7.12 (1H, m), 7.22 (1H, m), 7.29 (1H, m), 7.40 (1H, m), 9.14 (1H, br s).

IR (KBr)

ν 3420, 2218, 1605, 1491, 1460, 1323, 1290, 1036, 687 cm$^{-1}$.

Mass (FAB)

m/z 515 (M+H)$^+$.

Elementary analysis for $C_{33}H_{37}N_2O_8 \cdot 1.3H_2O$

Calculated: C, 64.65; H, 6.51; N, 4.57.

Found: C, 64.41; H, 6.41; N, 4.56.

Compound 174

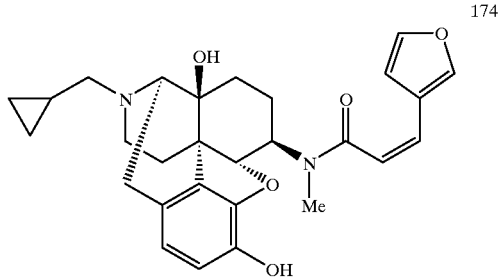

174 m.p. 165.0–175.5° C. (decomp., ethyl acetate)

NMR (400 MHz, CD$_3$OD)

δ 0.41–0.48 (2H, m), 0.67–0.79 (2H, m), 1.07 (1H, m), 1.20 (1H, m), 1.35 (0.75H, dt, J=13.4, 2.9 Hz), 1.48 (0.25H, m), 1.59 (1H, br d, J=9.8 Hz), 1.67 (0.75H, br d, 14.2 Hz), 1.80 (0.25H, br d, J=13.7 Hz), 2.18 (1H, m), 2.52–2.65 (2H, m), 2.84 (1H, m), 3.00–3.37 (3H, m), 3.04 (2.25H, s), 3.09 (0.75H, s), 3.77–3.87 (2H, m), 4.36 (1H, s), 4.71 (0.75H, d, J=8.3 Hz), 4.92 (0.25H, d, J=8.3 Hz), 6.02 (0.25H, d, J=12.2 Hz), 6.11 (0.75H, d, J=12.7 Hz), 6.25 (0.75H, d, J=12.2 Hz), 6.36 (0.75H, d, J=1.5 Hz), 6.58 (0.25H, d, J=12.7 Hz), 6.71–6.79 (2.25H, m), 7.40 (0.75H, d, J=1.5 Hz), 7.45 (0.25H, d, J=1.5 Hz), 7.50 (0.75H, br s), 7.74 (0.25H, br s).

IR (KBr)

ν 3426, 1605, 1508, 1313, 1129, 1035 cm$^{-1}$.

Mass (EI) (as free base)

m/z 476 (M$^+$).

Elementary analysis for $C_{30}H_{35}N_2O_8 \cdot 1.6H_2O$
Calculated: C, 62.08; H, 6.63; N, 4.83.
Found: C, 62.02; H, 6.51; N, 4.61.

Compound 175

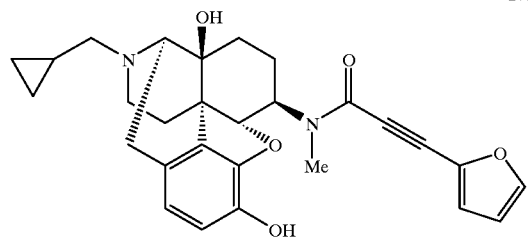

m.p. 189.0–199.0° C. (decomp.)
NMR (400 MHz, DMSO-$d_6$)
δ 0.36–0.47 (1H, m), 0.47–0.57 (1H, m), 0.57–0.63 (1H, m), 0.63–0.74 (1H, m), 1.00–1.14 (1H, m), 1.22–1.36 (0.3H, m), 1.36–1.54 (2.7H, m), 1.70–1.87 (1H, m), 2.06–2.30 (1H, m), 2.35–2.64 (2H, m), 2.78–2.93 (1H, m), 2.97 (2.1H, s), 2.99–3.17 (2H, m), 3.26 (0.9H, s), 3.27–3.43 (2H, m), 3.80–3.93 (1H, m), 3.93–4.03 (0.7H, m), 4.03–4.14 (0.3H, m), 4.87 (0.7H, d, J=8.3 Hz), 4.96 (0.3H, d, J=8.3 Hz), 6.45 (0.3H, br s), 6.58 (0.7H, br s), 6.59 (0.7H, dd, J=3.4, 2.0 Hz), 6.63 (0.7H, d, J=8.3 Hz), 6.64–6.68 (1.7H, m), 6.69 (0.3H, dd, J=3.4, 1.5 Hz), 6.72 (0.3H, d, J=8.3 Hz), 7.21 (0.3H, d, J=3.4 Hz), 7.80 (0.7H, d, J=1.5 Hz), 7.93 (0.3H, d, J=2.0 Hz), 8.85 (1H, br s), 9.24 (0.7H, s), 9.32 (0.3H, s).

IR (KBr)
ν 3410, 2210, 1620, 1504, 1460, 1410, 1377, 1319, 1127, 1035, 859 cm$^{-1}$.

Mass (FAB)
m/z 475 ((M+H)$^+$).

Elementary analysis for $C_{28}H_{31}N_2O_5Cl_1 \cdot 0.6H_2O$
Calculated: C, 64.45; H, 6.22; N, 5.37; Cl, 6.79
Found: C, 64.75; H, 6.24; N, 5.37; Cl, 6.71

Compound 176

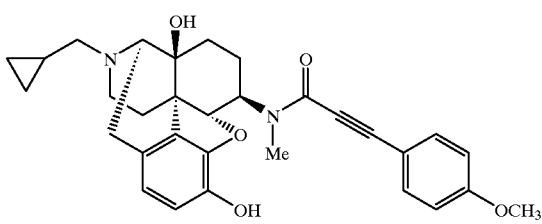

m.p. 200.0° C. (decomp.)
NMR (400 MHz, DMSO-$d_6$)
δ 0.33–0.48 (1H, m), 0.48–0.57 (1H, m), 0.57–0.63 (1H, m), 0.63–0.77 (1H, m), 0.98–1.14 (1H, m), 1.20–1.34 (0.25H, m), 1.34–1.52 (2.75H, m), 1.70–1.87 (1H, m), 2.03–2.30 (1H, m), 2.34–2.62 (2H, m), 2.80–2.93 (1H, m), 2.96 (2.25H, s), 2.99–3.18 (2H, m), 3.25–3.43 (2H, m), 3.29 (0.75H, s), 3.80 (2.25H, s), 3.82 (0.75H, s), 3.84–3.92 (1H, m), 4.03–4.13 (0.25H, m), 4.13–4.25 (0.75H, m), 4.90 (0.75H, d, J=7.8 Hz), 4.96 (0.25H, d, J=8.3 Hz), 6.46 (0.25H, br s), 6.59 (0.75H, br s), 6.65 (1H, d, J=8.3 Hz), 6.70 (1H, d, J=7.8 Hz), 6.91 (1.5H, d, J=8.8 Hz), 7.03 (0.5H, d, J=8.8 Hz), 7.11 (1.5H, d, J=8.8 Hz), 7.59 (0.5H, d, J=8.8 Hz), 8.85 (1H, br s), 9.33 (1H, s).

IR (KBr)
ν 3420, 2210, 1605, 1512, 1410, 1379, 1321, 1296, 1253, 1176, 1127, 1033, 837 cm$^{-1}$.

Mass (FAB)
m/z 515 ((M+H)$^+$).

Elementary analysis for $C_{31}H_{35}N_2O_5Cl_1 \cdot 0.3H_2O$
Calculated: C, 66.91; H, 6.45; N, 5.03; Cl, 6.37
Found: C, 66.97; H, 6.49; N, 5.11; Cl, 6.16

Compound 177

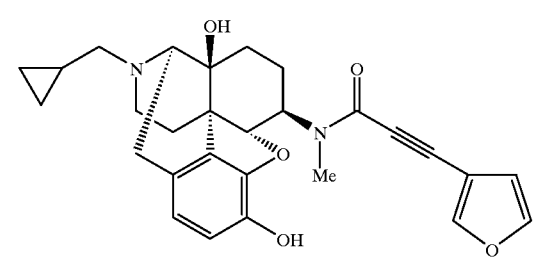

m.p. 161.0–165.0° C. (decomp., ethyl acetate)
NMR (400 MHz, CD$_3$OD)
δ 0.48–0.53 (2H, m), 0.73 (1H, m), 0.81 (1H, m), 1.10 (1H, m), 1.44–1.72 (3H, m), 1.79 (1H, m), 2.29 (1H, br q, J=l11.2 Hz), 2.57–2.71 (2H, m), 2.88 (1H, dd, J=13.7, 7.3 Hz), 3.02 (2.2H, s), 3.07–3.21 (2H, m), 3.34 (0,8H, s), 3.91 (1H, d, J=5.9 Hz), 4.29 (1H, m), 4.37 (1H, s), 4.79 (0.73H, d, J=8.3 Hz), 4.96 (0.27H, d, J=8.3 Hz), 6.35 (1H, d, J=1.0 Hz), 6.65 (1H, d, J=8.3 Hz), 6.75 (1H, d, J=8.3 Hz), 7.51 (0.73H, t, J=2.0 Hz), 7.61 (0.27H, t, J=2.0 Hz), 7.68 (0.73H, br s), 8.01 (0.27H, br s).

IR (KBr)
ν 3390, 2222, 1611, 1323, 1129, 1035, 872 cm$^{-1}$.

Mass (EI)
m/z 474 (M$^+$).

Elementary analysis for $C_{30}H_{33}N_2O_8 \cdot 2.5H_2O$
Calculated: C, 60.60; H, 6.44; N, 4.71.
Found: C, 60.72; H, 6.11; N, 4.63.

Compound 178

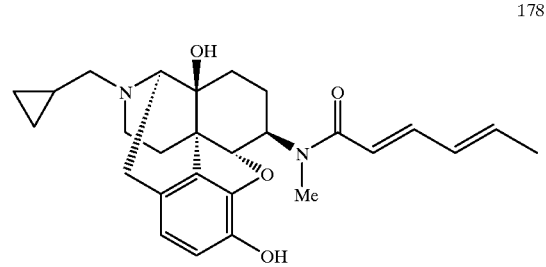

m.p. 160.0–162.0° C.
NMR (400 MHz, DMSO-$d_6$)
δ 0.12–0.31 (2H, m), 0.42–0.61 (2H, m), 0.82–0.98 (1H, m), 1.12–1.27 (0.4H, m), 1.27–1.45 (2.6H, m), 1.49–1.63 (1H, m), 1.77 (1.8H, d, J=5.4 Hz), 1.81 (1.2H, d, J=6.8 Hz), 1.98–2.20 (2H, m), 2.20–2.38 (1H, m), 2.40–2.58 (1H, m), 2.40–4.60 (2H, br s), 2.58–2.79

(3H, m), 2.83 (1.8H, s), 3.02 (1.2H, s), 3.03–3.17 (1H, m), 3.17–3.32 (1H, m), 3.48–3.62 (1.6H, m), 4.02 (1H, s),4.08–4.21 (0.4H, m), 4.62 (0.6H, d, J=7.8 Hz), 4.73 (0.4H, d, J=8.3 Hz), 5.95–6.19 (1H, m), 6.04 (0.6H, d, J=16.1 Hz), 6.13 (0.6H, d, J=14.6 Hz), 6.24–6.36 (0.4H, m), 6.45 (0.4H, d, J=14.6 Hz), 6.56 (0.4H, d, J=8.3 Hz), 6.61 (0.4H, d, J=7.8 Hz), 6.61 (0.6H, d, J=8.3 Hz), 6.73 (0.6H, d, J=8.3 Hz), 6.90 (0.6H, dd, J=15.1, 9.8 Hz), 7.03 (0.4H, dd, J=14.7, 10.8 Hz), 8.70–9.60 (1H, br s).

IR (KBr)

ν 3401, 1651, 1620, 1580, 1504, 1408, 1311, 1125, 1002, 922, 859 cm$^{-1}$.

Mass (FAB)

m/z 451 ((M+H)$^+$).

Elementary analysis for $C_{29}H_{37}N_2O_7 \cdot 0.7H_2O$

Calculated: C, 64.72; H, 7.19; N, 5.20

Found: C, 64.72; H, 7.23; M, 5.28

Compound 179

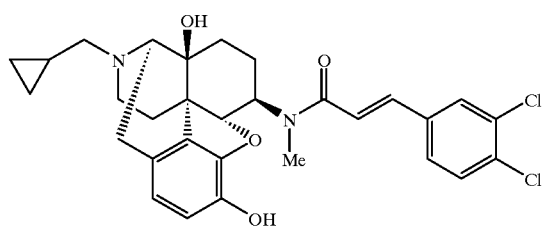

m.p . 201.0–210.0° C. (decomp.)

NMR (400 MHz, DMSO-d$_6$)

δ 0.33–0.47 (1H, m), 0.47–0.57 (1H, m), 0.57–0.64 (1H, m), 0.64–0.76 (1H, m), 1.00–1.14 (1H, m), 1.21–1.33 (0.3H, m), 1.33–1.59 (2.7H, m), 1.68–1.80 (1H, m), 2.04–2.27 (1H, m), 2.37–2.64 (2H, m), 2.80–2.93 (1H, m), 2.95 (2.1H, s), 3.00–3.14 (2H, m), 3.21 (0.9H, s), 3.26–3.45 (2H, m), 3.60–3.74 (0.7H, m), 3.80–3.92 (1H, m), 4.15–4.29 (0.3H, m), 4.86 (0.7H, d, J=7.8 Hz), 4.95 (0.3H, d, J=8.3 Hz), 6.43 (0.3H, br s), 6.54 (0.7H, br s), 6.65 (0.3H, d, J=8.3 Hz), 6.68 (0.7H, d, J=15.6 Hz), 6.72 (0.7H, d, J=7.8 Hz), 6.72 (0.3H, d, J=8.3 Hz), 6.88 (0.7H, d, J=7.8 Hz), 7.28 (0.7H, d, J=15.6 Hz), 7.30 (0.3H, d, J=15.1 Hz), 7.42 (0.3H, d, J=15.1 Hz), 7.48 (0.7H, dd, J=8.3, 1.5 Hz), 7.65 (0.7H, d, J=8.3 Hz), 7.67 (0.3H, d, J=8.3 Hz), 7.71 (0.7H, d, J=1.5 Hz). 7.73 (0.3H, dd, J=8.3, 1.5 Hz), 8.10 (0.3H, d, J=1.5 Hz), 8.85 (1H, br s), 9.31 (0.3H, s), 9.56 (0.7H, s).

IR (KBr)

ν 3425, 1649, 1475, 1460, 1323, 1127, 1033, 982, 926, 859, 814 cm$^-$.

Mass (FAB)

m/z 555 ((M+H)$^+$).

Elementary analysis for $C_{30}H_{33}N_2O_4Cl_3 \cdot 0.3H_2O$

Calculated: C, 60.32; H, 5.67; N, 4.69; Cl, 17.80

Found: C, 60.40; H, 5.82; N, 4.73; Cl, 17.72

Compound 180

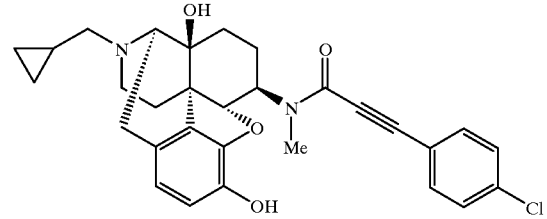

m.p. 201.0–211.0° C. (decomp.)

NMR (400 MHz, DMSO-d$_6$)

δ 0.34–0.47 (1H, m), 0.47–0.57 (1H, m), 0.57–0.64 (1H, m), 0.64–0.75 (1H, m), 1.00–1.16 (1H, m), 1.24–1.36 (0.2H, m), 1.36–1.53 (2.8H, m), 1.70–1.87 (1H, m), 2.08–2.31 (1H, m), 2.35–2.67 (2H, m), 2.80–2.94 (1H, m), 2.98 (2.4H, s), 3.01–3.16 (2H, m), 3.24–3.43 (2H, m), 3.31 (0.6H, s), 3.87 (1H, br d, J=3.4 Hz), 4.11 (1H, m), 4.91 (0.8H, d, J=8.3 Hz), 4.97 (0.2H, d, J=8.3 Hz), 6.50 (0.2H, br s), 6.60 (0.8H, d, J=8.3 Hz), 6.62 (0.8H, br s), 6.65 (0.2H, d, J=8.3 Hz), 6.67 (0.8H, d, J=8.3 Hz), 6.72 (0.2H, d, J=8.3 Hz), 7.21 (1.6H, d, J=8.3 Hz), 7.45 (1.6H, d, J=8.3 Hz), 7.56 (0.4H, d, J=8.3 Hz), 7.69 (0.4H, d, J=8.3 Hz), 8.86 (1H, br s), 9.33 (0.2H, s), 9.35 (0.8H, s).

IR (KBr)

ν 3420, 2220, 1620, 1491, 1460, 1319, 1127, 1091, 1035 cm$^{-1}$.

Mass (FAB)

m/z 519 ((M+H)$^+$).

Elementary analysis for $C_{30}H_{32}N_2O_4Cl_2 \cdot 0.3H_2O$

Calculated: C, 64.24; H, 5.86; N, 4.99; Cl, 12.64

Found: C, 66.21; H, 5.99; N, 4.97; Cl, 12.61

Compound 181

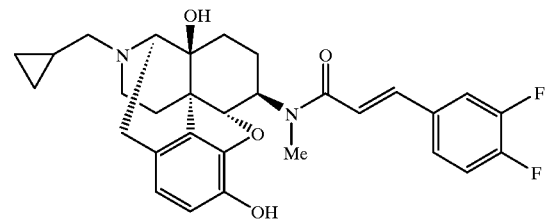

m.p. 161.0–167.0° C. (decomp.)

NMR (400 MHz, DMSO-d$_6$)

δ 0.15–0.33 (2H, m), 0.44–0.63 (2H, m), 0.82–1.02 (1H, m), 1.19–1.51 (3H, m), 1.53–1.67 (1H, m), 2.00–2.22 (2H, m), 2.22–2.39 (1H, m), 2.44–4.57 (3H, br s), 2.49–2.60 (1H, m), 2.60–2.85 (3H, m), 2.89 (2.1H, s), 3.03–3.14 (1H, m), 3.15 (0.9H, s), 3.57–3.74 (1.7H, m), 4.06 (1H, s), 4.11–4.27 (0.3H, m), 4.69 (0.7H, d, J=8.3 Hz), 4.80 (0.3H, d, J=8.3 Hz), 6.58 (0.3H, d, J=8.3 Hz), 6.62 (0.3H, d, J=8.3 Hz), 6.64 (0.7H, d, J=8.3 Hz), 6.64 (0.7H, d, J=15.6 Hz), 6.74 (0.7H, d, J=8.3 Hz), 7.23 (0.3H, d, J=15.6 Hz), 7.27 (0.7H, d, J=15.6 Hz), 7.32–7.63 (3H, m), 7.90–8.00 (0.3H, m), 8.75–9.27 (0.3H, br s), 9.27–9.65 (0.7H, br s).

IR (KBr)

ν 3420, 1649, 1605, 1518, 1410, 1296, 1116, 1069, 1035, 982, 861 cm$^{-1}$.

Mass (FAB)

m/z 523 ((M+H)+).

Elementary analysis for $C_{32}H_{35}N_2O_7F_2 \cdot 1.0H_2O$

Calculated: C, 62.43; H, 6.06; N, 4.55; F, 6.17

Found: C, 62.52; H, 6.12; N, 4.71; F, 6.02

Compound 182

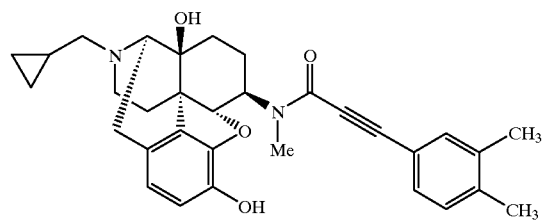

182 m.p. 194.0–204.0° C. (decomp.)

NMR (400 MHz, DMSO-$d_6$)

δ 0.35–0.47 (1H, m), 0.47–0.57 (1H, m), 0.57–0.64 (1H, m), 0.64–0.77 (1H, m), 1.00–1.15 (1H, m), 1.21–1.38 (0.6H, m), 1.38–1.52 (2.4H, m), 1.70–1.87 (1H, m), 2.05–2.28 (1H, m), 2.20 (2.1H, s), 2.23 (2.1H, s), 2.24 (0.9H, s), 2.27 (0.9H, s), 2.48–2.63 (2H, m), 2.80–2.93 (1H, m), 2.97 (2.1H, s), 2.99–3.18 (2H, m), 3.30 (0.9H, s), 3.21–3.43 (2H, m), 3.81–3.93 (1H, m), 4.02–4.13 (0.3H, m), 4.14–4.28 (0.7H, m), 4.90 (0.7H, d, J=8.1 Hz), 4.96 (0.3H, d, J=8.4 Hz), 6.43 (0.3H, br s), 6.57 (0.7H, br s), 6.64 (0.7H, d, J=8.1 Hz), 6.65 (0.3H, d, J=8.4 Hz), 6.69 (0.7H, d, J=8.4 Hz), 6.72 (0.3H, d, J=8.1 Hz), 6.88 (0.7H, s), 6.95 (0.7H, d, J=8.1 Hz), 7.12 (0.7H, d, J=8.1 Hz), 7.24 (0.3H, d, J=7.7 Hz), 7.36 (0.3H, d, J=7.7 Hz), 7.42 (0.3H, s), 8.84 (1H, br s), 9.31 (0.3H, s), 9.32 (0.7H, s).

IR (KBr)

ν 3410, 2212, 1611, 1504, 1410, 1377, 1247, 1176, 1033, 932, 859 cm$^{-1}$.

Mass (FAB)

m/z 513 ((M+H)+).

Elementary analysis for $C_{32}H_{37}N_2O_4Cl_1 \cdot 0.5H_2O$

Calculated: C, 69.09; H, 6.85; N, 5.04; Cl, 6.37

Found: C, 69.19; H, 6.93; N, 5.09; Cl, 6.17

Examples 173–179

The procedure of Example 114 was repeated, except that 17-cyclopropylmethyl-4,5α-epoxy-3,14β-dihydroxy-6α-methylaminomorphinan 4 was used instead of 17-cyclopropylmethyl-4,5α-epoxy-3,14β-dihydroxy-6β-methylaminomorphinan 10 and 3-(4-methylphenyl) propiolic acid, 3-(3-methoxyphenyl)propiolic acid, 3-(3-methylphenyl)propiolic acid, 3-(2-furyl)propiolic acid, 3-(4-methoxyphenyl)propiolic acid, 3-(3-furyl)propiolic acid and 3-(4-chlorophenyl)propiolic acid were used instead of 3-(3-trifluoromethylphenyl)propiolic acid, thereby preparing 17-cyclopropylmethyl-3,14β-dihydroxy-4,5α-epoxy-6α-[N-methyl-3-(4-methylphenyl)propiolamido]morphinan hydrochloride 183 (yield: 30%), 17-cyclopropylmethyl-3,14β-dihydroxy-4,5α-epoxy-6α-[N-methyl-3-(3-methoxyphenyl)propiolamido]morphinan tartrate 184 (yield: 73%), 17-cyclopropylmethyl-3,14β-dihydroxy-4,5α-epoxy-6α-[N-methyl-3-(3-methylphenyl)propiolamido] morphinan hydrochloride 185 (yield: 31%), 17-cyclopropylmethyl-3,14β-dihydroxy-4,5α-epoxy-6α-[N-methyl-3-(2-furyl)propiolamido]morphinan tartrate 186 (yield: 43%), 17-cyclopropylmethyl-3,14β-dihydroxy-4,5α-epoxy-6α-[N-methyl-3-(4-methoxyphenyl)propiolamido] morphinan tartrate 187 (yield: 71%), 17-cyclopropylmethyl-3,14β-dihydroxy-4,5α-epoxy-6α-[N-methyl-(3-furyl) propiolamido]morphinan tartrate 188 (yield: 80%) and 17-cyclopropylmethyl-3,14β-dihydroxy-4,5α-epoxy-6α-[N-methyl-3-(4-chlorophenyl)propiolamido]morphinan hydrochloride 189 (yield; 80%).

Compound 183

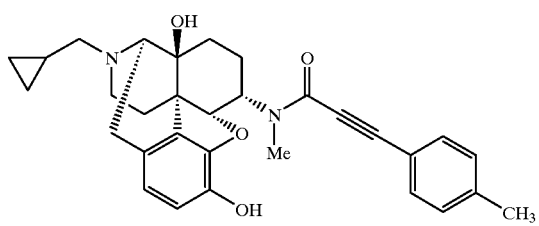

183 m.p. 243.0° C. (decomp.)

NMR (400 MHz, DMSO-$d_6$)

δ 0.28–0.44 (1H, m), 0.44–0.54 (1H, m), 0.54–0.65 (1H, m), 0.65–0.75 (1H, m), 0.98–1.13 (1H, m), 1.13–1.37 (1H, m), 1.40–1.75 (3H, m), 1.88–2.11 (1H, m), 2.36 (1.5H, s), 2.38 (1.5H, s), 2.40–2.57 (1H, m), 2.60–2.79 (1H, m), 2.85–3.19 (3H, m), 2.91 (1.5H, s), 3.19–3.47 (2H, m), 3.23 (1.5H, s), 3.89–4.02 (1H, m), 4.70 (0.5H, d, J=3.4 Hz), 4.80 (0.5H, d, J=3.4 Hz), 4.91 (0.5H, ddd, J=14.2, 3.4, 3.4 Hz), 5.08 (0.5H, ddd, J=13.7, 3.4, 3.4 Hz), 6.35 (0.5H, br s), 6.46 (0.5H, br s), 6.60 (0.5H, d, J=7.8 Hz), 6.61 (0.5H, d, J=8.3 Hz), 6.74 (0.5H, d, J=7.8 Hz), 6.75 (0.5H, d, J=7.8 Hz), 7.30 (1H, d, J=8.3 Hz), 7.33 (1H, d, J=8.3 Hz), 7.55 (1H, d, J=7.8 Hz), 7.61 (1H, d, J=7.8 Hz), 8.87 (0.5H, br s), 8.94 (0.5H, br s), 9.39 (1H, s).

IR (KBr)

ν 3420, 2214, 1603, 1510, 1460, 1406, 1319, 1120, 1036, 820 cm$^{-1}$.

Mass (FAB)

m/z 499 ((M+H)+).

Elementary analysis for $C_{31}H_{35}N_2O_4Cl_1 \cdot 1.1H_2O$

Calculated: C, 67.10; H, 6.78; N, 5.05; Cl, 6.39

Found: C, 67.20; H, 6.72; N, 5.32; Cl, 6.34

Compound 184

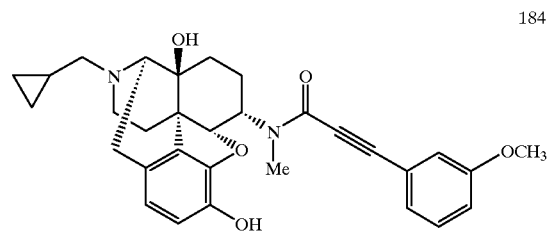

184 m.p. 159.0–162.0° C. (decomp., ethyl acetate)

NMR (400 MHz, DMSO-$d_6$)

δ 0.15–0.30 (2H, m), 0.44–0.60 (2H, m), 0.90 (1H, m), 1.32 (1H, m), 1.40 (2H, m), 1.61 (1H, m), 2.02–2.22 (2H, m), 2.31 (1H, m), 2.50 (1H, m), 2.58–2.81 (3H, m), 2.80–3.90 (3H, br), 2.88 (2.25H, s), 3.06 (0.75H, m), 3.10 (0.25H, m), 3.25 (1H, m), 3.26 (0.75H, s), 3.76 (2.25H, s), 3.80 (0.75H, s), 4.03 (1H, s), 4.08 (0.25H, m), 4.17 (0.75H, m), 4.71 (0.75H, d, J=7.8 Hz), 4.81 (0.25H, d, J=8.3 Hz), 6.51 (1H, d, J=8.3 Hz), 6.57 (1H, d, J=8.3 Hz), 6.62 (0.25H, d, J=7.8 Hz), 6.78 (1H, m), 7.02 (0.75H, dm, J=8.3 Hz), 7.11 (0.25H, dm, J=8.3 Hz), 7.21 (0.75H, d, J=7.8 Hz), 7.26 (0.75H, t, J=7.8 Hz), 7.39 (0.25H, t, J=7.8 Hz), 9.14 (1H, br s).

IR (KBr)

ν 3446, 2220, 1603, 1460, 1402, 1290, 1120, 1038, 795 cm$^{-1}$.

Mass (FAB)

m/z 515 (M+H)+.

Elementary analysis for $C_{33}H_{37}N_2O_8 \cdot 0.8H_2O$

Calculated: C, 65.61; H, 6.44; N, 4.64.

Found: C, 65.64; H, 6.39; N, 4.62.

Compound 185

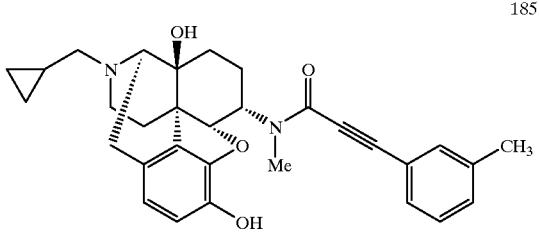

m.p. 182.0–183.0° C.

NMR (400 MHz, DMSO-d$_6$)

δ 0.33–0.47 (1H, m), 0.47–0.56 (1H, m), 0.56–0.64 (1H, m), 0.64–0.76 (1H, m), 1.00–1.15 (1H, m), 1.21–1.36 (0.6H, m), 1.36–1.55 (2.4H, m), 1.70–1.87 (1H, m), 2.05–2.28 (1H, m), 2.29 (2.4H, s), 2.34 (0.6H, s), 2.48–2.63 (2H, m), 2.78–2.93 (1H, m), 2.98 (2.4H, s), 2.99–3.18 (2H, m), 3.30 (0.6H, s), 3.21–3.43 (2H, m), 3.80–3.93 (1H, m), 4.02–4.14 (0.2H, m), 4.14–4.26 (0.8H, m), 4.91 (0.8H, d, J=7.8 Hz), 4.96 (0.2H, d, J=8.3 Hz), 6.45 (0.2H, br s), 6.58 (0.8H, br s), 6.63 (0.8H, d, J=8.3 Hz), 6.65 (0.2H, d, J=8.3 Hz), 6.69 (0.8H, d, J=8.3 Hz), 6.72 (0.2H, d, J=8.3 Hz), 6.92 (0.8H, s), 7.05 (0.8H, d, J=6.8 Hz), 7.20–7.32 (1.6H, m), 7.32–7.40 (0.4H, m), 7.40–7.51 (0.4H, m), 8.85 (1H, br s), 9.33 (0.2H, s), 9.36 (0.8H, s).

IR (KBr)

ν 3410, 2218, 1613, 1508, 1460, 1410, 1377, 1321, 1125, 1033, 930, 789, 690 cm$^{-1}$.

Mass (FAB)

m/z 499 ((M+H)$^+$).

Elementary analysis for $C_{31}H_{35}N_2O_4Cl_1 \cdot 0.4H_2O$

Calculated: C, 68.66; H, 6.65; N, 5.17; Cl, 6.54

Found: C, 68.86; H, 6.75; N, 5.22; Cl, 6.48

Compound 186

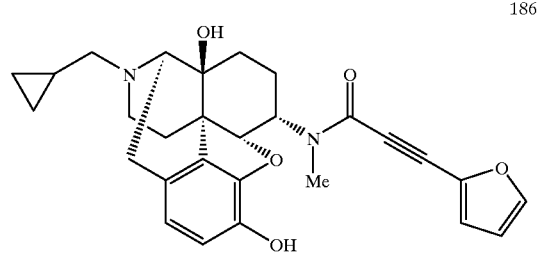

m.p. 141.0–155.0° C.

NMR (400 MHz, DMSO-d$_6$)

δ 0.10–0.28 (2H, m), 0.42–0.62 (2H, m), 0.82–0.99 (1H, m), 1.07–1.34 (1H, m), 1.38–1.60 (3H, m), 1.67–1.87 (1H, m), 2.14–2.36 (2H, m), 2.02–4.00 (3H, br s), 2.40–2.62 (2H, m), 2.62–2.82 (2H, m), 2.91 (1.2H, s), 2.98–3.12 (1H, m), 3.19 (1.8H, s), 3.21–3.37 (1H, m), 4.07 (1H, s), 4.61 (0.6H, d, J=3.9 Hz), 4.65 (0.4H, d, J=3.4 Hz), 4.82 (0.6H, ddd, J=14.1, 3.9, 3.4 Hz), 4.88 (0.4H,.ddd, J=13.7, 3.9, 3.4 Hz), 6.53 (1H, d, J=8.3 Hz), 6.63 (0.6H, d, J=8.3 Hz), 6.64 (0.4H, d, J=7.8 Hz), 6.69 (0.6H, dd, J=3.4, 2.0 Hz), 6.71 (0.4H, dd, J=3.4, 2.0 Hz), 7.21 (0.4H, d, J=3.4 Hz), 7.23 (0.6H, d, J=3.4 Hz), 7.93 (0.6H, d, J=1.5 Hz), 7.95 (0.4H, d, J=2.0 Hz), 8.32 (1H, br s).

IR (KBr)

ν 3420, 2208, 1611, 1508, 1460, 1402, 1311, 1120, 1071, 1036, 683 cm$^{-1}$.

Mass (FAB)

m/z 475 ((M+H)$^+$).

Elementary analysis for $C_{30}H_{33}N_2O_8 \cdot 0.2AcOEt \cdot 0.6H_2O$

Calculated: C, 63.79; H, 6.16; N, 4.89

Found: C, 63.74; H, 6.10; N, 4.87

Compound 187

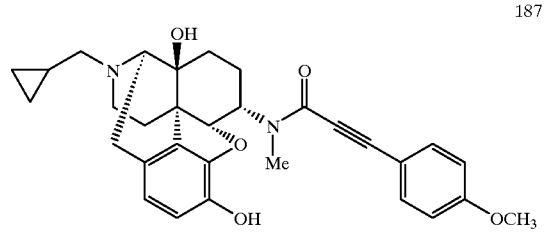

m.p. 167.0–174.0° C.

NMR (400 MHz, DMSO-d$_6$)

δ 0.12–0.28 (2H, m), 0.43–0.62 (2H, m), 0.82–1.00 (1H, m), 1.08–1.33 (1H, m), 1.38–1.60 (3H, m), 1.69–1.89 (1H, m), 2.10–4.20 (3H, br s), 2.13–2.37 (2H, m), 2.42–2.64 (2H, m), 2.64–2.83 (2H, m), 2.91 (1.8H, s), 3.00–3.13 (1H, m), 3.22 (1.2H, s), 3.25–3.38 (1H, m), 3.82 (1.2H, s), 3.83 (1.8H, s), 4.09 (1H, s), 4.61 (0.4H, d, J=3.4 Hz), 4.68 (0.6H, d, J=2.9 Hz), 4.84 (0.4H, ddd, J=14.2, 3.9, 3.4 Hz), 5.02 (0.6H, ddd, J=13.2, 3.9, 3.4 Hz), 6.53 (1H, d, J=7.81 Hz), 6.64 (0.4H, d, J=7.8 Hz), 6.65 (0.6H, d, J=8.3 Hz), 7.03 (1H, d, J=8.8 Hz), 7.06 (1H, d, J=8.8 Hz), 7.61 (1H, d, J=8.8 Hz), 7.66 (1H, d, J=8.8 Hz), 8.66–9.58 (1H, br s).

IR (KBr)

ν 3420, 2210, 1605, 1510, 1460, 1406, 1375, 1296, 1255, 1174, 1112, 1069, 1033, 839 cm$^{-1}$.

Mass (FAB)

m/z 515 ((M+H)$^+$).

Elementary analysis for $C_{33}H_{37}N_2O_8 \cdot 1.1H_2O$

Calculated: C, 66.01; H, 6.41; N, 4.67

Found: C, 65.93; H, 6.43; N, 4.60

Compound 188

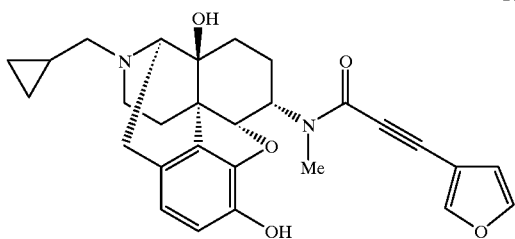

m.p. 139.0–143.0° C. (decomp., ethyl acetate)
NMR (400 MHz, CD$_3$OD)
δ 0.46–0.47 (2H, m), 0.73 (1H, m), 0.81 (1H, m), 1.09 (1H, m), 1.37–1.79 (4H, m), 1.97 (1H, m), 2.61 (1H, ddd, J=13.7, 13.7, 4.9 Hz), 2.86 (1H, dt, J=14.7, 3.4 Hz), 2.97 (1H, m), 3.03 (1.5H, s), 3.05–3.25 (4H, m), 3.32 (1.5H, s), 3.96 (1H, br t, J=7.3 Hz), 4.37 (1H, s), 4.83 (1H, m), 5.07 (0.5H, dt, J=14.2, 3.4 Hz), 5.24 (0.5H, dt, J=13.2, 3.4 Hz), 6.40 (0.5H, d, J=2.0 Hz), 6.67 (0.5H, d, J=8.3 Hz), 6.67 (0.5H, d, J=7.8 Hz), 6.71 (0.5H, d, J=1.5 Hz), 6.75 (0.5H, d, J=7.8 Hz), 6.76 (0.5H, d, J=8.3 Hz), 7.61 (0.5H, d, J=1.5 Hz), 7.62 (0.5H, d, J=2.0 Hz), 7.63 (0.5H, d, J=2.0 Hz), 7.63 (0.5H, d, J=1.5 Hz), 8.02 (0.5H, d, J=1.5 Hz), 8.08 (0.5H, br s).
IR (KBr)
ν 3380, 2222, 1607, 1510, 1404, 1120, 1069, 1036, 804 cm$^{-1}$.
Mass (EI)
m/z 474 (M$^+$).
Elementary analysis for C$_{30}$H$_{33}$N$_2$O$_8$•2.2H$_2$O
Calculated: C, 61.15; H, 6.40; N, 4.75.
Found: C, 61.06; H, 6.11; N, 4.59.

Compound 189

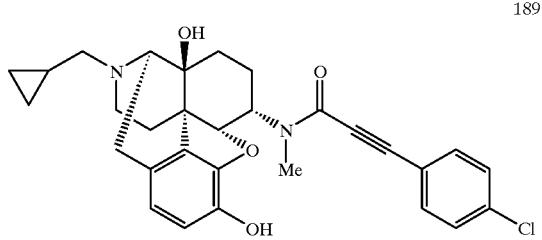

m.p. 195.0–205° C.
NMR (400 MHz, DMSO-d$_6$)
0.31–0.45 (1H, m), 0.45–0.52 (0.5H, m), 0.52–0.58 (0.5H, m), 0.58–0.66 (1H, m), 0.66–0.78 (1H, m), 1.00–1.37 (2H, m), 1.13–1.37 (1H, m), 1.42–1.74 (3H, m), 1.89–2.10 (1H, m), 2.39–2.58 (1H, m), 2.61–2.79 (1H, m), 2.83–3.19 (3H, m), 2.91 (1.5H, s), 3.19–3.45 (2H, m), 3.23 (1.5H, s),3.95 (0.5H, m), 3.99 (0.5H, m), 4.70 (0.5H, d, J=3.4 Hz), 4.80 (0.5H, d, J=3.4 Hz), 4.91 (0.5H, ddd, J=13.7, 3.4, 3.4 Hz), 5.11 (0.5H, ddd, J=13.7, 3.4, 3.4 Hz), 6.37 (0.5H, br s), 6.50 (0.5H, br s), 6.61 (1H, d, J=8.3 Hz), 7.56 (1H, d, J=8.3 Hz), 7.65 (1H, d, J=8.3 Hz), 7.70 (1H, d, J=8.3 Hz), 7.79 (1H, d, J=8.3 Hz), 8.88 (0.5H, br s), 9.12 (0.5H, br s), 9.39 (0.5H, s), 9.40 (0.5H, s).
IR (KBr)
ν 3420, 2218, 1611, 1491, 1460, 1402, 1321, 1172, 1120, 1089, 1035, 835 cm$^{-1}$.
Mass (FAB)
m/z 519 ((M+H)$^+$).
Elementary analysis for C$_{30}$H$_{32.1}$N$_2$O$_4$Cl$_{2.1}$•0.4H$_2$O
Calculated: C, 63.62; H, 5.86; N, 4.95; Cl, 13.15
Found: C, 63.58; H, 5.91; N, 4.96; Cl, 13.01

Example 180

The procedure of Example 118 was repeated, except that 3-tert-butyldimethylsilyloxy-17-cyclopropylmethyl-14β-hydroxy-4-methoxy-6α-(N-methyl-3,4-dichlorophenylacetamino)morphinan was used instead of 3-tert-butyldimethylsilyloxy-17-cyclopropylmethyl-4,5α-epoxy-14β-hydroxy-6α-(N-methyl-3,4-dichlorophenylmethanesulfonamido)morphinan 16, thereby preparing 17-cyclopropylmethyl-3,14β-dihydroxy-4-methoxy-6α-(N-methyl-3,4-dichlorophenylacetamido) morphinan tartrate 190 (yield: 80%).

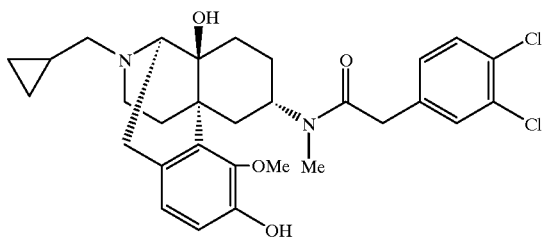

m.p. 190–197° C. (decomp.)
NMR (400 MHz, DMSO-d$_6$ +CD$_3$OD)
δ 0.33–0.73 (4H, m), 1.00–1.12 (1H, m), 1.43 (1H, brd, J=12.82 Hz), 1.50–1.63 (2H, m), 1.73–1.87 (2H, m), 2.08 (3H, s), 2.03–2.30 (2H, m), 2.42–2.53 (1H, m), 2.75–2.83 (1H, m), 2.95–3.08 (1H, m), 3.13–3.45 (6H, m), 3.57 (1H, d, J=16.2 Hz), 3.66 (3H, s), 3.65–3.75 (1H, m), 4.30–4.42 (1H, m), 5.68 (1H, s), 6.75 (1H, d, J=8.2 Hz), 6.86 (1H, d, J=8.2 Hz), 7.22 (1H, d, J=8.2, 1.5 Hz), 7.51–7.60 (2H, m), 7.60 (1H, d, J=1.5 Hz), 8.82 (1H, br), 9.50 (1H, s).
IR (KBr)
ν 3420, 3318, 1620, 1475, 1402, 1296, 1135, 1067, 687 cm$^{-1}$.
Mass (FAB)
m/z 559 ((M+H)$^+$).
Elementary analysis for C$_{30}$H$_{36}$N$_2$O$_4$Cl$_2$•HCl•0.55H$_2$O
Calculated: C, 59.47; H, 6.34; N, 4.62; Cl, 17.55
Found: C, 59.85; H, 6.30; N, 4.77; Cl, 17.16

Examples 181–184

The procedure of Example 4 was repeated, except that isopropylbenzylamine, isobutylbenzylamine, butylbenzylamine and pentylbenzylamine were used instead of benzylmethylamine, thereby preparing 17-cyclopropylmethyl-3,14β-dihydroxy-4,5α-epoxy-6β-(N-isopropylbenzylamino)morphinan dihydrochloride 191 (yield: 27%), 17-cyclopropylmethyl-3,14β-dihydroxy-4,5α-epoxy-6β-(N-isobutylbenzylamino)morphinan dihydrochloride 192 (yield: 60%), 17-cyclopropylmethyl-3,14β-dihydroxy-4,5α-epoxy-6β-(N-butylbenzylamino) morphinan dihydrochloride 193 (yield: 62%) and 17-cyclopropylmethyl-3,14β-dihydroxy-4,5α-epoxy-6β-(N-pentylbenzylamino)morphinan dihydrochloride 194 (yield: 92%).

Compound 191

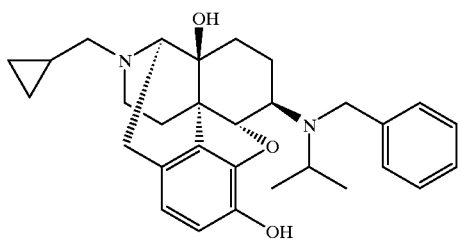

m.p. >165° C. (decomp.)
NMR (400 MHz, DMSO-d$_6$)
δ 0.41 (1H, m), 0.52 (1H, m), 0.59 (1H, m), 0.68 (1H, m), 1.07 (1H, m), 1.25 (2.1H, d, J=6.3 Hz), 1.34 (0.9H, d, J=6.3 Hz), 1.40 (3H, d, J=6.3 Hz), 1.40–1.52 (2H, m), 1.74 (1H, m), 1.88 (1H, m), 2.18 (1H, m), 2.45 (1H, m), 2.60 (1H, m), 2.86 (1H, m), 2.96–3.08 (2H, m), 3.25–3.48 (3H, m), 3.73 (1H, m), 3.92 (1H, m), 4.47 (0.7H, m), 4.61 (0.3H, m), 4.85 (0.7H, m), 4.91 (0.3H, m), 5.36 (1H, d, J=7.8 Hz), 6.68 (0.3H, d, J=8.3 Hz), 6.70 (0.7H, d, J=8.3 Hz), 6.81 (0.3H, d, J=8.3 Hz), 6.82 (1H, s, OH), 6.85 (0.7H, d, J=8.3 Hz), 7.40–7.48 (3H, m), 7.63–7.74 (2H, m), 8.92 (1H, br s, NH+), 9.63 (0.7H, br s, NH+), 9.63 (0.3H, br s, OH), 9.67 (0.7H, s, OH), 9.90 (0.3H, br s, NH+).
IR (KBr)
ν 3388, 1729, 1638, 1620, 1506, 1460, 1379, 1325, 1247, 1178, 1123, 1035, 922, 748, 700 cm$^{-1}$.
Mass (FAB)
m/z 475 ((M+H)$^+$).
Elementary analysis for C$_{30}$H$_{38}$N$_2$O$_3$•2HCl•0.6H$_2$O•0.3EtOAc
Calculated: C, 64.08; H, 7.51; Cl, 12.12; N, 4.79.
Found: C, 64.36; H, 7.77; Cl, 11.82; N, 4.85.

Compound 192

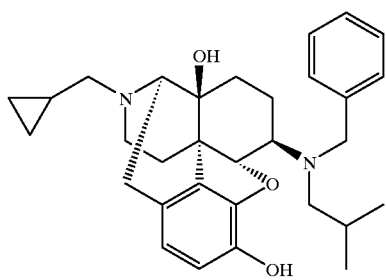

m.p. >190° C. (decomp.)
NMR (400 MHz, DMSO-d$_6$)
δ 0.42 (1H, m), 0.53 (2.1H, d, J=6.3 Hz), 0.55 (1H, m), 0.59 (1H, m), 0.68 (1H, m), 0.73 (0.9H, d, J=6.3 Hz), 0.88 (2.1H, d, J=6.5 Hz), 0.94 (0.9H, J=6.5 Hz), 1.08 (1H, m), 1.20–1.58 (2H, m), 1.80 (1H, m), 2.06–2.50 (3H, m), 2.66 (1H, m), 2.82–3.14 (4H, m), 3.30–3.60 (5H, m), 3.92 (1H, m), 4.45–4.75 (2H, m), 5.39 (0.7H, d, J=7.3 Hz), 5.48 (0.3H, d, J=7.3 Hz), 6.55–7.30 (1H, m, OH), 6.66 (0.3H, d, J=8.1 Hz), 6.72 (0.7H, d, J=8.1 Hz), 6.78 (0.3H, d, J=8.1 Hz), 6.81 (0.7H, d, J=8.1 Hz), 7.38–7.48 (3H, m), 7.72–7.92 (2H, m), 8.78 (0.3H, br s, NH+), 8.95 (0.7H, br s, NH+), 9.27 (0.3H, br s, OH), 9.55 (0.7H, br s, OH), 9.58 (0.3H, s, NH+), 9.93 (0.7H, br s, NH+).

IR (KBr)
ν 3378, 1721, 1638, 1626, 1504, 1462, 1377, 1325, 1274, 1176, 1125, 1035, 922 cm$^{-1}$.
Mass (FAB)
m/z 489 ((M+H)$^+$).
Elementary analysis for C$_{31}$H$_{40}$N$_2$O$_3$•2HCl•0.35EtOAc
Calculated: C, 65.69; H, 7.62; Cl, 11.97; N, 4.73.
Found: C, 65.96; H, 7.60; Cl, 11.72; N, 4.87.

Compound 193

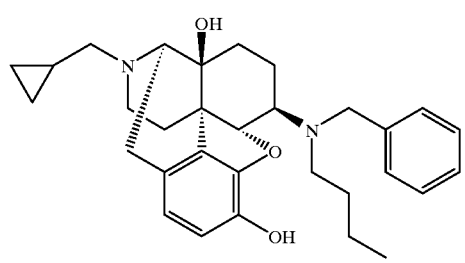

m.p. >180° C. (decomp.)
NMR (400 MHz, DMSO-d$_6$)
δ 0.41 (1H, m), 0.52 (1H, m), 0.60 (1H, m), 0.68 (1H, m), 0.78 (1.8H, t, J=7.3 Hz), 0.85 (1.2H, t, J=7.3 Hz), 1.07 (1H, m), 1.11–1.37 (3H, m), 1.60–1.77 (3H, m), 1.81 (1H, m), 2.14 (1H, m), 2.26 (1H, m), 2.45 (1H, m), 2.61 (1H, m), 2.88 (1H, m), 2.94–3.18 (3H, m), 3.20–3.45 (4H, m), 3.91 (1H, m), 4.36 (0.4H, m), 4.46 (0.6H, m), 4.57 (0.4H, m), 4.69 (0.6H, m), 5.38 (0.4H, d, J=7.3 Hz), 5.43 (0.6H, d, J=7.8 Hz), 6.66 (0.6H, d, J=8.1 Hz), 6.69 (0.4H, d, J=8.1 Hz), 6.72 (0.4H, s, OH), 6.79 (0.6H, d, J=8.1 Hz), 6.82 (0.6H, s, OH), 6.83 (0.4H, d, J=8.1 Hz), 7.38–7.47 (3H, m), 7.62–7.80 (2H, m), 8.95 (1H, br s, NH+), 9.62 (0.6H, s, OH), 9.66 (0.4H, s, OH), 10.48 (0.6H, br s, NH+), 10.54 (0.4H, br s, NH+).
IR (KBr)
ν 3330, 1729, 1642, 1626, 1506, 1462, 1383, 1325, 1249, 1176, 1125, 1035, 996, 922, 861, 812, 748, 702 cm$^{-1}$.
Mass (EI)
m/z 488 (M+).
Elementary analysis for C$_{31}$H$_{40}$N$_2$O$_3$•2HCl•0.2H$_2$O•0.2EtOAc
Calculated: C, 65.52; H, 7.61; Cl, 12.17; N, 4.81.
Found: C, 65.52; H, 7.81; Cl, 12.11; N, 4.81.

Compound 194

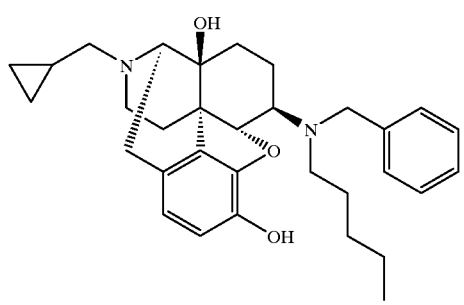

m.p. >185° C. (decomp.)
NMR (400 MHz, DMSO-d$_6$)
δ 0.41 (1H, m), 0.52 (1H, m), 0.59 (1H, m), 0.67 (1H, m), 0.78 (1.2H, t, J=7.1 Hz), 0.83 (1.8H, t, J=7.1 Hz), 1.05–1.85 (1OH, m), 2.14 (1H, m), 2.26 (1H, m), 2.45 (1H, m), 2.60 (1H, m), 2.82–3.46 (8H, m), 3.91 (1H, m), 4.37 (0.4H, m), 4.47 (0.6H, m), 4.58 (0.4H, m), 4.68 (0.6H, m), 5.37 (0.4H, d, J=7.3 Hz), 5.43 (0.6H, d, J=7.8 Hz), 6.66 (0.6H, d, J=8.3 Hz), 6.69 (0.4H, d, J=8.3 Hz), 6.72, 6.74 (1H, br s, OH), 6.78 (0.6H, d, J=8.3 Hz), 6.82 (0.4H, d, J=8.3 Hz), 7.38–7.48 (3H, m), 7.60–7.82 (2H, m), 8.95 (1H, br s, NH+), 9.60 (0.6H, s, OH), 9.65 (0.4H, s, OH), 10.46 (0.6H, br s, NH+), 10.54 (0.4H, br s, NH+).

IR (KBr)

ν 3350, 1649, 1638, 1626, 1508, 1460, 1365, 1323, 1270, 1251, 1125, 1033, 924, 748, 700 cm$^{-1}$.

Mass (FAB)

m/z 503 ((M+H)$^+$)

Elementary analysis for $C_{32}H_{42}N_2O_3 \cdot 2HCl$

Calculated: C, 66.77; H, 7.70; Cl, 12.32; N, 4.87.

Found: C, 66.91; H, 7.60; Cl, 12.17; N, 5.09.

Examples 185–188

The procedure of Example 6 was repeated, except that 17-cyclopropylmethyl-3,14β-dihydroxy-4,5α-epoxy-6β-(N-isopropylbenzylamino)morphinan dihydrochloride 191, 17-cyclopropylmethyl-3,14β-dihydroxy-4,5α-epoxy-6β-(N-isobutylbenzylamino)morphinan dihydrochloride 192, 17-cyclopropylmethyl-3,14β-dihydroxy-4,5α-epoxy-6β-(N-butylbenzylamino)morphinan dihydrochloride 193 and 17-cyclopropylmethyl-3,14β-dihydroxy-4,5α-epoxy-6β-(N-pentylbenzylamino)morphinan dihydrochloride 194 were used as the starting compound instead of 6β-(N-benzyl)methylamino-17-cyclopropylmethyl-4,5α-epoxy-3,14β-dihydroxymorphinan 8 hydrochloride, thereby preparing 17-cyclopropylmethyl-3,14β-dihydroxy-4,5α-epoxy-6β-isopropylaminomorphinan 195 (yield: 100%), 17-cyclopropylmethyl-3,14β-dihydroxy-4,5α-epoxy-6β-isobutylaminomorphinan 196 (yield: 100%), 17-cyclopropylmethyl-3,14β-dihydroxy-4,5α-epoxy-6β-butylaminomorphinan 197 (yield: 100%) and 17-cyclopropylmethyl-3,14β-dihydroxy-4,5α-epoxy-6β-pentylaminomorphinan 198 (yield: 100%).

Compound 195

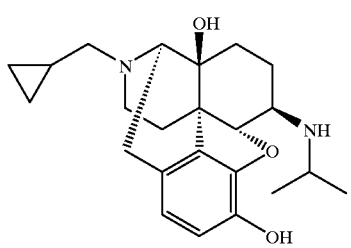

NMR (400 MHz, CDCl$_3$)

δ 0.12 (2H, m), 0.52 (2H, m), 0.83 (1H, m), 1.05 (3H, t, J=6.3 Hz) 1.13 (3H, d, J=6.3 Hz), 1.36 (1H, ddd, J=13.2, 13.2, 3.4 Hz), 1.43 (1H, br d, J=12.7 Hz), 1.59 (1H, ddd, J=13.2, 3.4, 3.0 Hz), 1.68 (1H, m), 1.78 (1H, m), 2.12 (1H, ddd, J=12.2, 12.2, 3.5 Hz), 2.20 (1H, ddd, J=12.2, 12.2, 4.4 Hz), 2.36 (2H, d, J=6.8 Hz), 2.40 (2H, br s, OH, NH), 2.52–2.64 (3H, m), 3.00 (1H, d, J=18.1 Hz), 3.03–3.09 (2H, m), 4.41 (1H, d, J=7.3 Hz), 5.05 (1H, br s, OH), 6.55 (1H, d, J=8.1 Hz), 6.69 (1H, d, J=8.1 Hz).

IR (neat)

ν 3288, 1636, 1609, 1506, 1458, 1388, 1334, 1151, 1120, 1036, 984, 752 cm$^{-1}$.

Mass (EI)

m/z 384 (M$^+$).

Compound 196

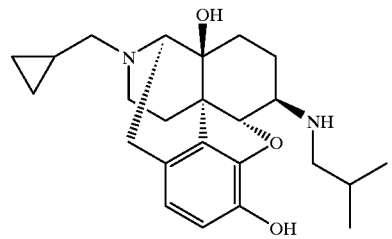

NMR (400 MHz, CDCl$_3$)

δ 0.12 (2H, m), 0.52 (2H, m), 0.83 (1H, m), 0.98 (3H, t, J=6.3 Hz), 1.01 (3H, d, J=6.3 Hz), 1.36–1.44 (2H, m), 1.57–1.70 (2H, m), 1.84 (1H, m), 1.94 (1H, m), 2.00 (2H, br s, OH, NH), 2.13 (1H, ddd, J=12.2, 12.2, 3.4 Hz), 2.21 (1H, ddd, J=12.2, 12.2, 4.4 Hz), 2.36 (2H, d, J=6.8 Hz), 2.47–2.68 (5H, m), 2.99 (1H, d, J=18.5 Hz), 3.05 (1H, d, J=5.9 Hz), 4.50 (1H, d, J=7.3 Hz), 5.15 (1H, br s, OH), 6.53 (1H, d, J=8.3 Hz), 6.63 (1H, d, J=8.3 Hz).

IR (neat)

ν 3318, 1607, 1456, 1394, 1334, 1257, 1149, 1120, 1036, 980, 915, 857, 750 cm$^{-1}$.

Mass (EI)

m/z 398 (M$^+$).

Compound 197

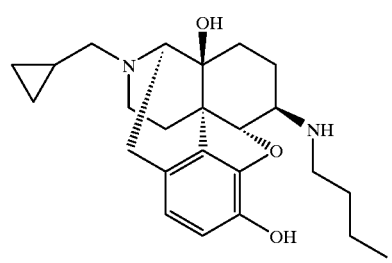

NMR (400 MHz, CDCl$_3$)

δ 0.12 (2H, m), 0.52 (2H, m), 0.83 (1H, m), 0.94 (3H, t, J=7.3 Hz), 1.34–1.48 (4H, m), 1.53–1.69 (4H, m), 1.94 (1H, m), 2.13 (1H, ddd, J=12.2, 12.2, 3.4 Hz), 2.21 (1H, ddd, J=12.2, 12.2, 4.9 Hz), 2.36 (2H, d, J=6.3 Hz), 2.40 (2H, br s, OH, NH), 2.53–2.77 (5H, m), 2.99 (1H, d, J=18.1 Hz), 3.04 (1H, d, J=5.6 Hz), 4.49 (1H, d, J=7.3 Hz), 5.12 (1H, br s, OH), 6.53 (1H, d, J=8.1 Hz), 6.63 (1H, d, J=8.1 Hz).

IR (neat)

ν 3302, 1636, 1609, 1506, 1458, 1396, 1334, 1257, 1218, 1149, 1114, 1036, 982, 915, 855, 803, 748 cm$^{-1}$.

Mass (EI)

m/z 398 (M$^+$).

Compound 198

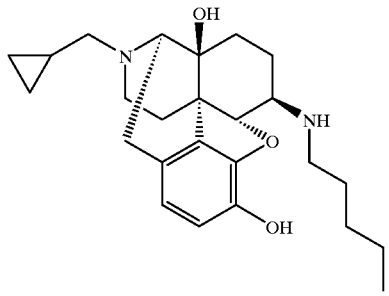

NMR (400 MHz, CDCl₃)

δ 0.12 (2H, m), 0.52 (2H, m), 0.83 (1H, m), 0.91 (3H, t, J=7.1 Hz), 1.28–1.45 (6H, m), 1.56–1.69 (4H, m), 1.94 (1H, m), 2.13 (1H, ddd, J=12.2, 12.2, 3.4 Hz), 2.21 (1H, ddd, J=12.2, 12.2, 4.4 Hz), 2.36 (2H, d, J=7.8 Hz), 2.52–2.73 (5H, m), 2.99 (1H, d, J=18.5 Hz), 3.04 (1H, d, J=5.4 Hz), 4.19 (1H, d, J=7.3 Hz), 5.12 (3H, br s, 2×OH+NH), 6.53 (1H, d, J=8.1 Hz), 6.63 (1H, d, J=8.1 Hz).

IR (neat)

ν 3386, 1638, 1607, 1504, 1460, 1398, 1334, 1255, 1149, 1116, 1036, 982, 915, 855, 801, 748 cm⁻¹.

Mass (EI)

m/z 412 (M⁺).

Examples 189–193

The procedure of Example 68 was repeated, except that 2,4,6-trichlorophenoxyacetyl chloride, 2,4,5-trichlorophenoxyacetyl chloride, 4-cyclohexylbutanoyl chloride, 6-phenylhexanoyl chloride and 5-phenylbutanoyl chloride were used instead of trans-3-(3-furyl)acryloyl chloride, thereby preparing 17-cyclopropylmethyl-3,14β-dihydroxy-4,5α-epoxy-6β-(N-methyl-2,4,6-trichlorophenoxyacetamido)morphinan hydrochloride 199 (yield: 79%), 17-cyclopropylmethyl-3,14β-dihydroxy-4,5α-epoxy-6β-(N-methyl-2,4,5-trichlorophenoxyacetamido) morphinan 0.5 tartrate 200 (yield: 58%), 17-cyclopropylmethyl-3,14β-dihydroxy-4,5α-epoxy-6β-(N-methyl-4-cyclohexylbutanoamido)morphinan hydrochloride 201 (yield: 79%), 17-cyclopropylmethyl-3,14β-dihydroxy-4,5α-epoxy-6β-(N-methyl-6-phenylhexanoamido)morphinan hydrochloride 202 (yield: 75%) and 17-cyclopropylmethyl-3,14β-dihydroxy-4,5α-epoxy-6β-(N-methyl-5-phenylpentanoamido)morphinan hydrochloride 203 (yield: 70%).

Compound 199

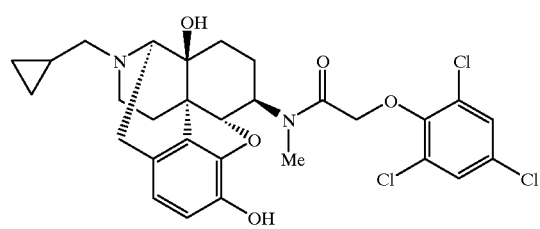

m.p. 207–210° C.

NMR (400 MHz, DMSO-d₆)

δ 0.41 (1H, m), 0.52 (1H, m), 0.60 (1H, m), 0.67 (1H, m), 1.06 (1H, m), 1.28 (0.3H, m), 1.35–1.50 (2.7H, m), 1.74 (1H, d, J=11.4 Hz), 2.20 (1H, m), 2.40–2.65 (2H, m), 2.80–3.00 (2H, m), 2.94 (2.1H, s), 3.03 (1H, m), 3.04 (0.9H, s), 3.25–3.45 (2H, m). 3.67 (1H, m), 3.86 (0.7H, m), 4.00 (0.3H, m), 4.26 (1H, d, J=11.7 Hz), 4.73 (1H, dd, J=13.6, 11.7 Hz), 4.86 (0.7H, d, J=7.7 Hz), 4.93 (0.3H, d, J=8.4 Hz), 6.65–6.75 (2H, m), 7.62 (1.4H, s), 7.71 (0.6H, s).

IR (KBr)

ν 3340, 1605, 1502, 1404, 1321, 1121, 1027, 870, 799 cm⁻¹.

Mass (FAB)

m/z 593 ((M+H)⁺).

Elementary analysis for C₂₉H₃₁N₂O₅Cl₃•HCl•0.1H₂O

Calculated: C, 55.10; H, 5.13; N, 4.43; Cl, 22.43

Found: C, 55.17; H, 5.35; N, 4.44; Cl, 22.21

Compound 200

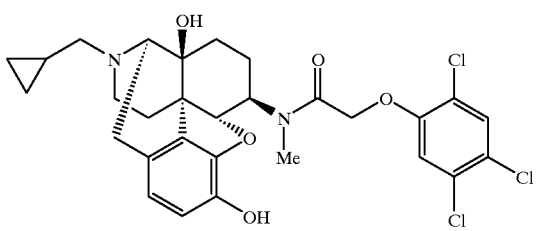

m.p. 180–182° C.

NMR (400 MHz, DMSO-d₆)

δ 0.16–0.28 (2H, m), 0.48–0.57 (2H, m), 0.85–0.97 (1H, m), 1.30–1.39 (1H, m), 1.40–1.52 (2H, m), 1.54–1.65 (1H, m), 2.03–2.20 (2H, m), 2.22–2.34 (1H, m), 2.40–2.56 (2H, m), 2.62–2.80 (2H, m), 3.06–3.16 (1H, m), 3.25–3.32 (1H, m), 3.32–3.43 (2H, m), 3.42–4.45 (2H, br), 4.05 (1H, s), 4.68 (0.8H, d, J=8.3 Hz), 4.75 (0.2H, d, J=8.3 Hz), 4.85 (0.2H, s), 4.89 (0.8H, s), 5.07 (0.5H, s), 5.11 (0.2H, s), 6.55 (0.2H, d, J=8.3 Hz), 6.59–6.63 (1H, m), 6.66 (0.8H, d, J=7.8 Hz), 7.22 (0.8H, s), 7.35 (0.2H, s), 7.77 (0.8H, s), 7.79 (0.2H, s), 9.39 (1H, br s).

IR (KBr)

ν 2932, 1719, 1702, 1595, 1249, 1129, 1081, 1035, 928, 859, 681 cm⁻¹.

Mass (FAB)

m/z 593 ((M+H)⁺).

Elementary analysis for C₂₉H₃₁N₂O₅Cl₃•0.5C₄H₆O₆•H₂O•0.1C₄H₁₀O•0.1C₄H₈O₂

Calculated: C, 54.31; H, 5.42; Cl, 15.12; N, 3.98.

Found: C, 54.67; H, 5.22; Cl, 14.80; N, 4.03.

Compound 201

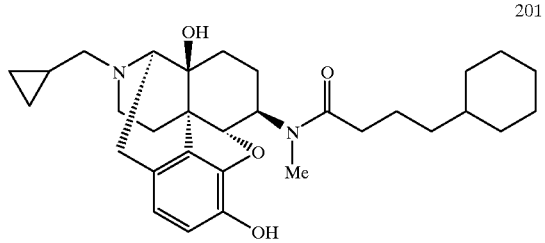

m.p. 180–183° C.
NMR (400 MHz, DMSO-$d_6$)
δ 0.36–0.46 (1H, m), 0.47–0.56 (1H, m), 0.56–0.64 (1H, m), 0.56–0.64 (1H, m), 0.64–0.73 (1H, m), 0.73–0.93 (2H, m), 0.93–1.26 (8H, m), 1.26–1.52 (5H, m), 1.53–1.78 (6H, m), 2.00–2.30 (3H, m), 2.40–2.58 (2H, m), 2.82 (2.1H, s), 2.83–2.93 (1H, m), 2.98 (0.9H, s), 3.00–3.08 (2H, m), 3.28–3.37 (2H, m), 3.40–3.49 (1H, m), 3.81–3.90 (1H, m), 4.77 (0.7H, d, J=7.8 Hz), 4.85 (0.3H, d, J=8.3 Hz), 6.37 (0.3H, s), 6.49 (0.7H, s), 6.63 (0.3H, d, J=8.3 Hz), 6.67 (0.3H, d, J=8.3 Hz), 6.69 (0.7H, d, J=8.3 Hz), 6.76 (0.7H, d, J=8.3 Hz), 8.84 (1H, s), 9.26 (0.3H, s), 9.44 (0.7H, s).
IR (KBr)
ν 2924, 2854, 1611, 1562, 1450, 1317, 1123, 1033, 859 cm$^{-1}$.
Mass (EI)
m/z 508 ((M)$^+$). (data for free base)
Elementary analysis for $C_{31}H_{44}N_2O_4 \cdot HCl \cdot 0.5H_2O$
Calculated: C, 67.19; H, 8.37; Cl, 6.40; N, 5.05.
Found: C, 67.14; H, 8.42; Cl, 6.44; N, 4.98.

Compound 202

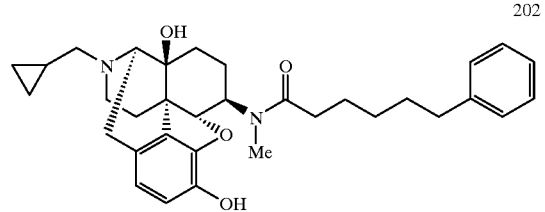

m.p. 227–229° C.
NMR (400 MHz, DMSO-$d_6$)
δ 0.37–0.46 (1H, m), 0.47–0.56 (1H, m), 0.56–0.64 (1H, m), 0.64–0.73 (1H, m), 1.02–1.12 (1H, m), 1.13–1.23 (2H, m), 1.24–1.61 (7H, m), 1.66–1.79 (1H, m), 2.00–2.32 (3H, m), 2.35–2.60 (5H, m), 2.82 (2.01H, s), 2.83–2.91 (1H, m), 2.98 (0.99H, s), 2.99–3.12 (2H, m), 3.26–3.37 (2H, m), 3.81–3.89 (1H, m), 4.78 (0.67H, d, J=8.3 Hz), 4.85 (0.33H, d, J=8.3 Hz), 6.39 (0.33H, s), 6.51 (0.67H, s), 6.62 (0.33H, d, J=8.3 Hz), 6.64 (0.67H, d, J=7.8 Hz), 6.70 (0.33H, d, J=8.3 Hz), 6.74 (0.67H, d, J=7.8 Hz), 7.23–7.30 (2H, m), 8.35 (1H, br, s), 9.27 (0.33H, s), 9.44 (0.67H, s).
IR (KBr)
ν 2934, 2858, 1702, 1613, 1499, 1450, 1317, 1125, 1033, 857, 748, 700 cm$^{-1}$.
Mass (EI)
m/z 530 ((M)$^+$). (data for free base)
Elementary analysis for $C_{33}H_{42}N_2O_4 \cdot HCl \cdot 0.2H_2O$
Calculated: C, 69.44; H, 7.67; Cl, 6.21; N, 4.91.
Found: C, 69.69; H, 7.73; Cl, 5.94; N, 4.70.

Compound 203

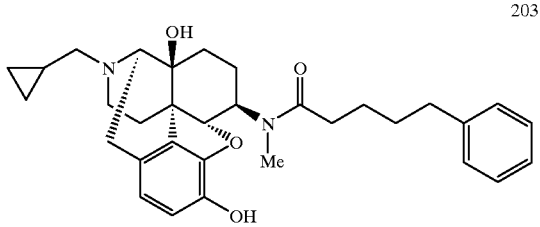

m.p. 251–253° C.
NMR (400 MHz, DMSO-$d_6$)
δ 0.37–0.47 (1H, m), 0.47–0.55 (1H, m), 0.55–0.64 (1H, m), 0.64–0.74 (1H, m), 1.01–1.14 (1H, m), 1.25–1.39 (2H, m), 1.39–1.53 (4H, m), 1.53–1.64 (1H, m), 1.65–1.76 (1H, m), 2.03–2.15 (2H, m), 2.15–2.35 (2H, m), 2.42–2.53 (4H, m), 2.59 (1H, t, J=6.83 Hz), 2.81 (2.1H, s), 2.85–2.91 (1H, m), 2.97 (0.9H, s), 3.00–3.12 (2H, m), 3.39–3.48 (1H, m), 3.83 (0.3H, d, J=5.37 Hz), 3.86 (0.7H, d, d, J=4.88 Hz), 4.76 (0.7H, d, J=7.81 Hz), 4.87 (0.3H, d, J=8.3 Hz), 6.37 (0.3H, s), 6.47 (0.7H, s), 6.63 (0.3H, d, J=8.3 Hz), 6.68 (0.7H, d, J=7.81 Hz), 6.69 (0.3H, d, J=8.3 Hz), 6.77 (0.7H, d, J=7.81 Hz), 7.08–7.22 (3H, m), 7.23–7.30 (2H, m), 8.83 (1H, br, s), 9.26 (0.3H, s), 9.50 (0.7H, s).
IR (KBr)
ν 2938, 1702, 1613, 1508, 1462, 1317, 1160, 1125, 1033, 922, 857, 808, 748, 700 cm$^{-1}$.
Mass (EI)
m/z 516 ((M)$^+$). (data for free base)
Elementary analysis for $C_{32}H_{40}N_2O_4 \cdot HCl \cdot 0.3H_2O$
Calculated: C, 68.81; H, 7.51; Cl, 6.35; N, 5.01.
Found: C, 69.12; H, 7.45; Cl, 5.96; N, 4.73.

Example 194

The procedure of Example 68 was repeated, except that 17-cyclopropylmethyl-4,5α-epoxy-14β-hydroxy-6β-(N-methylamino)morphinan was used as a starting compound instead of 17-cyclopropylmethyl-4,5α-epoxy-3,14β-dihydroxy-6-(N-methylamino)morphinan 10, thereby preparing 17-cyclopropylmethyl-4,5α-epoxy-14-hydroxy-6β-[N-methyl-trans-3-(3-furan)acrylamido]morphinan hydrochloride 204 (yield: 44%).

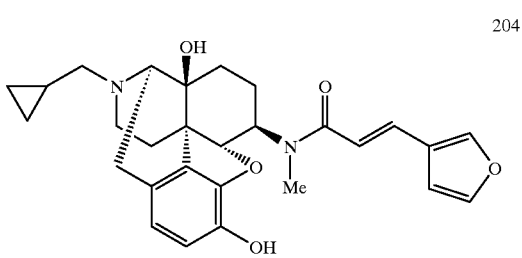

m.p. 190–195° C.
NMR (400 MHz, DMSO-$d_6$)
δ 0.44 (1H, m), 0.53 (1H, m), 0.60 (1H, m), 0.69 (1H, m), 1.09 (1H, m), 1.25 (0.5H, m), 1.35–1.45 (2H, m), 1.51 (0.5H, m), 1.75 (1H, m), 2.14 (1H, m), 2.35–2.60 (2H, m), 2.88 (1H, m), 2.93 (1.5H, s), 3.05 (1H, m), 3.16

(1.5H, s), 3.18 (1H, m), 3.43 (0.5H, d, J=7.3 Hz), 3.48 (0.5H, d, J=8.3 Hz), 3.63 (0.5H, m), 3.92 (1H, m), 4.24 (0.5H , m), 4.84 (0.5H, d, J=8.3 Hz), 4.91 (0.5H, d, J=8.3 Hz), 6.35 (0.5H, d, J=15.6 Hz), 6.50 (0.5H, s), 6.66 (0.5H, d, J=7.8 Hz), 6.70 (0.5H, d, J=7.8 Hz), 6.84 (0.5H, d, J=7.8 Hz), 6.85–7.00 (1.5H, m), 7.18 (0.5H, t, J=7.8 Hz), 7.21 (0.5H, t, T=7.8 Hz), 7.30 (0.5H, d, J=15.1 Hz), 7.36 (0.5H, d, J=15.1 Hz), 7.70 (0.5H, s), 7.72 (0.5H, s), 7.96 (0.5H, s), 8.03 (0.5H, s).

IR (KBr)
ν 3300, 1650, 1504, 1326, 1122, 1023, 871, 794 cm$^{-1}$.
Mass (FAB)
m/z 461 ((M+H)$^+$).
Elementary analysis for $C_{28}H_{32}N_2O_4 \cdot HCl \cdot 0.3H_2O$
Calculated: C, 66.93; H, 6.74; N, 5.57; Cl, 7.06
Found: C, 66.86; H, 6.81; N, 5.66; Cl, 6.96

Examples 195–200

The procedure of Example 11 was repeated, except that 17-cyclopropylmethyl-4,5α-epoxy-3,14β-dihydroxy-6β-isobutylaminomorphinan was used instead of 17-cyclopropylmethyl-4,5α-epoxy-3,14β-dihydroxy-6α-methylaminomorphinan 4 and 3-methylcinnamoyl chloride, 6-phenylhexanoyl chloride, 8-octanoyl chloride, 11-phenylundecanoyl chloride, 5-benzoylpentanoyl chloride and 5-cyclohexylpentanoyl chloride were used instead of 3,4-dichlorophenylacetyl chloride, thereby preparing 17-cyclopropylmethyl-3,14β-dihydroxy-4,5α-epoxy-6β-(N-isobutyl-3-methylcinnamamido)morphinan monotartrate 205 (yield: 91%), 17-cyclopropylmethyl-3,14β-dihydroxy-4,5α-epoxy-6β-(N-isobutyl-6-phenylhexanoamido) morphinan monotartrate 206 (yield: 85%), 17-cyclopropylmethyl-3,14β-dihydroxy-4,5α-epoxy-6β-(N-isobutyl-8-phenyloctanoamido)morphinan monotartrate 207 (yield: 82%), 17-cyclopropylmethyl-3,14β-dihydroxy-4,5α-epoxy-6β-(N-isobutyl-11-phenylundecanoamido) morphinan monotartrate 208 (yield: 74%), 17-cyclopropylmethyl-3,14β-dihydroxy-4,5α-epoxy-6β-(N-isobutyl-5-benzoylpentanoamido)morphinan methanesulfonate 209 (yield: 71%) and 17-cyclopropylmethyl-3,14β-dihydroxy-4,5α-epoxy-6β-(N-isobutyl-5-cyclohexylpentanoamido)morphinan phosphate 210 (yield: 82%).

Compound 205

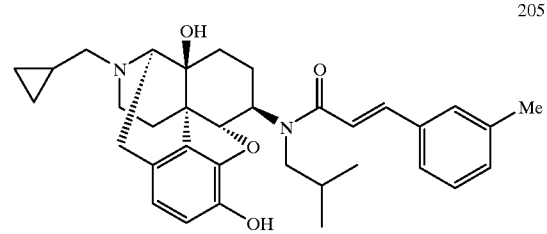

m.p. >103° C. (decomp.)
NMR (400 MHz, DMSO-d$_6$)
δ 0.26 (2H, m), 0.53 (2H, m), 0.83–0.98 (7H, m), 1.26–1.86 (4H, m), 2.13–2.34 (3H, m), 2.33 (3H, s), 2.50–2.85 (4H, m), 3.07–3.40 (5H, m) 3.60 (5H, br s, 5×OH), 3.67 (1H, m), 4.09 (2H, s), 4.58 (0.5H, m), 5.24 (0.5H, m), 6.57–6.67 (2H, m), 6.75 (0.5H, m), 7.08–7.33 (4H, m), 7.43–7.53 (1.5H, m), 9.15 (0.5H, m, NH+), 9.40 (0.5H, m, NH+).

IR (KBr)
ν 3318, 1736, 1638, 1593, 1460, 1377, 1315, 1245, 1125, 1069, 1033, 984, 922, 787 cm$^{-1}$.
Mass (FAB)
m/z 543 ((M+H)$^+$).
Elementary analysis for $C_{34}H_{42}N_2O_4 \cdot C_4H_6O_6 \cdot 0.4H_2O$
Calculated: C, 65.20; H, 7.03; N, 4.00.
Found: C, 65.13; H, 7.09; N, 3.96.

Compound 206

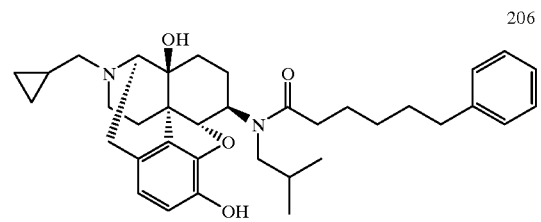

m.p. >110° C. (decomp.)
NMR (400 MHz, DMSO-d$_6$)
δ 0.24 (2H, m), 0.54 (2H, m), 0.78–0.88 (6H, m), 0.92 (1H, m), 1.14–1.76 (11H, m), 1.91–2.32 (5H, m), 2.46–2.83 (6H, m), 2.96–3.16 (2H, m), 3.26–3.38 (2H, m), 3.48 (1H, m), 3.60 (5H, br s, 5×OH), 4.09 (2H, s), 4.55 (0.5H, br d, J=7.8 Hz), 5.17 (0.5H, br d, J=7.3 Hz), 6.55 (0.5H, d, J=8.1 Hz), 6.56 (0.5H, d, J=8.1 Hz), 6.64 (0.5H, d, J=8.1 Hz), 6.65 (0.5H, d, J=8.1 Hz), 7.12–7.22 (3H, m), 7.22–7.29 (2H, m), 9.25 (1H, m, NH+).

IR (KBr)
ν 3300, 1738, 1622, 1504, 1460, 1421, 1388, 1365, 1319, 1270, 1123, 1071, 1033, 922, 748 cm$^{-1}$.
Mass (FAB)
m/z 573 ((M+H)$^+$).
Elementary analysis for $C_{36}H_{48}N_2O_4 \cdot C_4H_6O_6 \cdot 0.2H_2O$
Calculated: C, 66.13; H, 7.55; N, 3.86.
Found: C, 66.10; H, 7.52; N, 3.90.

Compound 207

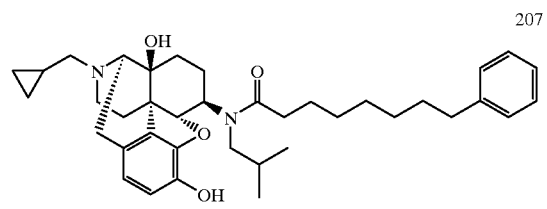

m.p. >110° C. (decomp.)
NMR (400 MHz, DMSO-d$_6$)
δ 0.24 (2H, d), 0.54 (2H, m), 0.79–0.88 (6H, m), 0.92 (1H, m), 1.10–1.78 (35H, m), 1.91–2.32 (5H, 9.) 2.48–2.83 (6H, m), 2.96–3.16 (2H, m), 3.26–3.38 (2H, 16), 3.47 (1H, m), 3.65 (5H, br s, 5×OH), 4.09 (2H, 1), 4.50 (0.5H, br d, J=7.8 Hz), 5.17 (0.5H, br d, J=7.3 Hz), 6.56 (0.5H, d, J=8.1 Hz), 6.56 (0.5H, d, J=8.1 Hz), 6.64 (0.5H, d, J=8.1 Hz), 6.65 (0.5H, d, J=8.1 Hz), 7.13–7.21 (3H, m), 7.23–7.29 (2H, m), 9.25 (1H, m, NH+).

IR (KBr)
ν 3323, 1731, 1611, 1504, 1460, 1421, 1388, 1365, 1321, 1276, 1123, 1069, 1033, 922, 748 cm$^{-1}$.
Mass (FAB)
m/z 601 ((M+H)$^+$).

Elementary analysis for $C_{38}H_{52}N_2O_4 \cdot C_4H_6O_6 \cdot 0.4H_2O$
Calculated: C, 66.54; H, 7.82; N, 3.70.
Found: C, 66.45; H, 7.77; N, 3.81.

Compound 208

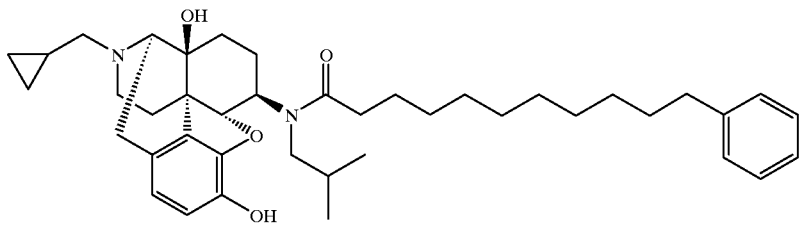

m.p. >105° C. (decomp.)
NMR (400 MHz, DMSO-$d_6$)
δ 0.24 (2H, m), 0.53 (2H, m), 0.76–0.88 (6H, m), 0.92 (1H, m), 0.96–1.78 (21H, m), 1.91–2.32 (5H, m), 2.48–2.83 (6H, m), 2.97–3.17 (2H, m), 3.26–3.38 (2H, m), 3.40 (5H, br s, 5×OH), 3.47 (1H, m), 4.10 (2H, s), 4.53 (0.5H, br d, J=7.3 Hz), 5.16 (0.5H, m), 6.55 (0.5H, d, J=7.8 Hz), 6.57 (0.5H, d, J=7.8 Hz), 6.64 (0.5H, d, J=7.8 Hz), 6.65 (0.5H, d, J=7.8 Hz), 7.10–7.22 (3H, m), 7.25–7.32 (2H, m), 9.20 (1H, m, NH+).

IR (KBr)
δ 3314, 1731, 1611, 1508, 1462, 1421, 1365, 1321, 1272, 1243, 1123, 1071, 1033, 922, 702 cm$^{-1}$.

Mass (FAB)
m/z 643 ((M+H)$^+$).
Elementary analysis for $C_{41}H_{58}N_2O_4 \cdot C_4H_6O_6 \cdot 0.5H_2O$
Calculated: C, 67.39; H, 8.17; N, 3.65.
Found: C, 67.33; H, 8.08; N, 3.65.

Compound 209

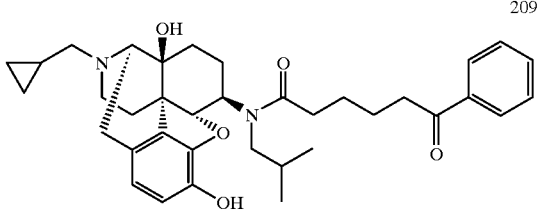

m.p. >125° C. (decomp.)
NMR (400 MHz, DMSO-$d_6$)
δ 0.42 (1H, m), 0.48 (1H, m), 0.59 (1H, m), 0.68 (1H, m), 0.82 (1.5H, d, J=6.3 Hz), 0.84 (1.5H, d, J=6.3 Hz), 0.86 (1.5H, d, J=6.3 Hz), 0.87 (1.5H, d, J=6.3 Hz), 1.15 (1H, m), 1.31 (1H, m), 1.38–1.77 (7H, m),1.91–2.69 (6H, m), 2.30 (3H, s), 2.82–3.12 (6H, m), 3.27–3.38 (2H, m), 3.42–3.54 (2H, m), 3.80 (1H, br dd, J=8.6, 5.4 Hz), 4.62 (0.5H, d, J=7.3 Hz), 5.23 (0.5H, d, J=7.3 Hz), 5.89 (0.5H, s, OH), 6.21 (0.5H, s, OH), 6.63 (0.5H, d, J=7.8 Hz), 6.64 (0.5H, d, J=7.8 Hz), 6.71 (0.5H, d, J=7.8 Hz), 6.73 (0.5H, d, J=7.8 Hz), 7.51–7.56 (2H, m), 7.64 (1H, ddd, J=7.3, 7.3, 2.0 Hz), 7.92 (1H, br d, J=7.3 Hz), 7.98 (1H, br d, J=7.3 Hz), 8.67 (0.5H, br s, NH+), 8.76 (0.5H, br s, NH+), 9.25 (0.5H, br s, OH), 9.47 (0.5H, br s, OH).

IR (KBr)
ν 3250, 1682, 1630, 1508, 1473, 1423, 1377, 1321, 1225, 1125, 1044, 924, 857, 810, 779, 649 cm$^{-1}$.

Mass (FAB)
m/z 587 ((M+H)$^+$).
Elementary analysis for $C_{36}H_{46}N_2O_5 \cdot CH_3SO_3H \cdot 0.5H_2O$
Calculated: C, 64.23; H, 7.43; N, 4.05; S, 4.63.
Found: C, 64.12; H, 7.16; N, 4.15; S, 4.89.

Compound 210

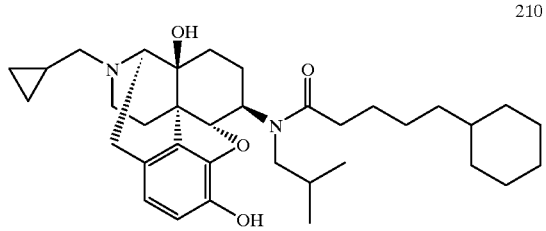

m.p. >147° C. (decomp.)
NMR (400 MHz, DMSO-$d_6$)
δ 0.22 (2H, m), 0.52 (2H, m), 0.73–0.95 (9H, m), 0.98–1.76 (20H, m), 1.93–2.33 (5H, m), 2.50–2.80 (5H, m), 2.94–3.52 (4H, m), 4.48 (0.6H, d, J=7.8 Hz), 5.16 (0.4H, d, J=6.8 Hz), 6.50 (5H, br S, 4×OH, NH+), 6.54 (0.4H, d, J=8.3 Hz), 6.58 (0.6H, d, J=8.3 Hz), 6.63 (0.4H, d, J=8.3 Hz), 6.66 (0.6H, d, J=8.3 Hz).

IR (KBr)
ν 3220, 1638, 1622, 1508, 1460, 1388, 1321, 1236, 1125, 1033, 926, 857 cm$^{-1}$.

Mass (FAB)
m/z 565 ((M+H)$^+$).
Elementary analysis for $C_{35}H_{52}N_2O_4 \cdot 0.95H_3PO_4 \cdot 0.9H_2O$
Calculated: C, 62.36; H, 8.47; N, 4.16; P, 4.36.
Found: C, 62.63; H, 8.22; N, 4.26; P, 4.02.

Example 201

The procedure of Example 11 was repeated, except that 17-isobutyl-4,5α-epoxy-3,14β-dihydroxy-6β-methylaminomorphinan was used instead of 17-cyclopropylmethyl-4,5α-epoxy-3,14β-dihydroxy-6α-methylaminomorphinan 4 and trans-3-(3-furan)acryloyl chloride was used instead of 3,4-dichlorophenylacetyl chloride, thereby preparing 17-isobutyl-3,14β-dihydroxy-4,5α-epoxy-6β-[N-methyl-3-(3-furan)acrylamido]morphinan tartrate 211 (yield: 76%).

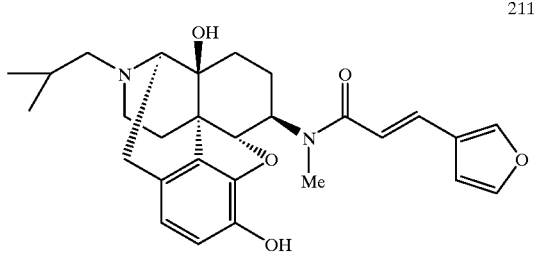

211 m.p. 158.0–162.0° C. (decomp., ethyl acetate)
NMR (400 MHz, DMSO-$d_6$)
δ 0.88 (3H, d, J=5,9 Hz), 0.90 (3H, d, J=6.3 Hz), 1.24–1.38 (3H, m), 1.54 (1H, br d, J=13.2 Hz), 1.78 (1H, m), 2.02–2.16 (2H, m), 2.20–2.37 (3H, m), 2.54 (1H, m), 2.65 (1H, m), 2.85 (2H, s), 2.88 (1H, m), 3.09 (1H, s), 3.00–3.80 (3H, br s), 3.04 (1H, d, J=18.6 Hz), 4.17 (1H, s), 4.17 (1H, m), 4.65 (0.67H, d, J=8.3 Hz), 4.75 (0.33H, d, J=8.8 Hz), 6.40 (0.67H, d, J=15.6 Hz), 6.56 (0.33H, d, J=7.8 Hz), 6.60 (0.33H, d, J=7.8 Hz), 6.62 (0.67H, d, J=8.3 Hz), 6.64 (0.67H, s), 6.73 (0.67H, d, J=8.3 Hz), 6.89 (0.33H, d, J=15.1 Hz), 6.99 (0.33H, s), 7.21 (0.67H, d, J=15.1 Hz), 7.36 (0.33H, d, J=15.1 Hz), 7.66 (0.67H, s), 7.72 (0.33H, s), 7.92 (0.67H, s), 8.02 (0.33H, s), 9.04 (0.33H, br s), 9.43 (0.67H, br s).
IR (KBr)
ν 3400, 2968, 1651, 1599, 1408, 1323, 1125, 1019, 872 cm$^{-1}$.
Mass (EI)
m/z 478 (M$^+$).
Elementary analysis for $C_{30}H_{37}N_2O_8 \cdot 0.7H_2O$
Calculated: C, 63.64; H, 6.83; N, 4.95.
Found: C, 63.68; H, 6.83; N, 4.88.

Examples 202–203

The procedure of Example 11 was repeated, except that 17-cyclopropylmethyl-4,5α-epoxy-3,14β-dihydroxy-6α-isobutylaminomorphinan and 17-cyclopropylmethyl-4,5α-epoxy-3,14β-dihydroxy-6β-pentylaminomorphinan 198 were used instead of 17-cyclopropylmethyl-4,5α-epoxy-3,14β-dihydroxy-6α-methylaminomorphinan 4 and 6-phenylhexanoyl chloride was used instead of 3,4-dichlorophenylacetyl chloride, thereby preparing 17-cyclopropylmethyl-3,14β-dihydroxy-4,5α-epoxy-6α-(N-isobutyl-6-phenylhexanoamido)morphinan methanesulfonate 212 (yield: 37%) and 17-cyclopropylmethyl-3,14β-dihydroxy-4,5α-epoxy-6β-(N-pentyl-6-phenylhexanoamido)morphinan methanesulfonate 213 (yield: 90%).
Compound 212

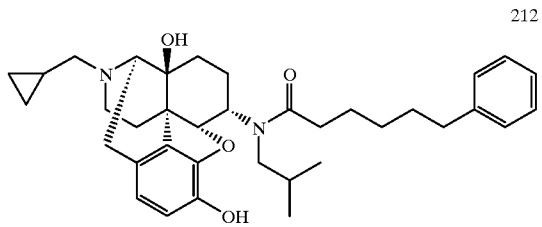

m.p. >120° C. (decomp.)
NMR (400 MHz, DMSO-$d_6$)
δ 0.43 (2H, m), 0.65 (2H, m), 0.73 (2H, dd, J=17.1, 6.8 Hz), 0.81 (4H, t, J=5.9 Hz), 0.98–1.25 (2H, m), 1.27–1.37 (2H, m), 1.45–1.66 (7H, m), 1.73–1.97 (2H, m), 2.3 (3H, s), 2.27–2.50 (3H, m), 2.54–2.62 (2H, m), 2.63–2.77 (1H, m), 2.85–3.48 (7H, m), 3.83–3.90 (1H, m), 4.47 (0.4H, m), 4.67–4.73 (1H, m), 5.01 (0.6H, m), 6.11 (0.6H, s), 6.29 (0.4H, s), 6.54–6.60 (1H, m), 6.69–6.74 (1H, m), 7.14–7.22 (3H, m), 7.24–7.31 (2H, m), 8.75 (1H, br s), 9.21 (0.6H, s), 9.26 (0.4H, s).
IR (KBr)
ν 3420, 1620, 1508, 1460, 1323, 1207, 1120, 1044 cm$^{-1}$.
Mass (FAB)
m/z 573 ((M+H)$^+$).
Elementary analysis for $C_{36}H_{48}N_2O_4 \cdot CH_4O_3S \cdot 0.4H_2O$
Calculated: C, 65.73; H, 7.87; N, 4.14; S, 4.74.
Found: C, 65.65; H, 7.73; N, 4.23; S, 4.81.
Compound 213

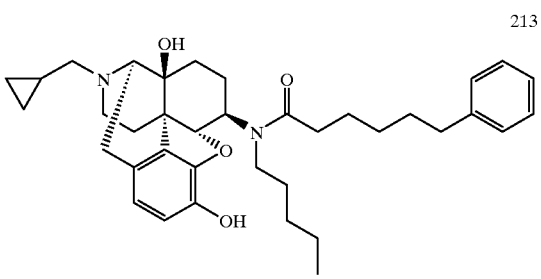

m.p. 104–115° C. (decomp.)
NMR (400 MHz, DMSO-$d_6$)
δ 0.42 (1H, m), 0.48 (1H, m), 0.59 (1H, m), 0.69 (1H, m), 0.85 (1.2H, t, J=7.3 Hz), 0.89 (1.8H, t, J=7.3 Hz), 1.15 (1H, m), 1.12–1.74 (17H, m), 1.94–2.28 (3H, m), 2.31 (3H, s), 2.41–2.60 (3H, m), 2.86 (1H, m), 2.96–3.23 (4H, m), 3.28–3.55 (3H, m), 3.77 (0.4H, br d, J=5.4 Hz), 3.81 (0.6H, br d, J=5.9 Hz), 4.62 (0.6H, d, J=7.8 Hz), 5.08 (0.4H, m), 5.94 (0.4H, br s, OH), 6.20 (0.6H, br s, OH), 6.62 (0.4H, dd J=8.1 Hz), 6.64 (0.6H, d, J=8.1 Hz), 6.71 (0.4H, d, J=8.1 Hz), 6.73 (0.6H, d, J=8.1 Hz), 7.13–7.21 (3H, m), 7.23–7.39 (2H, m), 8.68 (0.6H, br s, NH+), 8.74 (0.4H, br s, NH+), 9.28 (0.4H, br s, OH), 9.43 (0.6H, br s, OH).
IR (KBr)
ν 3232, 1638, 1508, 1460, 14331 1377, 1325, 1220, 1168, 1123, 1042, 922, 859, 772, 748, 700 cm$^{-1}$.
Mass (FAB)
m/z 587 ((M+H)$^+$).
Elementary analysis for $C_{37}H_{50}N_2O_4 \cdot 1.1CH_3SO_3H \cdot 0.2H_2O$
Calculated: C, 65.74; H, 7.93; M, 4.02; S, 5.07.
Found: C, 65.81; H, 7.93; N, 4.11; S, 5.06.

Example 204

The procedure of Example 114 was repeated, except that 17-cyclopropylmethyl-4,5α-epoxy-14β-hydroxy-6β-methylaminomorphinan was used instead of 17-cyclopropylmethyl-4,5α-epoxy-3,14β-dihydroxy-6β- methylaminomorphinan 10 and 3-(3-methylphenyl) propiolic acid was used instead of 3-(3-trifluoromethylphenyl)propiolic acid, thereby preparing 17-cyclopropylmethyl-4,5α-epoxy-14β-hydroxy-6β-[N-methyl-3-(3-methylphenyl)propiolamido]morphinan monotartrate 214 (yield: 46%).

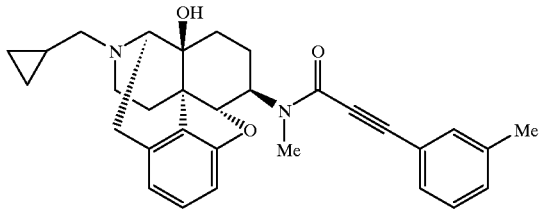

214 m.p. 128–134° C.
NMR (400 MHz, DMSO-$d_6$)
δ 0.26 (2H, m), 0.56 (2H, m), 0.95 (1H, m), 1.25–1.50 (3H, m), 1.70 (1H, m), 2.20–2.40 (3H, m), 2.28 (2.25H, s), 2.33 (0.75H, s), 2.59 (1H, m), 2.75–3.00 (3H, m), 2.92 (2.25H, s), 3.25–3.60 (2H, m), 3.25 (0.75H, s), 4.10 (1H, m), 4.12 (2H, s), 4.73 (0.75H, d, J=7.8 Hz), 4.80 (0.25H, d, J=8.3 Hz), 6.56 (0.75H, d, J=7.8 Hz), 6.78 (0.25H, d, J=7.8 Hz), 6.80–7.15 (4H, m), 7.25–7.45 (2H, m).
IR (KBr)
ν 3200, 2211, 1608, 1502, 1455, 1321, 1125, 931, 786 cm$^{-1}$.
Mass (FAB)
m/z 483 ((M+H)$^+$).
Elementary analysis for $C_{31}H_{34}N_2O_3 \cdot C_4H_6O_6$
Calculated: C, 66.44; H, 6.37; N, 4.43
Found: C, 66.42; H, 6.39; N, 4.45

Examples 205–206

The procedure of Example 125 was repeated, except that 17-cyclopropylmethyl-3,14β-dihydroxy-4,5α-epoxy-6β-(N-isobutyl-6-phenylhexanoylamido)morphinan and 17-cyclopropylmethyl-3,14β-dihydroxy-4,5α-epoxy-6α-(N-isobutyl-6-phenylhexanoylamido)morphinan were used instead of 17-cyclopropylmethyl-3,14β-dihydroxy-4,5α-epoxy-6α-(N-methyl-3,4-dichlorophenylacetamido)morphinan, thereby preparing 17-cyclopropylmethyl-3,14β-dihydroxy-4,5α-epoxy-6β-(N-isobutyl-N-6-phenylhexylainino)morphinan dihydrochloride 215 (yield: 85%) and 17-cyclopropylmethyl-3,14β-dihydroxy-4,5α-epoxy-6α-(N-isobutyl-N-6-phenylhexylamino)morphinan dihydrochloride 216 (yield: 90%).

Compound 215

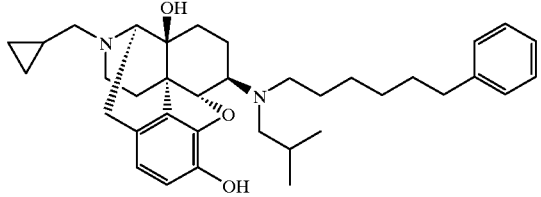

215 m.p. >174° C. (decomnp.)
NMR (400 MHz, DMSO-$d_6$)
δ 0.41 (1H, m), 0.52 (1H, m), 0.59 (1H, m), 0.68 (1H, m), 0.96–1.04 (6H, m), 1.08 (1H, m), 1.23–1.52 (6H, m), 1.53–1.83 (5H, m), 1.92–2.15 (3H, m), 2.38–2.68 (4H, m), 2.86–3.45 (10H, m), 3.92 (1H, m), 5.24 (0.7H, d, J=7.8 Hz), 5.29 (0.3H, d, J=7.3 Hz), 6.70 (0.3H, d, J=7.8 Hz), 6.70 (0.7H, d, J=7.8 Hz), 6.81 (0.3H, d, J=7.8 Hz), 6.83 (0.7H, d, J=7.8 Hz), 6.93 (1H, m, OH), 7.14–7.22 (3H, m), 7.25–7.31 (2H, m), 8.95 (1H, br s, NH+), 9.40 (0.3H, br s, NH+), 9.49 (0.7H, br s, NH+), 9.56 (0.3H, s, OH), 9.62 (0.7H, s, OH).
IR (KBr)
ν 3378, 3180, 1638, 1620, 1508, 1460, 1377, 1325, 1238, 1178, 1125, 1035, 998, 922, 861, 748, 700 cm$^{-1}$.
Mass (FAB)
m/z 559 ((M+H)$^+$).
Elementary analysis for $C_{36}H_{50}N_2O_3 \cdot 2HCl \cdot 0.2H_2O$
Calculated: C, 68.06; H, 8.31; Cl, 11.16; N, 4.41.
Found: C, 68.19; H, 8.15; Cl, 10.82; N, 4.56.

Compound 216

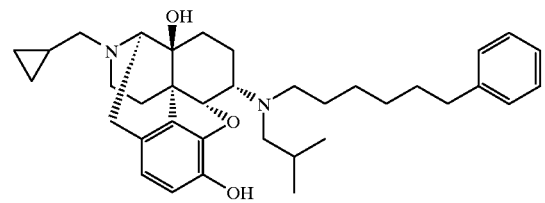

216 m.p. >172° C. (decomp.)
NMR (400 MHz, DMSO-$d_6$)
δ 0.40 (1H, m), 0.48 (1H, m), 0.61 (1H, m), 0.68 (1H, m), 0.98–1.04 (6H, m), 1.05–1.15 (2H, m), 1.28–1.42 (4H, m), 1.53–2.22 (9H, m), 2.40–2.75 (4H, m), 2.86–3.41 (9H, m), 3.90–4.02 (2H, m), 5.25 (0.6H, br s), 5.31 (0.4H, br s), 6.64 (1H, d, J=8.1 Hz), 6.75 (1H, m, OH), 6.64 (1H, d, J=8.1 Hz), 7.14–7.23 (3H, m), 7.24–7.31 (2H, m), 8.93 (1H, br s, NH+), 9.43 (0.6H, s, OH), 9.49 (0.4H, s, OH), 9.96 (0.6H, br s, NH+), 10.07 (0.4H, br s, NH+).
IR (KBr)
ν 3358, 3180, 1638, 1618, 1508, 1460, 1373, 1321, 1241, 1174, 1122, 1073, 1036, 994, 928, 748, 700 cm$^{-1}$.
Mass (FAB)
m/z 559 ((M+H)$^+$).
Elementary analysis for $C_{36}H_{50}N_2O_3 \cdot 2HCl \cdot 0.1H_2O$
Calculated: C, 68.25; H, 8.31; Cl, 11.19; N, 4.42.
Found: C, 68.21; H, 8.19; Cl, 11.05; N, 4.58.

Examples 207–208

The procedure of Example 132 was repeated, except that 17-cyclopropylmethyl-4,5α-epoxy-3,14β-dihydroxy-6β-[N-methyl-trans-3-(3-furan)acrylamido]morphinan (free base of 78) and 17-cyclopropylmethyl-4,5α-epoxy-3,14β-dihydroxy-6β-[N-methyl-3-(3-methylphenyl)propiolamido] morphinan (free base of 172) were used instead of 17-cyclopropylmethyl-4,5α-epoxy-3,14β-dihydroxy-6α-(N-methyl-3,4-dichlorophenylacetamido)morphinan (free base of 1), thereby preparing 17-cyclopropylmethyl-4,5α-epoxy-14β-hydroxy-3-methoxy-6β-[N-methyl-trans-3-(3-furan)acrylamido]morphinan hydrochloride 217 (yield: 49%) and 17-cyclopropylmethyl-4,5α-epoxy-14β-hydroxy-3-methoxy-6β-[N-methyl-3-(3-methylphenyl)propiolamido]morphinan hydrochloride 218 (yield: 76%).

Compound 217

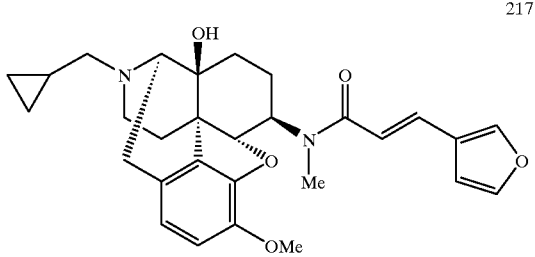

m.p. 235–245° C. (decomp.)
NMR (400 MHz, DMSO-$d_6$)
δ 0.42 (1H, m), 0.53 (1H, m), 0.60 (1H, m), 0.69 (1H, m), 1.08 (1H, m), 1.25 (0.5H, m), 1.36–1.53 (2.5H, m), 1.78 (1H, m), 2.15 (1H, m), 2.38–2.62 (3H, m), 2.88 (1H, m), 2.92 (1.5H, s), 3.02–3.15 (2H, m), 3.18 (1.5H, s), 3.35–3.45 (2H, m), 3.62 (1.5H, s), 3.66 (0.5H, m), 3.75 (1.5H, s), 3.90 (1H, m), 4.30 (0.5H, m), 4.88 (0.5H, d, J=7.8 Hz), 4.95 (0.5H, d, J=7.8 Hz), 6.38 (0.5H, d, J=15.6 Hz), 6.41 (0.5H, br s), 6.75–7.00 (3H, m), 7.28 (0.5H, d, J=15.6 Hz), 7.37 (0.5H, d, J=15.1 Hz), 7.69 (0.5H, s), 7.72 (0.5H, s), 7.92 (0.5H, s), 8.03 (0.5H, s).
IR (KBr)
ν 3350, 1651, 1505, 1405, 1323, 1156, 1122, 1029, 872, 800 cm$^{-1}$.
Mass (FAB)
m/z 491 (M+H).
Elementary analysis for $C_{29}H_{34}N_2O_5 \cdot HCl \cdot 0.3H_2O$
Calculated: C, 65.42; H, 6.74; N, 5.26; Cl, 6.66
Found: C, 65.25; H, 6.79; N, 5.53; Cl, 6.57

Compound 218

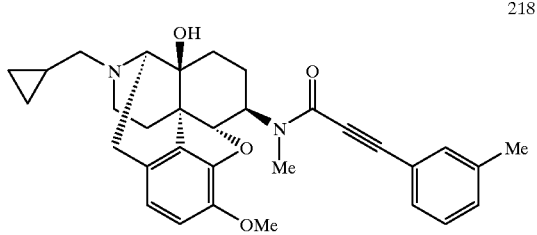

m.p. 225–235° C.
NMR (400 MHz, DMSO-$d_6$)
δ 0.38–0.47 (1H, m), 0.47–0.56 (1H, m), 0.56–0.64 (1H, m), 0.64–0.74 (1H, m), 1.05–1.13 (1H, m), 1.28–1.36 (0.3H, m), 1.36–1.52 (2.7H, m), 1.74–1.87 (1H, m), 2.08–2.25 (1H, m), 2.30 (2.1H, s), 2.34 (0.9H, s), 2.28–2.57 (2H, m), 2.83–2.92 (1H, m), 2.96 (2.1H, s), 3.00–3.24 (2H, m), 3.29 (0.9H, s), 3.34 (2.1H, s), 3.35–3.55 (2H, m), 3.77 (0.9H, s), 3.86–3.93 (1H, m), 4.15–4.25 (1H, m), 4.88 (0.7H, d, J=8.3 Hz), 4.94 (0.3H, d, J=8.3 Hz), 6.63 (0.7H, d, J=8.3 Hz), 6.77 (0.7H, s), 6.80 (0.3H, d, J=7.8 Hz), 6.83 (0.7H, d, J=8.3 Hz), 6.90 (0.3H, d, J=8.3 Hz), 6.97 (0.7H, d, J=7.8 Hz), 7.06 (0.3H, s), 7.25–7.46 (2.3H, m).
IR (KBr)
ν 3400, 2214, 1613, 1505, 1460, 1323, 1125, 932, 787 cm$^{-1}$.

Mass (FAB)
m/z 513 ((M+H)$^+$).
Elementary analysis for $C_{32}H_{37}N_2O_4Cl_1 \cdot 0.6H_2O$
Calculated: C, 68.64; H, 6.88; N, 5.00; Cl, 6.33
Found: C, 68.58; H, 7.00; N, 5.01; Cl, 6.38

Reference Example 12

The procedure of Example 11 was repeated, except that 17-trichloroethoxycarbonyl-4,5α-epoxy-14β-hydroxy-3-methoxy-6β-methylaminomorphinan was used instead of 17-cyclopropylmethyl-4,5α-epoxy-3,14β-dihydroxy-6α-methylaminomorphinan 4 and trans-3-(3-furan)acryloyl chloride was used instead of 3(4-dichlorophenylacetyl chloride , thereby preparing 17-trichoroethoxycarbonyl-4,5α-epoxy-14β-hydroxy-3-methoxy-6β[-trans-3-(3-furan)acrylamido]morphinan 219 (yield: 88%).

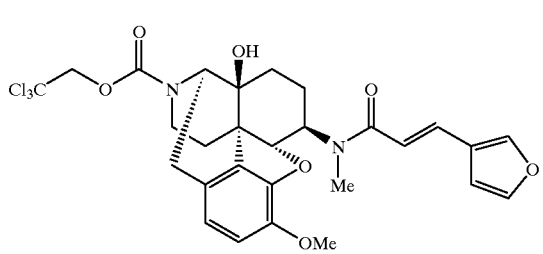

NMR (400 MHz, CDCl$_3$)
δ 1.56 (4H, m), 2.30 (3H, m), 2.90 (2H, m), 3.01 (2.1H, s), 3.15 (1H, m), 3.16 (0.9H, s), 3.75 (0.7H, s),3.82 (2.1H, m), 3.86 (0.9H, s), 4.08 (1H, m), 4.16 (0.3H, m), 4.47 (1H, m), 4.63 (0.7H, d, J=7.8 Hz), 4.82 (2.3H, m), 6.43 (0.7H, d, J=15.6 Hz), 6.47 (0.7H, s), 6.58 (0.3H, m), 6.59 (0.3H, s), 6.66 (0.3H, m), 6.72 (0.7H, d, J=8.3 Hz), 6.78 (0.3H, d, J=7.8 Hz), 6.85 (0.7H, d, J=8.3 Hz), 7.38 (0.7H, brs), 7.42 (0.3H, brs), 7.48 (0.7H, d, 15.6 Hz), 7.53 (0.3H, m), 7.56 (0.7H, s), 7.61 (0.3H, s).
IR (KBr)
ν 3400, 2960, 1704, 1652, 1593, 1510, 1410, 1377
Mass (EI)
m/z 610 ((M)$^+$).

Reference Example 13

17-Trichloroethoxycarbonyl-4,5α-epoxy-3,14β-dihydroxy-6β-[trans-3-(3-furan)acrylamido]morphinan 220

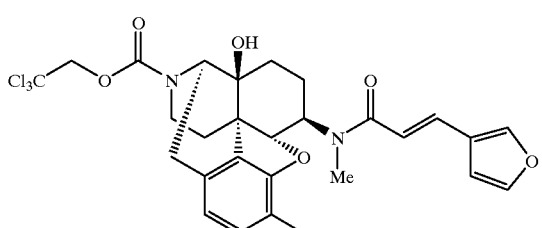

A 1 N boron tribromide-methylene chloride solution (8.7 ml) was cooled to 0° C. in an eggplant type flask purged with argon, and a solution (5 ml) of 17-trichloroethoxycarbonyl- 4,5α-epoxy-14β-hydroxy-3-methoxy-6β-[trans-3-(3-furan) acrylamido]morphinan 219 (532 mg) in methylene chloride was dropwise added thereto. After the completion of the dropwise addition, the temperature of the mixture was raised to room temperature, and the mixture was stirred at that temperature for 30 min. Ice water was added to the reaction mixture and the mixture was stirred. Aqueous ammonia (3 ml) was subsequently added, and the mixture was stirred for 5 min. Thereafter, the reaction mixture was subjected to phase separation, and the aqueous phase was extracted twice with methylene chloride (10 ml). The organic phase was dried over anhydrous sodium hydrogensulfate (5 g) and concentrated. The residue was purified by silica gel column chromatography (Merck 7734, 50 g, chloroform/methanol= 20/1) to give the title compound 220 (yield: 100%).

NMR (400 MHz, CDCl$_3$)

δ 1.57 (4H, m), 2.29 (3H, m), 2.94 (2H, m), 3.12 (1H, m), 3.02 (2.25H, s), 3.13 (0.75H, s), 3.74 (0.75H, m), 4.07 (1H, m), 4.45 (1.25H, m), 4.54 (0.75H, d, J=7.8 Hz), 4.64 (0.25H, d, J=7.8 Hz), 4.75 (1H, m), 4.85 (1H, m), 6.30 (0.75H, d, J=8.3 Hz), 6.60 (0.75H, m), 6.65 (0.75H, brs), 6.68 (0.75H, d, J=8.3 Hz), 6.82 (0.25H, d, J=8.3 Hz), 6.91 (0.75H, d, J=8.3 Hz), 7.31 (0.75H, brs), 7.35 (0.75H, m), 7.37 (0.75H, m), 7.43 (0.25H, br s), 7.58 (0.25H, d, J=15.1 Hz), 7.63 (0.25H, s), 8.20 (1H, m).

IR (KBr)

ν 3400, 2960, 1702, 1651, 1593, 1510, 1410, 1377, 1321, 1272, 1224, 1162, 1131, 1021, 872 cm$^{-1}$.

Mass (EI)

m/z 596 ((M)$^+$).

Example 209

4,5α-Epoxy-3,14β-dihydroxy-6β-[trans-3-(3-furan) acrylamido]morphinan tartrate 221

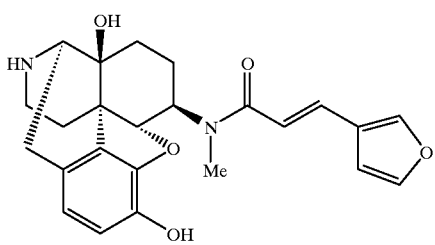

17-Trichloroethoxycarbonyl-4,5α-epoxy-3,14β-dihydroxy-6β-[trans-3-(3-furan)acrylamido]morphinan 220 (518 mg) was dissolved in acetic acid (6 ml), zinc powder (566 mg) was added thereto, and the mixture was vigorously stirred at room temperature. 2 hr after the initiation of stirring, zinc powder (590 mg) was additionally added, and stirring was continued for additional 1.5 hr. Thereafter, the zinc powder was removed through Celite®, and the filtrate was concentrated. Chloroform (25 ml), a saturated aqueous sodium hydrogencarbonate solution (25 ml) and aqueous ammonia (5 ml) were added to the residue. The mixture was subjected to phase separation, and the aqueous phase was extracted twice with chloroform/methanol=5/1 (12 ml). The organic phase was washed with a saturated sodium chloride solution (20 ml), dried over anhydrous sodium sulfate and then concentrated.

The residue was purified by silica gel column chromatography (Merck 7734, 30 g, ammonia-saturated chloroform/methanol=10/1 to 8/1) to give the title compound in a free base form (178 mg, 47%).

The free base (169 mg) was dissolved in methanol (2 ml), tartaric acid (60 mg) was added thereto to prepare a homogeneous solution which was then concentrated. The residue was reprecipitated from methanol-ethyl acetate to give the title compound (178 mg, 78% from the free form).

m.p. >160° C. (decomp.)

NMR (400 MHz, DMSO-d$_6$)

δ 1.36 (2H, m), 1.62 (1H, m), 2.07 (1H, m), 2.44 (2H, m), 2.89 (2H, s), 2.98 (1H, m), 3.11 (2H, m), 3.53 (1.5H, m), 3.90 (6H, brs, 6×OH), 3.85 (2H, s), 4.18 (0.5H, m), 4.71 (0.5H, d, J=7.8 Hz), 4.80 (0.5H, d, J=8.3 Hz), 6.36 (0.5H, d, J=15.6 Hz), 6.62 (1H, brs), 6.65 (0.5H, d, J=7.8 Hz), 6.69 (0.5H, d, J=7.8 Hz), 6.81 (0.5H, d, J=7.8 Hz), 6.89 (0.5H, d, J=15.6 Hz), 6.99 (0.5H, brs), 7.21 (0.5H, d, J=15.6 Hz), 7.36 (0.5H, d, J=15.6 Hz), 7.66 (0.5H, brs), 7.72 (0.5H, brs), 7.91 (0.5H, s), 8.03 (0.5H, s), 9.67 (1H, brs).

IR (KBr)

ν 3858, 1651, 1595, 1562, 1410, 1311, 1267, 1218, 1160, 1135, 681 cm$^{-1}$.

Mass (FAB)

m/z 423 ((M+H)$^+$).

Elementary analysis for $C_{24}H_{26}N_2O_5 \cdot C_4H_6O_6$

Calculated: C, 58.74; H, 5.63; N, 4.89.

Found: C, 58.66; H, 5.76; N, 4.93.

Examples 210–213

The procedure of Example 114 was repeated, except that 8-homo-17-cyclopropylmethyl-4,5α-epoxy-3,14β-dihydroxy-6α-methylaminomorphinan, 8-homo-17-cyclopropylmethyl-4,5α-epoxy-3,14βdihydroxy-6β-methylaminomorphinan, 17-cyclopropylmethyl-4,5α-epoxy- 3,14β-dihydroxy-10-keto-6α-methylaminomorphinan and 17-cyclopropylmethyl-4,5α-epoxy-3,14β-dihydroxy-10-keto-6α-methylaminomorphinan were used instead of 17-cyclopropylmethyl-4,5α-epoxy-3,14β-dihydroxy-6β-methylaminomorphinan 10 and 3-(4-trifluoromethylphenyl) propiolic acid was used instead of 3-(3-trifluoromethylphenyl)propiolic acid, thereby preparing 8-homo-17-cyclopropylmethyl-4,5α-epoxy-3,14β-dihydroxy-6α-[N-methyl-3-(4-trifluoromethylphenyl) propiolamido]morphinan hydrochloride 222 (yield: 68%), 8-homo-17-cyclopropylmethyl-4,5α-epoxy-3,14β-dihydroxy-6β-[N-methyl-3-(3-trifluoromethylphenyl) propiolamido]morphinan hydrochloride 223 (yield: 61%), 17-cyclopropylmethyl-4,5α-epoxy-3,14β-dihydroxy-10-keto-6α-[N-methyl-3-(4-trifluoromethylphenyl) propiolamido]morphinan hydrochloride 224 (yield: 69%) and 17-cyclopropylmethyl-4,5α-epoxy-3,14β-dihydroxy-10-keto-6β-[N-methyl-3-(4-trifluoromethylphenyl) propiolamido]morphinan hydrochloride 225 (yield: 65%).

Compound 222

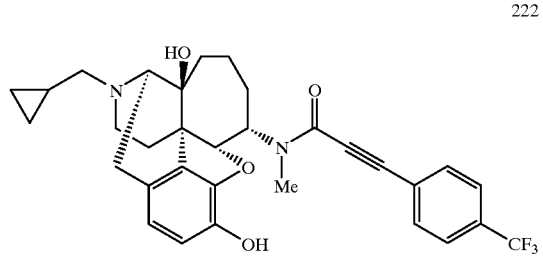

Mass (FAB)

m/z 567 ((M+H)$^+$).
Elementary analysis for $C_{32}H_{33}N_2O_4F_3$•HCl•0.2H$_2$O
Calculated: C, 63.35; H, 5.71; N, 4.62; F, 9.39; Cl, 5.84.
Found: C, 63.25; H, 5.75; N, 4.72; F. 9.21; Cl, 5.96.

Compound 223

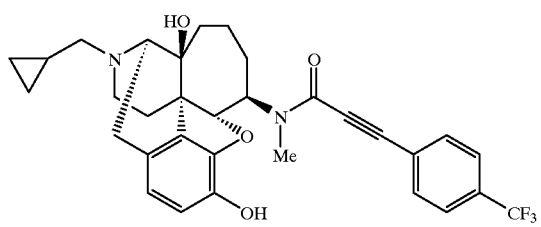

Mass (FAB)

m/z 567 ((M+H)$^+$).
Elementary analysis for $C_{32}H_{33}N_2O_4F_3$•HCl•0.3H$_2$O
Calculated: C, 63.17; H, 5.73; N, 4.60; F, 9.37; Cl, 5.83.
Found: C, 63.00; H, 5.78; N, 4.52; F, 9.41; Cl, 5.98.

Compound 224

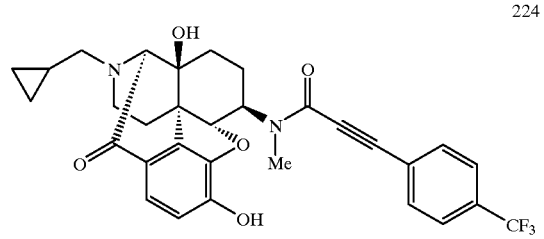

Mass (FAB)

m/z 567 ((M+H)$^+$).
Elementary analysis for $C_{31}H_{29}N_2O_5F_3$•HCl•0.4H$_2$O
Calculated: C, 61.02; H, 5.09; N, 4.59; F, 9.34; Cl, 5.81.
Found: C, 61.29; H, 5.11; N, 4.41; F, 9.43; Cl, 5.76.

Compound 225

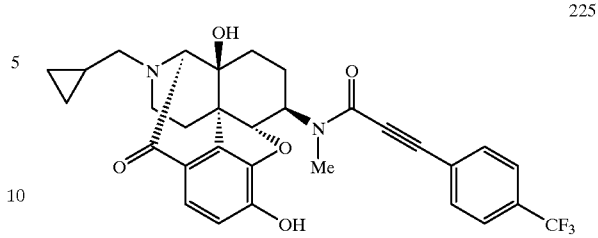

Mass (FAB)

m/z 567 ((M+H)$^+$).
Elementary analysis for $C_{31}H_{29}N_2O_5F_3$•HCl•0.3H$_2$O
Calculated: C, 61.20; H, 5.07; N, 4.60; F, 9.37; Cl, 5.83.
Found: C, 61.38; H, 5.18; N, 4.44; F, 9.27; Cl, 5.74.

Examples 214–217

The procedure of Example 114 was repeated, except that 8-homo-17-cyclopropylmethyl-4,5α-epoxy-3,14β-dihydroxy-7α-methylaminomorphinan, 8-homo-17-cyclopropylmethyl-4,5α-epoxy-3,14β-dihydroxy-7β-methylaminomorphinan, 17-cyclopropylmethyl-4,5α-epoxy-3,14β,15β-trihydroxy-6α-methylaminomorphinan and 17-cyclopropylmethyl-4,5α-epoxy-3,14β,15β-trihydroxy-6β-methylaminomorphinan were used instead of 17-cyclopropylmethyl-4,5α-epoxy-3,14β-dihydroxy-6β-methylaminomorphinan 10 and 3-(3-methylphenyl)propiolic acid was used instead of 3-(3-trifluoromethylphenyl)propiolic acid, thereby preparing 8-homo-17-cyclopropylmethyl-4,5α-epoxy-3,14β-dihydroxy-7α-[N-methyl-3-(3-methylphenyl)propiolamido]morphinan hydrochloride 226 (yield: 71%), 8-homo-17-cyclopropylmethyl-4,5α-epoxy-3,14β-dihydroxy-7β-[N-methyl-3-(3-methylphenyl)propiolamido]morphinan hydrochloride 227 (yield: 60%), 17-cyclopropylmethyl-4,5α-epoxy-3,14β,15β-trihydroxy-6α-[N-methyl-3-(3-methylphenyl)propiolamido]morphinan hydrochloride 228 (yield: 59%) and 17-cyclopropylmethyl-4,5α-epoxy-3,14β,15β-trihydroxy-6β-[N-methyl-3-(3-methylphenyl)propiolamido]morphinan hydrochloride 229 (yield: 63%).

Compound 226

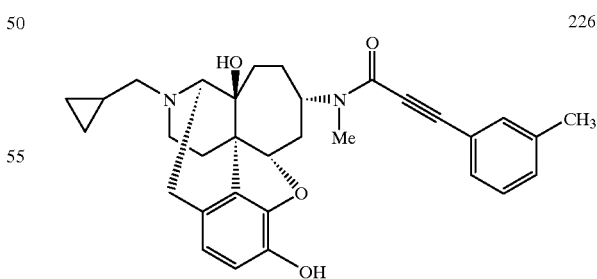

Mass (FAB)

m/z 513 ((M+H)$^+$).
Elementary analysis for $C_{32}H_{36}N_2O_4$•HCl•0.6H$_2$O
Calculated: C, 68.64; H, 6.88; N, 5.00; Cl, 6.33.
Found: C, 68.34; H, 6.95; N, 5.11; Cl, 6.19.

Compound 227

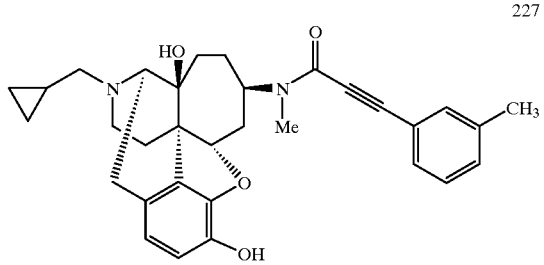

Mass (FAB)
m/z 513 ((M+H)$^+$).
Elementary analysis for $C_{32}H_{36}N_2O_4 \cdot HCl \cdot 0.3H_2O$
Calculated: C, 69.31; H, 6.83; N, 5.05; Cl, 6.39.
Found: C, 69.11; H, 6.74; N, 5.23; Cl, 6.44.

Compound 228

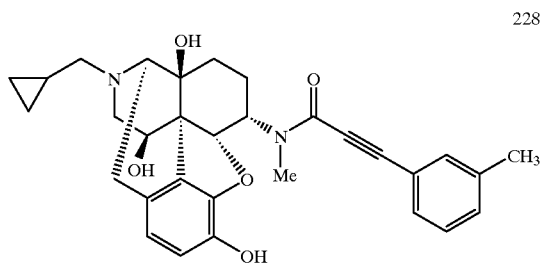

Mass (FAB)
m/z 515 ((M+H)$^+$).
Elementary analysis for $C_{31}H_{34}N_2O_5 \cdot HCl \cdot 0.4H_2O$
Calculated: C, 66.69; H, 6.46; N, 5.02; Cl, 6.35.
Found: C, 66.44; H, 6.51; N, 5.14; Cl, 6.22.

Compound 229

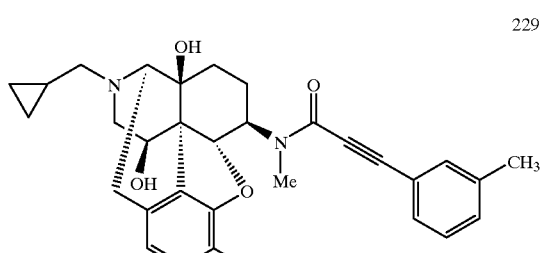

Mass (FAB)
m/z 515 ((M+H)$^+$).
Elementary analysis for $C_{31}H_{34}N_2O_5 \cdot HCl \cdot 0.1H_2O$
Calculated: C, 67.35; H, 6.42; N, 5.07; Cl, 6.41.
Found: C, 67.54; H, 6.51; N, 4.98; Cl, 6.37.

Examples 218–219

The procedure of Example 114 was repeated, except that 17-cyclopropylmethyl-4,5α-epoxy-3,14β-dihydroxy-8α-methylaminomorphinan and 17-cyclopropylmethyl-4,5α-epoxy-3,14β-dihydroxy-8β-methylaminomorphinan were used instead of 17-cyclopropylmethyl-4,5α-epoxy-3,14β-dihydroxy-6β-methylaminomorphinan 10 and 3-(3,4-dimethylphenyl)propiolic acid was used instead of 3-(3-trifluoromethylphenyl)propiolic acid, thereby preparing 17-cyclopropylmethyl-4,5α-epoxy-3,14β-dihydroxy-8α-[N-methyl-3-(3,4-dimethylphenyl)propiolamido]morphinan hydrochloride 230 (yield: 58%) and 17-cyclopropylmethyl-4,5α-epoxy-3,14β-dihydroxy-8β-[N-methyl-3-(3,4-dimethylphenyl)propiolamido]morphinan hydrochloride 231 (yield: 62%).

Compound 230

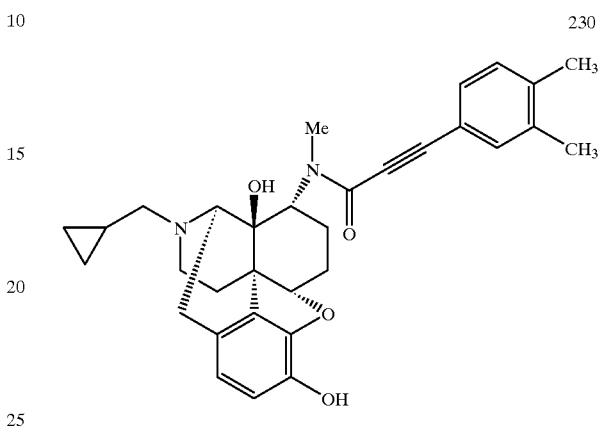

Mass (FAB)
m/z 513 ((M+H)$^+$).
Elementary analysis for $C_{32}H_{36}N_2O_4 \cdot HCl \cdot 0.3H_2O$
Calculated: C, 69.31; H, 6.83; N, 5.05; Cl, 6.39.
Found: C, 69.02; H, 6.87; N, 5.29; Cl, 6.50.

Compound 231

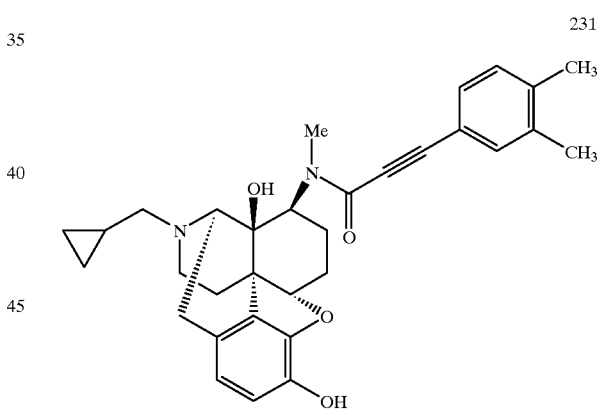

Mass (FAB)
m/z 513 ((M+H)$^+$).
Elementary analysis for $C_{32}H_{36}N_2O_4 \cdot HCl$
Calculated: C, 70.00; H, 6.79; N, 5.10; Cl, 6.46.
Found: C, 70.11; H, 6.73; N, 5.03; Cl, 6.61.

Examples 220–223

The procedure of Example 11 was repeated, except that 17-cyclopropylmethyl-4,5α-epoxy-3,14β-dihydroxy-7β-methyl-6α-methylaminomorphinan, 17-cyclopropylmethyl-4,5α-epoxy-3,14β-dihydroxy-7β-methyl-6β-methylaminomorphinan, 17-cyclopropylmethyl-16-cyano-4,5α-epoxy-3,14β-dihydroxy-6α-methylaminomorphinan and 17-cyclopropylmethyl-16-cyano-4,5α-epoxy-3,14β-dihydroxy-6β-methylaminomorphinan were used instead of 17-cyclopropylmethyl-4,5α-epoxy-3,14β-dihydroxy-6α- methylaminomorphinan 4 and 3-trifluoromethylcinnamoyl chloride was used instead of 3,4-dichlorophenylacetyl chloride, thereby preparing 17-cyclopropylmethyl-4,5α-epoxy-3,14β-dihydroxy-7β-methyl-6α-(N-methyl-3-trifluoromethylcinnamamido)morphinan hydrochloride 232 (yield: 75%), 17-cyclopropylmethyl-4,5α-epoxy-3,14β-dihydroxy-7β-methyl-6β-(N-methyl-3-trifluoromethylcinnamamido)morphinan hydrochloride 233 (yield: 73%), 17-cyclopropylmethyl-16-cyano-4,5α-epoxy-3,14β-dihydroxy-6α-(N-methyl-3-trifluoromethylcinnamamido)morphinan hydrochloride 234 (yield: 62%) and 17-cyclopropylmethyl-16-cyano-4,5α-epoxy-3,14β-dihydroxy-6β-(N-methyl-3-trifluoromethylcinnamamido)morphinan hydrochloride 235 (yield: 57%).

Compound 232

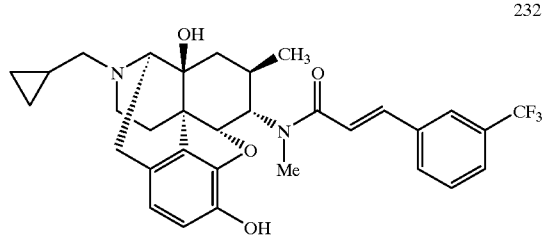

Mass (FAB)

m/z 569 ((M+H)$^+$).

Elementary analysis for $C_{32}H_{35}N_2O_4F_3 \cdot HCl \cdot 0.5H_2O$

Calculated: C, 62.59; H, 6.07; N, 4.56; F, 9.28; Cl, 5.77.

Found: C, 62.73; H, 6.11; N, 4.42; F, 9.21; Cl, 5.86.

Compound 233

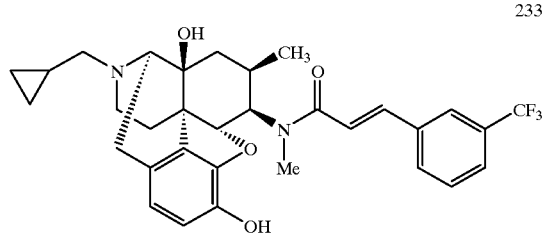

Mass (FAB)

m/z 569 ((M+H)$^+$).

Elementary analysis for $C_{32}H_{35}N_2O_4F_3 \cdot HCl \cdot 0.4H_2O$

Calculated: C, 62.77; H, 6.06; N, 4.58; F, 9.31; Cl, 5.79.

Found: C, 62.55; H, 6.15; N, 4.72; F, 9.23; Cl, 5.93.

Compound 234

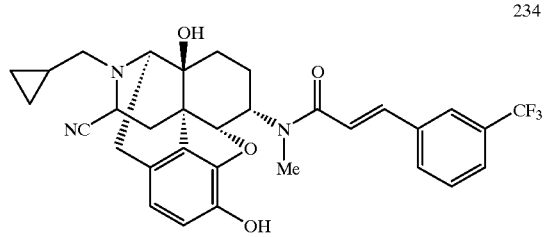

Mass (FAB)

m/z 580 ((M+H)$^+$).

Elementary analysis for $C_{32}H_{32}N_3O_4F_3 \cdot HCl \cdot 0.3H_2O$

Calculated: C, 61.84; H, 5.45; N, 6.76; F, 9.17; Cl, 5.70.

Found: C, 61.99; H, 5.53; N, 6.58; F, 9.11; Cl, 5.81.

Compound 235

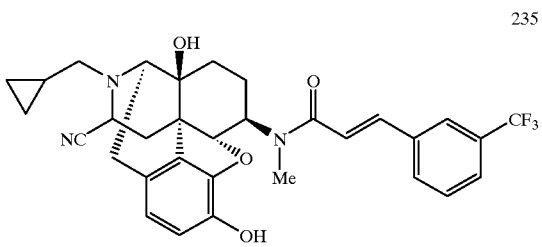

Mass (FAB)

m/z 580 ((M+H)$^+$).

Elementary analysis for $C_{32}H_{32}N_3O_4F_3 \cdot HCl \cdot 0.1H_2O$

Calculated: C, 62.20; H, 5.42; N, 6.80; F, 9.22; Cl, 5.74.

Found: C, 62.03; H, 5.48; N, 6.72; F, 9.31; Cl, 5.83.

Examples 224–226

The procedure of Example 11 was repeated, except that 17-cyclopropylmethyl-4,5α-epoxy-3,14β-dihydroxy-8β-methyl-6α-methylaminomorphinan, 17-cyclopropylmethyl-4,5α-epoxy-3,14β-dihydroxy-8β-methyl-6β-methylaminomorphinan and 17-cyclopropylmethyl-4,5α-epoxy-3,14β-dihydroxy-6β,8β-(bismethylamino)morphinan were used instead of 17-cyclopropylmethyl-4,5α-epoxy-3,14β-dihydroxy-6α-methylaminomorphinan 4 and trans-3-(3-furan)acryloyl chloride was used instead of 3,4-dichlorophenylacetyl chloride, thereby preparing 17-cyclopropyl-methyl-4,5α-epoxy-3,14β-dihydroxy-8β-methyl-6α-[N-methyl-trans-3-(3-furan)acrylamido]morphinan hydrochloride 236 (yield: 64%), 17-cyclopropylmethyl-4,5α-epoxy-3,14β-dihydroxy-8β-methyl-6β-[N-methyl-trans-3-(3-furan)acrylamido]morphinan hydrochloride 237 (yield: 58%) and 17-cyclopropylmethyl-4,5α-epoxy-3,14β-dihydroxy-6β,8β-bis[N-methyl-trans-3-(3-furan)acrylamido]morphinan hydrochloride 238 (yield: 53%).

Compound 236

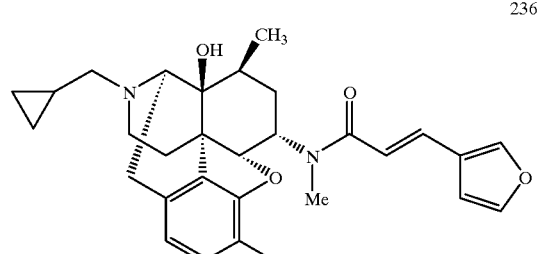

Mass (FAB)

m/z 491 ((M+H)$^+$).

Elementary analysis for $C_{29}H_{34}N_2O_5 \cdot HCl$

Calculated: C, 66.09; H, 6.69; N, 5.32; Cl, 6.73.

Found: C, 66.26; H, 6.73; N, 5.18; Cl, 6.66.

Compound 237

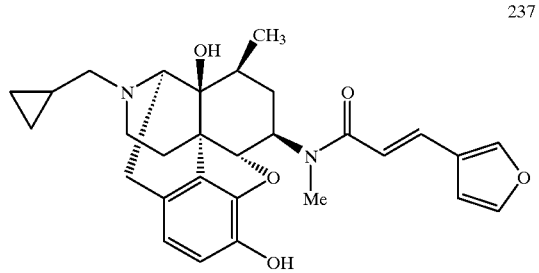

Mass (FAB)
m/z 491 ((M+H)$^+$).
Elementary analysis for $C_{29}H_{34}N_2O_5 \cdot HCl \cdot 0.2H_2O$
Calculated: C, 65.64; H, 6.72; N, 5.28; Cl, 6.68.
Found: C, 65.79; H, 6.67; N, 5.20; Cl, 6.56.

Compound 238

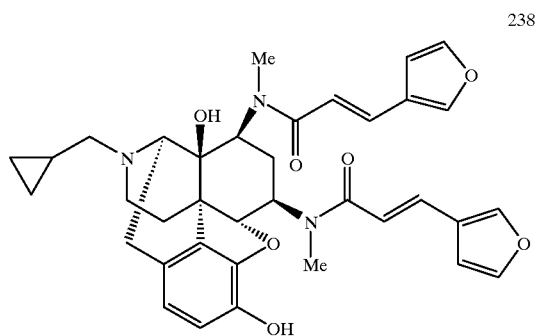

Mass (FAB)
m/z 626 ((M+H)$^+$).
Elementary analysis for $C_{36}H_{39}N_3O_7 \cdot HCl \cdot 0.5H_2O$
Calculated: C, 64.42; H, 6.16; N, 6.26; Cl, 5.28.
Found: C, 64.15; H, 6.25; N, 6.13; Cl, 5.41.

Examples 227–230

The procedure of Example 11 was repeated, except that 17-cyclopropylmethyl-4,5α-epoxy-3,14β-dihydroxy-1-nitro-6α-methylaminomorphinan, 17-cyclopropylmethyl-4,5α-epoxy-3,14β-dihydroxy-1-nitro-6β-methylaminomorphinan, 8-nor-17-cyclopropylmethyl-4,5α-epoxy-3,14β-dihydroxy-6α-methylaminomorphinan and 8-nor-17-cyclopropylmethyl-4,5α-epoxy-3,14β-dihydroxy-6β-methylaminomorphinan were used instead of 17-cyclopropylmethyl-4,5α-epoxy-3,14β-dihydroxy-6α-methylaminomorphinan 4 and 3-methylcinnamoyl chloride was used instead of 3,4-dichlorophenylacetyl chloride, thereby preparing 17-cyclopropylmethyl-4,5α-epoxy-3,14β-dihydroxy-1-nitro-6α-(N-methyl-3-methylcinnamamido)morphinan hydrochloride 239 (yield: 71%), 17-cyclopropylmethyl-4,5α-epoxy-3,14β-dihydroxy-1-nitro-6β-(N-methyl-3-methylcinnamamido)morphinan hydrochloride 240 (yield: 72%), 8-nor-17-cyclopropylmethyl-4,5α-epoxy-3,14β-dihydroxy-6α-(N-methyl-3-methylcinnamamido)morphinan hydrochloride 241 (yield: 63%) and 8-nor-17-cyclopropylmethyl-4,5α-epoxy-3,14β-dihydroxy-6β-(N-methyl-3-methylcinnamamido)morphinan hydrochloride 242 (yield: 57%).

Compound 239

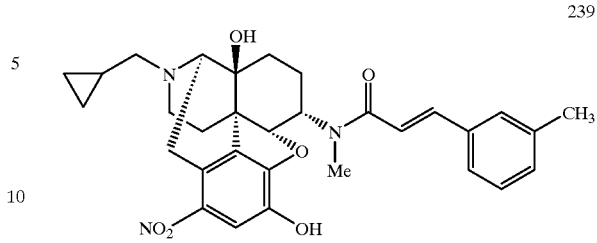

Mass (FAB)
m/z 546 ((M+H)$^+$).
Elementary analysis for $C_{31}H_{35}N_3O_6 \cdot HCl \cdot 0.1H_2O$
Calculated: C, 63.77; H, 6.25; N, 7.20; Cl, 6.07.
Found: C, 63.95; H, 6.31; N, 7.03; Cl, 5.93.

Compound 240

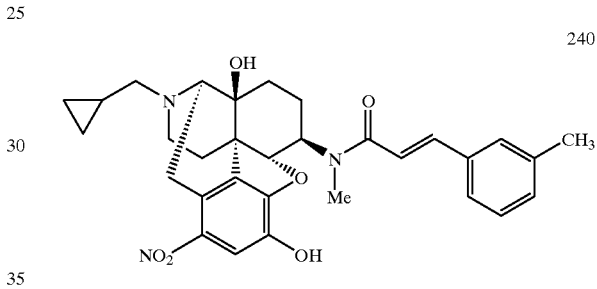

Mass (FAB)
m/z 546 ((M+H)$^+$).
Elementary analysis for $C_{31}H_{35}N_3O_6 \cdot HCl \cdot 0.3H_2O$
Calculated: C, 63.38; H, 6.28; N, 7.15; Cl, 6.03.
Found: C, 63.12; H, 6.31; N, 7.03; Cl, 6.31.

Compound 241

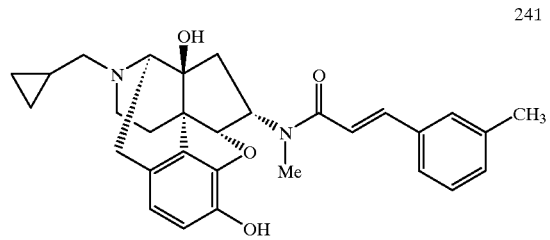

Mass (FAB)
m/z 487 ((M+H)$^+$)
Elementary analysis for $C_{30}H_{34}N_2O_4 \cdot HCl \cdot 0.1H_2O$
Calculated: C, 68.65; H, 6.76; N, 5.34; Cl, 6.75.
Found: C, 68.87; H, 6.75; N, 5.21; Cl, 6.59.

Compound 242

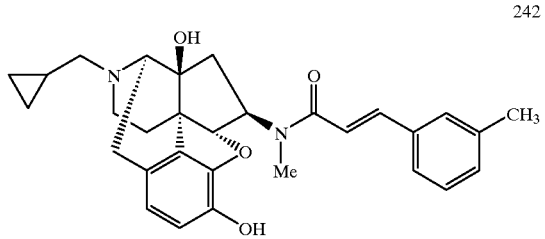

Mass (FAB)

m/z 487 ((M+H)$^+$).
Elementary analysis for $C_{30}H_{34}N_2O_4 \cdot HCl \cdot 0.1H_2O$
Calculated: C, 68.42; H, 6.77; N, 5.32; Cl, 6.73.
Found: C, 68.17; H, 6.75; N, 5.18; Cl, 6.89.

Examples 231–232

The procedure of Example 11 was repeated, except that 17-cyclopropylmethyl-4,5α-epoxy-3,14β-dihydroxy-7α-methylaminomorphinan and 17-cyclopropylmethyl-4,5α-epoxy-3,14β-dihydroxy-7β-methylaminomorphinan were used instead of 17-cyclopropylmethyl-4,5α-epoxy-3,14β-dihydroxy-6α-methylaminomorphinan 4 and 3-trifluoromethoxycinnamoyl chloride was used instead of 3,4-dichlorophenylacetyl chloride, thereby preparing 17-cyclopropylmethyl-4,5α-epoxy-3,14β-dihydroxy-7α-(N-methyl-3-trifluoromethoxycinnamamido)morphinan hydrochloride 243 (yield: 68%) and 17-cyclopropylmethyl-4,5α-epoxy-3,14β-dihydroxy-7β-(N-methyl-3-trifluoromethoxycinnamamido)morphinan hydrochloride 244 (yield: 71%).

Compound 243

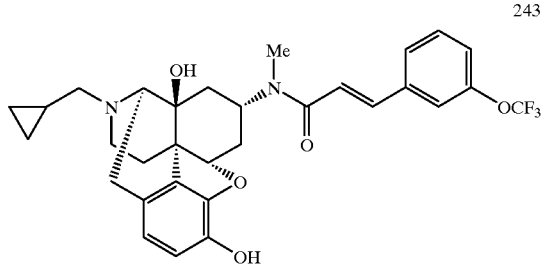

Mass (FAB)

m/z 571 ((M+H)$^+$).
Elementary analysis for $C_{31}H_{33}N_2O_5F_3 \cdot HCl$
Calculated: C, 61.33; H, 5.64; N, 4.61; F, 9.39; Cl, 5.84.
Found: C, 61.55; H, 5.69; N, 4.44; F, 9.22; Cl, 5.90.

Compound 244

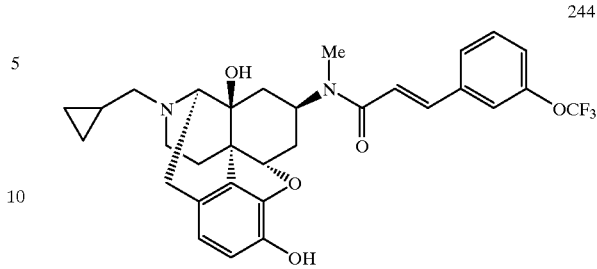

Mass (FAB)
m/z 571 ((M+H)$^+$).
Elementary analysis for $C_{31}H_{33}N_2O_5F_3 \cdot HCl \cdot 0.3H_2O$
Calculated: C, 60.79; H, 5.69; N, 4.57; F, 9.31; Cl, 5.79.
Found: C, 60.55; H, 5.75; N, 4.41; F, 9.42; Cl, 5.92.

Example 233

Opioid Activity Test Using an Extracted Guinea Pig Ileum Preparation

A male Hartley guinea pig was used in this test. After sacrificing the guinea pig and extracting the ileum, the lumen was washed with nutrient solution and only the longitudinal muscle was isolated. This longitudinal muscle was suspended in a Magnus tube filled with Krebes-Henseleit solution (NaCl 118 mM; KCl 4.7 mM; CaCl$_2$ 2.5 mM; KH$_2$PO$_4$ 1.2 mM; NaHCO$_3$ 25 mM; MgSO$_4$ 1.2 mM; Glucose 10 mM) warmed to 37° C. and ventilated with 5% carbon dioxide and 95% oxygen. Electrical stimulus was performed at 0.1 Hz for 5.0 ms by means of ring-shaped platinum electrodes located above and below. Tissue contractions were recorded on a polygraph using an isometric transducer.

Initially, the test drug was cumulatively added to a concentration at which specimen contractions caused by electrical stimulus were suppressed by 50% to calculate the IC$_{50}$ value. After adequately washing with nutrient solution and the contraction reaction stabilized, the μ agonist, naloxone, or the κ agonist, norBNI, was added after which the test compound was again cumulatively added after roughly 20 minutes. The Ke value was calculated using the following calculation formula from the difference in the efficacies of both agonists.

Ke=[Conc. of added agonist]/(IC$_{50}$ ratio−1)
IC$_{50}$ ratio=IC$_{50}$ in the presence of agonist/IC$_{50}$ in the absence of agonist As a result, when the ratio between the Ke value (μ) and the Ke value (κ) was taken, Ke(μ)/Ke(κ)=4063. It was thus found that the compounds of the present invention are highly selective agonists for κ receptors.

| | | Ke (nM) | |
|---|---|---|---|
| | IC$_{50}$ (nM) | Naloxone | norBNI |
| 1 | 0.026 | 650 | 0.16 |

Example 234

Opioid Activity Test Using an Extracted Mouse Vas Deferens Preparation

A male ddy mouse was used in this test. The vas deferens extracted from the animal was suspended in a Magnus tube filled with Krebes-Henseleit solution (NaCl 118 mM; KCl 4.7 mM; $CaCl_2$ 2.5 mM; $KH_2PO_4$ 1.1 mM; $NaHCO_3$ 25 mM; Glucose 11 mM) warmed to 37° C. and ventilated with 5% carbon dioxide and 95% oxygen. Electrical stimulus was performed at 0.1 Hz for 5.0 ms by means of ring-shaped platinum electrodes located above and below. Tissue contractions were recorded on a polygraph using an isometric transducer.

Initially, the test drug was cumulatively added to a concentration at which specimen contractions caused by electrical stimulus were suppressed by 50% to calculate the $IC_{50}$ value. After adequately washing with nutrient solution and the contraction reaction stabilized, the μ agonist, naloxone, the δ agonist, NTI, or the κ agonist, norBNI, was added after which the test compound was again cumulatively added after roughly 20 minutes. The Ke value was calculated using the following calculation formula from the difference in the efficacies of both agonists.

Ke=[Conc. of added agonist]/($IC_{50}$ ratio−1)

$IC_{50}$ ratio=$IC_{50}$ in the presence of agonist/$IC_{50}$ in the absence of agonist A portion of the evaluation results of the compounds of the present invention are shown in Table 1. In all cases, there were no large differences in $IC_{50}$ values before and after use of naltrexone, and agonist activity by means of μ receptors was found to be extremely weak. Namely, compounds 24, 84, 25, 97 and 126 are selective agonists for δ receptors, while compounds 1, 22, 38, 39, 42, 43, 45, 46, 47, 53, 57, 59, 60, 61, 62, 63, 68, 69, 70, 73, 89, 91, 98, 99, 100, 101, 102, 103, 104, 122, 140, 141, 150, 151, 152, 154, 156, 172 and 173 are selective agonists for κ receptors.

TABLE 1

Opioid Activity of Compounds

| | | Ke (nM) | | |
|---|---|---|---|---|
| | IC50 (nM) | Naloxone | NTI | norBNI |
| 1 | 0.395 | 53 | 17.3 | 0.548 |
| 22 | 1.20 | 800 | 545 | 5.53 |
| 24 | 0.121 | 16.5 | 0.426 | 4.90 |
| 38 | 0.349 | 411 | 16.6 | 4.65 |
| 39 | 0.568 | 89.9 | 99.3 | 1.01 |
| 42 | 0.251 | 186 | 63.5 | 0.905 |
| 43 | 0.650 | 409 | 22.5 | 5.31 |
| 45 | 0.185 | 26.5 | 135 | 0.416 |
| 46 | 1.05 | — | — | 0.440 |
| 47 | 0.439 | 63.5 | 10.4 | 0.140 |
| 53 | 10.3 | — | 1676 | 0.21 |
| 57 | 0.0254 | — | 747 | 0.0124 |
| 59 | 1.14 | 21.3 | 47.3 | 0.151 |
| 60 | 0.468 | — | 291 | 3.20 |
| 61 | 0.420 | 14000 | 41.6 | 0.164 |
| 62 | 14.7 | — | 90.2 | 0.203 |
| 63 | 0.746 | 60.9 | 96.9 | 1.60 |
| 68 | 0.457 | 5710 | 143 | 1.08 |
| 69 | 0.320 | 1780 | 64.5 | 1.95 |
| 70 | 0.545 | — | — | 0.198 |
| 73 | 0.072 | 524 | 78 | 0.272 |
| 84 | 2.07 | 35.4 | 0.309 | 5.69 |
| 89 | 0.0934 | 18.3 | 15.6 | 0.85 |
| 91 | 0.378 | — | 450 | 0.699 |
| 96 | 0.346 | 32.5 | 1.61 | 4.21 |
| 97 | 0.247 | 163 | 2.92 | 13.9 |
| 98 | 1.30 | — | — | 1.35 |
| 99 | 0.674 | 94.5 | — | 0.652 |
| 100 | 0.647 | 1797 | — | 0.0717 |
| 101 | 0.269 | 25.4 | 31.6 | 0.0425 |
| 102 | 1.60 | — | 276 | 2.37 |
| 103 | 11.0 | — | — | 0.657 |
| 104 | 0.227 | 185 | 89 | 1.40 |
| 122 | 3.01 | 59.5 | 42.7 | 0.358 |
| 126 | 0.969 | 40.2 | 0.0065 | 1.20 |
| 140 | 0.413 | 320 | 261 | 1.06 |
| 141 | 0.160 | 142 | 184 | 1.39 |
| 150 | 1.67 | 137 | 55.6 | 0.303 |
| 151 | 0.00026 | 0.94 | 1.65 | 0.028 |
| 152 | 0.0055 | 17.5 | 35.1 | 0.039 |
| 154 | 0.0022 | 43.1 | 31.5 | 0.133 |
| 156 | 0.0021 | — | — | 0.091 |
| 166 | 0.028 | 36.9 | 20.5 | 4.78 |
| 172 | 0.00178 | 16.16 | 17.57 | 0.163 |
| 173 | 0.02 | 19.6 | 21.3 | 0.11 |

Example 235

Analgesic Activity Test Using the Acetic Acid-Induced Writhing Method 5 week old ddy mice were used in this test. After intraperitoneal administration of 0.1 ml of 0.6% aqueous acetic acid per 10 g of body weight, the number of writhing reactions that occurred in 10 minutes starting 10 minutes after administration was evaluated for the indicator. The test drug was administered subcutaneously into the backs of the animals 15 minutes before administration of acetic acid. A portion of those results are shown in Table 2. In this test, compounds 42, 47, 63, 96, 154 and 178 demonstrated $ED_{50}$ values of 0.00136, 0.00052, 0.0011, 0.00086, 0.001 and 0.0016 mg/Kg, respectively, indicating particularly strong analgesic activity.

TABLE 2

Analgesic Activity According to Acetic Acid Writhing

| Compound | $ED_{50}$ (mg/Kg) | Compound | $ED_{50}$ (mg/kg) |
|---|---|---|---|
| 1 | 0.017 | 22 | 0.0051 |
| 23 | 0.67 | 24 | 0.00575 |
| 26 | 0.099 | 27 | 0.046 |
| 28 | 0.071 | 31 | 0.75 |
| 32 | 0.290 | 33 | 0.080 |
| 34 | 0.210 | 35 | 0.026 |
| 36 | 0.23 | 37 | 0.0041 |
| 38 | 0.00352 | 39 | 0.0088 |
| 41 | 0.39 | 42 | 0.00136 |
| 43 | 0.0055 | 44 | 0.084 |
| 45 | 0.0038 | 46 | 0.013 |
| 47 | 0.00052 | 48 | 0.019 |
| 49 | 0.026 | 50 | 0.011 |
| 51 | 0.19 | 53 | 0.46 |
| 54 | 0.72 | 55 | 0.980 |
| 56 | 0.00802 | 57 | 0.040 |
| 58 | 0.190 | 59 | 0.0028 |
| 60 | 0.0046 | 61 | 0.0044 |
| 62 | 0.077 | 63 | 0.0011 |
| 64 | 0.097 | 65 | 0.15 |
| 67 | 0.36 | 68 | 0.0042 |
| 69 | 0.0049 | 70 | 0.0016 |
| 71 | 0.0042 | 72 | 0.18 |
| 73 | 0.023 | 74 | 0.78 |
| 83 | 0.0080 | 84 | 0.0058 |
| 85 | 0.1128 | 86 | 0.0347 |
| 87 | 0.027 | 89 | 0.00471 |
| 91 | 0.019 | 94 | 0.013 |
| 95 | 0.0081 | 96 | 0.00086 |

TABLE 2-continued

Analgesic Activity According to Acetic Acid Writhing

| Compound | ED$_{50}$ (mg/Kg) | Compound | ED$_{50}$ (mg/kg) |
|---|---|---|---|
| 97 | 0.0019 | 98 | 0.0068 |
| 99 | 0.0018 | 100 | 0.024 |
| 101 | 0.0066 | 102 | 0.0019 |
| 103 | 0.069 | 104 | 0.017 |
| 105 | 0.098 | 106 | 0.25 |
| 107 | 0.023 | 108 | 0.0064 |
| 122 | 0.34 | 128 | 0.63 |
| 132 | 0.073 | 133 | 0.044 |
| 134 | 0.15 | 137 | 0.170 |
| 138 | 0.014 | 139 | 0.040 |
| 140 | 0.0034 | 141 | 0.010 |
| 142 | 0.78 | 144 | 0.024 |
| 149 | 0.013 | 150 | 0.035 |
| 151 | 0.0041 | 152 | 0.0038 |
| 153 | 0.13 | 154 | 0.001 |
| 155 | 0.012 | 156 | 0.0056 |
| 157 | 0.003 | 158 | 0.0071 |
| 159 | 0.0032 | 160 | 0.0027 |
| 162 | 0.018 | 163 | 0.37 |
| 171 | 0.038 | 172 | 0.0079 |
| 173 | 0.011 | 174 | 0.16 |
| 175 | 0.018 | 176 | 0.11 |
| 177 | 0.0096 | 178 | 0.0016 |
| 179 | 0.0028 | 183 | 0.013 |
| 184 | 0.0043 | 186 | 0.0061 |
| 187 | 0.026 | 188 | 0.002 |
| 199 | 0.017 | 202 | 0.083 |
| 203 | 0.38 | 204 | 0.013 |
| 217 | 0.018 | Morphine | 0.55 |

Example 236

Evaluation of Diuretic Action

7–8 week old male Wistar rats were used in this test after prohibiting from drinking water for 1 hour before the start of testing. After discharging any urine accumulated in the bladder by gently stimulating the lower abdomens of the animals, the drug was administered subcutaneously. After 30 minutes, the animals were then forcibly given 20 ml/kg of physiological saline orally. The animals were placed in metabolic cages immediately after administration of the drug (2 animals/cage) and urine output for 5 hours after loading with physiological saline was measured. Drug efficacy was expressed in the form of those doses resulting in urine outputs of 200 and 500, respectively, when the urine output of a non-dosed group was taken to be 100. Those doses were expressed as the ED$_{200}$ and ED$_{500}$ values, respectively. A portion of those results are shown in Table 3. In this test, the ED200 values of compounds 22, 24, 42, 43, 152 and 178 were 0.00095, 0.00069, 0.00085, 0.00054, 0.00071 and 0.00094 mg/kg, respectively, indicating that these compounds have extremely strong diuretic action.

TABLE 3

Diuretic Action

| Compound | ED$_{200}$ (mg/kg) | ED$_{500}$ (mg/kg) | Compound | ED$_{200}$ (mg/kg) | ED$_{500}$ (mg/kg) |
|---|---|---|---|---|---|
| 1 | 0.0027 | 0.0457 | 22 | 0.00095 | 0.0170 |
| 24 | 0.00069 | 0.0063 | 27 | 0.0248 | 2.075 |
| 28 | 0.0200 | 3.799 | 35 | 0.0245 | 5.19 |
| 37 | 0.365 | — | 38 | 0.0038 | 0.281 |
| 39 | 0.0041 | 0.228 | 42 | 0.00085 | 0.0061 |
| 43 | 0.00054 | 0.0044 | 45 | 0.0081 | 0.857 |
| 47 | 0.0016 | — | 50 | 0.0021 | 0.0325 |
| 53 | 0.135 | 0.658 | 56 | 0.0028 | 0.0518 |
| 57 | 0.0424 | 1.256 | 59 | 0.0105 | 2.364 |
| 60 | 0.0143 | 1.13 | 61 | 0.0032 | 0.157 |
| 62 | 0.101 | 7.04 | 63 | 0.0038 | 0.309 |
| 65 | 0.119 | 5.31 | 68 | 0.0016 | 0.0232 |
| 83 | 0.0261 | 2.99 | 84 | 0.0028 | 0.0469 |
| 86 | 0.0057 | 0.229 | 89 | 0.0012 | 0.0162 |
| 91 | 0.0094 | 0.960 | 95 | 0.0028 | 0.0968 |
| 96 | 0.0013 | 0.0549 | 97 | 0.0045 | 0.0939 |
| 98 | 0.0065 | 0.206 | 99 | 0.0011 | 0.0309 |
| 100 | 0.0159 | 0.811 | 101 | 0.0089 | 0.226 |
| 102 | 0.0014 | 0.0154 | 103 | 0.0827 | 5.65 |
| 105 | 0.0190 | 3.30 | 107 | 0.0061 | 0.20 |
| 108 | 0.0210 | 5.11 | 141 | 0.0319 | 3.45 |
| 150 | 0.0429 | 0.762 | 151 | 0.00445 | 1.56 |
| 152 | 0.00071 | 0.00953 | 154 | 0.00214 | 0.27 |
| 156 | 0.00545 | 0.355 | 172 | 0.00323 | 3.03 |
| 173 | 0.0275 | 1.55 | 178 | 0.00094 | 0.0045 |
| 184 | 0.00444 | 0.0326 | | | |

Example 237

Evaluation of Antitussive Action Using the Guinea Pig Respiratory Tract Stimulation Method Male Hartley guinea pigs having body weights of 330–380 g were used in this test in groups of 5 animals each. The animals were immobilized in the supine position under mild anesthesia by intraperitoneal administration of 15 mg/kg of sodium pentobarbital. An incision was made in the necks of the animals to expose the respiratory tract. A small hole was opened in the exposed respiratory tract, and stimulating hairs were inserted to a depth of roughly 3 cm and at an angle of 30 degrees to the respiratory tract through the opened hole to provide a stimulus to the inner wall of the respiratory tract. The animals were then examined for the presence of coughing. Only those animals that were reliably confirmed to demonstrate coughing were used in further testing. The test drug was administered subcutaneously, and stimuli were provided two times each 15, 30, 60 and 120 minutes after administration. The test drug was considered to be effective when the animal did not cough after both stimulations. Those evaluation results are shown in Table 4. All the test compounds were found to demonstrate strong antitussive action.

TABLE 4

Antitussive Activity of Compounds

| Compound | Dose (µg/kg) | No. of Animals in which Coughing was Suppressed/No. of Animals Tested | ED$_{50}$ (µg/kg) |
|---|---|---|---|
| 60 | 1 | 1/5 | 2.6 |
| | 3 | 3/5 | |
| | 30 | 5/5 | |
| 61 | 1 | 2/5 | 3.7 |
| | 3 | 3/5 | |
| | 30 | 5/5 | |

TABLE 4-continued

Antitussive Activity of Compounds

| Compound | Dose (μg/kg) | No. of Animals in which Coughing was Suppressed/No. of Animals Tested | $ED_{50}$ (μg/kg) |
|---|---|---|---|
| 69 | 1 | 1/5 | 12.5 |
|  | 3 | 1/5 |  |
|  | 30 | 4/5 |  |

Cultured Nerve Cell Protective Action Against Glutamic Acid Toxicity

When blood flow to the brain is temporarily interrupted due to transient cerebral ischemia, hypoglycemia, hypoxia or trauma, delayed neuronal death is known to be induced [T. Kirino, Brain Research, 239, 57 (1982)]. One of the possible causes of this nerve cell disorder is believed to be analeptic toxicity caused by analeptic neurotransmitters such as glutamic acid released in excess accompanying ischemia [S. M. Rotherman and J. W. Olney, Trends in Neuroscience, 10, 299 (1987)]. Compounds that protect nerve cells from this cytotoxicity caused by glutamic acid are considered to be promising for use as preventive and therapeutic agents for ischemic brain disorders, brain nerve cell disorders and dementia which are problems that the present invention is attempting to solve. The procedure described below was performed as a means of evaluating this protective action in vitro.

Fetuses were removed from the abdomens of female Wistar rats on days 18–19 of pregnancy under sterile conditions, and their brains were extracted after opening the skull. The brains were placed in ice-cooled L-15 medium and the cerebral cortex was isolated microscopically. After preparing thin sections of the cerebral cortex from the brains of roughly 30 fetuses, the thin sections were suspended in 10 ml of 0.25% trypsin and 0.2 ml of 0.01% DNTAase and cultured for 30 minutes at 37° C. Next, 2 ml of serum were added followed immediately by centrifuging for 2 minutes at 1200 rpm after which the sediment was isolated. 7 ml of DF medium (containing 20 nM of transferrin, 5 μg/ml of insulin, 20 nM of progesterone, 60 nM of selenite, 50 U/ml of penicillin and 50 U/ml of streptomycin added to a mixture of equal volumes of Dulbecco's modified Eagle medium and F-12 medium) was added to this sediment after which a cell suspension was obtained by repeating pipetting 20 times with a 10 ml plastic pipette. Moreover, isolated cells were removed by filtering with Nylon mesh (pore size: 43 μm). The resulting isolated cells were diluted with DF medium to a concentration of 6.0×10⁵ cells/ml. 500 μl aliquots of these diluted cells were then placed on a 48-hole culture plate precoated with polizine followed by culturing for 1 day at 37° C. in the presence of 5% $CO_2$. The medium was replaced with fresh DF medium on the second day and 10 μl aliquots of 0.5 M glutamic acid solution dissolved in distilled water were added to each hole (resulting in a final glutamic acid concentration of 10 mM). This was followed by additional culturing for 24 hours at 37° C. in the presence of 5% $CO_2$. The test compounds were dissolved in distilled water, 10% DMSO, 100% DMSO or 10% methanol, and 5 μl aliquots were added to each hole immediately before addition of glutamic acid. The enzyme activity of lactate dehydrogenase (LDH) that leaks into the medium from cells that have been damaged was measured as the indicator of nerve cell damage. The amount of leaked LDH was measured according to the respective concentrations of each test compound, and the dose reaction curve was determined according to the modified Cochrane-Armitige method. The 50% effective doses ($ED_{50}$) were then determined for each test compound from this curve. Those results are shown in Table 5.

TABLE 5

Cultured Nerve Cell Protective Action Against Glutamic Acid Toxicity

| Compound | $ED_{50}$ (μM) | Compound | $ED_{50}$ (μM) | Compound | $ED_{50}$ (μM) |
|---|---|---|---|---|---|
| 1 | 0.50 | 23 | 1.61 | 24 | 1.91 |
| 25 | 7.60 | 30 | 7.95 | 32 | 2.14 |
| 33 | 3.53 | 34 | 0.18 | 35 | 0.64 |
| 36 | 0.23 | 51 | 0.03 | 52 | 1.71 |
| 53 | 2.51 | 56 | 5.23 | 57 | 15.27 |
| 58 | 16.67 | 60 | 1.31 | 61 | 16.26 |
| 68 | 1.41 | 100 | 1.74 | 99 | 15.41 |
| 101 | 12.18 | 104 | 5.45 | 84 | 2.70 |
| 108 | 0.25 | 112 | 4.24 | 116 | 2.37 |
| 135 | 0.29 | 136 | 0.64 | 8 | 5.75 |

As a result, compounds 1, 23, 24, 25, 30, 32, 33, 34, 35, 36, 51, 52, 53, 56, 57, 58, 60, 61, 68, 100, 99, 101, 104, 84, 108, 112, 116, 135, 136 and 8 of the present invention clearly demonstrated action that protects nerve cells from cytotoxicity caused by glutamic acid.

Example 239

Delayed Neuronal Death Protective Action

Those compounds that provide protection from and suppress delayed neuronal death described in Example 238 are considered to be promising as preventive and therapeutic agents for ischemic brain disorders, brain nerve cell disorders and dementia, which are problems that the present invention is attempting to solve. The pharmacological activity of the compounds of the present invention was evaluated in the manner below using gerbils for the animal model.

A midline incision was made in gerbils having body weights of 50–70 g under ether anesthesia. Blood flow through the carotid arteries on both sides was interrupted to create an ischemic state by ligating the vessels for 5 minutes. The test compound was administered subcutaneously either 30 minutes or 1 hour prior to ligation ischemia, and the rectal temperature of the animals was controlled to 37±2° C. using a heating pad or heater starting 5 minutes before to 30 minutes after ligation ischemia. 1 week after ligation, 4% neutral buffered formalin was perfused from the heart throughout the body followed by extraction of the brain. After post-fixing the extracted brain in the same solution, the tissue was prepared into sections after embedding in paraffin. The sections were stained with hematoxylin and eosin stain, and the number of nerve cells in the region of the hippocampus CA1 over a width of 1 mm to the left and right was counted. The total number of nerve cells on the right and left sides was then used for evaluation. Those results are shown in Table 6.

TABLE 6

Late Brain Nerve Cell Necrosis Protective Action

| Compound | Dose (mg/kg) | No. of Residual Nerve Cells |
| --- | --- | --- |
| 36 | 0.03 (30 minutes before ischemia) | 38.8 ± 19.6 |
|  | 0.3 (30 minutes before ischemia) | 85.5 ± 34.9 |
|  | 3 (30 minutes, before ischemia) | 68.0 ± 45.3 |
| 51 | 0.03 (30 minutes before ischemia) | 17.8 ± 6.9 |
|  | 0.3 (30 minutes before ischemia) | 46.4 ± 15.1 |
|  | 3 (30 minutes before ischemia) | 203.8 ± 40.1 |
| 60 | 0.03 (1 hour before ischemia) | 52.1 ± 14.8 |
|  | 0.3 (1 hour before ischemia) | 148.3 ± 28.5 |
|  | 3 (1 hour before ischemia) | 284.5 ± 7.1 |
| 69 | 0.03 (30 minutes before ischemia) | 12.4 ± 3.0 |
|  | 0.3. (30 minutes before ischemia) | 43.3 ± 19.1 |
|  | 3 (30 minutes before ischemia) | 178.3 ± 30.4 |
| 104 | 0.03 (30 minutes before ischemia) | 12.0 ± 3.0 |
|  | 0.3 (30 minutes before ischemia) | 14.8 ± 1.2 |
|  | 3 (30 minutes before ischemia) | 106.2 ± 65.6 |
| Pseudo-surgical group | Not dosed | 323.4 ± 6.8 |
| Control group | 10% DMSO | 21.9 ± 8.5 |

As a result, compounds 36, 51, 60, 69 and 104 of the present invention were found to significantly suppress defluxion of brain nerve cells caused by ischemia, and clearly demonstrated cerebro-neuroprotective activity.

INDUSTRIAL APPLICABILITY

As a result of in vitro and in vivo tests of activity, the compounds of the present invention were found to have strong analgesic, diuretic and antitussive action as κ-agonists. On the other hand, since these compounds also demonstrated excellent protective effects against brain nerve cell necrosis, they can also be expected to be able to be used as brain cell protectors such as preventive and therapeutic agents for ischemic brain disorders and dementia based on damage to brain nerve cells. Moreover, based on the properties of κ-agonists, the compounds of the present invention can also be used as hypotensives and sedatives. What is more, it was also found that agonists highly selective for δ receptors are also included in the compounds of the present invention, thus suggesting the possibility of their use as immunoenhancers and anti-HIV agents.

What is claimed is:

1. A morphinan derivative represented by formula (I-A) below or a pharmaceutically acceptable acid addition salt thereof:

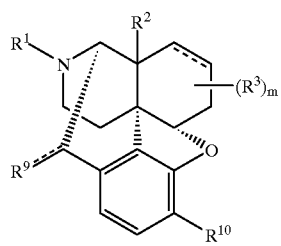

(I-A)

wherein

..... represents a single or double bond;

$R^1$ represents an alkyl group having 1 to 5 carbon atoms, a cycloalkylalkyl group having 4 to 7 carbon atoms, a cycloalkenylalkyl group having 5 to 7 carbon atoms, an aryl group having 6 to 12 carbon atoms including carbon atoms in any substituent group, an aralkyl group having 7 to 13 carbon atoms, an alkenyl group having 4 to 7 carbon atoms, or an allyl group;

$R^2$ represents a hydrogen atom, a hydroxy group, a nitro group, a straight chain alkanoyloxy group having 1 to 5 carbon atoms, a straight chain alkoxy group having 1 to 5 carbon atoms, a straight chain alkyl group having 1 to 5 carbon atoms, or the group $NR^{13}R^{14}$ wherein $R^{13}$ represents a hydrogen atom, a straight chain alkyl group having 1 to 5 carbon atoms, and $R^{14}$ represents a hydrogen atom, a straight chain alkyl group having 1 to 5 carbon atoms, or $-C(=O)R^{15}$ group wherein $R^{15}$ represents a hydrogen atom, a phenyl group, or a straight chain alkyl group having 1 to 5 carbon atoms;

$R^3$ represents $-A-B-R^{11}$ wherein

A represents $-NR^{12'}C(=O)-$, $-NR^{12'}C(=O)O-$, $-NR^{12'}C(=S)NR^{12}-$, or $-NR^{12'}C(=O)NR^{12}$, wherein $R^{12'}$ represents a straight chain alkyl group having 1 to 5 carbon atoms, a branched chain alkyl group having 3 to 5 carbon atoms, or an aryl group having 6 to 12 carbon atoms including carbon atoms in any substituent group, and $R^{12}$ represents a hydrogen atom, a straight chain alkyl group having 1 to 5 carbon atoms, a branched chain alkyl group having 3 to 5 carbon atoms, or an aryl group having 6 to 12 carbon atoms including carbon atoms in any substituent group;

B represents a valence bond, straight chain or branched chain alkylene group having 1 to 14, or 3 to 14 carbon atoms respectively which may be substituted with at least one substituent group selected from the group consisting of an alkoxy group having 1 to 5 carbon atoms, an alkanoyloxy group having 1 to 5 carbon atoms, a hydroxy group, an amino group, a cyano group, a trifluoromethyl group and a phenoxy group, a straight chain or branched chain acyclic unsaturated hydrocarbon group having 2 to 14, or 3 to 14 carbon atoms respectively and having 1 to 3 double bonds and/or triple bonds which may be substituted with at least one substituent group selected from the group consisting of an alkoxy group having 1 to 5 carbon atoms, an alkanoyloxy group having 1 to 5 carbon atoms, a hydroxy group, an amino group, a cyano group, a trifluoromethyl group and a phenoxy group, and wherein the number of carbon atoms is not less than twice the number of unsaturated bonds, or a divalent linking group comprising one or more of a straight chain or branched chain saturated or unsaturated hydrocarbon radical and 1 to 5 linkages selected from the group consisting of a thioether linkage, an ether linkage and an amino linkage wherein the total number of carbon atoms and linkages is from 2 to 14 and said linkages are not adjacent to one another and wherein any hetero atom is not bonded directly to A; and, $R^{11}$ represents a hydrogen atom, or an organic group having one of the following structures:

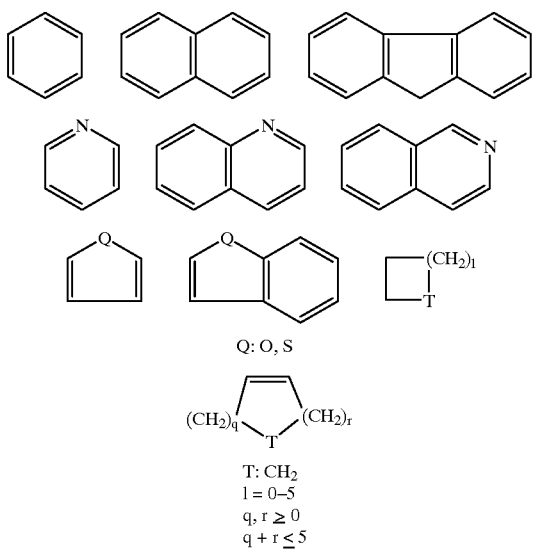

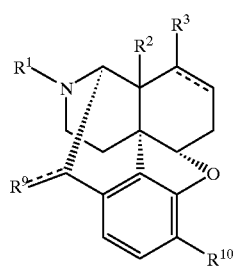

T: $CH_2$
l = 0–5
q, r ≥ 0
q + r ≤ 5 which may be substituted with at least one substituent group selected from the group consisting of an alkyl group having 1 to 5 carbon atoms, an alkoxy group having 1 to 5 carbon atoms, a hydroxy group, fluorine, chlorine, bromine, iodine, an amino group, a nitro group, a cyano group, an isothiocyanato group, a trifluoromethyl group, a trifluoromethoxy group and a methylenedioxy group;

m is an integer from 1 to 2, and $R^3$ may be identical or different in the case of m being equal to 2;

$R^9$ represents a hydroxy group, fluorine, chlorine, bromine, iodine, or a carbonyl group;

$R^{10}$ represents a hydrogen atom, a hydroxy group, an alkanoyloxy group having 1 to 5 carbon atoms, or an alkoxy group having 1 to 5 carbon atoms;

and, the formula (I-A) includes the (+) form, (–) form and (±) form.

2. The morphinan derivative according to claim 1, or its pharmaceutically acceptable acid addition salt, represented with the formula (I-G) or (I-H):

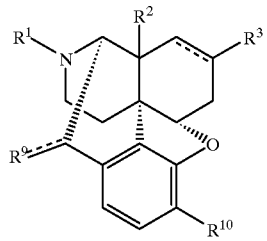
(I-G)

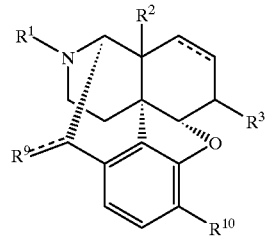
(I-H)

wherein ..... represents a double bond or single bond, $R^1$, $R^2$, $R^3$, $R^9$, and $R^{10}$ are the same as previously defined, and the formula (I-G) or (I-H) includes the (+) form, (–) form and (±) form.

3. The morphinan derivative according to claim 1, or its pharmaceutically acceptable acid addition salt, represented with the formula (I-J):

(I-J)

wherein ..... represents a double bond or single bond, $R^1$, $R^2$, $R^3$, $R^9$, and $R^{10}$ are the same as previously defined, and the general formula (I-J) includes the (+) form, (–) form and (±) form.

4. The morphinan derivative according to claim 3, or its pharmaceutically acceptable acid addition salt, wherein $R^1$ represents a methyl group, an ethyl group, a cyclopropylmethyl group, a cyclobutylmethyl group, an allyl group, a benzyl group, or a phenethyl group;

$R^2$ represents a hydrogen atom, a hydroxy group, an acetoxy group, or a methoxy group;

$R^3$ represents —A—B—$R^{11}$, wherein
A represents —$NR^{12'}C(=O)$—, —$NR^{12'}C(=O)O$—, —$NR^{12'}C(=S)NR^{12}$—, or —$NR^{12'}C(=O)NR^{12}$—, wherein
$R^{12'}$ represents a methyl group, an ethyl group, a propyl group, an isopropyl group, a butyl group, or an isobutyl group;
$R^{12}$ represents a hydrogen atom or a straight chain alkyl group having 1 to 5 carbon atoms;
B represents a straight chain alkyl group having 1 to 5 carbon atoms, —CH=CH—, —C≡C—, or —$CH_2O$—; and
$R^{11}$ represents a hydrogen atom or an organic group having one of the following structures:

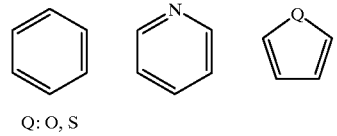

Q: O, S which may be substituted with at least one substituent group selected from the group consisting of an alkyl group having 1 to 5 carbon atoms, an alkoxy group having 1 to 5 carbon atoms, a hydroxy group, a fluorine atom, a chlorine atom, a bromine atom, an iodine atom, an amino group, a nitro group, a cyano group, an isothiocyanato group, a trifluoromethyl group, a trifluoromethoxy group and a methylenedioxy group;

$R^9$ is a hydroxy group or a carbonyl group; and $R^{10}$ represents a hydrogen atom, a hydroxy group, an acetoxy group, or a methoxy group.

5. A pharmaceutical composition comprising a pharmaceutically effective amount of the morphinan derivative according to claim 1, or its pharmaceutically acceptable acid addition salt, and a pharmaceutically acceptable carrier.

6. A method for treating pain which comprises administering to a patient in need thereof, an effective analgesic amount of a morphinan derivative according to claim 1, or its pharmaceutically acceptable acid addition salt.

* * * * *